(12) United States Patent
Houghton et al.

(10) Patent No.: US 12,048,742 B2
(45) Date of Patent: Jul. 30, 2024

(54) HEPATITIS C VIRUS PEPTIDE COMPOSITIONS AND METHODS OF USE THEREOF

(71) Applicant: The Governors of the University of Alberta, Edmonton (CA)

(72) Inventors: Michael Houghton, Danville, CA (US); Abdolamir Landi, Edmonton (CA); Michael Logan, Edmonton (CA); John L. Law, Edmonton (CA); Chao Chen, Edmonton (CA); Darren Hockman, Edmonton (CA)

(73) Assignee: The Governors of the University of Alberta, Edmonton (CA)

( * ) Notice: Subject to any disclaimer, the term of this patent is extended or adjusted under 35 U.S.C. 154(b) by 774 days.

(21) Appl. No.: 16/978,486

(22) PCT Filed: Mar. 14, 2019

(86) PCT No.: PCT/CA2019/050320
§ 371 (c)(1),
(2) Date: Sep. 4, 2020

(87) PCT Pub. No.: WO2019/173925
PCT Pub. Date: Sep. 19, 2019

(65) Prior Publication Data
US 2021/0052721 A1   Feb. 25, 2021

Related U.S. Application Data

(60) Provisional application No. 62/644,140, filed on Mar. 16, 2018.

(51) Int. Cl.
| | | |
|---|---|---|
| *A61K 39/29* | (2006.01) | |
| *A61K 39/00* | (2006.01) | |
| *A61P 31/14* | (2006.01) | |
| *A61P 37/04* | (2006.01) | |

(52) U.S. Cl.
CPC .............. *A61K 39/29* (2013.01); *A61P 31/14* (2018.01); *A61P 37/04* (2018.01); *A61K 2039/55505* (2013.01); *C12N 2770/24222* (2013.01); *C12N 2770/24234* (2013.01)

(58) Field of Classification Search
None
See application file for complete search history.

(56) References Cited

U.S. PATENT DOCUMENTS

| | | | |
|---|---|---|---|
| 5,639,594 A | | 6/1997 | Wang et al. |
| 6,977,144 B2 * | | 12/2005 | Legrain ................... A61P 31/12 435/5 |
| 2002/0151484 A1 * | | 10/2002 | Legrain ................ C07K 14/005 514/6.9 |
| 2004/0047877 A1 | | 3/2004 | Leroux-Roels et al. |
| 2004/0105868 A1 | | 6/2004 | Lauer et al. |

FOREIGN PATENT DOCUMENTS

| | | |
|---|---|---|
| CN | 1609213 A | 4/2005 |
| CN | 1984677 A | 6/2007 |
| CN | 104837498 A | 8/2015 |
| CN | 105263517 A | 1/2016 |
| EP | 0710294 A1 | 5/1996 |
| WO | WO 1993/025575 | 12/1993 |
| WO | WO 2014/060851 | 4/2014 |
| WO | WO 2017/006182 A1 | 1/2017 |
| WO | WO 2017/060857 | 4/2017 |
| WO | WO 2017/163083 A1 | 9/2017 |

OTHER PUBLICATIONS

Deering RP, Kommareddy S, Ulmer JB, Brito LA, Geall AJ. Nucleic acid vaccines: prospects for non-viral delivery of mRNA vaccines. Expert Opin Drug Deliv. Jun. 2014; 11(6):885-99. (Year: 2014).*

Vajdy et al. Hepatitis C virus polyprotein vaccine formulations capable of inducing broad antibody and cellular immune responses. J Gen Virol Aug. 2006;87(Pt 8):2253-2262. (Year: 2006).*

Chien DY, Arcangel P, Medina-Selby A, Coit D, Baumeister M, Nguyen S, George-Nascimento C, Gyenes A, Kuo G, Valenzuela P. Use of a novel hepatitis C virus (HCV) major-epitope chimeric polypeptide for diagnosis of HCV infection. J Clin Microbiol. May 1999;37(5):1393-7. (Year: 1999).*

Gededzha, et al.; "Prediction of T-cell epitopes of hepatitis C virus genotype 5a"; Virology Journal; vol. 11, No. 187, 13 pages (Nov. 8, 2014).

Shehzadi, et al.; "Promiscuous prediction and conservancy analysis of CTL binding epitopes of HCV 3a viral proteome from Punjab Pakistan: an In Silico Approach"; Virology Journal; vol. 8, No. 55, 13 pages (Feb. 8, 2011).

Yusim, et al.; "Hepatitis C Genotype 1 Mosaic Vaccines Are Immunogenic in Mice and Induce Stronger T-Cell Responses than Natural Strains"; Clinical and Vaccine Immunology; vol. 20, No. 2, pp. 302-305 (Feb. 2013).

(Continued)

*Primary Examiner* — Michelle S Horning

(74) *Attorney, Agent, or Firm* — Bozicevic, Field & Francis LLP; Shweta Chandra

(57) ABSTRACT

The present disclosure provides an immunogenic composition comprising: a) i) a hepatitis C virus (HCV) heterodimeric polypeptide that includes HCV E1 and E2 polypeptides; ii) an HCV E1 polypeptide; or iii) an HCV E2 polypeptide; b) a polypeptide (also referred to herein as a "T-cell epitope polypeptide" or an "HCV T-cell epitope polypeptide") comprising T-cell epitopes (e.g., CD4+ and CD8+ T-cell epitopes that are conserved among some HCV genotypes and that are presented through one or multiple HLA alleles common within the human population) present in an HCV protein other than E1 and E2; and c) a pharmaceutically acceptable excipient. The present disclosure provides a method of inducing an immune response, in an individual, to an HCV polypeptide.

18 Claims, 36 Drawing Sheets

Specification includes a Sequence Listing.

(56) References Cited

OTHER PUBLICATIONS

Zeng, et al.; "A novel combined vaccine candidate containing epitopes of HCV NS3, core and E1 proteins induces multi-specific immune responses in BALB/c mice"; Antiviral Research; vol. 84, pp. 23-30 (Jul. 21, 2009).

* cited by examiner

FIG. 5A
GenBank 3S7G_A
*Homo sapiens* IgG1 Fc
227 aa

```
  1 dkthtcppcp apellggpsv flfppkpkdt lmisrtpevt cvvvdvshed pevkfnwyvd
 61 gvevhnaktk preeqynsty rvvsvltvlh qdwlngkeyk ckvsnkalpa piektiskak
121 gqprepqvyt lppsrdeltk nqvsltclvk gfypsdiave wesngqpenn ykttppvlds
181 dgsfflyskl tvdksrwqqg nvfscsvmhe alhnhytqks lslspgk
```

GenBank AAN76044
*Homo sapiens* IgG2 Fc (amino acids 99-325)
227 aa

```
  1 stkgpsvfpl apcsrstses taalgclvkd yfpepvtvsw nsgaltsgvh tfpavlqssg
 61 lyslssvvtv pssnfgtqty tcnvdhkpsn tkvdktverk ccvecppcpa ppvagpsvfl
121 fppkpkdtlm isrtpevtcv vvdvshedpe vqfnwyvdgv evhnaktkpr eeqfnstfrv
181 vsvltvvhqd wlngkeykck vsnkglpapi ektisktkgq prepqvytlp psreemtknq
241 vsltclvkgf ypsdiavewe sngqpennyk ttppmldsdg sfflyskltv dksrwqqgnv
301 fscsvmheal hnhytqksls lspgk
```

GenBank AAW65947
*Homo sapiens* IgG3 Fc (amino acids 19-246)
238 aa

```
  1 hkpsntkvdk rvelktplgd tthtcppcpa pellggpsvf lfppkpkdtl misrtpevtc
 61 vvvdvshedp evkfnwyvdg vevhnaktkp reeqynstyr vvsvltvlhq dwlngkeykc
121 kvsnkalpap iektiskakg qprepqvytl ppsrdeltkn qvsltclvkg fypsdiavew
181 esngqpenny kttppvldsd gsfflysklt vdksrwqqgn vfscsvmhea lhnhytqksl
241 slspgk
```

FIG. 5B

GenBank AAA52770
*Homo sapiens* IgD Fc (amino acids 162-383)
222 aa

```
  1 ptkapdvfpi isgcrhpkdn spvvlaclit gyhptsvtvt wymgtqsqpg rtfpeiqrrd
 61 syymtssqls tplqqwrgge ykcvvqhtas kskkeifrwp espkaqassv ptaqpqaegs
121 lakattapat trntgrggee kkkekekeeq eeretktpec pshtqplgvy lltpavqdlw
181 lrdkatftcf vvgsdlkdah ltwevagkvp tggveeglle rhsngsqsqh srltlprslw
241 nagtsvtctl nhpslppqrl malrepaaqa pvklslnlla ssdppeaasw llcevsgfsp
301 pnillmwled qrevntsgfa parpppqprs ttfwawsvlr vpappspqpa tytcvvshed
361 srtllnasrs levsyvtdhg pmk
```

GenBank 0308221A
*Homo sapiens* IgM Fc
276 aa

```
  1 vtstltikzs dwlgesmftc rvdhrgltfq qnassmcvpd qdtairvfai ppsfasiflt
 61 kstkltclvt dlttybsvti swtreengav kthtnisesh pnatfsavge asicedbdws
121 gerftctvth tdlpsplkqt isrpkgvalh rpbvyllppa rzzlnlresa titclvtgfs
181 padvfvewmq rgeplspqky vtsapmpepq apgryfahsi ltvseeewnt ggtytcvvah
241 ealpnrvter tvdkstgkpt lynvslvmsd tagtcy
```

FIG. 5C

GenBank P01876
*Homo sapiens* IgA Fc (amino acids 120-353)
234 aa

```
  1 asptspkvfp lslcstqpdg nvviaclvgg ffpqeplsvt wsesgqgvta rnfppsqdas
 61 gdlyttssql tlpatqclag ksvtchvkhy tnpsqdvtvp cpvpstpptp spstpptpsp
121 scchprlslh rpaledlllg sealtctlt glrdasgvtf twtpssgksa vqgpperdlc
181 gcysvssvlp gcaepwnhgk tftctaaype sktplitatls ksgntfrpev hllpppseel
241 alnelvtltc largfspkdv lvrwlggsqe lprekyltwa srgepsqgtt tfavtsilrv
301 aaedwkkgdt fscmvghea1 plaftqktid rlagkpthvn vsvvmaevdg tcy
```

GenBank 1F6A_B
*Homo sapiens* IgE Fc (amino acids 6-222)
212 aa

```
  1 adpcdsnprg vsaylsrpsp fdlfirkspt itclvvdlap skgtvnltws rasgkpvnhs
 61 trkeekqrng tltvtstlpv gtrdwieget yqcrvthphl pralmrsttk tsgpraapev
121 yafatpewpg srdkrtlacl iqmfmpedis vqwlhnevql pdarhsttqp rktkgsgffv
181 fsrlevtrae weqkdeficr avheaaspsq tvqravsvnp gk
```

GenBank P01861
*Homo sapiens* IgG4 Fc (amino acids 100-327)
228 aa

```
  1 astkgpsvfp lapcsrstse staalgclvk dyfpepvtvs wnsgaltsgv htfpavlqss
 61 glyslssvvt vpsssl gtkt ytcnvdhkps ntkvdkrves kygppcpscp apeflgqpsv
121 flfppkpkdt lmisrtpevt cvvvdvsqed pevqfnwyvd gvevhnaktk preeqfnsty
181 rvvsvltvlh qdwlngkeyk ckvsnkglps siektiskak gqprepqvyt lppsqeemtk
241 nqvsltclvk gfypsdiave wesngqpenn ykttppvlds dgsfflysrl tvdksrwqeg
301 nvfscsvmhe alhnhytqks lslslgk
```

FIG. 6

| TP | Amino acid sequence | MW (g/m) | Expected Concentration (mg/ml) | Measured Concentration (mg/ml) | Solubility (%) |
|---|---|---|---|---|---|
| TP35-NS3 | KSTKVPAAYAAQGYKVLVLN PSVAATLGFGAYMSK | 3603 | 0.643 | 0.797 | 124% |
| TP35-NS3(Lys)₃ | KSTKVPAAYAAQGYKVLVLN PSVAATLGFGAYMSKKKK | 3988 | 0.667 | 0.654 | 98% |
| TP42 | GTEGEIPFYGKAIPLEQIKGGR HLIFCHSKKKCDELAAKLTG | 4585 | 0.655 | 0.079 | 12% |
| TP45 (C-terminal CNV replaced with KKK) | LNAVAYYRGLDVSVIPTSGDV VVVATDALMTGFTGDFDSVI DKKK | 4749 | 0.643 | 0.054 | 8% |
| TP48 | ILRRHVGPGEGAVQWMNRLI AFASRGNHVSPTHYVPESDA SARVTQIL | 5296 | 0.688 | 0.328 | 48% |
| TP48(Lys)₃ | ILRRHVGPGEGAVQWMNRLI AFASRGNHVSPTHYVPESDA SARVTQILKKK | 5680 | 0.688 | 0.685 | 100% |
| TP50-C | GVYLLPRRGPRLGVRATRKTS ERSQPRGRRQPIPKARRSEGR SWAQPGYP | 5741 | 0.688 | 0.814 | 118% |

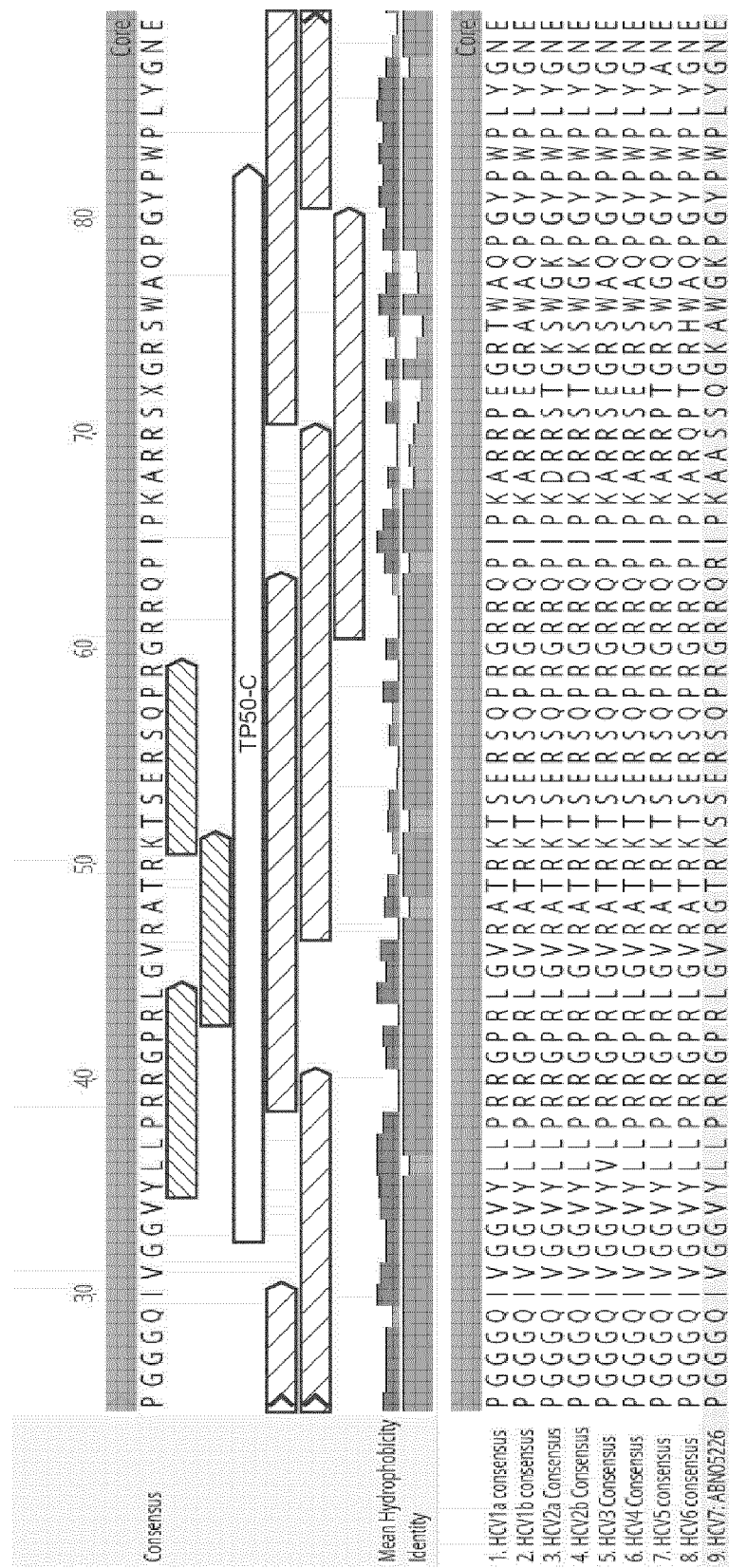
FIG. 7 – TP50-C

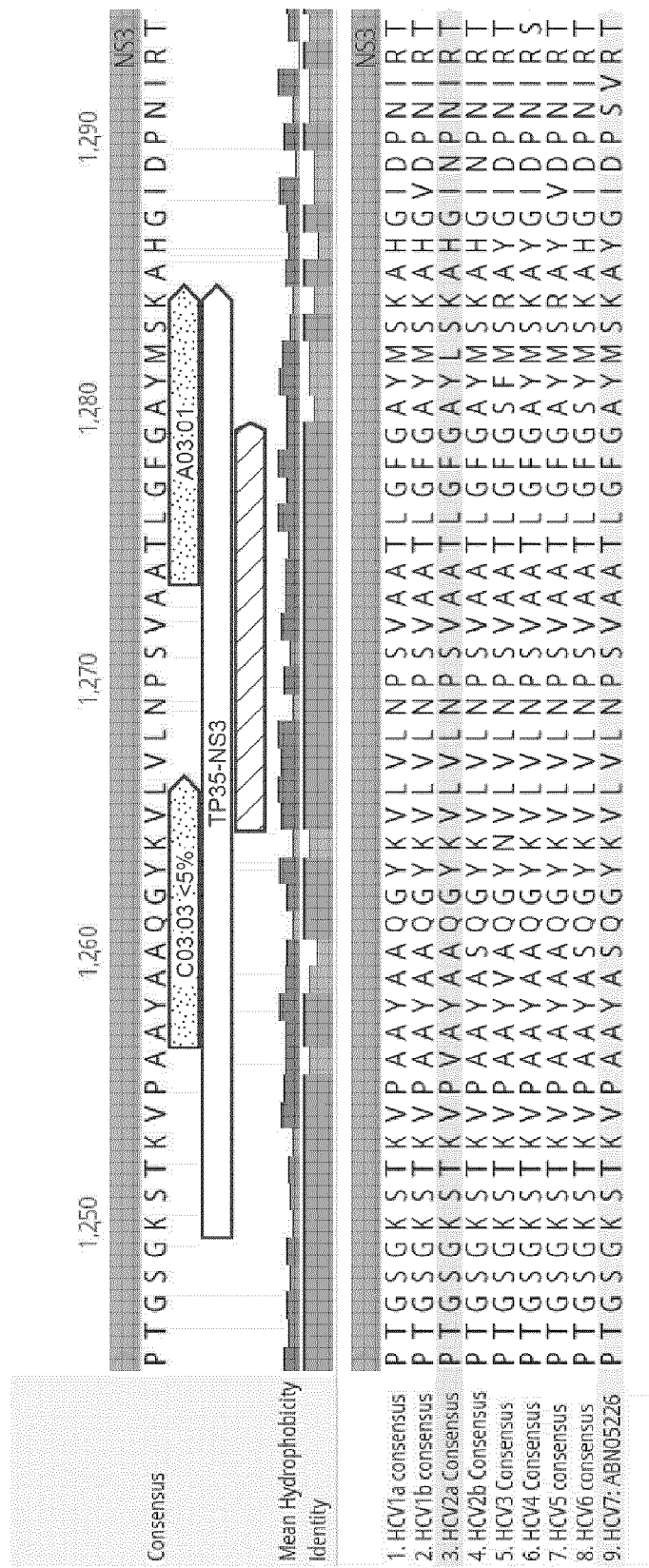
FIG. 8 – TP35-NS3

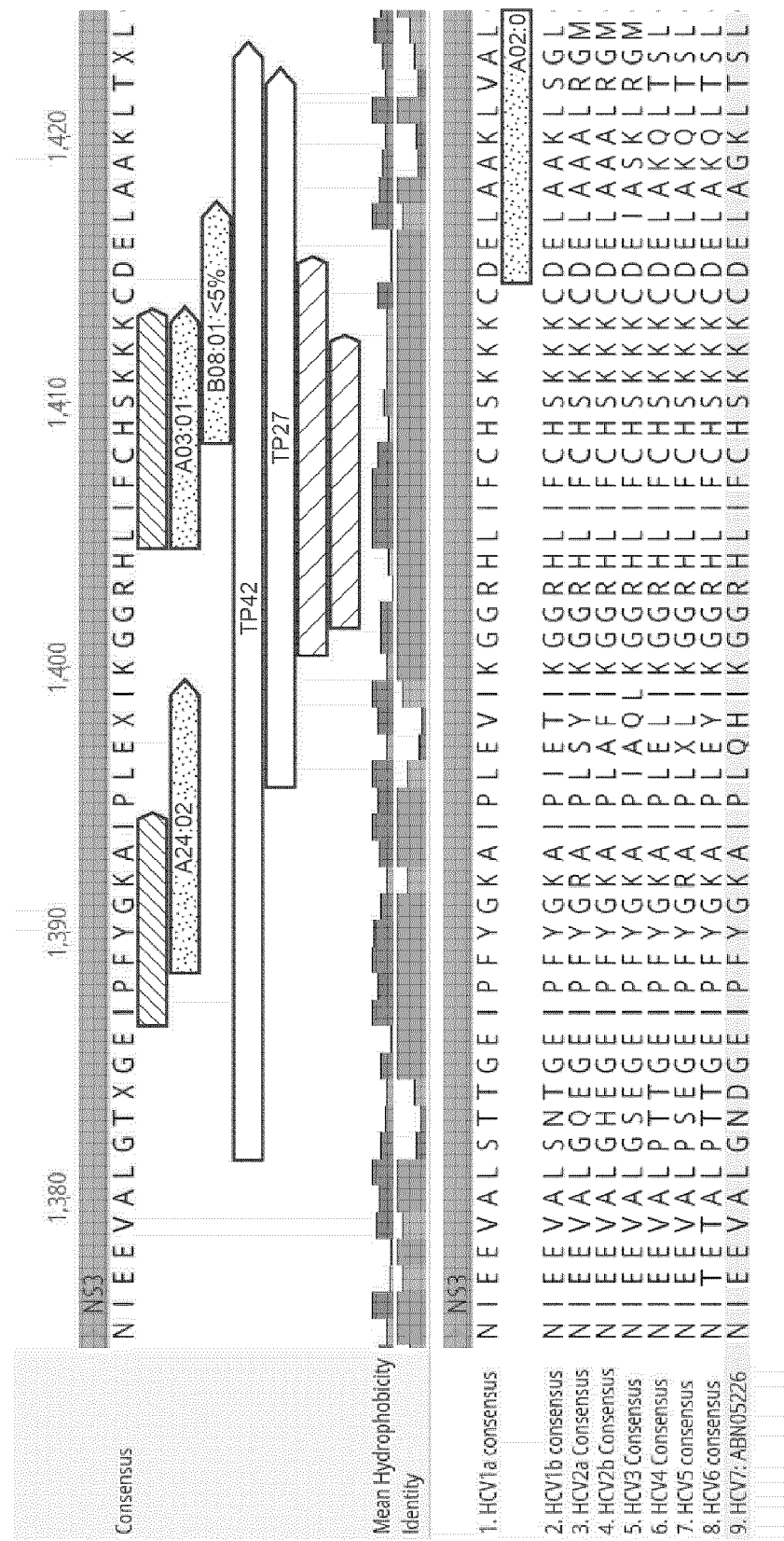
FIG. 9 – TP27 & TP42

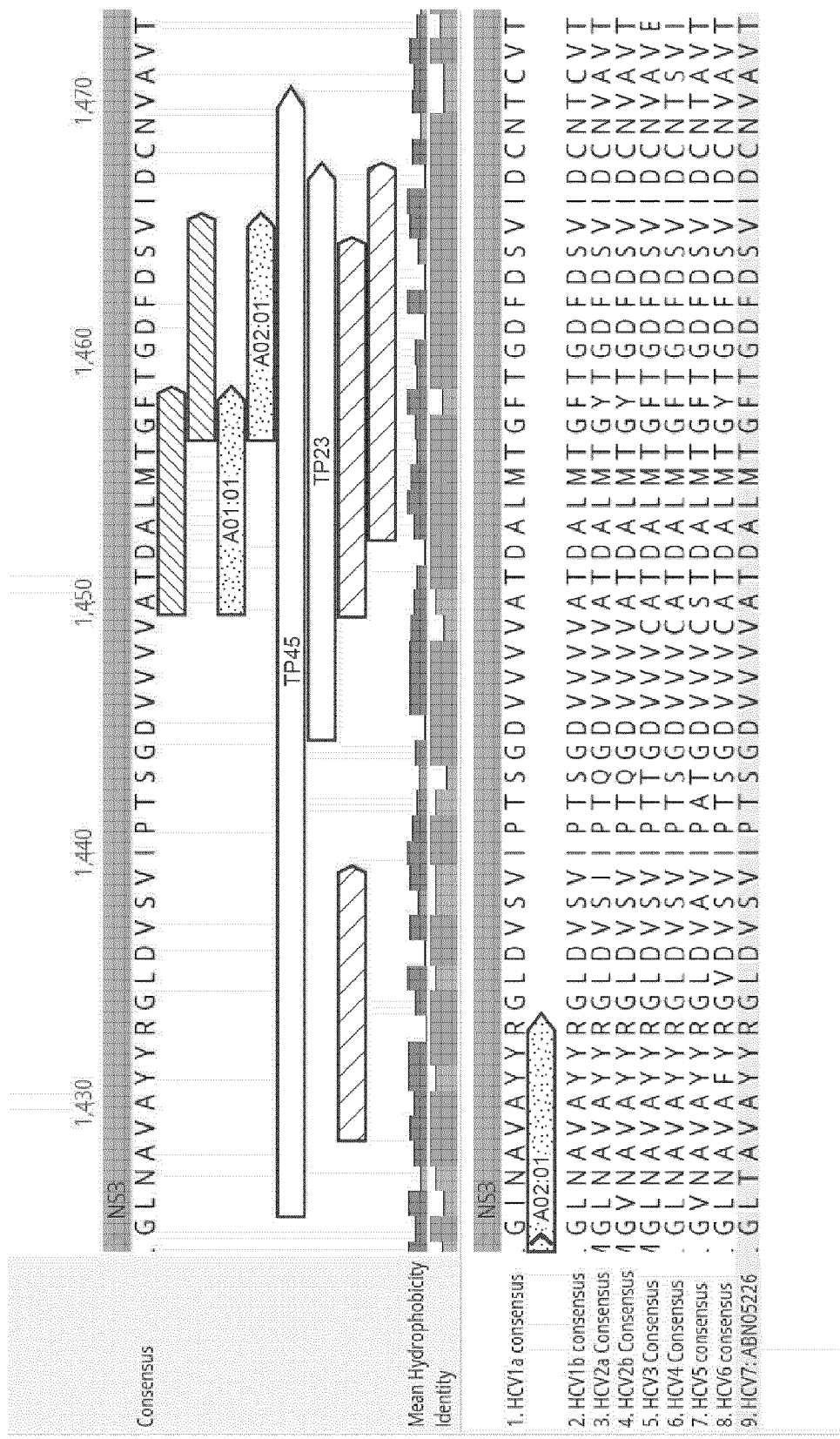
FIG. 10 – TP23 & TP45

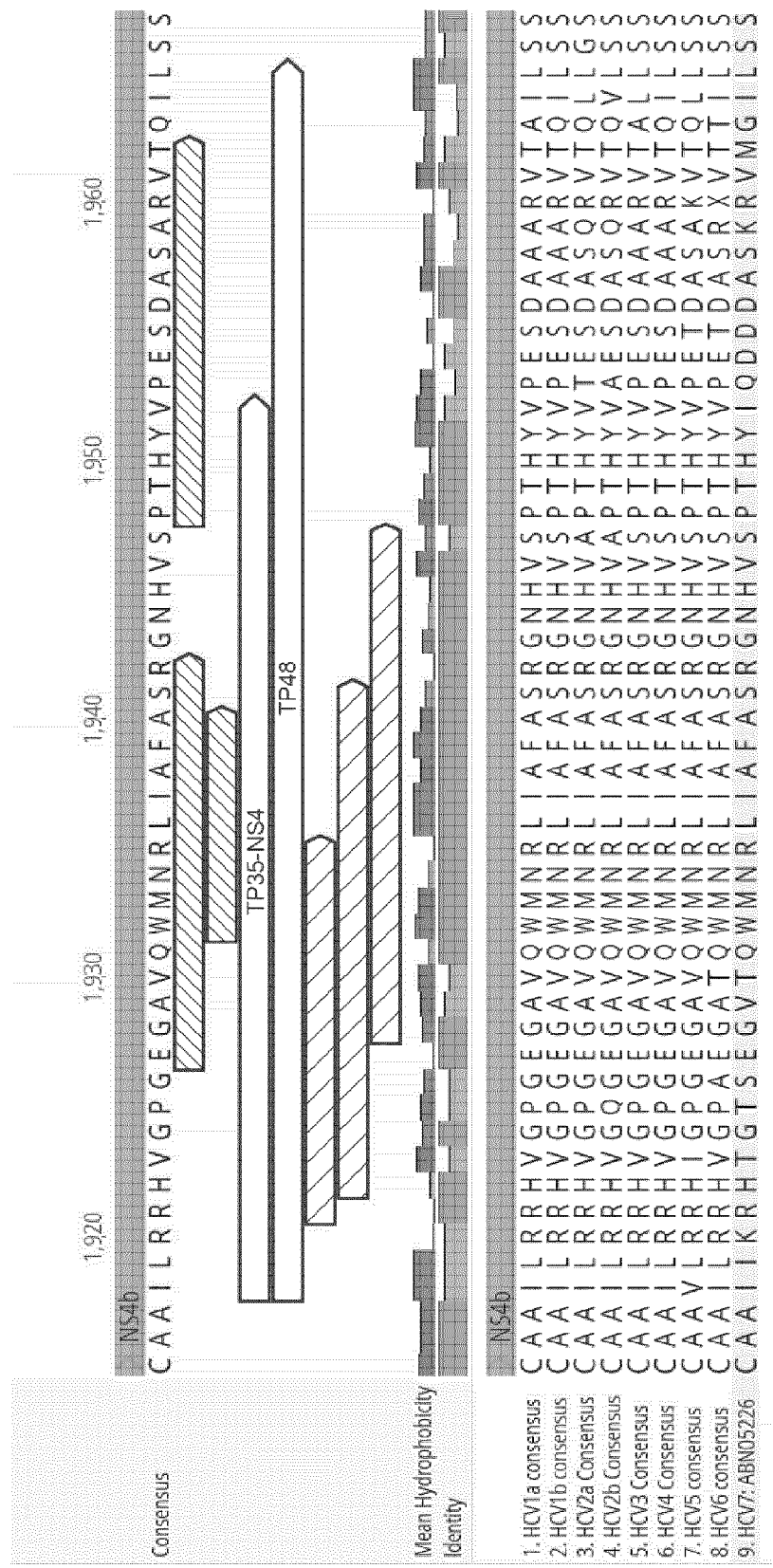
FIG. 11 – TP35-NS4 & TP48

FIG. 12

| TPs | Sequences | MW (g/m) | EC | Solubility (%) | Solubility (Visual) |
|---|---|---|---|---|---|
| TP45 | LNAVAYYRGLDVSVIPTSGDVVVVATDALMTGFTGDFDSVIDCNV | 4681 | 2560 | N/A | N/A |
| TP45+KKK | LNAVAYYRGLDVSVIPTSGDVVVVATDALMTGFTGDFDSVIDCNVKKK | 5066 | 2680 | - | Precipitation |
| TP23 | DVVVVATDALMTGFTGDFDSVID | 2388 | - | - | Precipitation |
| TP23+KKK | DVVVVATDALMTGFTGDFDSVIDKKK | 2772 | - | - | Precipitation |
| TP27 | LEQIKGGRHLIFCHSKKKCDELAAKLT | 3068 | 240 | - | Dissolved |
| TP27+KKK | LEQIKGGRHLIFCHSKKKCDELAAKLTKKK | 3452 | 240 | - | Dissolved |
| TP35-NS4 | ILRRHVGPGEGAVQWMNRLIAFASRGNHVSPTHYV | 3928 | 6970 | 64 | Mostly Dissolved |
| TP35-NS4+KKK | ILRRHVGPGEGAVQWMNRLIAFASRGNHVSPTHYVKKK | 4312 | 6970 | 107 | Dissolved |

FIG. 13

TP42: GTEGEIPFYGKAIPLEQIKGGRHLIFCHSKKKCDELAAKLTG
MW= 4585 g/m; EC=1280

| TP42 | Solubility | | | |
|---|---|---|---|---|
| Solution | Visual | Expected (mg/ml) | Measured (mg/ml) | Percent (%) |
| E1E2 Buffer | Dissolved | 1 | 2.1 | 210% |
| E1E2 Buffer w/o Tween | Dissolved | 1 | 1.4 | 140% |
| H2O | Dissolved | 1 | 0.9 | 90% |

TP45+KKK: LNAVAYYRGLDVSVIPTSGDVVVVATDALMTGFTGDFDSVIDCNVKKK
MW= 5066 g/m; EC= 2680

| TP45 | Solubility | | | |
|---|---|---|---|---|
| Solution | Visual | Expected (mg/ml) | Measured (mg/ml) | Percent (%) |
| E1E2 Buffer | Precipitation (medium) | 1 | 0.2 | 20% |
| E1E2 Buffer w/o Tween | Precipitation (low) | 1 | - | - |
| H2O | Precipitation (high) | 1 | 0.2 | 20% |

TP48: ILRRHVGPGEGAVQWMNRLIAFASRGNHVSPTHYVPESDASARVTQIL
MW= 5296 g/m; EC= 6970

| TP48 | Solubility | | | |
|---|---|---|---|---|
| Solution | Visual | Expected (mg/ml) | Measured (mg/ml) | Percent (%) |
| E1E2 Buffer | Precipitation (low) | 1 | 0.8 | 80% |
| E1E2 Buffer w/o Tween | Precipitation (low) | 1 | 0.5 | 50% |
| H2O | Dissolved | 1 | 0.9 | 90% |

FIG. 14

TP45+KKK: LNAVAYYRGLDVSVIPTSGDVVVVATDALMTGFTGDFDSVIDCNVKKK
MW= 5066 g/m; EC= 2680

| TP45 | Solubility | | | | |
|---|---|---|---|---|---|
| Solution | Visual | Expected (mg/ml) | Measured (mg/ml) | Percent (%) | 18.5 h incubation |
| E1E2 Buffer | Precipitation (medium) | 1 | 0.2 | 20% | 20% Precip. (Medium) |
| E1E2 Buffer w/o Tween | Precipitation (low) | 1 | - | - | - |
| H2O | Precipitation (high) | 1 | 0.2 | 20% | 77% Precip. (Medium) |

TP48: ILRRHVGPGEGAVQWMNRLIAFASRGNHVSPTHYVPESDASARVTQIL
MW= 5296 g/m; EC= 6970

| TP48 | Solubility | | | | |
|---|---|---|---|---|---|
| Solution | Visual | Expected (mg/ml) | Measured (mg/ml) | Percent (%) | 18.5 h incubation |
| E1E2 Buffer | Precipitation (low) | 1 | 0.8 | 80% | 81% Precip (very low) |
| E1E2 Buffer w/o Tween | Precipitation (low) | 1 | 0.5 | 50% | 50% Precip (very low) |
| H2O | Dissolved | 1 | 0.9 | 90% | 90% |

FIG. 19

Population Coverage Analysis

| Population | Reported Epitopes | | | Predicted Epitopes | | |
|---|---|---|---|---|---|---|
| | Coverage (%) | Average Hit* | PC90** | Coverage (%) | Average Hit* | PC90** |
| World | 87.38 | 3.86 | 0.79 | 100 | 13.71 | 5.25 |
| North America | 89.81 | 3.92 | 0.98 | 100 | 14.07 | 5.78 |
| USA | 89.81 | 3.95 | 0.98 | 100 | 14.22 | 5.83 |
| Europe | 92.47 | 4.82 | 1.66 | 99.99 | 16.4 | 5.74 |
| Oceania | 75.73 | 2.19 | 0.41 | 99.12 | 8.04 | 2.48 |
| China | 69.75 | 2.21 | 0.33 | 99.4 | 9.47 | 3.45 |
| India | 67.34 | 2.08 | 0.31 | 100 | 9.44 | 3.53 |
| Japan | 90.67 | 3.14 | 1.08 | 100 | 12.4 | 5.76 |

\* Average number of epitope hits / HLA combinations recognized by the population.
\*\* Minimum number of epitope hits / HLA combinations recognized by 90% the population.

FIG. 27

TP33: HSKKKCDELAAKLTGLGLNAVAVVRGLDVSVIP
MW= 3531 g/mol; EC= 3043 (secreted protein)

| TP33 | | Solubility | | |
|---|---|---|---|---|
| Solution | Visual | Expected (mg/ml) | Measured (mg/ml) | Percent (%) |
| E1E2 Buffer | Precipitation (Medium) | 0.5 | 0.296 | 59% |
| E1E2 Buffer w/o Tween | Precipitation (Medium) | 0.5 | 0.202 | 40% |
| H2O | Precipitation (Medium) | 0.5 | 0.139 | 28% |

TP42-2: KGGRHLIFCHSKKKCDELAAKLTGLGLNAVAVVRGLDVSVIP
MW= 4543 g/mol; EC= 3105 (secreted protein)

| TP42-2 | | Solubility | | |
|---|---|---|---|---|
| Solution | Visual | Expected (mg/ml) | Measured (mg/ml) | Percent (%) |
| E1E2 Buffer | Precipitation (low) | 0.5 | 0.415 | 83% |
| E1E2 Buffer w/o Tween | Precipitation (low) | 0.5 | 0.215 | 43% |
| H2O | Precipitation (low) | 0.5 | 0.233 | 47% |

SEQUENCE LISTING

<160> NUMBER OF SEQ ID NOS: 428

<210> SEQ ID NO 1
<211> LENGTH: 746
<212> TYPE: PRT
<213> ORGANISM: Hepatitis C virus
<220> FEATURE:
<221> NAME/KEY: misc_feature
<222> LOCATION: (248)..(248)
<223> OTHER INFORMATION: Xaa can be any amino acid
<220> FEATURE:
<221> NAME/KEY: misc_feature

```
<222> LOCATION: (262)..(262)
<223> OTHER INFORMATION: Xaa can be any amino acid
<220> FEATURE:
<221> NAME/KEY: misc_feature
<222> LOCATION: (270)..(270)
<223> OTHER INFORMATION: Xaa can be any amino acid
<220> FEATURE:
<221> NAME/KEY: misc_feature
<222> LOCATION: (275)..(275)
<223> OTHER INFORMATION: Xaa can be any amino acid
<220> FEATURE:
<221> NAME/KEY: misc_feature
<222> LOCATION: (399)..(399)
<223> OTHER INFORMATION: Xaa can be any amino acid
<220> FEATURE:
<221> NAME/KEY: misc_feature
<222> LOCATION: (408)..(408)
<223> OTHER INFORMATION: Xaa can be any amino acid
<220> FEATURE:
<221> NAME/KEY: misc_feature
<222> LOCATION: (524)..(524)
<223> OTHER INFORMATION: Xaa can be any amino acid
<220> FEATURE:
<221> NAME/KEY: misc_feature
<222> LOCATION: (580)..(580)
<223> OTHER INFORMATION: Xaa can be any amino acid
<220> FEATURE:
<221> NAME/KEY: misc_feature
<222> LOCATION: (641)..(641)
<223> OTHER INFORMATION: Xaa can be any amino acid
<220> FEATURE:
<221> NAME/KEY: misc_feature
<222> LOCATION: (709)..(709)
<223> OTHER INFORMATION: Xaa can be any amino acid
<220> FEATURE:
<221> NAME/KEY: misc_feature
<222> LOCATION: (733)..(733)
<223> OTHER INFORMATION: Xaa can be any amino acid

<400> SEQUENCE: 1

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Ser Gly Leu Tyr His Val Thr Asn Asp Cys Pro
        195                 200                 205
```

```
Asn Ser Ser Ile Val Tyr Glu Thr Ala Asp Thr Ile Leu His Ser Pro
    210                 215                 220

Gly Cys Val Pro Cys Val Arg Glu Gly Asn Ala Ser Arg Cys Trp Val
225                 230                 235                 240

Ala Leu Thr Pro Thr Val Ala Xaa Arg Asp Gly Ser Leu Pro Thr Thr
                245                 250                 255

Gln Leu Arg Arg His Xaa Asp Leu Leu Val Gly Ser Ala Xaa Leu Cys
            260                 265                 270

Ser Ala Xaa Tyr Val Gly Asp Leu Cys Gly Ser Val Phe Leu Val Gly
        275                 280                 285

Gln Leu Phe Thr Phe Ser Pro Arg Arg His Trp Thr Thr Gln Asp Cys
    290                 295                 300

Asn Cys Ser Ile Tyr Pro Gly His Ile Thr Gly His Arg Met Ala Trp
305                 310                 315                 320

Asp Met Met Met Asn Trp Ser Pro Thr Thr Ala Leu Val Val Ala Gln
                325                 330                 335

Leu Leu Arg Ile Pro Gln Ala Ile Leu Asp Met Ile Ala Gly Ala His
            340                 345                 350

Trp Gly Val Leu Ala Gly Ile Ala Tyr Phe Ser Met Val Gly Asn Trp
        355                 360                 365

Ala Lys Val Leu Val Val Leu Leu Phe Ala Gly Val Asp Ala Glu
    370                 375                 380

Thr His Val Thr Gly Gly Ser Ala Ala Arg Ala Thr Ser Gly Xaa Ala
385                 390                 395                 400

Ser Leu Phe Ser Pro Gly Ala Xaa Gln Asn Ile Gln Leu Ile Asn Thr
                405                 410                 415

Asn Gly Ser Trp His Ile Asn Arg Thr Ala Leu Asn Cys Asn Asp Ser
            420                 425                 430

Leu Asp Thr Gly Trp Val Ala Gly Leu Phe Tyr Tyr His Lys Phe Asn
        435                 440                 445

Ser Ser Gly Cys Pro Glu Arg Met Ala Ser Cys Arg Pro Leu Ala Asp
450                 455                 460

Phe Asp Gln Gly Trp Gly Pro Ile Ser Tyr Ala Asn Gly Ser Gly Pro
465                 470                 475                 480

Asp Gln Arg Pro Tyr Cys Trp His Tyr Pro Pro Lys Pro Cys Gly Ile
                485                 490                 495

Val Pro Ala Gln Gln Val Cys Gly Pro Val Tyr Cys Phe Thr Pro Ser
            500                 505                 510

Pro Val Val Val Gly Thr Thr Asp Arg Leu Gly Xaa Pro Thr Tyr Asn
        515                 520                 525

Trp Gly Glu Asn Glu Thr Asp Val Leu Val Leu Asn Asn Thr Arg Pro
530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Asn Ile Gly Gly Val Gly Asn
                565                 570                 575

Asn Thr Leu Xaa Cys Pro Thr Asp Cys Phe Arg Lys His Pro Glu Ala
            580                 585                 590

Thr Tyr Ser Arg Cys Gly Ser Gly Pro Trp Leu Thr Pro Arg Cys Leu
        595                 600                 605

Val Asp Tyr Pro Tyr Arg Leu Trp His Tyr Pro Cys Thr Val Asn Tyr
610                 615                 620
```

```
Thr Ile Phe Lys Val Arg Met Tyr Val Gly Val Glu His Arg Leu
625                 630                 635                 640

Xaa Ala Ala Cys Asn Trp Thr Arg Gly Glu Arg Cys Asp Leu Asp Asp
            645                 650                 655

Arg Asp Arg Ser Glu Leu Ser Pro Leu Leu Leu Ser Thr Thr Gln Trp
            660                 665                 670

Gln Val Leu Pro Cys Ser Phe Thr Thr Leu Pro Ala Leu Ser Thr Gly
            675                 680                 685

Leu Ile His Leu His Gln Asn Ile Val Asp Val Gln Tyr Leu Tyr Gly
            690                 695                 700

Val Gly Ser Ser Xaa Val Ser Trp Ala Ile Lys Trp Glu Tyr Val Ile
705                 710                 715                 720

Leu Leu Phe Leu Leu Leu Ala Asp Ala Arg Ile Cys Xaa Cys Leu Trp
            725                 730                 735

Met Met Leu Leu Ile Ser Gln Ala Glu Ala
            740                 745

<210> SEQ ID NO 2
<211> LENGTH: 746
<212> TYPE: PRT
<213> ORGANISM: Hepatitis C virus

<400> SEQUENCE: 2

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Thr Gly Leu Tyr His Val Thr Asn Asp Cys Pro
        195                 200                 205

Asn Ser Ser Ile Val Tyr Glu Ala Ala Asp Ala Ile Leu His Thr Pro
    210                 215                 220

Gly Cys Val Pro Cys Val Arg Glu Gly Asn Thr Ser Arg Cys Trp Val
225                 230                 235                 240

Ala Met Thr Pro Thr Val Ala Thr Arg Asp Gly Lys Leu Pro Thr Thr
                245                 250                 255
```

```
Gln Leu Arg Arg His Ile Asp Leu Leu Val Gly Ser Ala Thr Leu Cys
            260                 265                 270

Ser Ala Leu Tyr Val Gly Asp Leu Cys Gly Ser Ile Phe Leu Val Gly
        275                 280                 285

Gln Met Phe Thr Phe Ser Pro Arg Arg His Trp Thr Thr Gln Asp Cys
    290                 295                 300

Asn Cys Ser Leu Tyr Pro Gly His Ile Thr Gly His Arg Met Ala Trp
305                 310                 315                 320

Asp Met Met Met Asn Trp Ser Pro Thr Ala Ala Leu Ile Thr Ala Gln
                325                 330                 335

Leu Leu Arg Ile Pro Gln Ala Ile Leu Asp Met Ile Ala Gly Ala His
            340                 345                 350

Trp Gly Val Leu Ala Gly Ile Ala Tyr Phe Ser Met Val Gly Asn Trp
        355                 360                 365

Ala Lys Val Leu Val Val Leu Leu Phe Ala Gly Val Asp Ala Gln
370                 375                 380

Thr His Val Thr Gly Gly Arg Ala Ala His Ile Thr Ala Gly Leu Thr
385                 390                 395                 400

Ser Leu Phe Ser Pro Gly Pro Ser Gln Lys Leu Gln Leu Val Asn Thr
            405                 410                 415

Asn Gly Ser Trp His Ile Asn Ser Thr Ala Leu Asn Cys Asn Asp Ser
        420                 425                 430

Leu Lys Thr Gly Trp Ile Ala Gly Leu Leu Tyr Ser Tyr Lys Phe Asn
    435                 440                 445

Ser Ser Gly Cys Pro Glu Arg Leu Ala Ser Cys Arg Arg Leu Thr Asp
450                 455                 460

Phe Ala Gln Gly Trp Gly Pro Ile Ser His Ala Asn Gly Ser Gly Pro
465                 470                 475                 480

Asp Glu Arg Pro Tyr Cys Trp His Tyr Pro Arg Pro Cys Gly Ile
            485                 490                 495

Val Pro Ala Lys Ser Val Cys Gly Pro Val Tyr Cys Phe Thr Pro Ser
        500                 505                 510

Pro Val Val Val Gly Thr Thr Asp Lys Ser Gly Ala Pro Thr Tyr Asn
    515                 520                 525

Trp Gly Glu Asn Asp Thr Asp Val Phe Val Leu Asn Asn Thr Arg Pro
530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Ala Gly Asn
            565                 570                 575

Asn Thr Leu Arg Cys Pro Thr Asp Cys Phe Arg Lys His Pro Asp Ala
        580                 585                 590

Thr Tyr Ser Arg Cys Gly Ser Gly Pro Trp Ile Thr Pro Arg Cys Leu
    595                 600                 605

Val Asp Tyr Pro Tyr Arg Leu Trp His Tyr Pro Cys Thr Val Asn Tyr
    610                 615                 620

Ser Ile Phe Lys Ile Arg Met Tyr Leu Gly Gly Val Glu His Arg Leu
625                 630                 635                 640

Glu Ala Ala Cys Asn Trp Thr Arg Gly Glu Arg Cys Asp Leu Glu Asp
            645                 650                 655

Arg Asp Arg Ser Glu Leu Ser Pro Leu Leu Leu Ser Thr Thr Gln Trp
        660                 665                 670
```

```
Gln Val Leu Pro Cys Ser Phe Thr Thr Leu Pro Ala Leu Ser Thr Gly
            675                 680                 685

Leu Ile His Leu His Gln Asn Ile Val Asp Val Gln Tyr Leu Tyr Gly
            690                 695                 700

Val Gly Ser Ser Val Ala Ser Trp Ala Ile Lys Trp Asp Tyr Val Val
705                 710                 715                 720

Leu Leu Phe Leu Leu Leu Ala Asp Ala Arg Ile Cys Ser Cys Leu Trp
                725                 730                 735

Met Met Leu Leu Ile Ser Gln Ala Glu Ala
                740                 745

<210> SEQ ID NO 3
<211> LENGTH: 746
<212> TYPE: PRT
<213> ORGANISM: Hepatitis C virus

<400> SEQUENCE: 3

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Ser Gly Leu Tyr His Val Thr Asn Asp Cys Pro
        195                 200                 205

Asn Ser Ser Ile Val Tyr Glu Ala Ala Asp Ala Ile Leu His Thr Pro
    210                 215                 220

Gly Cys Val Pro Cys Val Arg Glu Gly Asn Ala Ser Arg Cys Trp Val
225                 230                 235                 240

Ala Val Thr Pro Thr Val Ala Thr Arg Asp Gly Lys Leu Pro Thr Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Val Gly
        275                 280                 285

Gln Leu Phe Thr Phe Ser Pro Arg Arg His Trp Thr Thr Gln Asp Cys
    290                 295                 300
```

```
Asn Cys Ser Ile Tyr Pro Gly His Ile Thr Gly His Arg Met Ala Trp
305                 310                 315                 320

Asp Met Met Met Asn Trp Ser Pro Thr Ala Leu Val Val Ala Gln
            325                 330                 335

Leu Leu Arg Ile Pro Gln Ala Ile Met Asp Met Ile Ala Gly Ala His
            340                 345                 350

Trp Gly Val Leu Ala Gly Ile Ala Tyr Phe Ser Met Val Gly Asn Trp
            355                 360                 365

Ala Lys Val Leu Val Leu Leu Phe Ala Gly Val Asp Ala Glu
370                 375                 380

Thr His Val Thr Gly Ser Ala Gly Arg Thr Thr Ala Gly Leu Val
385                 390                 395                 400

Gly Leu Leu Thr Pro Gly Ala Lys Gln Asn Ile Gln Leu Ile Asn Thr
                405                 410                 415

Asn Gly Ser Trp His Ile Asn Ser Thr Ala Leu Asn Cys Asn Glu Ser
                420                 425                 430

Leu Asn Thr Gly Trp Leu Ala Gly Leu Phe Tyr Gln His Lys Phe Asn
            435                 440                 445

Ser Ser Gly Cys Pro Glu Arg Leu Ala Ser Cys Arg Arg Leu Thr Asp
450                 455                 460

Phe Ala Gln Gly Trp Gly Pro Ile Ser Tyr Ala Asn Gly Ser Gly Leu
465                 470                 475                 480

Asp Glu Arg Pro Tyr Cys Trp His Tyr Pro Arg Pro Cys Gly Ile
            485                 490                 495

Val Pro Ala Lys Ser Val Cys Gly Pro Val Tyr Cys Phe Thr Pro Ser
            500                 505                 510

Pro Val Val Gly Thr Thr Asp Arg Ser Gly Ala Pro Thr Tyr Ser
            515                 520                 525

Trp Gly Ala Asn Asp Thr Asp Val Phe Val Leu Asn Asn Thr Arg Pro
530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Val Gly Asn
                565                 570                 575

Asn Thr Leu Leu Cys Pro Thr Asp Cys Phe Arg Lys His Pro Glu Ala
            580                 585                 590

Thr Tyr Ser Arg Cys Gly Ser Gly Pro Trp Ile Thr Pro Arg Cys Met
            595                 600                 605

Val Asp Tyr Pro Tyr Arg Leu Trp His Tyr Pro Cys Thr Ile Asn Tyr
            610                 615                 620

Thr Ile Phe Lys Val Arg Met Tyr Val Gly Gly Val Glu His Arg Leu
625                 630                 635                 640

Glu Ala Ala Cys Asn Trp Thr Arg Gly Glu Arg Cys Asp Leu Glu Asp
                645                 650                 655

Arg Asp Arg Ser Glu Leu Ser Pro Leu Leu Leu Ser Thr Thr Gln Trp
            660                 665                 670

Gln Val Leu Pro Cys Ser Phe Thr Thr Leu Pro Ala Leu Ser Thr Gly
            675                 680                 685

Leu Ile His Leu His Gln Asn Ile Val Asp Val Gln Tyr Leu Tyr Gly
            690                 695                 700

Val Gly Ser Ser Ile Ala Ser Trp Ala Ile Lys Trp Glu Tyr Val Val
705                 710                 715                 720
```

```
Leu Leu Phe Leu Leu Leu Ala Asp Ala Arg Val Cys Ser Cys Leu Trp
                    725                 730                 735

Met Met Leu Leu Ile Ser Gln Ala Glu Ala
            740                 745

<210> SEQ ID NO 4
<211> LENGTH: 746
<212> TYPE: PRT
<213> ORGANISM: Hepatitis C virus

<400> SEQUENCE: 4

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Val Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Ser Gly Ile Tyr His Val Thr Asn Asp Cys Pro
        195                 200                 205

Asn Ser Ser Ile Val Tyr Glu Thr Ala Asp Thr Ile Leu His Ser Pro
210                 215                 220

Gly Cys Val Pro Cys Val Arg Glu Gly Asn Ala Ser Lys Cys Trp Val
225                 230                 235                 240

Ala Leu Ala Pro Thr Val Ala Thr Arg Asp Gly Lys Leu Pro Thr Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Val Gly
        275                 280                 285

Gln Leu Phe Thr Phe Ser Pro Arg Arg His Trp Thr Thr Gln Asp Cys
290                 295                 300

Asn Cys Ser Ile Tyr Pro Gly His Ile Thr Gly His Arg Met Ala Trp
305                 310                 315                 320

Asp Met Met Met Asn Trp Ser Pro Thr Thr Ala Leu Val Val Ala Gln
                325                 330                 335

Leu Leu Arg Val Pro Gln Ala Ile Leu Asp Met Ile Ala Gly Ala His
            340                 345                 350
```

```
Trp Gly Val Leu Ala Gly Ile Ala Tyr Phe Ser Met Val Gly Asn Trp
        355                 360                 365

Ala Lys Val Leu Val Leu Leu Phe Ala Gly Val Asp Ala Glu
        370                 375                 380

Thr Tyr Thr Thr Gly Gly Ser Val Ala Gln Ala Phe Gly Leu Thr
385                 390                 395                 400

Ser Leu Phe Arg Pro Gly Pro Lys Gln Asp Ile Gln Leu Ile Asn Thr
                405                 410                 415

Asn Gly Ser Trp His Ile Asn Arg Thr Ala Leu Asn Cys Asn Ala Ser
                420                 425                 430

Leu Asp Thr Gly Trp Val Ala Gly Leu Phe Tyr Tyr His Lys Phe Asn
        435                 440                 445

Ser Ser Gly Cys Pro Glu Arg Met Ala Ser Cys Arg Ser Leu Ala Asp
        450                 455                 460

Phe Asp Gln Gly Trp Gly Pro Ile Ser Tyr Ala Asn Gly Ser Gly Pro
465                 470                 475                 480

Glu His Arg Pro Tyr Cys Trp His Tyr Pro Lys Pro Cys Gly Ile
                485                 490                 495

Val Pro Ala Gln Asn Val Cys Gly Pro Val Tyr Cys Phe Thr Pro Ser
        500                 505                 510

Pro Val Val Gly Thr Thr Asn Lys Leu Gly Val Pro Thr Tyr Ser
        515                 520                 525

Trp Gly Ser Asn Glu Thr Asp Val Leu Val Leu Asn Asn Thr Arg Pro
        530                 535                 540

Pro Leu Gly Asn Trp Phe Gly Cys Thr Trp Met Asn Ser Ser Gly Phe
545                 550                 555                 560

Thr Lys Val Cys Gly Ala Pro Pro Cys Val Ile Gly Gly Ala Gly Asn
                565                 570                 575

Arg Thr Leu His Cys Pro Thr Asp Cys Phe Arg Lys His Pro Glu Ala
                580                 585                 590

Thr Tyr Ser Arg Cys Gly Ser Gly Pro Trp Ile Thr Pro Arg Cys Leu
        595                 600                 605

Val His Tyr Pro Tyr Arg Leu Trp His Tyr Pro Cys Thr Val Asn Tyr
        610                 615                 620

Thr Met Phe Lys Val Arg Met Tyr Val Gly Gly Val Glu His Arg Leu
625                 630                 635                 640

Glu Val Ala Cys Asn Trp Thr Arg Gly Glu Arg Cys Asp Leu Asp Asp
                645                 650                 655

Arg Asp Arg Ser Glu Leu Ser Pro Leu Leu Leu Ser Thr Thr Gln Trp
                660                 665                 670

Gln Val Leu Pro Cys Ser Phe Thr Thr Leu Pro Ala Leu Thr Thr Gly
        675                 680                 685

Leu Ile His Leu His Gln Asn Ile Val Asp Val Gln Tyr Leu Tyr Gly
        690                 695                 700

Val Gly Ser Ser Ile Val Ser Trp Ala Ile Lys Trp Glu Tyr Val Ile
705                 710                 715                 720

Leu Leu Phe Leu Leu Leu Ala Asp Ala Arg Ile Cys Ser Cys Leu Trp
                725                 730                 735

Met Met Leu Leu Ile Ser Gln Ala Glu Ala
                740                 745

<210> SEQ ID NO 5
<211> LENGTH: 746
```

```
<212> TYPE: PRT
<213> ORGANISM: Hepatitis C virus

<400> SEQUENCE: 5

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Phe
            180                 185                 190

Gln Val Arg Asn Ser Ser Gly Leu Tyr His Val Thr Asn Asp Cys Pro
        195                 200                 205

Asn Ser Ser Ile Val Tyr Glu Thr Ala Asp Thr Ile Leu His Ser Pro
210                 215                 220

Gly Cys Val Pro Cys Val Arg Glu Asp Asn Thr Ser Arg Cys Trp Val
225                 230                 235                 240

Ala Val Ala Pro Thr Val Ala Thr Arg Asp Gly Arg Leu Pro Thr Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Val Gly
        275                 280                 285

Gln Leu Phe Thr Phe Ser Pro Arg Arg His Trp Thr Thr Gln Asp Cys
290                 295                 300

Asn Cys Ser Ile Tyr Pro Gly His Ile Thr Gly His Arg Met Ala Trp
305                 310                 315                 320

Asp Met Met Met Asn Trp Ser Pro Thr Thr Ala Leu Val Val Ala Gln
                325                 330                 335

Leu Leu Arg Val Pro Gln Ala Ile Leu Asp Met Ile Ala Gly Ala His
            340                 345                 350

Trp Gly Val Leu Ala Gly Ile Ala Tyr Phe Ser Met Val Gly Asn Trp
        355                 360                 365

Ala Lys Val Leu Val Val Leu Leu Phe Ala Ser Val Asp Ala Glu
370                 375                 380

Thr Tyr Thr Ser Gly Gly Ser Val Ala Arg Ala Thr Ala Gly Phe Ala
385                 390                 395                 400
```

-continued

Gly Ile Phe Asn Pro Gly Ala Lys Gln Asp Ile Gln Leu Ile Asn Thr
                405                 410                 415

Asn Gly Ser Trp His Ile Asn Arg Thr Ala Leu Asn Cys Asn Ala Ser
            420                 425                 430

Leu Asp Thr Gly Trp Val Ala Gly Leu Phe Tyr Tyr His Lys Phe Asn
        435                 440                 445

Ser Ser Gly Cys Pro Glu Arg Met Ala Ser Cys Lys Pro Leu Ala His
    450                 455                 460

Phe Ala Gln Gly Trp Gly Pro Ile Ser Tyr Ala Asn Gly Ser Gly Pro
465                 470                 475                 480

Asp His Arg Pro Tyr Cys Trp His Tyr Pro Pro Lys Pro Cys Gly Ile
                485                 490                 495

Val Pro Ala Gln Asn Val Cys Gly Pro Val Tyr Cys Phe Thr Pro Ser
            500                 505                 510

Pro Val Val Gly Thr Thr Asn Lys Leu Gly Ala Pro Thr Tyr Asn
        515                 520                 525

Trp Gly Ser Asn Asp Thr Asp Val Phe Ile Leu Asn Asn Thr Arg Pro
    530                 535                 540

Pro Gly Gly Asn Trp Phe Gly Cys Thr Trp Met Asn Ser Ser Gly Phe
545                 550                 555                 560

Thr Lys Val Cys Gly Ala Pro Pro Cys Thr Ile Gly Gly Val Gly Asn
                565                 570                 575

Asn Thr Leu Leu Cys Pro Thr Asp Cys Phe Arg Lys His Pro Glu Ala
            580                 585                 590

Thr Tyr Ser Arg Cys Gly Ser Gly Pro Trp Val Thr Pro Arg Phe Leu
        595                 600                 605

Val His Tyr Pro Tyr Arg Leu Trp His Tyr Pro Cys Thr Val Asn Tyr
    610                 615                 620

Thr Leu Phe Lys Val Arg Met Tyr Val Gly Gly Val Glu His Arg Leu
625                 630                 635                 640

Glu Val Ala Cys Asn Trp Thr Arg Gly Glu Arg Cys Asp Leu Asp Asp
                645                 650                 655

Arg Asp Arg Ser Glu Leu Ser Pro Leu Leu Leu Ser Thr Thr Gln Trp
            660                 665                 670

Gln Val Leu Pro Cys Ser Phe Thr Thr Leu Pro Ala Leu Thr Thr Gly
        675                 680                 685

Leu Ile His Leu His Gln Asn Ile Val Asp Val Gln Tyr Leu Tyr Gly
    690                 695                 700

Val Gly Ser Ser Leu Val Ser Trp Ala Ile Lys Trp Glu Tyr Val Ile
705                 710                 715                 720

Leu Leu Phe Leu Leu Leu Ala Asp Ala Arg Ile Cys Ser Cys Leu Trp
                725                 730                 735

Met Met Leu Leu Ile Ser Gln Ala Glu Ala
            740                 745

<210> SEQ ID NO 6
<211> LENGTH: 746
<212> TYPE: PRT
<213> ORGANISM: Hepatitis C virus

<400> SEQUENCE: 6

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly

```
            20                  25                  30
Gly Val Tyr Leu Leu Pro Arg Arg Gly Pro Arg Leu Gly Val Arg Ala
            35                  40                  45
Thr Arg Lys Thr Ser Glu Arg Ser Gln Pro Arg Gly Arg Arg Gln Pro
50                  55                  60
Ile Pro Lys Ala Arg Arg Pro Glu Gly Arg Thr Trp Ala Gln Pro Gly
65                  70                  75                  80
Tyr Pro Trp Pro Leu Tyr Gly Asn Glu Gly Cys Gly Trp Ala Gly Trp
                    85                  90                  95
Leu Leu Ser Pro Arg Gly Ser Arg Pro Ser Trp Gly Pro Thr Asp Pro
                100                 105                 110
Arg Arg Arg Ser Arg Asn Leu Gly Lys Val Ile Asp Thr Leu Thr Cys
                115                 120                 125
Gly Phe Ala Asp Leu Met Gly Tyr Ile Pro Leu Val Gly Ala Pro Leu
                130                 135                 140
Gly Gly Ala Ala Arg Ala Leu Ala His Gly Val Arg Val Leu Glu Asp
145                 150                 155                 160
Gly Val Asn Tyr Ala Thr Gly Asn Leu Pro Gly Cys Ser Phe Ser Ile
                    165                 170                 175
Phe Leu Leu Ala Leu Leu Ser Cys Leu Thr Val Pro Ala Ser Ala Tyr
                180                 185                 190
Gln Val Arg Asn Ser Ser Gly Leu Tyr His Val Thr Asn Asp Cys Pro
                195                 200                 205
Asn Ser Ser Ile Val Tyr Glu Thr Ala Asp Thr Ile Leu His Ser Pro
                210                 215                 220
Gly Cys Val Pro Cys Val Arg Glu Gly Asn Thr Ser Lys Cys Trp Val
225                 230                 235                 240
Ala Val Ala Pro Thr Val Ala Thr Arg Asp Gly Lys Leu Pro Thr Thr
                    245                 250                 255
Gln Leu Arg Arg His Ile Asp Leu Leu Val Gly Ser Ala Thr Leu Cys
                260                 265                 270
Ser Ala Leu Tyr Val Gly Asp Leu Cys Gly Ser Val Phe Leu Val Gly
                275                 280                 285
Gln Leu Phe Thr Phe Ser Pro Arg Arg His Trp Thr Thr Gln Asp Cys
                290                 295                 300
Asn Cys Ser Ile Tyr Pro Gly His Ile Thr Gly His Arg Met Ala Trp
305                 310                 315                 320
Asp Met Met Met Asn Trp Ser Pro Thr Ala Ala Leu Val Thr Ala Gln
                    325                 330                 335
Leu Leu Arg Val Pro Gln Ala Ile Leu Asp Met Ile Ala Gly Ala His
                340                 345                 350
Trp Gly Val Leu Ala Gly Ile Ala Tyr Phe Ser Met Ala Gly Asn Trp
                355                 360                 365
Ala Lys Val Leu Leu Val Leu Leu Leu Phe Ala Gly Val Asp Ala Glu
                370                 375                 380
Thr Tyr Thr Thr Gly Gly Ser Val Ala Arg Thr Thr Arg Gly Leu Ala
385                 390                 395                 400
Ser Leu Leu Gln Val Gly Pro Lys Gln Asp Ile Arg Leu Ile His Thr
                    405                 410                 415
Asn Gly Ser Trp His Ile Asn Arg Thr Ala Leu Asn Cys Asn Ala Ser
                420                 425                 430
Leu Asp Thr Gly Trp Leu Ala Gly Leu Leu Tyr Tyr His Lys Phe Asn
                435                 440                 445
```

```
Ser Ser Gly Cys Pro Glu Arg Met Ala Ser Cys Arg Pro Leu Ala Asp
    450                 455                 460

Phe Asp Gln Gly Trp Gly Pro Ile Ser Tyr Ala Asn Gly Ser Gly Pro
465                 470                 475                 480

Glu His Arg Pro Tyr Cys Trp His Tyr Pro Pro Lys Pro Cys Gly Ile
                485                 490                 495

Val Pro Ala Gln Thr Val Cys Gly Pro Val Tyr Cys Phe Thr Pro Ser
            500                 505                 510

Pro Val Val Val Gly Thr Thr Asn Lys Leu Gly Val Pro Thr Tyr Thr
        515                 520                 525

Trp Gly Ser Asn Asp Thr Asp Val Phe Val Leu Asn Asn Thr Arg Pro
    530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Gly Val Gly Asn
                565                 570                 575

Asn Thr Leu His Cys Pro Thr Asp Cys Phe Arg Lys His Pro Glu Ala
            580                 585                 590

Thr Tyr Ser Arg Cys Gly Ser Gly Pro Trp Ile Thr Pro Arg Cys Leu
        595                 600                 605

Val Asp Tyr Pro Tyr Arg Leu Trp His Tyr Pro Cys Thr Val Asn Tyr
    610                 615                 620

Thr Leu Phe Lys Val Arg Met Tyr Val Gly Val Glu His Arg Leu
625                 630                 635                 640

Gln Ala Ala Cys Asn Trp Thr Arg Gly Glu Arg Cys Asp Leu Asp Asp
                645                 650                 655

Arg Asp Arg Ser Glu Leu Ser Pro Leu Leu Leu Ser Thr Thr Gln Trp
            660                 665                 670

Gln Val Leu Pro Cys Ser Phe Thr Thr Leu Pro Ala Leu Thr Thr Gly
        675                 680                 685

Leu Ile His Leu His Gln Asn Ile Val Asp Val Gln Tyr Leu Tyr Gly
    690                 695                 700

Val Gly Ser Ser Ile Val Ser Trp Ala Ile Lys Trp Glu Tyr Val Ile
705                 710                 715                 720

Leu Leu Phe Leu Leu Leu Ala Asp Ala Arg Ile Cys Ser Cys Leu Trp
                725                 730                 735

Met Met Leu Leu Ile Ser Gln Ala Glu Ala
            740                 745

<210> SEQ ID NO 7
<211> LENGTH: 746
<212> TYPE: PRT
<213> ORGANISM: Hepatitis C virus

<400> SEQUENCE: 7

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Thr Trp Ala Gln Pro Gly
```

```
                65                  70                  75                  80
Tyr Pro Trp Pro Leu Tyr Gly Asn Glu Gly Cys Gly Trp Ala Gly Trp
                    85                  90                  95

Leu Leu Ser Pro Arg Gly Ser Arg Pro Ser Trp Gly Pro Thr Asp Pro
                    100                 105                 110

Arg Arg Arg Ser Arg Asn Leu Gly Lys Val Ile Asp Thr Leu Thr Cys
                    115                 120                 125

Gly Phe Ala Asp Leu Met Gly Tyr Ile Pro Leu Val Gly Ala Pro Leu
                    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                    165                 170                 175

Phe Leu Leu Ala Leu Leu Ser Cys Leu Thr Val Pro Ala Ser Ala Tyr
                    180                 185                 190

Gln Val Arg Asn Ser Ser Gly Leu Tyr His Val Thr Asn Asp Cys Pro
                    195                 200                 205

Asn Ser Ser Ile Val Tyr Glu Thr Ala Asp Thr Ile Leu His Ser Pro
210                 215                 220

Gly Cys Val Pro Cys Val Arg Glu Asp Asn Ala Ser Arg Cys Trp Val
225                 230                 235                 240

Pro Val Ala Pro Thr Val Ala Thr Arg Asp Gly Lys Leu Pro Thr Thr
                    245                 250                 255

Gln Leu Arg Arg His Ile Asp Leu Leu Val Gly Ser Ala Thr Leu Cys
                    260                 265                 270

Ser Ala Leu Tyr Val Gly Asp Leu Cys Gly Ser Val Phe Leu Val Ser
                    275                 280                 285

Gln Leu Phe Thr Phe Ser Pro Arg Arg His Trp Thr Thr Gln Asp Cys
                    290                 295                 300

Asn Cys Ser Ile Tyr Pro Gly His Ile Thr Gly His Arg Met Ala Trp
305                 310                 315                 320

Asp Met Met Met Asn Trp Ser Pro Thr Val Ala Leu Val Met Ala Gln
                    325                 330                 335

Leu Leu Arg Val Pro Gln Ala Ile Leu Asp Met Ile Ala Gly Ala His
                    340                 345                 350

Trp Gly Val Leu Ala Gly Ile Ala Tyr Phe Ser Met Val Gly Asn Trp
                    355                 360                 365

Ala Lys Val Leu Val Val Leu Leu Leu Phe Ala Gly Val Asp Ala Gln
                    370                 375                 380

Thr Tyr Val Thr Gly Gly Ser Ala Ala Arg Gly Ala Ser Gly Leu Ala
385                 390                 395                 400

Asn Leu Phe Thr Pro Gly Ala Lys Gln Asp Ile Gln Leu Ile Asn Thr
                    405                 410                 415

Asn Gly Ser Trp His Ile Asn Arg Thr Ala Leu Asn Cys Asn Ala Ser
                    420                 425                 430

Leu Asp Thr Gly Trp Val Ala Gly Leu Phe Tyr Tyr His Lys Phe Asn
                    435                 440                 445

Ser Ser Gly Cys Pro Glu Arg Met Ala Ser Cys Lys Pro Leu Ala Asp
                    450                 455                 460

Phe Asp Gln Gly Trp Gly Pro Ile Arg His Ala Asn Gly Ser Gly Pro
465                 470                 475                 480

Glu His Arg Pro Tyr Cys Trp His Tyr Pro Pro Lys Pro Cys Gly Ile
                    485                 490                 495
```

```
Val Ser Ala Gln Thr Val Cys Gly Pro Val Tyr Cys Phe Thr Pro Ser
            500                 505                 510

Pro Val Val Val Gly Thr Thr Asn Arg Leu Gly Val Pro Thr Tyr Ser
            515                 520                 525

Trp Gly Thr Asn Asp Thr Asp Val Phe Val Leu Asn Asn Thr Arg Pro
        530                 535                 540

Pro Leu Gly Asn Trp Phe Gly Cys Thr Trp Met Asn Ser Ser Gly Phe
545                 550                 555                 560

Thr Lys Val Cys Gly Ala Pro Pro Cys Val Ile Gly Val Gly Asn
                565                 570                 575

Asn Thr Leu His Cys Pro Thr Asp Cys Phe Arg Lys His Pro Glu Ala
            580                 585                 590

Thr Tyr Ser Arg Cys Gly Ser Gly Pro Trp Ile Thr Pro Arg Cys Leu
        595                 600                 605

Val His Tyr Pro Tyr Arg Leu Trp His Tyr Pro Cys Thr Val Asn Tyr
    610                 615                 620

Thr Leu Phe Lys Val Arg Met Tyr Val Gly Val Glu His Arg Leu
625                 630                 635                 640

Glu Val Ala Cys Asn Trp Thr Arg Gly Glu Arg Cys Asp Leu Asp Asp
                645                 650                 655

Arg Asp Arg Ser Glu Leu Ser Pro Leu Leu Leu Ser Thr Thr Gln Trp
            660                 665                 670

Gln Val Leu Pro Cys Ser Phe Thr Thr Leu Pro Ala Leu Thr Thr Gly
        675                 680                 685

Leu Ile His Leu His Gln Asn Ile Val Asp Val Gln Tyr Leu Tyr Gly
    690                 695                 700

Val Gly Ser Ser Ile Val Ser Trp Ala Ile Lys Trp Glu Tyr Val Ile
705                 710                 715                 720

Leu Leu Phe Leu Leu Leu Ala Asp Ala Arg Ile Cys Ser Cys Leu Trp
                725                 730                 735

Met Met Leu Leu Ile Ser Gln Ala Glu Ala
            740                 745

<210> SEQ ID NO 8
<211> LENGTH: 746
<212> TYPE: PRT
<213> ORGANISM: Hepatitis C virus

<400> SEQUENCE: 8

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Thr
        35                  40                  45

Thr Arg Lys Thr Ser Glu Arg Ser Glu Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
```

```
            115                 120                 125
Gly Phe Ala Asp Leu Met Gly Tyr Ile Pro Leu Val Gly Ala Pro Leu
130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
                180                 185                 190

Gln Val Arg Asn Ser Ser Gly Leu Tyr His Val Thr Asn Asp Cys Pro
                195                 200                 205

Asn Ser Ser Ile Val Tyr Glu Thr Lys Asp Thr Ile Leu His Ser Pro
210                 215                 220

Gly Cys Val Pro Cys Val Arg Glu Gly Asn Val Ser Lys Cys Trp Val
225                 230                 235                 240

Pro Val Ala Leu Thr Val Ala Thr Arg Asp Gly Asn Leu Pro Thr Thr
                245                 250                 255

Gln Leu Arg Arg His Ile Asp Leu Leu Val Gly Ser Ala Thr Leu Cys
                260                 265                 270

Ser Ala Leu Tyr Val Gly Asp Leu Cys Gly Ser Val Phe Leu Val Gly
                275                 280                 285

Gln Leu Phe Thr Phe Ser Pro Arg Arg His Trp Thr Thr Gln Asp Cys
290                 295                 300

Asn Cys Ser Met Tyr Pro Gly His Ile Thr Gly His Arg Met Ala Trp
305                 310                 315                 320

Asp Met Met Met Asn Trp Ser Pro Thr Ser Ala Leu Val Val Ala Gln
                325                 330                 335

Leu Leu Arg Val Pro Gln Ala Ile Leu Asp Met Ile Ala Gly Ala His
                340                 345                 350

Trp Gly Val Leu Ala Gly Leu Ala Tyr Phe Ser Met Val Gly Asn Trp
                355                 360                 365

Ala Lys Val Leu Val Val Leu Leu Leu Phe Ala Ser Val Asp Ala Gly
                370                 375                 380

Thr His Val Thr Gly Gly Ser Ala Ala His Asp Val Ser Ala Leu Ala
385                 390                 395                 400

Gly Phe Phe Arg Arg Gly Ala Lys Gln Asn Ile Gln Leu Ile Asn Thr
                405                 410                 415

Asn Gly Ser Trp His Val Asn Arg Thr Ala Leu Asn Cys Asn Ala Ser
                420                 425                 430

Leu Asp Thr Gly Trp Val Ala Gly Leu Leu Tyr Tyr His Arg Phe Asn
                435                 440                 445

Ser Ser Gly Cys Pro Glu Arg Met Ala Ser Cys Arg Pro Leu Ala Asp
                450                 455                 460

Phe Asp Gln Gly Trp Gly Pro Ile Thr Asn Val Asp Gly Gly Ser
465                 470                 475                 480

Glu Tyr Arg Pro Tyr Cys Trp His Tyr Pro Lys Pro Cys Gly Ile
                485                 490                 495

Glu Pro Ala Gln Asn Val Cys Gly Pro Val Tyr Cys Phe Thr Pro Ser
                500                 505                 510

Pro Val Val Val Gly Thr Thr Asp Lys Val Gly Val Pro Thr Tyr Asn
                515                 520                 525

Trp Gly Glu Asn Asp Thr Asp Val Phe Val Leu Asn Asn Thr Arg Pro
530                 535                 540
```

```
Pro Leu Gly Asn Trp Phe Gly Cys Thr Trp Met Asn Ser Ser Gly Phe
545                 550                 555                 560

Val Lys Val Cys Gly Ala Pro Pro Cys Ile Ile Gly Gly Ala Gly Asn
                565                 570                 575

Lys Thr Leu His Cys Pro Thr Asp Cys Phe Arg Lys His Pro Asp Ala
            580                 585                 590

Thr Tyr Ser Arg Cys Gly Ser Gly Pro Trp Leu Thr Pro Arg Cys Leu
            595                 600                 605

Val Asp Tyr Pro Tyr Arg Leu Trp His Tyr Pro Cys Thr Val Asn Tyr
610                 615                 620

Thr Leu Phe Lys Ile Arg Met Tyr Val Gly Gly Val Glu His Arg Leu
625                 630                 635                 640

Val Ala Ala Cys Asn Trp Thr Tyr Gly Glu Arg Cys Asn Leu Asp Asp
                645                 650                 655

Arg Asp Arg Ser Glu Leu Ser Pro Leu Leu Leu Ser Thr Thr Gln Trp
                660                 665                 670

Gln Val Leu Pro Cys Ser Phe Thr Thr Leu Pro Ala Leu Thr Thr Gly
            675                 680                 685

Leu Ile His Leu His Gln Asn Ile Val Asp Val Gln Tyr Leu Tyr Gly
            690                 695                 700

Val Gly Ser Ser Ile Val Ser Trp Ala Ile Lys Trp Glu Tyr Val Ile
705                 710                 715                 720

Leu Leu Phe Leu Leu Leu Ala Asp Ala Arg Ile Cys Ser Cys Leu Trp
                725                 730                 735

Met Met Leu Leu Ile Ser Gln Ala Glu Ala
            740                 745

<210> SEQ ID NO 9
<211> LENGTH: 746
<212> TYPE: PRT
<213> ORGANISM: Hepatitis C virus

<400> SEQUENCE: 9

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
            130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
```

```
                165                 170                 175
Phe Leu Leu Ala Leu Leu Ser Cys Leu Thr Val Pro Ala Ser Ala Tyr
            180                 185                 190

Gln Val Arg Asn Ser Ser Gly Leu Tyr His Val Thr Asn Asp Cys Pro
            195                 200                 205

Asn Ser Ser Ile Val Tyr Glu Thr Ala Asp Thr Ile Leu His Ser Pro
            210                 215                 220

Gly Cys Val Pro Cys Val Arg Glu Gly Asn Ala Ser Lys Cys Trp Val
225                 230                 235                 240

Ala Val Ala Pro Thr Val Ala Thr Arg Asp Gly Thr Leu Pro Thr Thr
                245                 250                 255

Gln Leu Arg Arg His Ile Asp Leu Leu Val Gly Gly Ala Thr Leu Cys
                260                 265                 270

Ser Ala Leu Tyr Val Gly Asp Leu Cys Gly Ser Val Phe Leu Val Gly
                275                 280                 285

Gln Leu Phe Thr Phe Ser Pro Arg Arg His Trp Thr Thr Gln Asp Cys
            290                 295                 300

Asn Cys Ser Ile Tyr Pro Gly His Ile Thr Gly His Arg Met Ala Trp
305                 310                 315                 320

Asp Met Met Met Asn Trp Ser Pro Thr Thr Ala Leu Ile Val Ala Gln
                325                 330                 335

Leu Leu Arg Val Pro Gln Ala Ile Leu Asp Met Ile Ala Gly Ala His
                340                 345                 350

Trp Gly Val Leu Ala Gly Ile Ala Tyr Phe Ser Met Val Gly Asn Trp
                355                 360                 365

Ala Lys Val Leu Val Val Leu Leu Leu Phe Ala Gly Val Asp Ala Glu
            370                 375                 380

Thr His Val Thr Gly Gly Ser Ala Ala Gln Val Thr Ser Arg Val Ala
385                 390                 395                 400

Gly Phe Phe Asn Pro Gly Pro Lys Gln Asn Val Gln Leu Ile Asn Thr
                405                 410                 415

Asn Gly Ser Trp His Ile Asn Arg Thr Ala Leu Asn Cys Asn Ala Ser
                420                 425                 430

Leu Asp Thr Gly Trp Val Ala Gly Leu Phe Tyr His Tyr Asn Phe Asn
            435                 440                 445

Ser Ser Gly Cys Pro Glu Arg Met Ala Ser Cys Arg Pro Leu Ala Asp
            450                 455                 460

Phe Asp Gln Gly Trp Gly Pro Ile Ser Tyr Ala Asn Gly Ser Gly Pro
465                 470                 475                 480

Glu His Arg Pro Tyr Cys Trp His Tyr Pro Pro Lys Pro Cys Gly Ile
                485                 490                 495

Val Pro Ala Gln Asn Val Cys Gly Pro Val Tyr Cys Phe Thr Pro Ser
                500                 505                 510

Pro Val Val Val Gly Thr Thr Asn Arg Leu Gly Val Pro Thr Tyr Asn
                515                 520                 525

Trp Gly Ser Asn Asp Thr Asp Val Phe Val Leu Asn Asn Thr Arg Pro
            530                 535                 540

Pro Leu Gly Asn Trp Phe Gly Cys Thr Trp Met Asn Ser Ser Gly Phe
545                 550                 555                 560

Thr Lys Val Cys Gly Ala Pro Pro Cys Val Ile Gly Gly Val Gly Asn
                565                 570                 575

Asn Thr Leu His Cys Pro Thr Asp Cys Phe Arg Lys His Pro Glu Ala
                580                 585                 590
```

```
Thr Tyr Ser Arg Cys Gly Ser Gly Pro Trp Ile Thr Pro Arg Cys Leu
            595                 600                 605

Val His Tyr Pro Tyr Arg Leu Trp His Tyr Pro Cys Thr Val Asn Tyr
        610                 615                 620

Thr Leu Phe Lys Val Arg Met Tyr Val Gly Gly Val Glu His Arg Leu
625                 630                 635                 640

Glu Ala Ala Cys Asn Trp Thr Arg Gly Glu Arg Cys Asp Leu Asp Asp
                645                 650                 655

Arg Asp Arg Ser Glu Leu Ser Pro Leu Leu Leu Ser Thr Thr Gln Trp
                660                 665                 670

Gln Val Leu Pro Cys Ser Phe Thr Thr Leu Pro Ala Leu Thr Thr Gly
            675                 680                 685

Leu Ile His Leu His Gln Asn Ile Val Asp Val Gln Tyr Leu Tyr Gly
            690                 695                 700

Val Gly Ser Ser Ile Val Ser Trp Ala Ile Lys Trp Glu Tyr Val Ile
705                 710                 715                 720

Leu Leu Phe Leu Leu Leu Ala Asp Ala Arg Ile Cys Ser Cys Leu Trp
                725                 730                 735

Met Met Leu Leu Ile Ser Gln Ala Glu Ala
            740                 745

<210> SEQ ID NO 10
<211> LENGTH: 746
<212> TYPE: PRT
<213> ORGANISM: Hepatitis C virus

<400> SEQUENCE: 10

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Ser Gly Ile Tyr His Val Thr Asn Asp Cys Pro
        195                 200                 205

Asn Ser Ser Ile Val Tyr Glu Thr Ala Asp Thr Ile Leu His Ser Pro
```

```
                210                 215                 220
Gly Cys Val Pro Cys Val Arg Glu Gly Asn Ala Ser Lys Cys Trp Val
225                 230                 235                 240

Ala Leu Ala Pro Thr Val Ala Thr Arg Asp Gly Arg Leu Pro Thr Thr
                245                 250                 255

Gln Leu Arg Arg His Ile Asp Leu Leu Val Gly Ser Ala Thr Leu Cys
                260                 265                 270

Ser Ala Leu Tyr Val Gly Asp Leu Cys Gly Ser Val Phe Leu Val Gly
                275                 280                 285

Gln Leu Phe Thr Phe Ser Pro Arg Arg His Trp Thr Thr Gln Asp Cys
                290                 295                 300

Asn Cys Ser Ile Tyr Pro Gly His Ile Thr Gly His Arg Met Ala Trp
305                 310                 315                 320

Asp Met Met Met Asn Trp Ser Pro Thr Thr Ala Leu Val Val Ala Gln
                325                 330                 335

Leu Leu Arg Ile Pro Gln Ala Ile Leu Asp Met Ile Ala Gly Ala His
                340                 345                 350

Trp Gly Val Leu Ala Gly Ile Ala Tyr Phe Ser Met Val Gly Asn Trp
                355                 360                 365

Ala Lys Val Leu Val Val Leu Leu Leu Phe Ala Gly Val Asp Ala His
                370                 375                 380

Thr Arg Val Thr Gly Gly Ser Ala Ala Arg Ala Thr Ala Arg Leu Thr
385                 390                 395                 400

Thr Leu Phe Ser Pro Gly Ala Lys Gln Asp Ile Gln Leu Ile Asn Thr
                405                 410                 415

Asn Gly Ser Trp His Ile Asn Arg Thr Ala Leu Asn Cys Asn Ala Ser
                420                 425                 430

Leu Asp Thr Gly Trp Val Ala Gly Leu Phe Tyr Tyr His Lys Phe Asn
                435                 440                 445

Ser Ser Gly Cys Pro Glu Arg Met Ala Ser Cys Arg Pro Leu Ala Asp
                450                 455                 460

Phe Asp Gln Gly Trp Gly Pro Ile Ser Tyr Ala Asn Gly Ser Gly Pro
465                 470                 475                 480

Glu His Arg Pro Tyr Cys Trp His Tyr Pro Pro Lys Pro Cys Gly Ile
                485                 490                 495

Ile Pro Ala Lys Thr Val Cys Gly Pro Val Tyr Cys Phe Thr Pro Ser
                500                 505                 510

Pro Val Val Val Gly Thr Thr Asp Arg Ser Gly Ala Pro Thr Phe Asn
                515                 520                 525

Trp Gly Asp Asn Asp Thr Asp Val Leu Val Leu Asn Asn Thr Arg Pro
530                 535                 540

Pro Leu Gly Asn Trp Phe Gly Cys Thr Trp Met Asn Ser Ser Gly Tyr
545                 550                 555                 560

Thr Lys Val Cys Gly Ala Pro Pro Cys Ile Ile Gly Gly Val Gly Asn
                565                 570                 575

Asn Thr Leu His Cys Pro Thr Asp Cys Phe Arg Lys His Pro Glu Ala
                580                 585                 590

Thr Tyr Ser Arg Cys Gly Ser Gly Pro Trp Ile Thr Pro Arg Cys Leu
                595                 600                 605

Val His Tyr Pro Tyr Arg Leu Trp His Tyr Pro Cys Thr Val Asn Tyr
                610                 615                 620

Thr Leu Phe Lys Val Arg Met Tyr Val Gly Gly Val Glu His Arg Leu
625                 630                 635                 640
```

-continued

Glu Ala Ala Cys Asn Trp Thr Arg Gly Glu Arg Cys Asn Leu Asp Asp
                645                 650                 655

Arg Asp Arg Ser Glu Leu Ser Pro Leu Leu Ser Thr Thr Gln Trp
            660                 665                 670

Gln Val Leu Pro Cys Ser Phe Thr Thr Leu Pro Ala Leu Thr Thr Gly
            675                 680                 685

Leu Ile His Leu His Gln Asn Ile Val Asp Val Gln Tyr Leu Tyr Gly
        690                 695                 700

Val Gly Ser Ser Ile Val Ser Trp Ala Ile Lys Trp Glu Tyr Val Ile
705                 710                 715                 720

Leu Leu Phe Leu Leu Leu Ala Asp Ala Arg Val Cys Ser Cys Leu Trp
                725                 730                 735

Met Met Leu Leu Ile Ser Gln Val Glu Ala
                740                 745

<210> SEQ ID NO 11
<211> LENGTH: 746
<212> TYPE: PRT
<213> ORGANISM: Hepatitis C virus

<400> SEQUENCE: 11

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
        130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
                180                 185                 190

Gln Val Arg Asn Ser Ser Gly Leu Tyr His Val Thr Asn Asp Cys Pro
            195                 200                 205

Asn Ser Ser Ile Val Tyr Glu Thr Ala Asp Thr Ile Leu His Ser Pro
        210                 215                 220

Gly Cys Val Pro Cys Val Arg Glu Gly Asn Ala Ser Lys Cys Trp Val
225                 230                 235                 240

Ala Val Thr Pro Thr Val Ala Thr Arg Asp Gly Arg Leu Pro Ala Thr
                245                 250                 255

Gln Leu Arg Arg His Ile Asp Leu Leu Val Gly Ser Ala Thr Leu Cys

```
                260                 265                 270
Ser Ala Leu Tyr Val Gly Asp Leu Cys Gly Ser Ile Phe Leu Val Gly
                275                 280                 285

Gln Leu Phe Thr Phe Ser Pro Arg Arg His Trp Thr Thr Gln Asp Cys
            290                 295                 300

Asn Cys Ser Ile Tyr Pro Gly His Ile Thr Gly His Arg Met Ala Trp
305                 310                 315                 320

Asp Met Met Met Asn Trp Ser Pro Thr Thr Ala Leu Val Val Ala Gln
                325                 330                 335

Leu Leu Arg Val Pro Gln Ala Ile Leu Asp Met Ile Ala Gly Ala His
                340                 345                 350

Trp Gly Val Leu Ala Gly Ile Ala Tyr Phe Ser Met Val Gly Asn Trp
            355                 360                 365

Ala Lys Val Leu Val Val Leu Leu Phe Ala Gly Val Asp Ala Gly
        370                 375                 380

Thr His Val Thr Gly Gly Ser Ala Ala Lys Asp Thr Ser Gly Phe Thr
385                 390                 395                 400

Ser Leu Phe Arg Ile Gly Ala Arg Gln Asn Ile Gln Leu Ile Asn Ser
                405                 410                 415

Asn Gly Ser Trp His Ile Asn Arg Thr Ala Leu Asn Cys Asn Glu Ser
            420                 425                 430

Leu Asp Thr Gly Trp Val Ala Gly Leu Leu Tyr Tyr His Lys Phe Asn
            435                 440                 445

Ser Ser Gly Cys Pro Glu Arg Met Ala Ser Cys Arg Ser Leu Ala Asp
        450                 455                 460

Phe Asp Gln Gly Trp Gly Pro Ile Ser Tyr Ala Asn Gly Ser Gly Pro
465                 470                 475                 480

Glu His Arg Pro Tyr Cys Trp His Tyr Pro Lys Pro Cys Gly Ile
                485                 490                 495

Val Pro Ala Gln Ser Val Cys Gly Pro Val Tyr Cys Phe Thr Pro Ser
            500                 505                 510

Pro Val Val Val Gly Thr Thr Asp Lys Ser Gly Ala Pro Thr Tyr Asn
            515                 520                 525

Trp Gly Cys Asn Glu Thr Asp Val Phe Val Leu Asn Asn Thr Arg Pro
            530                 535                 540

Pro Leu Gly Asn Trp Phe Gly Cys Thr Trp Met Asn Ser Ser Gly Phe
545                 550                 555                 560

Thr Lys Val Cys Gly Ala Pro Pro Cys Val Ile Gly Val Gly Asn
            565                 570                 575

Asn Thr Leu His Cys Pro Thr Asp Cys Phe Arg Lys His Pro Glu Ala
                580                 585                 590

Thr Tyr Ser Arg Cys Gly Ser Gly Pro Trp Ile Thr Pro Arg Cys Leu
            595                 600                 605

Val His Tyr Ala Tyr Arg Leu Trp His Tyr Pro Cys Thr Val Asn Tyr
            610                 615                 620

Thr Leu Phe Lys Val Arg Met Tyr Val Gly Gly Val Glu His Arg Leu
625                 630                 635                 640

Asp Val Ala Cys Asn Trp Thr Arg Gly Glu Arg Cys Asn Leu Asp Asp
                645                 650                 655

Arg Asp Arg Ser Glu Leu Ser Pro Leu Leu Leu Ser Thr Thr Gln Trp
            660                 665                 670

Gln Val Leu Pro Cys Ser Phe Thr Thr Leu Pro Ala Leu Ser Thr Gly
            675                 680                 685
```

```
Leu Ile His Leu His Gln Asn Ile Val Asp Val Gln Tyr Leu Tyr Gly
        690                 695                 700
Val Gly Ser Ser Ile Val Ser Trp Ala Ile Lys Trp Glu Tyr Val Ile
705                 710                 715                 720
Leu Leu Phe Leu Leu Leu Ala Asp Ala Arg Ile Cys Ser Cys Leu Trp
                725                 730                 735
Met Met Leu Leu Ile Ser Gln Ala Glu Ala
        740                 745

<210> SEQ ID NO 12
<211> LENGTH: 746
<212> TYPE: PRT
<213> ORGANISM: Hepatitis C virus

<400> SEQUENCE: 12

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Ser Gly Leu Tyr His Val Thr Asn Asp Cys Pro
        195                 200                 205

Asn Ser Ser Ile Val Tyr Glu Thr Ala Asp Thr Ile Leu His Ser Pro
210                 215                 220

Gly Cys Val Pro Cys Val Arg Glu Gly Asn Ala Ser Lys Cys Trp Val
225                 230                 235                 240

Ala Val Thr Pro Thr Val Ala Thr Arg Asp Gly Arg Leu Pro Ala Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Ile Phe Leu Val Gly
        275                 280                 285

Gln Leu Phe Thr Phe Ser Pro Arg Arg His Trp Thr Thr Gln Asp Cys
290                 295                 300

Asn Cys Ser Ile Tyr Pro Gly His Ile Thr Gly His Arg Met Ala Trp
```

```
                    305                 310                 315                 320
            Asp Met Met Met Asn Trp Ser Pro Thr Thr Ala Leu Val Val Ala Gln
                                325                 330                 335

Leu Leu Arg Val Pro Gln Ala Ile Leu Asp Met Ile Ala Gly Ala His
                                340                 345                 350

Trp Gly Val Leu Ala Gly Ile Ala Tyr Phe Ser Met Val Gly Asn Trp
                                355                 360                 365

Ala Lys Val Leu Val Leu Leu Phe Ala Gly Val Asp Ala Gly
                370                 375                 380

Thr His Val Thr Gly Gly Ser Ala Ala Lys Asp Thr Ser Gly Phe Thr
            385                 390                 395                 400

Ser Leu Phe Arg Ile Gly Ala Arg Gln Asn Ile Gln Leu Ile Asn Ser
                                405                 410                 415

Asn Gly Ser Trp His Ile Asn Arg Thr Ala Leu Asn Cys Asn Glu Ser
                                420                 425                 430

Leu Asp Thr Gly Trp Val Ala Gly Leu Leu Tyr Tyr His Lys Phe Asn
                                435                 440                 445

Ser Ser Gly Cys Pro Glu Arg Met Ala Ser Cys Arg Ser Leu Ala Asp
                                450                 455                 460

Phe Asp Gln Gly Trp Gly Pro Ile Ser Tyr Ala Asn Gly Ser Gly Pro
            465                 470                 475                 480

Glu His Arg Pro Tyr Cys Trp His Tyr Pro Pro Lys Pro Cys Gly Ile
                                485                 490                 495

Val Pro Ala Gln Ser Val Cys Gly Pro Val Tyr Cys Phe Thr Pro Ser
                                500                 505                 510

Pro Val Val Val Gly Thr Thr Asp Lys Ser Gly Ala Pro Thr Tyr Asn
                                515                 520                 525

Trp Gly Cys Asn Glu Thr Asp Val Phe Val Leu Asn Asn Thr Arg Pro
                                530                 535                 540

Pro Leu Gly Asn Trp Phe Gly Cys Thr Trp Met Asn Ser Ser Gly Phe
            545                 550                 555                 560

Thr Lys Val Cys Gly Ala Pro Pro Cys Val Ile Gly Gly Val Gly Asn
                                565                 570                 575

Asn Thr Leu His Cys Pro Thr Asp Cys Phe Arg Lys His Pro Glu Ala
                                580                 585                 590

Thr Tyr Ser Arg Cys Gly Ser Gly Pro Trp Ile Thr Pro Arg Cys Leu
                                595                 600                 605

Val His Tyr Ala Tyr Arg Leu Trp His Tyr Pro Cys Thr Val Asn Tyr
                                610                 615                 620

Thr Leu Phe Lys Val Arg Met Tyr Val Gly Gly Val Glu His Arg Leu
            625                 630                 635                 640

Asp Val Ala Cys Asn Trp Thr Arg Gly Glu Arg Cys Asn Leu Asp Asp
                                645                 650                 655

Arg Asp Arg Ser Glu Leu Ser Pro Leu Leu Leu Ser Thr Thr Gln Trp
                                660                 665                 670

Gln Val Leu Pro Cys Ser Phe Thr Thr Leu Pro Ala Leu Ser Thr Gly
                                675                 680                 685

Leu Ile His Leu His Gln Asn Ile Val Asp Val Gln Tyr Leu Tyr Gly
                                690                 695                 700

Val Gly Ser Ser Ile Val Ser Trp Ala Ile Lys Trp Glu Tyr Val Ile
            705                 710                 715                 720

Leu Leu Phe Leu Leu Leu Ala Asp Ala Arg Ile Cys Ser Cys Leu Trp
                                725                 730                 735
```

Met Met Leu Leu Ile Ser Gln Ala Glu Ala
            740                 745

<210> SEQ ID NO 13
<211> LENGTH: 746
<212> TYPE: PRT
<213> ORGANISM: Hepatitis C virus

<400> SEQUENCE: 13

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Ser Gly Leu Tyr His Val Thr Asn Asp Cys Pro
        195                 200                 205

Asn Ser Ser Ile Val Tyr Glu Thr Ala Asp Thr Ile Leu His Ser Pro
    210                 215                 220

Gly Cys Val Pro Cys Val Arg Glu Gly Asn Ala Ser Lys Cys Trp Val
225                 230                 235                 240

Ala Val Thr Pro Thr Val Ala Thr Arg Asp Gly Arg Leu Pro Ala Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Ile Phe Leu Val Gly
        275                 280                 285

Gln Leu Phe Thr Phe Ser Pro Arg Arg His Trp Thr Thr Gln Asp Cys
    290                 295                 300

Asn Cys Ser Ile Tyr Pro Gly His Ile Thr Gly His Arg Met Ala Trp
305                 310                 315                 320

Asp Met Met Met Asn Trp Ser Pro Thr Thr Ala Leu Val Val Ala Gln
                325                 330                 335

Leu Leu Arg Val Pro Gln Ala Ile Leu Asp Met Ile Ala Gly Ala His
            340                 345                 350

Trp Gly Val Leu Ala Gly Ile Ala Tyr Phe Ser Met Val Gly Asn Trp

```
                355                 360                 365
Ala Lys Val Leu Val Leu Leu Phe Ala Gly Val Asp Ala Gly
    370                 375                 380

Thr His Val Thr Gly Gly Ser Ala Ala Lys Asp Thr Ser Gly Phe Thr
385                 390                 395                 400

Ser Leu Phe Arg Ile Gly Ala Arg Gln Asn Ile Gln Leu Ile Asn Ser
                405                 410                 415

Asn Gly Ser Trp His Ile Asn Arg Thr Ala Leu Asn Cys Asn Glu Ser
            420                 425                 430

Leu Asp Thr Gly Trp Val Ala Gly Leu Leu Tyr Tyr His Lys Phe Asn
        435                 440                 445

Ser Ser Gly Cys Pro Glu Arg Met Ala Ser Cys Arg Ser Leu Ala Asp
    450                 455                 460

Phe Asp Gln Gly Trp Gly Pro Ile Ser Tyr Ala Asn Gly Ser Gly Pro
465                 470                 475                 480

Glu His Arg Pro Tyr Cys Trp His Tyr Pro Lys Pro Cys Gly Ile
                485                 490                 495

Val Pro Ala Gln Ser Val Cys Gly Pro Val Tyr Cys Phe Thr Pro Ser
            500                 505                 510

Pro Val Val Gly Thr Thr Asp Lys Ser Gly Ala Pro Thr Tyr Asn
        515                 520                 525

Trp Gly Cys Asn Glu Thr Asp Val Phe Val Leu Asn Asn Thr Arg Pro
    530                 535                 540

Pro Leu Gly Asn Trp Phe Gly Cys Thr Trp Met Asn Ser Ser Gly Phe
545                 550                 555                 560

Thr Lys Val Cys Gly Ala Pro Pro Cys Val Ile Gly Gly Val Gly Asn
                565                 570                 575

Asn Thr Leu His Cys Pro Thr Asp Cys Phe Arg Lys His Pro Glu Ala
            580                 585                 590

Thr Tyr Ser Arg Cys Gly Ser Gly Pro Trp Ile Thr Pro Arg Cys Leu
        595                 600                 605

Val His Tyr Ala Tyr Arg Leu Trp His Tyr Pro Cys Thr Val Asn Tyr
    610                 615                 620

Thr Leu Phe Lys Val Arg Met Tyr Val Gly Gly Val Glu His Arg Leu
625                 630                 635                 640

Asp Val Ala Cys Asn Trp Thr Arg Gly Glu Arg Cys Asn Leu Asp Asp
                645                 650                 655

Arg Asp Arg Ser Glu Leu Ser Pro Leu Leu Leu Ser Thr Thr Gln Trp
            660                 665                 670

Gln Val Leu Pro Cys Ser Phe Thr Thr Leu Pro Ala Leu Ser Thr Gly
        675                 680                 685

Leu Ile His Leu His Gln Asn Ile Val Asp Val Gln Tyr Leu Tyr Gly
    690                 695                 700

Val Gly Ser Ser Ile Val Ser Trp Ala Ile Lys Trp Glu Tyr Val Ile
705                 710                 715                 720

Leu Leu Phe Leu Leu Leu Ala Asp Ala Arg Ile Cys Ser Cys Leu Trp
                725                 730                 735

Met Met Leu Leu Ile Ser Gln Ala Glu Ala
            740                 745

<210> SEQ ID NO 14
<211> LENGTH: 746
<212> TYPE: PRT
<213> ORGANISM: Hepatitis C virus
```

<400> SEQUENCE: 14

```
Met Ser Thr Asn Pro Lys Pro Gln Arg Lys Thr Lys Arg Asn Thr Asn
1               5                   10                  15
Arg Arg Pro Gln Asp Val Lys Phe Pro Gly Gly Gln Ile Val Gly
            20                  25                  30
Gly Val Tyr Leu Leu Pro Arg Arg Gly Pro Arg Leu Gly Val Arg Ala
                35                  40                  45
Thr Arg Lys Thr Ser Glu Arg Ser Gln Pro Arg Gly Arg Arg Gln Pro
        50                  55                  60
Ile Pro Lys Ala Arg Arg Pro Glu Gly Arg Thr Trp Ala Gln Pro Gly
65                  70                  75                  80
Tyr Pro Trp Pro Leu Tyr Gly Asn Glu Gly Cys Gly Trp Ala Gly Trp
                85                  90                  95
Leu Leu Ser Pro Arg Gly Ser Arg Pro Ser Trp Gly Pro Thr Asp Pro
            100                 105                 110
Arg Arg Arg Ser Arg Asn Leu Gly Lys Val Ile Asp Thr Leu Thr Cys
        115                 120                 125
Gly Phe Ala Asp Leu Met Gly Tyr Ile Pro Leu Val Gly Ala Pro Leu
130                 135                 140
Gly Gly Ala Ala Arg Ala Leu Ala His Gly Val Arg Val Leu Glu Asp
145                 150                 155                 160
Gly Val Asn Tyr Ala Thr Gly Asn Leu Pro Gly Cys Ser Phe Ser Ile
                165                 170                 175
Phe Leu Leu Ala Leu Leu Ser Cys Leu Thr Val Pro Ala Ser Ala Tyr
            180                 185                 190
Gln Val Arg Asn Ser Ser Gly Leu Tyr His Val Thr Asn Asp Cys Pro
        195                 200                 205
Asn Ser Ser Ile Val Tyr Glu Thr Ala Asp Ser Ile Leu His Ser Pro
210                 215                 220
Gly Cys Val Pro Cys Val Arg Glu Gly Asn Ala Ser Lys Cys Trp Val
225                 230                 235                 240
Ala Val Ala Pro Thr Val Ala Thr Arg Asp Gly Lys Leu Pro Ala Thr
                245                 250                 255
Gln Leu Arg Arg His Ile Asp Leu Leu Val Gly Ser Ala Thr Leu Cys
            260                 265                 270
Ser Ala Leu Tyr Val Gly Asp Leu Cys Gly Ser Val Phe Leu Val Ser
        275                 280                 285
Gln Leu Phe Thr Phe Ser Pro Arg Arg His Trp Thr Thr Gln Asp Cys
    290                 295                 300
Asn Cys Ser Ile Tyr Pro Gly His Ile Thr Gly His Arg Met Ala Trp
305                 310                 315                 320
Asp Met Met Met Asn Trp Ser Pro Thr Thr Ala Leu Val Val Ser Gln
                325                 330                 335
Leu Leu Arg Val Pro Gln Ala Ile Leu Asp Met Ile Ala Gly Ala His
            340                 345                 350
Trp Gly Val Leu Ala Gly Ile Ala Tyr Phe Ser Met Val Gly Asn Trp
        355                 360                 365
Ala Lys Val Leu Val Val Leu Leu Phe Ala Gly Val Asp Ala Glu
    370                 375                 380
Thr His Thr Thr Gly Gly Ser Ala Ala Tyr Ala Thr Ser Gly Phe Val
385                 390                 395                 400
Gly Leu Phe Arg Gln Gly Ala Lys Gln Asn Ile Gln Leu Ile Asn Thr
```

```
                    405                 410                 415
Asn Gly Ser Trp His Val Asn Arg Thr Ala Leu Asn Cys Asn Ala Ser
                420                 425                 430

Leu Asp Thr Gly Trp Val Ala Gly Leu Phe Tyr Tyr His Lys Phe Asn
            435                 440                 445

Ser Ser Gly Cys Pro Glu Arg Leu Ala Ser Cys Lys Pro Leu Ala Asn
        450                 455                 460

Phe Asp Gln Gly Trp Gly Ser Ile Ser Tyr Thr Asn Gly Ser Gly Pro
465                 470                 475                 480

Glu His Arg Pro Tyr Cys Trp His Tyr Pro Pro Lys Pro Cys Gly Ile
                485                 490                 495

Val Pro Ala Gln Asn Val Cys Gly Pro Val Tyr Cys Phe Thr Pro Ser
                500                 505                 510

Pro Val Val Val Gly Thr Thr Asp Arg Leu Gly Ala Pro Thr Phe Asn
                515                 520                 525

Trp Gly Glu Asn Glu Ser Asp Val Phe Val Leu Asn Asn Thr Arg Pro
530                 535                 540

Pro Ser Gly Asn Trp Phe Gly Cys Thr Trp Met Asn Ser Ser Gly Phe
545                 550                 555                 560

Thr Lys Val Cys Gly Ala Pro Pro Cys Asn Ile Gly Val Gly Asn
                565                 570                 575

Asn Thr Leu His Cys Pro Thr Asp Cys Phe Arg Lys His Pro Glu Ala
                580                 585                 590

Thr Tyr Ser Arg Cys Gly Ser Gly Pro Trp Val Thr Pro Arg Cys Leu
                595                 600                 605

Val His Tyr Pro Tyr Arg Leu Trp His Tyr Pro Cys Thr Leu Asn Tyr
                610                 615                 620

Ser Leu Phe Lys Val Arg Met Tyr Val Gly Gly Ile Glu His Arg Leu
625                 630                 635                 640

Glu Val Ala Cys Asn Trp Thr Arg Gly Glu Arg Cys Asn Leu Asp Asp
                645                 650                 655

Arg Asp Arg Ser Glu Leu Ser Pro Leu Leu Leu Thr Thr Thr Gln Trp
                660                 665                 670

Gln Val Leu Pro Cys Ser Phe Thr Thr Leu Pro Ala Leu Thr Thr Gly
            675                 680                 685

Leu Ile His Leu His Gln Asn Val Val Asp Val Gln Tyr Leu Tyr Gly
            690                 695                 700

Val Gly Ser Ser Ile Val Ser Trp Ala Ile Lys Trp Glu Tyr Val Ile
705                 710                 715                 720

Leu Leu Phe Leu Leu Leu Ala Asp Ala Arg Ile Cys Ser Cys Leu Trp
                725                 730                 735

Met Met Leu Leu Ile Ser Gln Ala Glu Ala
                740                 745

<210> SEQ ID NO 15
<211> LENGTH: 746
<212> TYPE: PRT
<213> ORGANISM: Hepatitis C virus

<400> SEQUENCE: 15

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gln Ile Val Gly
            20                  25                  30
```

-continued

Gly Val Tyr Leu Leu Pro Arg Arg Gly Pro Arg Leu Gly Val Arg Ala
             35                  40                  45

Thr Arg Lys Thr Ser Glu Arg Ser Gln Pro Arg Gly Arg Gln Pro
 50                  55                  60

Ile Pro Lys Ala Arg Arg Pro Glu Gly Arg Thr Trp Ala Gln Pro Gly
 65                  70                  75                  80

Tyr Pro Trp Pro Leu Tyr Gly Asn Glu Gly Cys Gly Trp Ala Gly Trp
                 85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
                115                 120                 125

Gly Phe Ala Asp Leu Met Gly Tyr Ile Pro Leu Val Gly Ala Pro Leu
130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
                180                 185                 190

Gln Val Arg Asn Ser Ser Gly Leu Tyr His Val Thr Asn Asp Cys Pro
                195                 200                 205

Asn Ser Ser Ile Val Tyr Glu Thr Ala Asp Thr Ile Leu His Ser Pro
                210                 215                 220

Gly Cys Val Pro Cys Val Arg Glu Gly Asn Ala Ser Lys Cys Trp Val
225                 230                 235                 240

Ala Val Ala Pro Thr Val Ala Thr Arg Asp Gly Arg Leu Pro Thr Thr
                245                 250                 255

Gln Leu Arg Arg His Ile Asp Leu Leu Val Gly Ser Ala Thr Leu Cys
                260                 265                 270

Ser Ala Leu Tyr Val Gly Asp Leu Cys Gly Ser Val Phe Leu Val Gly
                275                 280                 285

Gln Leu Phe Thr Phe Ser Pro Arg Arg His His Trp Thr Thr Gln Asp Cys
                290                 295                 300

Asn Cys Ser Ile Tyr Pro Gly His Ile Thr Gly His Arg Met Ala Trp
305                 310                 315                 320

Asp Met Met Met Asn Trp Ser Pro Thr Thr Ala Leu Val Val Ala Gln
                325                 330                 335

Leu Leu Arg Val Pro Gln Ala Ile Leu Asp Met Ile Ala Gly Ala His
                340                 345                 350

Trp Gly Val Leu Ala Gly Ile Ala Tyr Phe Ser Met Val Gly Asn Trp
                355                 360                 365

Ala Lys Val Leu Val Val Leu Leu Leu Phe Ala Gly Val Asp Ala Thr
                370                 375                 380

Thr His Thr Thr Gly Gly Ala Val Ala His Asn Thr Arg Met Phe Thr
385                 390                 395                 400

Ser Ile Phe Ser Leu Gly Pro Arg Gln Glu Ile Gln Leu Val Asn Thr
                405                 410                 415

Asn Gly Ser Trp His Ile Asn Arg Thr Ala Leu Asn Cys Asn Ala Ser
                420                 425                 430

Leu Glu Thr Gly Trp Ile Ala Gly Leu Leu Tyr Ala Asn Arg Phe Asn
                435                 440                 445

Ser Ser Gly Cys Pro Glu Arg Met Ala Ser Cys Lys Pro Leu Ala Asp

```
                    450                 455                 460

Phe Asp Gln Gly Trp Gly Pro Ile Ser Tyr Ala Asn Gly Ser Gly Pro
        465                 470                 475                 480

Glu His Arg Pro Tyr Cys Trp His Tyr Pro Lys Pro Cys Gly Ile
                        485                 490                 495

Val Pro Ala Gln Asn Val Cys Gly Pro Val Tyr Cys Phe Thr Pro Ser
                        500                 505                 510

Pro Val Val Val Gly Thr Thr Asp Arg Leu Gly Thr Pro Thr Tyr Asp
                    515                 520                 525

Trp Gly Ser Asn Asp Thr Asp Val Phe Val Leu Asn Asn Thr Arg Pro
        530                 535                 540

Pro Ala Gly Asn Trp Phe Gly Cys Thr Trp Met Asn Ser Ser Gly Tyr
        545                 550                 555                 560

Thr Lys Val Cys Gly Ala Pro Pro Cys Val Ile Gly Gly Val Ser Asn
                        565                 570                 575

Asn Thr Leu His Cys Pro Thr Asp Cys Phe Arg Lys His Pro Glu Ala
                        580                 585                 590

Thr Tyr Ser Arg Cys Gly Ser Gly Pro Trp Ile Thr Pro Arg Cys Leu
                    595                 600                 605

Val His Tyr Ala Tyr Arg Leu Trp His Tyr Pro Cys Thr Val Asn Tyr
                    610                 615                 620

Thr Leu Phe Lys Val Arg Met Tyr Val Gly Gly Val Glu His Arg Leu
        625                 630                 635                 640

Glu Val Ala Cys Asn Trp Thr Arg Gly Glu Arg Cys Asn Leu Asp Asp
                        645                 650                 655

Arg Asp Arg Ser Glu Leu Ser Pro Leu Leu Leu Ser Thr Thr Gln Trp
                        660                 665                 670

Gln Val Leu Pro Cys Ser Phe Thr Thr Leu Pro Ala Leu Thr Thr Gly
                    675                 680                 685

Leu Ile His Leu His Gln Asn Ile Val Asp Val Gln Tyr Leu Tyr Gly
                    690                 695                 700

Val Gly Ser Ser Ile Val Ser Trp Ala Val Lys Trp Glu Tyr Val Ile
        705                 710                 715                 720

Leu Leu Phe Leu Leu Leu Ala Asp Ala Arg Ile Cys Ser Cys Leu Trp
                        725                 730                 735

Met Met Leu Leu Ile Ser Gln Ala Glu Ala
                        740                 745

<210> SEQ ID NO 16
<211> LENGTH: 746
<212> TYPE: PRT
<213> ORGANISM: Hepatitis C virus

<400> SEQUENCE: 16

Met Ser Thr Asn Pro Lys Pro Gln Arg Lys Thr Lys Arg Asn Thr Asn
        1               5                   10                  15

Arg Arg Pro Gln Asp Val Lys Phe Pro Gly Gly Gly Gln Ile Val Gly
                        20                  25                  30

Gly Val Tyr Leu Leu Pro Arg Arg Gly Pro Arg Leu Gly Val Arg Ala
                    35                  40                  45

Thr Arg Lys Thr Ser Glu Arg Ser Gln Pro Arg Gly Arg Arg Gln Pro
                50                  55                  60

Ile Pro Lys Ala Arg Gln Pro Glu Gly Arg Ala Trp Ala Gln Pro Gly
        65                  70                  75                  80
```

```
Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala Tyr
            180                 185                 190

Glu Val Arg Asn Val Ser Gly Val Tyr His Val Thr Asn Asp Cys Ser
        195                 200                 205

Asn Ala Ser Ile Val Tyr Glu Ala Ala Asp Met Ile Met His Thr Pro
    210                 215                 220

Gly Cys Val Pro Cys Val Arg Glu Asn Asn Ser Ser Arg Cys Trp Val
225                 230                 235                 240

Ala Leu Thr Pro Thr Leu Ala Ala Arg Asn Ala Ser Val Pro Thr Thr
                245                 250                 255

Thr Ile Arg Arg His Val Asp Leu Leu Val Gly Ala Ala Leu Cys
        260                 265                 270

Ser Ala Met Tyr Val Gly Asp Leu Cys Gly Ser Val Phe Leu Val Ala
        275                 280                 285

Gln Leu Phe Thr Phe Ser Pro Arg Arg His Glu Thr Val Gln Asp Cys
    290                 295                 300

Asn Cys Ser Ile Tyr Pro Gly His Val Thr Gly His Arg Met Ala Trp
305                 310                 315                 320

Asp Met Met Met Asn Trp Ser Pro Thr Ala Ala Leu Val Val Ser Gln
                325                 330                 335

Leu Leu Arg Ile Pro Gln Ala Val Val Asp Met Val Ala Gly Ala His
            340                 345                 350

Trp Gly Val Leu Ala Gly Leu Ala Tyr Tyr Ser Met Val Gly Asn Trp
        355                 360                 365

Ala Lys Val Leu Ile Val Met Leu Leu Phe Ala Gly Val Asp Gly Gly
    370                 375                 380

Thr Tyr Val Thr Gly Gly Thr Met Ala Lys Asn Thr Leu Gly Ile Thr
385                 390                 395                 400

Ser Leu Phe Ser Pro Gly Ser Ser Gln Lys Ile Gln Leu Val Asn Thr
                405                 410                 415

Asn Gly Ser Trp His Ile Asn Arg Thr Ala Leu Asn Cys Asn Asp Ser
            420                 425                 430

Leu Asn Thr Gly Phe Leu Ala Ala Leu Phe Tyr Val His Lys Phe Asn
        435                 440                 445

Ser Ser Gly Cys Pro Glu Arg Met Ala Ser Cys Ser Pro Ile Asp Ala
    450                 455                 460

Phe Ala Gln Gly Trp Gly Pro Ile Thr Tyr Asn Glu Ser His Ser Ser
465                 470                 475                 480

Asp Gln Arg Pro Tyr Cys Trp His Tyr Ala Pro Arg Pro Cys Gly Ile
                485                 490                 495

Val Pro Ala Ala Gln Val Cys Gly Pro Val Tyr Cys Phe Thr Pro Ser
```

```
                500                 505                 510
Pro Val Val Gly Thr Thr Asp Arg Phe Gly Val Pro Thr Tyr Ser
            515                 520                 525

Trp Gly Glu Asn Glu Thr Asp Val Leu Leu Asn Thr Arg Pro
        530                 535                 540

Pro Gln Gly Asn Trp Phe Gly Cys Thr Trp Met Asn Ser Thr Gly Phe
545                 550                 555                 560

Thr Lys Thr Cys Gly Gly Pro Pro Cys Asn Ile Gly Ile Gly Asn
            565                 570                 575

Lys Thr Leu Thr Cys Pro Thr Asp Cys Phe Arg Lys His Pro Glu Ala
        580                 585                 590

Thr Tyr Thr Lys Cys Gly Ser Gly Pro Trp Leu Thr Pro Arg Cys Leu
            595                 600                 605

Val His Tyr Pro Tyr Arg Leu Trp His Tyr Pro Cys Thr Val Asn Phe
        610                 615                 620

Thr Ile Phe Lys Val Arg Met Tyr Val Gly Gly Val Glu His Arg Leu
625                 630                 635                 640

Glu Ala Ala Cys Asn Trp Thr Arg Gly Glu Arg Cys Asn Leu Glu Asp
            645                 650                 655

Arg Asp Arg Ser Glu Leu Ser Pro Leu Leu Leu Ser Thr Thr Glu Trp
        660                 665                 670

Gln Val Leu Pro Cys Ser Phe Thr Thr Leu Pro Ala Leu Ser Thr Gly
        675                 680                 685

Leu Ile His Leu His Gln Asn Val Val Asp Val Gln Tyr Leu Tyr Gly
        690                 695                 700

Ile Gly Ser Ala Val Val Ser Phe Ala Ile Lys Trp Glu Tyr Val Leu
705                 710                 715                 720

Leu Leu Phe Leu Leu Leu Ala Asp Ala Arg Val Cys Ala Cys Leu Trp
            725                 730                 735

Met Met Leu Leu Ile Ala Gln Ala Glu Ala
            740                 745

<210> SEQ ID NO 17
<211> LENGTH: 746
<212> TYPE: PRT
<213> ORGANISM: Hepatitis C virus

<400> SEQUENCE: 17

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Gln Pro Glu Gly Arg Ala Trp Ala Gln Pro Gly
65                  70                  75                  80

Tyr Pro Trp Pro Leu Tyr Gly Asn Glu Gly Met Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125
```

-continued

Gly Phe Ala Asp Leu Met Gly Tyr Ile Pro Leu Val Gly Ala Pro Leu
130                 135                 140

Gly Gly Val Ala Arg Ala Leu Ala His Gly Val Arg Val Val Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala Tyr
                180                 185                 190

Glu Val Arg Asn Val Ser Gly Ile Tyr His Val Thr Asn Asp Cys Ser
                195                 200                 205

Asn Ser Ser Ile Val Tyr Glu Ala Ala Asp Met Ile Met His Thr Pro
210                 215                 220

Gly Cys Val Pro Cys Val Arg Glu Gly Asn Ser Ser Arg Cys Trp Val
225                 230                 235                 240

Ala Leu Thr Pro Thr Leu Ala Ala Arg Asn Ala Ser Val Pro Thr Thr
                245                 250                 255

Ala Ile Arg Arg His Val Asp Leu Leu Val Gly Ala Ala Ala Phe Cys
                260                 265                 270

Ser Ala Met Tyr Val Gly Asp Leu Cys Gly Ser Val Phe Leu Val Ser
                275                 280                 285

Gln Leu Phe Thr Phe Ser Pro Arg Arg His Glu Thr Ile Gln Asp Cys
290                 295                 300

Asn Cys Ser Ile Tyr Pro Gly His Val Ser Gly His Arg Met Ala Trp
305                 310                 315                 320

Asp Met Met Met Asn Trp Ser Pro Thr Thr Ala Leu Val Val Ser Gln
                325                 330                 335

Leu Leu Arg Ile Pro Gln Ala Ile Val Asp Met Val Ala Gly Ala His
                340                 345                 350

Trp Gly Val Leu Ala Gly Leu Ala Tyr Tyr Ser Met Val Gly Asn Trp
                355                 360                 365

Ala Lys Val Leu Ile Val Met Leu Leu Phe Ala Gly Val Asp Gly Glu
370                 375                 380

Thr Arg Val Thr Gly Gly Gln Ile Ala Arg Asn Ala Tyr Ser Leu Thr
385                 390                 395                 400

Thr Leu Phe Ser Ser Gly Ser Ala Gln Asn Ile Gln Leu Ile Asn Thr
                405                 410                 415

Asn Gly Ser Trp His Ile Asn Arg Thr Ala Leu Asn Cys Asn Asp Ser
                420                 425                 430

Leu Asn Thr Gly Phe Leu Ala Ala Leu Phe Tyr Thr His Lys Phe Asn
                435                 440                 445

Ala Ser Gly Cys Pro Glu Arg Leu Ala Ser Cys Arg Pro Ile Asp Lys
450                 455                 460

Phe Asp Gln Gly Trp Gly Pro Ile Thr Tyr Ala Glu Gln Gly Gly Gln
465                 470                 475                 480

Asp Gln Arg Pro Tyr Cys Trp His Tyr Ala Pro Lys Pro Cys Gly Ile
                485                 490                 495

Val Ser Ala Ser Lys Val Cys Gly Pro Val Tyr Cys Phe Thr Pro Ser
                500                 505                 510

Pro Val Val Gly Thr Thr Asp Arg Phe Gly Val Pro Thr Tyr Ser
                515                 520                 525

Trp Gly Glu Asn Glu Thr Asp Val Leu Leu Leu Asn Asn Thr Arg Pro
530                 535                 540

Pro Gln Gly Asn Trp Phe Gly Cys Thr Trp Met Asn Gly Thr Gly Phe

-continued

```
           545                 550                 555                 560
        Thr Lys Thr Cys Gly Gly Pro Pro Cys Asn Ile Gly Gly Gly Asn
                        565                 570                 575

Asn Thr Leu Thr Cys Pro Thr Asp Cys Phe Arg Lys His Pro Ala Ala
                        580                 585                 590

Thr Tyr Thr Lys Cys Gly Ser Gly Pro Trp Leu Thr Pro Arg Cys Leu
                        595                 600                 605

Val Asp Tyr Pro Tyr Arg Leu Trp His Tyr Pro Cys Thr Ala Asn Phe
                610                 615                 620

Thr Ile Phe Lys Val Arg Met Tyr Val Gly Val Glu His Arg Leu
        625                 630                 635                 640

Asp Ala Ala Cys Asn Trp Thr Arg Gly Glu Arg Cys Asn Leu Glu Asp
                        645                 650                 655

Arg Asp Arg Leu Glu Leu Ser Pro Leu Leu Leu Ser Thr Thr Glu Trp
                        660                 665                 670

Gln Val Leu Pro Cys Ser Phe Thr Thr Leu Pro Ala Leu Ser Thr Gly
                        675                 680                 685

Leu Ile His Leu His Gln Asn Ile Val Asp Val Gln Tyr Leu Tyr Gly
                        690                 695                 700

Ile Gly Ser Ala Val Val Ser Phe Ala Ile Lys Trp Asp Tyr Ile Val
        705                 710                 715                 720

Ile Leu Phe Leu Leu Leu Ala Asp Ala Arg Val Cys Ala Cys Leu Trp
                        725                 730                 735

Met Met Leu Leu Ile Ala Gln Ala Glu Ala
                        740                 745

<210> SEQ ID NO 18
<211> LENGTH: 747
<212> TYPE: PRT
<213> ORGANISM: Hepatitis C virus

<400> SEQUENCE: 18

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Ile Arg Lys Thr Ser Glu Arg Ser Gln Pro Arg Gly Arg Arg Gln Pro
        50                  55                  60

Ile Pro Lys Ala Arg Arg Pro Glu Gly Arg Ala Trp Ala Gln Pro Gly
65                  70                  75                  80

Tyr Pro Trp Pro Leu Tyr Gly Asn Glu Gly Met Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Leu Ala Asp Leu Met Gly Tyr Ile Pro Leu Val Gly Gly Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175
```

```
Phe Leu Leu Ala Leu Leu Ser Cys Leu Thr Val Pro Ala Ser Ala His
                180                 185                 190

Glu Val Arg Asn Ala Ser Gly Val Tyr His Val Thr Asn Asp Cys Ser
            195                 200                 205

Asn Ser Ser Ile Val Phe Glu Ala Ala Asp Leu Ile Met His Thr Pro
        210                 215                 220

Gly Cys Val Pro Cys Val Arg Glu Gly Asn Ser Ser Arg Cys Trp Val
225                 230                 235                 240

Ala Leu Thr Pro Thr Leu Ala Ala Arg Asn Ala Thr Ile Pro Thr Thr
                245                 250                 255

Thr Ile Arg His His Val Asp Leu Leu Val Gly Ala Ala Leu Cys
            260                 265                 270

Ser Ala Met Tyr Val Gly Asp Leu Cys Gly Ser Val Phe Leu Val Ser
                275                 280                 285

Gln Leu Phe Thr Phe Ser Pro Arg Arg His Ala Thr Leu Gln Asp Cys
        290                 295                 300

Asn Cys Ser Ile Tyr Pro Gly His Ala Ser Gly His Arg Met Ala Trp
305                 310                 315                 320

Asp Met Met Met Asn Trp Ser Pro Thr Thr Ala Leu Val Val Ser Gln
                325                 330                 335

Leu Leu Arg Ile Pro Gln Ala Val Ile Asp Met Val Ala Gly Ala His
            340                 345                 350

Trp Gly Val Leu Ala Gly Leu Ala Tyr Tyr Ser Met Ala Gly Asn Trp
        355                 360                 365

Ala Lys Val Leu Ile Val Met Leu Leu Phe Ala Gly Val Asp Gly His
370                 375                 380

Thr Leu Thr Thr Gly Gly His Ala Ala Arg Leu Thr Ser Gly Phe Ala
385                 390                 395                 400

Gly Leu Phe Thr Pro Gly Pro Ser Gln Arg Ile Gln Leu Ile Asn Thr
                405                 410                 415

Asn Gly Ser Trp His Ile Asn Arg Thr Ala Leu Asn Cys Asn Asp Ser
            420                 425                 430

Leu Gln Thr Gly Phe Leu Ala Ala Leu Phe Tyr Ala His Arg Phe Asn
        435                 440                 445

Ser Ser Gly Cys Pro Glu Arg Met Ala Ser Cys Arg Ser Ile Asp Lys
450                 455                 460

Phe Asp Gln Gly Trp Gly Pro Ile Thr Tyr Ala Glu Pro Thr Lys Asp
465                 470                 475                 480

Pro Asp Gln Arg Pro Tyr Cys Trp His Tyr Pro Pro Gln Gln Cys Gly
                485                 490                 495

Ile Val Pro Ala Ser Gln Val Cys Gly Pro Val Tyr Cys Phe Thr Pro
            500                 505                 510

Ser Pro Val Val Gly Thr Thr Asp Arg Leu Gly Asn Pro Thr Tyr
        515                 520                 525

Ser Trp Gly Glu Asn Asp Thr Asp Val Leu Leu Leu Asn Asn Thr Arg
            530                 535                 540

Pro Pro Gln Gly Asn Trp Phe Gly Cys Thr Trp Met Asn Ser Thr Gly
545                 550                 555                 560

Phe Thr Lys Thr Cys Gly Ala Pro Pro Cys Asn Ile Gly Gly Val Gly
                565                 570                 575

Asn Asn Thr Leu Thr Cys Pro Thr Asp Cys Phe Arg Lys His Pro Glu
            580                 585                 590

Ala Thr Tyr Ser Lys Cys Gly Ser Gly Pro Trp Leu Thr Pro Arg Cys
```

```
                    595                 600                 605
Met Val Asp Tyr Pro Tyr Arg Leu Trp His Tyr Pro Cys Thr Val Asn
610                 615                 620

Phe Ser Ile Phe Lys Val Arg Met Tyr Val Gly Gly Val Glu His Arg
625                 630                 635                 640

Leu Asn Ala Ala Cys Asn Trp Thr Arg Gly Glu Arg Cys Asn Leu Asp
                645                 650                 655

Asp Arg Asp Arg Ser Glu Leu Ser Pro Leu Leu Leu Ser Thr Thr Glu
                660                 665                 670

Trp Gln Val Leu Pro Cys Ser Phe Thr Thr Leu Pro Ala Leu Ser Thr
                675                 680                 685

Gly Leu Ile His Leu His Gln Asn Ile Val Asp Val Gln Tyr Leu Tyr
                690                 695                 700

Gly Ile Gly Ser Ala Val Val Ser Phe Ala Ile Lys Trp Glu Tyr Val
705                 710                 715                 720

Val Leu Leu Phe Leu Leu Leu Ala Asp Ala Arg Val Cys Ala Cys Leu
                725                 730                 735

Trp Met Met Leu Leu Ile Ala Gln Ala Glu Ala
                740                 745

<210> SEQ ID NO 19
<211> LENGTH: 746
<212> TYPE: PRT
<213> ORGANISM: Hepatitis C virus

<400> SEQUENCE: 19

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
                35                  40                  45

Thr Arg Lys Thr Ser Glu Arg Ser Gln Pro Arg Gly Arg Arg Gln Pro
50                  55                  60

Ile Pro Lys Ala Arg His Pro Glu Gly Arg Thr Trp Ala Gln Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
                115                 120                 125

Gly Phe Ala Asp Leu Met Gly Tyr Ile Pro Leu Val Gly Ala Pro Leu
                130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala Tyr
                180                 185                 190

Glu Val Arg Asn Val Ser Gly Val Tyr His Val Thr Asn Asp Cys Ser
                195                 200                 205

Asn Ser Ser Ile Val Tyr Glu Ala Ala Asp Val Ile Met His Thr Pro
                210                 215                 220
```

Gly Cys Val Pro Cys Val Gln Asp Gly Asn Thr Ser Arg Cys Trp Val
225                 230                 235                 240

Ala Leu Thr Pro Thr Leu Ala Ala Arg Asn Ala Ser Val Pro Val Thr
            245                 250                 255

Ala Ile Arg Arg His Val Asp Leu Leu Val Gly Thr Ala Ala Phe Cys
            260                 265                 270

Ser Ala Met Tyr Val Gly Asp Leu Cys Gly Ser Val Phe Pro Val Ser
            275                 280                 285

Gln Leu Phe Thr Phe Ser Pro Arg Arg His Gln Thr Val Gln Asp Cys
            290                 295                 300

Asn Cys Ser Ile Tyr Pro Gly His Ile Ser Gly His Arg Met Ala Trp
305                 310                 315                 320

Asp Met Met Met Asn Trp Ser Pro Thr Ala Ala Leu Val Val Ser Gln
                325                 330                 335

Leu Leu Arg Ile Pro Gln Ala Ile Val Asp Met Val Ala Gly Ala His
            340                 345                 350

Trp Gly Val Leu Ala Gly Leu Ala Tyr Tyr Ser Met Val Gly Asn Trp
            355                 360                 365

Ala Lys Val Met Ile Val Leu Leu Leu Phe Ala Gly Val Asp Gly Thr
            370                 375                 380

Thr His Thr Thr Gly Gly Ala Ala Ala Arg Ala Thr Gln Gly Phe Thr
385                 390                 395                 400

Ser Phe Phe Ser Leu Gly Pro Ser Gln Lys Ile Gln Leu Ile Asn Thr
                405                 410                 415

Asn Gly Ser Trp His Ile Asn Arg Thr Ala Leu Asn Cys Asn Asp Ser
            420                 425                 430

Leu Gln Thr Gly Phe Leu Ala Ala Leu Phe Tyr Thr Tyr Arg Phe Asn
            435                 440                 445

Ala Ser Gly Cys Pro Glu Arg Met Ala Ser Cys Arg Pro Ile Asp Lys
450                 455                 460

Phe Asp Gln Gly Trp Gly Pro Ile Thr Tyr Ala Glu Pro Asp Ser Ser
465                 470                 475                 480

Asp Gln Arg Pro Tyr Cys Trp His Tyr Ala Pro Arg Pro Cys Gly Ile
            485                 490                 495

Val Pro Ala Ser Gln Val Cys Gly Pro Val Tyr Cys Phe Thr Pro Ser
            500                 505                 510

Pro Val Val Val Gly Thr Thr Asp Arg Phe Gly Val Pro Thr Tyr Thr
        515                 520                 525

Trp Gly Glu Asn Glu Thr Asp Val Leu Leu Leu Asn Asn Thr Arg Pro
530                 535                 540

Pro Leu Gly Asn Trp Phe Gly Cys Thr Trp Met Asn Ser Thr Gly Phe
545                 550                 555                 560

Thr Lys Thr Cys Gly Gly Pro Pro Cys Asn Ile Gly Gly Ala Gly Asn
            565                 570                 575

Thr Thr Leu Thr Cys Pro Thr Asp Cys Phe Arg Lys His Pro Glu Ala
            580                 585                 590

Thr Tyr Thr Lys Cys Gly Ser Gly Pro Trp Leu Thr Pro Arg Cys Leu
            595                 600                 605

Val Asp Tyr Pro Tyr Arg Leu Trp His Tyr Pro Cys Ala Val Asn Phe
            610                 615                 620

Thr Ile Phe Lys Val Arg Met Tyr Val Gly Gly Val Glu His Arg Leu
625                 630                 635                 640

Asn Ala Ala Cys Asn Trp Thr Arg Gly Glu Arg Cys Asp Leu Glu Asp

```
                     645                 650                 655
Arg Asp Arg Ser Glu Leu Ser Pro Leu Leu Ser Thr Thr Glu Trp
                660                 665                 670

Gln Val Leu Pro Cys Ser Phe Thr Thr Leu Pro Ala Leu Ser Thr Gly
            675                 680                 685

Leu Ile His Leu His Gln Asn Ile Val Asp Val Gln Tyr Leu Tyr Gly
        690                 695                 700

Ile Gly Ser Ala Val Ile Pro Phe Ala Ile Lys Trp Glu Tyr Val Leu
705                 710                 715                 720

Leu Leu Phe Leu Leu Leu Ala Asp Ala Arg Val Cys Ala Cys Leu Trp
                725                 730                 735

Met Met Leu Leu Ile Ala Gln Ala Glu Ala
                740                 745

<210> SEQ ID NO 20
<211> LENGTH: 746
<212> TYPE: PRT
<213> ORGANISM: Hepatitis C virus

<400> SEQUENCE: 20

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Met Gly Trp Ala Gly Trp
                85                  90                  95

Leu Leu Ser Pro Arg Gly Ser Arg Pro Asn Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Thr Pro Ala Ser Ala Tyr
            180                 185                 190

Glu Val Arg Asn Val Ser Gly Ile Tyr His Val Thr Asn Asp Cys Ser
        195                 200                 205

Asn Ser Ser Ile Val Tyr Glu Ala Ala Asp Ile Ile Met His Thr Pro
    210                 215                 220

Gly Cys Val Pro Cys Val Arg Glu Lys Asn Ile Ser Arg Cys Trp Val
225                 230                 235                 240

Ala Leu Thr Pro Thr Leu Ala Ala Arg Asn Ile Ser Val Pro Thr Ala
                245                 250                 255

Thr Ile Arg Arg His Val Asp Leu Leu Val Gly Thr Ala Ala Phe Cys
            260                 265                 270
```

```
Ser Ala Met Tyr Val Gly Asp Leu Cys Gly Ser Val Phe Leu Val Ser
            275                 280                 285
Gln Leu Phe Thr Phe Ser Pro Arg Trp His Glu Thr Val Gln Asp Cys
290                 295                 300
Asn Cys Ser Leu Tyr Pro Gly His Val Ser Gly His Arg Met Ala Trp
305                 310                 315                 320
Asp Met Met Met Asn Trp Ser Pro Thr Ala Leu Val Val Ser Gln
                325                 330                 335
Leu Leu Arg Ile Pro Gln Ala Val Val Asp Met Val Ala Gly Ala His
            340                 345                 350
Trp Gly Val Leu Ala Gly Leu Ala Tyr Tyr Ser Met Ile Gly Asn Trp
        355                 360                 365
Ala Lys Val Leu Ile Val Met Leu Leu Phe Ala Gly Ala Asp Gly Thr
    370                 375                 380
Thr His Val Thr Gly Gly Val Gln Ala His Gly Ala Tyr Gly Leu Ala
385                 390                 395                 400
Ser Leu Phe Asn Val Gly Pro His Gln Lys Ile Gln Leu Val Asn Thr
                405                 410                 415
Asn Gly Ser Trp His Ile Asn Arg Thr Ala Leu Asn Cys Asn Asp Thr
            420                 425                 430
Leu Gln Thr Gly Phe Leu Ala Ala Leu Phe Tyr Lys His Arg Phe Asn
        435                 440                 445
Ala Ser Gly Cys Pro Glu Arg Met Ala Ser Cys Arg Pro Ile Asp Lys
    450                 455                 460
Phe Ala Gln Gly Trp Gly Pro Ile Thr Tyr Ala Glu Pro Asp Arg Leu
465                 470                 475                 480
Asp Gln Arg Pro Tyr Cys Trp His Tyr Pro Pro Arg Pro Cys Gly Ile
                485                 490                 495
Val Pro Ala Leu Glu Val Cys Gly Pro Val Tyr Cys Phe Thr Pro Ser
            500                 505                 510
Pro Val Val Val Gly Thr Thr Asp Arg Phe Gly Val Pro Thr Tyr Ser
        515                 520                 525
Trp Gly Glu Asn Glu Thr Asp Val Leu Leu Leu Asn Asn Thr Arg Pro
    530                 535                 540
Pro Gln Gly Asn Trp Phe Gly Cys Thr Trp Met Asn Ser Thr Gly Tyr
545                 550                 555                 560
Thr Lys Thr Cys Gly Pro Pro Cys Asn Ile Gly Gly Val Gly Asn
                565                 570                 575
Asn Thr Leu Thr Cys Pro Thr Asp Cys Phe Arg Lys His Pro Glu Ala
            580                 585                 590
Thr Tyr Thr Lys Cys Gly Ser Gly Pro Trp Leu Thr Pro Arg Cys Leu
        595                 600                 605
Val His Tyr Pro Tyr Arg Leu Trp His Tyr Pro Cys Thr Val Asn Phe
    610                 615                 620
Thr Ile Phe Lys Val Arg Met Tyr Val Gly Gly Ile Glu His Arg Leu
625                 630                 635                 640
Asp Ala Ala Cys Asn Trp Thr Arg Gly Glu Arg Cys Asp Leu Glu Asp
                645                 650                 655
Arg Asp Arg Ser Glu Leu Ser Pro Leu Leu Leu Ser Thr Thr Glu Trp
            660                 665                 670
Gln Ile Leu Pro Cys Ser Phe Thr Thr Leu Pro Ala Leu Ser Thr Gly
        675                 680                 685
Leu Ile His Leu His Arg Asn Ile Val Asp Val Gln Tyr Leu Tyr Gly
```

```
                690             695             700
Ile Gly Ser Ala Val Val Ser Phe Ala Ile Lys Trp Glu Tyr Val Leu
705                 710             715                 720

Leu Leu Phe Leu Leu Leu Ala Asp Ala Arg Val Cys Ala Cys Leu Trp
                725             730             735

Met Met Leu Leu Ile Ala Gln Ala Glu Ala
                740             745

<210> SEQ ID NO 21
<211> LENGTH: 746
<212> TYPE: PRT
<213> ORGANISM: Hepatitis C virus

<400> SEQUENCE: 21

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Asn Asp Pro
                100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
        130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala Tyr
                180                 185                 190

Glu Val Arg Asn Val Ser Gly Ile Tyr His Val Thr Asn Asp Cys Ser
            195                 200                 205

Asn Ser Ser Ile Val Tyr Glu Ala Ala Asp Val Ile Met His Ala Pro
210                 215                 220

Gly Cys Val Pro Cys Val Arg Glu Asn Asn Ser Ser Arg Cys Trp Val
225                 230                 235                 240

Ala Leu Thr Pro Thr Leu Ala Ala Arg Asn Ala Ser Val Pro Thr Thr
                245                 250                 255

Thr Leu Arg Arg His Val Asp Leu Leu Val Gly Thr Ala Ala Phe Cys
            260                 265                 270

Ser Ala Met Tyr Val Gly Asp Leu Cys Gly Ser Val Phe Leu Ile Ser
        275                 280                 285

Gln Leu Phe Thr Phe Ser Pro Arg Arg His Glu Thr Val Gln Asp Cys
    290                 295                 300

Asn Cys Ser Ile Tyr Pro Gly His Val Ser Gly His Arg Met Ala Trp
305                 310                 315                 320
```

```
Asp Met Met Met Asn Trp Ser Pro Thr Ala Leu Val Val Ser Gln
                325                 330                 335

Leu Leu Arg Ile Pro Gln Ala Val Met Asp Met Val Ala Gly Ala His
            340                 345                 350

Trp Gly Val Leu Ala Gly Leu Ala Tyr Tyr Ser Met Val Gly Asn Trp
                355                 360                 365

Ala Lys Val Leu Ile Val Met Leu Leu Phe Ala Gly Val Asp Gly His
    370                 375                 380

Thr Arg Val Thr Gly Val Gln Gly His Val Thr Ser Thr Leu Thr
385                 390                 395                 400

Ser Leu Phe Arg Pro Gly Ala Ser Gln Lys Ile Gln Leu Val Asn Thr
                405                 410                 415

Asn Gly Ser Trp His Ile Asn Arg Thr Ala Leu Asn Cys Asn Asp Ser
                420                 425                 430

Leu Lys Thr Gly Phe Leu Ala Ala Leu Phe Tyr Thr His Lys Phe Asn
            435                 440                 445

Ala Ser Gly Cys Pro Glu Arg Met Ala Ser Cys Arg Ser Ile Asp Lys
    450                 455                 460

Phe Asp Gln Gly Trp Gly Pro Ile Thr Tyr Ala Gln Pro Asp Asn Ser
465                 470                 475                 480

Asp Gln Arg Pro Tyr Cys Trp His Tyr Ala Pro Arg Gln Cys Gly Ile
                485                 490                 495

Val Pro Ala Ser Gln Val Cys Gly Pro Val Tyr Cys Phe Thr Pro Ser
                500                 505                 510

Pro Val Val Val Gly Thr Thr Asp Arg Phe Gly Ala Pro Thr Tyr Asn
            515                 520                 525

Trp Gly Asp Asn Glu Thr Asp Val Leu Leu Leu Asn Asn Thr Arg Pro
530                 535                 540

Pro His Gly Asn Trp Phe Gly Cys Thr Trp Met Asn Ser Thr Gly Phe
545                 550                 555                 560

Thr Lys Thr Cys Gly Gly Pro Pro Cys Asn Ile Arg Gly Val Gly Asn
                565                 570                 575

Asn Thr Leu Thr Cys Pro Thr Asp Cys Phe Arg Lys His Pro Asp Ala
            580                 585                 590

Thr Tyr Thr Lys Cys Gly Ser Gly Pro Trp Leu Thr Pro Arg Cys Leu
    595                 600                 605

Val Asp Tyr Pro Tyr Arg Leu Trp His Tyr Pro Cys Thr Val Asn Phe
            610                 615                 620

Thr Ile Phe Lys Val Arg Met Tyr Val Gly Gly Val Glu His Arg Leu
625                 630                 635                 640

Asp Ala Ala Cys Asn Trp Thr Arg Gly Glu Arg Cys Asp Leu Glu Asp
                645                 650                 655

Arg Asp Arg Ala Glu Leu Ser Pro Leu Leu Leu Ser Thr Thr Glu Trp
                660                 665                 670

Gln Ile Leu Pro Cys Ser Tyr Thr Thr Leu Pro Ala Leu Ser Thr Gly
            675                 680                 685

Leu Ile His Leu His Gln Asn Ile Val Asp Ile Gln Tyr Leu Tyr Gly
    690                 695                 700

Ile Gly Ser Ala Val Val Ser Ile Ala Ile Lys Trp Glu Tyr Val Val
705                 710                 715                 720

Leu Leu Phe Leu Leu Leu Ala Asp Ala Arg Val Cys Ala Cys Leu Trp
                725                 730                 735

Met Met Leu Leu Ile Ala Gln Ala Glu Ala
```

```
                        740                 745

<210> SEQ ID NO 22
<211> LENGTH: 746
<212> TYPE: PRT
<213> ORGANISM: Hepatitis C virus

<400> SEQUENCE: 22

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asp Glu Gly Met Gly Trp Ala Gly Trp
                85                  90                  95

Leu Leu Ser Pro Arg Gly Ser Arg Pro Asn Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Thr Pro Ala Ser Ala Tyr
            180                 185                 190

Glu Val Arg Asn Val Ser Gly Ile Tyr His Val Thr Asn Asp Cys Ser
        195                 200                 205

Asn Ser Ser Ile Val Tyr Glu Ala Ala Asp Ile Ile Met His Thr Pro
    210                 215                 220

Gly Cys Val Pro Cys Val Arg Glu Lys Asn Thr Ser Arg Cys Trp Val
225                 230                 235                 240

Ala Leu Thr Pro Thr Leu Ala Ala Arg Asn Ile Ser Val Pro Thr Thr
                245                 250                 255

Thr Ile Arg Arg His Val Asp Leu Leu Val Gly Thr Ala Ala Phe Cys
            260                 265                 270

Ser Ala Met Tyr Val Gly Asp Leu Cys Gly Ser Val Phe Leu Val Ser
        275                 280                 285

Gln Leu Phe Thr Phe Ser Pro Arg Arg His Glu Thr Val Gln Asp Cys
    290                 295                 300

Asn Cys Ser Leu Tyr Pro Gly His Val Ser Gly His Arg Met Ala Trp
305                 310                 315                 320

Asp Met Met Met Asn Trp Ser Pro Thr Ala Ala Leu Val Val Ser Gln
                325                 330                 335

Leu Leu Arg Ile Pro Gln Ala Ile Val Asp Met Val Ala Gly Ala His
            340                 345                 350

Trp Gly Val Leu Ala Gly Leu Ala Tyr Tyr Ser Met Val Gly Asn Trp
        355                 360                 365
```

```
Ala Lys Val Leu Ile Val Met Leu Leu Phe Ala Gly Ala Asp Gly Thr
    370                 375                 380
Thr His Val Thr Gly Gly Val Gln Ala His Gly Ala Tyr Gly Leu Ala
385                 390                 395                 400
Ser Leu Phe Asn Val Gly Pro His Gln Lys Ile Gln Leu Val Asn Thr
                405                 410                 415
Asn Gly Ser Trp His Ile Asn Arg Thr Ala Leu Asn Cys Asn Asp Thr
                420                 425                 430
Leu Gln Thr Gly Phe Leu Ala Ala Leu Phe Tyr Lys His Arg Phe Asn
            435                 440                 445
Ala Ser Gly Cys Pro Glu Arg Met Ala Ser Cys Arg Pro Ile Asp Lys
    450                 455                 460
Phe Ala Gln Gly Trp Gly Pro Ile Thr Tyr Ala Glu Pro Asp Arg Leu
465                 470                 475                 480
Asp Gln Arg Pro Tyr Cys Trp His Tyr Pro Arg Pro Cys Gly Ile
                485                 490                 495
Val Pro Ala Leu Glu Val Cys Gly Pro Val Tyr Cys Phe Thr Pro Ser
                500                 505                 510
Pro Val Val Gly Thr Thr Asp Arg Phe Gly Val Pro Thr Tyr Ser
    515                 520                 525
Trp Gly Glu Asn Glu Thr Asp Val Leu Leu Leu Asn Asn Thr Arg Pro
    530                 535                 540
Pro Gln Gly Asn Trp Phe Gly Cys Thr Trp Met Asn Asn Thr Gly Phe
545                 550                 555                 560
Thr Lys Thr Cys Gly Gly Pro Pro Cys Asn Ile Gly Gly Val Gly Asn
                565                 570                 575
Asn Thr Leu Thr Cys Pro Thr Asp Cys Phe Arg Lys His Pro Glu Ala
            580                 585                 590
Thr Tyr Thr Lys Cys Gly Ser Gly Pro Trp Leu Thr Pro Arg Cys Leu
        595                 600                 605
Val Asp Tyr Pro Tyr Arg Leu Trp His Tyr Pro Cys Thr Val Asn Phe
    610                 615                 620
Thr Val Phe Lys Val Arg Met Tyr Val Gly Gly Ile Glu His Arg Leu
625                 630                 635                 640
Asp Ala Ala Cys Asn Trp Thr Arg Gly Glu Arg Cys Asp Leu Glu Asp
                645                 650                 655
Arg Asp Arg Ser Glu Leu Ser Pro Leu Leu Leu Ser Thr Thr Glu Trp
            660                 665                 670
Gln Ile Leu Pro Cys Ser Phe Thr Thr Leu Pro Ala Leu Ser Thr Gly
        675                 680                 685
Leu Ile His Leu His Arg Asn Ile Val Asp Val Gln Tyr Leu Tyr Gly
    690                 695                 700
Ile Gly Ser Ala Val Val Ser Phe Ala Ile Lys Trp Glu Tyr Ile Leu
705                 710                 715                 720
Leu Leu Phe Leu Leu Leu Ala Asp Ala Arg Val Cys Ala Cys Leu Trp
                725                 730                 735
Met Met Leu Leu Ile Ala Gln Ala Glu Ala
            740                 745

<210> SEQ ID NO 23
<211> LENGTH: 746
<212> TYPE: PRT
<213> ORGANISM: Hepatitis C virus

<400> SEQUENCE: 23
```

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gln Ile Val Gly
            20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
    50                  55                  60

Ile Pro Lys Ala Arg Gln Pro Glu Gly Arg Ala Trp Ala Gln Pro Gly
65              70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
            130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala Tyr
                180                 185                 190

Glu Val Arg Asn Val Ser Gly Val Tyr His Val Thr Asn Asp Cys Ser
            195                 200                 205

Asn Ser Ser Ile Val Tyr Glu Ala Ala Asp Met Ile Met His Thr Pro
210                 215                 220

Gly Cys Val Pro Cys Val Arg Glu Asp Asn Ser Ser Arg Cys Trp Val
225                 230                 235                 240

Ala Leu Thr Pro Thr Leu Ala Ala Arg Asn Ser Ser Val Pro Thr Thr
                245                 250                 255

Thr Ile Arg Arg His Val Asp Leu Leu Val Gly Ala Ala Ala Phe Cys
            260                 265                 270

Ser Ala Met Tyr Val Gly Asp Leu Cys Gly Ser Val Phe Leu Ile Ser
            275                 280                 285

Gln Leu Phe Thr Phe Ser Pro Arg Arg Tyr Glu Thr Val Gln Asp Cys
    290                 295                 300

Asn Cys Ser Leu Tyr Pro Gly His Val Ser Gly His Arg Met Ala Trp
305                 310                 315                 320

Asp Met Met Met Asn Trp Ser Pro Thr Thr Ala Leu Val Val Ser Gln
                325                 330                 335

Leu Leu Arg Ile Pro Gln Ala Val Val Asp Met Val Ala Gly Ala His
            340                 345                 350

Trp Gly Val Leu Ala Gly Leu Ala Tyr Tyr Ser Met Val Gly Asn Trp
            355                 360                 365

Ala Lys Val Leu Ile Val Met Leu Leu Phe Ala Gly Val Asp Gly Asn
            370                 375                 380

Thr Arg Val Ser Gly Gly Glu Ala Ala Lys Asn Thr Met Gly Phe Ala
385                 390                 395                 400

Ser Leu Phe Val Ser Gly Pro Ser Gln Lys Ile Gln Leu Ile Asn Thr
                405                 410                 415
```

-continued

```
Asn Gly Ser Trp His Ile Asn Arg Thr Ala Leu Asn Cys Asp Asp Ser
            420                 425                 430

Leu His Thr Gly Phe Leu Ala Ala Leu Phe Tyr Ala His Lys Phe Asn
        435                 440                 445

Ser Ser Gly Cys Ser Gly Arg Met Ala Ser Cys Arg Pro Ile Asp Glu
    450                 455                 460

Phe Ala Gln Gly Trp Gly Pro Ile Thr His Gly Val Pro Asp Asn Leu
465                 470                 475                 480

Asp Gln Arg Pro Tyr Cys Trp His Tyr Ala Pro Arg Pro Cys Gly Ile
                485                 490                 495

Val Pro Ala Ser Gln Val Cys Gly Pro Val Tyr Cys Phe Thr Pro Ser
            500                 505                 510

Pro Val Val Val Gly Thr Thr Asp Arg Phe Gly Ala Pro Thr Tyr Ser
        515                 520                 525

Trp Gly Glu Asn Glu Thr Asp Val Leu Leu Leu Asn Asn Thr Arg Pro
    530                 535                 540

Pro Gln Gly Asn Trp Phe Gly Cys Thr Trp Met Asn Ser Thr Gly Phe
545                 550                 555                 560

Thr Lys Thr Cys Gly Gly Pro Pro Cys Asn Ile Gly Gly Val Gly Asn
                565                 570                 575

Asn Thr Leu Thr Cys Pro Thr Asp Cys Phe Arg Lys His Pro Glu Ala
            580                 585                 590

Thr Tyr Thr Lys Cys Gly Ser Gly Pro Trp Leu Thr Pro Arg Cys Met
        595                 600                 605

Val Asp Tyr Pro Tyr Arg Leu Trp His Tyr Pro Cys Thr Val Asn Phe
    610                 615                 620

Thr Ile Phe Lys Val Arg Met Tyr Val Gly Gly Val Glu His Arg Leu
625                 630                 635                 640

Asp Ala Ala Cys Asn Trp Thr Arg Gly Glu Arg Cys Asn Val Glu Asp
                645                 650                 655

Arg Asp Arg Ser Glu Leu Ser Pro Leu Leu Leu Ser Thr Thr Glu Trp
            660                 665                 670

Gln Ile Leu Pro Cys Ser Phe Thr Thr Leu Pro Ala Leu Ser Thr Gly
        675                 680                 685

Leu Ile His Leu His Gln Asn Ile Val Asp Val Gln Tyr Leu Tyr Gly
    690                 695                 700

Val Gly Ser Val Val Ser Val Val Ile Arg Trp Glu Tyr Val Val
705                 710                 715                 720

Leu Leu Phe Leu Leu Leu Ala Asp Ala Arg Val Cys Ala Cys Leu Trp
                725                 730                 735

Met Met Leu Leu Ile Ala Gln Ala Glu Ala
            740                 745

<210> SEQ ID NO 24
<211> LENGTH: 746
<212> TYPE: PRT
<213> ORGANISM: Hepatitis C virus

<400> SEQUENCE: 24

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45
```

```
Thr Arg Lys Thr Ser Glu Arg Ser Gln Pro Arg Gly Arg Gln Pro
    50                  55                  60

Ile Pro Lys Ala Arg Gln Pro Glu Gly Arg Ala Trp Ala Gln Pro Gly
65                  70                  75                  80

Tyr Pro Trp Pro Leu Tyr Gly Asn Glu Gly Met Gly Trp Ala Gly Trp
                85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala Tyr
                180                 185                 190

Glu Val Arg Asn Val Ser Gly Met Tyr His Val Thr Asn Asp Cys Ser
            195                 200                 205

Asn Ser Ser Ile Val Tyr Glu Ala Ala Asp Met Ile Leu His Ala Pro
    210                 215                 220

Gly Cys Val Pro Cys Val Arg Glu Asn Asn Ser Ser Arg Cys Trp Val
225                 230                 235                 240

Ala Leu Thr Pro Thr Leu Ala Ala Arg Asn Ala Ser Val Pro Thr Thr
                245                 250                 255

Ala Ile Arg Arg His Val Asp Leu Leu Val Gly Ala Ala Ala Phe Cys
            260                 265                 270

Ser Ala Met Tyr Val Gly Asp Leu Cys Gly Ser Val Leu Leu Val Ser
    275                 280                 285

Gln Ile Phe Thr Phe Ser Pro Arg Arg His Glu Thr Met Gln Asp Cys
290                 295                 300

Asn Cys Ser Ile Tyr Pro Gly His Ile Thr Gly His Arg Met Ala Trp
305                 310                 315                 320

Asp Met Met Met Asn Trp Ser Pro Thr Thr Ala Leu Val Val Ser Gln
                325                 330                 335

Leu Leu Arg Ile Pro Gln Ala Ile Val Asp Met Val Ala Gly Ala His
            340                 345                 350

Trp Gly Val Leu Ala Gly Leu Ala Tyr Tyr Ser Met Val Gly Asn Trp
    355                 360                 365

Ala Lys Val Leu Ile Val Met Leu Leu Phe Ala Gly Val Asp Gly Gly
    370                 375                 380

Thr Tyr Val Thr Gly Gly Glu Ala Gly Arg Arg Thr Ser Gly Phe Ala
385                 390                 395                 400

Ser Ile Phe Thr Pro Gly Ala Ser Gln Asn Ile Gln Leu Ile Asn Thr
                405                 410                 415

Asn Gly Ser Trp His Ile Asn Arg Thr Ala Leu Asn Cys Asn Asp Ser
            420                 425                 430

Leu His Thr Gly Phe Ile Ala Ala Leu Phe Tyr His His Lys Phe Asn
    435                 440                 445

Ala Ser Gly Cys Pro Glu Arg Met Ala Ser Cys Arg Pro Ile Gly Glu
450                 455                 460
```

-continued

```
Phe Ala Gln Gly Trp Gly Pro Ile Ser Tyr Thr Glu Pro Pro Ser Ser
465                 470                 475                 480

Asp Gln Arg Pro Tyr Cys Trp His Tyr Pro Arg Pro Cys Gly Ile
            485                 490                 495

Val Pro Ala Ser Gln Val Cys Gly Pro Val Tyr Cys Phe Thr Pro Ser
            500                 505                 510

Pro Val Val Val Gly Thr Thr Asp Arg Leu Gly Ala Pro Thr Tyr Asn
            515                 520                 525

Trp Gly Asp Asn Asp Thr Asp Val Leu Leu Asn Asn Thr Arg Pro
    530                 535                 540

Pro Gln Gly Asn Trp Phe Gly Cys Thr Trp Met Asn Gly Thr Gly Phe
545                 550                 555                 560

Thr Lys Thr Cys Gly Gly Pro Pro Cys Asn Ile Gly Gly Val Gly Asn
                565                 570                 575

Asn Thr Leu Thr Cys Pro Thr Asp Cys Phe Arg Lys His Pro Glu Ala
            580                 585                 590

Thr Tyr Thr Lys Cys Gly Ser Gly Pro Trp Leu Thr Pro Arg Cys Ile
            595                 600                 605

Val Asp Tyr Pro Tyr Arg Leu Trp His Tyr Pro Cys Thr Val Asn Phe
610                 615                 620

Thr Ile Thr Lys Ile Arg Met Tyr Val Gly Gly Val Glu His Arg Leu
625                 630                 635                 640

Thr Ala Ala Cys Asn Trp Thr Arg Gly Glu Arg Cys Asp Leu Glu Asp
                645                 650                 655

Arg Asp Arg Ser Glu Leu Ser Pro Leu Leu Leu Ser Thr Thr Glu Trp
            660                 665                 670

Gln Ile Met Pro Cys Ser Phe Thr Thr Leu Pro Ala Leu Ser Thr Gly
            675                 680                 685

Leu Ile His Leu His Gln Asn Ile Val Asp Ile Gln Tyr Leu Tyr Gly
            690                 695                 700

Ile Gly Ser Ala Ala Val Ser Phe Ala Ile Arg Trp Glu Tyr Val Leu
705                 710                 715                 720

Leu Leu Phe Leu Leu Leu Ala Asp Ala Arg Val Cys Ala Cys Leu Trp
                725                 730                 735

Met Met Leu Leu Ile Ala Gln Ala Glu Ala
                740                 745

<210> SEQ ID NO 25
<211> LENGTH: 746
<212> TYPE: PRT
<213> ORGANISM: Hepatitis C virus

<400> SEQUENCE: 25

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Gln Pro Glu Gly Arg Ala Trp Ala Gln Pro Gly
65                  70                  75                  80

Tyr Pro Trp Pro Leu Tyr Gly Asn Glu Gly Met Gly Trp Ala Gly Trp
                85                  90                  95
```

-continued

```
Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala Tyr
            180                 185                 190

Glu Val Arg Asn Val Ser Gly Met Tyr His Val Thr Asn Asp Cys Ser
        195                 200                 205

Asn Ser Ser Ile Val Tyr Glu Ala Ala Asp Met Ile Leu His Ala Pro
    210                 215                 220

Gly Cys Val Pro Cys Val Arg Glu Asn Asn Ser Ser Arg Cys Trp Val
225                 230                 235                 240

Ala Leu Thr Pro Thr Leu Ala Ala Arg Asn Ala Ser Val Pro Thr Thr
                245                 250                 255

Ala Ile Arg Arg His Val Asp Leu Leu Val Gly Ala Ala Ala Phe Cys
            260                 265                 270

Ser Ala Met Tyr Val Gly Asp Leu Cys Gly Ser Val Leu Leu Val Ser
        275                 280                 285

Gln Ile Phe Thr Phe Ser Pro Arg Arg His Glu Thr Met Gln Asp Cys
    290                 295                 300

Asn Cys Ser Ile Tyr Pro Gly His Ile Thr Gly His Arg Met Ala Trp
305                 310                 315                 320

Asp Met Met Met Asn Trp Ser Pro Thr Thr Ala Leu Val Val Ser Gln
                325                 330                 335

Leu Leu Arg Ile Pro Gln Ala Ile Val Asp Met Val Ala Gly Ala His
            340                 345                 350

Trp Gly Val Leu Ala Gly Leu Ala Tyr Tyr Ser Met Val Gly Asn Trp
        355                 360                 365

Ala Lys Val Leu Ile Val Met Leu Leu Phe Ala Gly Val Asp Gly Gly
    370                 375                 380

Thr Tyr Val Thr Gly Gly Glu Ala Gly Arg Arg Thr Ser Gly Phe Ala
385                 390                 395                 400

Ser Ile Phe Thr Pro Gly Ala Ser Gln Asn Ile Gln Leu Ile Asn Thr
                405                 410                 415

Asn Gly Ser Trp His Ile Asn Arg Thr Ala Leu Asn Cys Asn Asp Ser
            420                 425                 430

Leu His Thr Gly Phe Ile Ala Ala Leu Phe Tyr His His Lys Phe Asn
        435                 440                 445

Ala Ser Gly Cys Pro Glu Arg Met Ala Ser Cys Arg Pro Ile Gly Glu
    450                 455                 460

Phe Ala Gln Gly Trp Gly Pro Ile Ser Tyr Thr Glu Pro Pro Ser Ser
465                 470                 475                 480

Asp Gln Arg Pro Tyr Cys Trp His Tyr Pro Arg Pro Cys Gly Ile
                485                 490                 495

Val Pro Ala Ser Gln Val Cys Gly Pro Val Tyr Cys Phe Thr Pro Ser
            500                 505                 510
```

Pro Val Val Gly Thr Thr Asp Arg Leu Gly Ala Pro Thr Tyr Asn
                515                 520                 525

Trp Gly Asp Asn Asp Thr Asp Val Leu Leu Asn Asn Thr Arg Pro
            530                 535                 540

Pro Gln Gly Asn Trp Phe Gly Cys Thr Trp Met Asn Gly Thr Gly Phe
545                 550                 555                 560

Thr Lys Thr Cys Gly Gly Pro Pro Cys Asn Ile Gly Gly Val Gly Asn
                565                 570                 575

Asn Thr Leu Thr Cys Pro Thr Asp Cys Phe Arg Lys His Pro Glu Ala
                580                 585                 590

Thr Tyr Thr Lys Cys Gly Ser Gly Pro Trp Leu Thr Pro Arg Cys Ile
                595                 600                 605

Val Asp Tyr Pro Tyr Arg Leu Trp His Tyr Pro Cys Thr Val Asn Phe
610                 615                 620

Thr Ile Thr Lys Ile Arg Met Tyr Val Gly Val Glu His Arg Leu
625                 630                 635                 640

Thr Ala Ala Cys Asn Trp Thr Arg Gly Glu Arg Cys Asp Leu Glu Asp
                645                 650                 655

Arg Asp Arg Ser Glu Leu Ser Pro Leu Leu Leu Ser Thr Thr Glu Trp
                660                 665                 670

Gln Ile Met Pro Cys Ser Phe Thr Thr Leu Pro Ala Leu Ser Thr Gly
                675                 680                 685

Leu Ile His Leu His Gln Asn Ile Val Asp Ile Gln Tyr Leu Tyr Gly
                690                 695                 700

Ile Gly Ser Ala Ala Val Ser Phe Ala Ile Arg Trp Glu Tyr Val Leu
705                 710                 715                 720

Leu Leu Phe Leu Leu Leu Ala Asp Ala Arg Val Cys Ala Cys Leu Trp
                725                 730                 735

Met Met Leu Leu Ile Ala Gln Ala Glu Ala
                740                 745

<210> SEQ ID NO 26
<211> LENGTH: 746
<212> TYPE: PRT
<213> ORGANISM: Hepatitis C virus

<400> SEQUENCE: 26

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
                35                  40                  45

Thr Arg Lys Thr Ser Glu Arg Ser Gln Pro Arg Gly Arg Arg Gln Pro
                50                  55                  60

Ile Pro Lys Ala Arg Arg Pro Glu Gly Arg Ala Trp Ala Gln Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
                115                 120                 125

Gly Phe Ala Asp Leu Met Gly Tyr Ile Pro Leu Val Gly Ala Pro Leu
                130                 135                 140

```
Gly Gly Thr Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
            165                 170                 175

Phe Leu Leu Ala Leu Leu Ser Cys Leu Thr Ile Pro Ala Ser Ala Tyr
                180                 185                 190

Glu Val Arg Asn Val Ser Gly Val Tyr His Val Thr Asn Asp Cys Ser
            195                 200                 205

Asn Ser Ser Ile Val Tyr Glu Thr Ala Asp Met Ile Met His Thr Pro
        210                 215                 220

Gly Cys Val Pro Cys Val Arg Glu Asp Asn Phe Thr Arg Cys Trp Val
225                 230                 235                 240

Ala Leu Thr Pro Thr Leu Ala Ala Arg Asn Gly Ser Val Pro Thr Thr
                245                 250                 255

Ala Ile Arg Arg His Val Asp Leu Leu Val Gly Ala Ala Ala Phe Cys
            260                 265                 270

Ser Ala Met Tyr Val Gly Asp Leu Cys Gly Ser Val Phe Leu Val Ser
                275                 280                 285

Gln Leu Phe Thr Phe Ser Pro Arg Trp His Glu Thr Val Gln Glu Cys
            290                 295                 300

Asn Cys Ser Ile Tyr Pro Gly His Val Thr Gly His Arg Met Ala Trp
305                 310                 315                 320

Asp Met Met Met Asn Trp Ser Pro Thr Thr Ala Leu Val Val Ser Gln
                325                 330                 335

Leu Leu Arg Ile Pro Gln Ala Val Val Asp Met Val Ala Gly Ala His
            340                 345                 350

Trp Gly Val Leu Ala Gly Leu Ala Tyr Tyr Ser Met Val Gly Asn Trp
            355                 360                 365

Ala Lys Val Leu Ile Val Thr Leu Leu Phe Ala Gly Val Asp Gly Asn
        370                 375                 380

Thr His Thr Ile Gly Gly Lys Gln Ala Gln Ala Thr Gly Gly Phe Val
385                 390                 395                 400

Ala Trp Leu Ala Arg Gly Pro Ser Gln Glu Ile Gln Leu Ile Asn Thr
                405                 410                 415

Asn Gly Ser Trp His Ile Asn Arg Thr Ala Leu Asn Cys Asn Asp Ser
            420                 425                 430

Leu Lys Thr Gly Phe Ile Ala Ala Leu Phe Tyr Ala His Arg Phe Asn
        435                 440                 445

Ser Ser Gly Cys Pro Glu Arg Met Ala Ser Cys Arg Pro Ile Asp Lys
450                 455                 460

Phe Ala Gln Gly Trp Gly Pro Ile Thr Tyr Ala Lys Pro Asp Ser Leu
465                 470                 475                 480

Asp Gln Arg Pro Tyr Cys Trp His Tyr Ala Pro Gln Pro Cys Gly Ile
                485                 490                 495

Val Pro Ala Ser Glu Val Cys Gly Pro Val Tyr Cys Phe Thr Pro Ser
                500                 505                 510

Pro Val Val Val Gly Thr Thr Asp Arg Ser Gly Val Pro Thr Tyr Arg
            515                 520                 525

Trp Gly Glu Asn Glu Thr Asp Val Leu Leu Leu Asn Asn Thr Arg Pro
            530                 535                 540

Pro Gln Gly Asn Trp Phe Gly Cys Thr Trp Met Asn Ala Thr Gly Phe
545                 550                 555                 560
```

-continued

```
Thr Lys Thr Cys Gly Gly Pro Pro Cys Lys Ile Gly Gly Leu Gly Asn
                565                 570                 575

Asn Thr Leu Thr Cys Pro Thr Asp Cys Phe Arg Lys His Pro Glu Ala
            580                 585                 590

Thr Tyr Thr Lys Cys Gly Ser Gly Pro Trp Leu Thr Pro Arg Cys Ile
        595                 600                 605

Val Asp Tyr Pro Tyr Arg Leu Trp His Tyr Pro Cys Thr Val Asn Phe
    610                 615                 620

Thr Ile Phe Lys Val Arg Met Tyr Val Gly Ile Glu His Arg Leu
625                 630                 635                 640

Ser Ala Ala Cys Asn Trp Thr Arg Gly Glu Arg Cys Asp Leu Glu Asp
                645                 650                 655

Arg Asp Arg Ser Glu Leu Ser Pro Leu Leu Leu Ser Thr Thr Glu Trp
            660                 665                 670

Gln Ile Leu Pro Cys Ser Phe Thr Thr Leu Pro Ala Leu Ser Thr Gly
        675                 680                 685

Leu Ile His Leu His Gln Asn Thr Val Asp Val Gln Tyr Leu Tyr Gly
    690                 695                 700

Val Gly Ser Val Leu Val Ser Phe Ala Ile Lys Trp Glu Tyr Ile Leu
705                 710                 715                 720

Leu Phe Phe Leu Leu Leu Ala Asp Ala Arg Val Cys Ala Cys Leu Trp
                725                 730                 735

Met Met Leu Leu Ile Ala Gln Ala Glu Ala
            740                 745

<210> SEQ ID NO 27
<211> LENGTH: 746
<212> TYPE: PRT
<213> ORGANISM: Hepatitis C virus

<400> SEQUENCE: 27

Met Ser Thr Asn Pro Lys Pro Gln Arg Lys Thr Lys Arg Asn Thr Asn
1               5                   10                  15

Arg Arg Pro Gln Asn Val Lys Phe Pro Gly Gly Gly Gln Ile Val Gly
            20                  25                  30

Gly Val Cys Leu Leu Pro Arg Arg Gly Pro Arg Val Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Arg Gly Pro Ser Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Val
            180                 185                 190
```

```
Glu Val Arg Asn Ser Ser Gly Ile Tyr His Val Thr Asn Asp Cys Pro
        195                 200                 205

Asn Ala Ser Val Val Tyr Glu Thr Asp Ser Leu Ile Ile His Leu Pro
        210                 215                 220

Gly Cys Val Pro Cys Val Arg Glu Gly Asn Ala Ser Arg Cys Trp Val
225                 230                 235                 240

Ser Leu Ser Pro Thr Val Ala Ala Lys Asp Pro Gly Val Pro Val Asn
                245                 250                 255

Glu Ile Arg Arg His Val Asp Leu Ile Val Gly Ala Ala Ala Phe Cys
                260                 265                 270

Ser Ala Met Tyr Val Gly Asp Leu Cys Gly Ser Ile Phe Leu Val Gly
            275                 280                 285

Gln Leu Phe Thr Leu Ser Pro Arg Arg His Trp Thr Thr Gln Asp Cys
        290                 295                 300

Asn Cys Ser Ile Tyr Pro Gly His Val Thr Gly His Arg Met Ala Trp
305                 310                 315                 320

Asp Met Met Met Asn Trp Ser Pro Thr Gly Ala Leu Val Val Ala Gln
                325                 330                 335

Leu Leu Arg Ile Pro Gln Ala Val Leu Asp Met Ile Ala Gly Ala His
                340                 345                 350

Trp Gly Val Leu Ala Gly Pro Ala Tyr Tyr Ser Met Val Gly Asn Trp
            355                 360                 365

Ala Lys Val Leu Val Val Leu Leu Leu Phe Ala Gly Val Asp Ala Thr
        370                 375                 380

Thr Gln Val Thr Gly Gly Thr Ala Gly Arg Asn Ala Tyr Arg Leu Ala
385                 390                 395                 400

Ser Leu Phe Ser Thr Gly Pro Ser Gln Asn Ile Gln Leu Ile Asn Ser
                405                 410                 415

Asn Gly Ser Trp His Ile Asn Arg Thr Ala Leu Asn Cys Asn Asp Ser
                420                 425                 430

Leu His Thr Gly Trp Val Ala Ala Leu Phe Tyr Ser His Lys Phe Asn
            435                 440                 445

Ser Ser Gly Arg Pro Glu Arg Met Ala Ser Cys Arg Pro Leu Thr Ala
        450                 455                 460

Phe Asp Gln Gly Trp Gly Pro Ile Thr Tyr Gly Gly Lys Ala Ser Asn
465                 470                 475                 480

Asp Gln Arg Pro Tyr Cys Trp His Tyr Ala Pro Arg Pro Cys Gly Ile
                485                 490                 495

Val Pro Ala Lys Glu Val Cys Gly Pro Val Tyr Cys Phe Thr Pro Ser
            500                 505                 510

Pro Val Val Val Gly Thr Thr Asp Lys Tyr Gly Val Pro Thr Tyr Thr
        515                 520                 525

Trp Gly Glu Asn Glu Thr Asp Val Leu Leu Leu Asn Asn Ser Arg Pro
530                 535                 540

Pro Ile Gly Asn Trp Phe Gly Cys Thr Trp Met Asn Ser Thr Gly Phe
545                 550                 555                 560

Thr Lys Thr Cys Gly Ala Pro Ala Cys Asn Val Gly Gly Ser Glu Thr
                565                 570                 575

Asn Thr Leu Ser Cys Pro Thr Asp Cys Phe Arg Arg His Pro Asp Ala
            580                 585                 590

Thr Tyr Ala Lys Cys Gly Ser Gly Pro Trp Leu Asn Pro Arg Cys Met
        595                 600                 605
```

-continued

```
Val Asp Tyr Pro Tyr Arg Leu Trp His Tyr Pro Cys Thr Val Asn Tyr
610                 615                 620

Thr Ile Phe Lys Ile Arg Met Phe Val Gly Gly Ile Glu His Arg Leu
625                 630                 635                 640

Thr Ala Ala Cys Asn Trp Thr Arg Gly Glu Arg Cys Asp Leu Asp Asp
                645                 650                 655

Arg Asp Arg Ala Glu Leu Ser Pro Leu Leu Leu Ser Thr Thr Gln Trp
                660                 665                 670

Gln Val Leu Pro Cys Ser Phe Thr Thr Leu Pro Ala Leu Ser Thr Gly
                675                 680                 685

Leu Ile His Leu His Gln Asn Ile Val Asp Val Gln Tyr Leu Tyr Gly
690                 695                 700

Leu Ser Ser Val Val Thr Ser Trp Ala Ile Arg Trp Glu Tyr Val Val
705                 710                 715                 720

Leu Leu Phe Leu Leu Leu Ala Asp Ala Arg Ile Cys Ala Cys Leu Trp
                725                 730                 735

Met Met Leu Leu Ile Ser Gln Val Glu Ala
                740                 745

<210> SEQ ID NO 28
<211> LENGTH: 746
<212> TYPE: PRT
<213> ORGANISM: Hepatitis C virus

<400> SEQUENCE: 28

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Tyr
            115                 120                 125

Gly Phe Ala Asp Leu Met Gly Tyr Ile Pro Leu Val Gly Ala Pro Leu
130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Val
                180                 185                 190

Gly Val Arg Asn Ser Ser Gly Val Tyr His Val Thr Asn Asp Cys Pro
            195                 200                 205

Asn Ala Ser Val Val Tyr Glu Thr Asp Ser Leu Ile Ile His Leu Pro
210                 215                 220

Gly Cys Val Pro Cys Val Arg Glu Gly Asn Gly Ser Arg Cys Trp Val
225                 230                 235                 240
```

```
Ser Leu Ser Pro Thr Val Ala Ala Lys Asp Pro Gly Val Pro Val Asn
            245                 250                 255

Glu Ile Arg Arg His Val Asp Leu Ile Ala Gly Ala Ala Ala Phe Cys
            260                 265                 270

Ser Ala Met Tyr Val Gly His Leu Cys Gly Ser Ile Phe Leu Val Gly
            275                 280                 285

Gln Leu Phe Thr Leu Ser Pro Arg Arg His Trp Thr Thr Gln Asp Cys
            290                 295                 300

Asn Cys Ser Ile Tyr Pro Gly His Val Thr Gly His Arg Met Ala Trp
305                 310                 315                 320

Asp Met Met Met Asn Trp Ser Pro Thr Thr Ala Leu Val Val Ala Gln
                325                 330                 335

Leu Leu Arg Ile Pro Gln Ala Ile Leu Asp Met Ile Ala Gly Ala His
            340                 345                 350

Trp Gly Val Leu Ala Gly Ile Ala Tyr Phe Ser Met Val Gly Asn Trp
            355                 360                 365

Thr Lys Val Leu Val Val Leu Leu Phe Ala Gly Val Asp Ala Thr
            370                 375                 380

Thr Ile Val Ser Gly Gly Ser Ala Gly Arg Ser Thr Ala Gly Leu Val
385                 390                 395                 400

Gly Leu Phe Ser Pro Gly Ala Arg Gln Asn Ile Gln Leu Ile Asn Thr
            405                 410                 415

Asn Gly Ser Trp His Ile Asn Arg Thr Ala Leu Asn Cys Asn Asp Thr
            420                 425                 430

Leu Gln Thr Gly Trp Val Ala Gly Leu Phe Tyr Thr Asn Lys Phe Asn
            435                 440                 445

Ser Ser Gly Cys Pro Glu Arg Leu Ala Ser Cys Arg Pro Leu Ala Asp
450                 455                 460

Phe Asp Gln Gly Trp Gly Pro Ile Ser Tyr Thr Asn Gly Ser Gly Pro
465                 470                 475                 480

Asp Gln Arg Pro Tyr Cys Trp His Tyr Pro Pro Lys Pro Cys Gly Ile
            485                 490                 495

Val Pro Ala Glu Ser Val Cys Gly Pro Val Tyr Cys Phe Thr Pro Ser
            500                 505                 510

Pro Val Val Val Gly Thr Thr Asp Arg Ser Gly Ala Pro Thr Tyr Asn
            515                 520                 525

Trp Gly Glu Asn Glu Thr Asp Val Phe Val Leu Asn Asn Thr Arg Pro
530                 535                 540

Arg Leu Gly Asn Trp Phe Gly Gly Thr Trp Met Asn Ser Thr Gly Phe
545                 550                 555                 560

Thr Lys Val Cys Gly Ala Pro Pro Cys Ala Ile Gly Gly Val Gly Asn
            565                 570                 575

Asn Thr Leu Tyr Cys Pro Thr Asp Cys Phe Arg Lys His Pro Glu Ala
            580                 585                 590

Thr Tyr Ser Arg Cys Gly Ser Gly Pro Trp Ile Thr Pro Arg Cys Leu
            595                 600                 605

Ile His Tyr Pro Tyr Arg Leu Trp His Tyr Pro Cys Thr Ile Asn Tyr
            610                 615                 620

Thr Ile Phe Lys Ile Arg Met Phe Val Gly Gly Val Glu His Arg Leu
625                 630                 635                 640

Asp Ala Ala Cys Asn Trp Thr Arg Gly Glu Arg Cys Asp Leu Asp Asp
            645                 650                 655
```

```
Arg Asp Arg Ala Glu Leu Ser Pro Leu Leu Ser Thr Thr Gln Trp
            660                 665                 670

Gln Val Leu Pro Cys Ser Phe Thr Thr Leu Pro Ala Leu Ser Thr Gly
            675                 680                 685

Leu Ile His Leu His Gln Asn Ile Val Asp Val Gln Tyr Leu Tyr Gly
            690                 695                 700

Leu Ser Ser Ala Val Thr Ser Trp Val Ile Lys Trp Glu Tyr Val Val
705                 710                 715                 720

Leu Leu Phe Leu Leu Ala Asp Ala Arg Ile Cys Ala Cys Leu Trp
            725                 730                 735

Met Met Leu Leu Ile Ser Gln Val Glu Ala
            740                 745

<210> SEQ ID NO 29
<211> LENGTH: 746
<212> TYPE: PRT
<213> ORGANISM: Hepatitis C virus

<400> SEQUENCE: 29

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Val Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Ser Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Val
            180                 185                 190

Gly Val Arg Asn Ser Ser Gly Val Tyr His Val Thr Asn Asp Cys Pro
        195                 200                 205

Asn Ala Ser Val Val Tyr Glu Thr Glu Asn Leu Ile Met His Leu Pro
210                 215                 220

Gly Cys Val Pro Tyr Val Arg Glu Gly Asn Ala Ser Arg Cys Trp Val
225                 230                 235                 240

Ser Leu Ser Pro Thr Val Ala Ala Arg Asp Ser Arg Val Pro Val Ser
                245                 250                 255

Glu Val Arg Arg Arg Val Asp Ser Ile Val Gly Ala Ala Ala Phe Cys
            260                 265                 270

Ser Ala Met Tyr Val Gly Asp Leu Cys Gly Ser Ile Phe Leu Val Gly
        275                 280                 285
```

```
Gln Ile Phe Thr Phe Ser Pro Arg His His Trp Thr Thr Gln Asp Cys
    290                 295                 300

Asn Cys Ser Ile Tyr Pro Gly His Val Thr Gly His Arg Met Ala Trp
305                 310                 315                 320

Asp Met Met Met Asn Trp Ser Pro Thr Gly Ala Leu Val Val Ala Gln
                325                 330                 335

Leu Leu Arg Ile Pro Gln Ala Ile Val Asp Met Ile Ala Gly Ala His
            340                 345                 350

Trp Gly Val Leu Ala Gly Leu Ala Tyr Tyr Ser Met Val Gly Asn Trp
        355                 360                 365

Ala Lys Val Val Val Leu Leu Leu Phe Ala Gly Val Asp Ala Glu
    370                 375                 380

Thr Arg Val Thr Gly Gly Ala Ala Gly His Thr Ala Phe Gly Phe Ala
385                 390                 395                 400

Ser Phe Leu Ala Pro Gly Ala Lys Gln Lys Ile Gln Leu Ile Asn Thr
                405                 410                 415

Asn Gly Ser Trp His Ile Asn Arg Thr Ala Leu Asn Cys Asn Glu Ser
            420                 425                 430

Leu Asp Thr Gly Trp Leu Ala Gly Leu Leu Tyr Tyr His Lys Phe Asn
        435                 440                 445

Ser Ser Gly Cys Pro Glu Arg Met Ala Ser Cys Gln Pro Leu Thr Ala
    450                 455                 460

Phe Asp Gln Gly Trp Gly Pro Ile Thr His Glu Gly Asn Ala Ser Asp
465                 470                 475                 480

Asp Gln Arg Pro Tyr Cys Trp His Tyr Ala Leu Arg Pro Cys Gly Ile
                485                 490                 495

Val Pro Ala Lys Lys Val Cys Gly Pro Val Tyr Cys Phe Thr Pro Ser
            500                 505                 510

Pro Val Val Gly Thr Thr Asp Arg Ala Gly Val Pro Thr Tyr Arg
        515                 520                 525

Trp Gly Ala Asn Glu Thr Asp Val Leu Leu Leu Asn Asn Ser Arg Pro
    530                 535                 540

Pro Met Gly Asn Trp Phe Gly Cys Thr Trp Met Asn Ser Ser Gly Phe
545                 550                 555                 560

Thr Lys Thr Cys Gly Ala Pro Ala Cys Asn Ile Gly Gly Ser Gly Asn
                565                 570                 575

Asn Thr Leu Leu Cys Pro Thr Asp Cys Phe Arg Lys His Pro Asp Ala
            580                 585                 590

Thr Tyr Ser Arg Cys Gly Ser Gly Pro Trp Leu Thr Pro Arg Cys Leu
        595                 600                 605

Val Asp Tyr Pro Tyr Arg Leu Trp His Tyr Pro Cys Thr Val Asn Tyr
    610                 615                 620

Thr Ile Phe Lys Ile Arg Met Phe Val Gly Gly Val Glu His Arg Leu
625                 630                 635                 640

Asp Ala Ala Cys Asn Trp Thr Arg Gly Glu Arg Cys Asp Leu Asp Asp
                645                 650                 655

Arg Asp Arg Ala Glu Leu Ser Pro Leu Leu Leu Ser Thr Thr Gln Trp
            660                 665                 670

Gln Val Leu Pro Cys Ser Phe Thr Thr Leu Pro Ala Leu Ser Thr Gly
        675                 680                 685

Leu Ile His Leu His Gln Asn Ile Val Asp Val Gln Tyr Leu Tyr Gly
    690                 695                 700
```

-continued

```
Leu Ser Ser Ala Val Thr Ser Trp Val Ile Lys Trp Glu Tyr Val Val
705                 710                 715                 720

Leu Leu Phe Leu Leu Leu Ala Asp Ala Arg Ile Cys Ala Cys Leu Trp
            725                 730                 735

Met Met Leu Leu Ile Ser Gln Val Glu Ala
            740                 745

<210> SEQ ID NO 30
<211> LENGTH: 750
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (233)..(233)
<223> OTHER INFORMATION: Xaa can be any amino acid
<220> FEATURE:
<221> NAME/KEY: misc_feature
<222> LOCATION: (249)..(250)
<223> OTHER INFORMATION: Xaa can be any amino acid
<220> FEATURE:
<221> NAME/KEY: misc_feature
<222> LOCATION: (290)..(290)
<223> OTHER INFORMATION: Xaa can be any amino acid
<220> FEATURE:
<221> NAME/KEY: misc_feature
<222> LOCATION: (378)..(378)
<223> OTHER INFORMATION: Xaa can be any amino acid
<220> FEATURE:
<221> NAME/KEY: misc_feature
<222> LOCATION: (392)..(392)
<223> OTHER INFORMATION: Xaa can be any amino acid
<220> FEATURE:
<221> NAME/KEY: misc_feature
<222> LOCATION: (399)..(399)
<223> OTHER INFORMATION: Xaa can be any amino acid
<220> FEATURE:
<221> NAME/KEY: misc_feature
<222> LOCATION: (445)..(445)
<223> OTHER INFORMATION: Xaa can be any amino acid
<220> FEATURE:
<221> NAME/KEY: misc_feature
<222> LOCATION: (495)..(495)
<223> OTHER INFORMATION: Xaa can be any amino acid
<220> FEATURE:
<221> NAME/KEY: misc_feature
<222> LOCATION: (599)..(599)
<223> OTHER INFORMATION: Xaa can be any amino acid
<220> FEATURE:
<221> NAME/KEY: misc_feature
<222> LOCATION: (628)..(628)
<223> OTHER INFORMATION: Xaa can be any amino acid
<220> FEATURE:
<221> NAME/KEY: misc_feature
<222> LOCATION: (664)..(664)
<223> OTHER INFORMATION: Xaa can be any amino acid
<220> FEATURE:
<221> NAME/KEY: misc_feature
<222> LOCATION: (683)..(683)
<223> OTHER INFORMATION: Xaa can be any amino acid

<400> SEQUENCE: 30

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
50                  55                  60
```

```
Ile Pro Lys Asp Arg Arg Ser Thr Gly Lys Ser Trp Gly Lys Pro Gly
 65                  70                  75                  80

Tyr Pro Trp Pro Leu Tyr Gly Asn Glu Gly Leu Gly Trp Ala Gly Trp
                 85                  90                  95

Leu Leu Ser Pro Arg Gly Ser Arg Pro Ser Trp Gly Pro Thr Asp Pro
            100                 105                 110

Arg His Arg Ser Arg Asn Val Gly Lys Val Ile Asp Thr Leu Thr Cys
        115                 120                 125

Gly Phe Ala Asp Leu Met Gly Tyr Ile Pro Val Val Gly Ala Pro Leu
    130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Ile Thr Val Pro Val Ser Ala Val
            180                 185                 190

Glu Val Lys Asn Ile Ser Thr Ser Tyr Met Val Thr Asn Asp Cys Ser
        195                 200                 205

Asn Asp Ser Ile Thr Trp Gln Leu Gln Ala Ala Val Leu His Val Pro
    210                 215                 220

Gly Cys Val Pro Cys Glu Asn Asp Xaa Asn Thr Ser Arg Cys Trp Ile
225                 230                 235                 240

Pro Val Ser Pro Asn Val Ala Val Xaa Xaa Pro Gly Ala Leu Thr Gln
                245                 250                 255

Gly Leu Arg Thr His Ile Asp Met Val Val Met Ser Ala Thr Leu Cys
            260                 265                 270

Ser Ala Leu Tyr Val Gly Asp Leu Cys Gly Gly Val Met Leu Ala Ala
        275                 280                 285

Gln Xaa Phe Ile Val Ser Pro Gln Arg His Trp Phe Val Gln Glu Cys
    290                 295                 300

Asn Cys Ser Ile Tyr Pro Gly Thr Ile Thr Gly His Arg Met Ala Trp
305                 310                 315                 320

Asp Met Met Met Asn Trp Ser Pro Thr Ala Thr Met Ile Leu Ala Tyr
                325                 330                 335

Ala Met Arg Val Pro Glu Val Ile Ile Asp Ile Ile Phe Gly Ala His
            340                 345                 350

Trp Gly Val Met Phe Gly Leu Ala Tyr Phe Ser Met Gln Gly Ala Trp
        355                 360                 365

Ala Lys Val Ile Val Ile Leu Leu Leu Xaa Ala Gly Val Asp Ala Arg
    370                 375                 380

Thr His Thr Val Gly Gly Ser Xaa Gly Arg Thr Thr Ser Gly Xaa Ala
385                 390                 395                 400

Gly Leu Phe Ser Ser Gly Pro Lys Gln Asn Ile Gln Leu Ile Asn Thr
                405                 410                 415

Asn Gly Ser Trp His Ile Asn Arg Thr Ala Leu Asn Cys Asn Asp Ser
            420                 425                 430

Leu Gln Thr Gly Phe Ile Ala Ser Leu Phe Tyr Thr Xaa Asn Phe Asn
        435                 440                 445

Ser Ser Gly Cys Pro Glu Arg Leu Ser Ala Cys Arg Gly Ile Glu Ala
    450                 455                 460

Phe Arg Ile Gly Trp Gly Thr Leu Gln Tyr Glu Asp Asn Val Thr Asn
465                 470                 475                 480

Pro Glu Asp Met Arg Pro Tyr Cys Trp His Tyr Pro Pro Lys Xaa Cys
```

```
            485                 490                 495
Gly Ile Val Pro Ala Arg Ser Val Cys Gly Pro Val Tyr Cys Phe Thr
                500                 505                 510

Pro Ser Pro Val Val Gly Thr Thr Asp Arg Leu Gly Val Pro Thr
            515                 520                 525

Tyr Thr Trp Gly Glu Asn Glu Thr Asp Val Phe Leu Leu Asn Ser Thr
        530                 535                 540

Arg Pro Pro Arg Gly Ser Trp Phe Gly Cys Thr Trp Met Asn Ser Thr
545                 550                 555                 560

Gly Phe Thr Lys Thr Cys Gly Ala Pro Pro Cys Arg Ile Arg Ala Asp
                565                 570                 575

Phe Asn Ala Ser Thr Asp Leu Leu Cys Pro Thr Asp Cys Phe Arg Lys
            580                 585                 590

His Pro Asp Ala Thr Tyr Xaa Lys Cys Gly Ser Gly Pro Trp Leu Thr
        595                 600                 605

Pro Arg Cys Leu Val Asp Tyr Pro Tyr Arg Leu Trp His Tyr Pro Cys
    610                 615                 620

Thr Val Asn Xaa Thr Ile Phe Lys Ile Arg Met Tyr Val Gly Gly Val
625                 630                 635                 640

Glu His Arg Leu Thr Ala Ala Cys Asn Phe Thr Arg Gly Asp Arg Cys
                645                 650                 655

Asn Leu Glu Asp Arg Asp Arg Xaa Gln Leu Ser Pro Leu Leu His Ser
            660                 665                 670

Thr Thr Glu Trp Ala Ile Leu Pro Cys Ser Xaa Ser Asp Leu Pro Ala
        675                 680                 685

Leu Ser Thr Gly Leu Leu His Leu His Gln Asn Ile Val Asp Val Gln
    690                 695                 700

Tyr Met Tyr Gly Leu Ser Pro Ala Leu Thr Lys Tyr Ile Val Arg Trp
705                 710                 715                 720

Glu Trp Val Val Leu Leu Phe Leu Leu Leu Ala Asp Ala Arg Val Cys
                725                 730                 735

Ala Cys Leu Trp Met Leu Ile Leu Leu Gly Gln Ala Glu Ala
            740                 745                 750

<210> SEQ ID NO 31
<211> LENGTH: 750
<212> TYPE: PRT
<213> ORGANISM: Hepatitis C virus

<400> SEQUENCE: 31

Met Ser Thr Asn Pro Lys Pro Gln Arg Lys Thr Lys Arg Asn Thr Asn
1               5                   10                  15

Arg Arg Pro Glu Asp Val Lys Phe Pro Gly Gly Gly Gln Ile Val Gly
            20                  25                  30

Gly Val Tyr Leu Leu Pro Arg Arg Gly Pro Arg Leu Gly Val Arg Thr
        35                  40                  45

Thr Arg Lys Thr Ser Glu Arg Ser Gln Pro Arg Gly Arg Arg Gln Pro
    50                  55                  60

Ile Pro Lys Asp Arg Arg Ser Thr Gly Lys Ala Trp Gly Lys Pro Gly
65                  70                  75                  80

Arg Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
            100                 105                 110
```

```
Arg His Arg Ser Arg Asn Val Gly Lys Val Ile Asp Thr Leu Thr Cys
            115                 120                 125
Gly Phe Ala Asp Leu Met Gly Tyr Ile Pro Val Gly Ala Pro Leu
130                 135                 140
Ser Gly Ala Ala Arg Ala Val Ala His Gly Val Arg Val Leu Glu Asp
145                 150                 155                 160
Gly Val Asn Tyr Ala Thr Gly Asn Leu Pro Gly Phe Pro Phe Ser Ile
                165                 170                 175
Phe Leu Leu Ala Leu Leu Ser Cys Ile Thr Val Pro Val Ser Ala Ala
            180                 185                 190
Gln Val Lys Asn Thr Ser Ser Tyr Met Val Thr Asn Asp Cys Ser
        195                 200                 205
Asn Asp Ser Ile Thr Trp Gln Leu Glu Ala Ala Val Leu His Val Pro
210                 215                 220
Gly Cys Val Pro Cys Glu Arg Val Gly Asn Thr Ser Arg Cys Trp Val
225                 230                 235                 240
Pro Val Ser Pro Asn Met Ala Val Arg Gln Pro Gly Ala Leu Thr Gln
                245                 250                 255
Gly Leu Arg Thr His Ile Asp Met Val Val Met Ser Ala Thr Phe Cys
            260                 265                 270
Ser Ala Leu Tyr Val Gly Asp Leu Cys Gly Gly Val Met Leu Ala Ala
        275                 280                 285
Gln Val Phe Ile Val Ser Pro Gln Tyr His Trp Phe Val Gln Glu Cys
        290                 295                 300
Asn Cys Ser Ile Tyr Pro Gly Thr Ile Thr Gly His Arg Met Ala Trp
305                 310                 315                 320
Asp Met Met Met Asn Trp Ser Pro Thr Ala Thr Met Ile Leu Ala Tyr
                325                 330                 335
Val Met Arg Val Pro Glu Val Ile Ile Asp Ile Val Ser Gly Ala His
            340                 345                 350
Trp Gly Val Met Phe Gly Leu Ala Tyr Phe Ser Met Gln Gly Ala Trp
        355                 360                 365
Ala Lys Val Ile Val Ile Leu Leu Leu Ala Ala Gly Val Asp Ala Gly
370                 375                 380
Thr Thr Thr Val Gly Gly Ala Val Ala Arg Ser Thr Asn Val Ile Ala
385                 390                 395                 400
Gly Val Phe Ser His Gly Pro Gln Gln Asn Ile Gln Leu Ile Asn Thr
                405                 410                 415
Asn Gly Ser Trp His Ile Asn Arg Thr Ala Leu Asn Cys Asn Asp Ser
            420                 425                 430
Leu Asn Thr Gly Phe Leu Ala Ala Leu Phe Tyr Thr Asn Arg Phe Asn
        435                 440                 445
Ser Ser Gly Cys Pro Gly Arg Leu Ser Ala Cys Arg Asn Ile Glu Ala
450                 455                 460
Phe Arg Ile Gly Trp Gly Thr Leu Gln Tyr Glu Asp Asn Val Thr Asn
465                 470                 475                 480
Pro Glu Asp Met Arg Pro Tyr Cys Trp His Tyr Pro Pro Lys Pro Cys
                485                 490                 495
Gly Val Val Pro Ala Arg Ser Val Cys Gly Pro Val Tyr Cys Phe Thr
            500                 505                 510
Pro Ser Pro Val Val Val Gly Thr Thr Asp Arg Arg Gly Val Pro Thr
        515                 520                 525
Tyr Thr Trp Gly Glu Asn Glu Thr Asp Val Phe Leu Leu Asn Ser Thr
```

```
            530                 535                 540
Arg Pro Pro Gln Gly Ser Trp Phe Gly Cys Thr Trp Met Asn Ser Thr
545                 550                 555                 560

Gly Phe Thr Lys Thr Cys Gly Ala Pro Pro Cys Arg Thr Arg Ala Asp
                565                 570                 575

Phe Asn Ala Ser Thr Asp Leu Leu Cys Pro Thr Asp Cys Phe Arg Lys
                580                 585                 590

His Pro Asp Ala Thr Tyr Ile Lys Cys Gly Ser Gly Pro Trp Leu Thr
                595                 600                 605

Pro Lys Cys Leu Val His Tyr Pro Tyr Arg Leu Trp His Tyr Pro Cys
610                 615                 620

Thr Val Asn Phe Thr Ile Phe Lys Ile Arg Met Tyr Val Gly Gly Val
625                 630                 635                 640

Glu His Arg Leu Thr Ala Ala Cys Asn Phe Thr Arg Gly Asp Arg Cys
                645                 650                 655

Asp Leu Glu Asp Arg Asp Arg Ser Gln Leu Ser Pro Leu Leu His Ser
                660                 665                 670

Thr Thr Glu Trp Ala Ile Leu Pro Cys Thr Tyr Ser Asp Leu Pro Ala
                675                 680                 685

Leu Ser Thr Gly Leu Leu His Leu His Gln Asn Ile Val Asp Val Gln
690                 695                 700

Tyr Met Tyr Gly Leu Ser Pro Ala Ile Thr Lys Tyr Val Val Arg Trp
705                 710                 715                 720

Glu Trp Val Val Leu Leu Phe Leu Leu Leu Ala Asp Ala Arg Val Cys
                725                 730                 735

Ala Cys Leu Trp Met Leu Ile Leu Leu Gly Gln Ala Glu Ala
                740                 745                 750

<210> SEQ ID NO 32
<211> LENGTH: 749
<212> TYPE: PRT
<213> ORGANISM: Hepatitis C virus

<400> SEQUENCE: 32

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
                35                  40                  45

Thr Arg Lys Thr Ser Glu Arg Ser Gln Pro Arg Gly Arg Arg Gln Pro
                50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
                100                 105                 110

Arg His Arg Ser Arg Asn Val Gly Lys Val Ile Asp Thr Leu Thr Cys
                115                 120                 125

Gly Phe Ala Asp Leu Met Gly Tyr Ile Pro Val Val Gly Ala Pro Leu
                130                 135                 140

Gly Gly Val Ala Arg Ala Leu Ala His Gly Val Arg Val Leu Glu Asp
145                 150                 155                 160
```

```
Gly Val Asn Tyr Ala Thr Gly Asn Leu Pro Gly Cys Ser Phe Ser Ile
            165                 170                 175

Phe Leu Leu Ala Leu Leu Ser Cys Ile Thr Thr Pro Val Ser Ala Ala
            180                 185                 190

Gln Val Lys Asn Thr Ser Asp Ile Tyr Met Val Thr Asn Asp Cys Ser
            195                 200                 205

Asn Asp Ser Ile Thr Trp Gln Leu Gln Ala Ala Leu His Val Pro
            210                 215                 220

Gly Cys Val Pro Cys Glu Arg Val Gly Asn Thr Ser Arg Cys Trp Ile
225                 230                 235                 240

Pro Val Ser Pro Asn Val Ala Val Arg Gln Pro Gly Ala Leu Thr Gln
            245                 250                 255

Gly Leu Arg Thr His Ile Asp Met Val Val Met Ser Ala Thr Leu Cys
            260                 265                 270

Ser Ala Leu Tyr Val Gly Asp Leu Cys Gly Gly Val Met Leu Ala Ala
            275                 280                 285

Gln Met Phe Ile Ile Ser Pro Gln His His Trp Phe Val Gln Glu Cys
            290                 295                 300

Asn Cys Ser Ile Tyr Pro Gly Thr Ile Thr Gly His Arg Met Ala Trp
305                 310                 315                 320

Asp Met Met Met Asn Trp Ser Pro Thr Thr Thr Met Ile Leu Ala Tyr
            325                 330                 335

Val Met Arg Val Pro Glu Val Ile Ile Asp Ile Ile Gly Gly Ala His
            340                 345                 350

Trp Gly Val Met Phe Gly Leu Ala Tyr Phe Ser Met Gln Gly Ala Trp
            355                 360                 365

Ala Lys Val Val Ile Leu Leu Leu Ala Ala Gly Val Asp Ala His
            370                 375                 380

Thr Arg Thr Gly Ser Ser Val Gly Tyr Ala Thr Ser Gly Ile Val Gly
385                 390                 395                 400

Leu Phe Thr Ser Gly Pro Lys Gln Asn Ile Gln Leu Ile Asn Thr Asn
            405                 410                 415

Gly Ser Trp His Ile Asn Arg Thr Ala Leu Asn Cys Asn Asp Ser Leu
            420                 425                 430

Asn Thr Gly Phe Ile Val Ser Leu Phe Tyr Ala Arg Asn Phe Asn Ser
            435                 440                 445

Thr Gly Cys Pro Glu Arg Leu Ser Ala Cys Arg Gly Ile Glu Gly Phe
            450                 455                 460

Arg Ile Gly Trp Gly Thr Leu Gln Tyr Glu Asp Asn Val Thr Asn Pro
465                 470                 475                 480

Glu Asp Met Arg Pro Tyr Cys Trp His Tyr Pro Pro Lys Gln Cys Gly
            485                 490                 495

Ile Val Pro Ala Gly Ser Val Cys Gly Pro Val Tyr Cys Phe Thr Pro
            500                 505                 510

Ser Pro Val Val Val Gly Thr Thr Asp Arg Leu Gly Val Pro Thr Tyr
            515                 520                 525

Thr Trp Gly Glu Asn Glu Thr Asp Val Phe Leu Leu Asn Ser Thr Arg
            530                 535                 540

Pro Pro Val Gly Ser Trp Phe Gly Cys Thr Trp Met Asn Ser Thr Gly
545                 550                 555                 560

Phe Thr Lys Thr Cys Gly Ala Pro Pro Cys Arg Ile Arg Ala Asp Phe
            565                 570                 575

Asn Ala Ser Thr Asp Leu Leu Cys Pro Thr Asp Cys Phe Arg Lys His
```

```
                580                 585                 590
Pro Glu Ala Thr Tyr Ile Lys Cys Gly Ser Gly Pro Trp Leu Thr Pro
            595                 600                 605

Arg Cys Leu Val Asp Tyr Pro Tyr Arg Leu Trp His Tyr Pro Cys Thr
        610                 615                 620

Val Asn Tyr Ser Ile Phe Lys Ile Arg Met Tyr Val Gly Gly Val Glu
625                 630                 635                 640

His Arg Leu Thr Ala Ala Cys Asn Phe Thr Arg Gly Asp Arg Cys Asn
                645                 650                 655

Leu Glu Asp Arg Asp Arg Ser Gln Leu Thr Pro Leu Leu His Ser Thr
            660                 665                 670

Thr Glu Trp Ala Ile Leu Pro Cys Thr Tyr Ser Asp Leu Pro Ala Leu
        675                 680                 685

Ser Thr Gly Leu Leu His Leu His Gln Asn Ile Val Asp Val Gln Tyr
690                 695                 700

Met Tyr Gly Leu Ser Pro Ala Leu Thr Lys Tyr Val Val Arg Trp Glu
705                 710                 715                 720

Trp Val Val Leu Leu Phe Leu Leu Leu Ala Asp Ala Arg Val Cys Ala
                725                 730                 735

Cys Val Trp Met Leu Ile Leu Leu Gly Gln Ala Glu Ala
            740                 745

<210> SEQ ID NO 33
<211> LENGTH: 750
<212> TYPE: PRT
<213> ORGANISM: Hepatitis C virus
<220> FEATURE:
<221> NAME/KEY: misc_feature
<222> LOCATION: (458)..(458)
<223> OTHER INFORMATION: Xaa can be any amino acid

<400> SEQUENCE: 33

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
            100                 105                 110

Arg His Arg Ser Arg Asn Val Gly Lys Val Ile Asp Thr Leu Thr Cys
        115                 120                 125

Gly Phe Ala Asp Leu Met Gly Tyr Ile Pro Val Val Gly Ala Pro Leu
    130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Val Thr Val Pro Val Ser Ala Val
            180                 185                 190
```

```
Gln Val Lys Asn Thr Ser Glu Thr Tyr Met Val Thr Asn Asp Cys Ser
            195                 200                 205

Asn Asp Ser Ile Thr Trp Gln Leu Gln Ala Ala Val Leu His Val Pro
210                 215                 220

Gly Cys Val Pro Cys Glu Arg Thr Gly Asn Thr Ser Arg Cys Trp Ile
225                 230                 235                 240

Pro Val Ser Pro Asn Val Ala Val Gln Gln Pro Gly Ala Leu Thr Gln
            245                 250                 255

Gly Leu Arg Thr His Ile Asp Met Val Val Met Ser Ala Thr Leu Cys
                260                 265                 270

Ser Ala Leu Tyr Val Gly Asp Leu Cys Gly Val Val Leu Ala Ala
            275                 280                 285

Gln Leu Phe Ile Val Ser Pro Arg Arg His Trp Phe Val Gln Glu Cys
            290                 295                 300

Asn Cys Ser Ile Tyr Pro Gly Ala Ile Thr Gly His Arg Met Ala Trp
305                 310                 315                 320

Asp Met Met Met Asn Trp Ser Pro Thr Thr Thr Met Val Leu Ala Tyr
                325                 330                 335

Ala Met Arg Val Pro Glu Val Ile Ile Asp Ile Ile Ser Gly Ala His
            340                 345                 350

Trp Gly Val Met Phe Gly Leu Ala Tyr Phe Ser Met Gln Gly Ala Trp
                355                 360                 365

Ala Lys Val Ala Val Ile Leu Leu Leu Thr Ala Gly Val Glu Ala Arg
            370                 375                 380

Thr His Thr Thr Gly Ser Val Ala Gly Arg Thr Thr Ser Gly Phe Ala
385                 390                 395                 400

Gly Ile Phe Thr Ser Gly Pro Lys Gln Asn Ile Gln Leu Ile Asn Thr
                405                 410                 415

Asn Gly Ser Trp His Ile Asn Arg Thr Ala Leu Asn Cys Asn Asp Ser
                420                 425                 430

Leu Asn Thr Gly Phe Met Ala Ala Leu Phe Tyr Thr Lys Asn Phe Asn
            435                 440                 445

Ser Ser Gly Cys Pro Glu Arg Leu Ser Xaa Cys Arg Asn Ile Glu Ala
            450                 455                 460

Phe Arg Ile Gly Trp Gly Thr Leu Gln Tyr Glu Asp Asp Val Thr Asn
465                 470                 475                 480

Pro Glu Asp Met Arg Pro Tyr Cys Trp His Tyr Pro Pro Lys Gln Cys
                485                 490                 495

Gly Ile Phe Pro Ala Gly Ser Val Cys Gly Pro Val Tyr Cys Phe Thr
            500                 505                 510

Pro Ser Pro Val Val Gly Thr Thr Asn Lys Leu Gly Val Pro Thr
            515                 520                 525

Tyr Thr Trp Gly Glu Asn Glu Thr Asp Val Phe Ile Leu Asn Ser Thr
            530                 535                 540

Arg Pro Pro Arg Gly Ser Trp Phe Gly Cys Thr Trp Met Asn Ser Thr
545                 550                 555                 560

Gly Phe Thr Lys Thr Cys Gly Ala Pro Pro Cys Arg Ile Arg Ala Asp
                565                 570                 575

Phe Asn Ala Ser Thr Asp Leu Leu Cys Pro Thr Asp Cys Phe Arg Lys
            580                 585                 590

His Pro Glu Ala Thr Tyr Ile Lys Cys Gly Ser Gly Pro Trp Leu Thr
            595                 600                 605
```

Pro Arg Cys Leu Val Asp Tyr Pro Tyr Arg Leu Trp His Tyr Pro Cys
            610                 615                 620

Thr Val Asn Tyr Ser Ile Phe Lys Ile Arg Met Tyr Val Gly Gly Val
625                 630                 635                 640

Glu His Arg Leu Thr Ala Ala Cys Asn Phe Ser Arg Gly Asp Arg Cys
                    645                 650                 655

Asn Leu Glu Asp Arg Asp Arg Ser Gln Leu Thr Pro Leu Leu His Ser
            660                 665                 670

Thr Thr Glu Trp Ala Ile Leu Pro Cys Ser Tyr Ser Asp Leu Pro Ala
            675                 680                 685

Leu Ser Thr Gly Leu Leu His Leu His Gln Asn Ile Val Asp Val Gln
690                 695                 700

Tyr Met Tyr Gly Leu Thr Pro Ala Leu Thr Lys Tyr Val Val Arg Trp
705                 710                 715                 720

Glu Trp Val Val Leu Leu Phe Leu Leu Leu Ala Asp Ala Arg Val Cys
                    725                 730                 735

Ala Cys Leu Trp Met Leu Ile Leu Leu Gly Gln Ala Glu Ala
            740                 745                 750

<210> SEQ ID NO 34
<211> LENGTH: 750
<212> TYPE: PRT
<213> ORGANISM: Hepatitis C virus

<400> SEQUENCE: 34

Met Ser Thr Asn Pro Lys Pro Gln Arg Lys Thr Lys Arg Asn Thr Ser
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
            100                 105                 110

Arg His Arg Ser Arg Asn Val Gly Lys Val Ile Asp Thr Leu Thr Cys
        115                 120                 125

Gly Phe Ala Asp Leu Met Gly Tyr Ile Pro Val Val Gly Ala Pro Leu
130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Ile Thr Val Pro Val Ser Ala Val
            180                 185                 190

Gln Val Lys Asn Ile Ser Asp Ser Tyr Met Val Thr Asn Asp Cys Ser
        195                 200                 205

Asn Asp Ser Ile Thr Trp Gln Leu Gln Ala Ala Val Leu His Val Pro
210                 215                 220

Gly Cys Val Pro Cys Glu Lys Met Gly Asn Ile Ser Arg Cys Trp Ile
225                 230                 235                 240

-continued

```
Pro Val Ser Pro Asn Val Ala Val Gln Arg Pro Gly Ala Leu Thr Gln
                245                 250                 255

Gly Leu Arg Ala His Ile Asp Met Val Val Met Ser Ala Thr Leu Cys
            260                 265                 270

Ser Ala Leu Tyr Val Gly Asp Leu Cys Gly Val Met Leu Ala Ala
        275                 280                 285

Gln Met Phe Ile Val Ser Pro Gln His His Phe Val Gln Glu Cys
    290                 295                 300

Asn Cys Ser Ile Tyr Pro Gly Ala Ile Thr Gly His Arg Met Ala Trp
305                 310                 315                 320

Asp Met Met Met Asn Trp Ser Pro Thr Ala Thr Met Ile Leu Ala Tyr
                325                 330                 335

Ala Met Arg Val Pro Glu Val Ile Ile Asp Ile Ile Ser Gly Ala His
            340                 345                 350

Trp Gly Val Met Phe Gly Leu Ala Tyr Phe Ser Met Gln Gly Ala Trp
        355                 360                 365

Ala Lys Val Val Ile Leu Leu Leu Thr Ala Gly Val Asp Ala His
    370                 375                 380

Thr Arg Ser Ile Ala Gly Ser Val Ala His Ala Thr Ser Gly Leu Ala
385                 390                 395                 400

Gly Leu Phe Thr Ser Gly Ala Lys Gln Asn Ile Gln Leu Ile Asn Thr
                405                 410                 415

Asn Gly Ser Trp His Ile Asn Arg Thr Ala Leu Asn Cys Asn Asp Ser
            420                 425                 430

Leu Asn Thr Gly Phe Ile Ala Ser Leu Phe Tyr Thr Tyr Arg Phe Asn
        435                 440                 445

Ser Ser Gly Cys Pro Glu Arg Leu Ser Ala Cys Arg Gly Ile Gln Ala
    450                 455                 460

Phe Arg Ile Gly Trp Gly Thr Leu Arg Tyr Glu Asp Asn Val Thr Asn
465                 470                 475                 480

Pro Glu Asp Met Arg Pro Tyr Cys Trp His Tyr Pro Pro Lys Gln Cys
                485                 490                 495

Gly Ile Val Ser Ala Arg Ser Val Cys Gly Pro Val Tyr Cys Phe Thr
            500                 505                 510

Pro Ser Pro Val Val Val Gly Thr Thr Asp Arg Leu Gly Val Pro Thr
        515                 520                 525

Tyr Thr Trp Gly Glu Asn Glu Thr Asp Val Phe Ile Leu Asn Ser Thr
    530                 535                 540

Arg Pro Pro Gly Gly Ser Trp Phe Gly Cys Thr Trp Met Asn Ser Thr
545                 550                 555                 560

Gly Phe Thr Lys Thr Cys Gly Ala Pro Pro Cys Arg Ile Arg Ala Asp
                565                 570                 575

Phe Asn Ala Ser Met Asp Leu Leu Cys Pro Thr Asp Cys Phe Arg Lys
            580                 585                 590

His Pro Asp Ala Thr Tyr Ile Lys Cys Gly Ser Gly Pro Trp Leu Thr
        595                 600                 605

Pro Arg Cys Leu Val Asp Tyr Pro Tyr Arg Leu Trp His Tyr Pro Cys
    610                 615                 620

Thr Ile Asn Tyr Thr Ile Phe Lys Ile Arg Met Tyr Val Gly Gly Val
625                 630                 635                 640

Glu His Arg Leu Thr Ala Ala Cys Asn Phe Thr Arg Gly Asp Pro Cys
                645                 650                 655
```

```
Asn Leu Glu Asp Arg Asp Arg Ser Gln Leu Ser Pro Leu Leu His Ser
            660                 665                 670

Thr Thr Glu Trp Ala Ile Leu Pro Cys Ser Tyr Ser Asp Leu Pro Ala
            675                 680                 685

Leu Ser Thr Gly Leu Leu His Leu His Gln Asn Ile Val Asp Val Gln
            690                 695                 700

Tyr Met Tyr Gly Leu Ser Pro Ala Leu Thr Lys Tyr Ile Val Arg Trp
705                 710                 715                 720

Glu Trp Val Val Leu Phe Leu Leu Ala Asp Ala Arg Val Cys
                725                 730                 735

Ala Cys Leu Trp Met Leu Ile Leu Leu Gly Gln Ala Glu Ala
            740                 745                 750

<210> SEQ ID NO 35
<211> LENGTH: 751
<212> TYPE: PRT
<213> ORGANISM: Hepatitis C virus

<400> SEQUENCE: 35

Met Ser Thr Asn Pro Lys Pro Gln Arg Lys Thr Gln Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Thr
        35                  40                  45

Ala Arg Lys Thr Ser Glu Arg Ser Gln Pro Arg Gly Arg Arg Gln Pro
    50                  55                  60

Ile Pro Lys Asp Arg Arg Ser Thr Gly Lys Ser Trp Gly Arg Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
            100                 105                 110

Arg His Arg Ser Arg Asn Val Gly Lys Val Ile Asp Thr Leu Thr Cys
        115                 120                 125

Gly Phe Ala Asp Leu Met Gly Tyr Ile Pro Val Val Gly Ala Pro Leu
    130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Ile Thr Ile Pro Ala Ser Ala Val
            180                 185                 190

Glu Val Lys Asn Thr Ser Thr Gly Tyr Met Val Thr Asn Asp Cys Ala
        195                 200                 205

Asn Ser Ser Ile Thr Trp Gln Leu His Ala Ala Val Leu His Val Pro
    210                 215                 220

Gly Cys Val Pro Cys Glu Arg Val Asp Asn Asn Thr Ser Arg Cys Trp
225                 230                 235                 240

Ile Pro Val Ser Pro Asn Ile Ala Val Gln Arg Pro Gly Ala Leu Thr
                245                 250                 255

Gln Gly Leu Arg Ser His Ile Asp Ile Val Val Met Ser Ala Thr Leu
            260                 265                 270

Cys Ser Ala Leu Tyr Val Gly Asp Leu Cys Gly Gly Val Met Leu Ala
        275                 280                 285
```

```
Ala Gln Met Phe Val Ser Pro Glu His His Trp Phe Val Gln Glu
        290             295             300

Cys Asn Cys Ser Ile Tyr Pro Gly Thr Ile Thr Gly His Arg Met Ala
305             310             315             320

Trp Asp Met Met Met Asn Trp Ser Pro Thr Ala Thr Met Ile Leu Ala
                325             330             335

Tyr Ala Met Arg Val Pro Glu Val Ile Ile Asp Ile Ile Gly Gly Ala
        340             345             350

His Trp Gly Val Met Phe Gly Leu Ala Tyr Phe Ser Met Gln Gly Ala
        355             360             365

Trp Ala Lys Val Val Ile Leu Leu Leu Ala Ala Gly Val Asp Ala
        370             375             380

Tyr Thr His Thr Val Gly Gly Ala Ala Ala Ser Thr Ala Asn Ser Ile
385             390             395             400

Ala Gly Leu Leu Ser Arg Gly Pro Arg Gln Asn Leu Gln Leu Ile Asn
        405             410             415

Ser Asn Gly Ser Trp His Ile Asn Arg Thr Ala Leu Asn Cys His Asp
        420             425             430

Ser Leu Gln Thr Gly Phe Ile Thr Ala Leu Phe Tyr Ala Arg His Phe
        435             440             445

Asn Ser Ser Gly Cys Pro Glu Arg Leu Ala Ala Cys Arg Asn Ile Glu
450             455             460

Ala Phe Arg Val Gly Trp Gly Ala Leu Gln Tyr Glu Asp Asn Val Thr
465             470             475             480

Asn Pro Glu Asp Met Arg Pro Tyr Cys Trp His Tyr Pro Lys Gln
        485             490             495

Cys Gly Ile Val Pro Ala Arg Ser Val Cys Gly Pro Val Tyr Cys Phe
        500             505             510

Thr Pro Ser Pro Val Val Gly Thr Thr Asp Lys Leu Gly Val Pro
        515             520             525

Thr Tyr Thr Trp Gly Glu Asn Glu Thr Asp Val Phe Leu Leu Asn Ser
530             535             540

Thr Arg Pro Pro Gln Gly Pro Trp Phe Gly Cys Thr Trp Met Asn Ser
545             550             555             560

Thr Gly Phe Thr Lys Thr Cys Gly Ala Pro Pro Cys Arg Thr Arg Ala
        565             570             575

Asp Phe Asn Ala Ser Thr Asp Leu Leu Cys Pro Thr Asp Cys Phe Arg
        580             585             590

Lys His Pro Asp Ala Thr Tyr Asn Lys Cys Gly Ser Gly Pro Trp Leu
        595             600             605

Thr Pro Arg Cys Leu Ile Asp Tyr Pro Tyr Arg Leu Trp His Tyr Pro
        610             615             620

Cys Thr Val Asn Tyr Thr Thr Phe Lys Ile Arg Met Tyr Val Gly Gly
625             630             635             640

Val Glu His Arg Leu Met Ala Ala Cys Asn Phe Thr Arg Gly Asp Ser
        645             650             655

Cys Asp Leu Ser Gln Arg Asp Arg Gly Gln Leu Ser Pro Leu Leu His
        660             665             670

Ser Thr Thr Glu Trp Ala Ile Leu Pro Cys Ser Phe Ser Asp Leu Pro
        675             680             685

Ala Leu Ser Thr Gly Leu Leu His Leu His Gln Asn Ile Val Asp Val
        690             695             700
```

-continued

```
Gln Tyr Met Tyr Gly Leu Ser Pro Ala Leu Thr Lys Tyr Ile Val Arg
705                 710                 715                 720

Trp Glu Trp Val Val Leu Leu Phe Leu Leu Leu Ala Asp Ala Arg Val
                725                 730                 735

Cys Ala Cys Ile Trp Met Leu Ile Leu Leu Gly Gln Ala Glu Ala
            740                 745                 750

<210> SEQ ID NO 36
<211> LENGTH: 750
<212> TYPE: PRT
<213> ORGANISM: Hepatitis C virus

<400> SEQUENCE: 36

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Asn Asp Pro
            100                 105                 110

Arg His Arg Ser Arg Asn Val Gly Lys Val Ile Asp Thr Leu Thr Cys
        115                 120                 125

Gly Phe Ala Asp Leu Met Gly Tyr Ile Pro Val Val Gly Ala Pro Leu
130                 135                 140

Gly Gly Val Ala Arg Ala Leu Ala His Gly Val Arg Val Leu Glu Asp
145                 150                 155                 160

Gly Val Asn Phe Ala Thr Gly Asn Leu Pro Gly Cys Ser Phe Ser Ile
                165                 170                 175

Phe Leu Leu Ala Leu Leu Ser Cys Ile Thr Thr Pro Val Ser Ala Ala
            180                 185                 190

Glu Val Lys Asn Ile Ser Thr Gly Tyr Met Val Thr Asn Asp Cys Thr
        195                 200                 205

Asn Asp Ser Ile Thr Trp Gln Leu Gln Ala Ala Val Leu His Val Pro
210                 215                 220

Gly Cys Val Pro Cys Glu Lys Val Gly Asn Thr Ser Arg Cys Trp Ile
225                 230                 235                 240

Pro Val Ser Pro Asn Val Ala Val Gln Gln Pro Gly Ala Leu Thr Gln
                245                 250                 255

Gly Leu Arg Thr His Ile Asp Met Val Val Met Ser Ala Thr Leu Cys
            260                 265                 270

Ser Ala Leu Tyr Val Gly Asp Leu Cys Gly Gly Val Met Leu Ala Ala
        275                 280                 285

Gln Met Phe Ile Val Ser Pro Gln His His Trp Phe Val Gln Asp Cys
290                 295                 300

Asn Cys Ser Ile Tyr Pro Gly Thr Ile Thr Gly His Arg Met Ala Trp
305                 310                 315                 320

Asp Met Met Met Asn Trp Ser Pro Thr Ala Thr Met Ile Leu Ala Tyr
                325                 330                 335
```

```
Ala Met Arg Val Pro Glu Val Ile Ile Asp Ile Ile Gly Gly Ala His
            340                 345                 350
Trp Gly Val Met Phe Gly Leu Ala Tyr Phe Ser Met Gln Gly Ala Trp
            355                 360                 365
Ala Lys Val Val Val Ile Leu Leu Leu Ala Ala Gly Val Asp Ala Gln
            370                 375                 380
Thr His Thr Val Gly Gly Ser Thr Ala His Asn Ala Arg Thr Leu Thr
385                 390                 395                 400
Gly Met Phe Ser Leu Gly Ala Arg Gln Lys Ile Gln Leu Ile Asn Thr
                405                 410                 415
Asn Gly Ser Trp His Ile Asn Arg Thr Ala Leu Asn Cys Asn Asp Ser
            420                 425                 430
Leu His Thr Gly Phe Leu Ala Ser Leu Phe Tyr Thr His Ser Phe Asn
            435                 440                 445
Ser Ser Gly Cys Pro Glu Arg Met Ser Ala Cys Arg Ser Ile Glu Ala
            450                 455                 460
Phe Arg Val Gly Trp Gly Ala Leu Gln Tyr Glu Asp Asn Val Thr Asn
465                 470                 475                 480
Pro Glu Asp Met Arg Pro Tyr Cys Trp His Tyr Pro Pro Arg Gln Cys
                485                 490                 495
Gly Val Val Ser Ala Ser Ser Val Cys Gly Pro Val Tyr Cys Phe Thr
            500                 505                 510
Pro Ser Pro Val Val Val Gly Thr Thr Asp Arg Leu Gly Ala Pro Thr
            515                 520                 525
Tyr Thr Trp Gly Glu Asn Glu Thr Asp Val Phe Leu Leu Asn Ser Thr
            530                 535                 540
Arg Pro Pro Gln Gly Ser Trp Phe Gly Cys Thr Trp Met Asn Ser Thr
545                 550                 555                 560
Gly Tyr Thr Lys Thr Cys Gly Ala Pro Pro Cys Arg Ile Arg Ala Asp
                565                 570                 575
Phe Asn Ala Ser Met Asp Leu Leu Cys Pro Thr Asp Cys Phe Arg Lys
            580                 585                 590
His Pro Asp Thr Thr Tyr Ile Lys Cys Gly Ser Gly Pro Trp Leu Thr
            595                 600                 605
Pro Arg Cys Leu Ile Asp Tyr Pro Tyr Arg Leu Trp His Tyr Pro Cys
            610                 615                 620
Thr Val Asn Tyr Thr Ile Phe Lys Ile Arg Met Tyr Val Gly Gly Val
625                 630                 635                 640
Glu His Arg Leu Thr Ala Ala Cys Asn Phe Thr Arg Gly Asp Arg Cys
                645                 650                 655
Asn Leu Glu Asp Arg Asp Arg Ser Gln Leu Ser Pro Leu Leu His Ser
            660                 665                 670
Thr Thr Glu Trp Ala Ile Leu Pro Cys Thr Tyr Ser Asp Leu Pro Ala
            675                 680                 685
Leu Ser Thr Gly Leu Leu His Leu His Gln Asn Ile Val Asp Val Gln
            690                 695                 700
Phe Met Tyr Gly Leu Ser Pro Ala Leu Thr Lys Tyr Ile Val Arg Trp
705                 710                 715                 720
Glu Trp Val Val Leu Leu Phe Leu Leu Leu Ala Asp Ala Arg Val Cys
                725                 730                 735
Ala Cys Leu Trp Met Leu Ile Leu Leu Gly Gln Ala Glu Ala
            740                 745                 750
```

<210> SEQ ID NO 37
<211> LENGTH: 750
<212> TYPE: PRT
<213> ORGANISM: Hepatitis C virus

<400> SEQUENCE: 37

| | | | | | | | | | | | | | | |
|---|---|---|---|---|---|---|---|---|---|---|---|---|---|---|
| Met | Ser | Thr | Asn | Pro | Lys | Pro | Gln | Arg | Lys | Thr | Lys | Arg | Asn | Thr | Asn |
| 1 | | | | 5 | | | | | 10 | | | | | 15 | |
| Arg | Arg | Pro | Gln | Asp | Val | Lys | Phe | Pro | Gly | Gly | Gly | Gln | Ile | Val | Gly |
| | | | 20 | | | | | 25 | | | | | 30 | | |
| Gly | Val | Tyr | Leu | Leu | Pro | Arg | Arg | Gly | Pro | Arg | Leu | Gly | Val | Arg | Ala |
| | | | 35 | | | | | 40 | | | | | 45 | | |
| Thr | Arg | Lys | Thr | Ser | Glu | Arg | Ser | Gln | Pro | Arg | Gly | Arg | Arg | Gln | Pro |
| | 50 | | | | | 55 | | | | | 60 | | | | |
| Ile | Pro | Lys | Asp | Arg | Arg | Ser | Thr | Gly | Lys | Ser | Trp | Gly | Lys | Pro | Gly |
| 65 | | | | | 70 | | | | | 75 | | | | | 80 |
| Tyr | Pro | Trp | Pro | Leu | Tyr | Gly | Asn | Glu | Gly | Leu | Gly | Trp | Ala | Gly | Trp |
| | | | | 85 | | | | | 90 | | | | | 95 | |
| Leu | Leu | Ser | Pro | Arg | Gly | Ser | Arg | Pro | Ser | Trp | Gly | Pro | Asn | Asp | Pro |
| | | | 100 | | | | | 105 | | | | | 110 | | |
| Arg | His | Arg | Ser | Arg | Asn | Val | Gly | Lys | Val | Ile | Asp | Thr | Leu | Thr | Cys |
| | | | 115 | | | | | 120 | | | | | 125 | | |
| Gly | Phe | Ala | Asp | Leu | Met | Gly | Tyr | Ile | Pro | Val | Val | Gly | Ala | Pro | Leu |
| | 130 | | | | | 135 | | | | | 140 | | | | |
| Gly | Gly | Val | Ala | Arg | Ala | Leu | Ala | His | Gly | Val | Arg | Val | Leu | Glu | Asp |
| 145 | | | | | 150 | | | | | 155 | | | | | 160 |
| Gly | Val | Asn | Phe | Ala | Thr | Gly | Asn | Leu | Pro | Gly | Cys | Ser | Phe | Ser | Ile |
| | | | | 165 | | | | | 170 | | | | | 175 | |
| Phe | Leu | Leu | Ala | Leu | Leu | Ser | Cys | Ile | Thr | Thr | Pro | Val | Ser | Ala | Ala |
| | | | 180 | | | | | 185 | | | | | 190 | | |
| Glu | Val | Lys | Asn | Ile | Ser | Thr | Gly | Tyr | Met | Val | Thr | Asn | Asp | Cys | Thr |
| | | | 195 | | | | | 200 | | | | | 205 | | |
| Asn | Asp | Ser | Ile | Thr | Trp | Gln | Leu | Gln | Ala | Ala | Val | Leu | His | Val | Pro |
| | 210 | | | | | 215 | | | | | 220 | | | | |
| Gly | Cys | Val | Pro | Cys | Glu | Lys | Val | Gly | Asn | Ala | Ser | Gln | Cys | Trp | Ile |
| 225 | | | | | 230 | | | | | 235 | | | | | 240 |
| Pro | Val | Ser | Pro | Asn | Val | Ala | Val | Gln | Arg | Pro | Gly | Ala | Leu | Thr | Gln |
| | | | | 245 | | | | | 250 | | | | | 255 | |
| Gly | Leu | Arg | Thr | His | Ile | Asp | Met | Val | Val | Met | Ser | Ala | Thr | Leu | Cys |
| | | | 260 | | | | | 265 | | | | | 270 | | |
| Ser | Ala | Leu | Tyr | Val | Gly | Asp | Leu | Cys | Gly | Gly | Val | Met | Leu | Ala | Ala |
| | | | 275 | | | | | 280 | | | | | 285 | | |
| Gln | Met | Phe | Ile | Val | Ser | Pro | Gln | His | His | Trp | Phe | Val | Gln | Asp | Cys |
| | 290 | | | | | 295 | | | | | 300 | | | | |
| Asn | Cys | Ser | Ile | Tyr | Pro | Gly | Thr | Ile | Thr | Gly | His | Arg | Met | Ala | Trp |
| 305 | | | | | 310 | | | | | 315 | | | | | 320 |
| Asp | Met | Met | Met | Asn | Trp | Ser | Pro | Thr | Ala | Thr | Met | Ile | Leu | Ala | Tyr |
| | | | | 325 | | | | | 330 | | | | | 335 | |
| Ala | Met | Arg | Val | Pro | Glu | Val | Ile | Ile | Asp | Ile | Ser | Gly | Ala | His |
| | | | 340 | | | | | 345 | | | | | 350 | | |
| Trp | Gly | Val | Met | Phe | Gly | Leu | Ala | Tyr | Phe | Ser | Met | Gln | Gly | Ala | Trp |
| | | | 355 | | | | | 360 | | | | | 365 | | |
| Ala | Lys | Val | Val | Val | Ile | Leu | Leu | Leu | Ala | Ala | Gly | Val | Asp | Ala | Arg |
| | 370 | | | | | 375 | | | | | 380 | | | | |

```
Thr His Thr Val Gly Gly Ser Ala Ala Gln Thr Thr Gly Arg Leu Thr
385                 390                 395                 400

Ser Leu Phe Asp Met Gly Pro Arg Gln Lys Ile Gln Leu Val Asn Thr
            405                 410                 415

Asn Gly Ser Trp His Ile Asn Arg Thr Ala Leu Asn Cys Asn Asp Ser
        420                 425                 430

Leu His Thr Gly Phe Ile Ala Ser Leu Phe Tyr Thr His Ser Phe Asn
            435                 440                 445

Ser Ser Gly Cys Pro Glu Arg Met Ser Ala Cys Arg Ser Ile Glu Ala
        450                 455                 460

Phe Arg Val Gly Trp Gly Ala Leu Gln Tyr Glu Asp Asn Val Thr Asn
465                 470                 475                 480

Pro Glu Asp Met Arg Pro Tyr Cys Trp His Tyr Pro Pro Arg Gln Cys
            485                 490                 495

Gly Val Val Ser Ala Lys Thr Val Cys Gly Pro Val Tyr Cys Phe Thr
            500                 505                 510

Pro Ser Pro Val Val Gly Thr Thr Asp Arg Leu Gly Ala Pro Thr
            515                 520                 525

Tyr Thr Trp Gly Glu Asn Glu Thr Asp Val Phe Leu Leu Asn Ser Thr
530                 535                 540

Arg Pro Pro Leu Gly Ser Trp Phe Gly Cys Thr Trp Met Asn Ser Ser
545                 550                 555                 560

Gly Tyr Thr Lys Thr Cys Gly Ala Pro Pro Cys Arg Thr Arg Ala Asp
            565                 570                 575

Phe Asn Ala Ser Thr Asp Leu Leu Cys Pro Thr Asp Cys Phe Arg Lys
            580                 585                 590

His Pro Asp Thr Thr Tyr Leu Lys Cys Gly Ser Gly Pro Trp Leu Thr
            595                 600                 605

Pro Arg Cys Leu Ile Asp Tyr Pro Tyr Arg Leu Trp His Tyr Pro Cys
            610                 615                 620

Thr Val Asn Tyr Thr Ile Phe Lys Ile Arg Met Tyr Val Gly Gly Val
625                 630                 635                 640

Glu His Arg Leu Thr Ala Ala Cys Asn Phe Thr Arg Gly Asp Arg Cys
            645                 650                 655

Asn Leu Glu Asp Arg Asp Arg Ser Gln Leu Ser Pro Leu Leu His Ser
            660                 665                 670

Thr Thr Glu Trp Ala Ile Leu Pro Cys Ser Tyr Ser Asp Leu Pro Ala
            675                 680                 685

Leu Ser Thr Gly Leu Leu His Leu His Gln Asn Ile Val Asp Val Gln
            690                 695                 700

Phe Met Tyr Gly Leu Ser Pro Ala Leu Thr Lys Tyr Ile Val Arg Trp
705                 710                 715                 720

Glu Trp Val Ile Leu Leu Phe Leu Leu Leu Ala Asp Ala Arg Val Cys
            725                 730                 735

Ala Cys Leu Trp Met Leu Ile Leu Leu Gly Gln Ala Glu Ala
            740                 745                 750

<210> SEQ ID NO 38
<211> LENGTH: 750
<212> TYPE: PRT
<213> ORGANISM: Hepatitis C virus

<400> SEQUENCE: 38

Met Ser Thr Asn Pro Lys Pro Gln Arg Lys Thr Lys Arg Asn Thr Asn
```

-continued

```
1               5                   10                  15
Arg Arg Pro Gln Asp Val Lys Phe Pro Gly Gly Gln Ile Val Gly
                20                  25                  30
Gly Val Tyr Leu Leu Pro Arg Arg Gly Pro Arg Leu Gly Val Arg Ala
                35                  40                  45
Thr Arg Lys Thr Ser Glu Arg Ser Gln Pro Arg Gly Arg Arg Gln Pro
                50                  55                  60
Ile Pro Lys Asp Arg Arg Ser Thr Gly Lys Ser Trp Gly Lys Pro Gly
65                  70                  75                  80
Tyr Pro Trp Pro Leu Tyr Gly Asn Glu Gly Cys Gly Trp Ala Gly Trp
                        85                  90                  95
Leu Leu Ser Pro Arg Gly Ser Arg Pro Thr Trp Gly Pro Thr Asp Pro
                        100                 105                 110
Arg His Arg Ser Arg Asn Leu Gly Arg Val Ile Asp Thr Ile Thr Cys
                        115                 120                 125
Gly Phe Ala Asp Leu Met Gly Tyr Ile Pro Val Val Gly Ala Pro Val
                        130                 135                 140
Gly Gly Val Ala Arg Ala Leu Ala His Gly Val Arg Val Leu Glu Asp
145                 150                 155                 160
Gly Ile Asn Tyr Ala Thr Gly Asn Leu Pro Gly Cys Ser Phe Ser Ile
                        165                 170                 175
Phe Leu Leu Ala Leu Leu Ser Cys Val Thr Val Pro Val Ser Ala Val
                        180                 185                 190
Glu Val Arg Asn Ile Ser Ser Ser Tyr Tyr Ala Thr Asn Asp Cys Ser
                        195                 200                 205
Asn Asn Ser Ile Thr Trp Gln Leu Thr Asp Ala Val Leu His Leu Pro
210                 215                 220
Gly Cys Val Pro Cys Glu Asn Asp Asn Gly Thr Leu His Cys Trp Ile
225                 230                 235                 240
Gln Val Thr Pro Asn Val Ala Val Lys His Arg Gly Ala Leu Thr Arg
                        245                 250                 255
Ser Leu Arg Thr His Val Asp Met Ile Val Met Ala Ala Thr Ala Cys
                        260                 265                 270
Ser Ala Leu Tyr Val Gly Asp Val Cys Gly Ala Val Met Ile Leu Ser
                        275                 280                 285
Gln Ala Phe Met Val Ser Pro Gln Arg His Asn Phe Thr Gln Glu Cys
                        290                 295                 300
Asn Cys Ser Ile Tyr Gln Gly His Ile Thr Gly His Arg Met Ala Trp
305                 310                 315                 320
Asp Met Met Leu Ser Trp Ser Pro Thr Leu Thr Met Ile Leu Ala Tyr
                        325                 330                 335
Ala Ala Arg Val Pro Glu Leu Val Leu Glu Ile Ile Phe Gly Gly His
                        340                 345                 350
Trp Gly Val Val Phe Gly Leu Ala Tyr Phe Ser Met Gln Gly Ala Trp
                        355                 360                 365
Ala Lys Val Ile Ala Ile Leu Leu Leu Val Ala Gly Val Asp Ala Thr
                        370                 375                 380
Thr Tyr Ser Ser Gly Gln Glu Ala Gly Arg Thr Val Ala Gly Phe Ala
385                 390                 395                 400
Gly Leu Phe Thr Thr Gly Ala Lys Gln Asn Leu Tyr Leu Ile Asn Thr
                        405                 410                 415
Asn Gly Ser Trp His Ile Asn Arg Thr Ala Leu Asn Cys Asn Asp Ser
                        420                 425                 430
```

```
Leu Gln Thr Gly Phe Leu Ala Ser Leu Phe Tyr Thr His Lys Phe Asn
            435                 440                 445

Ser Ser Gly Cys Pro Glu Arg Leu Ser Cys Arg Gly Leu Asp Asp
    450                 455                 460

Phe Arg Ile Gly Trp Gly Thr Leu Glu Tyr Glu Thr Asn Val Thr Asn
465                 470                 475                 480

Asp Gly Asp Met Arg Pro Tyr Cys Trp His Tyr Pro Arg Pro Cys
                485                 490                 495

Gly Ile Val Pro Ala Arg Thr Val Cys Gly Pro Val Tyr Cys Phe Thr
                500                 505                 510

Pro Ser Pro Val Val Gly Thr Thr Asp Lys Gln Gly Val Pro Thr
            515                 520                 525

Tyr Thr Trp Gly Glu Asn Glu Thr Asp Val Phe Leu Leu Asn Ser Thr
            530                 535                 540

Arg Pro Pro Arg Gly Ala Trp Phe Gly Cys Thr Trp Met Asn Gly Thr
545                 550                 555                 560

Gly Phe Thr Lys Thr Cys Gly Ala Pro Pro Cys Arg Ile Arg Lys Asp
                565                 570                 575

Tyr Asn Ser Thr Ile Asp Leu Leu Cys Pro Thr Asp Cys Phe Arg Lys
            580                 585                 590

His Pro Asp Ala Thr Tyr Leu Lys Cys Gly Ala Gly Pro Trp Leu Thr
            595                 600                 605

Pro Arg Cys Leu Val Asp Tyr Pro Tyr Arg Leu Trp His Tyr Pro Cys
            610                 615                 620

Thr Val Asn Phe Thr Ile Phe Lys Ala Arg Met Tyr Val Gly Gly Val
625                 630                 635                 640

Glu His Arg Phe Ser Ala Ala Cys Asn Phe Thr Arg Gly Asp Arg Cys
                645                 650                 655

Arg Leu Glu Asp Arg Asp Arg Gly Gln Gln Ser Pro Leu Leu His Ser
                660                 665                 670

Thr Thr Glu Trp Ala Val Leu Pro Cys Ser Phe Ser Asp Leu Pro Ala
            675                 680                 685

Leu Ser Thr Gly Leu Leu His Leu His Gln Asn Ile Val Asp Val Gln
            690                 695                 700

Tyr Leu Tyr Gly Leu Ser Pro Ala Leu Thr Arg Tyr Ile Val Lys Trp
705                 710                 715                 720

Glu Trp Val Ile Leu Leu Phe Leu Leu Leu Ala Asp Ala Arg Ile Cys
                725                 730                 735

Ala Cys Leu Trp Met Leu Ile Ile Leu Gly Gln Ala Glu Ala
                740                 745                 750

<210> SEQ ID NO 39
<211> LENGTH: 750
<212> TYPE: PRT
<213> ORGANISM: Hepatitis C virus

<400> SEQUENCE: 39

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
```

```
              50                  55                  60
Ile Pro Lys Asp Arg Arg Ser Thr Gly Lys Ser Trp Gly Lys Pro Gly
 65                  70                  75                  80

Tyr Pro Trp Pro Leu Tyr Gly Asn Glu Gly Cys Gly Trp Ala Gly Trp
                 85                  90                  95

Leu Leu Ser Pro Arg Gly Ser Arg Pro His Trp Gly Pro Thr Asp Pro
                100                 105                 110

Arg His Arg Ser Arg Asn Leu Gly Lys Val Ile Asp Thr Ile Thr Cys
                115                 120                 125

Gly Phe Ala Asp Leu Met Gly Tyr Ile Pro Val Ile Gly Ala Pro Val
130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Val Thr Val Pro Val Ser Ala Val
                180                 185                 190

Glu Val Arg Asn Ile Ser Ser Tyr Tyr Ala Thr Asn Asp Cys Ser
                195                 200                 205

Asn Asn Ser Ile Thr Trp Gln Leu Glu Asn Ala Val Leu His Leu Pro
210                 215                 220

Gly Cys Val Pro Cys Glu Asn Asp Asn Gly Thr Leu Arg Cys Trp Thr
225                 230                 235                 240

Gln Val Thr Pro Asn Val Ala Val Lys His Arg Gly Ala Leu Thr Gln
                245                 250                 255

Asn Leu Arg Thr His Val Asp Val Ile Val Ala Ala Thr Val Cys
                260                 265                 270

Ser Ala Leu Tyr Val Gly Asp Val Cys Gly Ala Val Met Ile Ala Ser
                275                 280                 285

Gln Ala Leu Ile Val Ser Pro Ala Arg His Asn Phe Thr Gln Glu Cys
290                 295                 300

Asn Cys Ser Ile Tyr Gln Gly Arg Ile Thr Gly His His Met Ala Trp
305                 310                 315                 320

Asp Met Met Leu Asn Trp Ser Pro Thr Ile Thr Met Ile Leu Ala Tyr
                325                 330                 335

Ala Ala Arg Ile Pro Glu Leu Val Leu Glu Val Ile Phe Gly Gly His
                340                 345                 350

Trp Gly Val Met Phe Gly Leu Ala Tyr Phe Ser Met Gln Gly Ala Trp
                355                 360                 365

Ala Lys Val Ile Val Ile Leu Leu Leu Val Ala Gly Val Asp Ala Arg
370                 375                 380

His His Thr Thr Gly Leu Gln Ala Gly Lys Thr Leu Ala Arg Val Thr
385                 390                 395                 400

Ser Leu Phe Ser Ile Gly Ala Lys Gln Asn Ile Gln Leu Ile Asn Thr
                405                 410                 415

Asn Gly Ser Trp His Ile Asn Arg Thr Ala Leu Asn Cys Asn Asp Ser
                420                 425                 430

Leu Gln Thr Gly Phe Ile Ala Ser Leu Phe Tyr Val Asn Asn Ile Asn
                435                 440                 445

Ser Ser Gly Cys Pro Glu Arg Met Ser Ser Cys Arg Glu Leu Asp Asp
450                 455                 460

Phe Arg Ile Gly Trp Gly Thr Leu Glu Tyr Glu Thr Asn Val Thr Asn
465                 470                 475                 480
```

```
Asp Glu Asp Met Arg Pro Tyr Cys Trp His Tyr Pro Pro Lys Pro Cys
                485                 490                 495

Gly Ile Val Pro Ala Arg Thr Val Cys Gly Pro Val Tyr Cys Phe Thr
                500                 505                 510

Pro Ser Pro Ile Val Val Gly Thr Thr Asp Lys Gln Gly Val Pro Thr
                515                 520                 525

Tyr Ser Trp Gly Glu Asn Glu Thr Asp Val Phe Leu Leu Asn Ser Thr
                530                 535                 540

Arg Pro Pro Arg Gly Ser Trp Phe Gly Cys Thr Trp Met Asn Gly Thr
545                 550                 555                 560

Gly Phe Thr Lys Thr Cys Gly Ala Pro Pro Cys Arg Ile Arg Arg Asp
                565                 570                 575

Tyr Asn Ser Thr Leu Asp Leu Leu Cys Pro Thr Asp Cys Phe Arg Lys
                580                 585                 590

His Pro Asp Thr Thr Tyr Leu Lys Cys Gly Ser Gly Pro Trp Leu Thr
                595                 600                 605

Pro Lys Cys Leu Val Glu Tyr Pro Tyr Arg Leu Trp His Tyr Pro Cys
                610                 615                 620

Thr Val Asn Phe Thr Ile Phe Lys Val Arg Met Tyr Val Gly Ala Val
625                 630                 635                 640

Glu His Arg Phe Ser Ala Ala Cys Asn Phe Thr Arg Gly Asp Arg Cys
                645                 650                 655

Arg Leu Glu Asp Arg Asp Arg Gly Gln Gln Ser Pro Leu Leu His Ser
                660                 665                 670

Thr Thr Glu Trp Ala Val Leu Pro Cys Ser Phe Ser Asp Leu Pro Ala
                675                 680                 685

Leu Ser Thr Gly Leu Leu His Leu His Gln Asn Ile Val Asp Val Gln
                690                 695                 700

Tyr Leu Tyr Gly Leu Ser Pro Ala Ile Thr Arg Tyr Ile Val Lys Trp
705                 710                 715                 720

Glu Trp Val Val Leu Leu Phe Leu Leu Leu Ala Asp Ala Arg Val Cys
                725                 730                 735

Ala Cys Leu Trp Met Leu Ile Ile Leu Gly Gln Ala Glu Ala
                740                 745                 750

<210> SEQ ID NO 40
<211> LENGTH: 750
<212> TYPE: PRT
<213> ORGANISM: Hepatitis C virus

<400> SEQUENCE: 40

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
                35                  40                  45

Thr Arg Lys Thr Ser Glu Arg Ser Gln Pro Arg Gly Arg Arg Gln Pro
                50                  55                  60

Ile Pro Lys Asp Arg Arg Ser Thr Gly Lys Ser Trp Gly Lys Pro Gly
65              70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Thr Trp Gly Pro Thr Asp Pro
```

-continued

```
                100             105             110
Arg His Arg Ser Arg Asn Leu Gly Arg Val Ile Asp Thr Ile Thr Cys
            115             120             125

Gly Phe Ala Asp Leu Met Gly Tyr Ile Pro Val Val Gly Ala Pro Val
130             135             140

Gly Gly Val Ala Arg Ala Leu Ala His Gly Val Arg Val Leu Glu Asp
145             150             155             160

Gly Ile Asn Tyr Ala Thr Gly Asn Leu Pro Gly Cys Ser Phe Ser Ile
            165             170             175

Phe Leu Leu Ala Leu Leu Ser Cys Cys Thr Val Pro Val Ser Ala Val
            180             185             190

Glu Val Arg Asn Ile Ser Thr Ser Tyr Tyr Ala Thr Asn Asp Cys Ser
            195             200             205

Asn Thr Ser Ile Thr Trp Gln Leu Thr Asn Ala Val Leu His Leu Pro
            210             215             220

Gly Cys Val Pro Cys Glu Asn Asp Asn Gly Thr Leu Arg Cys Trp Ile
225             230             235             240

Gln Val Thr Pro Asn Val Ala Val Lys His Arg Gly Ala Leu Thr His
            245             250             255

Asn Leu Arg Thr His Val Asp Val Ile Val Met Ala Ala Thr Val Cys
            260             265             270

Ser Ala Leu Tyr Val Gly Asp Ile Cys Gly Ala Val Met Ile Val Ser
            275             280             285

Gln Ala Phe Ile Ile Ser Pro Glu Arg His Asn Phe Thr Gln Glu Cys
            290             295             300

Asn Cys Ser Met Tyr Gln Gly His Ile Thr Gly His Arg Met Ala Trp
305             310             315             320

Asp Met Met Leu Asn Trp Ser Pro Thr Leu Thr Met Ile Leu Ala Tyr
            325             330             335

Ala Ala Arg Val Pro Glu Leu Val Leu Glu Val Ile Phe Gly Gly His
            340             345             350

Trp Gly Val Val Phe Gly Leu Ala Tyr Phe Ser Met Gln Gly Ala Trp
            355             360             365

Ala Lys Val Ile Ala Ile Leu Leu Leu Val Ala Gly Val Asp Ala Asn
            370             375             380

Thr Tyr Ser Ser Gly Val Thr Gly His Thr Thr Ser Thr Phe Ala
385             390             395             400

Asn Ile Phe Ser Val Gly Pro Ser Gln Lys Ile Asn Leu Ile Asn Thr
            405             410             415

Asn Gly Ser Trp His Ile Asn Arg Thr Ala Leu Asn Cys Asn Asp Ser
            420             425             430

Leu Gln Thr Gly Phe Leu Ala Ser Leu Phe Tyr Val Arg Asn Phe Asn
            435             440             445

Ser Ser Gly Cys Arg Glu Arg Leu Ser Ser Cys Arg Arg Leu Asp Asp
450             455             460

Phe Arg Ile Gly Trp Gly Thr Leu Glu Tyr Glu Thr Asn Val Thr Asn
465             470             475             480

Asp Glu Asp Met Arg Pro Tyr Cys Trp His Tyr Pro Pro Lys Pro Cys
            485             490             495

Gly Ile Val Ser Ala Arg Thr Val Cys Gly Pro Val Tyr Cys Phe Thr
            500             505             510

Pro Ser Pro Val Val Gly Thr Thr Asp Arg Gln Gly Val Pro Thr
            515             520             525
```

```
Tyr Ser Trp Gly Glu Asn Glu Thr Asp Val Phe Leu Leu Asn Ser Thr
        530                 535                 540

Arg Pro Pro Arg Gly Ala Trp Phe Gly Cys Thr Trp Met Asn Gly Thr
545                 550                 555                 560

Gly Phe Thr Lys Thr Cys Gly Ala Pro Cys Arg Ile Arg Arg Asp
                565                 570                 575

Tyr Asn Ser Thr Leu Asp Leu Leu Cys Pro Thr Asp Cys Phe Arg Lys
                580                 585                 590

His Pro Asp Thr Thr Tyr Leu Lys Cys Gly Ala Gly Pro Trp Leu Thr
                595                 600                 605

Pro Lys Cys Leu Val Asp Tyr Pro Tyr Arg Leu Trp His Tyr Pro Cys
                610                 615                 620

Thr Val Asn Phe Thr Ile Phe Lys Val Arg Met Tyr Val Gly Gly Val
625                 630                 635                 640

Glu His Arg Leu Ser Ala Ala Cys Asn Phe Thr Arg Gly Asp Arg Cys
                645                 650                 655

Gly Leu Glu Asp Arg Asp Arg Gly Gln Gln Ser Pro Leu Leu His Ser
                660                 665                 670

Thr Thr Glu Trp Ala Val Leu Pro Cys Ser Phe Ser Asp Leu Pro Ala
                675                 680                 685

Leu Ser Thr Gly Leu Leu His Leu His Gln Asn Ile Val Asp Val Gln
690                 695                 700

Tyr Leu Tyr Gly Leu Ser Pro Ala Ile Thr Arg Tyr Ile Val Lys Trp
705                 710                 715                 720

Glu Trp Val Val Leu Leu Phe Leu Leu Leu Ala Asp Ala Arg Val Cys
                725                 730                 735

Ala Cys Leu Trp Met Leu Ile Ile Leu Gly Gln Ala Glu Ala
                740                 745                 750

<210> SEQ ID NO 41
<211> LENGTH: 750
<212> TYPE: PRT
<213> ORGANISM: Hepatitis C virus

<400> SEQUENCE: 41

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
                35                  40                  45

Thr Arg Lys Thr Ser Glu Arg Ser Gln Pro Arg Gly Arg Arg Gln Pro
        50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Thr Trp Gly Pro Ser Asp Pro
                100                 105                 110

Arg His Arg Ser Arg Asn Leu Gly Arg Val Ile Asp Thr Ile Thr Cys
                115                 120                 125

Gly Phe Ala Asp Leu Met Gly Tyr Ile Pro Val Val Gly Ala Pro Val
                130                 135                 140

Gly Gly Val Ala Arg Ala Leu Ala His Gly Val Arg Val Leu Glu Asp
```

```
            145                 150                 155                 160
Gly Ile Asn Tyr Ala Thr Arg Asn Leu Pro Gly Cys Ser Phe Ser Ile
                165                 170                 175

Phe Leu Leu Ala Leu Leu Ser Cys Val Thr Val Pro Val Ser Ser Val
                180                 185                 190

Glu Ile Arg Asn Ile Ser Thr Ser Tyr Tyr Ala Thr Asn Asp Cys Ser
                195                 200                 205

Asn Asn Ser Ile Thr Trp Gln Leu Thr Asn Ala Val Leu His Leu Pro
    210                 215                 220

Gly Cys Val Pro Cys Glu Asn Asp Asn Gly Thr Leu Arg Cys Trp Ile
225                 230                 235                 240

Gln Val Thr Pro Asn Val Ala Val Lys His Arg Gly Ala Leu Thr His
                245                 250                 255

Asn Leu Arg Ala His Val Asp Val Ile Val Met Ala Ala Thr Val Cys
                260                 265                 270

Ser Ala Leu Tyr Val Gly Asp Val Cys Gly Ala Val Met Ile Val Ser
                275                 280                 285

Gln Ala Leu Ile Val Ser Pro Glu Arg His Asn Phe Thr Gln Glu Cys
    290                 295                 300

Asn Cys Ser Ile Tyr Gln Gly His Ile Thr Gly Gln Arg Met Ala Trp
305                 310                 315                 320

Asp Met Met Leu Asn Trp Ser Pro Thr Leu Thr Met Ile Leu Ala Tyr
                325                 330                 335

Ala Ala Arg Val Pro Glu Leu Val Leu Glu Ile Val Phe Gly Gly His
                340                 345                 350

Trp Gly Val Val Phe Gly Leu Ala Tyr Phe Ser Met Gln Gly Ala Trp
                355                 360                 365

Ala Lys Val Ile Ala Ile Leu Leu Val Ala Gly Val Asp Ala Thr
                370                 375                 380

Thr Tyr Ser Thr Gly Ala Thr Val Gly Arg Thr Val Gly Ser Phe Ala
385                 390                 395                 400

Gly Leu Phe Lys Leu Gly Ala Gln Gln Asn Val Gln Leu Ile Asn Thr
                405                 410                 415

Asn Gly Ser Trp His Ile Asn Arg Thr Ala Leu Asn Cys Asn Asp Ser
                420                 425                 430

Leu His Thr Gly Phe Met Ala Ala Leu Phe Tyr Ala Asn Lys Phe Asn
                435                 440                 445

Ser Ser Gly Cys Pro Glu Arg Leu Ser Ser Cys Arg Gly Leu Asp Asp
    450                 455                 460

Phe Arg Ile Gly Trp Gly Thr Leu Glu Tyr Glu Thr Asn Val Thr Asn
465                 470                 475                 480

Val Glu Asp Met Arg Pro Tyr Cys Trp His Tyr Pro Pro Lys Pro Cys
                485                 490                 495

Gly Ile Val Pro Ala Gln Ser Val Cys Gly Pro Val Tyr Cys Phe Thr
                500                 505                 510

Pro Ser Pro Val Val Val Gly Thr Thr Asp Arg Gln Gly Val Pro Thr
                515                 520                 525

Tyr Asn Trp Gly Asp Asn Glu Thr Asp Val Phe Leu Leu Asn Ser Thr
                530                 535                 540

Arg Pro Pro Arg Gly Ala Trp Phe Gly Cys Thr Trp Met Asn Gly Thr
545                 550                 555                 560

Gly Phe Thr Lys Thr Cys Gly Ala Pro Pro Cys Arg Ile Arg Lys Asp
                565                 570                 575
```

```
Phe Asn Ser Thr Leu Asp Leu Leu Cys Pro Thr Asp Cys Phe Arg Lys
                580                 585                 590

His Pro Asp Ala Thr Tyr Val Lys Cys Gly Ala Gly Pro Trp Leu Thr
            595                 600                 605

Pro Arg Cys Leu Ile Asp Tyr Pro Tyr Arg Leu Trp His Tyr Pro Cys
        610                 615                 620

Thr Val Asn Phe Thr Ile Phe Lys Val Arg Met Tyr Val Gly Gly Val
625                 630                 635                 640

Glu His Arg Phe Ser Ala Ala Cys Asn Phe Thr Arg Gly Asp Arg Cys
                645                 650                 655

Arg Leu Glu Asp Arg Asp Arg Gly Gln Gln Ser Pro Leu Leu His Ser
            660                 665                 670

Thr Thr Glu Trp Ala Val Leu Pro Cys Ser Phe Ser Asp Leu Pro Ala
        675                 680                 685

Leu Ser Thr Gly Leu Leu His Leu His Gln Asn Ile Val Asp Val Gln
        690                 695                 700

Tyr Leu Tyr Gly Leu Ser Pro Ala Val Thr Lys Tyr Ile Val Lys Trp
705                 710                 715                 720

Glu Trp Val Val Leu Leu Phe Leu Leu Leu Ala Asp Ala Arg Ile Cys
                725                 730                 735

Ala Cys Leu Trp Met Leu Ile Ile Leu Gly Gln Ala Glu Ala
            740                 745                 750

<210> SEQ ID NO 42
<211> LENGTH: 750
<212> TYPE: PRT
<213> ORGANISM: Hepatitis C virus
<220> FEATURE:
<221> NAME/KEY: misc_feature
<222> LOCATION: (203)..(203)
<223> OTHER INFORMATION: Xaa can be any amino acid
<220> FEATURE:
<221> NAME/KEY: misc_feature
<222> LOCATION: (295)..(295)
<223> OTHER INFORMATION: Xaa can be any amino acid
<220> FEATURE:
<221> NAME/KEY: misc_feature
<222> LOCATION: (343)..(343)
<223> OTHER INFORMATION: Xaa can be any amino acid
<220> FEATURE:
<221> NAME/KEY: misc_feature
<222> LOCATION: (401)..(401)
<223> OTHER INFORMATION: Xaa can be any amino acid
<220> FEATURE:
<221> NAME/KEY: misc_feature
<222> LOCATION: (426)..(426)
<223> OTHER INFORMATION: Xaa can be any amino acid
<220> FEATURE:
<221> NAME/KEY: misc_feature
<222> LOCATION: (626)..(626)
<223> OTHER INFORMATION: Xaa can be any amino acid

<400> SEQUENCE: 42

Met Ser Thr Asp Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Ala Arg Lys Thr Ser Glu Arg Ser Gln Pro Arg Gly Arg Arg Gln Pro
    50                  55                  60

Ile Pro Lys Asp Arg Arg Ser Pro Gly Lys Ser Trp Gly Lys Pro Gly
```

|   |   |   |   |   |   |   |   |   |   |   |   |   |   |   |   |
|---|---|---|---|---|---|---|---|---|---|---|---|---|---|---|---|
| 65 | | | | 70 | | | | 75 | | | | 80 | | | |

Tyr Pro Trp Pro Leu Tyr Gly Asn Glu Gly Cys Gly Trp Ala Gly Trp
                  85                      90                  95

Leu Leu Ser Pro Arg Gly Ser Arg Pro Thr Trp Gly Pro Thr Asp Pro
        100              105                110

Arg His Arg Ser Arg Asn Leu Gly Lys Val Ile Asp Thr Ile Thr Cys
        115              120                125

Gly Phe Ala Asp Leu Met Gly Tyr Ile Pro Val Val Gly Ala Pro Val
130                135                  140

Gly Gly Val Ala Arg Ala Leu Ala His Gly Val Arg Val Leu Glu Asp
145                150              155                160

Gly Ile Asn Tyr Ala Thr Gly Asn Leu Pro Gly Cys Ser Phe Ser Ile
                165              170                175

Phe Leu Leu Ala Leu Leu Ser Cys Leu Thr Val Pro Ala Ser Ala Val
        180              185                190

Glu Val Arg Asn Ile Ser Ser Gly Tyr Tyr Xaa Thr Asn Asp Cys Ser
        195              200                205

Asn Ser Ser Ile Thr Trp Gln Leu Thr Asn Ala Val Leu His Leu Pro
210                215              220

Gly Cys Val Pro Cys Glu Asn Asp Asn Gly Thr Leu Arg Cys Trp Ile
225                230              235                240

Gln Val Thr Pro Asn Val Ala Val Lys Tyr Arg Gly Ala Leu Thr His
                245              250                255

Asn Leu Arg Thr His Val Asp Met Ile Val Met Ala Ala Thr Val Cys
        260              265                270

Ser Ala Leu Tyr Val Gly Asp Val Cys Gly Ala Val Met Ile Val Ser
        275              280                285

Gln Ala Phe Ile Met Ser Xaa Glu Arg His Asn Phe Thr Gln Glu Cys
        290              295                300

Asn Cys Ser Ile Tyr Gln Gly His Ile Thr Gly His Arg Met Ala Trp
305                310              315                320

Asp Met Met Leu Gly Trp Ser Pro Thr Leu Thr Met Ile Leu Ala Tyr
                325              330                335

Ala Ala Arg Val Pro Glu Xaa Val Leu Glu Val Val Phe Gly Gly His
        340              345                350

Trp Gly Val Val Phe Gly Leu Ala Tyr Phe Ser Met Gln Gly Ala Trp
                355              360                365

Ala Lys Val Ile Ala Ile Leu Leu Leu Val Ala Gly Val Asp Ala Gly
        370              375                380

Thr Tyr Ser Ser Gly Ala Thr Ile Gly Gln Gly Thr Arg Gly Leu Val
385                390              395                400

Xaa Leu Phe Ser Ala Gly Pro Ser Gln Lys Ile Ser Leu Ile Asn Thr
                405              410                415

Asn Gly Ser Trp His Ile Asn Arg Thr Xaa Leu Asn Cys Asn Asp Ser
                420              425                430

Leu Gln Thr Gly Phe Ile Ala Ser Leu Phe Tyr Ala Lys Ser Phe Asn
        435              440                445

Ser Ser Gly Cys Pro Glu Arg Leu Ser Ser Cys Arg Gly Leu Asp Asp
450                455              460

Phe Arg Ile Gly Trp Gly Thr Leu Glu Tyr Glu Asn Asn Val Thr Asn
465                470              475                480

Asp Glu Asp Met Arg Pro Tyr Cys Trp His Tyr Pro Pro Lys Pro Cys
                485              490                495

```
Gly Ile Val Pro Ala Arg Thr Val Cys Gly Pro Val Tyr Cys Phe Thr
            500                 505                 510
Pro Ser Pro Val Val Gly Thr Asp Lys Gln Gly Val Pro Thr
        515                 520                 525
Tyr Ser Trp Gly Glu Asn Glu Thr Asp Val Phe Leu Leu Asn Ser Thr
    530                 535                 540
Arg Pro Pro Gln Gly Ala Trp Phe Gly Cys Thr Trp Met Asn Gly Thr
545                 550                 555                 560
Gly Phe Thr Lys Thr Cys Gly Ala Pro Pro Cys Arg Ile Arg Arg Asp
                565                 570                 575
His Thr Ser Thr Leu Asp Leu Leu Cys Pro Thr Asp Cys Phe Arg Lys
            580                 585                 590
His Pro Asp Thr Thr Tyr Leu Lys Cys Gly Ala Gly Pro Trp Leu Thr
        595                 600                 605
Pro Lys Cys Leu Val Asp Tyr Pro Tyr Arg Leu Trp His Tyr Pro Cys
    610                 615                 620
Thr Xaa Asn Phe Thr Ile Phe Lys Val Arg Met Tyr Val Gly Gly Val
625                 630                 635                 640
Glu His Arg Phe Ser Ala Ala Cys Asn Phe Thr Arg Gly Asp Arg Cys
                645                 650                 655
Arg Leu Glu Asp Arg Asp Arg Gly Gln Gln Ser Pro Leu Leu His Ser
            660                 665                 670
Thr Thr Glu Trp Ala Val Leu Pro Cys Ser Phe Ser Asp Leu Pro Ala
        675                 680                 685
Leu Ser Thr Gly Leu Leu His Leu His Gln Asn Ile Val Asp Val Gln
    690                 695                 700
Tyr Leu Tyr Gly Leu Ser Pro Ala Ile Thr Lys Tyr Ile Val Lys Trp
705                 710                 715                 720
Glu Trp Val Ile Leu Leu Phe Leu Leu Leu Ala Asp Ala Arg Val Cys
                725                 730                 735
Ala Cys Leu Trp Met Leu Ile Ile Leu Gly Gln Ala Glu Ala
            740                 745                 750

<210> SEQ ID NO 43
<211> LENGTH: 752
<212> TYPE: PRT
<213> ORGANISM: Hepatitis C virus
<220> FEATURE:
<221> NAME/KEY: misc_feature
<222> LOCATION: (431)..(431)
<223> OTHER INFORMATION: Xaa can be any amino acid
<220> FEATURE:
<221> NAME/KEY: misc_feature
<222> LOCATION: (466)..(466)
<223> OTHER INFORMATION: Xaa can be any amino acid

<400> SEQUENCE: 43

Met Ser Thr Leu Pro Lys Pro Gln Arg Lys Thr Lys Arg Asn Thr Ile
1               5                   10                  15
Arg Arg Pro Gln Asp Val Lys Phe Pro Gly Gly Gly Gln Ile Val Gly
            20                  25                  30
Gly Val Tyr Val Leu Pro Arg Arg Gly Pro Arg Leu Gly Val Arg Ala
        35                  40                  45
Thr Arg Lys Thr Ser Glu Arg Ser Gln Pro Arg Gly Arg Arg Gln Pro
    50                  55                  60
Ile Pro Lys Ala Arg Arg Ser Glu Gly Arg Ser Trp Ala Gln Pro Gly
65                  70                  75                  80
```

```
Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Val
        130                 135                 140

Gly Gly Val Ala Arg Ala Leu Ala His Gly Val Arg Ala Leu Glu Asp
145                 150                 155                 160

Gly Ile Asn Phe Ala Thr Gly Asn Leu Pro Gly Cys Ser Phe Ser Ile
            165                 170                 175

Phe Leu Leu Ala Leu Phe Ser Cys Leu Ile His Pro Ala Ala Ser Leu
            180                 185                 190

Glu Trp Arg Asn Thr Ser Gly Leu Tyr Val Leu Thr Asn Asp Cys Ser
        195                 200                 205

Asn Ser Ser Ile Val Tyr Glu Ala Asp Val Ile Leu His Thr Pro
210                 215                 220

Gly Cys Val Pro Cys Val Gln Asp Gly Asn Thr Ser Thr Cys Trp Thr
225                 230                 235                 240

Pro Val Thr Pro Thr Val Ala Val Arg Tyr Val Gly Ala Thr Thr Ala
            245                 250                 255

Ser Ile Arg Ser His Val Asp Leu Leu Val Gly Ala Ala Thr Met Cys
            260                 265                 270

Ser Ala Leu Tyr Val Gly Asp Met Cys Gly Ala Val Phe Leu Val Gly
        275                 280                 285

Gln Ala Phe Thr Phe Arg Pro Arg Arg His Gln Thr Val Gln Thr Cys
        290                 295                 300

Asn Cys Ser Leu Tyr Pro Gly His Leu Ser Gly His Arg Met Ala Trp
305                 310                 315                 320

Asp Met Met Met Asn Trp Ser Pro Ala Val Gly Met Val Val Ala His
            325                 330                 335

Val Leu Arg Leu Pro Gln Thr Leu Phe Asp Ile Ile Ala Gly Ala His
            340                 345                 350

Trp Gly Ile Leu Ala Gly Leu Ala Tyr Tyr Ser Met Gln Gly Asn Trp
        355                 360                 365

Ala Lys Val Ala Ile Ile Met Val Met Phe Ser Gly Val Asp Ala Thr
        370                 375                 380

Thr Tyr Thr Thr Gly Gly Ser Ala Ala Arg Gly Ala Arg Gly Leu Thr
385                 390                 395                 400

Ser Leu Phe Ser Val Gly Ala Lys Gln Lys Leu Gln Leu Val Asn Thr
            405                 410                 415

Asn Gly Ser Trp His Ile Asn Ser Thr Ala Leu Asn Cys Asn Xaa Ser
        420                 425                 430

Ile Asn Thr Gly Phe Ile Ala Gly Leu Phe Tyr His Lys Phe Asn
        435                 440                 445

Ser Thr Gly Cys Pro Gln Arg Leu Ser Ser Cys Lys Pro Ile Thr Phe
450                 455                 460

Phe Xaa Gln Gly Trp Gly Pro Leu Thr Asp Ala Asn Ile Thr Gly Pro
465                 470                 475                 480

Ser Asp Asp Lys Pro Tyr Cys Trp His Tyr Ala Pro Arg Pro Cys Asp
            485                 490                 495
```

```
Val Val Pro Ala Ser Ser Val Cys Gly Pro Val Tyr Cys Phe Thr Pro
            500                 505                 510

Ser Pro Val Val Val Gly Thr Thr Asp Ala Lys Gly Val Pro Thr Tyr
        515                 520                 525

Thr Trp Gly Glu Asn Glu Thr Asp Val Phe Leu Leu Glu Ser Leu Arg
    530                 535                 540

Pro Pro Ser Gly Arg Trp Phe Gly Cys Thr Trp Met Asn Ser Thr Gly
545                 550                 555                 560

Phe Val Lys Thr Cys Gly Ala Pro Pro Cys Asn Ile Tyr Gly Gly Gly
                565                 570                 575

Gly Asn Pro His Asn Glu Ser Asp Leu Phe Cys Pro Thr Asp Cys Phe
            580                 585                 590

Arg Lys His Pro Glu Ala Thr Tyr Ser Arg Cys Gly Ala Gly Pro Trp
        595                 600                 605

Leu Thr Pro Arg Cys Met Val Asp Tyr Pro Tyr Arg Leu Trp His Tyr
    610                 615                 620

Pro Cys Thr Val Asn Phe Thr Leu Phe Lys Val Arg Met Phe Val Gly
625                 630                 635                 640

Gly Phe Glu His Arg Phe Thr Ala Ala Cys Asn Trp Thr Arg Gly Glu
                645                 650                 655

Arg Cys Asp Ile Glu Asp Arg Asp Arg Ser Glu Gln His Pro Leu Leu
            660                 665                 670

His Ser Thr Thr Glu Leu Ala Ile Leu Pro Cys Ser Phe Thr Pro Met
        675                 680                 685

Pro Ala Leu Ser Thr Gly Leu Ile His Leu His Gln Asn Ile Val Asp
690                 695                 700

Val Gln Tyr Leu Tyr Gly Val Gly Ser Gly Met Val Gly Trp Ala Leu
705                 710                 715                 720

Lys Trp Glu Phe Val Ile Leu Val Phe Leu Leu Ala Asp Ala Arg
                725                 730                 735

Val Cys Val Ala Leu Trp Leu Met Leu Met Ile Ser Gln Ala Glu Ala
            740                 745                 750
```

<210> SEQ ID NO 44
<211> LENGTH: 752
<212> TYPE: PRT
<213> ORGANISM: Hepatitis C virus

<400> SEQUENCE: 44

```
Met Ser Thr Leu Pro Lys Pro Gln Arg Lys Thr Lys Arg Asn Thr Ile
1               5                   10                  15

Arg Arg Pro Gln Asp Val Lys Phe Pro Gly Gly Gly Gln Ile Val Gly
            20                  25                  30

Gly Val Tyr Val Leu Pro Arg Arg Gly Pro Arg Leu Gly Val Arg Ala
        35                  40                  45

Thr Arg Lys Thr Ser Glu Arg Ser Gln Pro Arg Glu Arg Arg Gln Pro
    50                  55                  60

Ile Pro Lys Ala Arg Arg Ser Asp Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125
```

```
Gly Phe Ala Asp Leu Met Gly Tyr Ile Pro Ile Val Gly Ala Pro Val
            130                 135                 140

Gly Gly Val Ala Arg Ala Leu Ala His Gly Val Arg Ala Leu Glu Asp
145                 150                 155                 160

Gly Ile Asn Phe Ala Thr Gly Asn Leu Pro Gly Cys Ser Phe Ser Ile
                165                 170                 175

Phe Leu Leu Ala Leu Leu Ser Cys Leu Ile His Pro Ala Ala Ser Leu
            180                 185                 190

Glu Trp Arg Asn Thr Ser Gly Leu Tyr Ile Leu Thr Asn Asp Cys Pro
        195                 200                 205

Asn Ser Ser Ile Val Tyr Glu Ala Asp Val Ile Leu His Thr Pro
210                 215                 220

Gly Cys Ile Pro Cys Val Gln Asp Gly Asn Thr Ser Thr Cys Trp Thr
225                 230                 235                 240

Ser Val Ser Pro Thr Val Ala Val Arg Tyr Val Gly Ala Thr Thr Ala
                245                 250                 255

Ser Ile Arg Ser His Val Asp Leu Leu Val Gly Ala Ala Thr Leu Cys
                260                 265                 270

Ser Ala Leu Tyr Val Gly Asp Met Cys Gly Ala Val Phe Leu Val Gly
        275                 280                 285

Gln Ala Phe Thr Phe Arg Pro Arg Arg His Gln Thr Val Gln Thr Cys
    290                 295                 300

Asn Cys Ser Leu Tyr Pro Gly His Leu Thr Gly His Arg Met Ala Trp
305                 310                 315                 320

Asp Met Met Met Asn Trp Ser Pro Ala Val Gly Met Val Val Ala His
                325                 330                 335

Val Leu Arg Met Pro Gln Thr Val Phe Asp Ile Ile Ala Gly Ala His
                340                 345                 350

Trp Gly Ile Leu Ala Gly Leu Ala Tyr Tyr Ser Met Gln Gly Asn Trp
        355                 360                 365

Ala Lys Val Ala Ile Ile Met Val Met Phe Ser Gly Val Asp Ala Glu
    370                 375                 380

Thr His Thr Thr Gly Gly Thr Ala Ala Arg Asn Ala Phe Thr Leu Thr
385                 390                 395                 400

Gly Leu Phe Thr Gln Gly Ala Arg Gln Lys Leu Glu Leu Ile Asn Thr
                405                 410                 415

Asn Gly Ser Trp His Ile Asn Arg Thr Ala Leu Asn Cys Asn Glu Ser
                420                 425                 430

Leu Asn Thr Gly Phe Ile Ala Gly Leu Phe Tyr Leu His Lys Phe Asn
        435                 440                 445

Ser Thr Gly Cys Pro Glu Arg Leu Ser Ser Cys Lys Pro Ile Thr Phe
    450                 455                 460

Phe Arg Gln Gly Trp Gly Ser Leu Thr Asp Ala Asn Ile Thr Gly Pro
465                 470                 475                 480

Ser Asp Asp Lys Pro Tyr Cys Trp His Tyr Ala Pro Arg Pro Cys Glu
                485                 490                 495

Val Val Pro Ala Leu Asn Val Cys Gly Pro Val Tyr Cys Phe Thr Pro
                500                 505                 510

Ser Pro Val Val Val Gly Thr Thr Asp Arg Gln Gly Val Pro Thr Tyr
        515                 520                 525

Thr Trp Gly Glu Asn Glu Thr Asp Val Phe Leu Leu Arg Ser Leu Arg
530                 535                 540
```

```
Pro Pro Ser Gly Gln Trp Phe Gly Cys Thr Trp Met Asn Ser Thr Gly
545                 550                 555                 560

Phe Val Lys Thr Cys Gly Ala Pro Pro Cys Asp Ile Tyr Gly Gly Gly
                565                 570                 575

Gly Asn Arg Cys Asn Glu Ser Asp Leu Phe Cys Pro Thr Asp Cys Phe
            580                 585                 590

Arg Lys His Pro Glu Ala Thr Tyr Ser Arg Cys Gly Ala Gly Pro Trp
        595                 600                 605

Leu Thr Pro Arg Cys Leu Val Asp Tyr Pro Tyr Arg Leu Trp His Tyr
    610                 615                 620

Pro Cys Thr Val Asn Phe Thr Leu Phe Lys Val Arg Met Phe Val Gly
625                 630                 635                 640

Gly Phe Glu His Arg Phe Thr Ala Ala Cys Asn Trp Thr Arg Gly Glu
                645                 650                 655

Arg Cys Asn Ile Glu Asp Arg Asp Arg Ser Glu Gln His Pro Leu Leu
            660                 665                 670

His Ser Thr Thr Glu Leu Ala Ile Leu Pro Cys Ser Phe Thr Pro Met
        675                 680                 685

Pro Ala Leu Ser Thr Gly Leu Ile His Leu His Gln Asn Ile Val Asp
690                 695                 700

Val Gln Tyr Leu Tyr Gly Val Gly Ser Gly Val Val Gly Trp Ala Leu
705                 710                 715                 720

Arg Trp Glu Phe Val Val Leu Val Phe Leu Leu Ala Asp Ala Arg
                725                 730                 735

Val Cys Val Ala Leu Trp Leu Met Leu Met Ile Ser Gln Ala Glu Ala
            740                 745                 750

<210> SEQ ID NO 45
<211> LENGTH: 752
<212> TYPE: PRT
<213> ORGANISM: Hepatitis C virus

<400> SEQUENCE: 45

Met Ser Thr Leu Pro Lys Pro Gln Arg Lys Thr Lys Arg Asn Thr Ile
1               5                   10                  15

Arg Arg Pro Gln Asp Val Lys Phe Pro Gly Gly Gly Gln Ile Val Gly
            20                  25                  30

Gly Val Tyr Val Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Ser Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Val
    130                 135                 140

Gly Gly Val Ala Arg Ala Leu Ala His Gly Val Arg Ala Leu Glu Asp
145                 150                 155                 160

Gly Ile Asn Phe Ala Thr Gly Asn Leu Pro Gly Cys Ser Phe Ser Ile
                165                 170                 175
```

```
Phe Leu Leu Ala Leu Phe Ser Cys Leu Val His Pro Ala Ala Ser Leu
            180                 185                 190

Glu Trp Arg Asn Thr Ser Gly Leu Tyr Val Leu Thr Asn Asp Cys Ser
            195                 200                 205

Asn Ser Ser Ile Val Tyr Glu Ala Asp Asp Val Ile Leu His Thr Pro
        210                 215                 220

Gly Cys Val Pro Cys Val Gln Asp Asp Asn Thr Ser Thr Cys Trp Thr
225                 230                 235                 240

Pro Val Thr Pro Thr Val Ala Val Arg Tyr Val Gly Ala Thr Thr Ala
                245                 250                 255

Ser Ile Arg Ser His Val Asp Leu Leu Val Gly Ala Ala Thr Leu Cys
            260                 265                 270

Ser Ala Leu Tyr Val Gly Asp Met Cys Gly Ala Val Phe Leu Val Gly
            275                 280                 285

Gln Ala Phe Thr Phe Arg Pro Arg His Gln Thr Val Gln Thr Cys
        290                 295                 300

Asn Cys Ser Leu Tyr Pro Gly His Val Ser Gly His Arg Met Ala Trp
305                 310                 315                 320

Asp Met Met Met Asn Trp Ser Pro Ala Val Gly Met Val Ala His
                    325                 330                 335

Ile Leu Arg Leu Pro Gln Thr Leu Phe Asp Ile Leu Ala Gly Ala His
            340                 345                 350

Trp Gly Ile Leu Ala Gly Leu Ala Tyr Tyr Ser Met Gln Gly Asn Trp
            355                 360                 365

Ala Lys Val Ala Ile Val Met Ile Met Phe Ser Gly Val Asp Ala Glu
            370                 375                 380

Thr Tyr Val Thr Gly Gly Ser Val Ala His Ser Ala Arg Gly Leu Thr
385                 390                 395                 400

Ser Leu Phe Ser Met Gly Ala Lys Gln Lys Leu Gln Leu Val Asn Thr
                405                 410                 415

Asn Gly Ser Trp His Ile Asn Ser Thr Ala Leu Asn Cys Asn Glu Ser
                420                 425                 430

Ile Asn Thr Gly Phe Ile Ala Gly Leu Phe Tyr Tyr His Lys Phe Asn
            435                 440                 445

Ser Thr Gly Cys Pro Gln Arg Leu Ser Ser Cys Lys Pro Ile Ile Ser
        450                 455                 460

Phe Arg Gln Gly Trp Gly Pro Leu Thr Asp Ala Asn Ile Thr Gly Pro
465                 470                 475                 480

Ser Asp Asp Arg Pro Tyr Cys Trp His Tyr Ala Pro Arg Pro Cys Ser
                485                 490                 495

Val Val Pro Ala Ser Ser Val Cys Gly Pro Val Tyr Cys Phe Thr Pro
            500                 505                 510

Ser Pro Val Val Gly Thr Thr Asp Ile Lys Gly Lys Pro Thr Tyr
            515                 520                 525

Asn Trp Gly Glu Asn Glu Thr Asp Val Phe Leu Leu Glu Ser Leu Arg
            530                 535                 540

Pro Pro Ser Gly Arg Trp Phe Gly Cys Ala Trp Met Asn Ser Thr Gly
545                 550                 555                 560

Phe Leu Lys Thr Cys Gly Ala Pro Pro Cys Asn Ile Tyr Gly Gly Glu
                565                 570                 575

Gly Asp Pro Glu Asn Glu Thr Asp Leu Phe Cys Pro Thr Asp Cys Phe
                580                 585                 590
```

```
Arg Lys His Pro Glu Ala Thr Tyr Ser Arg Cys Gly Ala Gly Pro Trp
            595                 600                 605

Leu Thr Pro Arg Cys Met Val Asp Tyr Pro Tyr Arg Leu Trp His Tyr
610                 615                 620

Pro Cys Thr Val Asn Phe Thr Leu Phe Lys Val Arg Met Phe Val Gly
625                 630                 635                 640

Gly Phe Glu His Arg Phe Thr Ala Ala Cys Asn Trp Thr Arg Gly Glu
                645                 650                 655

Arg Cys Asn Ile Glu Asp Arg Asp Arg Ser Glu Gln His Pro Leu Leu
            660                 665                 670

His Ser Thr Thr Glu Leu Ala Ile Leu Pro Cys Ser Phe Thr Pro Met
        675                 680                 685

Pro Ala Leu Ser Thr Gly Leu Ile His Leu His Gln Asn Ile Val Asp
690                 695                 700

Val Gln Tyr Leu Tyr Gly Val Gly Ser Asp Met Val Gly Trp Ala Leu
705                 710                 715                 720

Lys Trp Glu Phe Val Ile Leu Val Phe Leu Leu Ala Asp Ala Arg
                725                 730                 735

Val Cys Val Ala Leu Trp Leu Met Leu Met Val Ser Gln Ala Glu Ala
            740                 745                 750

<210> SEQ ID NO 46
<211> LENGTH: 752
<212> TYPE: PRT
<213> ORGANISM: Hepatitis C virus

<400> SEQUENCE: 46

Met Ser Thr Leu Pro Lys Pro Gln Arg Lys Thr Lys Arg Asn Thr Ile
1               5                   10                  15

Arg Arg Pro Gln Asp Val Lys Phe Pro Gly Gly Gly Gln Ile Val Gly
                20                  25                  30

Gly Val Tyr Val Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Ser Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Val
130                 135                 140

Gly Gly Val Ala Arg Ala Leu Ala His Gly Val Arg Ala Leu Glu Asp
145                 150                 155                 160

Gly Ile Asn Phe Ala Thr Gly Asn Leu Pro Gly Cys Ser Phe Ser Ile
                165                 170                 175

Phe Leu Leu Ala Leu Phe Ser Cys Leu Ile His Pro Ala Ala Ser Leu
            180                 185                 190

Glu Trp Arg Asn Thr Ser Gly Leu Tyr Val Leu Thr Asn Asp Cys Ser
        195                 200                 205

Asn Ser Ser Ile Val Tyr Glu Ala Asp Asp Val Ile Leu His Thr Pro
210                 215                 220
```

```
Gly Cys Val Pro Cys Val Gln Asp Gly Asn Thr Ser Thr Cys Trp Thr
225                 230                 235                 240

Pro Val Thr Pro Thr Val Ala Val Arg Tyr Val Gly Ala Thr Thr Ala
            245                 250                 255

Ser Ile Arg Ser His Val Asp Leu Leu Val Gly Ala Ala Thr Met Cys
            260                 265                 270

Ser Ala Leu Tyr Val Gly Asp Met Cys Gly Ala Val Phe Leu Val Gly
            275                 280                 285

Gln Ala Phe Thr Phe Arg Pro Arg His Gln Thr Val Gln Thr Cys
            290                 295                 300

Asn Cys Ser Leu Tyr Pro Gly His Leu Ser Gly His Arg Met Ala Trp
305                 310                 315                 320

Asp Met Met Met Asn Trp Ser Pro Ala Val Gly Met Val Val Ala His
                325                 330                 335

Val Leu Arg Leu Pro Gln Thr Leu Phe Asp Ile Met Ala Gly Ala His
            340                 345                 350

Trp Gly Ile Leu Ala Gly Leu Ala Tyr Tyr Ser Met Gln Gly Asn Trp
            355                 360                 365

Ala Lys Val Ala Ile Ile Met Val Met Phe Ser Gly Val Asp Ala His
            370                 375                 380

Thr Tyr Thr Thr Gly Gly Thr Ala Ser Arg His Thr Gln Ala Phe Ala
385                 390                 395                 400

Gly Leu Phe Asp Ile Gly Pro Gln Gln Lys Leu Gln Leu Val Asn Thr
            405                 410                 415

Asn Gly Ser Trp His Ile Asn Ser Thr Ala Leu Asn Cys Asn Glu Ser
            420                 425                 430

Ile Asn Thr Gly Phe Ile Ala Gly Leu Phe Tyr Tyr His Lys Phe Asn
            435                 440                 445

Ser Thr Gly Cys Pro Gln Arg Leu Ser Ser Cys Lys Pro Ile Thr Phe
450                 455                 460

Phe Arg Gln Gly Trp Gly Pro Leu Thr Asp Ala Asn Ile Thr Gly Pro
465                 470                 475                 480

Ser Asp Asp Arg Pro Tyr Cys Trp His Tyr Ala Pro Arg Pro Cys Asp
                485                 490                 495

Ile Val Pro Ala Ser Ser Val Cys Gly Pro Val Tyr Cys Phe Thr Pro
            500                 505                 510

Ser Pro Val Val Val Gly Thr Thr Asp Ala Arg Gly Val Pro Thr Tyr
            515                 520                 525

Thr Trp Gly Glu Asn Glu Lys Asp Val Phe Leu Leu Lys Ser Gln Arg
530                 535                 540

Pro Pro Ser Gly Arg Trp Phe Gly Cys Ser Trp Met Asn Ser Thr Gly
545                 550                 555                 560

Phe Leu Lys Thr Cys Gly Ala Pro Pro Cys Asn Ile Tyr Gly Gly Glu
                565                 570                 575

Gly Asn Pro His Asn Glu Ser Asp Leu Phe Cys Pro Thr Asp Cys Phe
            580                 585                 590

Arg Lys His Pro Glu Thr Thr Tyr Ser Arg Cys Gly Ala Gly Pro Trp
            595                 600                 605

Leu Thr Pro Arg Cys Met Val Asp Tyr Pro Tyr Arg Leu Trp His Tyr
            610                 615                 620

Pro Cys Thr Val Asp Phe Arg Leu Phe Lys Val Arg Met Phe Val Gly
625                 630                 635                 640
```

```
Gly Phe Glu His Arg Phe Thr Ala Ala Cys Asn Trp Thr Arg Gly Glu
                645                 650                 655

Arg Cys Asp Ile Glu Asp Arg Asp Arg Ser Glu Gln His Pro Leu Leu
            660                 665                 670

His Ser Thr Thr Glu Leu Ala Ile Leu Pro Cys Ser Phe Thr Pro Met
        675                 680                 685

Pro Ala Leu Ser Thr Gly Leu Ile His Leu His Gln Asn Ile Val Asp
690                 695                 700

Val Gln Tyr Leu Tyr Gly Val Gly Ser Gly Met Val Gly Trp Ala Leu
705                 710                 715                 720

Lys Trp Glu Phe Val Ile Leu Val Phe Leu Leu Leu Ala Asp Ala Arg
                725                 730                 735

Val Cys Val Ala Leu Trp Leu Met Leu Met Ile Ser Gln Thr Glu Ala
            740                 745                 750

<210> SEQ ID NO 47
<211> LENGTH: 752
<212> TYPE: PRT
<213> ORGANISM: Hepatitis C virus

<400> SEQUENCE: 47

Met Ser Thr Leu Pro Lys Pro Gln Arg Lys Thr Lys Arg Asn Thr Ile
1               5                   10                  15

Arg Arg Pro Gln Asp Val Lys Phe Pro Gly Gly Gly Gln Ile Val Gly
            20                  25                  30

Gly Val Tyr Val Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
50                  55                  60

Ile Pro Lys Ala Arg Arg Ser Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Gln Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Val
    130                 135                 140

Gly Gly Val Ala Arg Ala Leu Ala His Gly Val Arg Ala Leu Glu Asp
145                 150                 155                 160

Gly Ile Asn Phe Ala Thr Gly Asn Leu Pro Gly Cys Ser Phe Ser Ile
                165                 170                 175

Phe Leu Leu Ala Leu Phe Ser Cys Leu Ile His Pro Ala Ala Ser Leu
            180                 185                 190

Glu Trp Arg Asn Thr Ser Gly Leu Tyr Val Leu Thr Asn Asp Cys Ser
        195                 200                 205

Asn Ser Ser Ile Val Tyr Glu Ala Asp Asp Val Ile Leu His Thr Pro
    210                 215                 220

Gly Cys Val Pro Cys Val Gln Asp Gly Asn Thr Ser Thr Cys Trp Thr
225                 230                 235                 240

Pro Val Thr Pro Thr Val Ala Val Arg Tyr Val Gly Ala Thr Thr Ala
                245                 250                 255

Ser Ile Arg Ser His Val Asp Leu Leu Val Gly Ala Ala Thr Met Cys
            260                 265                 270
```

```
Ser Ala Leu Tyr Val Gly Asp Met Cys Gly Ala Val Phe Leu Val Gly
    275                 280                 285

Gln Ala Phe Thr Phe Arg Pro Arg His Gln Thr Val Gln Thr Cys
290                 295                 300

Asn Cys Ser Leu Tyr Pro Gly His Leu Ser Gly His Arg Met Ala Trp
305                 310                 315                 320

Asp Met Met Met Asn Trp Ser Pro Ala Val Gly Met Val Val Ser His
                325                 330                 335

Val Leu Arg Leu Pro Gln Thr Leu Phe Asp Ile Ile Ala Gly Ala His
            340                 345                 350

Trp Gly Ile Leu Ala Gly Leu Ala Tyr Tyr Ser Met Gln Gly Asn Trp
        355                 360                 365

Ala Lys Val Ala Val Ile Met Val Met Phe Ser Gly Val Asp Ala Glu
    370                 375                 380

Thr Tyr Ile Thr Gly Gly Ser Ala Ala His Gly Val Ser Thr Leu Thr
385                 390                 395                 400

Ser Leu Phe Ser Ser Gly Pro Gln Gln Lys Leu Gln Leu Val Lys Thr
                405                 410                 415

Asn Gly Ser Trp His Ile Asn Ser Thr Ala Leu Asn Cys Asn Glu Ser
            420                 425                 430

Ile Asn Thr Gly Phe Ile Ala Gly Leu Phe Tyr Tyr His Lys Phe Asn
        435                 440                 445

Ser Thr Gly Cys Pro Gln Arg Leu Ser Ser Cys Lys Pro Ile Thr Phe
    450                 455                 460

Phe Arg Gln Gly Trp Gly Ser Leu Thr Asp Ala Asn Val Thr Gly Ala
465                 470                 475                 480

Ser Ala Asp Lys Pro Tyr Cys Trp His Tyr Ala Pro Arg Pro Cys Asp
                485                 490                 495

Val Val Pro Ala Leu Asn Val Cys Gly Pro Val Tyr Cys Phe Thr Pro
            500                 505                 510

Ser Pro Val Val Gly Thr Thr Asp Arg Lys Gly Val Pro Thr Tyr
        515                 520                 525

Asn Trp Gly Glu Asn Glu Ser Asp Val Phe Leu Leu Glu Ser Leu Arg
    530                 535                 540

Pro Pro Ser Gly Arg Trp Phe Gly Cys Ala Trp Met Asn Ser Thr Gly
545                 550                 555                 560

Phe Leu Lys Thr Cys Gly Ala Pro Pro Cys Asn Ile Tyr Gly Gly Gly
                565                 570                 575

Gly Asn Pro Asn Asn Glu Ser His Leu Phe Cys Pro Thr Asp Cys Phe
            580                 585                 590

Arg Lys His Pro Asp Ala Thr Tyr Ser Arg Cys Gly Ala Gly Pro Trp
        595                 600                 605

Leu Thr Pro Arg Cys Met Val Asp Tyr Pro Tyr Arg Leu Trp His Tyr
    610                 615                 620

Pro Cys Thr Val Asn Phe Thr Leu Phe Lys Val Arg Met Phe Val Gly
625                 630                 635                 640

Gly Phe Glu His Arg Phe Thr Ala Ala Cys Asn Trp Thr Arg Gly Glu
                645                 650                 655

Arg Cys Asn Ile Glu Asp Arg Asp Arg Ser Glu Gln His Pro Leu Leu
            660                 665                 670

His Ser Thr Thr Glu Leu Ala Ile Leu Pro Cys Ser Phe Thr Pro Met
        675                 680                 685
```

```
Pro Ala Leu Ser Thr Gly Leu Ile His Leu His Gln Asn Ile Val Asp
    690             695                 700

Val Gln Tyr Leu Tyr Gly Val Gly Ser Gly Met Val Gly Trp Ala Leu
705             710                 715                 720

Lys Trp Glu Phe Val Ile Leu Ile Phe Leu Leu Leu Ala Asp Ala Arg
                725                 730                 735

Val Cys Val Ala Leu Trp Leu Met Leu Met Ile Ser Gln Ala Glu Ala
            740                 745                 750

<210> SEQ ID NO 48
<211> LENGTH: 752
<212> TYPE: PRT
<213> ORGANISM: Hepatitis C virus

<400> SEQUENCE: 48

Met Ser Thr Leu Pro Lys Pro Gln Arg Lys Thr Lys Arg Asn Thr Ile
1               5                   10                  15

Arg Arg Pro Gln Asp Val Lys Phe Pro Gly Gly Gly Gln Ile Val Gly
                20                  25                  30

Gly Val Tyr Val Leu Pro Arg Arg Gly Pro Arg Leu Gly Val Cys Ala
            35                  40                  45

Thr Arg Lys Thr Ser Glu Arg Ser Gln Pro Arg Arg Arg Arg Gln Pro
    50                  55                  60

Ile Pro Lys Ala Arg Gln Ser Gly Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Val
    130                 135                 140

Gly Gly Val Ala Arg Ala Leu Ala His Gly Val Arg Ala Leu Glu Asp
145                 150                 155                 160

Gly Ile Asn Phe Ala Thr Gly Asn Leu Pro Gly Cys Ser Phe Ser Ile
                165                 170                 175

Phe Leu Leu Ala Leu Phe Ser Cys Leu Ile His Pro Ala Ala Ser Leu
            180                 185                 190

Glu Trp Arg Asn Thr Ser Gly Leu Tyr Val Leu Thr Asn Asp Cys Ser
        195                 200                 205

Asn Ser Ser Ile Val Tyr Glu Ala Asp Asp Val Ile Leu His Thr Pro
    210                 215                 220

Gly Cys Val Pro Cys Val Gln Asn Asp Asn Ile Ser Thr Cys Trp Thr
225                 230                 235                 240

Pro Val Thr Pro Thr Val Ala Val Arg Tyr Val Gly Ala Thr Thr Ala
                245                 250                 255

Ser Ile Arg Ser His Val Asp Leu Leu Val Gly Ala Ala Thr Met Cys
            260                 265                 270

Ser Ala Leu Tyr Val Gly Asp Met Cys Gly Ala Val Phe Leu Val Gly
        275                 280                 285

Gln Ala Phe Thr Phe Arg Pro Arg Arg His Gln Thr Val Gln Thr Cys
    290                 295                 300

Asn Cys Ser Leu Tyr Pro Gly His Leu Ser Gly His Arg Met Ala Trp
305                 310                 315                 320
```

```
Asp Met Met Met Asn Trp Phe Pro Ala Leu Gly Met Ala Val Ala His
            325                 330                 335

Val Leu Arg Val Pro Gln Thr Leu Phe Asp Ile Ile Ala Gly Ala His
            340                 345                 350

Trp Gly Ile Leu Ala Gly Leu Ala Tyr Tyr Ser Met Gln Gly Asn Trp
            355                 360                 365

Ala Lys Val Ala Ile Ile Met Val Met Phe Ser Gly Val Asp Ala Val
370                 375                 380

Thr Tyr Thr Thr Gly Gly Ser Ala Ala His Ala Thr Arg Gly Leu Thr
385                 390                 395                 400

Ser Leu Phe Ser Val Gly Ala Gln Gln Lys Leu Gln Leu Val Asn Thr
            405                 410                 415

Asn Gly Ser Trp His Ile Asn Ser Thr Ala Leu Asn Cys Asn Glu Ser
            420                 425                 430

Ile Asn Thr Gly Phe Ile Ala Gly Leu Phe Tyr Tyr His Arg Phe Asn
            435                 440                 445

Ser Thr Gly Cys Pro Gln Arg Leu Ser Ser Cys Lys Pro Ile Thr Phe
            450                 455                 460

Phe Lys Gln Gly Trp Gly Pro Leu Thr Asp Ala Asn Ile Ser Gly Pro
465                 470                 475                 480

Ser Asp Asp Lys Pro Tyr Cys Trp His Tyr Ala Pro Arg Pro Cys Lys
            485                 490                 495

Val Val Pro Ala Ser Gly Val Cys Gly Pro Val Tyr Cys Phe Thr Pro
            500                 505                 510

Ser Pro Val Val Gly Thr Thr Asp Ala Lys Gly Val Pro Thr Tyr
            515                 520                 525

Thr Trp Gly Ala Asn Asp Thr Asp Val Phe Leu Leu Glu Ser Leu Arg
            530                 535                 540

Pro Pro Gly Gly Arg Trp Phe Gly Cys Thr Trp Met Asn Ser Thr Gly
545                 550                 555                 560

Phe Val Lys Thr Cys Gly Ala Ser Pro Cys Asp Ile Tyr Gly Gly Gly
            565                 570                 575

Gly Asn Ser Gly Asn Glu Ser Asp Leu Phe Cys Pro Thr Asp Cys Phe
            580                 585                 590

Arg Lys His Pro Glu Ala Thr Tyr Ser Arg Cys Gly Ala Gly Pro Trp
            595                 600                 605

Leu Thr Pro Arg Cys Met Val Asp Tyr Pro Tyr Arg Leu Trp His Tyr
            610                 615                 620

Pro Cys Thr Val Asn Phe Thr Leu Phe Lys Val Arg Met Phe Val Gly
625                 630                 635                 640

Gly Phe Glu His Arg Phe Thr Ala Ala Cys Asn Trp Thr Arg Gly Glu
            645                 650                 655

Arg Cys Asp Ile Glu Asp Arg Asp Arg Ser Glu Gln His Pro Leu Leu
            660                 665                 670

His Ser Thr Thr Glu Leu Ala Ile Leu Pro Cys Ser Phe Thr Pro Met
            675                 680                 685

Pro Ala Leu Ser Thr Gly Leu Ile His Leu His Gln Asn Ile Val Asp
            690                 695                 700

Val Gln Tyr Leu Tyr Gly Val Gly Ser Gly Met Val Gly Trp Ala Leu
705                 710                 715                 720

Lys Trp Glu Phe Val Ile Leu Ile Phe Leu Leu Leu Ala Asp Arg Arg
            725                 730                 735
```

```
Val Cys Val Ala Leu Trp Leu Met Leu Met Ile Thr Gln Ala Glu Ala
                740                 745                 750
```

<210> SEQ ID NO 49
<211> LENGTH: 752
<212> TYPE: PRT
<213> ORGANISM: Hepatitis C virus

<400> SEQUENCE: 49

```
Met Ser Thr Leu Pro Lys Pro Gln Arg Lys Thr Lys Arg Asn Thr Val
1               5                   10                  15

Cys Arg Pro Gln Asp Val Lys Phe Pro Gly Gly Gly Gln Ile Val Gly
            20                  25                  30

Gly Val Tyr Val Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Ser Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Val
    130                 135                 140

Gly Gly Val Ala Arg Ala Leu Ala His Gly Val Arg Ala Leu Glu Asp
145                 150                 155                 160

Gly Ile Asn Phe Ala Thr Gly Asn Leu Pro Gly Cys Ser Phe Ser Ile
                165                 170                 175

Phe Leu Leu Ala Leu Phe Ser Cys Leu Ile His Pro Ala Ala Ser Leu
            180                 185                 190

Glu Trp Arg Asn Val Ser Gly Leu Tyr Ile Leu Thr Asn Asp Cys Pro
        195                 200                 205

Asn Ser Ser Ile Val Tyr Glu Ala Asp Asp Val Ile Leu His Thr Pro
    210                 215                 220

Gly Cys Ile Pro Cys Val Gln Asp Gly Asn Thr Ser Thr Cys Trp Thr
225                 230                 235                 240

Ala Leu Thr Pro Thr Val Ala Val Arg Tyr Val Gly Ala Thr Thr Ala
                245                 250                 255

Ser Ile Arg Ser His Val Asp Leu Leu Val Gly Ala Ala Thr Met Cys
            260                 265                 270

Ser Ala Leu Tyr Val Gly Asp Met Cys Gly Ala Val Phe Leu Val Gly
        275                 280                 285

Gln Ala Phe Thr Phe Arg Pro Arg Arg His Gln Thr Val Gln Thr Cys
    290                 295                 300

Asn Cys Ser Leu Tyr Pro Gly His Leu Thr Gly His Arg Met Ala Trp
305                 310                 315                 320

Asp Met Met Met Asn Trp Ser Pro Ala Val Gly Met Val Ala His
                325                 330                 335

Val Leu Arg Leu Pro Gln Thr Leu Phe Asp Ile Ile Ala Gly Ala His
            340                 345                 350

Trp Gly Ile Leu Ala Gly Leu Ala Tyr Tyr Ser Met Gln Gly Asn Trp
        355                 360                 365
```

```
Ala Lys Val Ile Ile Met Val Met Phe Ser Gly Val Asp Ala Thr
    370                 375                 380

Thr His Val Thr Gly Thr Ala Gly Leu Thr Ala Phe Arg Leu Thr
385                 390                 395                 400

Gly Leu Phe Thr Val Gly Pro Gln Gln Lys Leu Gln Leu Val Asn Thr
                405                 410                 415

Asn Gly Ser Trp His Ile Asn Arg Thr Ala Leu Asn Cys Asn Asp Ser
            420                 425                 430

Leu Asn Thr Gly Phe Ile Ala Gly Leu Phe Arg Phe His Lys Phe Asn
            435                 440                 445

Ser Thr Gly Cys Pro Glu Met Leu Ser Ser Cys Lys Pro Ile Thr Ser
    450                 455                 460

Phe Lys Gln Gly Trp Gly Pro Leu Thr Asp Ala Asn Ile Thr Ile Pro
465                 470                 475                 480

Ser Asp Asp Arg Pro Tyr Cys Trp His Tyr Pro Pro Arg Ser Cys Glu
                485                 490                 495

Val Val Pro Ala Leu Ser Val Cys Gly Pro Val Tyr Cys Phe Thr Pro
                500                 505                 510

Ser Pro Val Val Val Gly Thr Thr Asp Ala Lys Gly Val Pro Thr Tyr
    515                 520                 525

Thr Trp Gly Glu Asn Glu Thr Asp Val Phe Leu Leu Lys Ser Leu Arg
530                 535                 540

Pro Pro Gly Gly Arg Trp Phe Gly Cys Thr Trp Met Asn Ser Thr Gly
545                 550                 555                 560

Phe Val Gln Thr Cys Gly Ala Pro Pro Cys Asn Ile Tyr Gly Gly Gly
                565                 570                 575

Gly Asp Leu Lys Asn Glu Ser Asp Leu Phe Cys Pro Thr Asp Cys Phe
            580                 585                 590

Arg Lys His Pro Glu Ala Thr Tyr Ser Arg Cys Gly Ala Gly Pro Trp
            595                 600                 605

Leu Thr Pro Arg Cys Met Val Asp Tyr Pro Tyr Arg Leu Trp His Tyr
    610                 615                 620

Pro Cys Thr Val Asn Phe Thr Leu Phe Lys Val Arg Met Phe Val Gly
625                 630                 635                 640

Gly Phe Glu His Arg Phe Thr Ala Ala Cys Asn Trp Thr Arg Gly Glu
                645                 650                 655

Arg Cys Asp Ile Glu Asp Arg Asp Arg Ser Glu Leu His Pro Leu Leu
            660                 665                 670

His Ser Thr Thr Glu Leu Ala Ile Leu Pro Cys Ser Phe Thr Pro Met
    675                 680                 685

Pro Ala Leu Ser Thr Gly Leu Ile His Leu His Gln Asn Ile Val Asp
690                 695                 700

Val Gln Tyr Leu Tyr Gly Val Gly Ser Gly Met Val Gly Trp Ala Val
705                 710                 715                 720

Lys Trp Glu Phe Val Ile Leu Val Phe Leu Leu Ala Asp Ala Arg
                725                 730                 735

Val Cys Val Ala Leu Trp Leu Met Leu Met Ile Ser Gln Ala Glu Ala
    740                 745                 750

<210> SEQ ID NO 50
<211> LENGTH: 752
<212> TYPE: PRT
<213> ORGANISM: Hepatitis C virus
```

```
<400> SEQUENCE: 50

Met Ser Thr Leu Pro Lys Pro Gln Arg Lys Thr Lys Arg Asn Thr Ile
1               5                   10                  15

Arg Arg Pro Gln Asp Val Lys Phe Pro Gly Gly Gly Gln Ile Val Gly
            20                  25                  30

Gly Val Tyr Val Leu Pro Arg Gly Pro Arg Leu Gly Val Arg Ala
                35                  40                  45

Thr Arg Lys Thr Ser Glu Arg Ser Gln Pro Arg Gly Arg Arg Gln Pro
        50                  55                  60

Ile Pro Lys Ala Arg Arg Ser Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Val
130                 135                 140

Gly Gly Val Ala Arg Ala Leu Ala His Gly Val Arg Ala Leu Glu Asp
145                 150                 155                 160

Gly Ile Asn Phe Ala Thr Gly Asn Leu Pro Gly Cys Ser Phe Ser Ile
                165                 170                 175

Phe Leu Leu Ala Leu Phe Ser Cys Leu Ile His Pro Ala Ala Ser Leu
            180                 185                 190

Gln Trp Arg Asn Thr Ser Gly Leu Tyr Val Leu Thr Asn Asp Cys Ser
        195                 200                 205

Asn Ser Ser Ile Val Tyr Glu Ala Asp Asp Val Ile Leu His Thr Pro
210                 215                 220

Gly Cys Val Pro Cys Val Gln Asp Gly Asn Thr Ser Thr Cys Trp Thr
225                 230                 235                 240

Pro Val Thr Pro Thr Val Ala Val Arg Tyr Val Gly Ala Thr Thr Ala
                245                 250                 255

Ser Ile Arg Ser His Val Asp Leu Leu Val Gly Ala Ala Thr Met Cys
            260                 265                 270

Ser Ala Leu Tyr Val Gly Asp Met Cys Gly Ala Val Phe Leu Val Gly
        275                 280                 285

Gln Ala Phe Thr Phe Arg Pro Arg Arg His Gln Thr Val Gln Thr Cys
290                 295                 300

Asn Cys Ser Leu Tyr Pro Gly His Leu Ser Gly His Arg Met Ala Trp
305                 310                 315                 320

Asp Met Met Met Asn Trp Ser Pro Ala Ala Gly Met Val Val Ala His
                325                 330                 335

Ile Leu Arg Leu Pro Gln Thr Leu Phe Asp Ile Ile Ala Gly Ala His
            340                 345                 350

Trp Gly Ile Leu Ala Gly Leu Ala Tyr Tyr Ser Met Gln Gly Asn Trp
        355                 360                 365

Ala Lys Val Ala Ile Ile Met Val Met Phe Ser Gly Val Asp Ala Thr
370                 375                 380

Thr Tyr Thr Ser Gly Gly Ser Val Ala Gln Gln Ala Arg Gly Leu Ala
385                 390                 395                 400

Asp Leu Phe Ser Val Gly Ala Lys Gln Asn Leu Gln Leu Val Asn Thr
            405                 410                 415
```

Asn Gly Ser Trp His Ile Asn Ser Thr Ala Leu Asn Cys Asp Asp Ser
            420                 425                 430

Ile Asn Thr Gly Phe Ile Ala Gly Leu Phe Tyr Tyr His Lys Phe Asn
        435                 440                 445

Ser Thr Gly Cys Pro Gln Arg Leu Ser Asp Cys Lys Pro Ile Thr Phe
    450                 455                 460

Phe Lys Gln Gly Trp Gly Pro Leu Thr Asp Ala Asn Ile Thr Gly Pro
465                 470                 475                 480

Ser Asp Asp Lys Pro Tyr Cys Trp His Tyr Ala Pro Arg Arg Cys Gly
                485                 490                 495

Val Val Pro Ala Ser Ser Val Cys Gly Pro Val Tyr Cys Phe Thr Pro
            500                 505                 510

Ser Pro Val Val Val Gly Thr Thr Asp Ala Lys Gly Val Pro Thr Tyr
        515                 520                 525

Thr Trp Gly Ala Asn Glu Thr Asp Val Phe Leu Leu Glu Ser Leu Arg
    530                 535                 540

Pro Pro Ser Gly Arg Trp Phe Gly Cys Ala Trp Met Asn Ser Thr Gly
545                 550                 555                 560

Phe Leu Lys Thr Cys Gly Ala Pro Pro Cys Asn Ile Tyr Gly Gly Gly
                565                 570                 575

Gly Asn Pro His Asn Glu Ser Asp Leu Phe Cys Pro Thr Asp Cys Phe
            580                 585                 590

Arg Lys His Pro Glu Ala Thr Tyr Ser Arg Cys Gly Ala Gly Pro Trp
        595                 600                 605

Leu Thr Pro Arg Cys Met Val Asp Tyr Pro Tyr Arg Leu Trp His Tyr
    610                 615                 620

Pro Cys Thr Val Asn Phe Thr Leu Phe Lys Met Arg Thr Phe Val Gly
625                 630                 635                 640

Gly Phe Glu His Arg Phe Thr Ala Ala Cys Asn Trp Thr Arg Gly Glu
                645                 650                 655

Arg Cys Asp Ile Glu Asp Arg Asp Arg Ser Glu Gln His Pro Leu Leu
            660                 665                 670

His Ser Thr Thr Glu Leu Ala Ile Leu Pro Cys Ser Phe Thr Pro Met
        675                 680                 685

Pro Ala Leu Ser Thr Gly Leu Ile His Leu His Gln Asn Ile Val Asp
    690                 695                 700

Val Gln Tyr Leu Tyr Gly Val Gly Ser Gly Met Val Gly Trp Ala Leu
705                 710                 715                 720

Lys Trp Glu Phe Val Ile Leu Val Phe Leu Leu Ala Asp Ala Arg
                725                 730                 735

Val Cys Val Ala Leu Trp Leu Met Leu Met Ile Ser Gln Ala Glu Ala
            740                 745                 750

<210> SEQ ID NO 51
<211> LENGTH: 752
<212> TYPE: PRT
<213> ORGANISM: Hepatitis C virus

<400> SEQUENCE: 51

Met Ser Thr Leu Pro Lys Pro Gln Arg Lys Thr Lys Arg Asn Thr Ile
1               5                   10                  15

Arg Arg Pro Gln Asp Val Lys Phe Pro Gly Gly Gly Gln Ile Val Gly
            20                  25                  30

Gly Val Tyr Val Leu Pro Arg Arg Gly Pro Arg Leu Gly Val Arg Ala

```
                35                  40                  45
Thr Arg Lys Thr Ser Glu Arg Ser Gln Pro Arg Gly Arg Gln Pro
 50                  55                  60

Ile Pro Lys Ala Arg Arg Ser Glu Gly Arg Ser Trp Ala Gln Pro Gly
 65                  70                  75                  80

Tyr Pro Trp Pro Leu Tyr Gly Asn Glu Gly Cys Gly Trp Ala Gly Trp
                 85                  90                  95

Leu Leu Ser Pro Arg Gly Ser Arg Pro Ser Trp Gly Pro Asn Asp Pro
                100                 105                 110

Arg Arg Arg Ser Arg Asn Leu Gly Lys Val Ile Asp Thr Leu Thr Cys
                115                 120                 125

Gly Phe Ala Asp Leu Met Gly Tyr Ile Pro Leu Val Gly Ala Pro Val
                130                 135                 140

Gly Gly Val Ala Arg Ala Leu Ala His Gly Val Arg Ala Leu Glu Asp
145                 150                 155                 160

Gly Ile Asn Phe Ala Thr Gly Asn Leu Pro Gly Cys Ser Phe Ser Ile
                165                 170                 175

Phe Leu Leu Ala Leu Phe Ser Cys Leu Ile His Pro Ala Ala Ser Leu
                180                 185                 190

Gln Trp Arg Asn Thr Ser Gly Leu Tyr Val Leu Thr Asn Asp Cys Ser
                195                 200                 205

Asn Ser Ser Ile Val Tyr Glu Ala Asp Asp Val Ile Leu His Thr Pro
210                 215                 220

Gly Cys Val Pro Cys Val Gln Asp Gly Asn Thr Ser Thr Cys Trp Thr
225                 230                 235                 240

Pro Val Thr Pro Thr Val Ala Val Arg Tyr Val Gly Ala Thr Thr Ala
                245                 250                 255

Ser Ile Arg Ser His Val Asp Leu Leu Val Gly Ala Ala Thr Met Cys
                260                 265                 270

Ser Ala Leu Tyr Val Gly Asp Met Cys Gly Ala Val Phe Leu Val Gly
                275                 280                 285

Gln Ala Phe Thr Phe Arg Pro Arg Arg His Gln Thr Val Gln Thr Cys
290                 295                 300

Asn Cys Ser Leu Tyr Pro Gly His Leu Ser Gly His Arg Met Ala Trp
305                 310                 315                 320

Asp Met Met Met Asn Trp Ser Pro Ala Ala Gly Met Val Val Ala His
                325                 330                 335

Ile Leu Arg Leu Pro Gln Thr Leu Phe Asp Ile Ile Ala Gly Ala His
                340                 345                 350

Trp Gly Ile Leu Ala Gly Leu Ala Tyr Tyr Ser Met Gln Gly Asn Trp
                355                 360                 365

Ala Lys Val Ala Ile Ile Met Val Met Phe Ser Gly Val Asp Ala Thr
                370                 375                 380

Thr Tyr Thr Ser Gly Gly Ser Val Ala Gln Gln Ala Arg Gly Leu Ala
385                 390                 395                 400

Asp Leu Phe Ser Val Gly Ala Lys Gln Asn Leu Gln Leu Val Asn Thr
                405                 410                 415

Asn Gly Ser Trp His Ile Asn Ser Thr Ala Leu Asn Cys Asp Asp Ser
                420                 425                 430

Ile Asn Thr Gly Phe Ile Ala Gly Leu Phe Tyr Tyr His Lys Phe Asn
                435                 440                 445

Ser Thr Gly Cys Pro Gln Arg Leu Ser Asp Cys Lys Pro Ile Thr Phe
                450                 455                 460
```

```
Phe Lys Gln Gly Trp Gly Pro Leu Thr Asp Ala Asn Ile Thr Gly Pro
465                 470                 475                 480

Ser Asp Asp Lys Pro Tyr Cys Trp His Tyr Ala Pro Arg Arg Cys Gly
                485                 490                 495

Val Val Pro Ala Ser Ser Val Cys Gly Pro Val Tyr Cys Phe Thr Pro
            500                 505                 510

Ser Pro Val Val Val Gly Thr Thr Asp Ala Lys Gly Val Pro Thr Tyr
            515                 520                 525

Thr Trp Gly Ala Asn Glu Thr Asp Val Phe Leu Leu Glu Ser Leu Arg
        530                 535                 540

Pro Pro Ser Gly Arg Trp Phe Gly Cys Ala Trp Met Asn Ser Thr Gly
545                 550                 555                 560

Phe Leu Lys Thr Cys Gly Ala Pro Pro Cys Asn Ile Tyr Gly Gly Gly
                565                 570                 575

Gly Asn Pro His Asn Glu Ser Asp Leu Phe Cys Pro Thr Asp Cys Phe
            580                 585                 590

Arg Lys His Pro Glu Ala Thr Tyr Ser Arg Cys Gly Ala Gly Pro Trp
            595                 600                 605

Leu Thr Pro Arg Cys Met Val Asp Tyr Pro Tyr Arg Leu Trp His Tyr
        610                 615                 620

Pro Cys Thr Val Asn Phe Thr Leu Phe Lys Met Arg Thr Phe Val Gly
625                 630                 635                 640

Gly Phe Glu His Arg Phe Thr Ala Ala Cys Asn Trp Thr Arg Gly Glu
                645                 650                 655

Arg Cys Asp Ile Glu Asp Arg Asp Arg Ser Glu Gln His Pro Leu Leu
            660                 665                 670

His Ser Thr Thr Glu Leu Ala Ile Leu Pro Cys Ser Phe Thr Pro Met
            675                 680                 685

Pro Ala Leu Ser Thr Gly Leu Ile His Leu His Gln Asn Ile Val Asp
        690                 695                 700

Val Gln Tyr Leu Tyr Gly Val Gly Ser Gly Met Val Gly Trp Ala Leu
705                 710                 715                 720

Lys Trp Glu Phe Val Ile Leu Val Phe Leu Leu Leu Ala Asp Ala Arg
                725                 730                 735

Val Cys Val Ala Leu Trp Leu Met Leu Met Ile Ser Gln Ala Glu Ala
            740                 745                 750

<210> SEQ ID NO 52
<211> LENGTH: 752
<212> TYPE: PRT
<213> ORGANISM: Hepatitis C virus

<400> SEQUENCE: 52

Met Ser Thr Leu Pro Lys Pro Gln Arg Lys Thr Lys Arg Asn Thr Ile
1               5                   10                  15

Arg Arg Pro Gln Asp Val Lys Phe Pro Gly Gly Gly Gln Ile Val Gly
                20                  25                  30

Gly Val Tyr Val Leu Pro Arg Arg Gly Pro Arg Leu Gly Val Cys Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Ser Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
```

```
                    85                  90                  95
Leu Leu Ser Pro Arg Gly Ser Arg Pro Ser Trp Gly Pro Asn Asp Pro
                100                 105                 110

Arg Arg Arg Ser Arg Asn Leu Gly Lys Val Ile Asp Thr Leu Thr Cys
                115                 120                 125

Gly Phe Ala Asp Leu Met Gly Tyr Ile Pro Leu Val Gly Ala Pro Val
                130                 135                 140

Gly Gly Val Ala Arg Ala Leu Ala His Gly Val Arg Ala Leu Glu Asp
145                 150                 155                 160

Gly Ile Asn Phe Ala Thr Gly Asn Leu Pro Gly Cys Ser Phe Ser Ile
                165                 170                 175

Phe Leu Leu Ala Leu Phe Ser Cys Leu Val His Pro Ala Ala Ser Leu
                180                 185                 190

Glu Trp Arg Asn Thr Ser Gly Leu Tyr Val Leu Thr Asn Asp Cys Pro
                195                 200                 205

Asn Ser Ser Ile Val Tyr Glu Ala Asp Asp Val Ile Leu His Thr Pro
                210                 215                 220

Gly Cys Ile Pro Cys Val Gln Asp Gly Asn Lys Ser Thr Cys Trp Thr
225                 230                 235                 240

Ser Val Thr Pro Thr Val Ala Val Lys Tyr Val Gly Ala Thr Thr Ala
                245                 250                 255

Ser Ile Arg Ser His Val Asp Leu Leu Val Gly Ala Ala Thr Met Cys
                260                 265                 270

Ser Ala Leu Tyr Val Gly Asp Met Cys Gly Ala Val Phe Leu Val Gly
                275                 280                 285

Gln Ala Phe Thr Phe Arg Pro Arg Arg His Gln Thr Val Gln Thr Cys
                290                 295                 300

Asn Cys Ser Leu Tyr Pro Gly His Leu Ser Gly His Arg Met Ala Trp
305                 310                 315                 320

Asp Met Met Met Asn Trp Ser Pro Ala Val Gly Met Val Val Ala His
                325                 330                 335

Val Leu Arg Leu Pro Gln Thr Leu Phe Asp Ile Ile Ala Gly Ala His
                340                 345                 350

Trp Gly Ile Leu Ala Gly Leu Ala Tyr Tyr Ser Met Gln Gly Asn Trp
                355                 360                 365

Ala Lys Val Ala Ile Ile Met Val Met Phe Ser Gly Val Asp Ala Thr
                370                 375                 380

Thr Tyr Thr Thr Gly Gly Asn Ala Ala Arg Gly Ala Ser Gly Ile Val
385                 390                 395                 400

Ser Leu Phe Thr Pro Gly Ala Lys Gln Asn Leu Gln Leu Val Asn Thr
                405                 410                 415

Asn Gly Ser Trp His Ile Asn Arg Thr Ala Leu Asn Cys Asn Asp Ser
                420                 425                 430

Ile Asn Thr Gly Phe Ile Ala Gly Leu Ile Tyr Tyr His Lys Phe Asn
                435                 440                 445

Ser Thr Gly Cys Pro Gln Arg Leu Ser Ser Cys Lys Pro Ile Thr Phe
                450                 455                 460

Phe Arg Gln Gly Trp Gly Ser Leu Thr Asp Ala Asn Ile Thr Gly Pro
465                 470                 475                 480

Ser Asp Asp Lys Pro Tyr Cys Trp His Tyr Pro Pro Arg Pro Cys Asp
                485                 490                 495

Thr Ile Arg Ala Ser Ser Val Cys Gly Pro Val Tyr Cys Phe Thr Pro
                500                 505                 510
```

```
Ser Pro Val Val Gly Thr Thr Asp Ala Lys Gly Ala Pro Thr Tyr
        515                 520                 525

Asn Trp Gly Ala Asn Glu Thr Asp Met Phe Leu Leu Gln Ser Leu Arg
        530                 535                 540

Pro Pro Ser Gly Arg Trp Phe Gly Cys Thr Trp Met Asn Ser Thr Gly
545                 550                 555                 560

Phe Thr Lys Thr Cys Gly Ala Pro Pro Cys Asn Ile Tyr Gly Gly Gly
            565                 570                 575

Gly Asn Leu Asn Asn Glu Ser Asp Leu Phe Cys Pro Thr Asp Cys Phe
            580                 585                 590

Arg Lys His Pro Glu Ala Thr Tyr Ser Arg Cys Gly Ala Gly Pro Trp
            595                 600                 605

Leu Thr Pro Arg Cys Leu Val Asp Tyr Pro Tyr Arg Leu Trp His Tyr
            610                 615                 620

Pro Cys Thr Val Asn Phe Thr Leu Phe Arg Met Arg Thr Phe Val Gly
625                 630                 635                 640

Gly Phe Glu His Arg Phe Thr Ala Ala Cys Asn Trp Thr Arg Gly Glu
            645                 650                 655

Arg Cys Asn Ile Glu Asp Arg Asp Arg Ser Glu Gln His Pro Leu Leu
            660                 665                 670

His Ser Thr Thr Glu Leu Ala Ile Leu Pro Cys Ser Phe Thr Pro Met
            675                 680                 685

Pro Ala Leu Ser Thr Gly Leu Ile His Leu His Gln Asn Ile Val Asp
            690                 695                 700

Val Gln Tyr Leu Tyr Gly Ile Gly Ser Gly Val Gly Trp Ala Leu
705                 710                 715                 720

Lys Trp Glu Phe Val Ile Leu Val Phe Leu Leu Leu Ala Asp Ala Arg
            725                 730                 735

Val Cys Val Ala Leu Trp Leu Met Leu Met Ile Ser Gln Ala Glu Ala
                740                 745                 750

<210> SEQ ID NO 53
<211> LENGTH: 752
<212> TYPE: PRT
<213> ORGANISM: Hepatitis C virus

<400> SEQUENCE: 53

Met Ser Thr Leu Pro Lys Pro Gln Arg Lys Thr Lys Arg Asn Thr Ile
1               5                   10                  15

Arg Arg Pro Gln Asp Val Lys Phe Pro Gly Gly Gly Val Ile Tyr Val
                20                  25                  30

Gly Val Tyr Val Leu Pro Arg Arg Gly Pro Arg Leu Gly Val Arg Ala
            35                  40                  45

Thr Arg Lys Thr Ser Glu Arg Ser Gln Pro Arg Gly Arg Arg Lys Pro
        50                  55                  60

Ile Pro Lys Ala Arg Arg Ser Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Asn Trp Ala Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
```

```
                130                 135                 140
Gly Gly Ala Ala Arg Ala Leu Ala His Gly Val Arg Ala Leu Glu Asp
145                 150                 155                 160

Gly Ile Asn Phe Ala Thr Gly Asn Leu Pro Gly Cys Ser Phe Ser Ile
                165                 170                 175

Phe Leu Leu Ala Leu Phe Ser Cys Leu Ile His Pro Ala Ala Ser Leu
                180                 185                 190

Glu Trp Arg Asn Thr Ser Gly Leu Tyr Val Leu Thr Asn Asp Cys Ser
                195                 200                 205

Asn Ser Ser Ile Val Tyr Glu Ala Asp Asp Val Ile Leu His Thr Pro
210                 215                 220

Gly Cys Ile Pro Cys Val Gln Asp Gly Asn Thr Ser Thr Cys Trp Thr
225                 230                 235                 240

Pro Val Thr Pro Thr Val Ala Val Arg Tyr Val Gly Ala Thr Thr Ala
                245                 250                 255

Ser Ile Arg Ser His Val Asp Leu Leu Val Gly Ala Gly Thr Met Cys
                260                 265                 270

Ser Ala Leu Tyr Val Gly Asp Met Cys Gly Pro Val Phe Leu Val Gly
                275                 280                 285

Gln Ala Phe Thr Phe Arg Pro Arg Arg His Arg Thr Val Gln Thr Cys
                290                 295                 300

Asn Cys Ser Leu Tyr Pro Gly His Leu Ser Gly Gln Arg Met Ala Trp
305                 310                 315                 320

Asp Met Met Met Asn Trp Ser Pro Ala Val Gly Met Val Val Ala His
                325                 330                 335

Ile Leu Arg Leu Pro Gln Thr Leu Phe Asp Val Val Ala Gly Ala His
                340                 345                 350

Trp Gly Ile Ile Ala Gly Leu Ala Tyr Tyr Ser Met Gln Gly Asn Trp
                355                 360                 365

Ala Lys Val Ala Ile Ile Met Val Met Phe Ser Gly Val Asp Ala Ser
370                 375                 380

Thr His Val Thr Ala Gly Gln Ala Ala Arg Asn Ala Tyr Gly Ile Thr
385                 390                 395                 400

Ser Leu Phe Ser Val Gly Ala Lys Gln Asn Leu Gln Leu Ile Asn Thr
                405                 410                 415

Asn Gly Ser Trp His Ile Asn Arg Thr Ala Leu Asn Cys Asn Glu Ser
                420                 425                 430

Ile Asn Thr Gly Phe Ile Ala Gly Leu Phe Tyr Tyr His Lys Phe Asn
                435                 440                 445

Ser Thr Gly Cys Pro Gln Arg Leu Ser Ser Cys Lys Pro Ile Thr Phe
450                 455                 460

Phe Lys Gln Gly Trp Gly Pro Leu Thr Asp Ala Asn Ile Thr Gly Pro
465                 470                 475                 480

Ser Asp Asp Lys Pro Tyr Cys Trp His Tyr Ala Pro Arg Pro Cys Gly
                485                 490                 495

Ile Val Pro Ala Leu Asn Val Cys Gly Pro Val Tyr Cys Phe Thr Pro
                500                 505                 510

Ser Pro Val Val Val Gly Thr Thr Asp Ala Lys Gly Ala Pro Thr Tyr
                515                 520                 525

Thr Trp Gly Ala Asn Lys Thr Asp Val Phe Leu Leu Glu Ser Leu Arg
530                 535                 540

Pro Pro Ser Gly Arg Trp Phe Gly Cys Thr Trp Met Asn Ser Thr Gly
545                 550                 555                 560
```

Phe Val Lys Thr Cys Gly Ala Pro Pro Cys Asn Ile Tyr Gly Asp Gly
            565                 570                 575

Arg Asp Ala Gln Asn Glu Ser Asp Leu Phe Cys Pro Thr Asp Cys Phe
            580                 585                 590

Arg Lys His Pro Glu Ala Thr Tyr Ser Arg Cys Gly Ala Gly Pro Trp
            595                 600                 605

Leu Thr Pro Arg Cys Leu Val Asp Tyr Pro Tyr Arg Leu Trp His Tyr
            610                 615                 620

Pro Cys Thr Val Asn Phe Thr Leu Phe Lys Val Arg Met Phe Val Gly
625                 630                 635                 640

Gly Phe Glu His Arg Phe Thr Ala Ala Cys Asn Trp Thr Arg Gly Glu
            645                 650                 655

Arg Cys Asp Ile Glu Asp Arg Asp Arg Ser Glu Gln His Pro Leu Leu
            660                 665                 670

His Ser Thr Thr Glu Leu Ala Ile Leu Pro Cys Ser Phe Thr Pro Met
            675                 680                 685

Pro Ala Leu Ser Thr Gly Leu Ile His Leu His Gln Asn Ile Val Asp
690                 695                 700

Val Gln Tyr Leu Tyr Gly Ile Gly Ser Gly Met Val Gly Trp Ala Leu
705                 710                 715                 720

Lys Trp Glu Phe Val Ile Leu Ile Phe Leu Leu Leu Ala Asp Ala Arg
                725                 730                 735

Val Cys Val Ala Leu Trp Leu Ile Leu Thr Ile Ser Gln Ala Glu Ala
            740                 745                 750

<210> SEQ ID NO 54
<211> LENGTH: 754
<212> TYPE: PRT
<213> ORGANISM: Hepatitis C virus

<400> SEQUENCE: 54

Met Ser Thr Leu Pro Lys Pro Lys Arg Gln Thr Lys Arg Asn Thr Leu
1               5                   10                  15

Arg Arg Pro Lys Asn Val Lys Phe Pro Ala Gly Gly Gln Ile Val Gly
            20                  25                  30

Glu Val Tyr Val Leu Pro Arg Arg Gly Pro Gln Leu Gly Val Arg Glu
            35                  40                  45

Val Arg Lys Thr Ser Glu Arg Ser Gln Pro Arg Gly Arg Arg Gln Pro
50                  55                  60

Thr Pro Lys Ala Arg Pro Arg Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Pro Pro Arg Gly Ser Arg Pro Ser Trp Gly Gln Asn Asp Pro
            100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Ile Gly Ala Pro Val
            130                 135                 140

Gly Gly Val Ala Arg Ala Leu Ala His Gly Val Arg Ala Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Phe Ser Cys Leu Thr Cys Pro Ala Ser Ser Leu

```
            180                 185                 190
Glu Tyr Arg Asn Ala Ser Gly Leu Tyr Leu Leu Thr Asn Asp Cys Ser
            195                 200                 205

Asn Arg Ser Ile Val Tyr Glu Ala Asp Asp Val Ile Leu His Leu Pro
210                 215                 220

Gly Cys Val Pro Cys Val Glu Thr Asp Asn Asn Thr Ser Cys Trp
225                 230                 235                 240

Thr Pro Ile Ser Pro Thr Val Ala Val Lys His Pro Gly Val Thr Thr
                245                 250                 255

Ala Ser Ile Arg Asn His Val Asn Met Leu Val Ala Pro Pro Thr Leu
                260                 265                 270

Cys Ser Ala Leu Tyr Val Glu Asp Ala Phe Gly Ala Val Ser Leu Val
            275                 280                 285

Gly Gln Ala Phe Thr Phe Arg Pro Arg Gln His Lys Thr Val Gln Thr
            290                 295                 300

Cys Asn Cys Ser Ile Tyr Pro Gly His Val Ser Gly His Arg Met Ala
305                 310                 315                 320

Trp Asp Met Met Met Asn Trp Ser Pro Ala Ile Gly Leu Val Ile Ser
                325                 330                 335

His Leu Met Arg Leu Pro Gln Thr Phe Phe Asp Leu Val Val Gly Ala
                340                 345                 350

His Trp Gly Val Met Ala Gly Leu Ala Tyr Phe Ser Met Gln Gly Asn
            355                 360                 365

Trp Ala Lys Val Val Ile Val Leu Ile Met Phe Ser Gly Val Asp Ala
370                 375                 380

Thr Thr His Thr Thr Gly Gly Ser Ala Ala Gln Ala Thr Ala Gly Phe
385                 390                 395                 400

Thr Ser Phe Phe Thr Arg Gly Pro Ser Gln Asn Leu Gln Leu Val Asn
                405                 410                 415

Ser Asn Gly Ser Trp His Ile Asn Ser Thr Ala Leu Asn Cys Asn Asp
            420                 425                 430

Ser Leu Asn Thr Gly Phe Ile Ala Gly Leu Phe Tyr Tyr His Lys Phe
            435                 440                 445

Asn Ser Ser Gly Cys Pro Glu Arg Met Ser Ser Cys Lys Pro Ile Thr
450                 455                 460

Tyr Phe Asn Gln Gly Trp Gly Pro Leu Thr Asp Ala Asn Ile Asn Gly
465                 470                 475                 480

Pro Ser Glu Asp Arg Pro Tyr Cys Trp His Tyr Pro Arg Pro Cys
                485                 490                 495

Asn Ile Thr Lys Pro Leu Asn Val Cys Gly Pro Val Tyr Cys Phe Thr
            500                 505                 510

Pro Ser Pro Val Val Gly Thr Thr Asp Ile Lys Gly Leu Pro Thr
            515                 520                 525

Tyr Arg Phe Gly Val Asn Glu Ser Asp Val Phe Leu Leu Thr Ser Leu
            530                 535                 540

Arg Pro Pro Gln Gly Arg Trp Phe Gly Cys Val Trp Met Asn Ser Thr
545                 550                 555                 560

Gly Phe Val Lys Thr Cys Gly Ala Pro Pro Cys Asn Ile Tyr Gly Gly
                565                 570                 575

Met Lys Asp Ile Glu Ala Asn Gln Thr His Leu Lys Cys Pro Thr Asp
                580                 585                 590

Cys Phe Arg Lys His His Asp Ala Thr Phe Thr Arg Cys Gly Ser Gly
            595                 600                 605
```

-continued

```
Pro Trp Leu Thr Pro Arg Cys Leu Val Asp Tyr Pro Tyr Arg Leu Trp
    610                 615                 620

His Tyr Pro Cys Thr Val Asn Phe Ser Ile Phe Lys Val Arg Met Phe
625                 630                 635                 640

Val Gly Gly His Glu His Arg Phe Ser Ala Ala Cys Asn Trp Thr Arg
            645                 650                 655

Gly Glu Arg Cys Asp Leu Glu Asp Arg Asp Arg Ser Glu Gln Gln Pro
            660                 665                 670

Leu Leu His Ser Thr Thr Asp Ser Leu Ile Leu Pro Cys Ser Phe Thr
        675                 680                 685

Pro Met Arg Arg Leu Ser Thr Gly Leu Ile His Leu His Gln Asn Ile
    690                 695                 700

Val Asp Val Gln Tyr Leu Tyr Gly Val Gly Ser Ala Val Val Gly Trp
705                 710                 715                 720

Ala Leu Lys Trp Glu Phe Val Val Leu Val Phe Leu Leu Leu Ala Asp
                725                 730                 735

Ala Arg Val Cys Val Ala Leu Trp Met Met Leu Leu Ile Ser Gln Ala
            740                 745                 750

Glu Ala

<210> SEQ ID NO 55
<211> LENGTH: 750
<212> TYPE: PRT
<213> ORGANISM: Hepatitis C virus

<400> SEQUENCE: 55

Met Ser Thr Asn Pro Lys Pro Gln Arg Leu Thr Lys Arg Asn Thr Val
1               5                   10                  15

Arg Arg Pro Gln Asn Val Lys Phe Pro Gly Gly Gly Gln Ile Val Gly
                20                  25                  30

Gly Val Tyr Leu Leu Pro Arg Arg Gly Pro Arg Leu Gly Val Arg Gly
            35                  40                  45

Thr Arg Lys Ser Ser Glu Arg Ser Gln Pro Arg Gly Arg Arg Gln Arg
    50                  55                  60

Ile Pro Lys Ala Ala Ser Ser Gln Gly Lys Ala Trp Gly Lys Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Thr Trp Gly Pro Thr Asp Pro
            100                 105                 110

Arg His Arg Ser Arg Asn Leu Gly Lys Val Ile Asp Thr Met Thr Cys
        115                 120                 125

Gly Phe Ala Asp Leu Met Gly Tyr Ile Pro Val Leu Gly Ala Pro Leu
    130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Glu Val Arg Asn Ser Ser Gly Val Tyr His Leu Thr Asn Asp Cys Pro
        195                 200                 205

Asn Ala Ser Ile Val Tyr Glu Thr Asp Asn Ala Ile Leu His Glu Pro
    210                 215                 220
```

Gly Cys Val Pro Cys Val Arg Glu Gly Asn Thr Ser Arg Cys Trp Glu
225                 230                 235                 240

Pro Val Ala Pro Thr Leu Ala Val Arg Tyr Arg Gly Ala Leu Thr Asp
            245                 250                 255

Asp Leu Arg Thr His Ile Asp Leu Val Val Ala Ser Ala Thr Leu Cys
        260                 265                 270

Ser Ala Leu Tyr Val Gly Asp Ile Cys Gly Ala Ile Phe Ile Ala Ser
    275                 280                 285

Gln Ala Val Leu Trp Lys Pro Gly Gly Arg Ile Val Gln Asp Cys
290                 295                 300

Asn Cys Ser Ile Tyr Pro Gly His Val Thr Gly His Arg Met Ala Trp
305                 310                 315                 320

Asp Met Met Gln Asn Trp Ala Pro Ala Leu Ser Met Val Ala Ala Tyr
                325                 330                 335

Ala Val Arg Val Pro Gly Val Ile Ile Thr Val Ala Gly Gly His
            340                 345                 350

Trp Gly Val Leu Phe Gly Leu Ala Tyr Phe Gly Met Ala Gly Asn Trp
        355                 360                 365

Ala Lys Val Ile Leu Ile Met Leu Leu Met Ser Gly Val Asp Ala Glu
    370                 375                 380

Thr Met Ala Val Gly Ala Arg Ala Ala His Thr Thr Gly Ala Leu Val
385                 390                 395                 400

Ser Leu Leu Asn Pro Gly Pro Ser Gln Arg Leu Gln Leu Ile Asn Thr
                405                 410                 415

Asn Gly Ser Trp His Ile Asn Arg Thr Ala Leu Asn Cys Asn Asp Ser
            420                 425                 430

Leu Gln Thr Gly Phe Ile Ala Ala Leu Phe Tyr Thr His Arg Phe Asn
        435                 440                 445

Ser Ser Gly Cys Pro Glu Arg Met Ala Ser Cys Lys Pro Leu Ser Asp
    450                 455                 460

Phe Asp Gln Gly Trp Gly Pro Leu Trp Tyr Asn Ser Thr Glu Arg Pro
465                 470                 475                 480

Ser Asp Gln Arg Pro Tyr Cys Trp His Tyr Ala Pro Ser Pro Cys Gly
                485                 490                 495

Ile Val Pro Ala Lys Asp Val Cys Gly Pro Val Tyr Cys Phe Thr Pro
            500                 505                 510

Ser Pro Val Val Gly Thr Thr Asp Arg Arg Gly Val Pro Thr Tyr
        515                 520                 525

Thr Trp Gly Glu Asn Glu Ser Asp Val Phe Leu Leu Asn Ser Thr Arg
    530                 535                 540

Pro Pro Gln Gly Ser Trp Phe Gly Cys Ser Trp Met Asn Thr Thr Gly
545                 550                 555                 560

Phe Thr Lys Thr Cys Gly Gly Pro Pro Cys Lys Ile Arg Pro Gln Gly
                565                 570                 575

Ala Gln Ser Asn Thr Ser Leu Thr Cys Pro Thr Asp Cys Phe Arg Lys
            580                 585                 590

His Pro Arg Ala Thr Tyr Ser Ala Cys Gly Ser Gly Pro Trp Leu Thr
        595                 600                 605

Pro Arg Cys Met Val His Tyr Pro Tyr Arg Leu Trp His Tyr Pro Cys
    610                 615                 620

Thr Val Asn Phe Thr Ile His Lys Val Arg Leu Tyr Ile Gly Gly Val
625                 630                 635                 640

```
Glu His Arg Leu Asp Ala Ala Cys Asn Trp Thr Arg Gly Glu Arg Cys
                645                 650                 655

Asp Leu Glu Asp Arg Asp Arg Val Asp Met Ser Pro Leu Leu His Ser
            660                 665                 670

Thr Thr Glu Leu Ala Ile Leu Pro Cys Ser Phe Val Pro Leu Pro Ala
        675                 680                 685

Leu Ser Thr Gly Leu Ile His Leu His Gln Asn Ile Val Asp Ala Gln
    690                 695                 700

Tyr Leu Tyr Gly Leu Ser Pro Ala Ile Ile Ser Trp Ala Ile Arg Trp
705                 710                 715                 720

Glu Trp Val Val Leu Val Phe Leu Leu Leu Ala Asp Ala Arg Ile Cys
                725                 730                 735

Ala Cys Leu Trp Met Met Met Leu Met Ala Gln Ala Glu Ala
            740                 745                 750

<210> SEQ ID NO 56
<211> LENGTH: 227
<212> TYPE: PRT
<213> ORGANISM: Homo sapiens

<400> SEQUENCE: 56

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 57
<211> LENGTH: 325
<212> TYPE: PRT
<213> ORGANISM: Homo sapiens
```

<400> SEQUENCE: 57

```
Ser Thr Lys Gly Pro Ser Val Phe Pro Leu Ala Pro Cys Ser Arg Ser
1               5                   10                  15

Thr Ser Glu Ser Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Asn Phe Gly Thr Gln Thr Tyr
65                  70                  75                  80

Thr Cys Asn Val Asp His Lys Pro Ser Asn Thr Lys Val Asp Lys Thr
                85                  90                  95

Val Glu Arg Lys Cys Cys Val Glu Cys Pro Pro Cys Pro Ala Pro Pro
            100                 105                 110

Val Ala Gly Pro Ser Val Phe Leu Phe Pro Pro Lys Pro Lys Asp Thr
        115                 120                 125

Leu Met Ile Ser Arg Thr Pro Glu Val Thr Cys Val Val Val Asp Val
130                 135                 140

Ser His Glu Asp Pro Glu Val Gln Phe Asn Trp Tyr Val Asp Gly Val
145                 150                 155                 160

Glu Val His Asn Ala Lys Thr Lys Pro Arg Glu Glu Gln Phe Asn Ser
                165                 170                 175

Thr Phe Arg Val Val Ser Val Leu Thr Val Val His Gln Asp Trp Leu
            180                 185                 190

Asn Gly Lys Glu Tyr Lys Cys Lys Val Ser Asn Lys Gly Leu Pro Ala
        195                 200                 205

Pro Ile Glu Lys Thr Ile Ser Lys Thr Lys Gly Gln Pro Arg Glu Pro
    210                 215                 220

Gln Val Tyr Thr Leu Pro Pro Ser Arg Glu Glu Met Thr Lys Asn Gln
225                 230                 235                 240

Val Ser Leu Thr Cys Leu Val Lys Gly Phe Tyr Pro Ser Asp Ile Ala
                245                 250                 255

Val Glu Trp Glu Ser Asn Gly Gln Pro Glu Asn Asn Tyr Lys Thr Thr
            260                 265                 270

Pro Pro Met Leu Asp Ser Asp Gly Ser Phe Phe Leu Tyr Ser Lys Leu
        275                 280                 285

Thr Val Asp Lys Ser Arg Trp Gln Gln Gly Asn Val Phe Ser Cys Ser
    290                 295                 300

Val Met His Glu Ala Leu His Asn His Tyr Thr Gln Lys Ser Leu Ser
305                 310                 315                 320

Leu Ser Pro Gly Lys
                325
```

<210> SEQ ID NO 58
<211> LENGTH: 246
<212> TYPE: PRT
<213> ORGANISM: Homo sapiens

<400> SEQUENCE: 58

```
His Lys Pro Ser Asn Thr Lys Val Asp Lys Arg Val Glu Leu Lys Thr
1               5                   10                  15

Pro Leu Gly Asp Thr Thr His Thr Cys Pro Pro Cys Pro Ala Pro Glu
            20                  25                  30
```

```
Leu Leu Gly Gly Pro Ser Val Phe Leu Phe Pro Pro Lys Pro Lys Asp
            35                  40                  45

Thr Leu Met Ile Ser Arg Thr Pro Glu Val Thr Cys Val Val Val Asp
 50                  55                  60

Val Ser His Glu Asp Pro Glu Val Lys Phe Asn Trp Tyr Val Asp Gly
 65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
                100                 105                 110

Leu Asn Gly Lys Glu Tyr Lys Cys Lys Val Ser Asn Lys Ala Leu Pro
            115                 120                 125

Ala Pro Ile Glu Lys Thr Ile Ser Lys Ala Lys Gly Gln Pro Arg Glu
130                 135                 140

Pro Gln Val Tyr Thr Leu Pro Pro Ser Arg Asp Glu Leu Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
            195                 200                 205

Leu Thr Val Asp Lys Ser Arg Trp Gln Gln Gly Asn Val Phe Ser Cys
210                 215                 220

Ser Val Met His Glu Ala Leu His Asn His Tyr Thr Gln Lys Ser Leu
225                 230                 235                 240

Ser Leu Ser Pro Gly Lys
                245

<210> SEQ ID NO 59
<211> LENGTH: 383
<212> TYPE: PRT
<213> ORGANISM: Homo sapiens

<400> SEQUENCE: 59

Pro Thr Lys Ala Pro Asp Val Phe Pro Ile Ile Ser Gly Cys Arg His
 1               5                   10                  15

Pro Lys Asp Asn Ser Pro Val Val Leu Ala Cys Leu Ile Thr Gly Tyr
                20                  25                  30

His Pro Thr Ser Val Thr Val Thr Trp Tyr Met Gly Thr Gln Ser Gln
            35                  40                  45

Pro Gln Arg Thr Phe Pro Glu Ile Gln Arg Arg Asp Ser Tyr Tyr Met
 50                  55                  60

Thr Ser Ser Gln Leu Ser Thr Pro Leu Gln Gln Trp Arg Gln Gly Glu
 65                  70                  75                  80

Tyr Lys Cys Val Val Gln His Thr Ala Ser Lys Ser Lys Lys Glu Ile
                85                  90                  95

Phe Arg Trp Pro Glu Ser Pro Lys Ala Gln Ala Ser Ser Val Pro Thr
                100                 105                 110

Ala Gln Pro Gln Ala Glu Gly Ser Leu Ala Lys Ala Thr Thr Ala Pro
            115                 120                 125

Ala Thr Thr Arg Asn Thr Gly Arg Gly Gly Glu Glu Lys Lys Lys Glu
130                 135                 140

Lys Glu Lys Glu Glu Gln Glu Glu Arg Glu Thr Lys Thr Pro Glu Cys
```

```
                145                 150                 155                 160
Pro Ser His Thr Gln Pro Leu Gly Val Tyr Leu Leu Thr Pro Ala Val
                165                 170                 175

Gln Asp Leu Trp Leu Arg Asp Lys Ala Thr Phe Thr Cys Phe Val Val
                180                 185                 190

Gly Ser Asp Leu Lys Asp Ala His Leu Thr Trp Glu Val Ala Gly Lys
                195                 200                 205

Val Pro Thr Gly Gly Val Glu Glu Gly Leu Leu Glu Arg His Ser Asn
210                 215                 220

Gly Ser Gln Ser Gln His Ser Arg Leu Thr Leu Pro Arg Ser Leu Trp
225                 230                 235                 240

Asn Ala Gly Thr Ser Val Thr Cys Thr Leu Asn His Pro Ser Leu Pro
                245                 250                 255

Pro Gln Arg Leu Met Ala Leu Arg Glu Pro Ala Ala Gln Ala Pro Val
                260                 265                 270

Lys Leu Ser Leu Asn Leu Leu Ala Ser Ser Asp Pro Pro Glu Ala Ala
                275                 280                 285

Ser Trp Leu Leu Cys Glu Val Ser Gly Phe Ser Pro Pro Asn Ile Leu
                290                 295                 300

Leu Met Trp Leu Glu Asp Gln Arg Glu Val Asn Thr Ser Gly Phe Ala
305                 310                 315                 320

Pro Ala Arg Pro Pro Gln Pro Arg Ser Thr Thr Phe Trp Ala Trp
                325                 330                 335

Ser Val Leu Arg Val Pro Ala Pro Pro Ser Pro Gln Pro Ala Thr Tyr
                340                 345                 350

Thr Cys Val Val Ser His Glu Asp Ser Arg Thr Leu Leu Asn Ala Ser
                355                 360                 365

Arg Ser Leu Glu Val Ser Tyr Val Thr Asp His Gly Pro Met Lys
                370                 375                 380

<210> SEQ ID NO 60
<211> LENGTH: 276
<212> TYPE: PRT
<213> ORGANISM: Homo sapiens

<400> SEQUENCE: 60

Val Thr Ser Thr Leu Thr Ile Lys Glx Ser Asp Trp Leu Gly Glu Ser
1               5                   10                  15

Met Phe Thr Cys Arg Val Asp His Arg Gly Leu Thr Phe Gln Gln Asn
                20                  25                  30

Ala Ser Ser Met Cys Val Pro Asp Gln Asp Thr Ala Ile Arg Val Phe
                35                  40                  45

Ala Ile Pro Pro Ser Phe Ala Ser Ile Phe Leu Thr Lys Ser Thr Lys
                50                  55                  60

Leu Thr Cys Leu Val Thr Asp Leu Thr Thr Tyr Asx Ser Val Thr Ile
65                  70                  75                  80

Ser Trp Thr Arg Glu Glu Asn Gly Ala Val Lys Thr His Thr Asn Ile
                85                  90                  95

Ser Glu Ser His Pro Asn Ala Thr Phe Ser Ala Val Gly Glu Ala Ser
                100                 105                 110

Ile Cys Glu Asp Asx Asp Trp Ser Gly Glu Arg Phe Thr Cys Thr Val
                115                 120                 125

Thr His Thr Asp Leu Pro Ser Pro Leu Lys Gln Thr Ile Ser Arg Pro
                130                 135                 140
```

```
Lys Gly Val Ala Leu His Arg Pro Asx Val Tyr Leu Leu Pro Pro Ala
145                 150                 155                 160

Arg Glx Glx Leu Asn Leu Arg Glu Ser Ala Thr Ile Thr Cys Leu Val
            165                 170                 175

Thr Gly Phe Ser Pro Ala Asp Val Phe Val Glu Trp Met Gln Arg Gly
            180                 185                 190

Glu Pro Leu Ser Pro Gln Lys Tyr Val Thr Ser Ala Pro Met Pro Glu
            195                 200                 205

Pro Gln Ala Pro Gly Arg Tyr Phe Ala His Ser Ile Leu Thr Val Ser
            210                 215                 220

Glu Glu Glu Trp Asn Thr Gly Thr Tyr Thr Cys Val Val Ala His
225                 230                 235                 240

Glu Ala Leu Pro Asn Arg Val Thr Glu Arg Thr Val Asp Lys Ser Thr
            245                 250                 255

Gly Lys Pro Thr Leu Tyr Asn Val Ser Leu Val Met Ser Asp Thr Ala
            260                 265                 270

Gly Thr Cys Tyr
            275

<210> SEQ ID NO 61
<211> LENGTH: 353
<212> TYPE: PRT
<213> ORGANISM: Homo sapiens

<400> SEQUENCE: 61

Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
            35                  40                  45

Thr Ala Arg Asn Phe Pro Pro Ser Gln Asp Ala Ser Gly Asp Leu Tyr
50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
            100                 105                 110

Ser Thr Pro Pro Thr Pro Ser Pro Ser Cys Cys His Pro Arg Leu Ser
            115                 120                 125

Leu His Arg Pro Ala Leu Glu Asp Leu Leu Leu Gly Ser Glu Ala Asn
            130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
            165                 170                 175

Arg Asp Leu Cys Gly Cys Tyr Ser Val Ser Ser Val Leu Pro Gly Cys
            180                 185                 190

Ala Glu Pro Trp Asn His Gly Lys Thr Phe Thr Cys Thr Ala Ala Tyr
            195                 200                 205

Pro Glu Ser Lys Thr Pro Leu Thr Ala Thr Leu Ser Lys Ser Gly Asn
            210                 215                 220

Thr Phe Arg Pro Glu Val His Leu Leu Pro Pro Pro Ser Glu Glu Leu
225                 230                 235                 240
```

```
Ala Leu Asn Glu Leu Val Thr Leu Thr Cys Leu Ala Arg Gly Phe Ser
                245                 250                 255
Pro Lys Asp Val Leu Val Arg Trp Leu Gln Gly Ser Gln Glu Leu Pro
            260                 265                 270
Arg Glu Lys Tyr Leu Thr Trp Ala Ser Arg Gln Glu Pro Ser Gln Gly
        275                 280                 285
Thr Thr Thr Phe Ala Val Thr Ser Ile Leu Arg Val Ala Ala Glu Asp
    290                 295                 300
Trp Lys Lys Gly Asp Thr Phe Ser Cys Met Val Gly His Glu Ala Leu
305                 310                 315                 320
Pro Leu Ala Phe Thr Gln Lys Thr Ile Asp Arg Leu Ala Gly Lys Pro
                325                 330                 335
Thr His Val Asn Val Ser Val Val Met Ala Glu Val Asp Gly Thr Cys
                340                 345                 350
Tyr

<210> SEQ ID NO 62
<211> LENGTH: 222
<212> TYPE: PRT
<213> ORGANISM: Homo sapiens

<400> SEQUENCE: 62

Ala Asp Pro Cys Asp Ser Asn Pro Arg Gly Val Ser Ala Tyr Leu Ser
1               5                   10                  15
Arg Pro Ser Pro Phe Asp Leu Phe Ile Arg Lys Ser Pro Thr Ile Thr
            20                  25                  30
Cys Leu Val Val Asp Leu Ala Pro Ser Lys Gly Thr Val Asn Leu Thr
        35                  40                  45
Trp Ser Arg Ala Ser Gly Lys Pro Val Asn His Ser Thr Arg Lys Glu
    50                  55                  60
Glu Lys Gln Arg Asn Gly Thr Leu Thr Val Thr Ser Thr Leu Pro Val
65                  70                  75                  80
Gly Thr Arg Asp Trp Ile Glu Gly Glu Thr Tyr Gln Cys Arg Val Thr
                85                  90                  95
His Pro His Leu Pro Arg Ala Leu Met Arg Ser Thr Thr Lys Thr Ser
                100                 105                 110
Gly Pro Arg Ala Ala Pro Glu Val Tyr Ala Phe Ala Thr Pro Glu Trp
            115                 120                 125
Pro Gly Ser Arg Asp Lys Arg Thr Leu Ala Cys Leu Ile Gln Asn Phe
        130                 135                 140
Met Pro Glu Asp Ile Ser Val Gln Trp Leu His Asn Glu Val Gln Leu
145                 150                 155                 160
Pro Asp Ala Arg His Ser Thr Thr Gln Pro Arg Lys Thr Lys Gly Ser
                165                 170                 175
Gly Phe Phe Val Phe Ser Arg Leu Glu Val Thr Arg Ala Glu Trp Glu
                180                 185                 190
Gln Lys Asp Glu Phe Ile Cys Arg Ala Val His Glu Ala Ala Ser Pro
            195                 200                 205
Ser Gln Thr Val Gln Arg Ala Val Ser Val Asn Pro Gly Lys
        210                 215                 220

<210> SEQ ID NO 63
<211> LENGTH: 327
<212> TYPE: PRT
<213> ORGANISM: Homo sapiens
```

<400> SEQUENCE: 63

```
Ala Ser Thr Lys Gly Pro Ser Val Phe Pro Leu Ala Pro Cys Ser Arg
 1               5                  10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Ser Cys Pro Ala Pro
            100                 105                 110
Glu Phe Leu Gly Gly Pro Ser Val Phe Leu Phe Pro Pro Lys Pro Lys
        115                 120                 125
Asp Thr Leu Met Ile Ser Arg Thr Pro Glu Val Thr Cys Val Val Val
130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Gly Leu
        195                 200                 205
Pro Ser Ser Ile Glu Lys Thr Ile Ser Lys Ala Lys Gly Gln Pro Arg
210                 215                 220
Glu Pro Gln Val Tyr Thr Leu Pro Pro Ser Gln Glu Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
        275                 280                 285
Arg Leu Thr Val Asp Lys Ser Arg Trp Gln Glu Gly Asn Val Phe Ser
290                 295                 300
Cys Ser Val Met His Glu Ala Leu His Asn His Tyr Thr Gln Lys Ser
305                 310                 315                 320
Leu Ser Leu Ser Leu Gly Lys
                325
```

<210> SEQ ID NO 64
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 64

```
Gln Tyr Ile Lys Ala Asn Ser Lys Phe Ile Gly Ile Thr Glu
 1               5                  10
```

```
<210> SEQ ID NO 65
<211> LENGTH: 124
<212> TYPE: PRT
<213> ORGANISM: Artificial Sequence
<220> FEATURE:
<223> OTHER INFORMATION: Synthetic Sequence

<400> SEQUENCE: 65

Met Ile Lys Leu Lys Phe Gly Val Phe Phe Thr Val Leu Leu Ser Ser
1               5                   10                  15

Ala Tyr Ala His Gly Thr Pro Gln Asn Ile Thr Asp Leu Cys Ala Glu
            20                  25                  30

Tyr His Asn Thr Gln Ile His Thr Leu Asn Asp Lys Ile Phe Ser Tyr
        35                  40                  45

Thr Glu Ser Leu Ala Gly Lys Arg Glu Met Ala Ile Ile Thr Phe Lys
    50                  55                  60

Asn Gly Ala Thr Phe Gln Val Glu Val Pro Gly Ser Gln His Ile Asp
65                  70                  75                  80

Ser Gln Lys Lys Ala Ile Glu Arg Met Lys Asp Thr Leu Arg Ile Ala
                85                  90                  95

Tyr Leu Thr Glu Ala Lys Val Glu Lys Leu Cys Val Trp Asn Asn Lys
            100                 105                 110

Thr Pro His Ala Ile Ala Ala Ile Ser Met Ala Asn
        115                 120

<210> SEQ ID NO 66
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 66

Ile Leu Met Gln Tyr Ile Lys Ala Asn Ser Lys Phe Ile Gly Ile
1               5                   10                  15

<210> SEQ ID NO 67
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 67

Val Asn Asn Glu Ser Ser Glu
1               5

<210> SEQ ID NO 68
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 68

Pro Gly Ile Asn Gly Lys Ala Ile His Leu Val Asn Asn Glu Ser Ser
1               5                   10                  15

Glu

<210> SEQ ID NO 69
<211> LENGTH: 6
<212> TYPE: PRT
```

```
<213> ORGANISM: Artificial Sequence
<220> FEATURE:
<223> OTHER INFORMATION: Synthetic Sequence

<400> SEQUENCE: 69

Pro Asn Arg Asp Ile Leu
1               5

<210> SEQ ID NO 70
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 70

Phe Ile Gly Ile Thr Glu Leu
1               5

<210> SEQ ID NO 71
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 71

Ser Tyr Phe Pro Ser Val
1               5

<210> SEQ ID NO 72
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 72

Asn Ser Val Asp Asp Ala Leu Ile Asn Ser Thr Lys Ile Tyr Ser Tyr
1               5                   10                  15

Phe Pro Ser Val
            20

<210> SEQ ID NO 73
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 73

Ile Asp Lys Ile Ser Asp Val Ser Thr Ile Val Pro Tyr Ile Gly Pro
1               5                   10                  15

Ala Leu Asn Ile
            20

<210> SEQ ID NO 74
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 74

Gln Ser Ile Ala Leu Ser Ser Leu Met Val Ala Gln Ala Ile Pro
1               5                   10                  15
```

-continued

<210> SEQ ID NO 75
<211> LENGTH: 19
<212> TYPE: PRT
<213> ORGANISM: Artificial Sequence
<220> FEATURE:
<223> OTHER INFORMATION: Synthetic Sequence

<400> SEQUENCE: 75

Pro Val Phe Ala Gly Ala Asn Tyr Ala Ala Trp Ala Val Asn Val Ala
1               5                   10                  15

Gln Val Ile

<210> SEQ ID NO 76
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 76

Val His His Asn Thr Glu Glu Ile Val Ala Gln Ser Ile Ala Leu Ser
1               5                   10                  15

Ser Leu Met Val
            20

<210> SEQ ID NO 77
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 77

Gln Ser Ile Ala Leu Ser Ser Leu Met Val Ala Gln Ala Ile Pro Leu
1               5                   10                  15

Val Gly Glu Leu
            20

<210> SEQ ID NO 78
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 78

Val Asp Ile Gly Phe Ala Ala Tyr Asn Phe Val Glu Ser Ile Ile Asn
1               5                   10                  15

Leu Phe Gln Val
            20

<210> SEQ ID NO 79
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 79

Gln Gly Glu Ser Gly His Asp Ile Lys Ile Thr Ala Glu Asn Thr Pro
1               5                   10                  15

Leu Pro Ile Ala
            20

<210> SEQ ID NO 80
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 80

Gly Val Leu Leu Pro Thr Ile Pro Gly Lys Leu Asp Val Asn Lys Ser
1               5                   10                  15

Lys Thr His Ile
            20

<210> SEQ ID NO 81
<211> LENGTH: 534
<212> TYPE: PRT
<213> ORGANISM: Artificial Sequence
<220> FEATURE:
<223> OTHER INFORMATION: Synthetic Sequence

<400> SEQUENCE: 81

Ala Asp Asp Val Val Asp Ser Ser Lys Ser Phe Val Met Glu Asn Phe
1               5                   10                  15

Ser Ser Tyr His Gly Thr Lys Pro Gly Tyr Val Asp Ser Ile Gln Lys
                20                  25                  30

Gly Ile Gln Lys Pro Lys Ser Gly Thr Gln Gly Asn Tyr Asp Asp Asp
            35                  40                  45

Trp Lys Glu Phe Tyr Ser Thr Asp Asn Lys Tyr Asp Ala Ala Gly Tyr
    50                  55                  60

Ser Val Asp Asn Glu Asn Pro Leu Ser Gly Lys Ala Gly Val Val
65                  70                  75                  80

Lys Val Thr Tyr Pro Gly Leu Thr Lys Val Leu Ala Leu Lys Val Asp
                85                  90                  95

Asn Ala Glu Thr Ile Lys Lys Glu Leu Gly Leu Ser Leu Thr Glu Pro
            100                 105                 110

Leu Met Glu Gln Val Gly Thr Glu Glu Phe Ile Lys Arg Phe Gly Asp
        115                 120                 125

Gly Ala Ser Arg Val Val Leu Ser Leu Pro Phe Ala Glu Gly Ser Ser
    130                 135                 140

Ser Val Glu Tyr Ile Asn Asn Trp Glu Gln Ala Lys Ala Leu Ser Val
145                 150                 155                 160

Glu Leu Glu Ile Asn Phe Glu Thr Arg Gly Lys Arg Gly Gln Asp Ala
                165                 170                 175

Met Tyr Glu Tyr Met Ala Gln Ala Cys Ala Gly Asn Arg Val Arg Arg
            180                 185                 190

Ser Val Gly Ser Ser Leu Ser Cys Ile Asn Leu Asp Trp Asp Val Ile
        195                 200                 205

Arg Asp Lys Thr Lys Thr Lys Ile Glu Ser Leu Lys Glu His Gly Pro
    210                 215                 220

Ile Lys Asn Lys Met Ser Glu Ser Pro Asn Lys Thr Val Ser Glu Glu
225                 230                 235                 240

Lys Ala Lys Gln Tyr Leu Glu Glu Phe His Gln Thr Ala Leu Glu His
                245                 250                 255

Pro Glu Leu Ser Glu Leu Lys Thr Val Thr Gly Thr Asn Pro Val Phe
            260                 265                 270

Ala Gly Ala Asn Tyr Ala Ala Trp Ala Val Asn Val Ala Gln Val Ile

```
                    275                 280                 285
Asp Ser Glu Thr Ala Asp Asn Leu Glu Lys Thr Thr Ala Ala Leu Ser
    290                 295                 300

Ile Leu Pro Gly Ile Gly Ser Val Met Gly Ile Ala Asp Gly Ala Val
305                 310                 315                 320

His His Asn Thr Glu Glu Ile Val Ala Gln Ser Ile Ala Leu Ser Ser
                325                 330                 335

Leu Met Val Ala Gln Ala Ile Pro Leu Val Gly Glu Leu Val Asp Ile
            340                 345                 350

Gly Phe Ala Ala Tyr Asn Phe Val Glu Ser Ile Ile Asn Leu Phe Gln
        355                 360                 365

Val Val His Asn Ser Tyr Asn Arg Pro Ala Tyr Ser Pro Gly His Lys
    370                 375                 380

Thr Gln Pro Phe Leu His Asp Gly Tyr Ala Val Ser Trp Asn Thr Val
385                 390                 395                 400

Glu Asp Ser Ile Ile Arg Thr Gly Phe Gln Gly Glu Ser Gly His Asp
                405                 410                 415

Ile Lys Ile Thr Ala Glu Asn Thr Pro Leu Pro Ile Ala Gly Val Leu
            420                 425                 430

Leu Pro Thr Ile Pro Gly Lys Leu Asp Val Asn Lys Ser Lys Thr His
        435                 440                 445

Ile Ser Val Asn Gly Arg Lys Ile Arg Met Arg Cys Arg Ala Ile Asp
    450                 455                 460

Gly Asp Val Thr Phe Cys Arg Pro Lys Ser Pro Val Tyr Val Gly Asn
465                 470                 475                 480

Gly Val His Ala Asn Leu His Val Ala Phe His Arg Ser Ser Ser Glu
                485                 490                 495

Lys Ile His Ser Asn Glu Ile Ser Ser Asp Ser Ile Gly Val Leu Gly
            500                 505                 510

Tyr Gln Lys Thr Val Asp His Thr Lys Val Asn Ser Lys Leu Ser Leu
        515                 520                 525

Phe Phe Glu Ile Lys Ser
    530

<210> SEQ ID NO 82
<211> LENGTH: 26
<212> TYPE: PRT
<213> ORGANISM: Artificial Sequence
<220> FEATURE:
<223> OTHER INFORMATION: Synthetic Sequence

<400> SEQUENCE: 82

Ile Met Gln Tyr Ile Lys Ala Asn Ser Lys Phe Ile Gly Ile Gln Ser
1               5                   10                  15

Ile Ala Leu Ser Ser Leu Met Val Ala Gln
            20                  25

<210> SEQ ID NO 83
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 83

Leu Glu Val Leu Phe Gln
1               5
```

-continued

```
<210> SEQ ID NO 84
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 84

Ala Ala Ala Ala Ala Ala Ala Ala Ala Ala Ala Ala Ala Ala Ala Ala
1               5                   10                  15

Ala

<210> SEQ ID NO 85
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 85

Leu Val Pro Arg
1

<210> SEQ ID NO 86
<211> LENGTH: 4
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (2)..(2)
<223> OTHER INFORMATION: Xaa is E (Glu) or D (Asp)

<400> SEQUENCE: 86

Ile Xaa Gly Arg
1

<210> SEQ ID NO 87
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 87

Asp Asp Asp Asp Lys
1               5

<210> SEQ ID NO 88
<211> LENGTH: 5
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(5)
<223> OTHER INFORMATION: This stretch of residues may be repeated

<400> SEQUENCE: 88

Gly Ser Gly Gly Ser
1               5

<210> SEQ ID NO 89
<211> LENGTH: 6
<212> TYPE: PRT
```

```
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(6)
<223> OTHER INFORMATION: This stretch of residues may be repeated

<400> SEQUENCE: 89

Gly Gly Ser Gly Gly Ser
1               5

<210> SEQ ID NO 90
<211> LENGTH: 4
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(4)
<223> OTHER INFORMATION: This stretch of residues may be repeated

<400> SEQUENCE: 90

Gly Gly Gly Ser
1

<210> SEQ ID NO 91
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 91

Gly Gly Ser Gly
1

<210> SEQ ID NO 92
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 92

Gly Gly Ser Gly Gly
1               5

<210> SEQ ID NO 93
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 93

Gly Ser Gly Ser Gly
1               5

<210> SEQ ID NO 94
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 94
```

```
Gly Ser Gly Gly Gly
1               5

<210> SEQ ID NO 95
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 95

Gly Gly Gly Ser Gly
1               5

<210> SEQ ID NO 96
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 96

Gly Ser Ser Ser Gly
1               5

<210> SEQ ID NO 97
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 97

Leu Glu Val Leu Phe Gln Gly Pro
1               5

<210> SEQ ID NO 98
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 98

Glu Asn Leu Tyr Phe Gln Ser
1               5

<210> SEQ ID NO 99
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 99

Glu Asn Leu Tyr Phe Gln Gly
1               5

<210> SEQ ID NO 100
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 100

Leu Val Pro Arg Gly Ser
```

```
<210> SEQ ID NO 101
<211> LENGTH: 5
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (2)..(2)
<223> OTHER INFORMATION: Xaa can be E (Glu) or D (Asp)
<220> FEATURE:
<221> NAME/KEY: misc_feature
<222> LOCATION: (5)..(5)
<223> OTHER INFORMATION: Xaa can be any naturally occurring amino acid
      except R (Arg) or P (Pro)

<400> SEQUENCE: 101

Ile Xaa Gly Arg Xaa
1               5

<210> SEQ ID NO 102
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 102

Glu Asn Leu Tyr Phe Gln
1               5

<210> SEQ ID NO 103
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 103

Asp Tyr Lys Asp Asp Asp Asp Lys
1               5

<210> SEQ ID NO 104
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 104

Tyr Pro Tyr Asp Val Pro Asp Tyr Ala
1               5

<210> SEQ ID NO 105
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 105

Glu Gln Lys Leu Ile Ser Glu Glu Asp Leu
1               5                   10

<210> SEQ ID NO 106
<211> LENGTH: 24
```

```
<212> TYPE: DNA
<213> ORGANISM: Artificial Sequence
<220> FEATURE:
<223> OTHER INFORMATION: Synthetic Sequence

<400> SEQUENCE: 106
tcgtcgtttt gtcgttttgt cgtt                                            24

<210> SEQ ID NO 107
<211> LENGTH: 6
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (2)..(2)
<223> OTHER INFORMATION: Xaa is L (Leu) or Q (Gln)

<400> SEQUENCE: 107

Pro Xaa Gly Met Thr Ser
1               5

<210> SEQ ID NO 108
<211> LENGTH: 5
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (2)..(2)
<223> OTHER INFORMATION: Xaa is L (Leu) or Q (Gln)

<400> SEQUENCE: 108

Pro Xaa Gly Met Thr
1               5

<210> SEQ ID NO 109
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 109

Glu Asn Leu Tyr Thr Gln Ser
1               5

<210> SEQ ID NO 110
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 110

Cys Gly Leu Val Pro Ala Gly Ser Gly Pro
1               5                   10

<210> SEQ ID NO 111
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 111
```

Ser Leu Leu Lys Ser Arg Met Val Pro Asn Phe Asn
1               5                   10

<210> SEQ ID NO 112
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 112

Ser Leu Leu Ile Ala Arg Arg Met Pro Asn Phe Asn
1               5                   10

<210> SEQ ID NO 113
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 113

Ser Lys Leu Val Gln Ala Ser Ala Ser Gly Val Asn
1               5                   10

<210> SEQ ID NO 114
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 114

Ser Ser Tyr Leu Lys Ala Ser Asp Ala Pro Asp Asn
1               5                   10

<210> SEQ ID NO 115
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 115

Arg Pro Lys Pro Gln Gln Phe Phe Gly Leu Met Asn
1               5                   10

<210> SEQ ID NO 116
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 116

Ser Leu Arg Pro Leu Ala Leu Trp Arg Ser Phe Asn
1               5                   10

<210> SEQ ID NO 117
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 117

Ser Pro Gln Gly Ile Ala Gly Gln Arg Asn Phe Asn

<210> SEQ ID NO 118
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 118

Asp Val Asp Glu Arg Asp Val Arg Gly Phe Ala Ser Phe Leu
1               5                   10

<210> SEQ ID NO 119
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 119

Ser Leu Pro Leu Gly Leu Trp Ala Pro Asn Phe Asn
1               5                   10

<210> SEQ ID NO 120
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 120

Ser Leu Leu Ile Phe Arg Ser Trp Ala Asn Phe Asn
1               5                   10

<210> SEQ ID NO 121
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 121

Ser Gly Val Val Ile Ala Thr Val Ile Val Ile Thr
1               5                   10

<210> SEQ ID NO 122
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 122

Ser Leu Gly Pro Gln Gly Ile Trp Gly Gln Phe Asn
1               5                   10

<210> SEQ ID NO 123
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 123

Lys Lys Ser Pro Gly Arg Val Val Gly Gly Ser Val
1               5                   10

<210> SEQ ID NO 124
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 124

Pro Gln Gly Leu Leu Gly Ala Pro Gly Ile Leu Gly
1               5                   10

<210> SEQ ID NO 125
<211> LENGTH: 31
<212> TYPE: PRT
<213> ORGANISM: Artificial Sequence
<220> FEATURE:
<223> OTHER INFORMATION: Synthetic Sequence

<400> SEQUENCE: 125

His Gly Pro Glu Gly Leu Arg Val Gly Phe Tyr Glu Ser Asp Val Met
1               5                   10                  15

Gly Arg Gly His Ala Arg Leu Val His Val Glu Glu Pro His Thr
            20                  25                  30

<210> SEQ ID NO 126
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 126

Gly Pro Gln Gly Leu Ala Gly Gln Arg Gly Ile Val
1               5                   10

<210> SEQ ID NO 127
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 127

Gly Gly Ser Gly Gln Arg Gly Arg Lys Ala Leu Glu
1               5                   10

<210> SEQ ID NO 128
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 128

Ser Leu Ser Ala Leu Leu Ser Ser Asp Ile Phe Asn
1               5                   10

<210> SEQ ID NO 129
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 129

```
Ser Leu Pro Arg Phe Lys Ile Ile Gly Gly Phe Asn
1               5                   10
```

<210> SEQ ID NO 130
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 130

```
Ser Leu Leu Gly Ile Ala Val Pro Gly Asn Phe Asn
1               5                   10
```

<210> SEQ ID NO 131
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 131

```
Phe Phe Lys Asn Ile Val Thr Pro Arg Thr Pro Pro
1               5                   10
```

<210> SEQ ID NO 132
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 132

```
Gln Tyr Ile Lys Ala Asn Ser Lys Phe Ile Gly Ile Phe Glu
1               5                   10
```

<210> SEQ ID NO 133
<211> LENGTH: 35
<212> TYPE: PRT
<213> ORGANISM: Artificial Sequence
<220> FEATURE:
<223> OTHER INFORMATION: Synthetic sequence

<400> SEQUENCE: 133

```
Lys Ser Thr Lys Val Pro Ala Ala Tyr Ala Ala Gln Gly Tyr Lys Val
1               5                   10                  15

Leu Val Leu Asn Pro Ser Val Ala Ala Thr Leu Gly Phe Gly Ala Tyr
            20                  25                  30

Met Ser Lys
        35
```

<210> SEQ ID NO 134
<211> LENGTH: 35
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (7)..(7)
<223> OTHER INFORMATION: Xaa is A or V
<220> FEATURE:
<221> NAME/KEY: misc_feature
<222> LOCATION: (10)..(10)
<223> OTHER INFORMATION: Xaa is A or V
<220> FEATURE:
<221> NAME/KEY: misc_feature
<222> LOCATION: (11)..(11)

<223> OTHER INFORMATION: Xaa is A or S
<220> FEATURE:
<221> NAME/KEY: misc_feature
<222> LOCATION: (15)..(15)
<223> OTHER INFORMATION: Xaa is K or N
<220> FEATURE:
<221> NAME/KEY: misc_feature
<222> LOCATION: (31)..(31)
<223> OTHER INFORMATION: Xaa is A or S
<220> FEATURE:
<221> NAME/KEY: misc_feature
<222> LOCATION: (32)..(32)
<223> OTHER INFORMATION: Xaa is Y or F
<220> FEATURE:
<221> NAME/KEY: misc_feature
<222> LOCATION: (33)..(33)
<223> OTHER INFORMATION: Xaa is M or L
<220> FEATURE:
<221> NAME/KEY: misc_feature
<222> LOCATION: (35)..(35)
<223> OTHER INFORMATION: Xaa is K or R

<400> SEQUENCE: 134

Lys Ser Thr Lys Val Pro Xaa Ala Tyr Xaa Xaa Gln Gly Tyr Xaa Val
1               5                   10                  15

Leu Val Leu Asn Pro Ser Val Ala Ala Thr Leu Gly Phe Gly Xaa Xaa
            20                  25                  30

Xaa Ser Xaa
        35

<210> SEQ ID NO 135
<211> LENGTH: 35
<212> TYPE: PRT
<213> ORGANISM: Artificial Sequence
<220> FEATURE:
<223> OTHER INFORMATION: Synthetic sequence

<400> SEQUENCE: 135

Lys Ser Thr Lys Val Pro Val Ala Tyr Ala Ala Gln Gly Tyr Lys Val
1               5                   10                  15

Leu Val Leu Asn Pro Ser Val Ala Ala Thr Leu Gly Phe Gly Ala Tyr
            20                  25                  30

Leu Ser Lys
        35

<210> SEQ ID NO 136
<211> LENGTH: 35
<212> TYPE: PRT
<213> ORGANISM: Artificial Sequence
<220> FEATURE:
<223> OTHER INFORMATION: Synthetic sequence

<400> SEQUENCE: 136

Lys Ser Thr Lys Val Pro Ala Ala Tyr Ala Ser Gln Gly Tyr Lys Val
1               5                   10                  15

Leu Val Leu Asn Pro Ser Val Ala Ala Thr Leu Gly Phe Gly Ala Tyr
            20                  25                  30

Met Ser Lys
        35

<210> SEQ ID NO 137
<211> LENGTH: 35
<212> TYPE: PRT
<213> ORGANISM: Artificial Sequence
<220> FEATURE:
<223> OTHER INFORMATION: Synthetic sequence

```
<400> SEQUENCE: 137

Lys Ser Thr Lys Val Pro Ala Ala Tyr Val Ala Gln Gly Tyr Asn Val
1               5                   10                  15

Leu Val Leu Asn Pro Ser Val Ala Ala Thr Leu Gly Phe Gly Ser Phe
            20                  25                  30

Met Ser Arg
        35

<210> SEQ ID NO 138
<211> LENGTH: 35
<212> TYPE: PRT
<213> ORGANISM: Artificial Sequence
<220> FEATURE:
<223> OTHER INFORMATION: Synthetic sequence

<400> SEQUENCE: 138

Lys Ser Thr Lys Val Pro Ala Ala Tyr Ala Ala Gln Gly Tyr Lys Val
1               5                   10                  15

Leu Val Leu Asn Pro Ser Val Ala Ala Thr Leu Gly Phe Gly Ala Tyr
            20                  25                  30

Met Ser Arg
        35

<210> SEQ ID NO 139
<211> LENGTH: 35
<212> TYPE: PRT
<213> ORGANISM: Artificial Sequence
<220> FEATURE:
<223> OTHER INFORMATION: Synthetic sequence

<400> SEQUENCE: 139

Lys Ser Thr Lys Val Pro Ala Ala Tyr Ala Ser Gln Gly Tyr Lys Val
1               5                   10                  15

Leu Val Leu Asn Pro Ser Val Ala Ala Thr Leu Gly Phe Gly Ser Tyr
            20                  25                  30

Met Ser Lys
        35

<210> SEQ ID NO 140
<211> LENGTH: 10
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (3)..(3)
<223> OTHER INFORMATION: Xaa is A or V
<220> FEATURE:
<221> NAME/KEY: misc_feature
<222> LOCATION: (4)..(4)
<223> OTHER INFORMATION: Xaa is A or S
<220> FEATURE:
<221> NAME/KEY: misc_feature
<222> LOCATION: (8)..(8)
<223> OTHER INFORMATION: Xaa is K or N

<400> SEQUENCE: 140

Ala Tyr Xaa Xaa Gln Gly Tyr Xaa Val Leu
1               5                   10

<210> SEQ ID NO 141
<211> LENGTH: 11
<212> TYPE: PRT
<213> ORGANISM: Artificial Sequence
```

```
-continued

<220> FEATURE:
<223> OTHER INFORMATION: Synthetic sequence
<220> FEATURE:
<221> NAME/KEY: misc_feature
<222> LOCATION: (7)..(7)
<223> OTHER INFORMATION: Xaa is A or S
<220> FEATURE:
<221> NAME/KEY: misc_feature
<222> LOCATION: (8)..(8)
<223> OTHER INFORMATION: Xaa is Y or F
<220> FEATURE:
<221> NAME/KEY: misc_feature
<222> LOCATION: (9)..(9)
<223> OTHER INFORMATION: Xaa is M or L
<220> FEATURE:
<221> NAME/KEY: misc_feature
<222> LOCATION: (11)..(11)
<223> OTHER INFORMATION: Xaa is K or R

<400> SEQUENCE: 141

Ala Thr Leu Gly Phe Gly Xaa Xaa Xaa Ser Xaa
1               5                   10

<210> SEQ ID NO 142
<211> LENGTH: 10
<212> TYPE: PRT
<213> ORGANISM: Artificial Sequence
<220> FEATURE:
<223> OTHER INFORMATION: Synthetic sequence

<400> SEQUENCE: 142

Ala Tyr Ala Ala Gln Gly Tyr Lys Val Leu
1               5                   10

<210> SEQ ID NO 143
<211> LENGTH: 10
<212> TYPE: PRT
<213> ORGANISM: Artificial Sequence
<220> FEATURE:
<223> OTHER INFORMATION: Synthetic sequence

<400> SEQUENCE: 143

Ala Tyr Val Ala Gln Gly Tyr Asn Val Leu
1               5                   10

<210> SEQ ID NO 144
<211> LENGTH: 11
<212> TYPE: PRT
<213> ORGANISM: Artificial Sequence
<220> FEATURE:
<223> OTHER INFORMATION: Synthetic sequence

<400> SEQUENCE: 144

Ala Thr Leu Gly Phe Gly Ala Tyr Met Ser Lys
1               5                   10

<210> SEQ ID NO 145
<211> LENGTH: 15
<212> TYPE: PRT
<213> ORGANISM: Artificial Sequence
<220> FEATURE:
<223> OTHER INFORMATION: Synthetic sequence

<400> SEQUENCE: 145

Val Leu Val Leu Asn Pro Ser Val Ala Ala Thr Leu Gly Phe Gly
1               5                   10                  15

<210> SEQ ID NO 146
<211> LENGTH: 30
```

<212> TYPE: PRT
<213> ORGANISM: Artificial Sequence
<220> FEATURE:
<223> OTHER INFORMATION: Synthetic sequence

<400> SEQUENCE: 146

Pro Ala Ala Tyr Ala Ala Gln Gly Tyr Lys Val Leu Val Leu Asn Pro
1               5                   10                  15

Ser Val Ala Ala Thr Leu Gly Phe Gly Ala Tyr Met Ser Lys
            20                  25                  30

<210> SEQ ID NO 147
<211> LENGTH: 30
<212> TYPE: PRT
<213> ORGANISM: Artificial Sequence
<220> FEATURE:
<223> OTHER INFORMATION: Synthetic sequence

<400> SEQUENCE: 147

Lys Ser Thr Lys Val Pro Ala Ala Tyr Ala Ala Gln Gly Tyr Lys Val
1               5                   10                  15

Leu Val Leu Asn Pro Ser Val Ala Ala Thr Leu Gly Phe Gly
            20                  25                  30

<210> SEQ ID NO 148
<211> LENGTH: 50
<212> TYPE: PRT
<213> ORGANISM: Artificial Sequence
<220> FEATURE:
<223> OTHER INFORMATION: Synthetic sequence

<400> SEQUENCE: 148

Gly Val Tyr Leu Leu Pro Arg Arg Gly Pro Arg Leu Gly Val Arg Ala
1               5                   10                  15

Thr Arg Lys Thr Ser Glu Arg Ser Gln Pro Arg Gly Arg Arg Gln Pro
            20                  25                  30

Ile Pro Lys Ala Arg Arg Ser Glu Gly Arg Ser Trp Ala Gln Pro Gly
                35                  40                  45

Tyr Pro
    50

<210> SEQ ID NO 149
<211> LENGTH: 50
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (4)..(4)
<223> OTHER INFORMATION: Xaa is L or V
<220> FEATURE:
<221> NAME/KEY: misc_feature
<222> LOCATION: (16)..(16)
<223> OTHER INFORMATION: Xaa A or G
<220> FEATURE:
<221> NAME/KEY: misc_feature
<222> LOCATION: (20)..(20)
<223> OTHER INFORMATION: Xaa is T or S
<220> FEATURE:
<221> NAME/KEY: misc_feature
<222> LOCATION: (32)..(32)
<223> OTHER INFORMATION: Xaa is P or R
<220> FEATURE:
<221> NAME/KEY: misc_feature
<222> LOCATION: (36)..(36)
<223> OTHER INFORMATION: Xaa A or D
<220> FEATURE:

```
<221> NAME/KEY: misc_feature
<222> LOCATION: (37)..(37)
<223> OTHER INFORMATION: Xaa R or A
<220> FEATURE:
<221> NAME/KEY: misc_feature
<222> LOCATION: (38)..(38)
<223> OTHER INFORMATION: Xaa is R, Q or S
<220> FEATURE:
<221> NAME/KEY: misc_feature
<222> LOCATION: (39)..(39)
<223> OTHER INFORMATION: Xaa is S or P
<220> FEATURE:
<221> NAME/KEY: misc_feature
<222> LOCATION: (40)..(40)
<223> OTHER INFORMATION: Xaa is E, T, or Q
<220> FEATURE:
<221> NAME/KEY: misc_feature
<222> LOCATION: (42)..(42)
<223> OTHER INFORMATION: Xaa is R or K
<220> FEATURE:
<221> NAME/KEY: misc_feature
<222> LOCATION: (43)..(43)
<223> OTHER INFORMATION: Xaa is S, T, H, or A
<220> FEATURE:
<221> NAME/KEY: misc_feature
<222> LOCATION: (45)..(45)
<223> OTHER INFORMATION: Xaa is A or G
<220> FEATURE:
<221> NAME/KEY: misc_feature
<222> LOCATION: (46)..(46)
<223> OTHER INFORMATION: Xaa is Q or K

<400> SEQUENCE: 149

Gly Val Tyr Xaa Leu Pro Arg Arg Gly Pro Arg Leu Gly Val Arg Xaa
1               5                   10                  15

Thr Arg Lys Xaa Ser Glu Arg Ser Gln Pro Arg Gly Arg Gln Xaa
            20                  25                  30

Ile Pro Lys Xaa Xaa Xaa Xaa Xaa Gly Xaa Xaa Trp Xaa Xaa Pro Gly
        35                  40                  45

Tyr Pro
    50

<210> SEQ ID NO 150
<211> LENGTH: 50
<212> TYPE: PRT
<213> ORGANISM: Artificial Sequence
<220> FEATURE:
<223> OTHER INFORMATION: Synthetic sequence

<400> SEQUENCE: 150

Gly Val Tyr Leu Leu Pro Arg Arg Gly Pro Arg Leu Gly Val Arg Ala
1               5                   10                  15

Thr Arg Lys Thr Ser Glu Arg Ser Gln Pro Arg Gly Arg Gln Pro
            20                  25                  30

Ile Pro Lys Ala Arg Arg Pro Glu Gly Arg Thr Trp Ala Gln Pro Gly
        35                  40                  45

Tyr Pro
    50

<210> SEQ ID NO 151
<211> LENGTH: 50
<212> TYPE: PRT
<213> ORGANISM: Artificial Sequence
<220> FEATURE:
<223> OTHER INFORMATION: Synthetic sequence

<400> SEQUENCE: 151

Gly Val Tyr Leu Leu Pro Arg Arg Gly Pro Arg Leu Gly Val Arg Ala
```

```
                1               5                  10                  15
Thr Arg Lys Thr Ser Glu Arg Ser Gln Pro Arg Gly Arg Arg Gln Pro
                20                  25                  30

Ile Pro Lys Ala Arg Arg Pro Glu Gly Arg Ala Trp Ala Gln Pro Gly
            35                  40                  45

Tyr Pro
    50

<210> SEQ ID NO 152
<211> LENGTH: 50
<212> TYPE: PRT
<213> ORGANISM: Artificial Sequence
<220> FEATURE:
<223> OTHER INFORMATION: Synthetic sequence

<400> SEQUENCE: 152

Gly Val Tyr Leu Leu Pro Arg Arg Gly Pro Arg Leu Gly Val Arg Ala
1               5                   10                  15

Thr Arg Lys Thr Ser Glu Arg Ser Gln Pro Arg Gly Arg Gln Pro
                20                  25                  30

Ile Pro Lys Asp Arg Arg Ser Thr Gly Lys Ser Trp Gly Lys Pro Gly
            35                  40                  45

Tyr Pro
    50

<210> SEQ ID NO 153
<211> LENGTH: 50
<212> TYPE: PRT
<213> ORGANISM: Artificial Sequence
<220> FEATURE:
<223> OTHER INFORMATION: Synthetic sequence

<400> SEQUENCE: 153

Gly Val Tyr Val Leu Pro Arg Arg Gly Pro Arg Leu Gly Val Arg Ala
1               5                   10                  15

Thr Arg Lys Thr Ser Glu Arg Ser Gln Pro Arg Gly Arg Arg Gln Pro
                20                  25                  30

Ile Pro Lys Ala Arg Arg Ser Glu Gly Arg Ser Trp Ala Gln Pro Gly
            35                  40                  45

Tyr Pro
    50

<210> SEQ ID NO 154
<211> LENGTH: 50
<212> TYPE: PRT
<213> ORGANISM: Artificial Sequence
<220> FEATURE:
<223> OTHER INFORMATION: Synthetic sequence

<400> SEQUENCE: 154

Gly Val Tyr Leu Leu Pro Arg Arg Gly Pro Arg Leu Gly Val Arg Ala
1               5                   10                  15

Thr Arg Lys Thr Ser Glu Arg Ser Gln Pro Arg Gly Arg Arg Gln Pro
                20                  25                  30

Ile Pro Lys Ala Arg Arg Pro Thr Gly Arg Ser Trp Gly Gln Pro Gly
            35                  40                  45

Tyr Pro
    50

<210> SEQ ID NO 155
```

```
<211> LENGTH: 50
<212> TYPE: PRT
<213> ORGANISM: Artificial Sequence
<220> FEATURE:
<223> OTHER INFORMATION: Synthetic sequence

<400> SEQUENCE: 155

Gly Val Tyr Leu Leu Pro Arg Arg Gly Pro Arg Leu Gly Val Arg Ala
1               5                   10                  15

Thr Arg Lys Thr Ser Glu Arg Ser Gln Pro Arg Gly Arg Arg Gln Pro
            20                  25                  30

Ile Pro Lys Ala Arg Gln Pro Thr Gly Arg His Trp Ala Gln Pro Gly
        35                  40                  45

Tyr Pro
    50

<210> SEQ ID NO 156
<211> LENGTH: 50
<212> TYPE: PRT
<213> ORGANISM: Artificial Sequence
<220> FEATURE:
<223> OTHER INFORMATION: Synthetic sequence

<400> SEQUENCE: 156

Gly Val Tyr Leu Leu Pro Arg Arg Gly Pro Arg Leu Gly Val Arg Thr
1               5                   10                  15

Thr Arg Lys Ser Ser Glu Arg Ser Gln Pro Arg Gly Arg Arg Gln Arg
            20                  25                  30

Ile Pro Lys Ala Ala Ser Ser Gln Gly Lys Ala Trp Gly Lys Pro Gly
        35                  40                  45

Tyr Pro
    50

<210> SEQ ID NO 157
<211> LENGTH: 25
<212> TYPE: PRT
<213> ORGANISM: Artificial Sequence
<220> FEATURE:
<223> OTHER INFORMATION: Synthetic sequence

<400> SEQUENCE: 157

Arg Arg Gly Pro Arg Leu Gly Val Arg Ala Thr Arg Lys Thr Ser Glu
1               5                   10                  15

Arg Ser Gln Pro Arg Gly Arg Arg Gln
            20                  25

<210> SEQ ID NO 158
<211> LENGTH: 25
<212> TYPE: PRT
<213> ORGANISM: Artificial Sequence
<220> FEATURE:
<223> OTHER INFORMATION: Synthetic sequence

<400> SEQUENCE: 158

Arg Arg Gly Pro Arg Leu Gly Val Arg Gly Thr Arg Lys Ser Ser Glu
1               5                   10                  15

Arg Ser Gln Pro Arg Gly Arg Arg Gln
            20                  25

<210> SEQ ID NO 159
<211> LENGTH: 24
<212> TYPE: PRT
<213> ORGANISM: Artificial Sequence
```

<220> FEATURE:
<223> OTHER INFORMATION: Synthetic sequence

<400> SEQUENCE: 159

Arg Ala Thr Arg Lys Thr Ser Glu Arg Ser Gln Pro Arg Gly Arg Arg
1               5                   10                  15

Gln Pro Ile Pro Lys Ala Arg Arg
            20

<210> SEQ ID NO 160
<211> LENGTH: 24
<212> TYPE: PRT
<213> ORGANISM: Artificial Sequence
<220> FEATURE:
<223> OTHER INFORMATION: Synthetic sequence

<400> SEQUENCE: 160

Arg Gly Thr Arg Lys Ser Ser Glu Arg Ser Gln Pro Arg Gly Arg Arg
1               5                   10                  15

Gln Arg Ile Pro Lys Ala Ala Gln
            20

<210> SEQ ID NO 161
<211> LENGTH: 24
<212> TYPE: PRT
<213> ORGANISM: Artificial Sequence
<220> FEATURE:
<223> OTHER INFORMATION: Synthetic sequence

<400> SEQUENCE: 161

Arg Ala Thr Arg Lys Thr Ser Glu Arg Ser Gln Pro Arg Gly Arg Arg
1               5                   10                  15

Gln Pro Ile Pro Lys Ala Arg Gln
            20

<210> SEQ ID NO 162
<211> LENGTH: 24
<212> TYPE: PRT
<213> ORGANISM: Artificial Sequence
<220> FEATURE:
<223> OTHER INFORMATION: Synthetic sequence

<400> SEQUENCE: 162

Arg Ala Thr Arg Lys Thr Ser Glu Arg Ser Gln Pro Arg Gly Arg Arg
1               5                   10                  15

Gln Pro Ile Pro Lys Asp Arg Arg
            20

<210> SEQ ID NO 163
<211> LENGTH: 20
<212> TYPE: PRT
<213> ORGANISM: Artificial Sequence
<220> FEATURE:
<223> OTHER INFORMATION: Synthetic sequence

<400> SEQUENCE: 163

Arg Arg Gln Pro Ile Pro Lys Ala Arg Arg Ser Glu Gly Arg Ser Trp
1               5                   10                  15

Ala Gln Pro Gly
            20

<210> SEQ ID NO 164
<211> LENGTH: 20
<212> TYPE: PRT

```
<213> ORGANISM: Artificial Sequence
<220> FEATURE:
<223> OTHER INFORMATION: Synthetic sequence

<400> SEQUENCE: 164

Arg Arg Gln Pro Ile Pro Lys Ala Arg Pro Ser Glu Gly Arg Thr Trp
1               5                   10                  15

Ala Gln Pro Gly
            20

<210> SEQ ID NO 165
<211> LENGTH: 20
<212> TYPE: PRT
<213> ORGANISM: Artificial Sequence
<220> FEATURE:
<223> OTHER INFORMATION: Synthetic sequence

<400> SEQUENCE: 165

Arg Arg Gln Pro Ile Pro Lys Ala Arg Arg Pro Glu Gly Arg Ala Trp
1               5                   10                  15

Ala Gln Pro Gly
            20

<210> SEQ ID NO 166
<211> LENGTH: 20
<212> TYPE: PRT
<213> ORGANISM: Artificial Sequence
<220> FEATURE:
<223> OTHER INFORMATION: Synthetic sequence

<400> SEQUENCE: 166

Arg Arg Gln Pro Ile Pro Lys Asp Arg Arg Ser Thr Gly Lys Ser Trp
1               5                   10                  15

Gly Lys Pro Gly
            20

<210> SEQ ID NO 167
<211> LENGTH: 20
<212> TYPE: PRT
<213> ORGANISM: Artificial Sequence
<220> FEATURE:
<223> OTHER INFORMATION: Synthetic sequence

<400> SEQUENCE: 167

Arg Arg Gln Pro Ile Pro Lys Asp Arg Arg Ser Thr Gly Lys Ser Trp
1               5                   10                  15

Gly Lys Pro Gly
            20

<210> SEQ ID NO 168
<211> LENGTH: 20
<212> TYPE: PRT
<213> ORGANISM: Artificial Sequence
<220> FEATURE:
<223> OTHER INFORMATION: Synthetic sequence

<400> SEQUENCE: 168

Arg Arg Gln Pro Ile Pro Lys Ala Arg Arg Pro Thr Gly Arg Ser Trp
1               5                   10                  15

Gly Gln Pro Gly
            20

<210> SEQ ID NO 169
<211> LENGTH: 20
```

```
<212> TYPE: PRT
<213> ORGANISM: Artificial Sequence
<220> FEATURE:
<223> OTHER INFORMATION: Synthetic sequence

<400> SEQUENCE: 169

Arg Arg Gln Pro Ile Pro Lys Ala Arg Gln Pro Thr Gly Arg His Trp
1               5                   10                  15

Ala Gln Pro Gly
            20

<210> SEQ ID NO 170
<211> LENGTH: 20
<212> TYPE: PRT
<213> ORGANISM: Artificial Sequence
<220> FEATURE:
<223> OTHER INFORMATION: Synthetic sequence

<400> SEQUENCE: 170

Arg Arg Gln Arg Ile Pro Lys Ala Ala Ser Ser Gln Gly Lys Ala Trp
1               5                   10                  15

Gly Lys Pro Gly
            20

<210> SEQ ID NO 171
<211> LENGTH: 23
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (5)..(5)
<223> OTHER INFORMATION: Xaa is V or C
<220> FEATURE:
<221> NAME/KEY: misc_feature
<222> LOCATION: (6)..(6)
<223> OTHER INFORMATION: Xaa is A or S
<220> FEATURE:
<221> NAME/KEY: misc_feature
<222> LOCATION: (14)..(14)
<223> OTHER INFORMATION: Xaa is F or Y

<400> SEQUENCE: 171

Asp Val Val Val Xaa Xaa Thr Asp Ala Leu Met Thr Gly Xaa Thr Gly
1               5                   10                  15

Asp Phe Asp Ser Val Ile Asp
            20

<210> SEQ ID NO 172
<211> LENGTH: 23
<212> TYPE: PRT
<213> ORGANISM: Artificial Sequence
<220> FEATURE:
<223> OTHER INFORMATION: Synthetic sequence

<400> SEQUENCE: 172

Asp Val Val Val Val Ala Thr Asp Ala Leu Met Thr Gly Tyr Thr Gly
1               5                   10                  15

Asp Phe Asp Ser Val Ile Asp
            20

<210> SEQ ID NO 173
<211> LENGTH: 23
<212> TYPE: PRT
<213> ORGANISM: Artificial Sequence
<220> FEATURE:
```

<223> OTHER INFORMATION: Synthetic sequence

<400> SEQUENCE: 173

Asp Val Val Val Cys Ala Thr Asp Ala Leu Met Thr Gly Phe Thr Gly
1               5                   10                  15

Asp Phe Asp Ser Val Ile Asp
            20

<210> SEQ ID NO 174
<211> LENGTH: 23
<212> TYPE: PRT
<213> ORGANISM: Artificial Sequence
<220> FEATURE:
<223> OTHER INFORMATION: Synthetic sequence

<400> SEQUENCE: 174

Asp Val Val Val Cys Ser Thr Asp Ala Leu Met Thr Gly Phe Thr Gly
1               5                   10                  15

Asp Phe Asp Ser Val Ile Asp
            20

<210> SEQ ID NO 175
<211> LENGTH: 23
<212> TYPE: PRT
<213> ORGANISM: Artificial Sequence
<220> FEATURE:
<223> OTHER INFORMATION: Synthetic sequence

<400> SEQUENCE: 175

Asp Val Val Val Cys Ala Thr Asp Ala Leu Met Thr Gly Tyr Thr Gly
1               5                   10                  15

Asp Phe Asp Ser Val Ile Asp
            20

<210> SEQ ID NO 176
<211> LENGTH: 9
<212> TYPE: PRT
<213> ORGANISM: Artificial Sequence
<220> FEATURE:
<223> OTHER INFORMATION: Synthetic sequence

<400> SEQUENCE: 176

Ala Thr Asp Ala Leu Met Thr Gly Phe
1               5

<210> SEQ ID NO 177
<211> LENGTH: 9
<212> TYPE: PRT
<213> ORGANISM: Artificial Sequence
<220> FEATURE:
<223> OTHER INFORMATION: Synthetic sequence

<400> SEQUENCE: 177

Ser Thr Asp Ala Leu Met Thr Gly Phe
1               5

<210> SEQ ID NO 178
<211> LENGTH: 9
<212> TYPE: PRT
<213> ORGANISM: Artificial Sequence
<220> FEATURE:
<223> OTHER INFORMATION: Synthetic sequence

<400> SEQUENCE: 178

Ala Thr Asp Ala Leu Met Thr Gly Tyr

```
1               5

<210> SEQ ID NO 179
<211> LENGTH: 9
<212> TYPE: PRT
<213> ORGANISM: Artificial Sequence
<220> FEATURE:
<223> OTHER INFORMATION: Synthetic sequence

<400> SEQUENCE: 179

Gly Phe Thr Gly Asp Phe Asp Ser Val
1               5

<210> SEQ ID NO 180
<211> LENGTH: 9
<212> TYPE: PRT
<213> ORGANISM: Artificial Sequence
<220> FEATURE:
<223> OTHER INFORMATION: Synthetic sequence

<400> SEQUENCE: 180

Gly Tyr Thr Gly Asp Phe Asp Ser Val
1               5

<210> SEQ ID NO 181
<211> LENGTH: 15
<212> TYPE: PRT
<213> ORGANISM: Artificial Sequence
<220> FEATURE:
<223> OTHER INFORMATION: Synthetic sequence

<400> SEQUENCE: 181

Ala Thr Asp Ala Leu Met Thr Gly Phe Thr Gly Asp Phe Asp Ser
1               5                   10                  15

<210> SEQ ID NO 182
<211> LENGTH: 15
<212> TYPE: PRT
<213> ORGANISM: Artificial Sequence
<220> FEATURE:
<223> OTHER INFORMATION: Synthetic sequence

<400> SEQUENCE: 182

Ser Thr Asp Ala Leu Met Thr Gly Phe Thr Gly Asp Phe Asp Ser
1               5                   10                  15

<210> SEQ ID NO 183
<211> LENGTH: 15
<212> TYPE: PRT
<213> ORGANISM: Artificial Sequence
<220> FEATURE:
<223> OTHER INFORMATION: Synthetic sequence

<400> SEQUENCE: 183

Ala Thr Asp Ala Leu Met Thr Gly Tyr Thr Gly Asp Phe Asp Ser
1               5                   10                  15

<210> SEQ ID NO 184
<211> LENGTH: 15
<212> TYPE: PRT
<213> ORGANISM: Artificial Sequence
<220> FEATURE:
<223> OTHER INFORMATION: Synthetic sequence

<400> SEQUENCE: 184

Ala Leu Met Thr Gly Phe Thr Gly Asp Phe Asp Ser Val Ile Asp
1               5                   10                  15
```

<210> SEQ ID NO 185
<211> LENGTH: 15
<212> TYPE: PRT
<213> ORGANISM: Artificial Sequence
<220> FEATURE:
<223> OTHER INFORMATION: Synthetic sequence

<400> SEQUENCE: 185

Ala Leu Met Thr Gly Tyr Thr Gly Asp Phe Asp Ser Val Ile Asp
1               5                   10                  15

<210> SEQ ID NO 186
<211> LENGTH: 23
<212> TYPE: PRT
<213> ORGANISM: Artificial Sequence
<220> FEATURE:
<223> OTHER INFORMATION: Synthetic sequence

<400> SEQUENCE: 186

Asp Val Val Val Val Ala Thr Asp Ala Leu Met Thr Gly Phe Thr Gly
1               5                   10                  15

Asp Phe Asp Ser Val Ile Asp
            20

<210> SEQ ID NO 187
<211> LENGTH: 10
<212> TYPE: PRT
<213> ORGANISM: Artificial Sequence
<220> FEATURE:
<223> OTHER INFORMATION: Synthetic sequence

<400> SEQUENCE: 187

Ala Tyr Ala Ser Gln Gly Tyr Lys Val Leu
1               5                   10

<210> SEQ ID NO 188
<211> LENGTH: 27
<212> TYPE: PRT
<213> ORGANISM: Artificial Sequence
<220> FEATURE:
<223> OTHER INFORMATION: Synthetic sequence

<400> SEQUENCE: 188

Leu Glu Gln Ile Lys Gly Gly Arg His Leu Ile Phe Cys His Ser Lys
1               5                   10                  15

Lys Lys Cys Asp Glu Leu Ala Ala Lys Leu Thr
            20                  25

<210> SEQ ID NO 189
<211> LENGTH: 27
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: Xaa is L or I
<220> FEATURE:
<221> NAME/KEY: misc_feature
<222> LOCATION: (2)..(2)
<223> OTHER INFORMATION: Xaa is E, A, V, S, OR Q
<220> FEATURE:
<221> NAME/KEY: misc_feature
<222> LOCATION: (3)..(3)
<223> OTHER INFORMATION: Xaa is Q, T, Y, F, or L
<220> FEATURE:

```
<221> NAME/KEY: misc_feature
<222> LOCATION: (4)..(4)
<223> OTHER INFORMATION: Xaa is I or L
<220> FEATURE:
<221> NAME/KEY: misc_feature
<222> LOCATION: (22)..(22)
<223> OTHER INFORMATION: Xaa is L or I
<220> FEATURE:
<221> NAME/KEY: misc_feature
<222> LOCATION: (24)..(24)
<223> OTHER INFORMATION: Xaa is A, K, or S
<220> FEATURE:
<221> NAME/KEY: misc_feature
<222> LOCATION: (25)..(25)
<223> OTHER INFORMATION: Xaa is K, Q, or A
<220> FEATURE:
<221> NAME/KEY: misc_feature
<222> LOCATION: (27)..(27)
<223> OTHER INFORMATION: Xaa is T, R, or S

<400> SEQUENCE: 189

Xaa Xaa Xaa Xaa Lys Gly Gly Arg His Leu Ile Phe Cys His Ser Lys
1               5                   10                  15

Lys Lys Cys Asp Glu Xaa Ala Xaa Xaa Leu Xaa
            20                  25

<210> SEQ ID NO 190
<211> LENGTH: 27
<212> TYPE: PRT
<213> ORGANISM: Artificial Sequence
<220> FEATURE:
<223> OTHER INFORMATION: Synthetic sequence

<400> SEQUENCE: 190

Leu Glu Val Ile Lys Gly Gly Arg His Leu Ile Phe Cys His Ser Lys
1               5                   10                  15

Lys Lys Cys Asp Glu Leu Ala Ala Lys Leu Val
            20                  25

<210> SEQ ID NO 191
<211> LENGTH: 27
<212> TYPE: PRT
<213> ORGANISM: Artificial Sequence
<220> FEATURE:
<223> OTHER INFORMATION: Synthetic sequence

<400> SEQUENCE: 191

Ile Glu Thr Ile Lys Gly Gly Arg His Leu Ile Phe Cys His Ser Lys
1               5                   10                  15

Lys Lys Cys Asp Glu Leu Ala Ala Lys Leu Ser
            20                  25

<210> SEQ ID NO 192
<211> LENGTH: 27
<212> TYPE: PRT
<213> ORGANISM: Artificial Sequence
<220> FEATURE:
<223> OTHER INFORMATION: Synthetic sequence

<400> SEQUENCE: 192

Leu Ser Tyr Ile Lys Gly Gly Arg His Leu Ile Phe Cys His Ser Lys
1               5                   10                  15

Lys Lys Cys Asp Glu Leu Ala Ala Ala Leu Arg
            20                  25

<210> SEQ ID NO 193
<211> LENGTH: 26
```

```
<212> TYPE: PRT
<213> ORGANISM: Artificial Sequence
<220> FEATURE:
<223> OTHER INFORMATION: Synthetic sequence

<400> SEQUENCE: 193

Leu Ala Phe Ile Lys Gly Gly Arg His Leu Ile Phe Cys His Ser Lys
1               5                   10                  15

Lys Lys Cys Asp Glu Leu Ala Ala Leu Arg
            20                  25

<210> SEQ ID NO 194
<211> LENGTH: 27
<212> TYPE: PRT
<213> ORGANISM: Artificial Sequence
<220> FEATURE:
<223> OTHER INFORMATION: Synthetic sequence

<400> SEQUENCE: 194

Ile Ala Gln Leu Lys Gly Gly Arg His Leu Ile Phe Cys His Ser Lys
1               5                   10                  15

Lys Lys Cys Asp Glu Ile Ala Ser Lys Leu Arg
            20                  25

<210> SEQ ID NO 195
<211> LENGTH: 27
<212> TYPE: PRT
<213> ORGANISM: Artificial Sequence
<220> FEATURE:
<223> OTHER INFORMATION: Synthetic sequence

<400> SEQUENCE: 195

Ile Ala Gln Leu Lys Gly Gly Arg His Leu Ile Phe Cys His Ser Lys
1               5                   10                  15

Lys Lys Cys Asp Glu Ile Ala Ser Lys Leu Arg
            20                  25

<210> SEQ ID NO 196
<211> LENGTH: 26
<212> TYPE: PRT
<213> ORGANISM: Artificial Sequence
<220> FEATURE:
<223> OTHER INFORMATION: Synthetic sequence

<400> SEQUENCE: 196

Leu Glu Leu Ile Lys Gly Gly Arg His Leu Ile Phe Cys His Ser Lys
1               5                   10                  15

Lys Lys Cys Asp Glu Leu Ala Gln Leu Thr
            20                  25

<210> SEQ ID NO 197
<211> LENGTH: 27
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (2)..(2)
<223> OTHER INFORMATION: Xaa can be any naturally occurring amino acid

<400> SEQUENCE: 197

Leu Xaa Leu Ile Lys Gly Gly Arg His Leu Ile Phe Cys His Ser Lys
1               5                   10                  15

Lys Lys Cys Asp Glu Leu Ala Lys Gln Leu Thr
```

```
            20                  25

<210> SEQ ID NO 198
<211> LENGTH: 27
<212> TYPE: PRT
<213> ORGANISM: Artificial Sequence
<220> FEATURE:
<223> OTHER INFORMATION: Synthetic sequence

<400> SEQUENCE: 198

Leu Glu Tyr Ile Lys Gly Gly Arg His Leu Ile Phe Cys His Ser Lys
1               5                   10                  15

Lys Lys Cys Asp Glu Leu Ala Lys Gln Leu Thr
            20                  25

<210> SEQ ID NO 199
<211> LENGTH: 27
<212> TYPE: PRT
<213> ORGANISM: Artificial Sequence
<220> FEATURE:
<223> OTHER INFORMATION: Synthetic sequence

<400> SEQUENCE: 199

Leu Gln His Ile Lys Gly Gly Arg His Leu Ile Phe Cys His Ser Lys
1               5                   10                  15

Lys Lys Cys Asp Glu Leu Ala Gly Lys Leu Thr
            20                  25

<210> SEQ ID NO 200
<211> LENGTH: 9
<212> TYPE: PRT
<213> ORGANISM: Artificial Sequence
<220> FEATURE:
<223> OTHER INFORMATION: Synthetic sequence

<400> SEQUENCE: 200

Leu Ile Phe Cys His Ser Lys Lys Lys
1               5

<210> SEQ ID NO 201
<211> LENGTH: 9
<212> TYPE: PRT
<213> ORGANISM: Artificial Sequence
<220> FEATURE:
<223> OTHER INFORMATION: Synthetic sequence

<400> SEQUENCE: 201

His Ser Lys Lys Lys Cys Asp Glu Leu
1               5

<210> SEQ ID NO 202
<211> LENGTH: 16
<212> TYPE: PRT
<213> ORGANISM: Artificial Sequence
<220> FEATURE:
<223> OTHER INFORMATION: Synthetic sequence

<400> SEQUENCE: 202

Lys Gly Gly Arg His Leu Ile Phe Cys His Ser Lys Lys Lys Cys Asp
1               5                   10                  15

<210> SEQ ID NO 203
<211> LENGTH: 35
<212> TYPE: PRT
<213> ORGANISM: Artificial Sequence
<220> FEATURE:
```

<223> OTHER INFORMATION: Synthetic sequence

<400> SEQUENCE: 203

Ile Leu Arg Arg His Val Gly Pro Gly Glu Gly Ala Val Gln Trp Met
1               5                   10                  15

Asn Arg Leu Ile Ala Phe Ala Ser Arg Gly Asn His Val Ser Pro Thr
            20                  25                  30

His Tyr Val
        35

<210> SEQ ID NO 204
<211> LENGTH: 35
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: Xaa is I or V
<220> FEATURE:
<221> NAME/KEY: misc_feature
<222> LOCATION: (2)..(2)
<223> OTHER INFORMATION: Xaa is L or I
<220> FEATURE:
<221> NAME/KEY: misc_feature
<222> LOCATION: (3)..(3)
<223> OTHER INFORMATION: Xaa is R or K
<220> FEATURE:
<221> NAME/KEY: misc_feature
<222> LOCATION: (6)..(6)
<223> OTHER INFORMATION: Xaa is V, I, or T
<220> FEATURE:
<221> NAME/KEY: misc_feature
<222> LOCATION: (8)..(8)
<223> OTHER INFORMATION: Xaa is P, Q, or T
<220> FEATURE:
<221> NAME/KEY: misc_feature
<222> LOCATION: (9)..(9)
<223> OTHER INFORMATION: Xaa G, A, or S
<220> FEATURE:
<221> NAME/KEY: misc_feature
<222> LOCATION: (12)..(12)
<223> OTHER INFORMATION: Xaa is A or V
<220> FEATURE:
<221> NAME/KEY: misc_feature
<222> LOCATION: (13)..(13)
<223> OTHER INFORMATION: Xaa is V or T
<220> FEATURE:
<221> NAME/KEY: misc_feature
<222> LOCATION: (30)..(30)
<223> OTHER INFORMATION: Xaa is S or A
<220> FEATURE:
<221> NAME/KEY: misc_feature
<222> LOCATION: (35)..(35)
<223> OTHER INFORMATION: Xaa is V or I

<400> SEQUENCE: 204

Xaa Xaa Xaa Arg His Xaa Gly Xaa Xaa Glu Gly Xaa Xaa Gln Trp Met
1               5                   10                  15

Asn Arg Leu Ile Ala Phe Ala Ser Arg Gly Asn His Val Xaa Pro Thr
            20                  25                  30

His Tyr Xaa
        35

<210> SEQ ID NO 205
<211> LENGTH: 35
<212> TYPE: PRT
<213> ORGANISM: Artificial Sequence
<220> FEATURE:
<223> OTHER INFORMATION: Synthetic sequence

<400> SEQUENCE: 205

Ile Leu Arg Arg His Val Gly Pro Gly Glu Gly Ala Val Gln Trp Met
1               5                   10                  15

Asn Arg Leu Ile Ala Phe Ala Ser Arg Gly Asn His Val Ala Pro Thr
            20                  25                  30

His Tyr Val
        35

<210> SEQ ID NO 206
<211> LENGTH: 35
<212> TYPE: PRT
<213> ORGANISM: Artificial Sequence
<220> FEATURE:
<223> OTHER INFORMATION: Synthetic sequence

<400> SEQUENCE: 206

Ile Leu Arg Arg His Val Gly Gln Gly Glu Gly Ala Val Gln Trp Met
1               5                   10                  15

Asn Arg Leu Ile Ala Phe Ala Ser Arg Gly Asn His Val Ala Pro Thr
            20                  25                  30

His Tyr Val
        35

<210> SEQ ID NO 207
<211> LENGTH: 35
<212> TYPE: PRT
<213> ORGANISM: Artificial Sequence
<220> FEATURE:
<223> OTHER INFORMATION: Synthetic sequence

<400> SEQUENCE: 207

Val Leu Arg Arg His Ile Gly Pro Gly Glu Gly Ala Val Gln Trp Met
1               5                   10                  15

Asn Arg Leu Ile Ala Phe Ala Ser Arg Gly Asn His Val Ser Pro Thr
            20                  25                  30

His Tyr Val
        35

<210> SEQ ID NO 208
<211> LENGTH: 35
<212> TYPE: PRT
<213> ORGANISM: Artificial Sequence
<220> FEATURE:
<223> OTHER INFORMATION: Synthetic sequence

<400> SEQUENCE: 208

Ile Leu Arg Arg His Val Gly Pro Ala Glu Gly Ala Thr Gln Trp Met
1               5                   10                  15

Asn Arg Leu Ile Ala Phe Ala Ser Arg Gly Asn His Val Ser Pro Thr
            20                  25                  30

His Tyr Val
        35

<210> SEQ ID NO 209
<211> LENGTH: 35
<212> TYPE: PRT
<213> ORGANISM: Artificial Sequence
<220> FEATURE:
<223> OTHER INFORMATION: Synthetic sequence

<400> SEQUENCE: 209

Ile Ile Lys Arg His Thr Gly Thr Ser Glu Gly Val Thr Gln Trp Met
1               5                   10                  15

Asn Arg Leu Ile Ala Phe Ala Ser Arg Gly Asn His Val Ser Pro Thr
                20                  25                  30

His Tyr Ile
        35

<210> SEQ ID NO 210
<211> LENGTH: 16
<212> TYPE: PRT
<213> ORGANISM: Artificial Sequence
<220> FEATURE:
<223> OTHER INFORMATION: Synthetic sequence

<400> SEQUENCE: 210

Glu Gly Ala Val Gln Trp Met Asn Arg Leu Ile Ala Phe Ala Ser Arg
1               5                   10                  15

<210> SEQ ID NO 211
<211> LENGTH: 16
<212> TYPE: PRT
<213> ORGANISM: Artificial Sequence
<220> FEATURE:
<223> OTHER INFORMATION: Synthetic sequence

<400> SEQUENCE: 211

Glu Gly Ala Thr Gln Trp Met Asn Arg Leu Ile Ala Phe Ala Ser Arg
1               5                   10                  15

<210> SEQ ID NO 212
<211> LENGTH: 16
<212> TYPE: PRT
<213> ORGANISM: Artificial Sequence
<220> FEATURE:
<223> OTHER INFORMATION: Synthetic sequence

<400> SEQUENCE: 212

Glu Gly Val Thr Gln Trp Met Asn Arg Leu Ile Ala Phe Ala Ser Arg
1               5                   10                  15

<210> SEQ ID NO 213
<211> LENGTH: 9
<212> TYPE: PRT
<213> ORGANISM: Artificial Sequence
<220> FEATURE:
<223> OTHER INFORMATION: Synthetic sequence

<400> SEQUENCE: 213

Trp Met Asn Arg Leu Ile Ala Phe Ala
1               5

<210> SEQ ID NO 214
<211> LENGTH: 15
<212> TYPE: PRT
<213> ORGANISM: Artificial Sequence
<220> FEATURE:
<223> OTHER INFORMATION: Synthetic sequence

<400> SEQUENCE: 214

Arg His Val Gly Pro Gly Glu Gly Ala Val Gln Trp Met Asn Arg
1               5                   10                  15

<210> SEQ ID NO 215
<211> LENGTH: 15
<212> TYPE: PRT
<213> ORGANISM: Artificial Sequence

```
<220> FEATURE:
<223> OTHER INFORMATION: Synthetic sequence

<400> SEQUENCE: 215

Arg His Val Gly Gln Gly Glu Gly Ala Val Gln Trp Met Asn Arg
1               5                   10                  15

<210> SEQ ID NO 216
<211> LENGTH: 15
<212> TYPE: PRT
<213> ORGANISM: Artificial Sequence
<220> FEATURE:
<223> OTHER INFORMATION: Synthetic sequence

<400> SEQUENCE: 216

Arg His Ile Gly Pro Gly Glu Gly Ala Val Gln Trp Met Asn Arg
1               5                   10                  15

<210> SEQ ID NO 217
<211> LENGTH: 15
<212> TYPE: PRT
<213> ORGANISM: Artificial Sequence
<220> FEATURE:
<223> OTHER INFORMATION: Synthetic sequence

<400> SEQUENCE: 217

Arg His Val Gly Pro Ala Glu Gly Ala Thr Gln Trp Met Asn Arg
1               5                   10                  15

<210> SEQ ID NO 218
<211> LENGTH: 15
<212> TYPE: PRT
<213> ORGANISM: Artificial Sequence
<220> FEATURE:
<223> OTHER INFORMATION: Synthetic sequence

<400> SEQUENCE: 218

Arg His Thr Gly Thr Ser Glu Gly Val Thr Gln Trp Met Asn Arg
1               5                   10                  15

<210> SEQ ID NO 219
<211> LENGTH: 20
<212> TYPE: PRT
<213> ORGANISM: Artificial Sequence
<220> FEATURE:
<223> OTHER INFORMATION: Synthetic sequence

<400> SEQUENCE: 219

His Val Gly Pro Gly Glu Gly Ala Val Gln Trp Met Asn Arg Leu Ile
1               5                   10                  15

Ala Phe Ala Ser
            20

<210> SEQ ID NO 220
<211> LENGTH: 20
<212> TYPE: PRT
<213> ORGANISM: Artificial Sequence
<220> FEATURE:
<223> OTHER INFORMATION: Synthetic sequence

<400> SEQUENCE: 220

His Val Gly Gln Gly Glu Gly Ala Val Gln Trp Met Asn Arg Leu Ile
1               5                   10                  15

Ala Phe Ala Ser
            20
```

<210> SEQ ID NO 221
<211> LENGTH: 20
<212> TYPE: PRT
<213> ORGANISM: Artificial Sequence
<220> FEATURE:
<223> OTHER INFORMATION: Synthetic sequence

<400> SEQUENCE: 221

His Ile Gly Pro Gly Glu Gly Ala Val Gln Trp Met Asn Arg Leu Ile
1               5                   10                  15

Ala Phe Ala Ser
            20

<210> SEQ ID NO 222
<211> LENGTH: 20
<212> TYPE: PRT
<213> ORGANISM: Artificial Sequence
<220> FEATURE:
<223> OTHER INFORMATION: Synthetic sequence

<400> SEQUENCE: 222

His Val Gly Pro Ala Glu Gly Ala Thr Gln Trp Met Asn Arg Leu Ile
1               5                   10                  15

Ala Phe Ala Ser
            20

<210> SEQ ID NO 223
<211> LENGTH: 20
<212> TYPE: PRT
<213> ORGANISM: Artificial Sequence
<220> FEATURE:
<223> OTHER INFORMATION: Synthetic sequence

<400> SEQUENCE: 223

His Thr Gly Thr Ser Glu Gly Val Thr Gln Trp Met Asn Arg Leu Ile
1               5                   10                  15

Ala Phe Ala Ser
            20

<210> SEQ ID NO 224
<211> LENGTH: 20
<212> TYPE: PRT
<213> ORGANISM: Artificial Sequence
<220> FEATURE:
<223> OTHER INFORMATION: Synthetic sequence

<400> SEQUENCE: 224

Gly Ala Val Gln Trp Met Asn Arg Leu Ile Ala Phe Ala Ser Arg Gly
1               5                   10                  15

Asn His Val Ser
            20

<210> SEQ ID NO 225
<211> LENGTH: 20
<212> TYPE: PRT
<213> ORGANISM: Artificial Sequence
<220> FEATURE:
<223> OTHER INFORMATION: Synthetic sequence

<400> SEQUENCE: 225

Gly Ala Val Gln Trp Met Asn Arg Leu Ile Ala Phe Ala Ser Arg Gly
1               5                   10                  15

Asn His Val Ala
            20

```
<210> SEQ ID NO 226
<211> LENGTH: 20
<212> TYPE: PRT
<213> ORGANISM: Artificial Sequence
<220> FEATURE:
<223> OTHER INFORMATION: Synthetic sequence

<400> SEQUENCE: 226

Gly Ala Thr Gln Trp Met Asn Arg Leu Ile Ala Phe Ala Ser Arg Gly
1               5                   10                  15

Asn His Val Ser
            20

<210> SEQ ID NO 227
<211> LENGTH: 20
<212> TYPE: PRT
<213> ORGANISM: Artificial Sequence
<220> FEATURE:
<223> OTHER INFORMATION: Synthetic sequence

<400> SEQUENCE: 227

Gly Val Thr Gln Trp Met Asn Arg Leu Ile Ala Phe Ala Ser Arg Gly
1               5                   10                  15

Asn His Val Ser
            20

<210> SEQ ID NO 228
<211> LENGTH: 42
<212> TYPE: PRT
<213> ORGANISM: Artificial Sequence
<220> FEATURE:
<223> OTHER INFORMATION: Synthetic sequence

<400> SEQUENCE: 228

Gly Thr Glu Gly Glu Ile Pro Phe Tyr Gly Lys Ala Ile Pro Leu Glu
1               5                   10                  15

Gln Ile Lys Gly Gly Arg His Leu Ile Phe Cys His Ser Lys Lys Lys
            20                  25                  30

Cys Asp Glu Leu Ala Ala Lys Leu Thr Gly
        35                  40

<210> SEQ ID NO 229
<211> LENGTH: 43
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: Xaa is P, G, or S
<220> FEATURE:
<221> NAME/KEY: misc_feature
<222> LOCATION: (2)..(2)
<223> OTHER INFORMATION: Xaa is T, N, Q, H, or S
<220> FEATURE:
<221> NAME/KEY: misc_feature
<222> LOCATION: (3)..(3)
<223> OTHER INFORMATION: Xaa is E, T, or D
<220> FEATURE:
<221> NAME/KEY: misc_feature
<222> LOCATION: (11)..(11)
<223> OTHER INFORMATION: Xaa is K or R
<220> FEATURE:
<221> NAME/KEY: misc_feature
<222> LOCATION: (15)..(15)
<223> OTHER INFORMATION: Xaa is L or I
```

```
<220> FEATURE:
<221> NAME/KEY: misc_feature
<222> LOCATION: (16)..(16)
<223> OTHER INFORMATION: Xaa E, A, S, or Q
<220> FEATURE:
<221> NAME/KEY: misc_feature
<222> LOCATION: (17)..(17)
<223> OTHER INFORMATION: Xaa is Q, T, Y, F, or L
<220> FEATURE:
<221> NAME/KEY: misc_feature
<222> LOCATION: (18)..(18)
<223> OTHER INFORMATION: Xaa is I or L
<220> FEATURE:
<221> NAME/KEY: misc_feature
<222> LOCATION: (36)..(36)
<223> OTHER INFORMATION: Xaa is L or I
<220> FEATURE:
<221> NAME/KEY: misc_feature
<222> LOCATION: (38)..(38)
<223> OTHER INFORMATION: Xaa is A, K, or S
<220> FEATURE:
<221> NAME/KEY: misc_feature
<222> LOCATION: (39)..(39)
<223> OTHER INFORMATION: Xaa is K, Q, or A
<220> FEATURE:
<221> NAME/KEY: misc_feature
<222> LOCATION: (41)..(41)
<223> OTHER INFORMATION: Xaa is T, R, or S
<220> FEATURE:
<221> NAME/KEY: misc_feature
<222> LOCATION: (42)..(42)
<223> OTHER INFORMATION: Xaa is G or S
<220> FEATURE:
<221> NAME/KEY: misc_feature
<222> LOCATION: (43)..(43)
<223> OTHER INFORMATION: this stretch of residues may be repeated

<400> SEQUENCE: 229

Xaa Xaa Xaa Gly Glu Ile Pro Phe Tyr Gly Xaa Ala Ile Pro Xaa Xaa
1               5                   10                  15

Xaa Xaa Lys Gly Gly Arg His Leu Ile Phe Cys His Ser Lys Lys Lys
            20                  25                  30

Cys Asp Glu Xaa Ala Xaa Xaa Leu Xaa Xaa Lys
        35                  40

<210> SEQ ID NO 230
<211> LENGTH: 45
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: Xaa is P, G, or S
<220> FEATURE:
<221> NAME/KEY: misc_feature
<222> LOCATION: (2)..(2)
<223> OTHER INFORMATION: Xaa is T, N, Q, H, or S
<220> FEATURE:
<221> NAME/KEY: misc_feature
<222> LOCATION: (3)..(3)
<223> OTHER INFORMATION: Xaa is E, T, or D
<220> FEATURE:
<221> NAME/KEY: misc_feature
<222> LOCATION: (11)..(11)
<223> OTHER INFORMATION: Xaa is K or R
<220> FEATURE:
<221> NAME/KEY: misc_feature
<222> LOCATION: (15)..(15)
<223> OTHER INFORMATION: Xaa is L or I
<220> FEATURE:
<221> NAME/KEY: misc_feature
<222> LOCATION: (16)..(16)
<223> OTHER INFORMATION: Xaa E, A, S, or Q
```

```
<220> FEATURE:
<221> NAME/KEY: misc_feature
<222> LOCATION: (17)..(17)
<223> OTHER INFORMATION: Xaa is Q, T, Y, F, or L
<220> FEATURE:
<221> NAME/KEY: misc_feature
<222> LOCATION: (18)..(18)
<223> OTHER INFORMATION: Xaa is I or L
<220> FEATURE:
<221> NAME/KEY: misc_feature
<222> LOCATION: (36)..(36)
<223> OTHER INFORMATION: Xaa is L or I
<220> FEATURE:
<221> NAME/KEY: misc_feature
<222> LOCATION: (38)..(38)
<223> OTHER INFORMATION: Xaa is A, K, or S
<220> FEATURE:
<221> NAME/KEY: misc_feature
<222> LOCATION: (39)..(39)
<223> OTHER INFORMATION: Xaa is K, Q, or A
<220> FEATURE:
<221> NAME/KEY: misc_feature
<222> LOCATION: (41)..(41)
<223> OTHER INFORMATION: Xaa is T, R, or S
<220> FEATURE:
<221> NAME/KEY: misc_feature
<222> LOCATION: (42)..(42)
<223> OTHER INFORMATION: Xaa is G or S

<400> SEQUENCE: 230

Xaa Xaa Xaa Gly Glu Ile Pro Phe Tyr Gly Xaa Ala Ile Pro Xaa Xaa
1               5                   10                  15

Xaa Xaa Lys Gly Gly Arg His Leu Ile Phe Cys His Ser Lys Lys Lys
            20                  25                  30

Cys Asp Glu Xaa Ala Xaa Xaa Leu Xaa Xaa Lys Lys Lys
            35                  40                  45

<210> SEQ ID NO 231
<211> LENGTH: 45
<212> TYPE: PRT
<213> ORGANISM: Artificial Sequence
<220> FEATURE:
<223> OTHER INFORMATION: Synthetic sequence

<400> SEQUENCE: 231

Gly Thr Glu Gly Glu Ile Pro Phe Tyr Gly Lys Ala Ile Pro Leu Glu
1               5                   10                  15

Gln Ile Lys Gly Gly Arg His Leu Ile Phe Cys His Ser Lys Lys Lys
            20                  25                  30

Cys Asp Glu Leu Ala Ala Lys Leu Thr Gly Lys Lys Lys
            35                  40                  45

<210> SEQ ID NO 232
<211> LENGTH: 42
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: Xaa is P, G, or S
<220> FEATURE:
<221> NAME/KEY: misc_feature
<222> LOCATION: (2)..(2)
<223> OTHER INFORMATION: Xaa is T, N, Q, H, or S
<220> FEATURE:
<221> NAME/KEY: misc_feature
<222> LOCATION: (3)..(3)
<223> OTHER INFORMATION: Xaa is E, T, or D
<220> FEATURE:
```

```
<221> NAME/KEY: misc_feature
<222> LOCATION: (11)..(11)
<223> OTHER INFORMATION: Xaa is K or R
<220> FEATURE:
<221> NAME/KEY: misc_feature
<222> LOCATION: (15)..(15)
<223> OTHER INFORMATION: Xaa is L or I
<220> FEATURE:
<221> NAME/KEY: misc_feature
<222> LOCATION: (16)..(16)
<223> OTHER INFORMATION: Xaa E, A, S, or Q
<220> FEATURE:
<221> NAME/KEY: misc_feature
<222> LOCATION: (17)..(17)
<223> OTHER INFORMATION: Xaa is Q, T, Y, F, or L
<220> FEATURE:
<221> NAME/KEY: misc_feature
<222> LOCATION: (18)..(18)
<223> OTHER INFORMATION: Xaa is I or L
<220> FEATURE:
<221> NAME/KEY: misc_feature
<222> LOCATION: (36)..(36)
<223> OTHER INFORMATION: Xaa is L or I
<220> FEATURE:
<221> NAME/KEY: misc_feature
<222> LOCATION: (38)..(38)
<223> OTHER INFORMATION: Xaa is A, K, or S
<220> FEATURE:
<221> NAME/KEY: misc_feature
<222> LOCATION: (39)..(39)
<223> OTHER INFORMATION: Xaa is K, Q, or A
<220> FEATURE:
<221> NAME/KEY: misc_feature
<222> LOCATION: (41)..(41)
<223> OTHER INFORMATION: Xaa is T, R, or S
<220> FEATURE:
<221> NAME/KEY: misc_feature
<222> LOCATION: (42)..(42)
<223> OTHER INFORMATION: Xaa is G or S

<400> SEQUENCE: 232

Xaa Xaa Xaa Gly Glu Ile Pro Phe Tyr Gly Xaa Ala Ile Pro Xaa Xaa
1               5                   10                  15

Xaa Xaa Lys Gly Gly Arg His Leu Ile Phe Cys His Ser Lys Lys Lys
            20                  25                  30

Cys Asp Glu Xaa Ala Xaa Xaa Leu Xaa Xaa
        35                  40

<210> SEQ ID NO 233
<211> LENGTH: 42
<212> TYPE: PRT
<213> ORGANISM: Artificial Sequence
<220> FEATURE:
<223> OTHER INFORMATION: Synthetic sequence

<400> SEQUENCE: 233

Ser Thr Thr Gly Glu Ile Pro Phe Tyr Gly Lys Ala Ile Pro Leu Glu
1               5                   10                  15

Val Ile Lys Gly Gly Arg His Leu Ile Phe Cys His Ser Lys Lys Lys
            20                  25                  30

Cys Asp Glu Leu Ala Ala Lys Leu Val Ala
        35                  40

<210> SEQ ID NO 234
<211> LENGTH: 42
<212> TYPE: PRT
<213> ORGANISM: Artificial Sequence
<220> FEATURE:
<223> OTHER INFORMATION: Synthetic sequence

<400> SEQUENCE: 234
```

```
Ser Asn Thr Gly Glu Ile Pro Phe Tyr Gly Lys Ala Ile Pro Ile Glu
1               5                   10                  15

Thr Ile Lys Gly Gly Arg His Leu Ile Phe Cys His Ser Lys Lys Lys
            20                  25                  30

Cys Asp Glu Leu Ala Ala Lys Leu Ser Gly
        35                  40
```

<210> SEQ ID NO 235
<211> LENGTH: 42
<212> TYPE: PRT
<213> ORGANISM: Artificial Sequence
<220> FEATURE:
<223> OTHER INFORMATION: Synthetic sequence

<400> SEQUENCE: 235

```
Gly Gln Glu Gly Glu Ile Pro Phe Tyr Gly Arg Ala Ile Pro Leu Ser
1               5                   10                  15

Tyr Ile Lys Gly Gly Arg His Leu Ile Phe Cys His Ser Lys Lys Lys
            20                  25                  30

Cys Asp Glu Leu Ala Ala Ala Leu Arg Gly
        35                  40
```

<210> SEQ ID NO 236
<211> LENGTH: 41
<212> TYPE: PRT
<213> ORGANISM: Artificial Sequence
<220> FEATURE:
<223> OTHER INFORMATION: Synthetic sequence

<400> SEQUENCE: 236

```
Gly His Glu Gly Glu Ile Pro Phe Tyr Gly Lys Ala Ile Pro Leu Ala
1               5                   10                  15

Phe Ile Lys Gly Gly Arg His Leu Ile Phe Cys His Ser Lys Lys Lys
            20                  25                  30

Cys Asp Glu Leu Ala Ala Leu Arg Gly
        35                  40
```

<210> SEQ ID NO 237
<211> LENGTH: 42
<212> TYPE: PRT
<213> ORGANISM: Artificial Sequence
<220> FEATURE:
<223> OTHER INFORMATION: Synthetic sequence

<400> SEQUENCE: 237

```
Gly Ser Glu Gly Glu Ile Pro Phe Tyr Gly Lys Ala Ile Pro Ile Ala
1               5                   10                  15

Gln Leu Lys Gly Gly Arg His Leu Ile Phe Cys His Ser Lys Lys Lys
            20                  25                  30

Cys Asp Glu Ile Ala Ser Lys Leu Arg Gly
        35                  40
```

<210> SEQ ID NO 238
<211> LENGTH: 41
<212> TYPE: PRT
<213> ORGANISM: Artificial Sequence
<220> FEATURE:
<223> OTHER INFORMATION: Synthetic sequence

<400> SEQUENCE: 238

```
Pro Thr Thr Gly Glu Ile Pro Phe Tyr Gly Lys Ala Ile Pro Leu Glu
1               5                   10                  15
```

```
Leu Ile Lys Gly Gly Arg His Leu Ile Phe Cys His Ser Lys Lys Lys
            20                  25                  30

Cys Asp Glu Leu Ala Gln Leu Thr Ser
        35                  40

<210> SEQ ID NO 239
<211> LENGTH: 42
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (16)..(16)
<223> OTHER INFORMATION: Xaa can be any naturally occurring amino acid

<400> SEQUENCE: 239

Pro Ser Glu Gly Glu Ile Pro Phe Tyr Gly Arg Ala Ile Pro Leu Xaa
1               5                   10                  15

Leu Ile Lys Gly Gly Arg His Leu Ile Phe Cys His Ser Lys Lys Lys
            20                  25                  30

Cys Asp Glu Leu Ala Lys Gln Leu Thr Ser
        35                  40

<210> SEQ ID NO 240
<211> LENGTH: 42
<212> TYPE: PRT
<213> ORGANISM: Artificial Sequence
<220> FEATURE:
<223> OTHER INFORMATION: Synthetic sequence

<400> SEQUENCE: 240

Pro Thr Thr Gly Glu Ile Pro Phe Tyr Gly Lys Ala Ile Pro Leu Glu
1               5                   10                  15

Tyr Ile Lys Gly Gly Arg His Leu Ile Phe Cys His Ser Lys Lys Lys
            20                  25                  30

Cys Asp Glu Leu Ala Lys Gln Leu Thr Ser
        35                  40

<210> SEQ ID NO 241
<211> LENGTH: 42
<212> TYPE: PRT
<213> ORGANISM: Artificial Sequence
<220> FEATURE:
<223> OTHER INFORMATION: Synthetic sequence

<400> SEQUENCE: 241

Gly Asn Asp Gly Glu Ile Pro Phe Tyr Gly Lys Ala Ile Pro Leu Gln
1               5                   10                  15

His Ile Lys Gly Gly Arg His Leu Ile Phe Cys His Ser Lys Lys Lys
            20                  25                  30

Cys Asp Glu Leu Ala Gly Lys Leu Thr Ser
        35                  40

<210> SEQ ID NO 242
<211> LENGTH: 11
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (4)..(4)
<223> OTHER INFORMATION: Xaa is K or R
```

```
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa is E, S, A, Q, or V
<220> FEATURE:
<221> NAME/KEY: misc_feature
<222> LOCATION: (10)..(10)
<223> OTHER INFORMATION: Xaa is L or I
<220> FEATURE:
<221> NAME/KEY: misc_feature
<222> LOCATION: (10)..(10)
<223> OTHER INFORMATION: Xaa is Q, T, Y, F, I, or H
<220> FEATURE:
<221> NAME/KEY: misc_feature
<222> LOCATION: (11)..(11)
<223> OTHER INFORMATION: Xaa is I or L

<400> SEQUENCE: 242

Phe Tyr Gly Xaa Ala Ile Pro Xaa Xaa Xaa Xaa
1               5                   10

<210> SEQ ID NO 243
<211> LENGTH: 11
<212> TYPE: PRT
<213> ORGANISM: Artificial Sequence
<220> FEATURE:
<223> OTHER INFORMATION: Synthetic sequence

<400> SEQUENCE: 243

Phe Tyr Gly Lys Ala Ile Pro Leu Glu Gln Ile
1               5                   10

<210> SEQ ID NO 244
<211> LENGTH: 11
<212> TYPE: PRT
<213> ORGANISM: Artificial Sequence
<220> FEATURE:
<223> OTHER INFORMATION: Synthetic sequence

<400> SEQUENCE: 244

Gly Arg His Leu Ile Phe Cys His Ser Lys Lys
1               5                   10

<210> SEQ ID NO 245
<211> LENGTH: 37
<212> TYPE: PRT
<213> ORGANISM: Artificial Sequence
<220> FEATURE:
<223> OTHER INFORMATION: Synthetic sequence

<400> SEQUENCE: 245

Ile Pro Phe Tyr Gly Lys Ala Ile Pro Leu Glu Gln Ile Lys Gly Gly
1               5                   10                  15

Arg His Leu Ile Phe Cys His Ser Lys Lys Lys Cys Asp Glu Leu Ala
                20                  25                  30

Ala Lys Leu Thr Gly
            35

<210> SEQ ID NO 246
<211> LENGTH: 37
<212> TYPE: PRT
<213> ORGANISM: Artificial Sequence
<220> FEATURE:
<223> OTHER INFORMATION: Synthetic sequence
```

```
<400> SEQUENCE: 246

Gly Thr Glu Gly Glu Ile Pro Phe Tyr Gly Lys Ala Ile Pro Leu Glu
1               5                   10                  15

Gln Ile Lys Gly Gly Arg His Leu Ile Phe Cys His Ser Lys Lys Lys
            20                  25                  30

Cys Asp Glu Leu Ala
        35

<210> SEQ ID NO 247
<211> LENGTH: 45
<212> TYPE: PRT
<213> ORGANISM: Artificial Sequence
<220> FEATURE:
<223> OTHER INFORMATION: Synthetic sequence

<400> SEQUENCE: 247

Leu Asn Ala Val Ala Tyr Tyr Arg Gly Leu Asp Val Ser Val Ile Pro
1               5                   10                  15

Thr Ser Gly Asp Val Val Val Ala Thr Asp Ala Leu Met Thr Gly
            20                  25                  30

Phe Thr Gly Asp Phe Asp Ser Val Ile Asp Cys Asn Val
        35                  40                  45

<210> SEQ ID NO 248
<211> LENGTH: 45
<212> TYPE: PRT
<213> ORGANISM: Artificial Sequence
<220> FEATURE:
<223> OTHER INFORMATION: Synthetic sequence

<400> SEQUENCE: 248

Leu Asn Ala Val Ala Tyr Tyr Arg Gly Leu Asp Val Ser Val Ile Pro
1               5                   10                  15

Thr Ser Gly Asp Val Val Val Ala Thr Asp Ala Leu Met Thr Gly
            20                  25                  30

Phe Thr Gly Asp Phe Asp Ser Val Ile Asp Lys Lys Lys
        35                  40                  45

<210> SEQ ID NO 249
<211> LENGTH: 46
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: Xaa is L or V
<220> FEATURE:
<221> NAME/KEY: misc_feature
<222> LOCATION: (2)..(2)
<223> OTHER INFORMATION: Xaa is N or T
<220> FEATURE:
<221> NAME/KEY: misc_feature
<222> LOCATION: (6)..(6)
<223> OTHER INFORMATION: Xaa is Y or F
<220> FEATURE:
<221> NAME/KEY: misc_feature
<222> LOCATION: (10)..(10)
<223> OTHER INFORMATION: Xaa is L or V
<220> FEATURE:
<221> NAME/KEY: misc_feature
<222> LOCATION: (13)..(13)
<223> OTHER INFORMATION: Xaa is S or A
<220> FEATURE:
<221> NAME/KEY: misc_feature
<222> LOCATION: (14)..(14)
```

<223> OTHER INFORMATION: Xaa is V or I
<220> FEATURE:
<221> NAME/KEY: misc_feature
<222> LOCATION: (17)..(17)
<223> OTHER INFORMATION: Xaa is T or A
<220> FEATURE:
<221> NAME/KEY: misc_feature
<222> LOCATION: (18)..(18)
<223> OTHER INFORMATION: Xaa is S, Q, or T
<220> FEATURE:
<221> NAME/KEY: misc_feature
<222> LOCATION: (24)..(24)
<223> OTHER INFORMATION: Xaa is V or C
<220> FEATURE:
<221> NAME/KEY: misc_feature
<222> LOCATION: (25)..(25)
<223> OTHER INFORMATION: Xaa is A or S
<220> FEATURE:
<221> NAME/KEY: misc_feature
<222> LOCATION: (33)..(33)
<223> OTHER INFORMATION: Xaa is F or Y
<220> FEATURE:
<221> NAME/KEY: misc_feature
<222> LOCATION: (43)..(43)
<223> OTHER INFORMATION: Xaa is C or K
<220> FEATURE:
<221> NAME/KEY: misc_feature
<222> LOCATION: (44)..(44)
<223> OTHER INFORMATION: Xaa is N or K
<220> FEATURE:
<221> NAME/KEY: misc_feature
<222> LOCATION: (45)..(45)
<223> OTHER INFORMATION: Xaa is V or K
<220> FEATURE:
<221> NAME/KEY: misc_feature
<222> LOCATION: (46)..(46)
<223> OTHER INFORMATION: this stretch of residues may be repeated

<400> SEQUENCE: 249

Xaa Xaa Ala Val Ala Xaa Tyr Arg Gly Xaa Asp Val Xaa Xaa Ile Pro
1               5                   10                  15

Xaa Xaa Gly Asp Val Val Val Xaa Xaa Thr Asp Ala Leu Met Thr Gly
            20                  25                  30

Xaa Thr Gly Asp Phe Asp Ser Val Ile Asp Xaa Xaa Xaa Lys
        35                  40                  45

<210> SEQ ID NO 250
<211> LENGTH: 48
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: Xaa is L or V
<220> FEATURE:
<221> NAME/KEY: misc_feature
<222> LOCATION: (2)..(2)
<223> OTHER INFORMATION: Xaa is N or T
<220> FEATURE:
<221> NAME/KEY: misc_feature
<222> LOCATION: (6)..(6)
<223> OTHER INFORMATION: Xaa is Y or F
<220> FEATURE:
<221> NAME/KEY: misc_feature
<222> LOCATION: (10)..(10)
<223> OTHER INFORMATION: Xaa is L or V
<220> FEATURE:
<221> NAME/KEY: misc_feature
<222> LOCATION: (13)..(13)
<223> OTHER INFORMATION: Xaa is S or A
<220> FEATURE:
<221> NAME/KEY: misc_feature
<222> LOCATION: (14)..(14)

```
<223> OTHER INFORMATION: Xaa is V or I
<220> FEATURE:
<221> NAME/KEY: misc_feature
<222> LOCATION: (17)..(17)
<223> OTHER INFORMATION: Xaa is T or A
<220> FEATURE:
<221> NAME/KEY: misc_feature
<222> LOCATION: (18)..(18)
<223> OTHER INFORMATION: Xaa is S, Q, or T
<220> FEATURE:
<221> NAME/KEY: misc_feature
<222> LOCATION: (24)..(24)
<223> OTHER INFORMATION: Xaa is V or C
<220> FEATURE:
<221> NAME/KEY: misc_feature
<222> LOCATION: (25)..(25)
<223> OTHER INFORMATION: Xaa is A or S
<220> FEATURE:
<221> NAME/KEY: misc_feature
<222> LOCATION: (33)..(33)
<223> OTHER INFORMATION: Xaa is F or Y
<220> FEATURE:
<221> NAME/KEY: misc_feature
<222> LOCATION: (43)..(43)
<223> OTHER INFORMATION: Xaa is C or K
<220> FEATURE:
<221> NAME/KEY: misc_feature
<222> LOCATION: (44)..(44)
<223> OTHER INFORMATION: Xaa is N or K
<220> FEATURE:
<221> NAME/KEY: misc_feature
<222> LOCATION: (45)..(45)
<223> OTHER INFORMATION: Xaa is V or K

<400> SEQUENCE: 250

Xaa Xaa Ala Val Ala Xaa Tyr Arg Gly Xaa Asp Val Xaa Xaa Ile Pro
1               5                   10                  15

Xaa Xaa Gly Asp Val Val Val Xaa Xaa Thr Asp Ala Leu Met Thr Gly
            20                  25                  30

Xaa Thr Gly Asp Phe Asp Ser Val Ile Asp Xaa Xaa Xaa Lys Lys Lys
        35                  40                  45

<210> SEQ ID NO 251
<211> LENGTH: 48
<212> TYPE: PRT
<213> ORGANISM: Artificial Sequence
<220> FEATURE:
<223> OTHER INFORMATION: Synthetic sequence

<400> SEQUENCE: 251

Leu Asn Ala Val Ala Tyr Tyr Arg Gly Leu Asp Val Ser Val Ile Pro
1               5                   10                  15

Thr Ser Gly Asp Val Val Val Ala Thr Asp Ala Leu Met Thr Gly
            20                  25                  30

Phe Thr Gly Asp Phe Asp Ser Val Ile Asp Cys Asn Val Lys Lys Lys
        35                  40                  45

<210> SEQ ID NO 252
<211> LENGTH: 45
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: Xaa is L or V
<220> FEATURE:
<221> NAME/KEY: misc_feature
<222> LOCATION: (2)..(2)
<223> OTHER INFORMATION: Xaa is N or T
```

```
<220> FEATURE:
<221> NAME/KEY: misc_feature
<222> LOCATION: (6)..(6)
<223> OTHER INFORMATION: Xaa is Y or F
<220> FEATURE:
<221> NAME/KEY: misc_feature
<222> LOCATION: (10)..(10)
<223> OTHER INFORMATION: Xaa is L or V
<220> FEATURE:
<221> NAME/KEY: misc_feature
<222> LOCATION: (13)..(13)
<223> OTHER INFORMATION: Xaa is S or A
<220> FEATURE:
<221> NAME/KEY: misc_feature
<222> LOCATION: (14)..(14)
<223> OTHER INFORMATION: Xaa is V or I
<220> FEATURE:
<221> NAME/KEY: misc_feature
<222> LOCATION: (17)..(17)
<223> OTHER INFORMATION: Xaa is T or A
<220> FEATURE:
<221> NAME/KEY: misc_feature
<222> LOCATION: (18)..(18)
<223> OTHER INFORMATION: Xaa is S, Q, or T
<220> FEATURE:
<221> NAME/KEY: misc_feature
<222> LOCATION: (24)..(24)
<223> OTHER INFORMATION: Xaa is V or C
<220> FEATURE:
<221> NAME/KEY: misc_feature
<222> LOCATION: (25)..(25)
<223> OTHER INFORMATION: Xaa is A or S
<220> FEATURE:
<221> NAME/KEY: misc_feature
<222> LOCATION: (33)..(33)
<223> OTHER INFORMATION: Xaa is F or Y
<220> FEATURE:
<221> NAME/KEY: misc_feature
<222> LOCATION: (43)..(43)
<223> OTHER INFORMATION: Xaa is C or K
<220> FEATURE:
<221> NAME/KEY: misc_feature
<222> LOCATION: (44)..(44)
<223> OTHER INFORMATION: Xaa is N or K
<220> FEATURE:
<221> NAME/KEY: misc_feature
<222> LOCATION: (45)..(45)
<223> OTHER INFORMATION: Xaa is V or K

<400> SEQUENCE: 252

Xaa Xaa Ala Val Ala Xaa Tyr Arg Gly Xaa Asp Val Xaa Xaa Ile Pro
1               5                   10                  15

Xaa Xaa Gly Asp Val Val Xaa Xaa Thr Asp Ala Leu Met Thr Gly
            20                  25                  30

Xaa Thr Gly Asp Phe Asp Ser Val Ile Asp Xaa Xaa Xaa
        35                  40                  45

<210> SEQ ID NO 253
<211> LENGTH: 42
<212> TYPE: PRT
<213> ORGANISM: Artificial Sequence
<220> FEATURE:
<223> OTHER INFORMATION: Synthetic sequence

<400> SEQUENCE: 253

Leu Asn Ala Val Ala Tyr Tyr Arg Gly Leu Asp Val Ser Val Ile Pro
1               5                   10                  15

Thr Ser Gly Asp Val Val Val Ala Thr Asp Ala Leu Met Thr Gly
            20                  25                  30

Phe Thr Gly Asp Phe Asp Ser Val Ile Asp
        35                  40
```

<210> SEQ ID NO 254
<211> LENGTH: 48
<212> TYPE: PRT
<213> ORGANISM: Artificial Sequence
<220> FEATURE:
<223> OTHER INFORMATION: Synthetic sequence

<400> SEQUENCE: 254

Ile Leu Arg Arg His Val Gly Pro Gly Glu Gly Ala Val Gln Trp Met
1               5                   10                  15

Asn Arg Leu Ile Ala Phe Ala Ser Arg Gly Asn His Val Ser Pro Thr
            20                  25                  30

His Tyr Val Pro Glu Ser Asp Ala Ser Ala Arg Val Thr Gln Ile Leu
        35                  40                  45

<210> SEQ ID NO 255
<211> LENGTH: 49
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: Xaa is I or V
<220> FEATURE:
<221> NAME/KEY: misc_feature
<222> LOCATION: (2)..(2)
<223> OTHER INFORMATION: Xaa is L or I
<220> FEATURE:
<221> NAME/KEY: misc_feature
<222> LOCATION: (3)..(3)
<223> OTHER INFORMATION: Xaa is R or K
<220> FEATURE:
<221> NAME/KEY: misc_feature
<222> LOCATION: (6)..(6)
<223> OTHER INFORMATION: Xaa is V, I, or T
<220> FEATURE:
<221> NAME/KEY: misc_feature
<222> LOCATION: (8)..(8)
<223> OTHER INFORMATION: Xaa is P, Q, or T
<220> FEATURE:
<221> NAME/KEY: misc_feature
<222> LOCATION: (9)..(9)
<223> OTHER INFORMATION: Xaa is G, A, or S
<220> FEATURE:
<221> NAME/KEY: misc_feature
<222> LOCATION: (12)..(12)
<223> OTHER INFORMATION: Xaa is A or V
<220> FEATURE:
<221> NAME/KEY: misc_feature
<222> LOCATION: (13)..(13)
<223> OTHER INFORMATION: Xaa V or T
<220> FEATURE:
<221> NAME/KEY: misc_feature
<222> LOCATION: (30)..(30)
<223> OTHER INFORMATION: Xaa S or A
<220> FEATURE:
<221> NAME/KEY: misc_feature
<222> LOCATION: (35)..(35)
<223> OTHER INFORMATION: Xaa is V or I
<220> FEATURE:
<221> NAME/KEY: misc_feature
<222> LOCATION: (36)..(36)
<223> OTHER INFORMATION: Xaa iS P, T, A, or Q
<220> FEATURE:
<221> NAME/KEY: misc_feature
<222> LOCATION: (37)..(37)
<223> OTHER INFORMATION: Xaa is E or D
<220> FEATURE:
<221> NAME/KEY: misc_feature
<222> LOCATION: (38)..(38)
<223> OTHER INFORMATION: Xaa is S, T, or D
<220> FEATURE:

```
<221> NAME/KEY: misc_feature
<222> LOCATION: (41)..(41)
<223> OTHER INFORMATION: Xaa is S or A
<220> FEATURE:
<221> NAME/KEY: misc_feature
<222> LOCATION: (42)..(42)
<223> OTHER INFORMATION: Xaa is A, Q, R, or K
<220> FEATURE:
<221> NAME/KEY: misc_feature
<222> LOCATION: (43)..(43)
<223> OTHER INFORMATION: Xaa R or K
<220> FEATURE:
<221> NAME/KEY: misc_feature
<222> LOCATION: (45)..(45)
<223> OTHER INFORMATION: Xaa is T or M
<220> FEATURE:
<221> NAME/KEY: misc_feature
<222> LOCATION: (46)..(46)
<223> OTHER INFORMATION: Xaa Q, A, T, or G
<220> FEATURE:
<221> NAME/KEY: misc_feature
<222> LOCATION: (47)..(47)
<223> OTHER INFORMATION: Xaa is I, L or V
<220> FEATURE:
<221> NAME/KEY: misc_feature
<222> LOCATION: (49)..(49)
<223> OTHER INFORMATION: this stretch of residues may be repeated

<400> SEQUENCE: 255

Xaa Xaa Xaa Arg His Xaa Gly Xaa Xaa Glu Gly Xaa Xaa Gln Trp Met
 1               5                  10                  15

Asn Arg Leu Ile Ala Phe Ala Ser Arg Gly Asn His Val Xaa Pro Thr
            20                  25                  30

His Tyr Xaa Xaa Xaa Xaa Asp Ala Xaa Xaa Xaa Val Xaa Xaa Xaa Leu
        35                  40                  45

Lys

<210> SEQ ID NO 256
<211> LENGTH: 51
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: Xaa is I or V
<220> FEATURE:
<221> NAME/KEY: misc_feature
<222> LOCATION: (2)..(2)
<223> OTHER INFORMATION: Xaa is L or I
<220> FEATURE:
<221> NAME/KEY: misc_feature
<222> LOCATION: (3)..(3)
<223> OTHER INFORMATION: Xaa is R or K
<220> FEATURE:
<221> NAME/KEY: misc_feature
<222> LOCATION: (6)..(6)
<223> OTHER INFORMATION: Xaa is V, I, or T
<220> FEATURE:
<221> NAME/KEY: misc_feature
<222> LOCATION: (8)..(8)
<223> OTHER INFORMATION: Xaa is P, Q, or T
<220> FEATURE:
<221> NAME/KEY: misc_feature
<222> LOCATION: (9)..(9)
<223> OTHER INFORMATION: Xaa is G, A, or S
<220> FEATURE:
<221> NAME/KEY: misc_feature
<222> LOCATION: (12)..(12)
<223> OTHER INFORMATION: Xaa is A or V
<220> FEATURE:
<221> NAME/KEY: misc_feature
<222> LOCATION: (13)..(13)
```

```
<223> OTHER INFORMATION: Xaa V or T
<220> FEATURE:
<221> NAME/KEY: misc_feature
<222> LOCATION: (30)..(30)
<223> OTHER INFORMATION: Xaa S or A
<220> FEATURE:
<221> NAME/KEY: misc_feature
<222> LOCATION: (35)..(35)
<223> OTHER INFORMATION: Xaa is V or I
<220> FEATURE:
<221> NAME/KEY: misc_feature
<222> LOCATION: (36)..(36)
<223> OTHER INFORMATION: Xaa iS P, T, A, or Q
<220> FEATURE:
<221> NAME/KEY: misc_feature
<222> LOCATION: (37)..(37)
<223> OTHER INFORMATION: Xaa is E or D
<220> FEATURE:
<221> NAME/KEY: misc_feature
<222> LOCATION: (38)..(38)
<223> OTHER INFORMATION: Xaa is S, T, or D
<220> FEATURE:
<221> NAME/KEY: misc_feature
<222> LOCATION: (41)..(41)
<223> OTHER INFORMATION: Xaa is S or A
<220> FEATURE:
<221> NAME/KEY: misc_feature
<222> LOCATION: (42)..(42)
<223> OTHER INFORMATION: Xaa is A, Q, R, or K
<220> FEATURE:
<221> NAME/KEY: misc_feature
<222> LOCATION: (43)..(43)
<223> OTHER INFORMATION: Xaa R, K, or any amino acid residue
<220> FEATURE:
<221> NAME/KEY: misc_feature
<222> LOCATION: (45)..(45)
<223> OTHER INFORMATION: Xaa is T or M
<220> FEATURE:
<221> NAME/KEY: misc_feature
<222> LOCATION: (46)..(46)
<223> OTHER INFORMATION: Xaa Q, A, T, or G
<220> FEATURE:
<221> NAME/KEY: misc_feature
<222> LOCATION: (47)..(47)
<223> OTHER INFORMATION: Xaa is I, L or V

<400> SEQUENCE: 256

Xaa Xaa Xaa Arg His Xaa Gly Xaa Xaa Glu Gly Xaa Xaa Gln Trp Met
1               5                   10                  15

Asn Arg Leu Ile Ala Phe Ala Ser Arg Gly Asn His Val Xaa Pro Thr
            20                  25                  30

His Tyr Xaa Xaa Xaa Xaa Asp Ala Xaa Xaa Xaa Val Xaa Xaa Xaa Leu
                35                  40                  45

Lys Lys Lys
    50

<210> SEQ ID NO 257
<211> LENGTH: 51
<212> TYPE: PRT
<213> ORGANISM: Artificial Sequence
<220> FEATURE:
<223> OTHER INFORMATION: Synthetic sequence

<400> SEQUENCE: 257

Ile Leu Arg Arg His Val Gly Pro Gly Glu Gly Ala Val Gln Trp Met
1               5                   10                  15

Asn Arg Leu Ile Ala Phe Ala Ser Arg Gly Asn His Val Ser Pro Thr
            20                  25                  30

His Tyr Val Pro Glu Ser Asp Ala Ser Ala Arg Val Thr Gln Ile Leu
                35                  40                  45
```

Lys Lys Lys
    50

<210> SEQ ID NO 258
<211> LENGTH: 51
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (51)..(51)
<223> OTHER INFORMATION: This stretch of amino acid residues may be
      repeated

<400> SEQUENCE: 258

Gly Val Tyr Leu Leu Pro Arg Arg Gly Pro Arg Leu Gly Val Arg Ala
1               5                   10                  15

Thr Arg Lys Thr Ser Glu Arg Ser Gln Pro Arg Gly Arg Arg Gln Pro
            20                  25                  30

Ile Pro Lys Ala Arg Arg Ser Glu Gly Arg Ser Trp Ala Gln Pro Gly
        35                  40                  45

Tyr Pro Lys
    50

<210> SEQ ID NO 259
<211> LENGTH: 53
<212> TYPE: PRT
<213> ORGANISM: Artificial Sequence
<220> FEATURE:
<223> OTHER INFORMATION: Synthetic sequence

<400> SEQUENCE: 259

Gly Val Tyr Leu Leu Pro Arg Arg Gly Pro Arg Leu Gly Val Arg Ala
1               5                   10                  15

Thr Arg Lys Thr Ser Glu Arg Ser Gln Pro Arg Gly Arg Arg Gln Pro
            20                  25                  30

Ile Pro Lys Ala Arg Arg Ser Glu Gly Arg Ser Trp Ala Gln Pro Gly
        35                  40                  45

Tyr Pro Lys Lys Lys
    50

<210> SEQ ID NO 260
<211> LENGTH: 24
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (24)..(24)
<223> OTHER INFORMATION: This stretch of amino acid residues may be
      repeated

<400> SEQUENCE: 260

Asp Val Val Val Val Ala Thr Asp Ala Leu Met Thr Gly Phe Thr Gly
1               5                   10                  15

Asp Phe Asp Ser Val Ile Asp Lys
            20

<210> SEQ ID NO 261
<211> LENGTH: 26
<212> TYPE: PRT
<213> ORGANISM: Artificial Sequence
<220> FEATURE:

```
<223> OTHER INFORMATION: Synthetic sequence

<400> SEQUENCE: 261

Asp Val Val Val Ala Thr Asp Ala Leu Met Thr Gly Phe Thr Gly
1               5                   10                  15

Asp Phe Asp Ser Val Ile Asp Lys Lys Lys
            20                  25

<210> SEQ ID NO 262
<211> LENGTH: 28
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (28)..(28)
<223> OTHER INFORMATION: This stretch of amino acid residues may be
      repeated

<400> SEQUENCE: 262

Leu Glu Gln Ile Lys Gly Gly Arg His Leu Ile Phe Cys His Ser Lys
1               5                   10                  15

Lys Lys Cys Asp Glu Leu Ala Ala Lys Leu Thr Lys
            20                  25

<210> SEQ ID NO 263
<211> LENGTH: 30
<212> TYPE: PRT
<213> ORGANISM: Artificial Sequence
<220> FEATURE:
<223> OTHER INFORMATION: Synthetic sequence

<400> SEQUENCE: 263

Leu Glu Gln Ile Lys Gly Gly Arg His Leu Ile Phe Cys His Ser Lys
1               5                   10                  15

Lys Lys Cys Asp Glu Leu Ala Ala Lys Leu Thr Lys Lys Lys
            20                  25                  30

<210> SEQ ID NO 264
<211> LENGTH: 36
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (36)..(36)
<223> OTHER INFORMATION: This stretch of amino acid residues may be
      repeated

<400> SEQUENCE: 264

Ile Leu Arg Arg His Val Gly Pro Gly Glu Gly Ala Val Gln Trp Met
1               5                   10                  15

Asn Arg Leu Ile Ala Phe Ala Ser Arg Gly Asn His Val Ser Pro Thr
            20                  25                  30

His Tyr Val Lys
        35

<210> SEQ ID NO 265
<211> LENGTH: 38
<212> TYPE: PRT
<213> ORGANISM: Artificial Sequence
<220> FEATURE:
<223> OTHER INFORMATION: Synthetic sequence
```

<400> SEQUENCE: 265

Ile Leu Arg Arg His Val Gly Pro Gly Glu Gly Ala Val Gln Trp Met
1               5                   10                  15

Asn Arg Leu Ile Ala Phe Ala Ser Arg Gly Asn His Val Ser Pro Thr
                20                  25                  30

His Tyr Val Lys Lys Lys
                35

<210> SEQ ID NO 266
<211> LENGTH: 48
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: Xaa is I or V
<220> FEATURE:
<221> NAME/KEY: misc_feature
<222> LOCATION: (2)..(2)
<223> OTHER INFORMATION: Xaa is L or I
<220> FEATURE:
<221> NAME/KEY: misc_feature
<222> LOCATION: (3)..(3)
<223> OTHER INFORMATION: Xaa is R or K
<220> FEATURE:
<221> NAME/KEY: misc_feature
<222> LOCATION: (6)..(6)
<223> OTHER INFORMATION: Xaa is V, I, or T
<220> FEATURE:
<221> NAME/KEY: misc_feature
<222> LOCATION: (8)..(8)
<223> OTHER INFORMATION: Xaa is P, Q, or T
<220> FEATURE:
<221> NAME/KEY: misc_feature
<222> LOCATION: (9)..(9)
<223> OTHER INFORMATION: Xaa is G, A, or S
<220> FEATURE:
<221> NAME/KEY: misc_feature
<222> LOCATION: (12)..(12)
<223> OTHER INFORMATION: Xaa is A or V
<220> FEATURE:
<221> NAME/KEY: misc_feature
<222> LOCATION: (13)..(13)
<223> OTHER INFORMATION: Xaa V or T
<220> FEATURE:
<221> NAME/KEY: misc_feature
<222> LOCATION: (30)..(30)
<223> OTHER INFORMATION: Xaa S or A
<220> FEATURE:
<221> NAME/KEY: misc_feature
<222> LOCATION: (35)..(35)
<223> OTHER INFORMATION: Xaa is V or I
<220> FEATURE:
<221> NAME/KEY: misc_feature
<222> LOCATION: (36)..(36)
<223> OTHER INFORMATION: Xaa iS P, T, A, or Q
<220> FEATURE:
<221> NAME/KEY: misc_feature
<222> LOCATION: (37)..(37)
<223> OTHER INFORMATION: Xaa is E or D
<220> FEATURE:
<221> NAME/KEY: misc_feature
<222> LOCATION: (38)..(38)
<223> OTHER INFORMATION: Xaa is S, T, or D
<220> FEATURE:
<221> NAME/KEY: misc_feature
<222> LOCATION: (41)..(41)
<223> OTHER INFORMATION: Xaa is S or A
<220> FEATURE:
<221> NAME/KEY: misc_feature
<222> LOCATION: (42)..(42)
<223> OTHER INFORMATION: Xaa is A, Q, R, or K
<220> FEATURE:

```
<221> NAME/KEY: misc_feature
<222> LOCATION: (43)..(43)
<223> OTHER INFORMATION: Xaa R, K, or any amino acid residue
<220> FEATURE:
<221> NAME/KEY: misc_feature
<222> LOCATION: (45)..(45)
<223> OTHER INFORMATION: Xaa is T or M
<220> FEATURE:
<221> NAME/KEY: misc_feature
<222> LOCATION: (46)..(46)
<223> OTHER INFORMATION: Xaa Q, A, T, or G
<220> FEATURE:
<221> NAME/KEY: misc_feature
<222> LOCATION: (47)..(47)
<223> OTHER INFORMATION: Xaa is I, L or V

<400> SEQUENCE: 266

Xaa Xaa Xaa Arg His Xaa Gly Xaa Xaa Glu Gly Xaa Xaa Gln Trp Met
1               5                   10                  15

Asn Arg Leu Ile Ala Phe Ala Ser Arg Gly Asn His Val Xaa Pro Thr
            20                  25                  30

His Tyr Xaa Xaa Xaa Xaa Asp Ala Xaa Xaa Xaa Val Xaa Xaa Xaa Leu
        35                  40                  45

<210> SEQ ID NO 267
<211> LENGTH: 48
<212> TYPE: PRT
<213> ORGANISM: Artificial Sequence
<220> FEATURE:
<223> OTHER INFORMATION: Synthetic sequence

<400> SEQUENCE: 267

Ile Leu Arg Arg His Val Gly Pro Gly Glu Gly Ala Val Gln Trp Met
1               5                   10                  15

Asn Arg Leu Ile Ala Phe Ala Ser Arg Gly Asn His Val Ser Pro Thr
            20                  25                  30

His Tyr Val Pro Glu Ser Asp Ala Ala Ala Arg Val Thr Ala Ile Leu
        35                  40                  45

<210> SEQ ID NO 268
<211> LENGTH: 48
<212> TYPE: PRT
<213> ORGANISM: Artificial Sequence
<220> FEATURE:
<223> OTHER INFORMATION: Synthetic sequence

<400> SEQUENCE: 268

Ile Leu Arg Arg His Val Gly Pro Gly Glu Gly Ala Val Gln Trp Met
1               5                   10                  15

Asn Arg Leu Ile Ala Phe Ala Ser Arg Gly Asn His Val Ser Pro Thr
            20                  25                  30

His Tyr Val Pro Glu Ser Asp Ala Ala Ala Arg Val Thr Gln Ile Leu
        35                  40                  45

<210> SEQ ID NO 269
<211> LENGTH: 48
<212> TYPE: PRT
<213> ORGANISM: Artificial Sequence
<220> FEATURE:
<223> OTHER INFORMATION: Synthetic sequence

<400> SEQUENCE: 269

Ile Leu Arg Arg His Val Gly Pro Gly Glu Gly Ala Val Gln Trp Met
1               5                   10                  15

Asn Arg Leu Ile Ala Phe Ala Ser Arg Gly Asn His Val Ala Pro Thr
```

His Tyr Val Thr Glu Ser Asp Ala Ser Gln Arg Val Thr Gln Leu Leu
            35                  40                  45

<210> SEQ ID NO 270
<211> LENGTH: 48
<212> TYPE: PRT
<213> ORGANISM: Artificial Sequence
<220> FEATURE:
<223> OTHER INFORMATION: Synthetic sequence

<400> SEQUENCE: 270

Ile Leu Arg Arg His Val Gly Gln Gly Glu Gly Ala Val Gln Trp Met
1               5                   10                  15

Asn Arg Leu Ile Ala Phe Ala Ser Arg Gly Asn His Val Ala Pro Thr
            20                  25                  30

His Tyr Val Ala Glu Ser Asp Ala Ser Gln Arg Val Thr Gln Val Leu
            35                  40                  45

<210> SEQ ID NO 271
<211> LENGTH: 48
<212> TYPE: PRT
<213> ORGANISM: Artificial Sequence
<220> FEATURE:
<223> OTHER INFORMATION: Synthetic sequence

<400> SEQUENCE: 271

Ile Leu Arg Arg His Val Gly Pro Gly Glu Gly Ala Val Gln Trp Met
1               5                   10                  15

Asn Arg Leu Ile Ala Phe Ala Ser Arg Gly Asn His Val Ser Pro Thr
            20                  25                  30

His Tyr Val Pro Glu Ser Asp Ala Ala Ala Arg Val Thr Ala Leu Leu
            35                  40                  45

<210> SEQ ID NO 272
<211> LENGTH: 48
<212> TYPE: PRT
<213> ORGANISM: Artificial Sequence
<220> FEATURE:
<223> OTHER INFORMATION: Synthetic sequence

<400> SEQUENCE: 272

Val Leu Arg Arg His Ile Gly Pro Gly Glu Gly Ala Val Gln Trp Met
1               5                   10                  15

Asn Arg Leu Ile Ala Phe Ala Ser Arg Gly Asn His Val Ser Pro Thr
            20                  25                  30

His Tyr Val Pro Glu Thr Asp Ala Ser Ala Lys Val Thr Gln Leu Leu
            35                  40                  45

<210> SEQ ID NO 273
<211> LENGTH: 48
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (43)..(43)
<223> OTHER INFORMATION: Xaa can be any naturally occurring amino acid

<400> SEQUENCE: 273

Ile Leu Arg Arg His Val Gly Pro Ala Glu Gly Ala Thr Gln Trp Met
1               5                   10                  15

```
Asn Arg Leu Ile Ala Phe Ala Ser Arg Gly Asn His Val Ser Pro Thr
            20                  25                  30

His Tyr Val Pro Glu Thr Asp Ala Ser Arg Xaa Val Thr Thr Ile Leu
        35                  40                  45
```

<210> SEQ ID NO 274
<211> LENGTH: 48
<212> TYPE: PRT
<213> ORGANISM: Artificial Sequence
<220> FEATURE:
<223> OTHER INFORMATION: Synthetic sequence

<400> SEQUENCE: 274

```
Ile Ile Lys Arg His Thr Gly Thr Ser Glu Gly Val Thr Gln Trp Met
1               5                   10                  15

Asn Arg Leu Ile Ala Phe Ala Ser Arg Gly Asn His Val Ser Pro Thr
            20                  25                  30

His Tyr Ile Gln Asp Asp Asp Ala Ser Lys Arg Val Met Gly Ile Leu
        35                  40                  45
```

<210> SEQ ID NO 275
<211> LENGTH: 96
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (91)..(91)
<223> OTHER INFORMATION: Xaa can be any naturally occurring amino acid

<400> SEQUENCE: 275

```
Ile Ile Lys Arg His Thr Gly Thr Ser Glu Gly Val Thr Gln Trp Met
1               5                   10                  15

Asn Arg Leu Ile Ala Phe Ala Ser Arg Gly Asn His Val Ser Pro Thr
            20                  25                  30

His Tyr Ile Gln Asp Asp Asp Ala Ser Lys Arg Val Met Gly Ile Leu
        35                  40                  45

Ile Leu Arg Arg His Val Gly Pro Ala Glu Gly Ala Thr Gln Trp Met
    50                  55                  60

Asn Arg Leu Ile Ala Phe Ala Ser Arg Gly Asn His Val Ser Pro Thr
65                  70                  75                  80

His Tyr Val Pro Glu Thr Asp Ala Ser Arg Xaa Val Thr Thr Ile Leu
            85                  90                  95
```

<210> SEQ ID NO 276
<211> LENGTH: 15
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (5)..(5)
<223> OTHER INFORMATION: Xaa is V or I
<220> FEATURE:
<221> NAME/KEY: misc_feature
<222> LOCATION: (6)..(6)
<223> OTHER INFORMATION: Xaa P, T, A, or Q
<220> FEATURE:
<221> NAME/KEY: misc_feature
<222> LOCATION: (7)..(7)
<223> OTHER INFORMATION: Xaa is E or D
<220> FEATURE:
<221> NAME/KEY: misc_feature
<222> LOCATION: (8)..(8)

```
<223> OTHER INFORMATION: Xaa is S, T, or D
<220> FEATURE:
<221> NAME/KEY: misc_feature
<222> LOCATION: (11)..(11)
<223> OTHER INFORMATION: Xaa is S or A
<220> FEATURE:
<221> NAME/KEY: misc_feature
<222> LOCATION: (12)..(12)
<223> OTHER INFORMATION: Xaa is A, Q, R, or K
<220> FEATURE:
<221> NAME/KEY: misc_feature
<222> LOCATION: (13)..(13)
<223> OTHER INFORMATION: Xaa is R, K, or any amino acid residue
<220> FEATURE:
<221> NAME/KEY: misc_feature
<222> LOCATION: (15)..(15)
<223> OTHER INFORMATION: Xaa is T or M

<400> SEQUENCE: 276

Pro Thr His Tyr Xaa Xaa Xaa Xaa Asp Ala Xaa Xaa Xaa Val Xaa
1               5                   10                  15

<210> SEQ ID NO 277
<211> LENGTH: 45
<212> TYPE: PRT
<213> ORGANISM: Artificial Sequence
<220> FEATURE:
<223> OTHER INFORMATION: Synthetic sequence

<400> SEQUENCE: 277

Arg His Val Gly Pro Gly Glu Gly Ala Val Gln Trp Met Asn Arg Leu
1               5                   10                  15

Ile Ala Phe Ala Ser Arg Gly Asn His Val Ser Pro Thr His Tyr Val
            20                  25                  30

Pro Glu Ser Asp Ala Ser Ala Arg Val Thr Gln Ile Leu
        35                  40                  45

<210> SEQ ID NO 278
<211> LENGTH: 45
<212> TYPE: PRT
<213> ORGANISM: Artificial Sequence
<220> FEATURE:
<223> OTHER INFORMATION: Synthetic sequence

<400> SEQUENCE: 278

Ile Leu Arg Arg His Val Gly Pro Gly Glu Gly Ala Val Gln Trp Met
1               5                   10                  15

Asn Arg Leu Ile Ala Phe Ala Ser Arg Gly Asn His Val Ser Pro Thr
            20                  25                  30

His Tyr Val Pro Glu Ser Asp Ala Ser Ala Arg Val Thr
        35                  40                  45

<210> SEQ ID NO 279
<211> LENGTH: 33
<212> TYPE: PRT
<213> ORGANISM: Artificial Sequence
<220> FEATURE:
<223> OTHER INFORMATION: Synthetic sequence

<400> SEQUENCE: 279

His Ser Lys Lys Lys Cys Asp Glu Leu Ala Ala Lys Leu Thr Gly Leu
1               5                   10                  15

Gly Leu Asn Ala Val Ala Tyr Tyr Arg Gly Leu Asp Val Ser Val Ile
            20                  25                  30

Pro
```

```
<210> SEQ ID NO 280
<211> LENGTH: 19
<212> TYPE: PRT
<213> ORGANISM: Artificial Sequence
<220> FEATURE:
<223> OTHER INFORMATION: Synthetic sequence

<400> SEQUENCE: 280

Asp Glu Leu Ala Ala Lys Leu Thr Gly Leu Gly Leu Asn Ala Val Ala
1               5                   10                  15

Tyr Tyr Arg

<210> SEQ ID NO 281
<211> LENGTH: 19
<212> TYPE: PRT
<213> ORGANISM: Artificial Sequence
<220> FEATURE:
<223> OTHER INFORMATION: Synthetic sequence

<400> SEQUENCE: 281

Asp Glu Leu Ala Ala Lys Leu Val Ala Leu Gly Ile Asn Ala Val Ala
1               5                   10                  15

Tyr Tyr Arg

<210> SEQ ID NO 282
<211> LENGTH: 19
<212> TYPE: PRT
<213> ORGANISM: Artificial Sequence
<220> FEATURE:
<223> OTHER INFORMATION: Synthetic sequence

<400> SEQUENCE: 282

Asp Glu Leu Ala Ala Lys Leu Ser Gly Leu Gly Leu Asn Ala Val Ala
1               5                   10                  15

Tyr Tyr Arg

<210> SEQ ID NO 283
<211> LENGTH: 19
<212> TYPE: PRT
<213> ORGANISM: Artificial Sequence
<220> FEATURE:
<223> OTHER INFORMATION: Synthetic sequence

<400> SEQUENCE: 283

Asp Glu Leu Ala Ala Ala Leu Arg Gly Met Gly Leu Asn Ala Val Ala
1               5                   10                  15

Tyr Tyr Arg

<210> SEQ ID NO 284
<211> LENGTH: 19
<212> TYPE: PRT
<213> ORGANISM: Artificial Sequence
<220> FEATURE:
<223> OTHER INFORMATION: Synthetic sequence

<400> SEQUENCE: 284

Asp Glu Leu Ala Ala Ala Leu Arg Gly Met Gly Val Asn Ala Val Ala
1               5                   10                  15

Tyr Tyr Arg

<210> SEQ ID NO 285
<211> LENGTH: 19
<212> TYPE: PRT
```

```
<213> ORGANISM: Artificial Sequence
<220> FEATURE:
<223> OTHER INFORMATION: Synthetic sequence

<400> SEQUENCE: 285

Asp Glu Leu Ala Ser Lys Leu Arg Gly Met Gly Leu Asn Ala Val Ala
1               5                   10                  15

Tyr Tyr Arg

<210> SEQ ID NO 286
<211> LENGTH: 19
<212> TYPE: PRT
<213> ORGANISM: Artificial Sequence
<220> FEATURE:
<223> OTHER INFORMATION: Synthetic sequence

<400> SEQUENCE: 286

Asp Glu Leu Ala Ala Lys Leu Arg Gly Met Gly Leu Asn Ala Val Ala
1               5                   10                  15

Tyr Tyr Arg

<210> SEQ ID NO 287
<211> LENGTH: 33
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (11)..(11)
<223> OTHER INFORMATION: Xaa is A or S
<220> FEATURE:
<221> NAME/KEY: misc_feature
<222> LOCATION: (12)..(12)
<223> OTHER INFORMATION: Xaa is K or A
<220> FEATURE:
<221> NAME/KEY: misc_feature
<222> LOCATION: (14)..(14)
<223> OTHER INFORMATION: Xaa is V, S, R, or T
<220> FEATURE:
<221> NAME/KEY: misc_feature
<222> LOCATION: (15)..(15)
<223> OTHER INFORMATION: Xaa is A or G
<220> FEATURE:
<221> NAME/KEY: misc_feature
<222> LOCATION: (16)..(16)
<223> OTHER INFORMATION: Xaa is L or M
<220> FEATURE:
<221> NAME/KEY: misc_feature
<222> LOCATION: (18)..(18)
<223> OTHER INFORMATION: Xaa is I, L, or V
<220> FEATURE:
<221> NAME/KEY: misc_feature
<222> LOCATION: (31)..(31)
<223> OTHER INFORMATION: Xaa is V or I

<400> SEQUENCE: 287

His Ser Lys Lys Lys Cys Asp Glu Leu Ala Xaa Xaa Leu Xaa Xaa Xaa
1               5                   10                  15

Gly Xaa Asn Ala Val Ala Tyr Tyr Arg Gly Leu Asp Val Ser Xaa Ile
                20                  25                  30

Pro

<210> SEQ ID NO 288
<211> LENGTH: 33
<212> TYPE: PRT
<213> ORGANISM: Artificial Sequence
<220> FEATURE:
<223> OTHER INFORMATION: Synthetic sequence
```

```
<220> FEATURE:
<221> NAME/KEY: misc_feature
<222> LOCATION: (14)..(14)
<223> OTHER INFORMATION: Xaa is V, S, R, or T
<220> FEATURE:
<221> NAME/KEY: misc_feature
<222> LOCATION: (15)..(15)
<223> OTHER INFORMATION: Xaa is A or G
<220> FEATURE:
<221> NAME/KEY: misc_feature
<222> LOCATION: (16)..(16)
<223> OTHER INFORMATION: Xaa is L or M
<220> FEATURE:
<221> NAME/KEY: misc_feature
<222> LOCATION: (18)..(18)
<223> OTHER INFORMATION: Xaa is I, L or V

<400> SEQUENCE: 288

His Ser Lys Lys Lys Cys Asp Glu Leu Ala Ala Lys Leu Xaa Xaa Xaa
1               5                   10                  15

Gly Xaa Asn Ala Val Ala Tyr Tyr Arg Gly Leu Asp Val Ser Val Ile
            20                  25                  30

Pro

<210> SEQ ID NO 289
<211> LENGTH: 33
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (18)..(18)
<223> OTHER INFORMATION: Xaa is I, L or V
<220> FEATURE:
<221> NAME/KEY: misc_feature
<222> LOCATION: (31)..(31)
<223> OTHER INFORMATION: Xaa is V or I

<400> SEQUENCE: 289

His Ser Lys Lys Lys Cys Asp Glu Leu Ala Ala Ala Leu Arg Gly Met
1               5                   10                  15

Gly Xaa Asn Ala Val Ala Tyr Tyr Arg Gly Leu Asp Val Ser Xaa Ile
            20                  25                  30

Pro

<210> SEQ ID NO 290
<211> LENGTH: 33
<212> TYPE: PRT
<213> ORGANISM: Artificial Sequence
<220> FEATURE:
<223> OTHER INFORMATION: Synthetic sequence

<400> SEQUENCE: 290

His Ser Lys Lys Lys Cys Asp Glu Leu Ala Ala Lys Leu Arg Gly Met
1               5                   10                  15

Gly Leu Asn Ala Val Ala Tyr Tyr Arg Gly Leu Asp Val Ser Val Ile
            20                  25                  30

Pro

<210> SEQ ID NO 291
<211> LENGTH: 42
<212> TYPE: PRT
<213> ORGANISM: Artificial Sequence
<220> FEATURE:
<223> OTHER INFORMATION: Synthetic sequence
```

<400> SEQUENCE: 291

Lys Gly Gly Arg His Leu Ile Phe Cys His Ser Lys Lys Cys Asp
1               5                   10                  15

Glu Leu Ala Ala Lys Leu Thr Gly Leu Gly Leu Asn Ala Val Ala Tyr
            20                  25                  30

Tyr Arg Gly Leu Asp Val Ser Val Ile Pro
        35                  40

<210> SEQ ID NO 292
<211> LENGTH: 42
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (20)..(20)
<223> OTHER INFORMATION: Xaa is A or S
<220> FEATURE:
<221> NAME/KEY: misc_feature
<222> LOCATION: (21)..(21)
<223> OTHER INFORMATION: Xaa is K or A
<220> FEATURE:
<221> NAME/KEY: misc_feature
<222> LOCATION: (23)..(23)
<223> OTHER INFORMATION: Xaa is V, S, R, or T
<220> FEATURE:
<221> NAME/KEY: misc_feature
<222> LOCATION: (24)..(24)
<223> OTHER INFORMATION: Xaa is A or G
<220> FEATURE:
<221> NAME/KEY: misc_feature
<222> LOCATION: (25)..(25)
<223> OTHER INFORMATION: Xaa is L or M
<220> FEATURE:
<221> NAME/KEY: misc_feature
<222> LOCATION: (27)..(27)
<223> OTHER INFORMATION: Xaa is I, L, or V
<220> FEATURE:
<221> NAME/KEY: misc_feature
<222> LOCATION: (40)..(40)
<223> OTHER INFORMATION: Xaa is V or I

<400> SEQUENCE: 292

Lys Gly Gly Arg His Leu Ile Phe Cys His Ser Lys Lys Cys Asp
1               5                   10                  15

Glu Leu Ala Xaa Xaa Leu Xaa Xaa Xaa Gly Xaa Asn Ala Val Ala Tyr
            20                  25                  30

Tyr Arg Gly Leu Asp Val Ser Xaa Ile Pro
        35                  40

<210> SEQ ID NO 293
<211> LENGTH: 42
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (23)..(23)
<223> OTHER INFORMATION: Xaa is V, S, R, or T
<220> FEATURE:
<221> NAME/KEY: misc_feature
<222> LOCATION: (24)..(24)
<223> OTHER INFORMATION: Xaa A or G
<220> FEATURE:
<221> NAME/KEY: misc_feature
<222> LOCATION: (25)..(25)
<223> OTHER INFORMATION: Xaa is L or M
<220> FEATURE:
<221> NAME/KEY: misc_feature

```
<222> LOCATION: (27)..(27)
<223> OTHER INFORMATION: Xaa is I L, or V

<400> SEQUENCE: 293

Lys Gly Gly Arg His Leu Ile Phe Cys His Ser Lys Lys Cys Asp
1               5                   10                  15

Glu Leu Ala Ala Lys Leu Xaa Xaa Xaa Gly Xaa Asn Ala Val Ala Tyr
            20                  25                  30

Tyr Arg Gly Leu Asp Val Ser Val Ile Pro
        35                  40

<210> SEQ ID NO 294
<211> LENGTH: 42
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (27)..(27)
<223> OTHER INFORMATION: Xaa is I, L, or V
<220> FEATURE:
<221> NAME/KEY: misc_feature
<222> LOCATION: (40)..(40)
<223> OTHER INFORMATION: Xaa is V or I

<400> SEQUENCE: 294

Lys Gly Gly Arg His Leu Ile Phe Cys His Ser Lys Lys Cys Asp
1               5                   10                  15

Glu Leu Ala Ala Ala Leu Arg Gly Met Gly Xaa Asn Ala Val Ala Tyr
            20                  25                  30

Tyr Arg Gly Leu Asp Val Ser Xaa Ile Pro
        35                  40

<210> SEQ ID NO 295
<211> LENGTH: 85
<212> TYPE: PRT
<213> ORGANISM: Artificial Sequence
<220> FEATURE:
<223> OTHER INFORMATION: Synthetic sequence

<400> SEQUENCE: 295

Lys Ser Thr Lys Val Pro Ala Ala Tyr Ala Ala Gln Gly Tyr Lys Val
1               5                   10                  15

Leu Val Leu Asn Pro Ser Val Ala Ala Thr Leu Gly Phe Gly Ala Tyr
            20                  25                  30

Met Ser Lys Gly Val Tyr Leu Leu Pro Arg Arg Gly Pro Arg Leu Gly
        35                  40                  45

Val Arg Ala Thr Arg Lys Thr Ser Glu Arg Ser Gln Pro Arg Gly Arg
    50                  55                  60

Arg Gln Pro Ile Pro Lys Ala Arg Arg Ser Glu Gly Arg Ser Trp Ala
65                  70                  75                  80

Gln Pro Gly Tyr Pro
                85

<210> SEQ ID NO 296
<211> LENGTH: 85
<212> TYPE: PRT
<213> ORGANISM: Artificial Sequence
<220> FEATURE:
<223> OTHER INFORMATION: Synthetic sequence

<400> SEQUENCE: 296
```

-continued

```
Gly Val Tyr Leu Leu Pro Arg Arg Gly Pro Arg Leu Gly Val Arg Ala
1               5                   10                  15

Thr Arg Lys Thr Ser Glu Arg Ser Gln Pro Arg Gly Arg Gln Pro
            20                  25                  30

Ile Pro Lys Ala Arg Arg Ser Glu Gly Arg Ser Trp Ala Gln Pro Gly
            35                  40                  45

Tyr Pro Lys Ser Thr Lys Val Pro Ala Ala Tyr Ala Ala Gln Gly Tyr
        50                  55                  60

Lys Val Leu Val Leu Asn Pro Ser Val Ala Ala Thr Leu Gly Phe Gly
65                  70                  75                  80

Ala Tyr Met Ser Lys
                85
```

<210> SEQ ID NO 297
<211> LENGTH: 27
<212> TYPE: PRT
<213> ORGANISM: Artificial Sequence
<220> FEATURE:
<223> OTHER INFORMATION: Synthetic sequence

<400> SEQUENCE: 297

```
Leu Glu Gln Ile Lys Gly Gly Arg His Leu Ile Phe Cys His Ser Lys
1               5                   10                  15

Lys Lys Cys Asp Glu Leu Ala Ala Lys Leu Thr
            20                  25
```

<210> SEQ ID NO 298
<211> LENGTH: 135
<212> TYPE: PRT
<213> ORGANISM: Artificial Sequence
<220> FEATURE:
<223> OTHER INFORMATION: Synthetic sequence

<400> SEQUENCE: 298

```
Lys Ser Thr Lys Val Pro Ala Ala Tyr Ala Ala Gln Gly Tyr Lys Val
1               5                   10                  15

Leu Val Leu Asn Pro Ser Val Ala Ala Thr Leu Gly Phe Gly Ala Tyr
            20                  25                  30

Met Ser Lys Gly Val Tyr Leu Leu Pro Arg Arg Gly Pro Arg Leu Gly
            35                  40                  45

Val Arg Ala Thr Arg Lys Thr Ser Glu Arg Ser Gln Pro Arg Gly Arg
    50                  55                  60

Arg Gln Pro Ile Pro Lys Ala Arg Arg Ser Glu Gly Arg Ser Trp Ala
65                  70                  75                  80

Gln Pro Gly Tyr Pro Asp Val Val Val Ala Thr Asp Ala Leu Met
                85                  90                  95

Thr Gly Phe Thr Gly Asp Phe Asp Ser Val Ile Asp Leu Glu Gln Ile
            100                 105                 110

Lys Gly Gly Arg His Leu Ile Phe Cys His Ser Lys Lys Lys Cys Asp
            115                 120                 125

Glu Leu Ala Ala Lys Leu Thr
        130                 135
```

<210> SEQ ID NO 299
<211> LENGTH: 170
<212> TYPE: PRT
<213> ORGANISM: Artificial Sequence
<220> FEATURE:
<223> OTHER INFORMATION: Synthetic sequence

<400> SEQUENCE: 299

Lys Ser Thr Lys Val Pro Ala Ala Tyr Ala Ala Gln Gly Tyr Lys Val
1               5                   10                  15

Leu Val Leu Asn Pro Ser Val Ala Ala Thr Leu Gly Phe Gly Ala Tyr
            20                  25                  30

Met Ser Lys Gly Val Tyr Leu Leu Pro Arg Arg Gly Pro Arg Leu Gly
        35                  40                  45

Val Arg Ala Thr Arg Lys Thr Ser Glu Arg Ser Gln Pro Arg Gly Arg
    50                  55                  60

Arg Gln Pro Ile Pro Lys Ala Arg Arg Ser Glu Gly Arg Ser Trp Ala
65              70                  75                  80

Gln Pro Gly Tyr Pro Asp Val Val Val Ala Thr Asp Ala Leu Met
                85                  90                  95

Thr Gly Phe Thr Gly Asp Phe Asp Ser Val Ile Asp Leu Glu Gln Ile
                100                 105                 110

Lys Gly Gly Arg His Leu Ile Phe Cys His Ser Lys Lys Lys Cys Asp
            115                 120                 125

Glu Leu Ala Ala Lys Leu Thr Ile Leu Arg Arg His Val Gly Pro Gly
130                 135                 140

Glu Gly Ala Val Gln Trp Met Asn Arg Leu Ile Ala Phe Ala Ser Arg
145                 150                 155                 160

Gly Asn His Val Ser Pro Thr His Tyr Val
                165                 170

<210> SEQ ID NO 300
<211> LENGTH: 36
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (36)..(36)
<223> OTHER INFORMATION: This stretch of amino acid residues may be
      repeated

<400> SEQUENCE: 300

Lys Ser Thr Lys Val Pro Ala Ala Tyr Ala Ala Gln Gly Tyr Lys Val
1               5                   10                  15

Leu Val Leu Asn Pro Ser Val Ala Ala Thr Leu Gly Phe Gly Ala Tyr
            20                  25                  30

Met Ser Lys Lys
        35

<210> SEQ ID NO 301
<211> LENGTH: 43
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (43)..(43)
<223> OTHER INFORMATION: This stretch of amino acid residues may be
      repeated

<400> SEQUENCE: 301

Gly Thr Glu Gly Glu Ile Pro Phe Tyr Gly Lys Ala Ile Pro Leu Glu
1               5                   10                  15

Gln Ile Lys Gly Gly Arg His Leu Ile Phe Cys His Ser Lys Lys Lys
            20                  25                  30

```
Cys Asp Glu Leu Ala Ala Lys Leu Thr Gly Lys
        35                  40
```

<210> SEQ ID NO 302
<211> LENGTH: 38
<212> TYPE: PRT
<213> ORGANISM: Artificial Sequence
<220> FEATURE:
<223> OTHER INFORMATION: Synthetic sequence

<400> SEQUENCE: 302

```
Lys Ser Thr Lys Val Pro Ala Ala Tyr Ala Ala Gln Gly Tyr Lys Val
1               5                   10                  15

Leu Val Leu Asn Pro Ser Val Ala Ala Thr Leu Gly Phe Gly Ala Tyr
            20                  25                  30

Met Ser Lys Lys Lys Lys
        35
```

<210> SEQ ID NO 303
<211> LENGTH: 49
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (49)..(49)
<223> OTHER INFORMATION: This stretch of amino acid residues may be
      repeated

<400> SEQUENCE: 303

```
Ile Leu Arg Arg His Val Gly Pro Gly Glu Gly Ala Val Gln Trp Met
1               5                   10                  15

Asn Arg Leu Ile Ala Phe Ala Ser Arg Gly Asn His Val Ser Pro Thr
            20                  25                  30

His Tyr Val Pro Glu Ser Asp Ala Ser Ala Arg Val Thr Gln Ile Leu
        35                  40                  45

Lys
```

<210> SEQ ID NO 304
<211> LENGTH: 46
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (46)..(46)
<223> OTHER INFORMATION: This stretch of amino acid residues may be
      repeated

<400> SEQUENCE: 304

```
Leu Asn Ala Val Ala Tyr Tyr Arg Gly Leu Asp Val Ser Val Ile Pro
1               5                   10                  15

Thr Ser Gly Asp Val Val Val Ala Thr Asp Ala Leu Met Thr Gly
            20                  25                  30

Phe Thr Gly Asp Phe Asp Ser Val Ile Asp Cys Asn Val Lys
        35                  40                  45
```

<210> SEQ ID NO 305
<211> LENGTH: 43
<212> TYPE: PRT
<213> ORGANISM: Artificial Sequence
<220> FEATURE:

<223> OTHER INFORMATION: Synthetic sequence
<220> FEATURE:
<221> NAME/KEY: Misc_feature
<222> LOCATION: (43)..(43)
<223> OTHER INFORMATION: This stretch of amino acid residues may be
      repeated

<400> SEQUENCE: 305

Leu Asn Ala Val Ala Tyr Tyr Arg Gly Leu Asp Val Ser Val Ile Pro
1               5                   10                  15

Thr Ser Gly Asp Val Val Val Ala Thr Asp Ala Leu Met Thr Gly
            20                  25                  30

Phe Thr Gly Asp Phe Asp Ser Val Ile Asp Lys
        35                  40

<210> SEQ ID NO 306
<211> LENGTH: 49
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (49)..(49)
<223> OTHER INFORMATION: This stretch of amino acid residues may be
      repeated

<400> SEQUENCE: 306

Ile Leu Arg Arg His Val Gly Pro Gly Glu Gly Ala Val Gln Trp Met
1               5                   10                  15

Asn Arg Leu Ile Ala Phe Ala Ser Arg Gly Asn His Val Ser Pro Thr
            20                  25                  30

His Tyr Val Pro Glu Ser Asp Ala Ser Ala Arg Val Thr Gln Ile Leu
        35                  40                  45

Lys

<210> SEQ ID NO 307
<211> LENGTH: 35
<212> TYPE: PRT
<213> ORGANISM: Artificial Sequence
<220> FEATURE:
<223> OTHER INFORMATION: Synthetic sequence

<400> SEQUENCE: 307

Ile Leu Arg Arg His Val Gly Pro Gly Glu Gly Ala Val Gln Trp Met
1               5                   10                  15

Asn Arg Leu Ile Ala Phe Ala Ser Arg Gly Asn His Val Ser Pro Thr
            20                  25                  30

His Tyr Val
        35

<210> SEQ ID NO 308
<211> LENGTH: 49
<212> TYPE: PRT
<213> ORGANISM: Artificial Sequence
<220> FEATURE:
<223> OTHER INFORMATION: Synthetic sequence
<220> FEATURE:
<221> NAME/KEY: Misc_feature
<222> LOCATION: (49)..(49)
<223> OTHER INFORMATION: This stretch of amino acid residues may be
      repeated

<400> SEQUENCE: 308

Ile Leu Arg Arg His Val Gly Pro Gly Glu Gly Ala Val Gln Trp Met

```
                1               5                  10                 15
Asn Arg Leu Ile Ala Phe Ala Ser Arg Gly Asn His Val Ser Pro Thr
                20                 25                 30

His Tyr Val Pro Glu Ser Asp Ala Ser Ala Arg Val Thr Gln Ile Leu
        35                 40                 45

Lys

<210> SEQ ID NO 309
<211> LENGTH: 64
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (47)..(47)
<223> OTHER INFORMATION: Xaa can be any naturally occurring amino acid

<400> SEQUENCE: 309

Pro Gly Gly Gly Gln Ile Val Gly Gly Val Tyr Leu Leu Pro Arg Arg
1               5                  10                 15

Gly Pro Arg Leu Gly Val Arg Ala Thr Arg Lys Thr Ser Glu Arg Ser
                20                 25                 30

Gln Pro Arg Gly Arg Arg Gln Pro Ile Pro Lys Ala Arg Arg Xaa Gly
        35                 40                 45

Arg Ser Trp Ala Gln Pro Gly Tyr Pro Trp Pro Leu Tyr Gly Asn Glu
    50                 55                 60

<210> SEQ ID NO 310
<211> LENGTH: 65
<212> TYPE: PRT
<213> ORGANISM: Artificial Sequence
<220> FEATURE:
<223> OTHER INFORMATION: Synthetic sequence

<400> SEQUENCE: 310

Pro Gly Gly Gly Gln Ile Val Gly Gly Val Tyr Leu Leu Pro Arg Arg
1               5                  10                 15

Gly Pro Arg Leu Gly Val Arg Ala Thr Arg Lys Thr Ser Glu Arg Ser
                20                 25                 30

Gln Pro Arg Gly Arg Arg Gln Pro Ile Pro Lys Ala Arg Arg Pro Glu
        35                 40                 45

Gly Arg Thr Trp Ala Gln Pro Gly Tyr Pro Trp Pro Leu Tyr Gly Asn
    50                 55                 60

Glu
65

<210> SEQ ID NO 311
<211> LENGTH: 65
<212> TYPE: PRT
<213> ORGANISM: Artificial Sequence
<220> FEATURE:
<223> OTHER INFORMATION: Synthetic sequence

<400> SEQUENCE: 311

Pro Gly Gly Gly Gln Ile Val Gly Gly Val Tyr Leu Leu Pro Arg Arg
1               5                  10                 15

Gly Pro Arg Leu Gly Val Arg Ala Thr Arg Lys Thr Ser Glu Arg Ser
                20                 25                 30

Gln Pro Arg Gly Arg Arg Gln Pro Ile Pro Lys Ala Arg Arg Pro Glu
        35                 40                 45
```

```
Gly Arg Ala Trp Ala Gln Pro Gly Tyr Pro Trp Pro Leu Tyr Gly Asn
    50                  55                  60

Glu
65

<210> SEQ ID NO 312
<211> LENGTH: 65
<212> TYPE: PRT
<213> ORGANISM: Artificial Sequence
<220> FEATURE:
<223> OTHER INFORMATION: Synthetic sequence

<400> SEQUENCE: 312

Pro Gly Gly Gly Gln Ile Val Gly Gly Val Tyr Leu Leu Pro Arg Arg
1               5                   10                  15

Gly Pro Arg Leu Gly Val Arg Ala Thr Arg Lys Thr Ser Glu Arg Ser
            20                  25                  30

Gln Pro Arg Gly Arg Arg Gln Pro Ile Pro Lys Asp Arg Arg Ser Thr
        35                  40                  45

Gly Lys Ser Trp Gly Lys Pro Gly Tyr Pro Trp Pro Leu Tyr Gly Asn
    50                  55                  60

Glu
65

<210> SEQ ID NO 313
<211> LENGTH: 65
<212> TYPE: PRT
<213> ORGANISM: Artificial Sequence
<220> FEATURE:
<223> OTHER INFORMATION: Synthetic sequence

<400> SEQUENCE: 313

Pro Gly Gly Gly Gln Ile Val Gly Gly Val Tyr Leu Leu Pro Arg Arg
1               5                   10                  15

Gly Pro Arg Leu Gly Val Arg Ala Thr Arg Lys Thr Ser Glu Arg Ser
            20                  25                  30

Gln Pro Arg Gly Arg Arg Gln Pro Ile Pro Lys Asp Arg Arg Ser Thr
        35                  40                  45

Gly Lys Ser Trp Gly Lys Pro Gly Tyr Pro Trp Pro Leu Tyr Gly Asn
    50                  55                  60

Glu
65

<210> SEQ ID NO 314
<211> LENGTH: 65
<212> TYPE: PRT
<213> ORGANISM: Artificial Sequence
<220> FEATURE:
<223> OTHER INFORMATION: Synthetic sequence

<400> SEQUENCE: 314

Pro Gly Gly Gly Gln Ile Val Gly Gly Val Tyr Val Leu Pro Arg Arg
1               5                   10                  15

Gly Pro Arg Leu Gly Val Arg Ala Thr Arg Lys Thr Ser Glu Arg Ser
            20                  25                  30

Gln Pro Arg Gly Arg Arg Gln Pro Ile Pro Lys Ala Arg Arg Ser Glu
        35                  40                  45

Gly Arg Ser Trp Ala Gln Pro Gly Tyr Pro Trp Pro Leu Tyr Gly Asn
    50                  55                  60
```

Glu
65

<210> SEQ ID NO 315
<211> LENGTH: 65
<212> TYPE: PRT
<213> ORGANISM: Artificial Sequence
<220> FEATURE:
<223> OTHER INFORMATION: Synthetic sequence

<400> SEQUENCE: 315

Pro Gly Gly Gly Gln Ile Val Gly Gly Val Tyr Leu Leu Pro Arg Arg
1               5                   10                  15

Gly Pro Arg Leu Gly Val Arg Ala Thr Arg Lys Thr Ser Glu Arg Ser
            20                  25                  30

Gln Pro Arg Gly Arg Arg Gln Pro Ile Pro Lys Ala Arg Arg Ser Glu
        35                  40                  45

Gly Arg Ser Trp Ala Gln Pro Gly Tyr Pro Trp Pro Leu Tyr Gly Asn
    50                  55                  60

Glu
65

<210> SEQ ID NO 316
<211> LENGTH: 65
<212> TYPE: PRT
<213> ORGANISM: Artificial Sequence
<220> FEATURE:
<223> OTHER INFORMATION: Synthetic sequence

<400> SEQUENCE: 316

Pro Gly Gly Gly Gln Ile Val Gly Gly Val Tyr Leu Leu Pro Arg Arg
1               5                   10                  15

Gly Pro Arg Leu Gly Val Arg Ala Thr Arg Lys Thr Ser Glu Arg Ser
            20                  25                  30

Gln Pro Arg Gly Arg Arg Gln Pro Ile Pro Lys Ala Arg Arg Pro Thr
        35                  40                  45

Gly Arg Ser Trp Gly Gln Pro Gly Tyr Pro Trp Pro Leu Tyr Ala Asn
    50                  55                  60

Glu
65

<210> SEQ ID NO 317
<211> LENGTH: 65
<212> TYPE: PRT
<213> ORGANISM: Artificial Sequence
<220> FEATURE:
<223> OTHER INFORMATION: Synthetic sequence

<400> SEQUENCE: 317

Pro Gly Gly Gly Gln Ile Val Gly Gly Val Tyr Leu Leu Pro Arg Arg
1               5                   10                  15

Gly Pro Arg Leu Gly Val Arg Ala Thr Arg Lys Thr Ser Glu Arg Ser
            20                  25                  30

Gln Pro Arg Gly Arg Arg Gln Pro Ile Pro Lys Ala Arg Gln Pro Thr
        35                  40                  45

Gly Arg His Trp Ala Gln Pro Gly Tyr Pro Trp Pro Leu Tyr Gly Asn
    50                  55                  60

Glu
65

```
<210> SEQ ID NO 318
<211> LENGTH: 65
<212> TYPE: PRT
<213> ORGANISM: Artificial Sequence
<220> FEATURE:
<223> OTHER INFORMATION: Synthetic sequence

<400> SEQUENCE: 318

Pro Gly Gly Gly Gln Ile Val Gly Gly Val Tyr Leu Leu Pro Arg Arg
1               5                   10                  15

Gly Pro Arg Leu Gly Val Arg Gly Thr Arg Lys Ser Ser Glu Arg Ser
            20                  25                  30

Gln Pro Arg Gly Arg Arg Gln Arg Ile Pro Lys Ala Ala Ser Ser Gln
        35                  40                  45

Gly Lys Ala Trp Lys Gly Pro Gly Tyr Pro Trp Pro Leu Tyr Gly Asn
    50                  55                  60

Glu
65

<210> SEQ ID NO 319
<211> LENGTH: 50
<212> TYPE: PRT
<213> ORGANISM: Artificial Sequence
<220> FEATURE:
<223> OTHER INFORMATION: Synthetic sequence

<400> SEQUENCE: 319

Pro Thr Gly Ser Gly Lys Ser Thr Lys Val Pro Ala Ala Tyr Ala Ala
1               5                   10                  15

Gln Gly Tyr Lys Val Leu Val Leu Asn Pro Ser Val Ala Ala Thr Leu
            20                  25                  30

Gly Phe Gly Ala Tyr Met Ser Lys Ala His Gly Ile Asp Pro Asn Ile
        35                  40                  45

Arg Thr
    50

<210> SEQ ID NO 320
<211> LENGTH: 50
<212> TYPE: PRT
<213> ORGANISM: Artificial Sequence
<220> FEATURE:
<223> OTHER INFORMATION: Synthetic sequence

<400> SEQUENCE: 320

Pro Thr Gly Ser Gly Lys Ser Thr Lys Val Pro Ala Ala Tyr Ala Ala
1               5                   10                  15

Gln Gly Tyr Lys Val Leu Val Leu Asn Pro Ser Val Ala Ala Thr Leu
            20                  25                  30

Gly Phe Gly Ala Tyr Met Ser Lys Ala His Gly Ile Asp Pro Asn Ile
        35                  40                  45

Arg Thr
    50

<210> SEQ ID NO 321
<211> LENGTH: 50
<212> TYPE: PRT
<213> ORGANISM: Artificial Sequence
<220> FEATURE:
<223> OTHER INFORMATION: Synthetic sequence

<400> SEQUENCE: 321

Pro Thr Gly Ser Gly Lys Ser Thr Lys Val Pro Ala Ala Tyr Ala Ala
```

```
                1               5                  10                  15
Gln Gly Tyr Lys Val Leu Val Leu Asn Pro Ser Val Ala Ala Thr Leu
            20                  25                  30

Gly Phe Gly Ala Tyr Met Ser Lys Ala His Gly Val Asp Pro Asn Ile
        35                  40                  45

Arg Thr
    50

<210> SEQ ID NO 322
<211> LENGTH: 50
<212> TYPE: PRT
<213> ORGANISM: Artificial Sequence
<220> FEATURE:
<223> OTHER INFORMATION: Synthetic sequence

<400> SEQUENCE: 322

Pro Thr Gly Ser Gly Lys Ser Thr Lys Val Pro Val Ala Tyr Ala Ala
1               5                   10                  15

Gln Gly Tyr Lys Val Leu Val Leu Asn Pro Ser Val Ala Ala Thr Leu
            20                  25                  30

Gly Phe Gly Ala Tyr Leu Ser Lys Ala His Gly Ile Asn Pro Asn Ile
        35                  40                  45

Arg Thr
    50

<210> SEQ ID NO 323
<211> LENGTH: 50
<212> TYPE: PRT
<213> ORGANISM: Artificial Sequence
<220> FEATURE:
<223> OTHER INFORMATION: Synthetic sequence

<400> SEQUENCE: 323

Pro Thr Gly Ser Gly Lys Ser Thr Lys Val Pro Ala Ala Tyr Ala Ser
1               5                   10                  15

Gln Gly Tyr Lys Val Leu Val Leu Asn Pro Ser Val Ala Ala Thr Leu
            20                  25                  30

Gly Phe Gly Ala Tyr Met Ser Lys Ala His Gly Ile Asn Pro Asn Ile
        35                  40                  45

Arg Thr
    50

<210> SEQ ID NO 324
<211> LENGTH: 50
<212> TYPE: PRT
<213> ORGANISM: Artificial Sequence
<220> FEATURE:
<223> OTHER INFORMATION: Synthetic sequence

<400> SEQUENCE: 324

Pro Thr Gly Ser Gly Lys Ser Thr Lys Val Pro Ala Ala Tyr Val Ala
1               5                   10                  15

Gln Gly Tyr Asn Val Leu Val Leu Asn Pro Ser Val Ala Ala Thr Leu
            20                  25                  30

Gly Phe Gly Ser Phe Met Ser Arg Ala Tyr Gly Ile Asp Pro Asn Ile
        35                  40                  45

Arg Thr
    50

<210> SEQ ID NO 325
```

<211> LENGTH: 51
<212> TYPE: PRT
<213> ORGANISM: Artificial Sequence
<220> FEATURE:
<223> OTHER INFORMATION: Synthetic sequence

<400> SEQUENCE: 325

Pro Thr Gly Ser Gly Lys Ser Thr Lys Val Pro Ala Ala Tyr Ala Ala
1               5                   10                  15

Gln Gly Tyr Lys Val Leu Val Leu Asn Pro Ser Val Ala Ala Thr Leu
            20                  25                  30

Gly Phe Gly Ala Tyr Met Ser Lys Ala Ala Tyr Gly Ile Asp Pro Asn
        35                  40                  45

Ile Arg Ser
    50

<210> SEQ ID NO 326
<211> LENGTH: 50
<212> TYPE: PRT
<213> ORGANISM: Artificial Sequence
<220> FEATURE:
<223> OTHER INFORMATION: Synthetic sequence

<400> SEQUENCE: 326

Pro Thr Gly Ser Gly Lys Ser Thr Lys Val Pro Ala Ala Tyr Ala Ala
1               5                   10                  15

Gln Gly Tyr Lys Val Leu Val Leu Asn Pro Ser Val Ala Ala Thr Leu
            20                  25                  30

Gly Phe Gly Ala Tyr Met Ser Arg Ala Tyr Gly Val Asp Pro Asn Ile
        35                  40                  45

Arg Thr
    50

<210> SEQ ID NO 327
<211> LENGTH: 50
<212> TYPE: PRT
<213> ORGANISM: Artificial Sequence
<220> FEATURE:
<223> OTHER INFORMATION: Synthetic sequence

<400> SEQUENCE: 327

Pro Thr Gly Ser Gly Lys Ser Thr Lys Val Pro Ala Ala Tyr Ala Ser
1               5                   10                  15

Gln Gly Tyr Lys Val Leu Val Leu Asn Pro Ser Val Ala Ala Thr Leu
            20                  25                  30

Gly Phe Gly Ser Tyr Met Ser Lys Ala His Gly Ile Asp Pro Asn Ile
        35                  40                  45

Arg Thr
    50

<210> SEQ ID NO 328
<211> LENGTH: 50
<212> TYPE: PRT
<213> ORGANISM: Artificial Sequence
<220> FEATURE:
<223> OTHER INFORMATION: Synthetic sequence

<400> SEQUENCE: 328

Pro Thr Gly Ser Gly Lys Ser Thr Lys Val Pro Ala Ala Tyr Ala Ser
1               5                   10                  15

Gln Gly Tyr Lys Val Leu Val Leu Asn Pro Ser Val Ala Ala Thr Leu
            20                  25                  30

```
Gly Phe Gly Ala Tyr Met Ser Lys Ala Tyr Gly Ile Asp Pro Ser Val
            35                  40                  45

Arg Thr
     50

<210> SEQ ID NO 329
<211> LENGTH: 50
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid

<400> SEQUENCE: 329

Asn Ile Glu Glu Val Ala Leu Gly Thr Xaa Gly Glu Ile Pro Phe Tyr
1               5                   10                  15

Gly Lys Ala Ile Pro Leu Glu Xaa Ile Lys Gly Gly Arg His Leu Ile
            20                  25                  30

Phe Cys His Ser Lys Lys Lys Cys Asp Glu Leu Ala Ala Lys Leu Thr
            35                  40                  45

Xaa Leu
     50

<210> SEQ ID NO 330
<211> LENGTH: 49
<212> TYPE: PRT
<213> ORGANISM: Artificial Sequence
<220> FEATURE:
<223> OTHER INFORMATION: Synthetic sequence

<400> SEQUENCE: 330

Asn Ile Glu Glu Val Ala Leu Ser Thr Thr Gly Glu Ile Pro Phe Tyr
1               5                   10                  15

Gly Lys Ala Ile Pro Leu Glu Val Ile Lys Gly Gly Arg His Leu Ile
            20                  25                  30

Phe Cys His Ser Lys Lys Cys Asp Glu Leu Ala Ala Lys Leu Val Ala
            35                  40                  45

Leu

<210> SEQ ID NO 331
<211> LENGTH: 50
<212> TYPE: PRT
<213> ORGANISM: Artificial Sequence
<220> FEATURE:
<223> OTHER INFORMATION: Synthetic sequence

<400> SEQUENCE: 331

Asn Ile Glu Glu Val Ala Leu Ser Asn Thr Gly Glu Ile Pro Phe Tyr
1               5                   10                  15

Gly Lys Ala Ile Pro Ile Glu Thr Ile Lys Gly Gly Arg His Leu Ile
            20                  25                  30

Phe Cys His Ser Lys Lys Lys Cys Asp Glu Leu Ala Ala Lys Leu Ser
```

Gly Leu
    50

<210> SEQ ID NO 332
<211> LENGTH: 50
<212> TYPE: PRT
<213> ORGANISM: Artificial Sequence
<220> FEATURE:
<223> OTHER INFORMATION: Synthetic sequence

<400> SEQUENCE: 332

Asn Ile Glu Glu Val Ala Leu Gly Gln Glu Gly Glu Ile Pro Phe Tyr
1               5                   10                  15

Gly Arg Ala Ile Pro Leu Ser Tyr Ile Lys Gly Gly Arg His Leu Ile
            20                  25                  30

Phe Cys His Ser Lys Lys Lys Cys Asp Glu Leu Ala Ala Ala Leu Arg
        35                  40                  45

Gly Met
    50

<210> SEQ ID NO 333
<211> LENGTH: 50
<212> TYPE: PRT
<213> ORGANISM: Artificial Sequence
<220> FEATURE:
<223> OTHER INFORMATION: Synthetic sequence

<400> SEQUENCE: 333

Asn Ile Glu Glu Val Ala Leu Gly His Glu Gly Glu Ile Pro Phe Tyr
1               5                   10                  15

Gly Lys Ala Ile Pro Leu Ala Phe Ile Lys Gly Gly Arg His Leu Ile
            20                  25                  30

Phe Cys His Ser Lys Lys Lys Cys Asp Glu Leu Ala Ala Ala Leu Arg
        35                  40                  45

Gly Met
    50

<210> SEQ ID NO 334
<211> LENGTH: 50
<212> TYPE: PRT
<213> ORGANISM: Artificial Sequence
<220> FEATURE:
<223> OTHER INFORMATION: Synthetic sequence

<400> SEQUENCE: 334

Asn Ile Glu Glu Val Ala Leu Gly Ser Glu Gly Glu Ile Pro Phe Tyr
1               5                   10                  15

Gly Lys Ala Ile Pro Ile Ala Gln Leu Lys Gly Gly Arg His Leu Ile
            20                  25                  30

Phe Cys His Ser Lys Lys Lys Cys Asp Glu Ile Ala Ser Lys Leu Arg
        35                  40                  45

Gly Met
    50

<210> SEQ ID NO 335
<211> LENGTH: 50
<212> TYPE: PRT
<213> ORGANISM: Artificial Sequence
<220> FEATURE:
<223> OTHER INFORMATION: Synthetic sequence -continued

```
<400> SEQUENCE: 335

Asn Ile Glu Glu Val Ala Leu Pro Thr Thr Gly Glu Ile Pro Phe Tyr
1               5                   10                  15

Gly Lys Ala Ile Pro Leu Glu Leu Ile Lys Gly Gly Arg His Leu Ile
            20                  25                  30

Phe Cys His Ser Lys Lys Lys Cys Asp Glu Leu Ala Lys Gln Leu Thr
        35                  40                  45

Ser Leu
    50

<210> SEQ ID NO 336
<211> LENGTH: 50
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (23)..(23)
<223> OTHER INFORMATION: Xaa can be any naturally occurring amino acid

<400> SEQUENCE: 336

Asn Ile Glu Glu Val Ala Leu Pro Ser Glu Gly Glu Ile Pro Phe Tyr
1               5                   10                  15

Gly Arg Ala Ile Pro Leu Xaa Leu Ile Lys Gly Gly Arg His Leu Ile
            20                  25                  30

Phe Cys His Ser Lys Lys Lys Cys Asp Glu Leu Ala Lys Gln Leu Thr
        35                  40                  45

Ser Leu
    50

<210> SEQ ID NO 337
<211> LENGTH: 50
<212> TYPE: PRT
<213> ORGANISM: Artificial Sequence
<220> FEATURE:
<223> OTHER INFORMATION: Synthetic sequence

<400> SEQUENCE: 337

Asn Ile Thr Glu Thr Ala Leu Pro Thr Thr Gly Glu Ile Pro Phe Tyr
1               5                   10                  15

Gly Lys Ala Ile Pro Leu Glu Tyr Ile Lys Gly Gly Arg His Leu Ile
            20                  25                  30

Phe Cys His Ser Lys Lys Lys Cys Asp Glu Leu Ala Lys Gln Leu Thr
        35                  40                  45

Ser Leu
    50

<210> SEQ ID NO 338
<211> LENGTH: 50
<212> TYPE: PRT
<213> ORGANISM: Artificial Sequence
<220> FEATURE:
<223> OTHER INFORMATION: Synthetic sequence

<400> SEQUENCE: 338

Asn Ile Glu Glu Val Ala Leu Gly Asn Asp Gly Glu Ile Pro Phe Tyr
1               5                   10                  15

Gly Lys Ala Ile Pro Leu Gln His Ile Lys Gly Gly Arg His Leu Ile
            20                  25                  30

Phe Cys His Ser Lys Lys Lys Cys Asp Glu Leu Ala Gly Lys Leu Thr
```

-continued

```
                35                  40                  45

Ser Leu
    50

<210> SEQ ID NO 339
<211> LENGTH: 49
<212> TYPE: PRT
<213> ORGANISM: Artificial Sequence
<220> FEATURE:
<223> OTHER INFORMATION: Synthetic sequence

<400> SEQUENCE: 339

Gly Leu Asn Ala Val Ala Tyr Tyr Arg Gly Leu Asp Val Ser Val Ile
1               5                   10                  15

Pro Thr Ser Gly Asp Val Val Val Ala Thr Asp Ala Leu Met Thr
            20                  25                  30

Gly Phe Thr Gly Asp Phe Asp Ser Val Ile Asp Cys Asn Val Ala Val
        35                  40                  45

Thr

<210> SEQ ID NO 340
<211> LENGTH: 49
<212> TYPE: PRT
<213> ORGANISM: Artificial Sequence
<220> FEATURE:
<223> OTHER INFORMATION: Synthetic sequence

<400> SEQUENCE: 340

Gly Ile Asn Ala Val Ala Tyr Tyr Arg Gly Leu Asp Val Ser Val Ile
1               5                   10                  15

Pro Thr Ser Gly Asp Val Val Val Ala Thr Asp Ala Leu Met Thr
            20                  25                  30

Gly Phe Thr Gly Asp Phe Asp Ser Val Ile Asp Cys Asn Thr Cys Val
        35                  40                  45

Thr

<210> SEQ ID NO 341
<211> LENGTH: 49
<212> TYPE: PRT
<213> ORGANISM: Artificial Sequence
<220> FEATURE:
<223> OTHER INFORMATION: Synthetic sequence

<400> SEQUENCE: 341

Gly Leu Asn Ala Val Ala Tyr Tyr Arg Gly Leu Asp Val Ser Val Ile
1               5                   10                  15

Pro Thr Ser Gly Asp Val Val Val Ala Thr Asp Ala Leu Met Thr
            20                  25                  30

Gly Phe Thr Gly Asp Phe Asp Ser Val Ile Asp Cys Asn Thr Cys Val
        35                  40                  45

Thr

<210> SEQ ID NO 342
<211> LENGTH: 49
<212> TYPE: PRT
<213> ORGANISM: Artificial Sequence
<220> FEATURE:
<223> OTHER INFORMATION: Synthetic sequence

<400> SEQUENCE: 342

Gly Leu Asn Ala Val Ala Tyr Tyr Arg Gly Leu Asp Val Ser Ile Ile
```

```
                1               5                  10                  15
Pro Thr Gln Gly Asp Val Val Val Ala Thr Asp Ala Leu Met Thr
                20                  25                  30

Gly Tyr Thr Gly Asp Phe Asp Ser Val Ile Asp Cys Asn Val Ala Val
        35                  40                  45

Thr
```

<210> SEQ ID NO 343
<211> LENGTH: 49
<212> TYPE: PRT
<213> ORGANISM: Artificial Sequence
<220> FEATURE:
<223> OTHER INFORMATION: Synthetic sequence

<400> SEQUENCE: 343

```
Gly Val Asn Ala Val Ala Tyr Tyr Arg Gly Leu Asp Val Ser Val Ile
1               5                  10                  15

Pro Thr Gln Gly Asp Val Val Val Ala Thr Asp Ala Leu Met Thr
                20                  25                  30

Gly Tyr Thr Gly Asp Phe Asp Ser Val Ile Asp Cys Asn Val Ala Val
        35                  40                  45

Thr
```

<210> SEQ ID NO 344
<211> LENGTH: 49
<212> TYPE: PRT
<213> ORGANISM: Artificial Sequence
<220> FEATURE:
<223> OTHER INFORMATION: Synthetic sequence

<400> SEQUENCE: 344

```
Gly Leu Asn Ala Val Ala Tyr Tyr Arg Gly Leu Asp Val Ser Val Ile
1               5                  10                  15

Pro Thr Thr Gly Asp Val Val Val Cys Ala Thr Asp Ala Leu Met Thr
                20                  25                  30

Gly Phe Thr Gly Asp Phe Asp Ser Val Ile Asp Cys Asn Val Ala Val
        35                  40                  45

Glu
```

<210> SEQ ID NO 345
<211> LENGTH: 49
<212> TYPE: PRT
<213> ORGANISM: Artificial Sequence
<220> FEATURE:
<223> OTHER INFORMATION: Synthetic sequence

<400> SEQUENCE: 345

```
Gly Leu Asn Ala Val Ala Tyr Tyr Arg Gly Leu Asp Val Ser Val Ile
1               5                  10                  15

Pro Thr Ser Gly Asp Val Val Val Cys Ala Thr Asp Ala Leu Met Thr
                20                  25                  30

Gly Phe Thr Gly Asp Phe Asp Ser Val Ile Asp Cys Asn Thr Ser Val
        35                  40                  45

Ile
```

<210> SEQ ID NO 346
<211> LENGTH: 49
<212> TYPE: PRT
<213> ORGANISM: Artificial Sequence
<220> FEATURE:

<223> OTHER INFORMATION: Synthetic sequence

<400> SEQUENCE: 346

Gly Val Asn Ala Val Ala Tyr Tyr Arg Gly Leu Asp Val Ala Val Ile
1               5                   10                  15

Pro Ala Thr Gly Asp Val Val Cys Ser Thr Asp Ala Leu Met Thr
            20                  25                  30

Gly Phe Thr Gly Asp Phe Asp Ser Val Ile Asp Cys Asn Thr Ala Val
        35                  40                  45

Thr

<210> SEQ ID NO 347
<211> LENGTH: 49
<212> TYPE: PRT
<213> ORGANISM: Artificial Sequence
<220> FEATURE:
<223> OTHER INFORMATION: Synthetic sequence

<400> SEQUENCE: 347

Gly Leu Asn Ala Val Ala Phe Tyr Arg Gly Val Asp Val Ser Val Ile
1               5                   10                  15

Pro Thr Ser Gly Asp Val Val Cys Ala Thr Asp Ala Leu Met Thr
            20                  25                  30

Gly Tyr Thr Gly Asp Phe Asp Ser Val Ile Asp Cys Asn Val Ala Val
        35                  40                  45

Thr

<210> SEQ ID NO 348
<211> LENGTH: 49
<212> TYPE: PRT
<213> ORGANISM: Artificial Sequence
<220> FEATURE:
<223> OTHER INFORMATION: Synthetic sequence

<400> SEQUENCE: 348

Gly Leu Thr Ala Val Ala Tyr Tyr Arg Gly Leu Asp Val Ser Val Ile
1               5                   10                  15

Pro Thr Ser Gly Asp Val Val Val Ala Thr Asp Ala Leu Met Thr
            20                  25                  30

Gly Phe Thr Gly Asp Phe Asp Ser Val Ile Asp Cys Asn Val Ala Val
        35                  40                  45

Thr

<210> SEQ ID NO 349
<211> LENGTH: 53
<212> TYPE: PRT
<213> ORGANISM: Artificial Sequence
<220> FEATURE:
<223> OTHER INFORMATION: Synthetic sequence

<400> SEQUENCE: 349

Cys Ala Ala Ile Leu Arg Arg His Val Gly Pro Gly Glu Gly Ala Val
1               5                   10                  15

Gln Trp Met Asn Arg Leu Ile Ala Phe Ala Ser Arg Gly Asn His Val
            20                  25                  30

Ser Pro Thr His Tyr Val Pro Glu Ser Asp Ala Ser Ala Arg Val Thr
        35                  40                  45

Gln Ile Leu Ser Ser
    50

<210> SEQ ID NO 350
<211> LENGTH: 53
<212> TYPE: PRT
<213> ORGANISM: Artificial Sequence
<220> FEATURE:
<223> OTHER INFORMATION: Synthetic sequence

<400> SEQUENCE: 350

Cys Ala Ala Ile Leu Arg Arg His Val Gly Pro Gly Glu Gly Ala Val
1               5                   10                  15

Gln Trp Met Asn Arg Leu Ile Ala Phe Ala Ser Arg Gly Asn His Val
            20                  25                  30

Ser Pro Thr His Tyr Val Pro Glu Ser Asp Ala Ala Ala Arg Val Thr
        35                  40                  45

Ala Ile Leu Ser Ser
    50

<210> SEQ ID NO 351
<211> LENGTH: 53
<212> TYPE: PRT
<213> ORGANISM: Artificial Sequence
<220> FEATURE:
<223> OTHER INFORMATION: Synthetic sequence

<400> SEQUENCE: 351

Cys Ala Ala Ile Leu Arg Arg His Val Gly Pro Gly Glu Gly Ala Val
1               5                   10                  15

Gln Trp Met Asn Arg Leu Ile Ala Phe Ala Ser Arg Gly Asn His Val
            20                  25                  30

Ser Pro Thr His Tyr Val Pro Glu Ser Asp Ala Ala Ala Arg Val Thr
        35                  40                  45

Gln Ile Leu Ser Ser
    50

<210> SEQ ID NO 352
<211> LENGTH: 53
<212> TYPE: PRT
<213> ORGANISM: Artificial Sequence
<220> FEATURE:
<223> OTHER INFORMATION: Synthetic sequence

<400> SEQUENCE: 352

Cys Ala Ala Ile Leu Arg Arg His Val Gly Pro Gly Glu Gly Ala Val
1               5                   10                  15

Gln Trp Met Asn Arg Leu Ile Ala Phe Ala Ser Arg Gly Asn His Val
            20                  25                  30

Ala Pro Thr His Tyr Val Thr Glu Ser Asp Ala Ser Gln Arg Val Thr
        35                  40                  45

Gln Leu Leu Gly Ser
    50

<210> SEQ ID NO 353
<211> LENGTH: 53
<212> TYPE: PRT
<213> ORGANISM: Artificial Sequence
<220> FEATURE:
<223> OTHER INFORMATION: Synthetic sequence

<400> SEQUENCE: 353

Cys Ala Ala Ile Leu Arg Arg His Val Gly Gln Gly Glu Gly Ala Val
1               5                   10                  15

Gln Trp Met Asn Arg Leu Ile Ala Phe Ala Ser Arg Gly Asn His Val
            20                  25                  30

Ala Pro Thr His Tyr Val Ala Glu Ser Asp Ala Ser Gln Arg Val Thr
        35                  40                  45

Gln Val Leu Ser Ser
    50

<210> SEQ ID NO 354
<211> LENGTH: 53
<212> TYPE: PRT
<213> ORGANISM: Artificial Sequence
<220> FEATURE:
<223> OTHER INFORMATION: Synthetic sequence

<400> SEQUENCE: 354

Cys Ala Ala Ile Leu Arg Arg His Val Gly Pro Gly Glu Gly Ala Val
1               5                   10                  15

Gln Trp Met Asn Arg Leu Ile Ala Phe Ala Ser Arg Gly Asn His Val
            20                  25                  30

Ser Pro Thr His Tyr Val Pro Glu Ser Asp Ala Ala Ala Arg Val Thr
        35                  40                  45

Ala Leu Leu Ser Ser
    50

<210> SEQ ID NO 355
<211> LENGTH: 53
<212> TYPE: PRT
<213> ORGANISM: Artificial Sequence
<220> FEATURE:
<223> OTHER INFORMATION: Synthetic sequence

<400> SEQUENCE: 355

Cys Ala Ala Ile Leu Arg Arg His Val Gly Pro Gly Glu Gly Ala Val
1               5                   10                  15

Gln Trp Met Asn Arg Leu Ile Ala Phe Ala Ser Arg Gly Asn His Val
            20                  25                  30

Ser Pro Thr His Tyr Val Pro Glu Ser Asp Ala Ala Ala Arg Val Thr
        35                  40                  45

Gln Ile Leu Ser Ser
    50

<210> SEQ ID NO 356
<211> LENGTH: 53
<212> TYPE: PRT
<213> ORGANISM: Artificial Sequence
<220> FEATURE:
<223> OTHER INFORMATION: Synthetic sequence

<400> SEQUENCE: 356

Cys Ala Ala Val Leu Arg Arg His Ile Gly Pro Gly Glu Gly Ala Val
1               5                   10                  15

Gln Trp Met Asn Arg Leu Ile Ala Phe Ala Ser Arg Gly Asn His Val
            20                  25                  30

Ser Pro Thr His Tyr Val Pro Glu Thr Asp Ala Ser Ala Lys Val Thr
        35                  40                  45

Gln Leu Leu Ser Ser
    50

<210> SEQ ID NO 357
<211> LENGTH: 53
<212> TYPE: PRT

```
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (46)..(46)
<223> OTHER INFORMATION: Xaa can be any naturally occurring amino acid

<400> SEQUENCE: 357

Cys Ala Ala Ile Leu Arg Arg His Val Gly Pro Ala Glu Gly Ala Thr
1               5                   10                  15

Gln Trp Met Asn Arg Leu Ile Ala Phe Ala Ser Arg Gly Asn His Val
            20                  25                  30

Ser Pro Thr His Tyr Val Pro Glu Thr Asp Ala Ser Arg Xaa Val Thr
        35                  40                  45

Thr Ile Leu Ser Ser
    50

<210> SEQ ID NO 358
<211> LENGTH: 53
<212> TYPE: PRT
<213> ORGANISM: Artificial Sequence
<220> FEATURE:
<223> OTHER INFORMATION: Synthetic sequence

<400> SEQUENCE: 358

Cys Ala Ala Ile Ile Lys Arg His Thr Gly Thr Ser Glu Gly Val Thr
1               5                   10                  15

Gln Trp Met Asn Arg Leu Ile Ala Phe Ala Ser Arg Gly Asn His Val
            20                  25                  30

Ser Pro Thr His Tyr Ile Gln Asp Asp Ala Ser Lys Arg Val Met
        35                  40                  45

Gly Ile Leu Ser Ser
    50

<210> SEQ ID NO 359
<211> LENGTH: 72
<212> TYPE: PRT
<213> ORGANISM: Artificial Sequence
<220> FEATURE:
<223> OTHER INFORMATION: Synthetic sequence

<400> SEQUENCE: 359

Tyr Gln Val Gly Tyr Leu His Ala Pro Thr Gly Ser Gly Lys Ser Thr
1               5                   10                  15

Lys Val Pro Ala Ala Tyr Ala Ala Gln Gly Tyr Lys Val Leu Val Leu
            20                  25                  30

Asn Pro Ser Val Ala Ala Thr Leu Gly Phe Gly Ala Tyr Met Ser Lys
        35                  40                  45

Ala His Gly Ile Asp Pro Asn Ile Arg Thr Gly Val Arg Thr Val Thr
    50                  55                  60

Thr Gly Ala Pro Ile Thr Tyr Ser
65                  70

<210> SEQ ID NO 360
<211> LENGTH: 72
<212> TYPE: PRT
<213> ORGANISM: Artificial Sequence
<220> FEATURE:
<223> OTHER INFORMATION: Synthetic sequence

<400> SEQUENCE: 360
```

```
Phe Gln Val Ala His Leu His Ala Pro Thr Gly Ser Gly Lys Ser Thr
1               5                   10                  15

Lys Val Pro Ala Ala Tyr Ala Ala Gln Gly Tyr Lys Val Leu Val Leu
            20                  25                  30

Asn Pro Ser Val Ala Ala Thr Leu Gly Phe Gly Ala Tyr Met Ser Lys
        35                  40                  45

Ala His Gly Ile Asp Pro Asn Ile Arg Thr Gly Val Arg Thr Ile Thr
    50                  55                  60

Thr Gly Ser Pro Ile Thr Tyr Ser
65                  70
```

<210> SEQ ID NO 361
<211> LENGTH: 72
<212> TYPE: PRT
<213> ORGANISM: Artificial Sequence
<220> FEATURE:
<223> OTHER INFORMATION: Synthetic sequence

<400> SEQUENCE: 361

```
Phe Gln Val Ala His Leu His Ala Pro Thr Gly Ser Gly Lys Ser Thr
1               5                   10                  15

Lys Val Pro Ala Ala Tyr Ala Ala Gln Gly Tyr Lys Val Leu Val Leu
            20                  25                  30

Asn Pro Ser Val Ala Ala Thr Leu Gly Phe Gly Ala Tyr Met Ser Lys
        35                  40                  45

Ala His Gly Val Asp Pro Asn Ile Arg Thr Gly Val Arg Thr Ile Thr
    50                  55                  60

Thr Gly Ala Pro Ile Thr Tyr Ser
65                  70
```

<210> SEQ ID NO 362
<211> LENGTH: 72
<212> TYPE: PRT
<213> ORGANISM: Artificial Sequence
<220> FEATURE:
<223> OTHER INFORMATION: Synthetic sequence

<400> SEQUENCE: 362

```
Tyr Gln Val Gly Tyr Leu His Ala Pro Thr Gly Ser Gly Lys Ser Thr
1               5                   10                  15

Lys Val Pro Val Ala Tyr Ala Ala Gln Gly Tyr Lys Val Leu Val Leu
            20                  25                  30

Asn Pro Ser Val Ala Ala Thr Leu Gly Phe Gly Ala Tyr Leu Ser Lys
        35                  40                  45

Ala His Gly Ile Asn Pro Asn Ile Arg Thr Gly Val Arg Thr Val Thr
    50                  55                  60

Thr Gly Glu Ala Ile Thr Tyr Ser
65                  70
```

<210> SEQ ID NO 363
<211> LENGTH: 72
<212> TYPE: PRT
<213> ORGANISM: Artificial Sequence
<220> FEATURE:
<223> OTHER INFORMATION: Synthetic sequence

<400> SEQUENCE: 363

```
Tyr Gln Val Gly Tyr Leu His Ala Pro Thr Gly Ser Gly Lys Ser Thr
1               5                   10                  15

Lys Val Pro Ala Ala Tyr Ala Ser Gln Gly Tyr Lys Val Leu Val Leu
```

```
                    20                  25                  30

Asn Pro Ser Val Ala Ala Thr Leu Gly Phe Gly Ala Tyr Met Ser Lys
                35                  40                  45

Ala His Gly Ile Asn Pro Asn Ile Arg Thr Gly Val Arg Thr Val Thr
        50                  55                  60

Thr Gly Asp Ser Ile Thr Tyr Ser
65                  70

<210> SEQ ID NO 364
<211> LENGTH: 72
<212> TYPE: PRT
<213> ORGANISM: Artificial Sequence
<220> FEATURE:
<223> OTHER INFORMATION: Synthetic sequence

<400> SEQUENCE: 364

Tyr Gln Val Gly Tyr Leu His Ala Pro Thr Gly Ser Gly Lys Ser Thr
1               5                   10                  15

Lys Val Pro Ala Ala Tyr Val Ala Gln Gly Tyr Asn Val Leu Val Leu
                20                  25                  30

Asn Pro Ser Val Ala Ala Thr Leu Gly Phe Gly Ser Phe Met Ser Arg
                35                  40                  45

Ala Tyr Gly Ile Asp Pro Asn Ile Arg Thr Gly Asn Arg Thr Val Thr
        50                  55                  60

Thr Gly Ala Lys Leu Thr Tyr Ser
65                  70

<210> SEQ ID NO 365
<211> LENGTH: 71
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (31)..(32)
<223> OTHER INFORMATION: Xaa can be any naturally occurring amino acid

<400> SEQUENCE: 365

Gly Ser Val Thr Val Pro His Pro Asn Ile Glu Glu Val Ala Leu Gly
1               5                   10                  15

Xaa Glu Gly Glu Ile Pro Phe Tyr Gly Lys Ala Ile Pro Leu Xaa Xaa
                20                  25                  30

Ile Lys Gly Gly Arg His Leu Ile Phe Cys His Ser Lys Lys Lys Cys
        35                  40                  45

Asp Glu Leu Ala Ala Lys Leu Arg Gly Met Gly Leu Asn Ala Val Ala
        50                  55                  60

Tyr Tyr Arg Gly Leu Asp Val
65                  70

<210> SEQ ID NO 366
<211> LENGTH: 71
<212> TYPE: PRT
<213> ORGANISM: Artificial Sequence
<220> FEATURE:
<223> OTHER INFORMATION: Synthetic sequence

<400> SEQUENCE: 366
```

```
Gly Ser Val Thr Val Pro His Pro Asn Ile Glu Val Ala Leu Ser
1               5                   10                  15

Thr Thr Gly Glu Ile Pro Phe Tyr Gly Lys Ala Ile Pro Leu Glu Val
            20                  25                  30

Ile Lys Gly Gly Arg His Leu Ile Phe Cys His Ser Lys Lys Lys Cys
                35                  40                  45

Asp Glu Leu Ala Ala Lys Leu Val Ala Leu Gly Ile Asn Ala Val Ala
        50                  55                  60

Tyr Tyr Arg Gly Leu Asp Val
65                  70
```

<210> SEQ ID NO 367
<211> LENGTH: 71
<212> TYPE: PRT
<213> ORGANISM: Artificial Sequence
<220> FEATURE:
<223> OTHER INFORMATION: Synthetic sequence

<400> SEQUENCE: 367

```
Gly Ser Val Thr Val Pro His Pro Asn Ile Glu Val Ala Leu Ser
1               5                   10                  15

Asn Thr Gly Glu Ile Pro Phe Tyr Gly Lys Ala Ile Pro Ile Glu Thr
            20                  25                  30

Ile Lys Gly Gly Arg His Leu Ile Phe Cys Asp Ser Lys Lys Lys Cys
                35                  40                  45

Asp Glu Leu Ala Ala Lys Leu Ser Gly Leu Gly Leu Asn Ala Val Ala
        50                  55                  60

Tyr Tyr Arg Gly Leu Asp Val
65                  70
```

<210> SEQ ID NO 368
<211> LENGTH: 71
<212> TYPE: PRT
<213> ORGANISM: Artificial Sequence
<220> FEATURE:
<223> OTHER INFORMATION: Synthetic sequence

<400> SEQUENCE: 368

```
Gly Ser Val Thr Thr Pro His Pro Asn Ile Glu Val Ala Leu Gly
1               5                   10                  15

Gln Glu Gly Glu Ile Pro Phe Tyr Gly Arg Ala Ile Pro Leu Ser Tyr
            20                  25                  30

Ile Lys Gly Gly Arg His Leu Ile Phe Cys His Ser Lys Lys Lys Cys
                35                  40                  45

Asp Glu Leu Ala Ala Ala Leu Arg Gly Met Gly Leu Asn Ala Val Ala
        50                  55                  60

Tyr Tyr Arg Gly Leu Asp Val
65                  70
```

<210> SEQ ID NO 369
<211> LENGTH: 71
<212> TYPE: PRT
<213> ORGANISM: Artificial Sequence
<220> FEATURE:
<223> OTHER INFORMATION: Synthetic sequence

<400> SEQUENCE: 369

```
Gly Thr Val Thr Thr Pro His Ser Asn Ile Glu Glu Val Ala Leu Gly
1               5                   10                  15

His Glu Gly Glu Ile Pro Phe Tyr Gly Lys Ala Ile Pro Leu Ala Phe
```

```
                        20                  25                  30

Ile Lys Gly Gly Arg His Leu Ile Phe Cys His Ser Lys Lys Cys
            35                  40                  45

Asp Glu Leu Ala Ala Ala Leu Arg Gly Met Gly Val Asn Ala Val Ala
        50                  55                  60

Tyr Tyr Arg Gly Leu Asp Val
65                  70

<210> SEQ ID NO 370
<211> LENGTH: 71
<212> TYPE: PRT
<213> ORGANISM: Artificial Sequence
<220> FEATURE:
<223> OTHER INFORMATION: Synthetic sequence

<400> SEQUENCE: 370

Gly Ser Ile Thr Val Pro His Ser Asn Ile Glu Val Ala Leu Gly
1               5                   10                  15

Ser Glu Gly Glu Ile Pro Phe Tyr Gly Lys Ala Ile Pro Ile Ala Leu
                20                  25                  30

Leu Lys Gly Gly Arg His Leu Ile Phe Cys His Ser Lys Lys Cys
            35                  40                  45

Asp Glu Leu Ala Ser Lys Leu Arg Gly Met Gly Leu Asn Ala Val Ala
        50                  55                  60

Tyr Tyr Arg Gly Leu Asp Val
65                  70

<210> SEQ ID NO 371
<211> LENGTH: 71
<212> TYPE: PRT
<213> ORGANISM: Artificial Sequence
<220> FEATURE:
<223> OTHER INFORMATION: Synthetic sequence

<400> SEQUENCE: 371

Val Lys Phe Pro Gly Gly Gly Gln Ile Val Gly Gly Val Tyr Leu Leu
1               5                   10                  15

Pro Arg Arg Gly Pro Arg Leu Gly Val Arg Ala Thr Arg Lys Thr Ser
                20                  25                  30

Glu Arg Ser Gln Pro Arg Gly Arg Arg Gln Pro Ile Pro Lys Ala Arg
            35                  40                  45

Arg Ser Glu Gly Arg Ser Trp Ala Gln Pro Gly Tyr Pro Trp Pro Leu
        50                  55                  60

Tyr Gly Asn Glu Gly Cys Gly
65                  70

<210> SEQ ID NO 372
<211> LENGTH: 71
<212> TYPE: PRT
<213> ORGANISM: Artificial Sequence
<220> FEATURE:
<223> OTHER INFORMATION: Synthetic sequence

<400> SEQUENCE: 372

Val Lys Phe Pro Gly Gly Gly Gln Ile Val Gly Gly Val Tyr Leu Leu
1               5                   10                  15

Pro Arg Arg Gly Pro Arg Leu Gly Val Arg Ala Thr Arg Lys Thr Ser
                20                  25                  30

Glu Arg Ser Gln Pro Arg Gly Arg Arg Gln Pro Ile Pro Lys Ala Arg
            35                  40                  45
```

```
Arg Pro Glu Gly Arg Thr Trp Ala Gln Pro Gly Tyr Pro Trp Pro Leu
        50                  55                  60

Tyr Gly Asn Glu Gly Cys Gly
65                  70

<210> SEQ ID NO 373
<211> LENGTH: 71
<212> TYPE: PRT
<213> ORGANISM: Artificial Sequence
<220> FEATURE:
<223> OTHER INFORMATION: Synthetic sequence

<400> SEQUENCE: 373

Val Lys Phe Pro Gly Gly Gln Ile Val Gly Val Tyr Leu Leu
1               5                   10                  15

Pro Arg Arg Gly Pro Arg Leu Gly Val Arg Ala Thr Arg Lys Thr Ser
            20                  25                  30

Glu Arg Ser Gln Pro Arg Gly Arg Arg Gln Pro Ile Pro Lys Ala Arg
        35                  40                  45

Arg Pro Glu Gly Arg Ala Trp Ala Gln Pro Gly Tyr Pro Trp Pro Leu
        50                  55                  60

Tyr Gly Asn Glu Gly Met Gly
65                  70

<210> SEQ ID NO 374
<211> LENGTH: 71
<212> TYPE: PRT
<213> ORGANISM: Artificial Sequence
<220> FEATURE:
<223> OTHER INFORMATION: Synthetic sequence

<400> SEQUENCE: 374

Val Lys Phe Pro Gly Gly Gln Ile Val Gly Val Tyr Leu Leu
1               5                   10                  15

Pro Arg Arg Gly Pro Arg Leu Gly Val Arg Ala Thr Arg Lys Thr Ser
            20                  25                  30

Glu Arg Ser Gln Pro Arg Gly Arg Arg Gln Pro Ile Pro Lys Asp Arg
        35                  40                  45

Arg Ser Thr Gly Lys Ser Trp Gly Lys Pro Gly Tyr Pro Trp Pro Leu
        50                  55                  60

Tyr Gly Asn Glu Gly Leu Gly
65                  70

<210> SEQ ID NO 375
<211> LENGTH: 71
<212> TYPE: PRT
<213> ORGANISM: Artificial Sequence
<220> FEATURE:
<223> OTHER INFORMATION: Synthetic sequence

<400> SEQUENCE: 375

Val Lys Phe Pro Gly Gly Gly Gln Ile Val Gly Val Tyr Leu Leu
1               5                   10                  15

Pro Arg Arg Gly Pro Arg Leu Gly Val Arg Ala Thr Arg Lys Thr Ser
            20                  25                  30

Glu Arg Ser Gln Pro Arg Gly Arg Arg Gln Pro Ile Pro Lys Asp Arg
        35                  40                  45

Arg Ser Thr Gly Lys Ser Trp Gly Lys Pro Gly Tyr Pro Trp Pro Leu
        50                  55                  60
```

Tyr Gly Asn Glu Gly Cys Gly
65                  70

<210> SEQ ID NO 376
<211> LENGTH: 71
<212> TYPE: PRT
<213> ORGANISM: Artificial Sequence
<220> FEATURE:
<223> OTHER INFORMATION: Synthetic sequence

<400> SEQUENCE: 376

Val Lys Phe Pro Gly Gly Gln Ile Val Gly Val Tyr Val Leu
1               5                   10                  15

Pro Arg Arg Gly Pro Arg Leu Gly Val Arg Ala Thr Arg Lys Thr Ser
            20                  25                  30

Glu Arg Ser Gln Pro Arg Gly Arg Arg Gln Pro Ile Pro Lys Ala Arg
        35                  40                  45

Arg Ser Glu Gly Arg Ser Trp Ala Gln Pro Gly Tyr Pro Trp Pro Leu
    50                  55                  60

Tyr Gly Asn Glu Gly Cys Gly
65                  70

<210> SEQ ID NO 377
<211> LENGTH: 70
<212> TYPE: PRT
<213> ORGANISM: Artificial Sequence
<220> FEATURE:
<223> OTHER INFORMATION: Synthetic sequence

<400> SEQUENCE: 377

Pro Gly Ala Leu Val Val Gly Val Ile Cys Ala Ala Ile Leu Arg Arg
1               5                   10                  15

His Val Gly Pro Gly Glu Gly Ala Val Gln Trp Met Asn Arg Leu Ile
            20                  25                  30

Ala Phe Ala Ser Arg Gly Asn His Val Ser Pro Thr His Tyr Val Pro
        35                  40                  45

Glu Ser Asp Ala Ala Ala Arg Val Thr Gln Leu Ser Ser Leu Thr Ile
    50                  55                  60

Thr Ser Leu Leu Arg Arg
65                  70

<210> SEQ ID NO 378
<211> LENGTH: 71
<212> TYPE: PRT
<213> ORGANISM: Artificial Sequence
<220> FEATURE:
<223> OTHER INFORMATION: Synthetic sequence

<400> SEQUENCE: 378

Pro Gly Ala Leu Val Val Gly Val Val Cys Ala Ala Ile Leu Arg Arg
1               5                   10                  15

His Val Gly Pro Gly Glu Gly Ala Val Gln Trp Met Asn Arg Leu Ile
            20                  25                  30

Ala Phe Ala Ser Arg Gly Asn His Val Ser Pro Thr His Tyr Val Pro
        35                  40                  45

Glu Ser Asp Ala Ala Ala Arg Val Thr Ala Ile Leu Ser Ser Leu Thr
    50                  55                  60

Val Thr Gln Leu Leu Arg Arg
65                  70

<210> SEQ ID NO 379
<211> LENGTH: 71
<212> TYPE: PRT
<213> ORGANISM: Artificial Sequence
<220> FEATURE:
<223> OTHER INFORMATION: Synthetic sequence

<400> SEQUENCE: 379

```
Pro Gly Ala Leu Val Val Gly Val Val Cys Ala Ala Ile Leu Arg Arg
1               5                   10                  15

His Val Gly Pro Gly Glu Gly Ala Val Gln Trp Met Asn Arg Leu Ile
            20                  25                  30

Ala Phe Ala Ser Arg Gly Asn His Val Ser Pro Thr His Tyr Val Pro
        35                  40                  45

Glu Ser Asp Ala Ala Ala Arg Val Thr Gln Ile Leu Ser Ser Leu Thr
    50                  55                  60

Ile Thr Gln Leu Leu Lys Arg
65                  70
```

<210> SEQ ID NO 380
<211> LENGTH: 71
<212> TYPE: PRT
<213> ORGANISM: Artificial Sequence
<220> FEATURE:
<223> OTHER INFORMATION: Synthetic sequence

<400> SEQUENCE: 380

```
Pro Gly Ala Leu Val Val Gly Val Ile Cys Ala Ala Ile Leu Arg Arg
1               5                   10                  15

His Val Gly Pro Gly Glu Gly Ala Val Gln Trp Met Asn Arg Leu Ile
            20                  25                  30

Ala Phe Ala Ser Arg Gly Asn His Val Ala Pro Thr His Tyr Val Thr
        35                  40                  45

Glu Ser Asp Ala Ser Gln Arg Val Thr Gln Leu Leu Gly Ser Leu Thr
    50                  55                  60

Ile Thr Ser Leu Leu Arg Arg
65                  70
```

<210> SEQ ID NO 381
<211> LENGTH: 71
<212> TYPE: PRT
<213> ORGANISM: Artificial Sequence
<220> FEATURE:
<223> OTHER INFORMATION: Synthetic sequence

<400> SEQUENCE: 381

```
Pro Gly Ala Leu Val Val Gly Val Ile Cys Ala Ala Ile Leu Arg Arg
1               5                   10                  15

His Val Gly Gln Gly Glu Gly Ala Val Gln Trp Met Asn Arg Leu Ile
            20                  25                  30

Ala Phe Ala Ser Arg Gly Asn His Val Ala Pro Thr His Tyr Val Ala
        35                  40                  45

Glu Ser Asp Ala Ser Gln Arg Val Thr Gln Val Leu Ser Ser Leu Thr
    50                  55                  60

Ile Thr Ser Leu Leu Arg Arg
65                  70
```

<210> SEQ ID NO 382
<211> LENGTH: 71
<212> TYPE: PRT
<213> ORGANISM: Artificial Sequence

```
<220> FEATURE:
<223> OTHER INFORMATION: Synthetic sequence

<400> SEQUENCE: 382

Pro Gly Ala Leu Val Gly Val Ile Cys Ala Ala Ile Leu Arg Arg
1               5                   10                  15

His Val Gly Pro Gly Glu Gly Ala Val Gln Trp Met Asn Arg Leu Ile
            20                  25                  30

Ala Phe Ala Ser Arg Gly Asn His Val Ser Pro Thr His Tyr Val Pro
        35                  40                  45

Glu Ser Asp Ala Ala Ala Arg Val Thr Ala Leu Leu Ser Ser Leu Thr
    50                  55                  60

Val Thr Ser Leu Leu Arg Arg
65                  70

<210> SEQ ID NO 383
<211> LENGTH: 93
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (17)..(18)
<223> OTHER INFORMATION: Xaa can be any naturally occurring amino acid
<220> FEATURE:
<221> NAME/KEY: misc_feature
<222> LOCATION: (63)..(63)
<223> OTHER INFORMATION: Xaa can be any naturally occurring amino acid

<400> SEQUENCE: 383

Leu Gly Xaa Glu Gly Glu Ile Pro Phe Tyr Gly Lys Ala Ile Pro Leu
1               5                   10                  15

Xaa Xaa Ile Lys Gly Gly Arg His Leu Ile Phe Cys His Ser Lys Lys
            20                  25                  30

Lys Cys Asp Glu Leu Ala Ala Lys Leu Arg Gly Met Gly Leu Asn Ala
        35                  40                  45

Val Ala Tyr Tyr Arg Gly Leu Asp Val Ser Val Ile Pro Thr Xaa Gly
    50                  55                  60

Asp Val Val Val Ala Thr Asp Ala Leu Met Thr Gly Tyr Thr Gly
65                  70                  75                  80

Asp Phe Asp Ser Val Ile Asp Cys Asn Val Ala Val Thr
                85                  90

<210> SEQ ID NO 384
<211> LENGTH: 93
<212> TYPE: PRT
<213> ORGANISM: Artificial Sequence
<220> FEATURE:
<223> OTHER INFORMATION: Synthetic sequence

<400> SEQUENCE: 384

Leu Ser Thr Thr Gly Glu Ile Pro Phe Tyr Gly Lys Ala Ile Pro Leu
1               5                   10                  15

Glu Val Ile Lys Gly Gly Arg His Leu Ile Phe Cys His Ser Lys Lys
            20                  25                  30

Lys Cys Asp Glu Leu Ala Ala Lys Leu Val Ala Leu Gly Ile Asn Ala
        35                  40                  45
```

```
Val Ala Tyr Tyr Arg Gly Leu Asp Val Ser Val Ile Pro Thr Ser Gly
 50                  55                  60

Asp Val Val Val Ala Thr Asp Ala Leu Met Thr Gly Tyr Thr Gly
 65                  70                  75                  80

Asp Phe Asp Ser Val Ile Asp Cys Asn Thr Cys Val Thr
                 85                  90

<210> SEQ ID NO 385
<211> LENGTH: 93
<212> TYPE: PRT
<213> ORGANISM: Artificial Sequence
<220> FEATURE:
<223> OTHER INFORMATION: Synthetic sequence

<400> SEQUENCE: 385

Leu Ser Asn Thr Gly Glu Ile Pro Phe Tyr Gly Lys Ala Ile Pro Ile
 1               5                  10                  15

Glu Thr Ile Lys Gly Gly Arg His Leu Ile Phe Cys His Ser Lys Lys
                 20                  25                  30

Lys Cys Asp Glu Leu Ala Ala Lys Leu Ser Gly Leu Gly Leu Asn Ala
             35                  40                  45

Val Ala Tyr Tyr Arg Gly Leu Asp Val Ser Val Ile Pro Thr Ser Gly
 50                  55                  60

Asp Val Val Val Ala Thr Asp Ala Leu Met Thr Gly Phe Thr Gly
 65                  70                  75                  80

Asp Phe Asp Ser Val Ile Asp Cys Asn Thr Cys Val Thr
                 85                  90

<210> SEQ ID NO 386
<211> LENGTH: 93
<212> TYPE: PRT
<213> ORGANISM: Artificial Sequence
<220> FEATURE:
<223> OTHER INFORMATION: Synthetic sequence

<400> SEQUENCE: 386

Leu Gly Gln Glu Gly Glu Ile Pro Phe Tyr Gly Arg Ala Ile Pro Leu
 1               5                  10                  15

Ser Tyr Ile Lys Gly Gly Arg His Leu Ile Phe Cys His Ser Lys Lys
                 20                  25                  30

Lys Cys Asp Glu Leu Ala Ala Ala Leu Arg Gly Met Gly Leu Asn Ala
             35                  40                  45

Val Ala Tyr Tyr Arg Gly Leu Asp Val Ser Ile Ile Pro Thr Gln Gly
 50                  55                  60

Asp Val Val Val Ala Thr Asp Ala Leu Met Thr Gly Tyr Thr Gly
 65                  70                  75                  80

Asp Phe Asp Ser Val Ile Asp Cys Asn Val Ala Val Thr
                 85                  90

<210> SEQ ID NO 387
<211> LENGTH: 93
<212> TYPE: PRT
<213> ORGANISM: Artificial Sequence
<220> FEATURE:
<223> OTHER INFORMATION: Synthetic sequence

<400> SEQUENCE: 387

Leu Gly His Glu Gly Glu Ile Pro Phe Tyr Gly Lys Ala Ile Pro Leu
 1               5                  10                  15

Ala Phe Ile Lys Gly Gly Arg His Leu Ile Phe Cys His Ser Lys Lys
```

```
                    20                  25                  30

Lys Cys Asp Glu Leu Ala Ala Ala Leu Arg Gly Met Gly Val Asn Ala
                35                  40                  45

Val Ala Tyr Tyr Arg Gly Leu Asp Val Ser Val Ile Pro Thr Gln Gly
    50                  55                  60

Asp Val Val Val Ala Thr Asp Ala Leu Met Thr Gly Tyr Thr Gly
65                  70                  75                  80

Asp Phe Asp Ser Val Ile Asp Cys Asn Val Ala Val Thr
                85                  90

<210> SEQ ID NO 388
<211> LENGTH: 93
<212> TYPE: PRT
<213> ORGANISM: Artificial Sequence
<220> FEATURE:
<223> OTHER INFORMATION: Synthetic sequence

<400> SEQUENCE: 388

Leu Gly Ser Glu Gly Glu Ile Pro Phe Tyr Gly Lys Ala Ile Pro Ile
1               5                   10                  15

Ala Leu Leu Lys Gly Gly Arg His Leu Ile Phe Cys His Ser Lys Lys
                20                  25                  30

Lys Cys Asp Glu Leu Ala Ser Lys Leu Arg Gly Met Gly Leu Asn Ala
                35                  40                  45

Val Ala Tyr Tyr Arg Gly Leu Asp Val Ser Val Ile Pro Thr Thr Gly
    50                  55                  60

Asp Val Val Val Cys Ala Thr Asp Ala Leu Met Thr Gly Phe Thr Gly
65                  70                  75                  80

Asp Phe Asp Ser Val Ile Asp Cys Asn Val Ala Val Glu
                85                  90

<210> SEQ ID NO 389
<211> LENGTH: 50
<212> TYPE: PRT
<213> ORGANISM: Artificial Sequence
<220> FEATURE:
<223> OTHER INFORMATION: Synthetic sequence

<400> SEQUENCE: 389

Gly Val Tyr Leu Leu Pro Arg Arg Gly Pro Arg Leu Gly Val Arg Ala
1               5                   10                  15

Thr Arg Lys Thr Ser Glu Arg Ser Gln Pro Arg Gly Arg Arg Gln Pro
                20                  25                  30

Ile Pro Lys Ala Arg Arg Pro Glu Gly Arg Thr Trp Ala Gln Pro Gly
                35                  40                  45

Tyr Pro
    50

<210> SEQ ID NO 390
<211> LENGTH: 50
<212> TYPE: PRT
<213> ORGANISM: Artificial Sequence
<220> FEATURE:
<223> OTHER INFORMATION: Synthetic sequence

<400> SEQUENCE: 390

Gly Val Tyr Leu Leu Pro Arg Arg Gly Pro Arg Leu Gly Val Arg Ala
1               5                   10                  15

Thr Arg Lys Thr Ser Glu Arg Ser Gln Pro Arg Gly Arg Arg Gln Pro
                20                  25                  30
```

Ile Pro Lys Ala Arg Arg Pro Glu Gly Arg Ala Trp Ala Gln Pro Gly
            35                  40                  45

Tyr Pro
    50

<210> SEQ ID NO 391
<211> LENGTH: 50
<212> TYPE: PRT
<213> ORGANISM: Artificial Sequence
<220> FEATURE:
<223> OTHER INFORMATION: Synthetic sequence

<400> SEQUENCE: 391

Gly Val Tyr Leu Leu Pro Arg Arg Gly Pro Arg Leu Gly Val Arg Ala
1               5                   10                  15

Thr Arg Lys Thr Ser Glu Arg Ser Gln Pro Arg Gly Arg Arg Gln Pro
            20                  25                  30

Ile Pro Lys Ala Arg Arg Pro Glu Gly Arg Ala Trp Ala Gln Pro Gly
            35                  40                  45

Tyr Pro
    50

<210> SEQ ID NO 392
<211> LENGTH: 50
<212> TYPE: PRT
<213> ORGANISM: Artificial Sequence
<220> FEATURE:
<223> OTHER INFORMATION: Synthetic sequence

<400> SEQUENCE: 392

Gly Val Tyr Leu Leu Pro Arg Arg Gly Pro Arg Leu Gly Val Arg Ala
1               5                   10                  15

Thr Arg Lys Thr Ser Glu Arg Ser Gln Pro Arg Gly Arg Arg Gln Pro
            20                  25                  30

Ile Pro Lys Asp Arg Arg Ser Thr Gly Lys Ser Trp Gly Lys Pro Gly
            35                  40                  45

Tyr Pro
    50

<210> SEQ ID NO 393
<211> LENGTH: 50
<212> TYPE: PRT
<213> ORGANISM: Artificial Sequence
<220> FEATURE:
<223> OTHER INFORMATION: Synthetic sequence

<400> SEQUENCE: 393

Gly Val Tyr Val Leu Pro Arg Arg Gly Pro Arg Leu Gly Val Arg Ala
1               5                   10                  15

Thr Arg Lys Thr Ser Glu Arg Ser Gln Pro Arg Gly Arg Arg Gln Pro
            20                  25                  30

Ile Pro Lys Ala Arg Arg Ser Glu Gly Arg Ser Trp Ala Gln Pro Gly
            35                  40                  45

Tyr Pro
    50

<210> SEQ ID NO 394
<211> LENGTH: 50
<212> TYPE: PRT
<213> ORGANISM: Artificial Sequence
<220> FEATURE:

<223> OTHER INFORMATION: Synthetic sequence

<400> SEQUENCE: 394

Gly Val Tyr Leu Leu Pro Arg Arg Gly Pro Arg Leu Gly Val Arg Ala
1               5                   10                  15

Thr Arg Lys Thr Ser Glu Arg Ser Gln Pro Arg Gly Arg Arg Gln Pro
            20                  25                  30

Ile Pro Lys Ala Arg Arg Ser Glu Gly Arg Ser Trp Ala Gln Pro Gly
        35                  40                  45

Tyr Pro
    50

<210> SEQ ID NO 395
<211> LENGTH: 50
<212> TYPE: PRT
<213> ORGANISM: Artificial Sequence
<220> FEATURE:
<223> OTHER INFORMATION: Synthetic sequence

<400> SEQUENCE: 395

Gly Val Tyr Leu Leu Pro Arg Arg Gly Pro Arg Leu Gly Val Arg Ala
1               5                   10                  15

Thr Arg Lys Thr Ser Glu Arg Ser Gln Pro Arg Gly Arg Arg Gln Pro
            20                  25                  30

Ile Pro Lys Ala Arg Arg Ser Glu Gly Arg Ser Trp Ala Gln Pro Gly
        35                  40                  45

Tyr Pro
    50

<210> SEQ ID NO 396
<211> LENGTH: 50
<212> TYPE: PRT
<213> ORGANISM: Artificial Sequence
<220> FEATURE:
<223> OTHER INFORMATION: Synthetic sequence

<400> SEQUENCE: 396

Gly Val Tyr Leu Leu Pro Arg Arg Gly Pro Arg Leu Gly Val Arg Ala
1               5                   10                  15

Thr Arg Lys Thr Ser Glu Arg Ser Gln Pro Arg Gly Arg Arg Gln Pro
            20                  25                  30

Ile Pro Lys Ala Arg Arg Ser Glu Gly Arg Ser Trp Ala Gln Pro Gly
        35                  40                  45

Tyr Pro
    50

<210> SEQ ID NO 397
<211> LENGTH: 35
<212> TYPE: PRT
<213> ORGANISM: Artificial Sequence
<220> FEATURE:
<223> OTHER INFORMATION: Synthetic sequence

<400> SEQUENCE: 397

Lys Ser Thr Lys Val Pro Ala Ala Tyr Ala Ala Gln Gly Tyr Lys Val
1               5                   10                  15

Leu Val Leu Asn Pro Ser Val Ala Ala Thr Leu Gly Phe Gly Ala Tyr
            20                  25                  30

Met Ser Lys
    35

<210> SEQ ID NO 398
<211> LENGTH: 35
<212> TYPE: PRT
<213> ORGANISM: Artificial Sequence
<220> FEATURE:
<223> OTHER INFORMATION: Synthetic sequence

<400> SEQUENCE: 398

```
Lys Ser Thr Lys Val Pro Ala Ala Tyr Ala Ala Gln Gly Tyr Lys Val
1               5                   10                  15

Leu Val Leu Asn Pro Ser Val Ala Ala Thr Leu Gly Phe Gly Ala Tyr
            20                  25                  30

Met Ser Lys
        35
```

<210> SEQ ID NO 399
<211> LENGTH: 35
<212> TYPE: PRT
<213> ORGANISM: Artificial Sequence
<220> FEATURE:
<223> OTHER INFORMATION: Synthetic sequence

<400> SEQUENCE: 399

```
Lys Ser Thr Lys Val Pro Val Ala Tyr Ala Ala Gln Gly Tyr Lys Val
1               5                   10                  15

Leu Val Leu Asn Pro Ser Val Ala Ala Thr Leu Gly Phe Gly Ala Tyr
            20                  25                  30

Leu Ser Lys
        35
```

<210> SEQ ID NO 400
<211> LENGTH: 35
<212> TYPE: PRT
<213> ORGANISM: Artificial Sequence
<220> FEATURE:
<223> OTHER INFORMATION: Synthetic sequence

<400> SEQUENCE: 400

```
Lys Ser Thr Lys Val Pro Ala Ala Tyr Ala Ser Gln Gly Tyr Lys Val
1               5                   10                  15

Leu Val Leu Asn Pro Ser Val Ala Ala Thr Leu Gly Phe Gly Ala Tyr
            20                  25                  30

Met Ser Lys
        35
```

<210> SEQ ID NO 401
<211> LENGTH: 35
<212> TYPE: PRT
<213> ORGANISM: Artificial Sequence
<220> FEATURE:
<223> OTHER INFORMATION: Synthetic sequence

<400> SEQUENCE: 401

```
Lys Ser Thr Lys Val Pro Ala Ala Tyr Val Ala Gln Gly Tyr Asn Val
1               5                   10                  15

Leu Val Leu Asn Pro Ser Val Ala Ala Thr Leu Gly Phe Gly Ser Phe
            20                  25                  30

Met Ser Arg
        35
```

<210> SEQ ID NO 402
<211> LENGTH: 35

```
<212> TYPE: PRT
<213> ORGANISM: Artificial Sequence
<220> FEATURE:
<223> OTHER INFORMATION: Synthetic sequence

<400> SEQUENCE: 402

Lys Ser Thr Lys Val Pro Ala Ala Tyr Ala Ala Gln Gly Tyr Lys Val
1               5                   10                  15

Leu Val Leu Asn Pro Ser Val Ala Ala Thr Leu Gly Phe Gly Ala Tyr
            20                  25                  30

Met Ser Lys
        35

<210> SEQ ID NO 403
<211> LENGTH: 35
<212> TYPE: PRT
<213> ORGANISM: Artificial Sequence
<220> FEATURE:
<223> OTHER INFORMATION: Synthetic sequence

<400> SEQUENCE: 403

Lys Ser Thr Lys Val Pro Ala Ala Tyr Ala Ala Gln Gly Tyr Lys Val
1               5                   10                  15

Leu Val Leu Asn Pro Ser Val Ala Ala Thr Leu Gly Phe Gly Ala Tyr
            20                  25                  30

Met Ser Lys
        35

<210> SEQ ID NO 404
<211> LENGTH: 35
<212> TYPE: PRT
<213> ORGANISM: Artificial Sequence
<220> FEATURE:
<223> OTHER INFORMATION: Synthetic sequence

<400> SEQUENCE: 404

Lys Ser Thr Lys Val Pro Ala Ala Tyr Ala Ala Gln Gly Tyr Lys Val
1               5                   10                  15

Leu Val Leu Asn Pro Ser Val Ala Ala Thr Leu Gly Phe Gly Ala Tyr
            20                  25                  30

Met Ser Lys
        35

<210> SEQ ID NO 405
<211> LENGTH: 42
<212> TYPE: PRT
<213> ORGANISM: Artificial Sequence
<220> FEATURE:
<223> OTHER INFORMATION: Synthetic sequence

<400> SEQUENCE: 405

Ser Thr Thr Gly Glu Ile Pro Phe Tyr Gly Lys Ala Ile Pro Leu Glu
1               5                   10                  15

Val Ile Lys Gly Gly Arg His Leu Ile Phe Cys His Ser Lys Lys Lys
            20                  25                  30

Cys Asp Glu Leu Ala Ala Lys Leu Val Ala
        35                  40

<210> SEQ ID NO 406
<211> LENGTH: 42
<212> TYPE: PRT
<213> ORGANISM: Artificial Sequence
<220> FEATURE:
```

<223> OTHER INFORMATION: Synthetic sequence

<400> SEQUENCE: 406

Ser Asn Thr Gly Glu Ile Pro Phe Tyr Gly Lys Ala Ile Pro Ile Glu
1               5                   10                  15

Thr Ile Lys Gly Gly Arg His Leu Ile Phe Cys His Ser Lys Lys Lys
            20                  25                  30

Cys Asp Glu Leu Ala Ala Lys Leu Ser Gly
        35                  40

<210> SEQ ID NO 407
<211> LENGTH: 42
<212> TYPE: PRT
<213> ORGANISM: Artificial Sequence
<220> FEATURE:
<223> OTHER INFORMATION: Synthetic sequence

<400> SEQUENCE: 407

Gly Gln Glu Gly Glu Ile Pro Phe Tyr Gly Arg Ala Ile Pro Leu Ser
1               5                   10                  15

Tyr Ile Lys Gly Gly Arg His Leu Ile Phe Cys His Ser Lys Lys Lys
            20                  25                  30

Cys Asp Glu Leu Ala Ala Ala Leu Arg Gly
        35                  40

<210> SEQ ID NO 408
<211> LENGTH: 42
<212> TYPE: PRT
<213> ORGANISM: Artificial Sequence
<220> FEATURE:
<223> OTHER INFORMATION: Synthetic sequence

<400> SEQUENCE: 408

Gly His Glu Gly Glu Ile Pro Phe Tyr Gly Lys Ala Ile Pro Leu Ala
1               5                   10                  15

Phe Ile Lys Gly Gly Arg His Leu Ile Phe Cys His Ser Lys Lys Lys
            20                  25                  30

Cys Asp Glu Leu Ala Ala Ala Leu Arg Gly
        35                  40

<210> SEQ ID NO 409
<211> LENGTH: 42
<212> TYPE: PRT
<213> ORGANISM: Artificial Sequence
<220> FEATURE:
<223> OTHER INFORMATION: Synthetic sequence

<400> SEQUENCE: 409

Gly Ser Glu Gly Glu Ile Pro Phe Tyr Gly Lys Ala Ile Pro Ile Ala
1               5                   10                  15

Leu Leu Lys Gly Gly Arg His Leu Ile Phe Cys His Ser Lys Lys Lys
            20                  25                  30

Cys Asp Glu Leu Ala Ser Lys Leu Arg Gly
        35                  40

<210> SEQ ID NO 410
<211> LENGTH: 44
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature

```
<222> LOCATION: (2)..(2)
<223> OTHER INFORMATION: Xaa can be any naturally occurring amino acid
<220> FEATURE:
<221> NAME/KEY: misc_feature
<222> LOCATION: (18)..(19)
<223> OTHER INFORMATION: Xaa can be any naturally occurring amino acid

<400> SEQUENCE: 410

Gly Xaa Glu Gly Glu Gly Ile Pro Phe Tyr Gly Lys Ala Ile Pro
1               5                   10                  15

Leu Xaa Xaa Ile Lys Gly Arg His Leu Ile Phe Cys His Ser Lys
            20                  25                  30

Lys Lys Cys Asp Glu Leu Ala Ala Lys Leu Arg Gly
        35                  40

<210> SEQ ID NO 411
<211> LENGTH: 42
<212> TYPE: PRT
<213> ORGANISM: Artificial Sequence
<220> FEATURE:
<223> OTHER INFORMATION: Synthetic sequence

<400> SEQUENCE: 411

Gly Thr Glu Gly Glu Ile Pro Phe Tyr Gly Lys Ala Ile Pro Leu Glu
1               5                   10                  15

Gln Ile Lys Gly Gly Arg His Leu Ile Phe Cys His Ser Lys Lys Lys
            20                  25                  30

Cys Asp Glu Leu Ala Ala Lys Leu Thr Gly
        35                  40

<210> SEQ ID NO 412
<211> LENGTH: 42
<212> TYPE: PRT
<213> ORGANISM: Artificial Sequence
<220> FEATURE:
<223> OTHER INFORMATION: Synthetic sequence

<400> SEQUENCE: 412

Gly Thr Glu Gly Glu Ile Pro Phe Tyr Gly Lys Ala Ile Pro Leu Glu
1               5                   10                  15

Gln Ile Lys Gly Gly Arg His Leu Ile Phe Cys His Ser Lys Lys Lys
            20                  25                  30

Cys Asp Glu Leu Ala Ala Lys Leu Arg Gly
        35                  40

<210> SEQ ID NO 413
<211> LENGTH: 42
<212> TYPE: PRT
<213> ORGANISM: Artificial Sequence
<220> FEATURE:
<223> OTHER INFORMATION: Synthetic sequence

<400> SEQUENCE: 413

Lys Gly Gly Arg His Leu Ile Phe Cys His Ser Lys Lys Lys Cys Asp
1               5                   10                  15

Glu Leu Ala Ala Lys Leu Val Ala Leu Gly Ile Asn Ala Val Ala Tyr
            20                  25                  30

Tyr Arg Gly Leu Asp Val Ser Val Ile Pro
        35                  40

<210> SEQ ID NO 414
<211> LENGTH: 42
<212> TYPE: PRT
```

```
<213> ORGANISM: Artificial Sequence
<220> FEATURE:
<223> OTHER INFORMATION: Synthetic sequence

<400> SEQUENCE: 414

Lys Gly Gly Arg His Leu Ile Phe Cys His Ser Lys Lys Cys Asp
1               5                   10                  15

Glu Leu Ala Ala Lys Leu Ser Gly Leu Gly Leu Asn Ala Val Ala Tyr
            20                  25                  30

Tyr Arg Gly Leu Asp Val Ser Val Ile Pro
        35                  40

<210> SEQ ID NO 415
<211> LENGTH: 42
<212> TYPE: PRT
<213> ORGANISM: Artificial Sequence
<220> FEATURE:
<223> OTHER INFORMATION: Synthetic sequence

<400> SEQUENCE: 415

Lys Gly Gly Arg His Leu Ile Phe Cys His Ser Lys Lys Cys Asp
1               5                   10                  15

Glu Leu Ala Ala Ala Leu Arg Gly Met Gly Leu Asn Ala Val Ala Tyr
            20                  25                  30

Tyr Arg Gly Leu Asp Val Ser Ile Ile Pro
        35                  40

<210> SEQ ID NO 416
<211> LENGTH: 42
<212> TYPE: PRT
<213> ORGANISM: Artificial Sequence
<220> FEATURE:
<223> OTHER INFORMATION: Synthetic sequence

<400> SEQUENCE: 416

Lys Gly Gly Arg His Leu Ile Phe Cys His Ser Lys Lys Cys Asp
1               5                   10                  15

Glu Leu Ala Ala Ala Leu Arg Gly Met Gly Val Asn Ala Val Ala Tyr
            20                  25                  30

Tyr Arg Gly Leu Asp Val Ser Val Ile Pro
        35                  40

<210> SEQ ID NO 417
<211> LENGTH: 42
<212> TYPE: PRT
<213> ORGANISM: Artificial Sequence
<220> FEATURE:
<223> OTHER INFORMATION: Synthetic sequence

<400> SEQUENCE: 417

Lys Gly Gly Arg His Leu Ile Phe Cys His Ser Lys Lys Cys Asp
1               5                   10                  15

Glu Leu Ala Ser Lys Leu Arg Gly Met Gly Leu Asn Ala Val Ala Tyr
            20                  25                  30

Tyr Arg Gly Leu Asp Val Ser Val Ile Pro
        35                  40

<210> SEQ ID NO 418
<211> LENGTH: 42
<212> TYPE: PRT
<213> ORGANISM: Artificial Sequence
<220> FEATURE:
<223> OTHER INFORMATION: Synthetic sequence
```

-continued

<400> SEQUENCE: 418

Lys Gly Gly Arg His Leu Ile Phe Cys His Ser Lys Lys Lys Cys Asp
1               5                   10                  15

Glu Leu Ala Ala Lys Leu Arg Gly Met Gly Leu Asn Ala Val Ala Tyr
            20                  25                  30

Tyr Arg Gly Leu Asp Val Ser Val Ile Pro
        35                  40

<210> SEQ ID NO 419
<211> LENGTH: 42
<212> TYPE: PRT
<213> ORGANISM: Artificial Sequence
<220> FEATURE:
<223> OTHER INFORMATION: Synthetic sequence

<400> SEQUENCE: 419

Lys Gly Gly Arg His Leu Ile Phe Cys His Ser Lys Lys Lys Cys Asp
1               5                   10                  15

Glu Leu Ala Ala Lys Leu Thr Gly Leu Gly Leu Asn Ala Val Ala Tyr
            20                  25                  30

Tyr Arg Gly Leu Asp Val Ser Val Ile Pro
        35                  40

<210> SEQ ID NO 420
<211> LENGTH: 42
<212> TYPE: PRT
<213> ORGANISM: Artificial Sequence
<220> FEATURE:
<223> OTHER INFORMATION: Synthetic sequence

<400> SEQUENCE: 420

Lys Gly Gly Arg His Leu Ile Phe Cys His Ser Lys Lys Lys Cys Asp
1               5                   10                  15

Glu Leu Ala Ala Lys Leu Arg Gly Met Gly Leu Asn Ala Val Ala Tyr
            20                  25                  30

Tyr Arg Gly Leu Asp Val Ser Val Ile Pro
        35                  40

<210> SEQ ID NO 421
<211> LENGTH: 48
<212> TYPE: PRT
<213> ORGANISM: Artificial Sequence
<220> FEATURE:
<223> OTHER INFORMATION: Synthetic sequence

<400> SEQUENCE: 421

Ile Leu Arg Arg His Val Gly Pro Gly Glu Gly Ala Val Gln Trp Met
1               5                   10                  15

Asn Arg Leu Ile Ala Phe Ala Ser Arg Gly Asn His Val Ser Pro Thr
            20                  25                  30

His Tyr Val Pro Glu Ser Asp Ala Ala Ala Arg Val Thr Ala Ile Leu
        35                  40                  45

<210> SEQ ID NO 422
<211> LENGTH: 48
<212> TYPE: PRT
<213> ORGANISM: Artificial Sequence
<220> FEATURE:
<223> OTHER INFORMATION: Synthetic sequence

<400> SEQUENCE: 422

Ile Leu Arg Arg His Val Gly Pro Gly Glu Gly Ala Val Gln Trp Met
1               5                   10                  15

Asn Arg Leu Ile Ala Phe Ala Ser Arg Gly Asn His Val Ser Pro Thr
                20                  25                  30

His Tyr Val Pro Glu Ser Asp Ala Ala Ala Arg Val Thr Gln Ile Leu
            35                  40                  45

<210> SEQ ID NO 423
<211> LENGTH: 48
<212> TYPE: PRT
<213> ORGANISM: Artificial Sequence
<220> FEATURE:
<223> OTHER INFORMATION: Synthetic sequence

<400> SEQUENCE: 423

Ile Leu Arg Arg His Val Gly Pro Gly Glu Gly Ala Val Gln Trp Met
1               5                   10                  15

Asn Arg Leu Ile Ala Phe Ala Ser Arg Gly Asn His Val Ala Pro Thr
                20                  25                  30

His Tyr Val Thr Glu Ser Asp Ala Ser Gln Arg Val Thr Gln Leu Leu
            35                  40                  45

<210> SEQ ID NO 424
<211> LENGTH: 47
<212> TYPE: PRT
<213> ORGANISM: Artificial Sequence
<220> FEATURE:
<223> OTHER INFORMATION: Synthetic sequence

<400> SEQUENCE: 424

Ile Leu Arg Arg His Val Gly Gln Gly Glu Gly Ala Val Gln Trp Met
1               5                   10                  15

Asn Arg Leu Ile Ala Phe Ala Ser Arg Gly Asn His Ala Pro Thr His
                20                  25                  30

Tyr Val Ala Glu Ser Asp Ala Ser Gln Arg Val Thr Gln Val Leu
            35                  40                  45

<210> SEQ ID NO 425
<211> LENGTH: 48
<212> TYPE: PRT
<213> ORGANISM: Artificial Sequence
<220> FEATURE:
<223> OTHER INFORMATION: Synthetic sequence

<400> SEQUENCE: 425

Ile Leu Arg Arg His Val Gly Pro Gly Glu Gly Ala Val Gln Trp Met
1               5                   10                  15

Asn Arg Leu Ile Ala Phe Ala Ser Arg Gly Asn His Val Ser Pro Thr
                20                  25                  30

His Tyr Val Pro Glu Ser Asp Ala Ala Ala Arg Val Thr Ala Leu Leu
            35                  40                  45

<210> SEQ ID NO 426
<211> LENGTH: 47
<212> TYPE: PRT
<213> ORGANISM: Artificial Sequence
<220> FEATURE:
<223> OTHER INFORMATION: Synthetic sequence

<400> SEQUENCE: 426

Ile Leu Arg Arg His Val Gly Pro Gly Glu Gly Ala Val Gln Trp Met
1               5                   10                  15

```
Asn Arg Leu Ile Ala Phe Ala Ser Arg Gly Asn His Val Ser Pro Thr
            20                  25                  30

His Tyr Val Pro Glu Ser Asp Ala Ala Ala Arg Val Thr Gln Leu
        35                  40                  45

<210> SEQ ID NO 427
<211> LENGTH: 48
<212> TYPE: PRT
<213> ORGANISM: Artificial Sequence
<220> FEATURE:
<223> OTHER INFORMATION: Synthetic sequence

<400> SEQUENCE: 427

Ile Leu Arg Arg His Val Gly Pro Gly Glu Gly Ala Val Gln Trp Met
1               5                   10                  15

Asn Arg Leu Ile Ala Phe Ala Ser Arg Gly Asn His Val Ser Pro Thr
            20                  25                  30

His Tyr Val Pro Glu Ser Asp Ala Ser Ala Arg Val Thr Gln Ile Leu
        35                  40                  45

<210> SEQ ID NO 428
<211> LENGTH: 48
<212> TYPE: PRT
<213> ORGANISM: Artificial Sequence
<220> FEATURE:
<223> OTHER INFORMATION: Synthetic sequence

<400> SEQUENCE: 428

Ile Leu Arg Arg His Val Gly Pro Gly Glu Gly Ala Val Gln Trp Met
1               5                   10                  15

Asn Arg Leu Ile Ala Phe Ala Ser Arg Gly Asn His Val Ser Pro Thr
            20                  25                  30

His Tyr Val Pro Glu Ser Asp Ala Ala Ala Arg Val Thr Gln Ile Leu
        35                  40                  45
```

HEPATITIS C VIRUS PEPTIDE COMPOSITIONS AND METHODS OF USE THEREOF

CROSS-REFERENCE

This application is a national stage filing under 35 U.S.C. § 371 of PCT/CA2019/050320, filed Mar. 14, 2019, which claims the benefit of U.S. Provisional Patent Application No. 62/644,140, filed Mar. 16, 2018, each of which applications is incorporated herein by reference in its entirety.

INCORPORATION BY REFERENCE OF SEQUENCE LISTING PROVIDED AS A TEXT FILE

A Sequence Listing is provided herewith as a text file, "UALB-041WO_SEQ_LISTING_ST25.txt" created on Mar. 13, 2019 and having a size of 547 KB. The contents of the text file are incorporated by reference herein in their entirety.

INTRODUCTION

Hepatitis C virus (HCV) is a blood-borne pathogen that is estimated to infect 150-200 million people worldwide. Infection by HCV may be non-symptomatic, and can be cleared by patients, sometimes without medical intervention. However, the majority of patients develop a chronic HCV infection, which may lead to liver inflammation, scarring, and even to liver failure or liver cancer. In the United States alone, over 3 million people have a chronic infection.

The HCV virion contains a positive-sense single stranded RNA genome of about 9.5 kb. The genome encodes a single polyprotein of 3,010 to 3,030 amino acids. The structural proteins comprise a core protein forming the viral nucleocapsid and two envelope glycoproteins, E1 and E2.

A vaccine based on the recombinant envelope glycoproteins (rE1E2) from a single genotype 1a strain (HCV-1) protected chimpanzees from chronic infection following homologous and heterologous genotype 1a (gt1a) viral challenge (reviewed in Houghton, Immunol Rev 2011) Antisera from the immunized chimpanzees were shown to exhibit in vitro cross-neutralizing activity (Meunier et al. (2011) *J. Infect. Dis.* 204:1186). A phase I clinical trial was conducted in human volunteers with a similar antigen (Frey et al. (2010) *Vaccine* 28:6367). Antisera from selected vaccinated individuals were similarly capable of neutralizing chimeric cell culture-derived viruses (HCVcc) expressing the structural proteins of strains representing all 7 major HCV genotypes in vitro (Law et al. (2013) *PLoS One* 8:e59776) and to be able to compete with the binding of numerous discrete monoclonal antibodies with broad cross-neutralizing activities (Wong et al. (2014) *J. Virol.* 88:14278).

There is a need in the art for compositions and methods for inducing immune responses to HCV.

SUMMARY

The present disclosure provides an immunogenic composition comprising: a) i) a hepatitis C virus (HCV) heterodimeric polypeptide that includes HCV E1 and E2 polypeptides; ii) an HCV E1 polypeptide; or iii) an HCV E2 polypeptide; b) a polypeptide (also referred to herein as a "T-cell epitope polypeptide" or an "HCV T-cell epitope polypeptide") comprising T-cell epitopes (e.g., CD4$^+$ and CD8$^+$ T-cell epitopes that are conserved among some HCV genotypes and that are presented through one or multiple HLA alleles common within the human population) present in an HCV protein other than E1 and E2; and c) a pharmaceutically acceptable excipient. The present disclosure provides a method of inducing an immune response, in an individual, to an HCV polypeptide. The present disclosure provides an immunogenic composition comprising: a) a polypeptide that comprises one or more T-cell epitopes (e.g., CD4$^+$ and CD8$^+$ T-cell epitopes that are conserved among some HCV genotypes and that are presented through one or multiple HLA alleles common within the human population) present in an HCV protein other than E1 and E2; and b) a pharmaceutically acceptable excipient.

BRIEF DESCRIPTION OF THE DRAWINGS

FIG. 1A-1C provide an amino acid sequence alignment of examples of the core-E1-E2 coding regions of a HCV genotype 1 virus, specifically representative HCV 1A, 1B and 1C genotypes. Genbank database sequences for the coding region core-E1-E2 were aligned using Geneious software v5.6.4. Numbering of amino acids is according to strain NP_671941 (H77). Consensus: SEQ ID NO:1; AVI1a129: SEQ ID NO:2; NP_671491 (H77): SEQ ID NO:3; EU155269: SEQ ID NO:4; EU781810: SEQ ID NO:5; EU781771: SEQ ID NO:6; AB250610: SEQ ID NO:7; EU781752: SEQ ID NO:8; EU781759: SEQ ID NO:9; EF407439: SEQ ID NO:10; EF407427: SEQ ID NO:11; EU362905: SEQ ID NO:12; EF407413: SEQ ID NO:13; EU781808: SEQ ID NO:14; EU78170: SEQ ID NO:15; AJ238799 (Con1): SEQ ID NO:16; AAK97744: SEQ ID NO:17; AF139594: SEQ ID NO:18; AF176573: SEQ ID NO:19; BAA19625: SEQ ID NO:20; BAA25076: SEQ ID NO:21; BAC54896: SEQ ID NO:22; BAD91386: SEQ ID NO:23; BAF46764: SEQ ID NO:24; BAG30950: SEQ ID NO:25; CAB41951: SEQ ID NO:26; AAK95832: SEQ ID NO:27; AAT69968: SEQ ID NO:28; and BAA03581: SEQ ID NO:29.

FIG. 2A-2C provide an alignment of amino acid sequences of the core-E1-E2 coding region of representative HCV 2A and HCV2B subtypes. Genbank database sequences for the coding region core-E1-E2 were aligned using Geneious software v5.6.4. The amino acid numbering depicted is in accordance to the common HCV strains: AB047639 (JFH1) and HPCJ8G-J8 (J8) for HCV2A and HCV2B, respectively. AB047639 (JFH1): SEQ ID NO:30; AB047645: SEQ ID NO:31; AF169003: SEQ ID NO:32; AF169005: SEQ ID NO:33; AF238482: SEQ ID NO:34; AY746460: SEQ ID NO:35; HPCPOLP: SEQ ID NO:36; NC_009823: SEQ ID NO:37; HPCJ8G HC-J8: SEQ ID NO:38; AB030907: SEQ ID NO:39; AY232730: SEQ ID NO:40; AY232747: SEQ ID NO:41; and DQ430817: SEQ ID NO:42.

FIG. 3A-3C provide an amino acid sequence alignment of the core-E1-E2 coding region for representative HCV 3A, 3B and 3K genotypes. Genbank database sequences for the coding region core-E1-E2 were aligned using Geneious software v5.6.4. Consensus: SEQ ID NO:43; AVI3a177: SEQ ID NO:44; YP_0014696: SEQ ID NO:45; CAA54244: SEQ ID NO:46; AAC03058: SEQ ID NO:47; AAY29642: SEQ ID NO:48; ABD85062: SEQ ID NO:49; ABD85063: SEQ ID NO:50; ABD97104: SEQ ID NO:51; BAA06044: SEQ ID NO:52; BAA08372: SEQ ID NO:53; and BAA09890: SEQ ID NO:54.

FIG. 5A-5C provide amino acid sequences of immunoglobulin Fc regions for GenBank 3S7G_A *Homo sapiens* IgG1 Fc: SEQ ID NO:56; GenBank AAN76044 *Homo sapiens* IgG2 Fc: SEQ ID NO: 57; GenBank AAW65947 *Homo sapiens* IgG3 Fc: SEQ ID NO:58; GenBank AAA52770 *Homo sapiens* IgD Fc: SEQ ID NO:59; GenBank 0308221A *Homo sapiens* IgM Fc: SEQ ID NO:60; GenBank P01876 *Homo sapiens* IgA Fc: SEQ ID NO:61; GenBank IF6A_B *Homo sapiens* IgE Fc: SEQ ID NO:62; and GenBank P01861 *Homo sapiens* IgG4 Fc: SEQ ID NO:63.

FIG. 6 provides the solubility of various T-cell epitope polypeptides in an aqueous buffer. TP35-NS3: SEQ ID NO:133; TP35-NS3(Lys)$_3$: SEQ ID NO:302; TP42: SEQ ID NO:228; TP45 (C-terminal CNV replaced with KKK): SEQ ID NO:248; TP48: SEQ ID NO:254; TP48(Lys)$_3$: SEQ ID NO:257; and TP50-C: SEQ ID NO:148.

FIG. 7 provides an alignment of amino acid sequences of HCV polypeptides; and shows the positions of TP50-C, conserved MHC class II CD4-specific HCV epitopes, and conserved MHC class I CD8-specific HCV epitopes. Top to bottom: SEQ ID NOs: 309-318.

FIG. 8 provides an alignment of amino acid sequences of HCV polypeptides; and shows the positions of TP35-NS3, conserved MHC class II CD4-specific HCV epitopes, conserved MHC class I CD8-specific HCV epitopes, and MHC class I CD8-specific HCV epitopes with corresponding HLA specificity. Top to bottom: SEQ ID NOs: 319-328.

FIG. 9 provides an alignment of amino acid sequences of HCV polypeptides; and shows the positions of TP27, TP42, conserved MHC class II CD4-specific HCV epitopes, conserved MHC class I CD8-specific HCV epitopes, and MHC class I CD8-specific HCV epitopes with corresponding HLA specificity. Top to bottom: SEQ ID NOs: 329-338.

FIG. 10 provides an alignment of amino acid sequences of HCV polypeptides; and shows the positions of TP23, TP45, conserved MHC class II CD4-specific HCV epitopes, conserved MHC class I CD8-specific HCV epitopes, and MHC class I CD8-specific HCV epitopes with corresponding HLA specificity. Top to bottom: SEQ ID NOs: 339-348.

FIG. 11 provides an alignment of amino acid sequences of HCV polypeptides; and shows the positions of TP35-NS4, TP48, conserved MHC class II CD4-specific HCV epitopes, and conserved MHC class I CD8-specific HCV epitopes. Top to bottom: SEQ ID NOs: 349-358.

FIG. 12 provides the solubility of various T-cell epitope polypeptides. TP35-NS3: SEQ ID NO:133; TP35-NS3+KKK: SEQ ID NO:302; TP42 SEQ ID NO:228; TP45(-last 3aa)+KKK SEQ ID NO:248; TP45+KKK SEQ ID NO:251; TP48 SEQ ID NO:254; TP48+KKK: SEQ ID NO:257; TP50-C: SEQ ID NO:148; TP23: SEQ ID NO:186; TP23+KKK: SEQ ID NO:261; TP27: SEQ ID NO:188; TP27+KKK: SEQ ID NO:263; TP35-NS4: SEQ ID NO:203; and TP35-NS4+KKK: SEQ ID N0265.

FIG. 13 provides the solubility of various T-cell epitope polypeptides. TP42: SEQ ID NO:228; TP45+KKK: SEQ ID NO:251; TP48: SEQ ID NO:254.

FIG. 14 provides the solubility of various T-cell epitope polypeptides. TP45+KKK: SEQ ID NO:251; TP48: SEQ ID NO:254.

FIG. 19 provides a table showing population coverage (PC) analysis of reported and predicted epitopes.

FIG. 27 depicts solubility data for a TP33 T-cell epitope polypeptide (SEQ ID NO:279) and a TP42-2 T-cell epitope polypeptide (SEQ ID NO:291).

DEFINITIONS

Figure 4A:
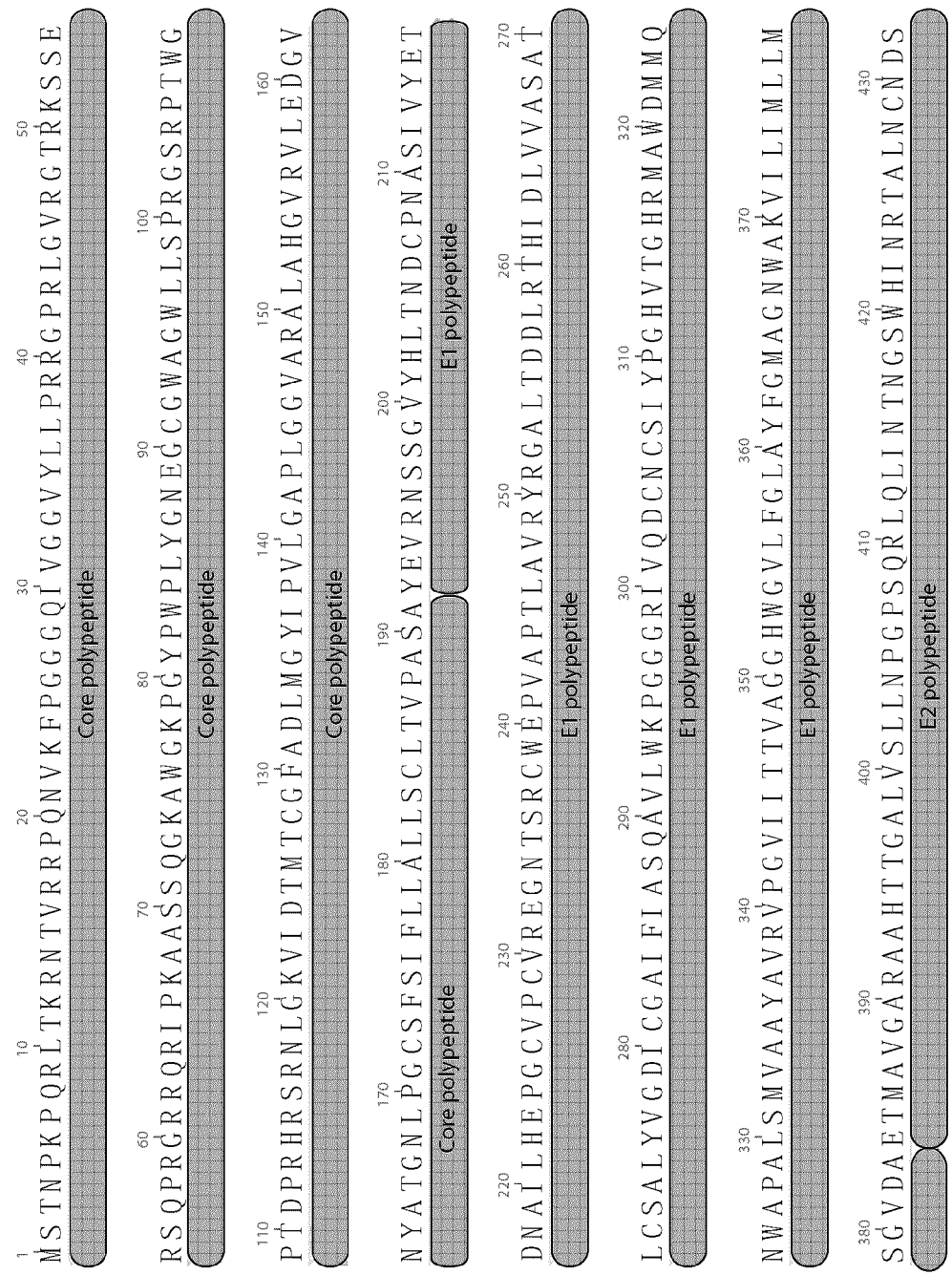
FIG. 4A-4B provide an amino acid sequence of the core-E1-E2 coding region for HCV genotype 7a. Amino acid sequence for the coding region core-E1-E2 of genotype 7a (isolate QC69; Genbank: ABN05226.1; SEQ ID NO:55) is shown according to the numbering scheme of the reference strain, NP_671941 (H77).

The term "hepatitis C virus" ("HCV"), as used herein, refers to any one of a number of different genotypes and isolates of hepatitis C virus. Thus, "HCV" encompasses any of a number of genotypes, subtypes, or quasispecies, of HCV, including, e.g., genotype 1, 2, 3, 4, 6, 7, etc. and subtypes (e.g., 1a, 1b, 2a, 2b, 3a, 4a, 4c, etc.), and quasispecies. Representative HCV genotypes and isolates include: HCV-1, H77, J6, Con1, isolate 1, BK, EC1, EC10, HC-J2, HC-J5; HC-J6, HC-J7, HC-J8, HC-JT, HCT18, HCT27, HCV-476, HCV-KF, "Hunan", "Japanese", "Taiwan", TH, type 1, type 1a, H77 type 1b, type 1c, type 1d, type 1e, type 1f, type 10, type 2, type 2a, type 2b, type 2c, type 2d, type 2f, type 3, type 3a, type 3b, type 3g, type 4, type 4a, type 4c, type 4d, type 4f, type 4h, type 4k, type 5, type 5a, type 6, type 6a, and type 7a.

The terms "individual," "host," "subject," and "patient" are used interchangeably herein, and refer to a mammal, including, but not limited to, non-human primates (e.g., simians), equines (e.g., horses), rodents (e.g., rats; mice), and humans.

As used herein, the term "isolated," in reference to a polypeptide, refers to a polypeptide that is in an environment different from that in which the polypeptide naturally occurs. An isolated polypeptide can be purified. By "purified" is meant a compound of interest (e.g., a polypeptide) has been separated from components that accompany it in nature. "Purified" can also be used to refer to a polypeptide separated from components that can accompany it during production of the polypeptide (e.g., during synthesis in vitro, etc.). In some embodiments, a polypeptide (or a mixture of polypeptides) is substantially pure when the polypeptide (or mixture of polypeptides) is at least 60% or at least 75% by weight free from organic molecules with which it is naturally associated or with which it is associated during production. In some cases, the polypeptide is from 30% to 60% pure. In some cases, the polypeptide (or mixture of polypeptides) is at least 60%, at least 75%, at least 80%, at least 85%, at least 90%, at least 95%, or at least 99%, by weight, pure. For example, in some cases, an E1 or an E2 polypeptide (or a mixture of E1 and E2 polypeptides, e.g., an E1/E2 heterodimer) is substantially pure when the E1 or E2 polypeptide (or mixture of E1 and E2 polypeptides) is at least 60% or at least 75% by weight free from organic molecules with which the polypeptide(s) is naturally associated or with which it is associated during production. In some cases, the E1 or E2 polypeptide (or mixture of E1 and E2 polypeptides) is at least 60%, at least 75%, at least 80%, at least 85%, at least 90%, at least 95%, or at least 99%, by weight, pure. In some cases, where a composition comprises an E2 polypeptide, the E2 polypeptide is at least 60%, at least 75%, at least 80%, at least 85%, at least 90%, at least 95%, or at least 99%, by weight, pure. In some cases, where a composition comprises an E1/E2 heterodimeric complex polypeptide, the E1/E2 heterodimeric complex polypeptide is at least 60%, at least 75%, at least 80%, at least 85%, at least 90%, at least 95%, or at least 99%, by weight, pure. In some cases, where a composition comprises a T-cell epitope polypeptide, the T-cell epitope polypeptide is at least 60%, at least 75%, at least 80%, at least 85%, at least 90%, at least 95%, or at least 99%, by weight, pure.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. In some cases, a polynucleotide is RNA. In some cases, a polynucleotide is DNA. A "polynucleotide" includes a nucleic acid that is incorporated into a viral vector or a bacterial vector.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones. The term "polypeptide" includes glycosylated polypeptides.

The term "heterologous" refers to two components that are defined by structures derived from different sources. For example, where "heterologous" is used in the context of a polypeptide, where the polypeptide includes operably linked amino acid sequences that can be derived from one or more different polypeptides, e.g., amino acid sequences that are not operably linked to the polypeptide in nature. As another example, where a composition comprises an HCV E1/E2 heterodimer and a "heterologous" polypeptide, the "heterologous polypeptide is a polypeptide other than HCV E1 or HCV E2. As another example, where a composition comprises an HCV E1 polypeptide and a "heterologous" polypeptide, the "heterologous polypeptide" is a polypeptide other than HCV E1. As another example, where a composition comprises an HCV E2 polypeptide and a "heterologous" polypeptide, the "heterologous polypeptide is a polypeptide other than HCV E2. As another example, where a fusion polypeptide comprises: a) a T-cell epitope polypeptide; and b) a heterologous fusion partner polypeptide, the "heterologous fusion partner polypeptide" is one that is not found associated with the T-cell epitope polypeptide in nature.

A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well known to those of skill in the art. See, e.g., Pearson (1994) Methods Mol. Biol. 24: 307-331, herein incorporated by reference. Examples of groups of amino acids that have side chains with similar chemical properties, and that thus constitute conservative amino acid substitution groups, include: 1) aliphatic side chain-containing amino acids: glycine, alanine, valine, leucine and isoleucine; 2) aliphatic-hydroxyl side chain-containing amino acids: serine and threonine; 3) amino acids with amide-containing side chains: asparagine and glutamine; 4) aromatic side chain-containing amino acids: phenylalanine, tyrosine, and tryptophan; 5) amino acids with basic side chains: lysine, arginine, and histidine; 6) amino acids with acidic side chains: aspartate and glutamate, and 7) amino acids with sulfur-containing side chains: cysteine and methionine. Examples of conservative amino acid substitution groups are: valine-leucine-isoleucine, phenylalanine-tyrosine, lysine-arginine, alanine-valine, glutamate-aspartate, and asparagine-glutamine.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a T-cell epitope" includes a plurality of such epitopes and reference to "the E1/E2 heterodimer" includes reference to one or more E1/E2 heterodimers and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides an immunogenic composition comprising: a) a polypeptide that comprises one or more T-cell epitopes (e.g., $CD4^+$ and/or $CD8^+$ T-cell epitopes that are conserved between or among two or more HCV genotypes and that are presented through one or multiple HLA alleles common within the human population) present in an HCV protein other than E1 and E2; and b) a pharmaceutically acceptable excipient. The present disclosure provides an immunogenic composition comprising: a) i) a hepatitis C virus (HCV) heterodimeric polypeptide that includes HCV E1 and E2 polypeptides; ii) an HCV E1 polypeptide; or iii) an HCV E2 polypeptide; b) a heterologous polypeptide (also referred to herein as a "T-cell epitope polypeptide" or an "HCV T-cell epitope polypeptide") comprising T-cell epitopes (e.g., $CD4^+$ and/or $CD8^+$ T-cell epitopes that are conserved between or among two or more HCV genotypes and that are presented through one or multiple HLA alleles common within the human population) present in an HCV protein other than E1 and E2; and c) a pharmaceutically acceptable excipient. The present disclosure provides a method of inducing an immune response in an individual to an HCV polypeptide.

An immunogenic composition of the present disclosure, when administered to an individual (e.g., an individual in need thereof), induces an immune response to HCV in the individual. In some cases, an immunogenic composition of the present disclosure, when administered to an individual (e.g., an individual in need thereof), induces a protective immune response to HCV in the individual. A protective immune response to HCV can include one or both of: i) an HCV-specific T cell response, which can include an HCV-specific $CD8^+$ T cell response and/or an HCV-specific $CD4^+$ T cell response; and ii) production of cross-neutralizing antibodies to HCV.

In some cases, an immunogenic composition of the present disclosure comprises, as separate entities (i.e., not in covalent linkage to one another): a) an HCV E1/E2 heterodimer; and b) a T-cell epitope polypeptide comprising a T-cell epitope present in an HCV protein other than E1 and E2. In some cases, an immunogenic composition of the present disclosure comprises, as separate entities (i.e., not in covalent linkage to one another): a) an HCV E2 polypeptide; and b) a T-cell epitope polypeptide comprising a T-cell epitope present in an HCV protein other than E1 and E2. In some cases, an immunogenic composition of the present disclosure comprises, as separate entities (i.e., not in covalent linkage to one another): a) an HCV E1 polypeptide; and b) a T-cell epitope polypeptide comprising a T-cell epitope present in an HCV protein other than E1 and E2.

As noted above, T-cell epitopes that are present in a heterologous polypeptide suitable for inclusion in an immunogenic composition of the present disclosure include $CD4^+$ and/or $CD8^+$ T-cell epitopes that are conserved between or among two or more HCV genotypes and that are presented through one or multiple HLA alleles common within the human population. Thus, a heterologous polypeptide suitable for inclusion in an immunogenic composition of the present disclosure comprises multiple (e.g., 2, 3, 4, 5, or more than 5) CD4$^+$ and/or CD8$^+$ T-cell epitopes that are conserved among some HCV genotypes and that are presented through one or multiple HLA alleles common within the human population. In some cases, a T-cell epitope polypeptide includes epitopes that are conserved among a subset of HCV genotypes. For example, in some cases, a T-cell epitope polypeptide includes epitopes that are conserved among at least 3 HCV genotypes. For example, in some cases, a T-cell epitope polypeptide includes epitopes that are conserved among only HCV genotypes 1a, 1b, and 3 (but not genotypes 4, 5, 6, or 7, for example). In some cases, one or more of the epitopes presented by a T-cell epitope polypeptide is/are conserved among all HCV genotypes. A T-cell epitope polypeptide can include: i) one or more epitopes that are conserved among a subset of HCV genotypes; and ii) one or more epitopes that are conserved among all HCV genotypes. For example, a T-cell epitope polypeptide can include: i) one or more epitopes that are conserved among only HCV genotypes 1a, 1b, and 3 (but not genotypes 4, 5, 6, or 7, for example); and ii) one or more epitopes that are conserved among all HCV genotypes.

Suitable T-cell epitope polypeptides are described in detail below. The T-cell epitope polypeptide can be expressed in any suitable host cell, e.g., a bacterial host cell, a yeast host cell, an insect host cell, a mammalian host cell) as a separate polypeptide, then combined with a E1/E2 heterodimer, an E2 polypeptide, or an E1 polypeptide, to form and immunogenic composition. The T-cell epitope polypeptides serve to elicit broad spectrum CD4$^+$ and CD8$^+$ T cell responses to multiple HCV genotypes because the T-cell epitope polypeptides have been selected to contain a plurality of T cell epitopes that are highly conserved among at least some genotypes of the hepacivirus genus, and which may in some cases be immunodominant. The T-cell epitope polypeptides also contain T cell epitopes presented by various MHC alleles common in the human population. The E1/E2 antigens will also elicit cross-reactive T cell responses; however, the T-cell epitope polypeptides will elicit broader T cell responses that are cross-reactive with multiple HCV genotypes in the general human population. Both neutralizing antibodies and T cell responses are known to be protective against HCV; thus, this combination of antigens, optionally along with a suitable adjuvant (e.g., AS01 or MF59 or Alum/MPL) will optimize the protective effects of a HCV vaccine.

The T-cell epitope polypeptides can be chemically-synthesized, e.g., using standard methods of chemical synthesis of polypeptides. The T-cell epitope polypeptides can also be produced using recombinant means. The T-cell epitope polypeptides may be expressed alone (e.g., without any heterologous polypeptide appended thereto), and then purified conventionally. Alternatively, the T-cell epitope polypeptides can be expressed downstream of, or upstream of, an immunoglobulin (Ig) Fc fragment (or other affinity tag) separated by a protease cleavage site (e.g., a Precision protease cleavage site) and then purified.

Immunogenic Compositions Comprising: A) an HCV E1/E2 Heterodimer, an HCV E2 Polypeptide, or an HCV E1 Polypeptide; and/or B) a Heterologous Polypeptide Comprising a T-Cell Epitope (a "T-Cell Epitope Polypeptide")

The present disclosure provides an immunogenic composition comprising: a) a T-cell epitope polypeptide (a polypeptide other than an HCV E1 or E2 polypeptide) comprising T-cell epitopes (e.g., CD4$^+$ and/or CD8$^+$ T-cell epitopes that are conserved between or among two or more HCV genotypes and that are presented through one or multiple HLA alleles common within the human population) present in an HCV protein other than E1 and E2; and b) a pharmaceutically acceptable excipient. In some cases, the immunogenic composition comprises an adjuvant. The present disclosure provides an immunogenic composition comprising: a) i) an HCV heterodimeric polypeptide that includes HCV E1 and E2 polypeptides; ii) an HCV E1 polypeptide; or iii) an HCV E2 polypeptide; b) a T-cell epitope polypeptide (a polypeptide other than an HCV E1 or E2 polypeptide) comprising T-cell epitopes (e.g., CD4$^+$ and/or CD8$^+$ T-cell epitopes that are conserved between or among two or more HCV genotypes and that are presented through one or multiple HLA alleles common within the human population) present in an HCV protein other than E1 and E2; and c) a pharmaceutically acceptable excipient. In some cases, the immunogenic composition comprises an adjuvant.

As noted above, T-cell epitopes that are present in a T-cell epitope polypeptide suitable for inclusion in an immunogenic composition of the present disclosure include CD4$^+$ and/or CD8$^+$ T-cell epitopes that are conserved between or among two or more HCV genotypes and that are presented through one or multiple HLA alleles common within the human population. Thus, a T-cell epitope polypeptide suitable for inclusion in an immunogenic composition of the present disclosure comprises multiple (e.g., 2, 3, 4, or 5, or more than 5) CD4$^+$ and/or CD8$^+$ T-cell epitopes that are conserved between or among two or more HCV genotypes and that are presented through one or multiple HLA alleles common within the human population. In some cases, the immunogenic composition comprises an adjuvant. In some cases, a CD8 epitope present in a T-cell epitope polypeptide of the present disclosure presented through a single HLA allele (a single HLA haplotype). In some cases, a CD4 epitope present in a T-cell epitope polypeptide of the present disclosure presented through multiple different HLA alleles (multiple different HLA haplotypes).

In some cases, an immunogenic composition of the present disclosure, when administered to an individual in need thereof, induces an immune response in the individual to one or more HCV genotypes. In some cases, an immunogenic composition of the present disclosure, when administered to an individual in need thereof, induces an immune response in the individual to one or more HCV genotypes, where the immune response is greater than the immune response induced by administration of a control composition comprising the HCV E1/E2 heterodimer (or E1 polypeptide, or E2 polypeptide) but lacking the heterologous polypeptide.

In some cases, an immunogenic composition of the present disclosure, when administered to an individual in need thereof, increases one or both of: a) the number of antigen-specific proliferating T cells; and b) the number of antigen-specific cytokine-secreting T-cells.

In some cases, an immunogenic composition of the present disclosure, when administered to an individual in need thereof, induces CD8$^+$ CTLs specific for HCV, where the number of HCV-specific CD8$^+$ CTLs induced is at least 10%, at least 15%, at least 20%, at least 25%, at least 30%, at least 40%, at least 50%, at least 75%, at least 100% (or 2-fold), at least 2.5-fold, at least 5-fold, at least 7.5-fold, at least 10-fold, at least 20-fold, at least 50-fold, or at least 100-fold, or more than 100-fold, higher than the number of HCV-specific CD8$^+$ CTLs induced by administration of a control composition (e.g., a composition comprising the HCV E1/E2 heterodimer but lacking the T-cell epitope polypeptide; a composition comprising an E1 polypeptide but lacking the T-cell epitope polypeptide; a composition comprising an E2 polypeptide but lacking the T-cell epitope polypeptide).

In some cases, an immunogenic composition of the present disclosure, when administered to an individual in need thereof, induces CD4$^+$ T cells specific for HCV, where the number of HCV-specific CD4$^+$ T cells induced is at least 10%, at least 15%, at least 20%, at least 25%, at least 30%, at least 40%, at least 50%, at least 75%, at least 100% (or 2-fold), at least 2.5-fold, at least 5-fold, at least 7.5-fold, at least 10-fold, at least 20-fold, at least 50-fold, or at least 100-fold, or more than 100-fold, higher than the number of HCV-specific CD4$^+$ T cells induced by administration of a control composition (e.g., a composition comprising the HCV E1/E2 heterodimer but lacking the T-cell epitope polypeptide; a composition comprising an E1 polypeptide but lacking the T-cell epitope polypeptide; a composition comprising an E2 polypeptide but lacking the T-cell epitope polypeptide).

In some cases, an immunogenic composition of the present disclosure, when administered to an individual in need thereof, induces production of HCV-specific CD4$^+$ T cells and CD8$^+$ T cells in the individual, where the number of HCV-specific CD4$^+$ T cells and/or CD8$^+$ T cells is increased, such that the percent of total peripheral CD4$^+$ and/or CD8$^+$ T cells that is HCV-specific is from 0.01% to 0.05%, from 0.05% to 0.10%, from 0.10% to 0.125%, from 0.125% to 0.25%, from 0.25% to from 0.50%, or 0.5% to 10% (e.g., from 0.5% to 1%, from 1% to 2%, from 2% to 5%, or from 5% to 10%). The number of HCV-specific CD4$^+$ T cells and CD8$^+$ T cells in a control individual (e.g., an individual not infected with HCV) not treated with the immunogenic composition would be undetectable.

In some cases, an immunogenic composition of the present disclosure, when administered to an individual in need thereof, induces production of HCV NS3-specific CD4$^+$ T cells and/or CD8$^+$ T cells in the individual, where the number of HCV NS3-specific CD4$^+$ T cells and/or CD8$^+$ T cells is increased, such that the percent of the total peripheral blood T cells (i.e., the total number of CD4$^+$ T cells+CD8$^+$ T cells in the peripheral blood) that are HCV NS3-specific CD4$^+$ T cells and CD8$^+$ T cells is from 0.01% to 10% (e.g., from 0.01% to 0.05%, from 0.05% to 0.1%, from 0.1% to 0.25%, from 0.25% to 0.5%, from 0.5% to 1%, from 1% to 2%, from 2% to 5%, or from 5% to 10%). The number of HCV NS3-specific CD4$^+$ T cells and CD8$^+$ T cells in a control individual (e.g., an individual not infected with HCV) not treated with the immunogenic composition would be undetectable.

In some cases, an immunogenic composition of the present disclosure, when administered to an individual in need thereof, induces production of HCV NS4-specific CD4$^+$ T cells and/or CD8$^+$ T cells in the individual, where the number of HCV NS4-specific CD4$^+$ T cells and/or CD8$^+$ T cells is increased, such that the percent of the total peripheral blood T cells (i.e., the total number of CD4$^+$ T cells+CD8$^+$ T cells in the peripheral blood) that are HCV NS4-specific CD4$^+$ T cells and CD8$^+$ T cells is from 0.01% to 10% (e.g., from 0.01% to 0.05%, from 0.05% to 0.1%, from 0.1% to 0.25%, from 0.25% to 0.5%, from 0.5% to 1%, from 1% to 2%, from 2% to 5%, or from 5% to 10%). The number of HCV NS4-specific CD4$^+$ T cells and CD8$^+$ T cells in a control individual (e.g., an individual not infected with HCV) not treated with the immunogenic composition would be undetectable.

In some cases, an immunogenic composition of the present disclosure, when administered to an individual in need thereof, induces production of HCV core-specific CD4$^+$ T cells and/or CD8$^+$ T cells in the individual, where the number of HCV core-specific CD4$^+$ T cells and/or CD8$^+$ T cells is increased, such that the percent of the total peripheral blood T cells (i.e., the total number of CD4$^+$ T cells+CD8$^+$ T cells in the peripheral blood) that are HCV core-specific CD4$^+$ T cells and CD8$^+$ T cells is from 0.01% to 10% (e.g., from 0.01% to 0.05%, from 0.05% to 0.1%, from 0.1% to 0.25%, from 0.25% to 0.5%, from 0.5% to 1%, from 1% to 2%, from 2% to 5%, or from 5% to 10%). The number of HCV core-specific CD4$^+$ T cells and CD8$^+$ T cells in a control individual (e.g., an individual not infected with HCV) not treated with the immunogenic composition would be undetectable.

In some cases, an immunogenic composition of the present disclosure, when administered to an individual in need thereof, increases the number of HCV E1/E2-specific CD4$^+$ T cells and CD8$^+$ T cells in the individual by at least 10%, at least 15%, at least 20%, at least 25%, at least 30%, at least 40%, at least 50%, at least 75%, at least 100% (or 2-fold), at least 2.5-fold, at least 5-fold, at least 7.5-fold, at least 10-fold, at least 20-fold, at least 50-fold, or at least 100-fold, or more than 100-fold, compared to the number of HCV E1/E2-specific CD4$^+$ T cells and CD8$^+$ T cells in the individual induced by administration of a control composition comprising the HCV E1/E2 heterodimer but lacking the T-cell epitope polypeptide, or compared to the number of HCV E1/E2-specific CD4$^+$ T cells and CD8$^+$ T cells in the individual before administration of the immunogenic composition.

In some cases, an immunogenic composition of the present disclosure, when administered to an individual in need thereof, induces helper T lymphocytes (e.g., CD4$^+$ T cells) specific for HCV, where the number of HCV-specific helper T lymphocytes induced is at least 10%, at least 15%, at least 20%, at least 25%, at least 30%, at least 40%, at least 50%, at least 75%, at least 100% (or 2-fold), at least 2.5-fold, at least 5-fold, at least 7.5-fold, at least 10-fold, at least 20-fold, at least 50-fold, or at least 100-fold, or more than 100-fold, higher than the number of HCV-specific helper T cells induced by administration of a control composition comprising the HCV E1/E2 heterodimer but lacking the T-cell epitope polypeptide, or compared to the number of HCV-specific CD4$^+$ T cells in the individual before administration of the immunogenic composition.

In some cases, an immunogenic composition of the present disclosure, when administered to an individual in need thereof, induces antibody specific for HCV, where the level of HCV-specific antibody induced is at least as high as the level of HCV-specific antibody induced by administration of a control composition comprising the HCV E1/E2 heterodimer but lacking the T-cell epitope polypeptide.

In some cases, an immunogenic composition of the present disclosure, when administered to an individual in need thereof, induces antibody specific for HCV, where the level of HCV-specific antibody induced is at least equivalent to the level of HCV-specific antibody induced by administration of a control composition comprising the HCV E1/E2 heterodimer but lacking the T-cell epitope polypeptide, or to the level of HCV-specific antibody in the individual before administration of the immunogenic composition. In some cases, an immunogenic composition of the present disclosure, when administered to an individual in need thereof, induces antibody specific for HCV, where the level of HCV-specific antibody induced is at least 10%, at least 15%, at least 20%, at least 25%, at least 30%, at least 40%, at least 50%, at least 75%, at least 100% (or 2-fold), at least 2.5-fold, at least 5-fold, at least 7.5-fold, at least 10-fold, at least 20-fold, at least 50-fold, or at least 100-fold, or more than 100-fold, higher than the level of HCV-specific antibody induced by administration of a control composition comprising the HCV E1/E2 heterodimer but lacking the T-cell epitope polypeptide, or compared the level of HCV-specific antibody in the individual before administration of the immunogenic composition.

An immunogenic composition of the present disclosure, when administered to an individual in need thereof, induces an immune response (e.g., a cellular immune response) in the individual to one or more HCV genotypes. In some cases, an immunogenic composition of the present disclosure, when administered to an individual in need thereof, induces an immune response in the individual to HCV genotype 1. In some cases, an immunogenic composition of the present disclosure, when administered to an individual in need thereof, induces an immune response in the individual to HCV genotype 2. In some cases, an immunogenic composition of the present disclosure, when administered to an individual in need thereof, induces an immune response in the individual to HCV genotype 3. In some cases, an immunogenic composition of the present disclosure, when administered to an individual in need thereof, induces an immune response in the individual to HCV genotype 1 and HCV genotype 3. In some cases, an immunogenic composition of the present disclosure, when administered to an individual in need thereof, induces an immune response in the individual to HCV genotype 1, HCV genotype 2, and HCV genotype 3. In some cases, an immunogenic composition of the present disclosure, when administered to an individual in need thereof, induces an immune response in the individual to HCV genotype 1, HCV genotype 2, HCV genotype 3, and HCV genotype 7. In some cases, an immunogenic composition of the present disclosure, when administered to an individual in need thereof, induces an immune response in the individual to HCV genotype 1, HCV genotype 2, HCV genotype 3, HCB genotype 4, HCV genotype 5, HCV genotype 6, and HCV genotype 7. In some cases, an immunogenic composition of the present disclosure, when administered to an individual in need thereof, induces an immune response in the individual to HCV genotype 1, HCV genotype 2, HCV genotype 3, HCV genotype 4, HCV genotype 5, and HCV genotype 6.

T-Cell Epitope Polypeptides

A T-cell epitope polypeptide suitable for inclusion in a composition of the present disclosure exhibits one or more of the following features: 1) displays immunodominant epitopes; 2) displays epitopes that are conserved between or among two or more different HCV genotypes; 3) displayed through human leukocyte antigen (HLA) alleles that are common within the human population; 4) good yields by chemical synthesis; and 5) good solubility in a buffered aqueous solution.

In some cases, a T-cell epitope polypeptide suitable for inclusion in a composition of the present disclosure displays 1, 2, 3, 4, 5, or from 5 to 10, different epitopes displayed by an HCV polypeptide other than E1 and E2. In some cases, the epitopes are immunodominant epitopes.

In some cases, a T-cell epitope polypeptide suitable for inclusion in a composition of the present disclosure displays one or more epitopes that are conserved between or among two or more HCV genotypes. For example, in some cases, a T-cell epitope polypeptide suitable for inclusion in a composition of the present disclosure displays 1, 2, 3, 4, 5, or from 5 to 10, epitopes that are conserved between HCV genotype 1 and HCV genotype 3. As another example, in some cases, a T-cell epitope polypeptide suitable for inclusion in a composition of the present disclosure displays 1, 2, 3, 4, 5, or from 5 to 10, epitopes that are conserved between HCV genotype 1 and HCV genotype 2. As another example, in some cases, a T-cell epitope polypeptide suitable for inclusion in a composition of the present disclosure displays 1, 2, 3, 4, 5, or from 5 to 10, epitopes that are conserved among HCV genotypes 1, 2, and 3. As another example, in some cases, a T-cell epitope polypeptide suitable for inclusion in a composition of the present disclosure displays 1, 2, 3, 4, 5, or from 5 to 10, epitopes that are conserved among HCV genotypes 1, 2, 3, and 6.

In some cases, a T-cell epitope polypeptide suitable for inclusion in a composition of the present disclosure is presented through one or multiple HLA alleles common within the human population. Examples of such alleles are described in Example 1.

In some cases, a T-cell epitope polypeptide suitable for inclusion in a composition of the present disclosure can be chemically synthesized using standard methods (e.g., a solid-phase peptide synthesis (SPPS) method), where the yield is at least 50%, at least 55%, at least 60%, at least 70%, at least 80%, at least 85%, at least 90%, at least 95%, at least 96%, at least 97%, at least 98%, or more than 98%. In some cases, the yield is 95%. In some cases, the yield is 96%. In some cases, the yield is 97%.

In some cases, a T-cell epitope polypeptide suitable for inclusion in a composition of the present disclosure exhibits solubility in a buffered aqueous solution. As one non-limiting example, a T-cell epitope polypeptide suitable for inclusion in a composition of the present disclosure exhibits solubility of at least 1 mg/ml in the following buffer ("E1E2" buffer): 10 mM sodium citrate, 250 mM NaCl, 1 mM ethylenediaminetetraacetic acid (EDTA), 0.1% non-ionic detergent TWEEN® 80, pH 6.0. For example, the peptides TP35-NS3 and TP50C are soluble in E1E2 buffer at a concentration of at least 1 mg/ml. The peptides TP35-NS3 and TP50C are soluble in E1E2 buffer at a concentration of at least 1 mg/ml, without the need for adding dimethylsulfoxide (DMS). Solubility of various T-cell epitope polypeptides are shown in FIGS. 6 and 12-14. In some cases, a T-cell epitope polypeptide suitable for inclusion in a composition of the present disclosure is soluble in E1E2 buffer at a concentration of at least 25 μg/ml, at least 30 μg/ml, at least 35 g/ml, at least 50 μg/ml, at least 75 μg/ml, at least 100 μg/ml, at least 250 μg/ml, at least 500 g/ml, at least 750 μg/ml, or at least 1 mg/ml. In some cases, a T-cell epitope polypeptide suitable for inclusion in a composition of the present disclosure exhibits good solubility in E1E2 buffer following lyophilization of the T-cell epitope polypeptide; in other words, in some cases, the T-cell epitope polypeptide is lyophilized, then reconstituted in E1E2 buffer, where the T-cell epitope polypeptide exhibits good solubility in the E1E2 buffer following reconstitution.

In some cases, a T-cell epitope polypeptide suitable for inclusion in a composition of the present disclosure exhibits good solubility in water. In some cases, a T-cell epitope polypeptide suitable for inclusion in a composition of the present disclosure is soluble in water at a concentration of at least 25 μg/ml, at least 30 μg/ml, at least 35 μg/ml, at least 50 μg/ml, at least 75 μg/ml, at least 100 μg/ml, at least 250 μg/ml, at least 500 μg/ml, at least 750 μg/ml, or at least 1 mg/ml.

In some cases, T-cell epitopes present in a T-cell epitope polypeptide can be provided in two peptide fragments. For example, for TP35-NS3 or for TP50C, a mixture of two shorter peptides can be used. The peptide fragments can be partially overlapping (e.g., overlapping by from 2 to 10 amino acids), or non-overlapping. The peptide fragments can have a length of from 18 amino acids to 30 amino acids, e.g., can have a length of 18 amino acids (aa), 19 aa, 20 aa, 21 aa, 22 aa, 23 aa, 24 aa, 25 aa, 26 aa, 27 aa, 28 aa, 29 aa, or 30 aa.

A T-cell epitope polypeptide suitable for inclusion in a composition of the present disclosure can include one or more conservative amino acid substitutions compared to, e.g., the amino acid designated "consensus" in one of FIGS. 7-11, e.g., an amino acid sequence labeled "consensus" and corresponding to TP35-NS3, TP50C, TP23, TP27, TP35-NS4, TP42, TP45, or TP48 (open bars in FIGS. 7-11). Examples of TP35-NS3, TP50C, TP23, TP27, TP35-NS4, TP42, TP45, and TP48 amino acid sequences with conservative amino acid substitutions are provided in FIGS. 7-11.

As described in detail below, a T-cell epitope polypeptide suitable for inclusion in a composition of the present disclosure can include one or more CD8 and/or CD4 epitopes. Examples of CD8 and CD4 epitopes are described below, and depicted in FIGS. 7-11. In FIGS. 7-11, bars with right-slanting hash marks denote conserved MHC class I CD8-specific HCV epitopes; bars with left-slanting hash marks denote conserved MHC class II CD4-specific HCV epitopes; stippled bars denote MHC class I CD8-specific HCV epitopes with corresponding HLA specificity. Stippled bars with "<5%" indicate the least common HLA alleles (less than 5%) in the U.S. population; the remainder of the stippled bars indicate an HLA frequency of >5% in the U.S. population. The corresponding alleles shown are: HLA-A01:01; HLA-A02:01; HLA-A03:01; HLA-A24:02; HLA-B08:01; and HLA-C03:03.

Those skilled in the art are aware of "anchor" amino acid positions, i.e., that are more likely to be conserved in a particular CD8 epitope (binding to HLA Class I) for various HLA alleles. For example, in a 9-amino acid peptide comprising a CD8 epitope (and binding to HLA class I), residues 2 and 9 are likely to be "anchor" amino acids and are therefore likely conserved, for HLA alleles HLA-A01:01, HLA-A02:01, HLA-A03:01, and HLA-A24:02.

TP35-NS3

In some cases, a T-cell epitope polypeptide suitable for inclusion in a composition of the present disclosure comprises an amino acid sequence having at least 20% (e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, or 100%) amino acid sequence identity to the following amino acid sequence: KSTKVPAAYAAQGYKVLVLNPSVAATLGFGAYMSK (SEQ ID NO:133; also referred to herein as "TP35-NS3"); where the T-cell epitope polypeptide has a length of from 28 amino acids to 35 amino acids (e.g., the T-cell epitope polypeptide has a length of 28 amino acids (aa), 29 aa, 30 aa, 31 aa, 32 aa, 33 aa, 34 aa, or 35 aa). In some cases, the T-cell epitope polypeptide has a length of 35 amino acids. In some cases, the T-cell epitope polypeptide is part of a fusion polypeptide, as described in detail below.

In some cases, a TP35-NS3 T-cell epitope polypeptide suitable for inclusion in a composition of the present disclosure comprises the following amino acid sequence: KSTKVPX$_1$AYX$_2$X$_3$QGYX$_4$VLVLNPSVAATLG FGX$_5$X$_6$X$_7$SX$_8$ (SEQ ID NO:134), where X$_1$ is A or V; X$_2$ is A or V; X$_3$ is A or S; X$_4$ is K or N; X$_5$ is A or S; X$_6$ is Y or F; X$_7$ is M or L; and X$_8$ is K or R; where the TP35-NS3 T-cell epitope polypeptide has a length of from 28 amino acids to 35 amino acids (e.g., the T-cell epitope polypeptide has a length of 28 amino acids (aa), 29 aa, 30 aa, 31 aa, 32 aa, 33 aa, 34 aa, or 35 aa). In some cases, the T-cell epitope polypeptide has a length of 35 amino acids. In some cases, the T-cell epitope polypeptide is part of a fusion polypeptide, as described in detail below.

In some cases, a TP35-NS3 T-cell epitope polypeptide suitable for inclusion in a composition of the present disclosure comprises the following amino acid sequence: KSTKVPVAYAAQGYKVLVLNPSVAATLGFGAYLSK (SEQ ID NO:135); where the TP35-NS3 T-cell epitope polypeptide has a length of from 28 amino acids to 35 amino acids (e.g., the T-cell epitope polypeptide has a length of 28 amino acids (aa), 29 aa, 30 aa, 31 aa, 32 aa, 33 aa, 34 aa, or 35 aa). In some cases, the T-cell epitope polypeptide has a length of 35 amino acids. In some cases, the T-cell epitope polypeptide is part of a fusion polypeptide, as described in detail below.

In some cases, a TP35-NS3 T-cell epitope polypeptide suitable for inclusion in a composition of the present disclosure comprises the following amino acid sequence: KSTKVPAAYASQGYKVLVLNPSVAATLGFGAYMSK (SEQ ID NO:136); where the TP35-NS3 T-cell epitope polypeptide has a length of from 28 amino acids to 35 amino acids (e.g., the T-cell epitope polypeptide has a length of 28 amino acids (aa), 29 aa, 30 aa, 31 aa, 32 aa, 33 aa, 34 aa, or 35 aa). In some cases, the T-cell epitope polypeptide has a length of 35 amino acids. In some cases, the T-cell epitope polypeptide is part of a fusion polypeptide, as described in detail below.

In some cases, a TP35-NS3 T-cell epitope polypeptide suitable for inclusion in a composition of the present disclosure comprises the following amino acid sequence: KSTKVPAAYVAQGYNVLVLNPSVAATLGFGSFMSR (SEQ ID NO:137); where the TP35-NS3 T-cell epitope polypeptide has a length of from 28 amino acids to 35 amino acids (e.g., the T-cell epitope polypeptide has a length of 28 amino acids (aa), 29 aa, 30 aa, 31 aa, 32 aa, 33 aa, 34 aa, or 35 aa). In some cases, the T-cell epitope polypeptide has a length of 35 amino acids. In some cases, the T-cell epitope polypeptide is part of a fusion polypeptide, as described in detail below.

In some cases, a TP35-NS3 T-cell epitope polypeptide suitable for inclusion in a composition of the present disclosure comprises the following amino acid sequence: KSTKVPAAYAAQGYKVLVLNPSVAATLGFGAYMSR (SEQ ID NO:138); where the TP35-NS3 T-cell epitope polypeptide has a length of from 28 amino acids to 35 amino acids (e.g., the T-cell epitope polypeptide has a length of 28 amino acids (aa), 29 aa, 30 aa, 31 aa, 32 aa, 33 aa, 34 aa, or 35 aa). In some cases, the T-cell epitope polypeptide has a length of 35 amino acids. In some cases, the T-cell epitope polypeptide is part of a fusion polypeptide, as described in detail below.

In some cases, a TP35-NS3 T-cell epitope polypeptide suitable for inclusion in a composition of the present disclosure comprises the following amino acid sequence: KSTKVPAAYASQGYKVLVLNPSVAATLGFGSYMSK (SEQ ID NO:139); where the TP35-NS3 T-cell epitope polypeptide has a length of from 28 amino acids to 35 amino acids (e.g., the T-cell epitope polypeptide has a length of 28 amino acids (aa), 29 aa, 30 aa, 31 aa, 32 aa, 33 aa, 34 aa, or 35 aa). In some cases, the T-cell epitope polypeptide has a length of 35 amino acids. In some cases, the T-cell epitope polypeptide is part of a fusion polypeptide, as described in detail below.

In some cases, a TP35-NS3 T-cell epitope polypeptide suitable for inclusion in a composition of the present disclosure comprises the following amino acid sequence: KSTKVPAAYASQGYKVLVLNPSVAATLGFGAYMSK (SEQ ID NO:136); where the TP35-NS3 T-cell epitope polypeptide has a length of from 28 amino acids to 35 amino acids (e.g., the T-cell epitope polypeptide has a length of 28 amino acids (aa), 29 aa, 30 aa, 31 aa, 32 aa, 33 aa, 34 aa, or 35 aa). In some cases, the T-cell epitope polypeptide has a length of 35 amino acids. In some cases, the T-cell epitope polypeptide is part of a fusion polypeptide, as described in detail below.

A TP35-NS3 T-cell epitope polypeptide suitable for inclusion in a composition of the present disclosure can include a CD8 epitope, e.g., a stretch of 10 contiguous amino acids having the amino acid sequence AYX$_1$X$_2$QGYX$_3$VL (SEQ ID NO:140), where X$_1$ is A or V; X$_2$ is A or S; and X$_3$ is K or N; and/or a stretch of 11 contiguous amino acids having the amino acid sequence ATLGFGX$_1$X$_2$X$_3$SX$_4$ (SEQ ID NO:141), where X$_1$ is A or S; X$_2$ is Y or F; X$_3$ is M or L; and X$_4$ is K or R. In some cases, the CD8 epitope is a stretch of 10 contiguous amino acids having the amino acid sequence AYAAQGYKVL (SEQ ID NO:142). In some cases, the CD8 epitope is a stretch of 10 contiguous amino acids having the amino acid sequence AYASQGYKVL (SEQ ID NO:187). In some cases, the CD8 epitope is a stretch of 10 contiguous amino acids having the amino acid sequence AYVAQGYNVL (SEQ ID NO:143). A TP35-NS3 T-cell epitope polypeptide suitable for inclusion in a composition of the present disclosure can include a CD8 epitope, e.g., a stretch of 10 contiguous amino acids having the amino acid sequence AYAAQGYKVL (SEQ ID NO:142) and/or a stretch of 11 contiguous amino acids having the amino acid sequence ATLGFGAYMSK (SEQ ID NO:144). A TP35-NS3 T-cell epitope polypeptide suitable for inclusion in a composition of the present disclosure can include: i) a stretch of 10 contiguous amino acids having the amino acid sequence AYAAQGYKVL (SEQ ID NO:142); and ii) a stretch of 11 contiguous amino acids having the amino acid sequence ATLGFGAYMSK (SEQ ID NO:144).

A TP35-NS3 T-cell epitope polypeptide suitable for inclusion in a composition of the present disclosure can include a CD4 epitope, e.g., a stretch of about 15 contiguous amino acids having the amino acid sequence: VLVLNPSVAATLGFG (SEQ ID NO:145).

A TP35-NS3 T-cell epitope polypeptide suitable for inclusion in a composition of the present disclosure can include: i) a CD4 epitope, e.g., a stretch of about 15 contiguous amino acids having the amino acid sequence: VLVLNPSVAATLGFG (SEQ ID NO:145); ii) a first CD8 epitope, e.g., a stretch of 10 contiguous amino acids having the amino acid sequence AYX$_1$X$_2$QGYX$_3$VL (SEQ ID NO:140), where X$_1$ is A or V; X$_2$ is A or S; and X$_3$ is K or N; and iii) a second CD8 epitope, e.g., a stretch of 11 contiguous amino acids having the amino acid sequence ATLGFGX$_1$X$_2$X$_3$SX$_4$ (SEQ ID NO:141), where X$_1$ is A or S; X$_2$ is Y or F; X$_3$ is M or L; and X$_4$ is K or R. A TP35-NS3 T-cell epitope polypeptide suitable for inclusion in a composition of the present disclosure can include: i) a CD4 epitope, e.g., a stretch of about 15 contiguous amino acids having the amino acid sequence: VLVLNPSVAATLGFG (SEQ ID NO:145); ii) a first CD8 epitope, e.g., a stretch of 10 contiguous amino acids having the amino acid sequence AYAAQGYKVL (SEQ ID NO:142); and iii) a second CD8 epitope, e.g., a stretch of 11 contiguous amino acids having the amino acid sequence ATLGFGAYMSK (SEQ ID NO:144).

In some cases, a T-cell epitope polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: KSTKVPAAYAAQGYKVLVLNPSVAATLGFGAYMSK (SEQ ID NO:133); and has a length of from 35 amino acids to 40 amino acids (e.g., 35 amino acids (aa), 36 aa, 37 aa, 38 aa, 39 aa, or 40 aa).

In some cases, a T-cell epitope polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: KSTKVPAAYAAQGYKVLVLNPSVAATLGFGAYMSK (SEQ ID NO:133); and has a length of 35 amino acids. In some cases, a T-cell epitope polypeptide suitable for inclusion in a composition of the present disclosure comprises the amino acid sequence KSTKVPAAYAAQGYKVLVLNPSVAATLGFGAYMSK (SEQ ID NO:133); and has a length of 35 amino acids.

In some cases, a suitable T-cell epitope polypeptide is a TP35-NS3 polypeptide with from 1 amino acid to 5 amino acids removed from the N-terminus and/or from 1 amino acid to 5 amino acids removed from the C-terminus. Thus, e.g., a suitable T-cell epitope polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: PAAYAAQGYKVLVLNPSVAATLGFGAYMSK (SEQ ID NO:146); and has a length of 30 amino acids. As another example, a suitable T-cell epitope polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: KSTKVPAAYAAQGYKVLVLNPSVAATLGFG (SEQ ID NO:147); and has a length of 30 amino acids.

TP50-C

In some cases, a T-cell epitope polypeptide suitable for inclusion in a composition of the present disclosure comprises an amino acid sequence having at least 20% (e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, or 100%) amino acid sequence identity to the following amino acid sequence: GVYLLPRRGPRLGVRATRKTSERSQPRGRRQPIPKARRSEGRSWAQPGYP (SEQ ID NO:148); also referred to herein as "TP50C"); where the T-cell epitope polypeptide has a length of from 40 amino acids to 50 amino acids (e.g., T-cell epitope polypeptide has a length of 40 amino acids (aa), 41 aa, 42 aa, 43 aa, 44 aa, 45 aa, 46 aa, 47 aa, 48 aa, 49 aa, or 50 aa). In some cases, the T-cell epitope polypeptide is part of a fusion polypeptide, as described in detail below.

In some cases, a TP50-C T-cell epitope polypeptide suitable for inclusion in a composition of the present disclosure comprises the following amino acid sequence: GVYX$_1$LPRRGPRLGVRX$_2$TRKX$_3$SERSQPR GRRQX$_4$IPKX$_5$X$_6$X$_7$X$_8$X$_9$GX$_{10}$X$_{11}$WX$_{12}$X$_{13}$PGY P (SEQ ID NO:149), where X$_1$ is L or V; X$_2$ is A or G; X$_3$ is T or S; X$_4$ is P or R; X$_5$ is A or D; X$_6$ is R or A; X$_7$ is R, Q, or S; X$_8$ is S or P; X$_9$ is E, T, or Q; X$_{10}$ is R or K; X$_1$ is S, T, H, or A; X$_{12}$ is A or G; and X$_{13}$ is Q or K; where the T-cell epitope polypeptide has a length of from 40 amino acids to 50 amino acids (e.g., the T-cell epitope polypeptide has a length of 40 amino acids (aa), 41 aa, 42 aa, 43 aa, 44 aa, 45 aa, 46 aa, 47 aa, 48 aa, 49 aa, or 50 aa). In some cases, the T-cell epitope polypeptide has a length of 50 amino acids. In some cases, the T-cell epitope polypeptide is part of a fusion polypeptide, as described in detail below.

In some cases, a TP50-C T-cell epitope polypeptide suitable for inclusion in a composition of the present disclosure comprises the following amino acid sequence: GVYX$_1$LPRRGPRLGVRX$_2$TRKX$_3$SERSQPRGRRQX$_4$ IPKX$_5$X$_6$X$_7$X$_8$X$_9$GX$_{10}$X$_{11}$WX$_{12}$X$_{13}$PGY P (SEQ ID NO:149), where X$_1$ is L or V; X$_2$ is A; X$_3$ is T; X$_4$ is P; X$_5$ is A or D; X$_6$ is R; X$_7$ is R or Q; X$_8$ is S or P; X$_9$ is E or T; X$_{10}$ is R or K; X$_{11}$ is S, T, H, or A; X$_{12}$ is A or G; and X$_{13}$ is Q or K; where the T-cell epitope polypeptide has a length of from 40 amino acids to 50 amino acids (e.g., the T-cell epitope polypeptide has a length of 40 amino acids (aa), 41 aa, 42 aa, 43 aa, 44 aa, 45 aa, 46 aa, 47 aa, 48 aa, 49 aa, or 50 aa). In some cases, the T-cell epitope polypeptide has a length of 50 amino acids. In some cases, the T-cell epitope polypeptide is part of a fusion polypeptide, as described in detail below.

In some cases, a TP50-C T-cell epitope polypeptide suitable for inclusion in a composition of the present disclosure comprises the following amino acid sequence: GVYLLPRRGPRLGVRATRKTSERSQPR-GRRQPIPKARRPEGRTWAQPGYP (SEQ ID NO:150); where the T-cell epitope polypeptide has a length of from 40 amino acids to 50 amino acids (e.g., the T-cell epitope polypeptide has a length of 40 amino acids (aa), 41 aa, 42 aa, 43 aa, 44 aa, 45 aa, 46 aa, 47 aa, 48 aa, 49 aa, or 50 aa). In some cases, the T-cell epitope polypeptide has a length of 50 amino acids. In some cases, the T-cell epitope polypeptide is part of a fusion polypeptide, as described in detail below.

In some cases, a TP50-C T-cell epitope polypeptide suitable for inclusion in a composition of the present disclosure comprises the following amino acid sequence: GVYLLPRRGPRLGVRATRKTSERSQPR-GRRQPIPKARRPEGRAWAQPGYP (SEQ ID NO:151); where the T-cell epitope polypeptide has a length of from 40 amino acids to 50 amino acids (e.g., the T-cell epitope polypeptide has a length of 40 amino acids (aa), 41 aa, 42 aa, 43 aa, 44 aa, 45 aa, 46 aa, 47 aa, 48 aa, 49 aa, or 50 aa). In some cases, the T-cell epitope polypeptide has a length of 50 amino acids. In some cases, the T-cell epitope polypeptide is part of a fusion polypeptide, as described in detail below.

In some cases, a TP50-C T-cell epitope polypeptide suitable for inclusion in a composition of the present disclosure comprises the following amino acid sequence: GVYLLPRRGPRLGVRATRKTSERSQPR-
GRRQPIPKDRRSTGKSWGKPGYP (SEQ ID NO:152); where the T-cell epitope polypeptide has a length of from 40 amino acids to 50 amino acids (e.g., the T-cell epitope polypeptide has a length of 40 amino acids (aa), 41 aa, 42 aa, 43 aa, 44 aa, 45 aa, 46 aa, 47 aa, 48 aa, 49 aa, or 50 aa). In some cases, the T-cell epitope polypeptide has a length of 50 amino acids. In some cases, the T-cell epitope polypeptide is part of a fusion polypeptide, as described in detail below.

In some cases, a TP50-C T-cell epitope polypeptide suitable for inclusion in a composition of the present disclosure comprises the following amino acid sequence: GVYLLPRRGPRLGVRATRKTSERSQPR-GRRQPIPKDRRSTGKSWGKPGYP (SEQ ID NO:152); where the T-cell epitope polypeptide has a length of from 40 amino acids to 50 amino acids (e.g., the T-cell epitope polypeptide has a length of 40 amino acids (aa), 41 aa, 42 aa, 43 aa, 44 aa, 45 aa, 46 aa, 47 aa, 48 aa, 49 aa, or 50 aa). In some cases, the T-cell epitope polypeptide has a length of 50 amino acids. In some cases, the T-cell epitope polypeptide is part of a fusion polypeptide, as described in detail below.

In some cases, a TP50-C T-cell epitope polypeptide suitable for inclusion in a composition of the present disclosure comprises the following amino acid sequence: GVYVLPRRGPRLGVRATRKTSERSQPR-GRRQPIPKARRSEGRSWAQPGYP (SEQ ID NO:153); where the T-cell epitope polypeptide has a length of from 40 amino acids to 50 amino acids (e.g., the T-cell epitope polypeptide has a length of 40 amino acids (aa), 41 aa, 42 aa, 43 aa, 44 aa, 45 aa, 46 aa, 47 aa, 48 aa, 49 aa, or 50 aa). In some cases, the T-cell epitope polypeptide has a length of 50 amino acids. In some cases, the T-cell epitope polypeptide is part of a fusion polypeptide, as described in detail below.

In some cases, a TP50-C T-cell epitope polypeptide suitable for inclusion in a composition of the present disclosure comprises the following amino acid sequence: GVYLLPRRGPRLGVRATRKTSERSQPR-GRRQPIPKARRPTGRSWGQPGYP (SEQ ID NO:154); where the T-cell epitope polypeptide has a length of from 40 amino acids to 50 amino acids (e.g., the T-cell epitope polypeptide has a length of 40 amino acids (aa), 41 aa, 42 aa, 43 aa, 44 aa, 45 aa, 46 aa, 47 aa, 48 aa, 49 aa, or 50 aa). In some cases, the T-cell epitope polypeptide has a length of 50 amino acids. In some cases, the T-cell epitope polypeptide is part of a fusion polypeptide, as described in detail below.

In some cases, a TP50-C T-cell epitope polypeptide suitable for inclusion in a composition of the present disclosure comprises the following amino acid sequence: GVYLLPRRGPRLGVRATRKTSERSQPR-GRRQPIPKARQPTGRHWAQPGYP (SEQ ID NO:155); where the T-cell epitope polypeptide has a length of from 40 amino acids to 50 amino acids (e.g., the T-cell epitope polypeptide has a length of 40 amino acids (aa), 41 aa, 42 aa, 43 aa, 44 aa, 45 aa, 46 aa, 47 aa, 48 aa, 49 aa, or 50 aa). In some cases, the T-cell epitope polypeptide has a length of 50 amino acids. In some cases, the T-cell epitope polypeptide is part of a fusion polypeptide, as described in detail below.

In some cases, a TP50-C T-cell epitope polypeptide suitable for inclusion in a composition of the present disclosure comprises the following amino acid sequence: GVYLLPRRGPRLGVRTTRKSSERSQPRGRRQRIP-KAASSQGKAWGKPGYP (SEQ ID NO:156); where the T-cell epitope polypeptide has a length of from 40 amino acids to 50 amino acids (e.g., the T-cell epitope polypeptide has a length of 40 amino acids (aa), 41 aa, 42 aa, 43 aa, 44 aa, 45 aa, 46 aa, 47 aa, 48 aa, 49 aa, or 50 aa). In some cases, the T-cell epitope polypeptide has a length of 50 amino acids. In some cases, the T-cell epitope polypeptide is part of a fusion polypeptide, as described in detail below.

A TP50-C T-cell epitope polypeptide suitable for inclusion in a composition of the present disclosure can include one or more CD4 epitopes, e.g., one or more of: i) a stretch of about 25 contiguous amino acids having the amino acid sequence: RRGPRLGVRATRKTSERSQPRGRRQ (SEQ ID NO:157) or RRGPRLGVRGTRKSSERSQPRGRRQ (SEQ ID NO:158); ii) a stretch of about 24 contiguous amino acids having the amino acid sequence: RATRKTSERSQPRGRRQPIPKARR (SEQ ID NO:159), or RGTRKSSERSQPRGRRQRIPKAAQ (SEQ ID NO:160), or RATRKTSERSQPRGRRQPIPKARQ (SEQ ID NO:161), or RATRKTSERSQPRGRRQPIPKDRR (SEQ ID NO:162); or iii) a stretch of about 20 contiguous amino acids having the amino acid sequence: RRQPIPKARRSEGRSWAQPG (SEQ ID NO:163), or RRQPIPKARPSEGRTWAQPG (SEQ ID NO:164), or RRQPIPKARRPEGRAWAQPG (SEQ ID NO:165), or RRQPIPKDRRSTGKSWGKPG (SEQ ID NO:166), or RRQPIPKDRRSTGKSWGKPG (SEQ ID NO:167), or RRQPIPKARRPTGRSWGQPG (SEQ ID NO:168), or RRQPIPKARQPTGRHWAQPG (SEQ ID NO:169), or RRQRIPKAASSQGKAWGKPG (SEQ ID NO:170).

In some cases, a T-cell epitope polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: GVYLLPRRGPRLGVRATRKTSERSQPRGRRQPIPKARRSEGRSWAQPGYP (SEQ ID NO:148); and has a length of from 50 amino acids to about 60 amino acids.

In some cases, a T-cell epitope polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: GVYLLPRRGPRLGVRATRKTSERSQPRGRRQPIPKARRSEGRSWAQPGYP (SEQ ID NO:148); and has a length of 50 amino acids. In some cases, a T-cell epitope polypeptide suitable for inclusion in a composition of the present disclosure comprises the amino acid sequence GVYLLPRRGPRLGVRATRKTSERSQPRGRRQPIPKARRSEGRSWAQPGYP (SEQ ID NO:148); and has a length of 50 amino acids.

TP23

In some cases, a T-cell epitope polypeptide suitable for inclusion in a composition of the present disclosure comprises an amino acid sequence having at least 20% (e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, or 100%) amino acid sequence identity to the following amino acid sequence: DVVVVATDALMTGFTGDFDSVID (SEQ ID NO:186; also referred to herein as "TP23"); where the T-cell epitope polypeptide has a length of from 18 amino acids to 23 amino acids (e.g., T-cell epitope polypeptide has a length of 18 amino acids (aa), 19 aa, 20 aa, 21 aa, 22 aa, or 23 aa). In some cases, the TP23 T-cell epitope polypeptide has a length of 23 amino acids. In some cases, the T-cell epitope polypeptide is part of a fusion polypeptide, as described in detail below.

In some cases, a TP23 T-cell epitope polypeptide suitable for inclusion in a composition of the present disclosure comprises the following amino acid sequence: DVVV$X_1X_2$TDALMTG$X_3$TGDFDSVID (SEQ ID NO:171), where $X_1$ is V or C; $X_2$ is A or S; and $X_3$ is F or Y; where the TP23 T-cell epitope polypeptide has a length of from 18 amino acids to 23 amino acids (e.g., T-cell epitope polypeptide has a length of 18 amino acids (aa), 19 aa, 20 aa, 21 aa, 22 aa, or 23 aa). In some cases, the TP23 T-cell epitope polypeptide has a length of 23 amino acids. In some cases, the TP23 T-cell epitope polypeptide is part of a fusion polypeptide, as described in detail below.

In some cases, a TP23 T-cell epitope polypeptide suitable for inclusion in a composition of the present disclosure comprises the following amino acid sequence: DVVVVATDALMTGYTGDFDSVID (SEQ ID NO:172); where the TP23 T-cell epitope polypeptide has a length of from 18 amino acids to 23 amino acids (e.g., T-cell epitope polypeptide has a length of 18 amino acids (aa), 19 aa, 20 aa, 21 aa, 22 aa, or 23 aa). In some cases, the TP23 T-cell epitope polypeptide has a length of 23 amino acids. In some cases, the TP23 T-cell epitope polypeptide is part of a fusion polypeptide, as described in detail below.

In some cases, a TP23 T-cell epitope polypeptide suitable for inclusion in a composition of the present disclosure comprises the following amino acid sequence: DVVVCATDALMTGFTGDFDSVID (SEQ ID NO:173); where the TP23 T-cell epitope polypeptide has a length of from 18 amino acids to 23 amino acids (e.g., T-cell epitope polypeptide has a length of 18 amino acids (aa), 19 aa, 20 aa, 21 aa, 22 aa, or 23 aa). In some cases, the TP23 T-cell epitope polypeptide has a length of 23 amino acids. In some cases, the TP23 T-cell epitope polypeptide is part of a fusion polypeptide, as described in detail below.

In some cases, a TP23 T-cell epitope polypeptide suitable for inclusion in a composition of the present disclosure comprises the following amino acid sequence: DVVVCSTDALMTGFTGDFDSVID (SEQ ID NO:174); where the TP23 T-cell epitope polypeptide has a length of from 18 amino acids to 23 amino acids (e.g., T-cell epitope polypeptide has a length of 18 amino acids (aa), 19 aa, 20 aa, 21 aa, 22 aa, or 23 aa). In some cases, the TP23 T-cell epitope polypeptide has a length of 23 amino acids. In some cases, the TP23 T-cell epitope polypeptide is part of a fusion polypeptide, as described in detail below.

In some cases, a TP23 T-cell epitope polypeptide suitable for inclusion in a composition of the present disclosure comprises the following amino acid sequence: DVVVCATDALMTGYTGDFDSVID (SEQ ID NO:175); where the TP23 T-cell epitope polypeptide has a length of from 18 amino acids to 23 amino acids (e.g., T-cell epitope polypeptide has a length of 18 amino acids (aa), 19 aa, 20 aa, 21 aa, 22 aa, or 23 aa). In some cases, the TP23 T-cell epitope polypeptide has a length of 23 amino acids. In some cases, the TP23 T-cell epitope polypeptide is part of a fusion polypeptide, as described in detail below.

A TP23 T-cell epitope polypeptide suitable for inclusion in a composition of the present disclosure can include one or more CD8 epitopes, e.g., one or both of: i) a stretch of about 9 contiguous amino acids having the amino acid sequence: ATDALMTGF (SEQ ID NO:176), or STDALMTGF (SEQ ID NO:177), or ATDALMTGY (SEQ ID NO:178); or ii) a stretch of about 9 contiguous amino acids having the amino acid sequence GFTGDFDSV (SEQ ID NO:179), or GYTGDFDSV (SEQ ID NO:180).

A TP23 T-cell epitope polypeptide suitable for inclusion in a composition of the present disclosure can include one or more CD4 epitopes, e.g., a stretch of about 15 contiguous amino acids having the amino acid sequence: ATDALMTGFTGDFDS (SEQ ID NO:181), or STDALMTGFTGDFDS (SEQ ID NO:182), or ATDALMTGYTGDFDS (SEQ ID NO:183), or ALMTGFTGDFDSVID (SEQ ID NO:184), or ALMTGYTGDFDSVID (SEQ ID NO:185).

In some cases, a TP23 T-cell epitope polypeptide suitable for inclusion in a composition of the present disclosure includes: a) one or more CD8 epitopes, e.g., one or both of: i) a stretch of about 9 contiguous amino acids having the amino acid sequence: ATDALMTGF (SEQ ID NO:176), or STDALMTGF (SEQ ID NO:177), or ATDALMTGY (SEQ ID NO:178); or ii) a stretch of about 9 contiguous amino acids having the amino acid sequence GFTGDFDSV (SEQ ID NO:179), or GYTGDFDSV (SEQ ID NO:180); and b) one or more CD4 epitopes, e.g., a stretch of about 15 contiguous amino acids having the amino acid sequence: ATDALMTGFTGDFDS (SEQ ID NO:181), or STDALMTGFTGDFDS (SEQ ID NO:182), or ATDALMTGYTGDFDS (SEQ ID NO:183), or ALMTGFTGDFDSVID (SEQ ID NO:184), or ALMTGYTGDFDSVID (SEQ ID NO:185).

In some cases, an immunogenic composition of the present disclosure includes only a T-cell epitope polypeptide comprising an amino acid sequence having at least 20% (e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, or 100%) amino acid sequence identity to the following amino acid sequence: DVVV-VATDALMTGFTGDFDSVID (SEQ ID NO:186; "TP23"); where the T-cell epitope polypeptide has a length of from 23 amino acids to 30 amino acids (e.g., T-cell epitope polypeptide has a length of 23 amino acids (aa), 24 aa, 25 aa, 26 aa, 27 aa, 28 aa, 29 aa, or 30 aa).

In some cases, a T-cell epitope polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: DVVVVATDALMTGFTGDFDSVID (SEQ ID NO:186); and has a length of 23 amino acids. In some cases, a T-cell epitope polypeptide suitable for inclusion in a composition of the present disclosure comprises the amino acid sequence DVVVVATDALMTGFTGDFDSVID (SEQ ID NO:186); and has a length of 23 amino acids.

TP27

In some cases, a T-cell epitope polypeptide suitable for inclusion in a composition of the present disclosure comprises an amino acid sequence having at least 20% (e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, or 100%) amino acid sequence identity to the following amino acid sequence: LEQIKGGRHLIFCHSKKKCDE-LAAKLT (SEQ ID NO:188; also referred to herein as "TP27"); where the T-cell epitope polypeptide has a length of from 22 amino acids to 27 amino acids (e.g., T-cell epitope polypeptide has a length of 22 amino acids (aa), 23 aa, 24 aa, 25 aa, 26 aa, or 27 aa). In some cases, the T-cell epitope polypeptide is part of a fusion polypeptide, as described in detail below.

In some cases, a TP27 T-cell epitope polypeptide suitable for inclusion in a composition of the present disclosure comprises the following amino acid sequence: $X_1X_2X_3X_4$KGGRHLIFCHSKKKCDEX$_5$AX$_6$X$_7$LX$_8$ (SEQ ID NO:189), where $X_1$ is L or I; $X_2$ is E, A, S, V, or Q; $X_3$ is Q, T, Y, F, or L; $X_4$ is I or L; $X_5$ is L or I; $X_6$ is A, K, or S; $X_7$ is K, Q, or A; and $X_8$ is T, R, or S; where the T-cell epitope polypeptide has a length of from 22 amino acids to 27 amino acids (e.g., T-cell epitope polypeptide has a length of 22 amino acids (aa), 23 aa, 24 aa, 25 aa, 26 aa, or 27 aa). In some cases, the T-cell epitope polypeptide has a length of 27 amino acids. In some cases, the T-cell epitope polypeptide is part of a fusion polypeptide, as described in detail below.

In some cases, a TP27 T-cell epitope polypeptide suitable for inclusion in a composition of the present disclosure comprises the following amino acid sequence: LEVIKG-GRHLIFCHSKKKCDELAAKLV (SEQ ID NO:190); where the T-cell epitope polypeptide has a length of from 22 amino acids to 27 amino acids (e.g., T-cell epitope polypeptide has a length of 22 amino acids (aa), 23 aa, 24 aa, 25 aa, 26 aa, or 27 aa). In some cases, the T-cell epitope polypeptide has a length of 27 amino acids. In some cases, the T-cell epitope polypeptide is part of a fusion polypeptide, as described in detail below.

In some cases, a TP27 T-cell epitope polypeptide suitable for inclusion in a composition of the present disclosure comprises the following amino acid sequence: IETIKG-GRHLIFCHSKKKCDELAAKLS (SEQ ID NO:191); where the T-cell epitope polypeptide has a length of from 22 amino acids to 27 amino acids (e.g., T-cell epitope polypeptide has a length of 22 amino acids (aa), 23 aa, 24 aa, 25 aa, 26 aa, or 27 aa). In some cases, the T-cell epitope polypeptide has a length of 27 amino acids. In some cases, the T-cell epitope polypeptide is part of a fusion polypeptide, as described in detail below.

In some cases, a TP27 T-cell epitope polypeptide suitable for inclusion in a composition of the present disclosure comprises the following amino acid sequence: LSYIKG-GRHLIFCHSKKKCDELAAALR (SEQ ID NO:192); where the T-cell epitope polypeptide has a length of from 22 amino acids to 27 amino acids (e.g., T-cell epitope polypeptide has a length of 22 amino acids (aa), 23 aa, 24 aa, 25 aa, 26 aa, or 27 aa). In some cases, the T-cell epitope polypeptide has a length of 27 amino acids. In some cases, the T-cell epitope polypeptide is part of a fusion polypeptide, as described in detail below.

In some cases, a TP27 T-cell epitope polypeptide suitable for inclusion in a composition of the present disclosure comprises the following amino acid sequence: LAFIKG-GRHLIFCHSKKKCDELAALR (SEQ ID NO:193); where the T-cell epitope polypeptide has a length of from 22 amino acids to 27 amino acids (e.g., T-cell epitope polypeptide has a length of 22 amino acids (aa), 23 aa, 24 aa, 25 aa, 26 aa, or 27 aa). In some cases, the T-cell epitope polypeptide has a length of 27 amino acids. In some cases, the T-cell epitope polypeptide is part of a fusion polypeptide, as described in detail below.

In some cases, a TP27 T-cell epitope polypeptide suitable for inclusion in a composition of the present disclosure comprises the following amino acid sequence: IAQLKG- GRHLIFCHSKKKCDEIASKLR (SEQ ID NO:195); where the T-cell epitope polypeptide has a length of from 22 amino acids to 27 amino acids (e.g., T-cell epitope polypeptide has a length of 22 amino acids (aa), 23 aa, 24 aa, 25 aa, 26 aa, or 27 aa). In some cases, the T-cell epitope polypeptide has a length of 27 amino acids. In some cases, the T-cell epitope polypeptide is part of a fusion polypeptide, as described in detail below.

In some cases, a TP27 T-cell epitope polypeptide suitable for inclusion in a composition of the present disclosure comprises the following amino acid sequence: LELIKG-GRHLIFCHSKKKCDELAQLT (SEQ ID NO:196); where the T-cell epitope polypeptide has a length of from 22 amino acids to 27 amino acids (e.g., T-cell epitope polypeptide has a length of 22 amino acids (aa), 23 aa, 24 aa, 25 aa, 26 aa, or 27 aa). In some cases, the T-cell epitope polypeptide has a length of 27 amino acids. In some cases, the T-cell epitope polypeptide is part of a fusion polypeptide, as described in detail below.

In some cases, a TP27 T-cell epitope polypeptide suitable for inclusion in a composition of the present disclosure comprises the following amino acid sequence: LXLIKG-GRHLIFCHSKKKCDELAKQLT (SEQ ID NO:197); where the T-cell epitope polypeptide has a length of from 22 amino acids to 27 amino acids (e.g., T-cell epitope polypeptide has a length of 22 amino acids (aa), 23 aa, 24 aa, 25 aa, 26 aa, or 27 aa). In some cases, the T-cell epitope polypeptide has a length of 27 amino acids. In some cases, the T-cell epitope polypeptide is part of a fusion polypeptide, as described in detail below.

In some cases, a TP27 T-cell epitope polypeptide suitable for inclusion in a composition of the present disclosure comprises the following amino acid sequence: LEYIKG-GRHLIFCHSKKKCDELAKQLT (SEQ ID NO:198); where the T-cell epitope polypeptide has a length of from 22 amino acids to 27 amino acids (e.g., T-cell epitope polypeptide has a length of 22 amino acids (aa), 23 aa, 24 aa, 25 aa, 26 aa, or 27 aa). In some cases, the T-cell epitope polypeptide has a length of 27 amino acids. In some cases, the T-cell epitope polypeptide is part of a fusion polypeptide, as described in detail below.

In some cases, a TP27 T-cell epitope polypeptide suitable for inclusion in a composition of the present disclosure comprises the following amino acid sequence: LQHIKG-GRHLIFCHSKKKCDELAGKLT (SEQ ID NO:199); where the T-cell epitope polypeptide has a length of from 22 amino acids to 27 amino acids (e.g., T-cell epitope polypeptide has a length of 22 amino acids (aa), 23 aa, 24 aa, 25 aa, 26 aa, or 27 aa). In some cases, the T-cell epitope polypeptide has a length of 27 amino acids. In some cases, the T-cell epitope polypeptide is part of a fusion polypeptide, as described in detail below.

A TP27 T-cell epitope polypeptide suitable for inclusion in a composition of the present disclosure can include one or more CD8 epitopes, e.g., one or both of: i) a stretch of about 9 contiguous amino acids having the amino acid sequence: LIFCHSKKK (SEQ ID NO:200); and ii) a stretch of about 9 contiguous amino acids having the amino acid sequence: HSKKKCDEL (SEQ ID NO:201). In some cases, a TP27 T-cell epitope polypeptide suitable for inclusion in a composition of the present disclosure includes the following CD8 epitopes: i) a stretch of about 9 contiguous amino acids having the amino acid sequence: LIFCHSKKK (SEQ ID NO:200); and ii) a stretch of about 9 contiguous amino acids having the amino acid sequence: HSKKKCDEL (SEQ ID NO:201).

A TP27 T-cell epitope polypeptide suitable for inclusion in a composition of the present disclosure can include one or more CD4 epitopes, e.g., a stretch of about 15 contiguous amino acids having the amino acid sequence: KGGRHLIFCHSKKKCD (SEQ ID NO:202), or a stretch of about 11 contiguous amino acids having the amino acid sequence: GRHLIFCHSKK (SEQ ID NO:244).

A TP27 T-cell epitope polypeptide suitable for inclusion in a composition of the present disclosure can include: a) the following CD8 epitopes: i) a stretch of about 9 contiguous amino acids having the amino acid sequence: LIFCHSKKK (SEQ ID NO:200); and ii) a stretch of about 9 contiguous amino acids having the amino acid sequence: HSKKKCDEL (SEQ ID NO:201); and b) the following CD4 epitope: a stretch of about 11 contiguous amino acids having the amino acid sequence: GRHLIFCHSKK (SEQ ID NO:244). A TP27 T-cell epitope polypeptide suitable for inclusion in a composition of the present disclosure can include: a) the following CD8 epitopes: i) a stretch of about 9 contiguous amino acids having the amino acid sequence: LIFCHSKKK (SEQ ID NO:200); and ii) a stretch of about 9 contiguous amino acids having the amino acid sequence: HSKKKCDEL (SEQ ID NO:201); and b) the following CD4 epitope: a stretch of about 15 contiguous amino acids having the amino acid sequence: KGGRHLIFCHSKKKCD (SEQ ID NO:202).

In some cases, an immunogenic composition of the present disclosure includes only a T-cell epitope polypeptide comprising an amino acid sequence having at least 20% (e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, or 100%) amino acid sequence identity to the following amino acid sequence: LEQIKGGRHLIFCHSKKKCDE-LAAKLT (SEQ ID NO:188; "TP27"); where the T-cell epitope polypeptide has a length of from 27 amino acids to 34 amino acids (e.g., T-cell epitope polypeptide has a length of 27 amino acids (aa), 28 aa, 29 aa, 30 aa, 31 aa, 32 aa, 33 aa, or 34 aa).

In some cases, a T-cell epitope polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: LEQIKGGRHLIFCHSKKKCDELAAKLT (SEQ ID NO:188); and has a length of 27 amino acids. In some cases, a T-cell epitope polypeptide suitable for inclusion in a composition of the present disclosure comprises the amino acid sequence LEQIKGGRHLIFCHSKKKCDE-LAAKLT (SEQ ID NO:188); and has a length of 27 amino acids.

TP35-NS4

In some cases, a T-cell epitope polypeptide suitable for inclusion in a composition of the present disclosure comprises an amino acid sequence having at least 20% (e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, or 100%) amino acid sequence identity to the following amino acid sequence: ILRRHVGPGEGAVQWMNRLIA-FASRGNHVSPTHYV (SEQ ID NO:203; also referred to herein as "TP35-NS4"); where the T-cell epitope polypeptide has a length of from 28 amino acids to 35 amino acids (e.g., the T-cell epitope polypeptide has a length of 28 amino acids (aa), 29 aa, 30 aa, 31 aa, 32 aa, 33 aa, 34 aa, or 35 aa). In some cases, the T-cell epitope polypeptide is part of a fusion polypeptide, as described in detail below.

In some cases, a TP35-NS4 T-cell epitope polypeptide suitable for inclusion in a composition of the present disclosure comprises the following amino acid sequence: $X_1X_2X_3RHX_4GX_5X_6EGX_7X_8QWMNRLIAFAS$ $RGNHVX_9PTHYX_{10}$ (SEQ ID NO:204), where $X_1$ is I or V; $X_2$ is L or I; $X_3$ is R or K; $X_4$ is V, I, or T; $X_5$ is P, Q, or T; $X_6$ is G, A, or S; $X_7$ is A or V; $X_8$ is V or T; $X_9$ is S or A; and $X_{10}$ is V or I; where the TP35-NS4 T-cell epitope polypeptide has a length of from 28 amino acids to 35 amino acids (e.g., the T-cell epitope polypeptide has a length of 28 amino acids (aa), 29 aa, 30 aa, 31 aa, 32 aa, 33 aa, 34 aa, or 35 aa). In some cases, the TP35-NS4 T-cell epitope polypeptide has a length of 35 amino acids. In some cases, the T-cell epitope polypeptide is part of a fusion polypeptide, as described in detail below.

In some cases, a TP35-NS4 T-cell epitope polypeptide suitable for inclusion in a composition of the present disclosure comprises the following amino acid sequence: $X_1X_2X_3RHX_4GX_5X_6EGX_7X_8QWMNRLIAFASRGN$ $HVX_9PTHYX_{10}$ (SEQ ID NO:204), where $X_1$ is I or V; $X_2$ is L; $X_3$ is R; $X_4$ is V or I; $X_5$ is P or Q; $X_6$ is G or A; $X_7$ is A; $X_8$ is V or T; $X_9$ is S or A; and $X_{10}$ is V; where the TP35-NS4 T-cell epitope polypeptide has a length of from 28 amino acids to 35 amino acids (e.g., the T-cell epitope polypeptide has a length of 28 amino acids (aa), 29 aa, 30 aa, 31 aa, 32 aa, 33 aa, 34 aa, or 35 aa). In some cases, the TP35-NS4 T-cell epitope polypeptide has a length of 35 amino acids. In some cases, the T-cell epitope polypeptide is part of a fusion polypeptide, as described in detail below.

In some cases, a TP35-NS4 T-cell epitope polypeptide suitable for inclusion in a composition of the present disclosure comprises the following amino acid sequence: ILR-RHVGPGEGAVQWMNRLIAFASRGNHVAPTHYV (SEQ ID NO:205); where the TP35-NS4 T-cell epitope polypeptide has a length of from 28 amino acids to 35 amino acids (e.g., the T-cell epitope polypeptide has a length of 28 amino acids (aa), 29 aa, 30 aa, 31 aa, 32 aa, 33 aa, 34 aa, or 35 aa). In some cases, the TP35-NS4 T-cell epitope polypeptide has a length of 35 amino acids. In some cases, the T-cell epitope polypeptide is part of a fusion polypeptide, as described in detail below.

In some cases, a TP35-NS4 T-cell epitope polypeptide suitable for inclusion in a composition of the present disclosure comprises the following amino acid sequence: ILR-RHVGQGEGAVQWMNRLIAFASRGNHVAPTHYV (SEQ ID NO:206); where the TP35-NS4 T-cell epitope polypeptide has a length of from 28 amino acids to 35 amino acids (e.g., the T-cell epitope polypeptide has a length of 28 amino acids (aa), 29 aa, 30 aa, 31 aa, 32 aa, 33 aa, 34 aa, or 35 aa). In some cases, the TP35-NS4 T-cell epitope polypeptide has a length of 35 amino acids. In some cases, the T-cell epitope polypeptide is part of a fusion polypeptide, as described in detail below.

In some cases, a TP35-NS4 T-cell epitope polypeptide suitable for inclusion in a composition of the present disclosure comprises the following amino acid sequence: VLR-RHIGPGEGAVQWMNRLIAFASRGNHVSPTHYV (SEQ ID NO:207); where the TP35-NS4 T-cell epitope polypeptide has a length of from 28 amino acids to 35 amino acids (e.g., the T-cell epitope polypeptide has a length of 28 amino acids (aa), 29 aa, 30 aa, 31 aa, 32 aa, 33 aa, 34 aa, or 35 aa). In some cases, the TP35-NS4 T-cell epitope polypeptide has a length of 35 amino acids. In some cases, the T-cell epitope polypeptide is part of a fusion polypeptide, as described in detail below.

In some cases, a TP35-NS4 T-cell epitope polypeptide suitable for inclusion in a composition of the present disclosure comprises the following amino acid sequence: ILR-RHVGPAEGATQWMNRLIAFASRGNHVSPTHYV (SEQ ID NO:208); where the TP35-NS4 T-cell epitope polypeptide has a length of from 28 amino acids to 35 amino acids (e.g., the T-cell epitope polypeptide has a length of 28 amino acids (aa), 29 aa, 30 aa, 31 aa, 32 aa, 33 aa, 34 aa, or 35 aa). In some cases, the TP35-NS4 T-cell epitope polypeptide has a length of 35 amino acids. In some cases, the T-cell epitope polypeptide is part of a fusion polypeptide, as described in detail below.

In some cases, a TP35-NS4 T-cell epitope polypeptide suitable for inclusion in a composition of the present disclosure comprises the following amino acid sequence: IIKRHTGTSEGVTQWMNRLIAFASRGNHVSPTHYI (SEQ ID NO:209); where the TP35-NS4 T-cell epitope polypeptide has a length of from 28 amino acids to 35 amino acids (e.g., the T-cell epitope polypeptide has a length of 28 amino acids (aa), 29 aa, 30 aa, 31 aa, 32 aa, 33 aa, 34 aa, or 35 aa). In some cases, the TP35-NS4 T-cell epitope polypeptide has a length of 35 amino acids. In some cases, the T-cell epitope polypeptide is part of a fusion polypeptide, as described in detail below.

A TP35-NS4 T-cell epitope polypeptide suitable for inclusion in a composition of the present disclosure can include one or more CD8 epitopes, e.g., a stretch of about 16 contiguous amino acids having the amino acid sequence: EGAVQWMNRLIAFASR (SEQ ID NO:210), or EGATQWMNRLIAFASR (SEQ ID NO:211), or EGVTQWMNRLIAFASR (SEQ ID NO:212); or a stretch of about 9 contiguous amino acids having the amino acid sequence: WMNRLIAFA (SEQ ID NO:213).

A TP35-NS4 T-cell epitope polypeptide suitable for inclusion in a composition of the present disclosure can include one or more CD4 epitopes, e.g., a stretch of about 15 contiguous amino acids having the amino acid sequence: RHVGPGEGAVQWMNR (SEQ ID NO:214), or RHVGQGEGAVQWMNR (SEQ ID NO:215), or RHIGPGEGAVQWMNR (SEQ ID NO:216), or RHVG-PAEGATQWMNR (SEQ ID NO:217), or RHTGT-SEGVTQWMNR (SEQ ID NO:218); or a stretch of about 20 contiguous amino acids having the amino acid sequence: HVGPGEGAVQWMNRLIAFAS (SEQ ID NO:219), or HVGQGEGAVQWMNRLIAFAS (SEQ ID NO:220), or HIGPGEGAVQWMNRLIAFAS (SEQ ID NO:221), or HVGPAEGATQWMNRLIAFAS (SEQ ID NO:222), or HTGTSEGVTQWMNRLIAFAS (SEQ ID NO:223); or a stretch of about 20 contiguous amino acids having the amino acid sequence: GAVQWMNRLIAFASRGNHVS (SEQ ID NO:224), or GAVQWMNRLIAFASRGNHVA (SEQ ID NO:225), or GATQWMNRLIAFASRGNHVS (SEQ ID NO:226), or GVTQWMNRLIAFASRGNHVS (SEQ ID NO:227).

In some cases, TP35-NS4 T-cell epitope polypeptide suitable for inclusion in a composition of the present disclosure includes: a) one or more CD8 epitopes, e.g., a stretch of about 16 contiguous amino acids having the amino acid sequence: EGAVQWMNRLIAFASR (SEQ ID NO:210), or EGATQWMNRLIAFASR (SEQ ID NO:211), or EGVTQWMNRLIAFASR (SEQ ID NO:212); or a stretch of about 9 contiguous amino acids having the amino acid sequence: WMNRLIAFA (SEQ ID NO:213); and b) one or more CD4 epitopes, e.g., a stretch of about 15 contiguous amino acids having the amino acid sequence: RHVGPGEGAVQWMNR (SEQ ID NO:214), or RHVGQGEGAVQWMNR (SEQ ID NO:215), or RHIGPGEGAVQWMNR (SEQ ID NO:216), or RHVGPAEGATQWMNR (SEQ ID NO:217), or RHTGTSEGVTQWMNR (SEQ ID NO:218); or a stretch of about 20 contiguous amino acids having the amino acid sequence: HVGPGEGAVQWMNRLIAFAS (SEQ ID NO:219), or HVGQGEGAVQWMNRLIAFAS (SEQ ID NO:220), or HIGPGEGAVQWMNRLIAFAS (SEQ ID NO:221), or HVGPAEGATQWMNRLIAFAS (SEQ ID NO:222), or HTGTSEGVTQWMNRLIAFAS (SEQ ID NO:223); or a stretch of about 20 contiguous amino acids having amino acid sequence: GAVQWMNRLIAFASRGNHVS (SEQ ID NO:224), or GAVQWMNRLIAFASRGNHVA (SEQ ID NO:225), or GATQWMNRLIAFASRGNHVS (SEQ ID NO:226), or GVTQWMNRLIAFASRGNHVS (SEQ ID NO:227).

In some cases, a T-cell epitope polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: ILRRHVGPGEGAVQWMNRLIAFASRGNHVSPTHYV (SEQ ID NO:203); and has a length of from 35 amino acids to 40 amino acids (e.g., 35 amino acids (aa), 36 aa, 37 aa, 38 aa, 39 aa, or 40 aa).

In some cases, a T-cell epitope polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: ILRRHVGPGEGAVQWMNRLIAFASRGNHVSPTHYV (SEQ ID NO:203); and has a length of 35 amino acids. In some cases, a T-cell epitope polypeptide suitable for inclusion in a composition of the present disclosure comprises the amino acid sequence ILRRHVGPGEGAVQWMNRLIAFASRGNHVSPTHYV (SEQ ID NO:203); and has a length of 35 amino acids.

TP42

In some cases, a T-cell epitope polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: GTEGEIPFYGKAIPLEQIKGGRHLIFCHSKKKCDELAAKLTG (SEQ ID NO:228); and has a length of from 33 amino acids to about 50 amino acids (e.g., 33 amino acids (aa), 34 aa, 35 aa, 36 aa, 37 aa, 38 aa, 39 aa, 40 aa, 41 aa, 42 aa, or from 42 aa to 50 aa). In some cases, a T-cell epitope polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: GTEGEIPFYGKAIPLEQIKGGRHLIFCHSKKKCDELAAKLTG (SEQ ID NO:228); and has a length of 42 amino acids. In some cases, a T-cell epitope polypeptide suitable for inclusion in a composition of the present disclosure comprises the amino acid sequence GTEGEIPFYGKAIPLEQIKGGRHLIFCHSKKKCDELAAKLTG (SEQ ID NO:228); and has a length of 42 amino acids.

In some cases, a TP42 T-cell epitope polypeptide suitable for inclusion in a composition of the present disclosure comprises the following amino acid sequence: $X_1X_2X_3$GEIPFYG$X_4$AIP$X_5X_6X_7X_8$KGGRHLIFCHSKKKCDEX$_9$A$X_{10}X_{11}$L$X_{12}X_{13}$(K)n (SEQ ID NO:229), where $X_1$ is G, P, or S; $X_2$ is T, N, Q, H, or S; $X_3$ is E, T, or D; $X_4$ is K or R; $X_5$ is L or I; $X_6$ is E, A, S, or Q; $X_7$ is Q, T, Y, F, or L; $X_8$ is I or L; $X_9$ is L or I; $X_{10}$ is A, K, or S; $X_{11}$ is K, Q, or A; $X_{12}$ is T, R, or S; and $X_{13}$ is G or S, wherein n is an integer from 2 to 10, and where the TP42 T-cell epitope polypeptide has a length of from 34 amino acids to 52 amino acids (e.g., 34 amino acids (aa), 35 aa, 36 aa, 37 aa, 38 aa, 39 aa, 40 aa, 41 aa, 42 aa, 43 aa, 44 aa, 45 aa, 46 aa, 47 aa, 48 aa, 49 aa, 50 aa, 51 aa, or 52 aa. In some cases, a TP42 T-cell epitope polypeptide suitable for inclusion in a composition of the present disclosure comprises the following amino acid sequence: $X_1X_2X_3$GEIPFYG$X_4$AIP$X_5X_6X_7X_8$KGGRHLIFCHSKKKCDEX$_9$A$X_{10}X_{11}$L$X_{12}X_{13}$KKK (SEQ ID NO:230), where $X_1$ is G, P, or S; $X_2$ is T, N, Q, H, or S; $X_3$ is E, T, or D; $X_4$ is K or R; $X_5$ is L or I; $X_6$ is E, A, S, or Q; $X_7$ is Q, T, Y, F, or L; $X_8$ is I or L; $X_9$ is L or I; $X_{10}$ is A, K, or S; $X_{11}$ is K, Q, or A; $X_{12}$ is T, R, or S; and $X_{13}$ is G or S. In some cases, a TP42 T-cell epitope polypeptide suitable for inclusion in a composition of the present disclosure comprises the following amino acid sequence: $X_1X_2X_3$GEIPFYG$X_4$AIP$X_5X_6X_7X_8$KGGRHLIFCHSKKKCDEX$_9$A$X_{10}X_{11}$L$X_{12}X_{13}$(K)n (SEQ ID NO:229), where $X_1$ is G, P, or S; $X_2$ is T, N, Q, H, or S; $X_3$ is E, T, or D; $X_4$ is K or R; $X_5$ is L or I; $X_6$ is E, A, S, or Q; $X_7$ is Q, T, Y, F, V, or L; $X_8$ is I or L; $X_9$ is L or I; $X_{10}$ is A, K, or S; $X_{11}$ is K, Q, or A; $X_{12}$ is T, R, V, or S; and $X_{13}$ is G or S, wherein n is an integer from 2 to 10, and where the TP42 T-cell epitope polypeptide has a length of from 34 amino acids to 52 amino acids (e.g., 34 amino acids (aa), 35 aa, 36 aa, 37 aa, 38 aa, 39 aa, 40 aa, 41 aa, 42 aa, 43 aa, 44 aa, 45 aa, 46 aa, 47 aa, 48 aa, 49 aa, 50 aa, 51 aa, or 52 aa. In some cases, a TP42 T-cell epitope polypeptide suitable for inclusion in a composition of the present disclosure comprises the following amino acid sequence: $X_1X_2X_3$GEIPFYG$X_4$AIP$X_5X_6X_7X_8$KGGRHLIFCHSKKKCDEX$_9$A$X_{10}X_{11}$L$X_{12}X_{13}$KKK (SEQ ID NO:230), where $X_1$ is G, P, or S; $X_2$ is T, N, Q, H, or S; $X_3$ is E, T, or D; $X_4$ is K or R; $X_5$ is L or I; $X_6$ is E, A, S, or Q; $X_7$ is Q, T, Y, F, V, or L; $X_8$ is I or L; $X_9$ is L or I; $X_{10}$ is A, K, or S; $X_{11}$ is K, Q, or A; $X_{12}$ is T, R, V, or S; and $X_{13}$ is G or S. In some cases, the TP42 T-cell epitope polypeptide has a length of 45 amino acids. In some cases, the TP42 T-cell epitope polypeptide comprises the following amino acid sequence: GTEGEIPFYGKAIPLEQIKGGRHLIFCHSKKKCDELAAKLTGKKK (SEQ ID NO:231) and has a length of 45 amino acids.

In some cases, a TP42 T-cell epitope polypeptide suitable for inclusion in a composition of the present disclosure comprises the following amino acid sequence: $X_1X_2X_3$GEIPFYG$X_4$AIP$X_5X_6X_7X_8$KGGRHLIFC HSKKKCDEX$_9$AX$_{10}$X$_{11}$LX$_{12}$X$_{13}$ (SEQ ID NO:232), where X$_1$ is G, P, or S; X$_2$ is T, N, Q, H, or S; X$_3$ is E, T, or D; X$_4$ is K or R; X$_5$ is L or I; X$_6$ is E, A, S, or Q; X$_7$ is Q, T, Y, F, or L; X$_8$ is I or L; X$_9$ is L or I; X$_{10}$ is A, K, or S; X$_{11}$ is K, Q, or A; X$_{12}$ is T, R, or S; and X$_{13}$ is G or S; where the TP42 T-cell epitope polypeptide has a length of from 33 amino acids to 42 amino acids (e.g., 33 amino acids (aa), 34 aa, 35 aa, 36 aa, 37 aa, 38 aa, 39 aa, 40 aa, 41 aa, or 42 aa). In some cases, the TP42 T-cell epitope polypeptide has a length of 42 amino acids. In some cases, the T-cell epitope polypeptide has a length of 42 amino acids. In some cases, the T-cell epitope polypeptide is part of a fusion polypeptide, as described in detail below.

In some cases, a TP42 T-cell epitope polypeptide suitable for inclusion in a composition of the present disclosure comprises the following amino acid sequence: STT-GEIPFYGKAIPLEVIKGGRHLIFCHSKKKCDELAAK-LVA (SEQ ID NO:233); where the TP42 T-cell epitope polypeptide has a length of from 33 amino acids to 42 amino acids (e.g., 33 amino acids (aa), 34 aa, 35 aa, 36 aa, 37 aa, 38 aa, 39 aa, 40 aa, 41 aa, or 42 aa). In some cases, the TP42 T-cell epitope polypeptide has a length of 42 amino acids. In some cases, the T-cell epitope polypeptide has a length of 42 amino acids. In some cases, the T-cell epitope polypeptide is part of a fusion polypeptide, as described in detail below.

In some cases, a TP42 T-cell epitope polypeptide suitable for inclusion in a composition of the present disclosure comprises the following amino acid sequence: SNT-GEIPFYGKAIPIETIKGGRHLIFCHSKKKCDELAAK-LSG (SEQ ID NO:234); where the TP42 T-cell epitope polypeptide has a length of from 33 amino acids to 42 amino acids (e.g., 33 amino acids (aa), 34 aa, 35 aa, 36 aa, 37 aa, 38 aa, 39 aa, 40 aa, 41 aa, or 42 aa). In some cases, the TP42 T-cell epitope polypeptide has a length of 42 amino acids. In some cases, the T-cell epitope polypeptide has a length of 42 amino acids. In some cases, the T-cell epitope polypeptide is part of a fusion polypeptide, as described in detail below.

In some cases, a TP42 T-cell epitope polypeptide suitable for inclusion in a composition of the present disclosure comprises the following amino acid sequence: GQEGEIPFYGRAIPLSYIKGGRHLIFCHSKKKCDE-LAAALRG (SEQ ID NO:235); where the TP42 T-cell epitope polypeptide has a length of from 33 amino acids to 42 amino acids (e.g., 33 amino acids (aa), 34 aa, 35 aa, 36 aa, 37 aa, 38 aa, 39 aa, 40 aa, 41 aa, or 42 aa). In some cases, the TP42 T-cell epitope polypeptide has a length of 42 amino acids. In some cases, the T-cell epitope polypeptide has a length of 42 amino acids. In some cases, the T-cell epitope polypeptide is part of a fusion polypeptide, as described in detail below.

In some cases, a TP42 T-cell epitope polypeptide suitable for inclusion in a composition of the present disclosure comprises the following amino acid sequence: GHEGEIPFYGKAIPLAFIKGGRHLIFCHSKKKCDE-LAALRG (SEQ ID NO:236); where the TP42 T-cell epitope polypeptide has a length of from 33 amino acids to 42 amino acids (e.g., 33 amino acids (aa), 34 aa, 35 aa, 36 aa, 37 aa, 38 aa, 39 aa, 40 aa, 41 aa, or 42 aa). In some cases, the TP42 T-cell epitope polypeptide has a length of 42 amino acids. In some cases, the T-cell epitope polypeptide has a length of 42 amino acids. In some cases, the T-cell epitope polypeptide is part of a fusion polypeptide, as described in detail below.

In some cases, a TP42 T-cell epitope polypeptide suitable for inclusion in a composition of the present disclosure comprises the following amino acid sequence: GSEGEIPFYGKAIPIAQLKGGRHLIFCHSKKKCDE-IASKLRG (SEQ ID NO:237); where the TP42 T-cell epitope polypeptide has a length of from 33 amino acids to 42 amino acids (e.g., 33 amino acids (aa), 34 aa, 35 aa, 36 aa, 37 aa, 38 aa, 39 aa, 40 aa, 41 aa, or 42 aa). In some cases, the TP42 T-cell epitope polypeptide has a length of 42 amino acids. In some cases, the T-cell epitope polypeptide has a length of 42 amino acids. In some cases, the T-cell epitope polypeptide is part of a fusion polypeptide, as described in detail below.

In some cases, a TP42 T-cell epitope polypeptide suitable for inclusion in a composition of the present disclosure comprises the following amino acid sequence: PTT-GEIPFYGKAIPLELIKGGRHLIFCHSKKKCDELAQLTS (SEQ ID NO:238); where the TP42 T-cell epitope polypeptide has a length of from 33 amino acids to 42 amino acids (e.g., 33 amino acids (aa), 34 aa, 35 aa, 36 aa, 37 aa, 38 aa, 39 aa, 40 aa, 41 aa, or 42 aa). In some cases, the TP42 T-cell epitope polypeptide has a length of 42 amino acids. In some cases, the T-cell epitope polypeptide has a length of 42 amino acids. In some cases, the T-cell epitope polypeptide is part of a fusion polypeptide, as described in detail below.

In some cases, a TP42 T-cell epitope polypeptide suitable for inclusion in a composition of the present disclosure comprises the following amino acid sequence: PSEGEIPFYGRAIPLXLIKGGRHLIFCHS-KKKCDELAKQLTS (SEQ ID NO:239); where the TP42 T-cell epitope polypeptide has a length of from 33 amino acids to 42 amino acids (e.g., 33 amino acids (aa), 34 aa, 35 aa, 36 aa, 37 aa, 38 aa, 39 aa, 40 aa, 41 aa, or 42 aa). In some cases, the TP42 T-cell epitope polypeptide has a length of 42 amino acids. In some cases, the T-cell epitope polypeptide has a length of 42 amino acids. In some cases, the T-cell epitope polypeptide is part of a fusion polypeptide, as described in detail below.

In some cases, a TP42 T-cell epitope polypeptide suitable for inclusion in a composition of the present disclosure comprises the following amino acid sequence: PTT-GEIPFYGKAIPLEYIKGGRHLIFCHS-KKKCDELAKQLTS (SEQ ID NO:240); where the TP42 T-cell epitope polypeptide has a length of from 33 amino acids to 42 amino acids (e.g., 33 amino acids (aa), 34 aa, 35 aa, 36 aa, 37 aa, 38 aa, 39 aa, 40 aa, 41 aa, or 42 aa). In some cases, the TP42 T-cell epitope polypeptide has a length of 42 amino acids. In some cases, the T-cell epitope polypeptide has a length of 42 amino acids. In some cases, the T-cell epitope polypeptide is part of a fusion polypeptide, as described in detail below.

In some cases, a TP42 T-cell epitope polypeptide suitable for inclusion in a composition of the present disclosure comprises the following amino acid sequence: GNDGEIPFYGKAIPLQHIKGGRHLIFCHS-KKKCDELAGKLTS (SEQ ID NO:241); where the TP42 T-cell epitope polypeptide has a length of from 33 amino acids to 42 amino acids (e.g., 33 amino acids (aa), 34 aa, 35 aa, 36 aa, 37 aa, 38 aa, 39 aa, 40 aa, 41 aa, or 42 aa). In some cases, the TP42 T-cell epitope polypeptide has a length of 42 amino acids. In some cases, the T-cell epitope polypeptide has a length of 42 amino acids. In some cases, the T-cell epitope polypeptide is part of a fusion polypeptide, as described in detail below.

A TP42 T-cell epitope polypeptide suitable for inclusion in a composition of the present disclosure can include one or more CD8 epitopes, e.g., one or more of: i) a stretch of about 11 contiguous amino acids having the amino acid sequence: FYGX$_1$AIPX$_2$X$_3$X$_4$X$_5$(SEQ ID NO:242), where X$_1$ is K or R; X$_2$ is L or I; X$_3$ is E, S, A, Q, or V; X$_4$ is Q, T, Y, F, L, or H; and X$_5$ is I or L; ii) a stretch of about 9 contiguous amino acids having the amino acid sequence: LIFCHSKKK (SEQ ID NO:200); and iii) a stretch of about 9 contiguous amino acids having the amino acid sequence: HSKKKCDEL (SEQ ID NO:201). In some cases, a TP42 T-cell epitope polypeptide suitable for inclusion in a composition of the present disclosure includes the following CD8 epitopes: i) a stretch of about 11 contiguous amino acids having the amino acid sequence: FYGKAIPLEQI (SEQ ID NO:243); ii) ii) a stretch of about 9 contiguous amino acids having the amino acid sequence: LIFCHSKKK (SEQ ID NO:200); and iii) a stretch of about 9 contiguous amino acids having the amino acid sequence: HSKKKCDEL (SEQ ID NO:201).

A TP42 T-cell epitope polypeptide suitable for inclusion in a composition of the present disclosure can include one or more CD4 epitopes, e.g., a stretch of about 15 contiguous amino acids having the amino acid sequence: KGGRHLIFCHSKKKCD (SEQ ID NO:202), or a stretch of about 11 contiguous amino acids having the amino acid sequence: GRHLIFCHSKKK (SEQ ID NO:244).

A TP42 T-cell epitope polypeptide suitable for inclusion in a composition of the present disclosure can include: a) the following CD8 epitopes: i) a stretch of about 11 contiguous amino acids having the amino acid sequence: FYGKAIPLEQI (SEQ ID NO:243); ii) ii) a stretch of about 9 contiguous amino acids having the amino acid sequence: LIFCHSKKK (SEQ ID NO:200); and iii) a stretch of about 9 contiguous amino acids having the amino acid sequence: HSKKKCDEL (SEQ ID NO:201); and b) the following CD4 epitope: a stretch of about 11 contiguous amino acids having the amino acid sequence: GRHLIFCHSKKK (SEQ ID NO:244). A TP42 T-cell epitope polypeptide suitable for inclusion in a composition of the present disclosure can include: a) the following CD8 epitopes: i) a stretch of about 11 contiguous amino acids having the amino acid sequence: FYGKAIPLEQI (SEQ ID NO:243); ii) ii) a stretch of about 9 contiguous amino acids having the amino acid sequence: LIFCHSKKK (SEQ ID NO:200); and iii) a stretch of about 9 contiguous amino acids having the amino acid sequence: HSKKKCDEL (SEQ ID NO:201); and b) the following CD4 epitope: a stretch of about 15 contiguous amino acids having the amino acid sequence: KGGRHLIFCHSKKKCD (SEQ ID NO:202).

In some cases, a suitable T-cell epitope polypeptide is a TP42 polypeptide with from 1 amino acid to 5 amino acids removed from the N-terminus and/or from 1 amino acid to 5 amino acids removed from the C-terminus. Thus, e.g., a suitable T-cell epitope polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: IPFYGKAIPLEQIKGGRHLIFCHSKKKCDELAAKLTG (SEQ ID NO:245); and has a length of 37 amino acids. As another example, a suitable T-cell epitope polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: GTEGEIPFYGKAIPLEQIKGGRHLIFCHSKKKCDELA (SEQ ID NO:246); and has a length of 37 amino acids.

TP45

In some cases, a T-cell epitope polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: LNAVAYYRGLDVSVIPTSGDVVV-VATDALMTGFTGDFDSVIDCNV (SEQ ID NO:247);

and has a length of from 45 amino acids to about 50 amino acids. In some cases, a T-cell epitope polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: LNAVAYYRGLDVSVIPTSGDVVV-VATDALMTGFTGDFDSVIDCNV (SEQ ID NO:247);

and has a length of 45 amino acids. In some cases, a T-cell epitope polypeptide suitable for inclusion in a composition of the present disclosure comprises the amino acid sequence LNAVAYYRGLDVSVIPTSGDVVV-VATDALMTGFTGDFDSVIDCNV (SEQ ID NO:247);

and has a length of 45 amino acids. In some cases, a T-cell epitope polypeptide suitable for inclusion in a composition of the present disclosure comprises the amino acid sequence LNAVAYYRGLDVSVIPTSGDVVV-VATDALMTGFTGDFDSVIDKKK (SEQ ID NO:248);

and has a length of 45 amino acids.

In some cases, a TP45 T-cell epitope polypeptide suitable for inclusion in a composition of the present disclosure comprises the following amino acid sequence: $X_1X_2AVAX_3YRGX_4DVX_5X_6IPX_7X_8GDVVVX_9X_{10}TDALMTGX_{11}TGDFDSVIDX_{12}X_{13}$ $X_{14}(K)n$ (SEQ ID NO:249), where $X_1$ is L or V; $X_2$ is N or T; $X_3$ is Y or F; $X_4$ is L or V; $X_5$ is S or A; $X_6$ is V or I; $X_7$ is T or A; $X_8$ is S, Q, or T; $X_9$ is V or C; $X_1$ is A or S; $X_{11}$ is F or Y; $X_{12}$ is C or K; $X_{13}$ is N or K; and $X_{14}$ is V or K, wherein n is an integer from 2 to 10, and where the TP45 T-cell epitope polypeptide has a length of from 36 amino acids to 55 amino acids. In some cases, a TP45 T-cell epitope polypeptide suitable for inclusion in a composition of the present disclosure comprises the following amino acid sequence: $X_1X_2AVAX_3YRGX_4DVX_5X_6IPX_7X_8GDVVVX_9X_{10}TDALMTGX_{11}TGDFDSVIDX_{12}X_{13}$ $X_{14}KKK$ (SEQ ID NO:250), where $X_1$ is L or V; $X_2$ is N or T; $X_3$ is Y or F; $X_4$ is L or V; $X_5$ is S or A; $X_6$ is V or I; $X_7$ is T or A; $X_1$ is S, Q, or T; $X_9$ is V or C; $X_{10}$ is A or S; $X_{11}$ is F or Y; $X_{12}$ is C or K; $X_{13}$ is N or K; and $X_{14}$ is V or K; where the TP45 T-cell epitope polypeptide has a length of 48 amino acids. In some cases, the TP45 T-cell epitope polypeptide comprises the following amino acid sequence: LNAVAYYR-GLDVSVIPTSGDVVV-VATDALMTGFTGDFDSVIDCNVKKK (SEQ ID NO:251) and has a length of 48 amino acids.

In some cases, a TP45 T-cell epitope polypeptide suitable for inclusion in a composition of the present disclosure comprises the following amino acid sequence:

$X_1X_2AVAX_3YRGX_4DVX_5X_6IPX_7X_8GDVVVX_9X_{10}$
TDALMTGX$_{11}$TGDFDSVIDX$_{12}X_{13}$ X$_{14}$ (SEQ ID NO:252), where $X_1$ is L or V; $X_2$ is N or T; $X_3$ is Y or F; $X_4$ is L or V; $X_5$ is S or A; $X_6$ is V or I; $X_7$ is T or A; $X_8$ is S, Q, or T; $X_9$ is V or C; $X_{10}$ is A or S; $X_{11}$ is F or Y; $X_{12}$ is C or K; $X_{13}$ is N or K; and $X_{14}$ is V or K; where the TP23 T-cell epitope polypeptide has a length of from 18 amino acids to 23 amino acids (e.g., T-cell epitope polypeptide has a length of 18 amino acids (aa), 19 aa, 20 aa, 21 aa, 22 aa, or 23 aa). In some cases, the TP23 T-cell epitope polypeptide has a length of 23 amino acids. In some cases, the TP23 T-cell epitope polypeptide is part of a fusion polypeptide, as described in detail below.

In some cases, a TP45 T-cell epitope polypeptide suitable for inclusion in a composition of the present disclosure comprises the following amino acid sequence: $X_1X_2AVAX_3YRGX_4DVX_5X_6IPX_7X_8GDVVVX_9X_{10}$ TDALMTGX$_{11}$TGDFDSVIDX$_{12}X_{13}$ X$_{14}$ (SEQ ID NO:252), where $X_1$ is L; $X_2$ is N; $X_3$ is Y; $X_4$ is L; $X_5$ is S; $X_6$ is V; $X_7$ is T; $X_8$ is S, Q, or T; $X_9$ is V or C; $X_{10}$ is A; $X_{11}$ is F or Y; $X_{12}$ is K; $X_{13}$ is K; and $X_{14}$ is K; where the TP23 T-cell epitope polypeptide has a length of from 18 amino acids to 23 amino acids (e.g., T-cell epitope polypeptide has a length of 18 amino acids (aa), 19 aa, 20 aa, 21 aa, 22 aa, or 23 aa). In some cases, the TP23 T-cell epitope polypeptide has a length of 23 amino acids. In some cases, the TP23 T-cell epitope polypeptide is part of a fusion polypeptide, as described in detail below.

In some cases, a suitable T-cell epitope polypeptide is a TP45 polypeptide with from 1 amino acid to 5 amino acids removed from the N-terminus and/or from 1 amino acid to 5 amino acids removed from the C-terminus. Thus, for example, in some cases, a T-cell epitope polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: LNAVAYYR-GLDVSVIPTSGDVVVVATDALMTGFTGDFDSVID (SEQ ID NO:253); and has a length of 43 amino acids. For example, in some cases, a T-cell epitope polypeptide suitable for inclusion in a composition of the present disclosure comprises the amino acid sequence LNAVAYYR-GLDVSVIPTSGDVVVVATDALMTGFTGDFDSVID (SEQ ID NO:253); and has a length of 43 amino acids.
TP48

In some cases, a T-cell epitope polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: ILRRHVGPGEGAVQWMNRLIAFAS-RGNHVSPTHYVPESDASARVTQIL (SEQ ID NO:254); and has a length of from 48 amino acids to about 55 amino acids, or has a length of from 40 amino acids to about 48 amino acids (e.g., has a length of 40 amino acids (aa), 41 aa, 42 aa, 43 aa, 44 aa, 45 aa, 46 aa, 47 aa, or 48 aa). In some cases, a T-cell epitope polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: ILRRHVGPGEGAVQWMNRLIAFAS-RGNHVSPTHYVPESDASARVTQIL (SEQ ID NO:254); and has a length of 48 amino acids. In some cases, a T-cell epitope polypeptide suitable for inclusion in a composition of the present disclosure comprises the amino acid sequence ILRRHVGPGEGAVQWMNRLIAFAS-RGNHVSPTHYVPESDASARVTQIL (SEQ ID NO:254); and has a length of 48 amino acids.

In some cases, a TP48 T-cell epitope polypeptide suitable for inclusion in a composition of the present disclosure comprises the following amino acid sequence: $X_1X_2X_3RHX_4GX_5X_6EGX_7X_8QWMNRLIAFASRGNH$ $VX_9PTHYX_{10}X_{11}X_{12}X_{13}DAX_{14}X_{15}X_{16}VX_{17}X_{18}X_{19}L$ (K)n (SEQ ID NO:255), wherein $X_1$ is I or V; $X_2$ is L or I; $X_3$ is R or K; $X_4$ is V, I, or T; $X_5$ is P, Q, or T; $X_6$ is G, A, or S; $X_7$ is A or V; $X_8$ is V or T; $X_9$ is S or A; $X_{10}$ is V or I; $X_1$ is P, T, A, or Q, $X_{12}$ is E or D; $X_{13}$ is S, T, or D; $X_{14}$ is S or A; $X_{15}$ is A, Q, R, or K; $X_{16}$ is R, K, or X; $X_{17}$ is T or M; $X_{18}$ is Q, A, T, or G; and $X_{19}$ is I, L, or V, where n is an integer from 2 to 10, and where the TP48 T-cell epitope polypeptide has a length of from 38 amino acids to 58 amino acids. In some cases, a TP48 T-cell epitope polypeptide suitable for inclusion in a composition of the present disclosure comprises the following amino acid sequence: $X_1X_2X_3RHX_4GX_5X_6EGX_7X_8QWMNRLIAFASRG$ $NHVX_9PTHYX_{10}X_{11}X_{12}X_{13}DAX_{14}X_{15}X_{16}VX_{17}X_{18}X_{19}$ LKKK (SEQ ID NO:256), wherein $X_1$ is I or V; $X_2$ is L or I; $X_3$ is R or K; $X_4$ is V, I, or T; $X_5$ is P, Q, or T; $X_6$ is G, A, or S; $X_7$ is A or V; $X_8$ is V or T; $X_9$ is S or A; $X_{10}$ is V or I; $X_1$ is P, T, A, or Q, $X_{12}$ is E or D; $X_{13}$ is S, T, or D; $X_{14}$ is S or A; $X_{15}$ is A, Q, R, or K; $X_{16}$ is R, K, or X; $X_{17}$ is T or M; $X_{18}$ is Q, A, T, or G; and $X_{19}$ is I, L, or V, where the TP48 T-cell epitope polypeptide has a length of 51 amino acids. In some cases, the TP48 T-cell epitope polypeptide comprises the amino acid sequence: ILR-RHVGPGEGAVQWMNRLIAFASRGNHVSPTHYVPES-DASARVTQILKKK (SEQ ID NO:257) and has a length of 51 amino acids.

In some cases, a TP48 T-cell epitope polypeptide suitable for inclusion in a composition of the present disclosure comprises the following amino acid sequence: $X_1X_2X_3RHX_4GX_5X_6EGX_7X_8QWMNRLIAFASR$ $GNHVX_9PTHYX_{10}X_{11}X_{12}X_{13}DAX_{14}X_{15}X_{16}VX_{17}X_{18}X_{19}L$ (SEQ ID NO:266), where $X_1$ is I or V; $X_2$ is L or I; $X_3$ is R or K; $X_4$ is V, I, or T; $X_5$ is P, Q, or T; $X_6$ is G, A, or S; $X_7$ is A or V; $X_8$ is V or T; $X_9$ is S or A; $X_{10}$ is V or I; $X_1$ is P, T, A, or Q, $X_{12}$ is E or D; $X_{13}$ is S, T, or D; $X_{14}$ is S or A; $X_{15}$ is A, Q, R, or K; $X_{16}$ is R, K, or X; $X_{17}$ is T or M; $X_{18}$ is Q, A, T, or G; and $X_{19}$ is I, L, or V; where the TP48 T-cell epitope polypeptide has a length of from 40 amino acids to about 48 amino acids (e.g., has a length of 40 amino acids (aa), 41 aa, 42 aa, 43 aa, 44 aa, 45 aa, 46 aa, 47 aa, or 48 aa). In some cases, the TP48 T-cell epitope polypeptide has a length of 48 amino acids. In some cases, the T-cell epitope polypeptide is part of a fusion polypeptide, as described in detail below.

In some cases, a TP48 T-cell epitope polypeptide suitable for inclusion in a composition of the present disclosure comprises the following amino acid sequence: $X_1X_2X_3RHX_4GX_5X_6EGX_7X_8QWMNRLIAFASR$ GNHVX$_9$PTHYX$_{10}$X$_{11}$X$_{12}$X$_{13}$DAX$_{14}$X$_{15}$X$_{16}$VX$_{17}$X$_{18}$X$_{19}$L (SEQ ID NO:266), where X$_1$ is I or V; X$_2$ is L; X$_3$ is R; X$_4$ is V or I; X$_5$ is P or Q; X$_6$ is G or A; X$_7$ is A; X$_8$ is V or T; X$_9$ is S or A; X$_{10}$ is V; X$_{11}$ is P, T, or A; X$_{12}$ is E; X$_{13}$ is S or T; X$_{14}$ is S or A; X$_{15}$ is A, Q, or R; X$_{16}$ is R or K; X$_{17}$ is T; X$_{18}$ is Q, A, or T; and X$_{19}$ is I, L, or V; where the TP48 T-cell epitope polypeptide has a length of from 40 amino acids to about 48 amino acids (e.g., has a length of 40 amino acids (aa), 41 aa, 42 aa, 43 aa, 44 aa, 45 aa, 46 aa, 47 aa, or 48 aa). In some cases, the TP48 T-cell epitope polypeptide has a length of 48 amino acids. In some cases, the T-cell epitope polypeptide is part of a fusion polypeptide, as described in detail below.

In some cases, a TP48 T-cell epitope polypeptide suitable for inclusion in a composition of the present disclosure comprises the following amino acid sequence: ILRRHVGPGEGAVQWMNRLIAFASRGNHVSPTHYVPESDAAARVTAIL (SEQ ID NO:267); where the TP48 T-cell epitope polypeptide has a length of from 40 amino acids to about 48 amino acids (e.g., has a length of 40 amino acids (aa), 41 aa, 42 aa, 43 aa, 44 aa, 45 aa, 46 aa, 47 aa, or 48 aa). In some cases, the TP48 T-cell epitope polypeptide has a length of 48 amino acids. In some cases, the T-cell epitope polypeptide is part of a fusion polypeptide, as described in detail below.

In some cases, a TP48 T-cell epitope polypeptide suitable for inclusion in a composition of the present disclosure comprises the following amino acid sequence: ILRRHVGPGEGAVQWMNRLIAFASRGNHVSPTHYVPESDAAARVTQIL (SEQ ID NO:268); where the TP48 T-cell epitope polypeptide has a length of from 40 amino acids to about 48 amino acids (e.g., has a length of 40 amino acids (aa), 41 aa, 42 aa, 43 aa, 44 aa, 45 aa, 46 aa, 47 aa, or 48 aa). In some cases, the TP48 T-cell epitope polypeptide has a length of 48 amino acids. In some cases, the T-cell epitope polypeptide is part of a fusion polypeptide, as described in detail below.

In some cases, a TP48 T-cell epitope polypeptide suitable for inclusion in a composition of the present disclosure comprises the following amino acid sequence: ILRRHVGPGEGAVQWMNRLIAFASRGNHVAPTHYVTESDASQRVTQLL (SEQ ID NO:269); where the TP48 T-cell epitope polypeptide has a length of from 40 amino acids to about 48 amino acids (e.g., has a length of 40 amino acids (aa), 41 aa, 42 aa, 43 aa, 44 aa, 45 aa, 46 aa, 47 aa, or 48 aa). In some cases, the TP48 T-cell epitope polypeptide has a length of 48 amino acids. In some cases, the T-cell epitope polypeptide is part of a fusion polypeptide, as described in detail below.

In some cases, a TP48 T-cell epitope polypeptide suitable for inclusion in a composition of the present disclosure comprises the following amino acid sequence: ILRRHVGQGEGAVQWMNRLIAFASRGNHVAPTHYVAESDASQRVTQVL (SEQ ID NO:270); where the TP48 T-cell epitope polypeptide has a length of from 40 amino acids to about 48 amino acids (e.g., has a length of 40 amino acids (aa), 41 aa, 42 aa, 43 aa, 44 aa, 45 aa, 46 aa, 47 aa, or 48 aa). In some cases, the TP48 T-cell epitope polypeptide has a length of 48 amino acids. In some cases, the T-cell epitope polypeptide is part of a fusion polypeptide, as described in detail below.

In some cases, a TP48 T-cell epitope polypeptide suitable for inclusion in a composition of the present disclosure comprises the following amino acid sequence: ILRRHVGPGEGAVQWMNRLIAFASRGNHVSPTHYVPESDAAARVTALL (SEQ ID NO:271); where the TP48 T-cell epitope polypeptide has a length of from about 48 amino acids (e.g., has a length of 40 amino acids (aa), 41 aa, 42 aa, 43 aa, 44 aa, 45 aa, 46 aa, 47 aa, or 48 aa). In some cases, the TP48 T-cell epitope polypeptide has a length of 48 amino acids. In some cases, the T-cell epitope polypeptide is part of a fusion polypeptide, as described in detail below.

In some cases, a TP48 T-cell epitope polypeptide suitable for inclusion of the present disclosure comprises the following amino acid sequence: ILRRHVGPGEGAVQWMNRLIAFASRGNHVSPTHYVPESDAAARVTQIL (SEQ ID NO:268); where the TP48 T-cell epitope polypeptide has a length of from 40 amino acids to about 48 amino acids (e.g., has a length of 40 amino acids (aa), 41 aa, 42 aa, 43 aa, 44 aa, 45 aa, 46 aa, 47 aa, or 48 aa). In some cases, the TP48 T-cell epitope polypeptide has a length of 48 amino acids. In some cases, the T-cell epitope polypeptide is part of a fusion polypeptide, as described in detail below.

In some cases, a TP48 T-cell epitope polypeptide suitable for inclusion of the present disclosure comprises the following amino acid sequence: VLRRHIGPGEGAVQWMNRLIAFASRGNHVSPTHYVPETDASAKVTQLL (SEQ ID NO:272); where the TP48 T-cell epitope polypeptide has a length of from 40 amino acids to about 48 amino acids (e.g., has a length of 40 amino acids (aa), 41 aa, 42 aa, 43 aa, 44 aa, 45 aa, 46 aa, 47 aa, or 48 aa). In some cases, the TP48 T-cell epitope polypeptide has a length of 48 amino acids. In some cases, the T-cell epitope polypeptide is part of a fusion polypeptide, as described in detail below.

In some cases, a TP48 T-cell epitope polypeptide suitable for inclusion of the present disclosure comprises the following amino acid sequence: ILRRHVGPAEGATQWMNRLIAFASRGNHVSPTHYVPETDASRX$V$TTIL (SEQ ID NO:273); where the TP48 T-cell epitope polypeptide has a length of from 40 amino acids to about 48 amino acids (e.g., has a length of 40 amino acids (aa), 41 aa, 42 aa, 43 aa, 44 aa, 45 aa, 46 aa, 47 aa, or 48 aa). In some cases, the TP48 T-cell epitope polypeptide has a length of 48 amino acids. In some cases, the T-cell epitope polypeptide is part of a fusion polypeptide, as described in detail below.

In some cases, a TP48 T-cell epitope polypeptide suitable for inclusion of the present disclosure comprises the following amino acid sequence: IIKRHTGTSEGVTQWMNRLIAFASRGNHVSPTHYIQDDDASKRVMGIL (SEQ ID NO:274); where the TP48 T-cell epitope polypeptide has a length of from 40 amino acids to about 48 amino acids (e.g., has a length of 40 amino acids (aa), 41 aa, 42 aa, 43 aa, 44 aa, 45 aa, 46 aa, 47 aa, or 48 aa). In some cases, the TP48 T-cell epitope polypeptide has a length of 48 amino acids. In some cases, the T-cell epitope polypeptide is part of a fusion polypeptide, as described in detail below.

In some cases, a TP48 T-cell epitope polypeptide suitable for inclusion of the present disclosure comprises the following amino acid sequence: ILRRHVGPAEGATQWMNRLIAFASRGNHVSPTHYVPETDASRX$V$TTIL (SEQ ID NO:273), where X is R or K; where the TP48 T-cell epitope polypeptide has a length of from 40 amino acids to about 48 amino acids (e.g., has a length of 40 amino acids (aa), 41 aa, 42 aa, 43 aa, 44 aa, 45 aa, 46 aa, 47 aa, or 48 aa). In some cases, the TP48 T-cell epitope polypeptide has a length of 48 amino acids. In some cases, the T-cell epitope polypeptide is part of a fusion polypeptide, as described in detail below.

A TP48 T-cell epitope polypeptide suitable for inclusion in a composition of the present disclosure can include one or more CD8 epitopes, e.g., a stretch of about 16 contiguous amino acids having the amino acid sequence: EGAVQWMNRLIAFASR (SEQ ID NO:210), or EGATQWMNRLIAFASR (SEQ ID NO:211), or EGVTQWMNRLIAFASR (SEQ ID NO:212); or a stretch of about 9 contiguous amino acids having the amino acid sequence: WMNRLIAFA (SEQ ID NO:213); or a stretch of about 15 contiguous amino acids having the amino acid sequence: PTHYX$_1$X$_2$X$_3$X$_4$DAX$_5$X$_6$X$_7$VX$_8$ (SEQ ID NO:276), where X$_1$ is V or I; X$_2$ is P, T, A, or Q, X$_3$ is E or D; X$_4$ is S, T, or D; X$_5$ is S or A; X$_6$ is A, Q, R, or K; X$_7$ is R, K, or X; and X$_8$ is T or M.

A TP48 T-cell epitope polypeptide suitable for inclusion in a composition of the present disclosure can include one or more CD8 epitopes, e.g., a stretch of about 16 contiguous amino acids having the amino acid sequence: EGAVQWMNRLIAFASR (SEQ ID NO:210), or EGATQWMNRLIAFASR (SEQ ID NO:211), or EGVTQWMNRLIAFASR (SEQ ID NO:212); or a stretch of about 9 contiguous amino acids having the amino acid sequence: WMNRLIAFA (SEQ ID NO:213); or a stretch of about 15 contiguous amino acids having the amino acid sequence: PTHYX$_1$X$_2$X$_3$X$_4$DAX$_5$X$_6$X$_7$VX$_8$ (SEQ ID NO:276), where X$_1$ is V; X$_2$ is P, T, or A, X$_3$ is E; X$_4$ is S or T; X$_5$ is S or A; X$_6$ is A, Q, or R; X$_7$ is R or K; and X$_8$ is T.

A TP48 T-cell epitope polypeptide suitable for inclusion in a composition of the present disclosure can include one or more CD4 epitopes, e.g., a stretch of about 15 contiguous amino acids having the amino acid sequence: RHVGPGEGAVQWMNR (SEQ ID NO:214), or RHVGQGEGAVQWMNR (SEQ ID NO:215), or RHIGPGEGAVQWMNR (SEQ ID NO:216), or RHVGPAEGATQWMNR (SEQ ID NO:217), or RHTGTSEGVTQWMNR (SEQ ID NO:218); or a stretch of about 20 contiguous amino acids having the amino acid sequence: HVGPGEGAVQWMNRLIAFAS (SEQ ID NO:219), or HVGQGEGAVQWMNRLIAFAS (SEQ ID NO:220), or HIGPGEGAVQWMNRLIAFAS (SEQ ID NO:221), or HVGPAEGATQWMNRLIAFAS (SEQ ID NO:222), or HTGTSEGVTQWMNRLIAFAS (SEQ ID NO:223); or a stretch of about 20 contiguous amino acids having amino acid sequence: GAVQWMNRLIAFASRGNHVS (SEQ ID NO:224), or GAVQWMNRLIAFASRGNHVA (SEQ ID NO:225), or GATQWMNRLIAFASRGNHVS (SEQ ID NO:226), or GVTQWMNRLIAFASRGNHVS (SEQ ID NO:227).

In some cases, TP48 T-cell epitope polypeptide suitable for inclusion in a composition of the present disclosure includes: a) one or more CD8 epitopes, e.g., a stretch of about 16 contiguous amino acids having the amino acid sequence: EGAVQWMNRLIAFASR (SEQ ID NO:210), or EGATQWMNRLIAFASR (SEQ ID NO:211), or EGVTQWMNRLIAFASR (SEQ ID NO:212); or a stretch of about 9 contiguous amino acids having the amino acid sequence: WMNRLIAFA (SEQ ID NO:213); or a stretch of about 15 contiguous amino acids having the amino acid sequence: PTHYX$_1$X$_2$X$_3$X$_4$DAX$_5$X$_6$X$_7$VX$_8$ (SEQ ID NO:276), where X$_1$ is V or I; X$_2$ is P, T, A, or Q, X$_3$ is E or D; X$_4$ is S, T, or D; X$_5$ is S or A; X$_6$ is A, Q, R, or K; X$_7$ is R, K, or X; and X$_8$ is T or M; or a stretch of about 15 contiguous amino acids having the amino acid sequence: PTHYX$_1$X$_2$X$_3$X$_4$DAX$_5$X$_6$X$_7$VX$_8$ (SEQ ID NO:276), where X$_1$ is V; X$_2$ is P, T, or A, X$_3$ is E; X$_4$ is S or T; X$_5$ is S or A; X$_6$ is A, Q, or R; X$_7$ is R or K; and X$_8$ is T; and b) one or more CD4 epitopes, e.g., a stretch of about 15 contiguous amino acids having the amino acid sequence: RHVGPGEGAVQWMNR (SEQ ID NO:214), or RHVGQGEGAVQWMNR (SEQ ID NO:215), or RHIGPGEGAVQWMNR (SEQ ID NO:216), or RHVGPAEGATQWMNR (SEQ ID NO:217), or RHTGTSEGVTQWMNR (SEQ ID NO:218); or a stretch of about 20 contiguous amino acids having the amino acid sequence: HVGPGEGAVQWMNRLIAFAS (SEQ ID NO:219), or HVGQGEGAVQWMNRLIAFAS (SEQ ID NO:220), or HIGPGEGAVQWMNRLIAFAS (SEQ ID NO:221), or HVGPAEGATQWMNRLIAFAS (SEQ ID NO:222), or HTGTSEGVTQWMNRLIAFAS (SEQ ID NO:223); or a stretch of about 20 contiguous amino acids having amino acid sequence: GAVQWMNRLIAFASRGNHVS (SEQ ID NO:224), or GAVQWMNRLIAFASRGNHVA (SEQ ID NO:225), or GATQWMNRLIAFASRGNHVS (SEQ ID NO:226), or GVTQWMNRLIAFASRGNHVS (SEQ ID NO:227).

In some cases, a suitable T-cell epitope polypeptide is a TP48 polypeptide with from 1 amino acid to 5 amino acids removed from the N-terminus and/or from 1 amino acid to 5 amino acids removed from the C-terminus. Thus, e.g., a suitable T-cell epitope polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: RHVGPGEGAVQWMNRLIAFASRGNHVSPTHYVPES-DASARVTQIL (SEQ ID NO:277); and has a length of 45 amino acids. As another example, a suitable T-cell epitope polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: ILR-RHVGPGEGAVQWMNRLIAFASRGNHVSPTHYVPES-DASARVT (SEQ ID NO:278); and has a length of 45 amino acids.

TP33

In some cases, a T-cell epitope polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: HSKKKCDELAAKLTGLGLNAVAYYR-GLDVSVIP (SEQ ID NO:279); and has a length of from 33 amino acids to about 37 amino acids (e.g., has a length of 33 amino acids (aa), 34 aa, 35 aa, 36 aa, or 37 aa), or has a length of from 30 amino acids to about 33 amino acids (e.g., has a length of 30 amino acids (aa), 31 aa, 32 aa, or 33 aa). In some cases, a T-cell epitope polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: HSKKKCDELAAKLTGLGLNAVAYYR-GLDVSVIP (SEQ ID NO:279); and has a length of 33 amino acids. In some cases, a T-cell epitope polypeptide suitable for inclusion in a composition of the present disclosure comprises the amino acid sequence HSKKKCDE-LAAKLTGLGLNAVAYYRGLDVSVIP (SEQ ID NO:279); and has a length of 33 amino acids. Such T-cell epitope polypeptides are also referred to herein as "TP33" polypeptides. In some cases, a TP33 T-cell epitope polypeptide comprises a CD8 epitope comprising a contiguous stretch of 19 amino acids of one of the following amino acid sequences: i) DELAAKLTGLGLNAVAYYR (SEQ ID NO:280); ii) DELAAKLVALGINAVAYYR (SEQ ID NO:281); iii) DELAAKLSGLGLNAVAYYR (SEQ ID NO:282); iv) DELAAALRGMGLNAVAYYR (SEQ ID NO:283); v) DELAAALRGMGVNAVAYYR (SEQ ID NO:284); vi) DELASKLRGMGLNAVAYYR (SEQ ID NO:285); vii) DELAAKLRGMGLNAVAYYR (SEQ ID NO:286).

In some cases, a TP33 T-cell epitope polypeptide suitable for inclusion in a composition of the present disclosure comprises the following amino acid sequence: HSKKKCDELAX$_1$X$_2$LX$_3$X$_4$X$_5$GX$_6$NAVAYYRGL DVSX$_7$IP (SEQ ID NO:287), where X$_1$ is A or S; X$_2$ is K or A; X$_3$ is V, S, R, or T; X$_4$ is A or G; X$_5$ is L or M; X$_6$ is I, L, or V; and X$_7$ is V or I; and has a length of from 33 amino acids to about 37 amino acids (e.g., has a length of 33 amino acids (aa), 34 aa, 35 aa, 36 aa, or 37 aa), or has a length of from 30 amino acids to about 33 amino acids (e.g., has a length of 30 amino acids (aa), 31 aa, 32 aa, or 33 aa). In some cases, a TP33 T-cell epitope polypeptide suitable for inclusion in a composition of the present disclosure comprises the following amino acid sequence: HSKKKCDELAX$_1$X$_2$LX$_3$X$_4$X$_5$GX$_6$NAVAYYRG LDVSX$_7$IP (SEQ ID NO:287), where X$_1$ is A or S; X$_2$ is K or A; X$_3$ is V, S, R, or T; X$_4$ is A or G; X$_5$ is L or M; X$_6$ is I, L, or V; and X$_7$ is V or I; where the TP33 T-cell epitope polypeptide has a length of 33 amino acids.

In some cases, a TP33 T-cell epitope polypeptide suitable for inclusion in a composition of the present disclosure comprises the following amino acid sequence: HSKKKCDELAAKLX$_1$X$_2$X$_3$GX$_4$NAVAYYRGLDVSVIP (SEQ ID NO:288), where X$_1$ is V, S, R, or T; X$_2$ is A or G; X$_3$ is L or M; and X$_4$ is I, L, or V; and has a length of from 33 amino acids to about 37 amino acids (e.g., has a length of 33 amino acids (aa), 34 aa, 35 aa, 36 aa, or 37 aa), or has a length of from 30 amino acids to about 33 amino acids (e.g., has a length of 30 amino acids (aa), 31 aa, 32 aa, or 33 aa). In some cases, a TP33 T-cell epitope polypeptide suitable for inclusion in a composition of the present disclosure comprises the following amino acid sequence: HSKKKCDELAAKLX$_1$X$_2$X$_3$GX$_4$NAVAYYRGLDVSVIP (SEQ ID NO:288), where X$_1$ is V, S, R, or T; X$_2$ is A or G; X$_3$ is L or M; and X$_4$ is I, L, or V; where the TP33 T-cell epitope polypeptide has a length of 33 amino acids.

In some cases, a TP33 T-cell epitope polypeptide suitable for inclusion in a composition of the present disclosure comprises the following amino acid sequence: HSKKKCDELAAALRGMGX$_1$NAVAYYRGLDVSX$_1$IP (SEQ ID NO:289), where X$_1$ is I, L, or V; and X$_2$ is V or I; and has a length of from 33 amino acids to about 37 amino acids (e.g., has a length of 33 amino acids (aa), 34 aa, 35 aa, 36 aa, or 37 aa), or has a length of from 30 amino acids to about 33 amino acids (e.g., has a length of 30 amino acids (aa), 31 aa, 32 aa, or 33 aa). In some cases, a TP33 T-cell epitope polypeptide suitable for inclusion in a composition of the present disclosure comprises the following amino acid sequence: HSKKKCDELAAALRGMGX$_1$NAVAYYRGLDVSX$_1$IP (SEQ ID NO:289), where X$_1$ is I, L, or V; and X$_2$ is V or I; where the TP33 T-cell epitope polypeptide has a length of 33 amino acids.

In some cases, a T-cell epitope polypeptide suitable for inclusion in a composition of the present disclosure comprises the amino acid sequence HSKKKCDELAAK-LRGMGLNAVAYYRGLDVSVIP (SEQ ID NO:290); and has a length of 33 amino acids.

TP42-2

In some cases, a T-cell epitope polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: KGGRHLIFCHSKKKCDELAAK-LTGLGLNAVAYYRGLDVSVIP (SEQ ID NO:291); and has a length of from 42 amino acids to about 46 amino acids (e.g., has a length of 42 amino acids (aa), 43 aa, 44 aa, 45 aa, or 46 aa), or has a length of from 38 amino acids to about 42 amino acids (e.g., has a length of 38 amino acids (aa), 39 aa, 40 aa, 41 aa, or 42 aa). In some cases, a T-cell epitope polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: KGGRHLIFCHS-KKKCDELAAKLTGLGLNAVAYYRGLDVSVIP (SEQ ID NO:291); and has a length of 42 amino acids. In some cases, a T-cell epitope polypeptide suitable for inclusion in a composition of the present disclosure comprises the amino acid sequence KGGRHLIFCHSKKKCDELAAKLTGLGL-NAVAYYRGLDVSVIP (SEQ ID NO:291); and has a length of 42 amino acids. Such T-cell epitope polypeptides are also referred to herein as "TP42-2" polypeptides. In some cases, a TP42-2 T-cell epitope polypeptide comprises a CD8 epitope comprising a contiguous stretch of 19 amino acids of one of the following amino acid sequences: i) DELAAK-LTGLGLNAVAYYR (SEQ ID NO:280); ii) DELAAK-LVALGINAVAYYR (SEQ ID NO:281); iii) DELAAK-LSGLGLNAVAYYR (SEQ ID NO:282); iv) DELAAALRGMGLNAVAYYR (SEQ ID NO:283); v) DELAAALRGMGVNAVAYYR (SEQ ID NO:284); vi) DELASKLRGMGLNAVAYYR (SEQ ID NO:285); vii) DELAAKLRGMGLNAVAYYR (SEQ ID NO:286).

In some cases, a TP42-2 T-cell epitope polypeptide suitable for inclusion in a composition of the present disclosure comprises the following amino acid sequence: KGGRHLIFCHSKKKCDELAX$_1$X$_2$LX$_3$X$_4$X$_5$GX$_6$N AVAYYRGLDVSX$_7$IP (SEQ ID NO:292), where X$_1$ is A or S; X$_2$ is K or A; X$_3$ is V, S, R, or T; X$_4$ is A or G; X$_5$ is L or M; X$_6$ is I, L, or V; and X$_7$ is V or I; and has a length of from 42 amino acids to about 46 amino acids (e.g., has a length of 42 amino acids (aa), 43 aa, 44 aa, 45 aa, or 46 aa), or has a length of from 38 amino acids to about 42 amino acids (e.g., has a length of 38 amino acids (aa), 39 aa, 40 aa, 41 aa, or 42 aa). In some cases, a TP42-2 T-cell epitope polypeptide suitable for inclusion in a composition of the present disclosure comprises the following amino acid sequence: KGGRHLIFCHSKKKCDELAX₁X₂LX₃X₄X₅GX₆NAVAYYRGLDVSX₇IP (SEQ ID NO:292), where X₁ is A or S; X₂ is K or A; X₃ is V, S, R, or T; X₄ is A or G; X₅ is L or M; X₆ is I, L, or V; and X₇ is V or I; where the TP42-2 T-cell epitope polypeptide has a length of 42 amino acids.

In some cases, a TP42-2 T-cell epitope polypeptide suitable for inclusion in a composition of the present disclosure comprises the following amino acid sequence: KGGRHLIFCHSKKKCDELAAKLX₁X₂X₃GX₄NAVAYYRGLDVSVIP (SEQ ID NO:293), where X₁ is V, S, R, or T; X₂ is A or G; X₃ is L or M; and X₄ is I, L, or V; and has a length of from 42 amino acids to about 46 amino acids (e.g., has a length of 42 amino acids (aa), 43 aa, 44 aa, 45 aa, or 46 aa), or has a length of from 38 amino acids to about 42 amino acids (e.g., has a length of 38 amino acids (aa), 39 aa, 40 aa, 41 aa, or 42 aa). In some cases, a TP42-2 T-cell epitope polypeptide suitable for inclusion in a composition of the present disclosure comprises the following amino acid sequence: KGGRHLIFCHSKKKCDELAAKLX₁X₂X₃GX₄NAVAYYRGLDVSVIP (SEQ ID NO:293), where X₁ is V, S, R, or T; X₂ is A or G; X₃ is L or M; and X₄ is I, L, or V; where the TP42-2 T-cell epitope polypeptide has a length of 42 amino acids.

In some cases, a TP42-2 T-cell epitope polypeptide suitable for inclusion in a composition of the present disclosure comprises the following amino acid sequence: KGGRHLIFCHSKKKCDELAAALRGMGX₁NAVAYYRGLDVSX₁IP (SEQ ID NO:294), where X₁ is I, L, or V; and X₂ is V or I; and has a length of from 42 amino acids to about 46 amino acids (e.g., has a length of 42 amino acids (aa), 43 aa, 44 aa, 45 aa, or 46 aa), or has a length of from 38 amino acids to about 42 amino acids (e.g., has a length of 38 amino acids (aa), 39 aa, 40 aa, 41 aa, or 42 aa). In some cases, a TP42-2 T-cell epitope polypeptide suitable for inclusion in a composition of the present disclosure comprises the following amino acid sequence: HSKKKCDELAAALRGMGX₁NAVAYYRGLDVSX₁IP (SEQ ID NO:289), where X₁ is I, L, or V; and X₂ is V or I; where the TP42-2 T-cell epitope polypeptide has a length of 42 amino acids.

In some cases, a TP42-2 T-cell epitope polypeptide suitable for inclusion in a composition of the present disclosure comprises the amino acid sequence KGGRHLIFCHSKKKCDELAAKLRGMGLNAVAYYRGLDVSVIP (SEQ ID NO:290); and has a length of 42 amino acids.

Multiple T-Cell Epitope Polypeptides in a Single Polypeptide Chain

The present disclosure provides a T-cell epitope polypeptide comprising 2, 3, 4, or 5 of the aforementioned T-cell epitope polypeptides in a single polypeptide chain. In other words, the present disclosure provides a fusion polypeptide comprising 2, 3, 4, or 5 of the aforementioned T-cell epitope polypeptides in a single polypeptide chain. Such a fusion polypeptide can be synthesized recombinantly, e.g., where a nucleic acid (e.g., a recombinant expression vector) comprising a nucleotide sequence encoding the fusion polypeptide is introduced into a host cell in vitro, generating a genetically modified host cell; and the host cell synthesizes the encoded fusion polypeptide. Suitable host cells include, e.g., prokaryotic host cells (e.g., *E. coli*); and eukaryotic host cells (e.g., yeast, such as *Saccharomyces cerevisiae*, *Pichia*, and the like; mammalian host cells; and insect cells). The present disclosure further provides a nucleic acid comprising a nucleotide sequence encoding a fusion polypeptide of the present disclosure (e.g., a T-cell epitope polypeptide comprising 2, 3, 4, or 5 of the aforementioned T-cell epitope polypeptides in a single polypeptide chain). The nucleic acid can be present in: i) a recombinant expression vector, e.g., for production of the fusion polypeptide, e.g., in a cell in vitro); ii) in an RNA, e.g., for administration to an individual; or iii) in a DNA, e.g., for administration to an individual).

For example, in some cases, an immunogenic composition of the present disclosure comprises: a) i) an HCV E1/E2 heterodimeric polypeptide; ii) an HCV E2 polypeptide; or iii) an HCV E1 polypeptide; b) a T-cell epitope comprising, in order from N-terminus to C-terminus: i) a TP35-NS3 polypeptide, as described above (e.g., a polypeptide having the following amino acid sequence: KSTKVPAAYAAQGYKVLVLNPSVAATLGFGAYMSK (SEQ ID NO:133); and having a length of 35 amino acids); and ii) a TP50C polypeptide, as described above (e.g., a polypeptide having the following amino acid sequence: GVYLLPRRGPRLGVRATRKTSERSQPR-GRRQPIPKARRSEGRSWAQPGYP (SEQ ID NO:148); and having a length of 50 amino acids. Thus, e.g., in some cases, an immunogenic composition of the present disclosure comprises: a) i) an HCV E1/E2 heterodimeric polypeptide; ii) an HCV E2 polypeptide; or iii) an HCV E1 polypeptide; b) a T-cell epitope comprising a polypeptide having at least 20% (at least 20%, at least 30%, at least 40%, at least 50%, at least 60%, at least 70%, at least 80%, at least 90%, at least 95%, at least 98%, or 100%) amino acid identity to: KSTKVPAAYAAQGYKVLVLNPSVAATLGF-GAYMSKGVYLLPRRGPRLGVRATRKTSE RSQPR-GRRQPIPKARRSEGRSWAQPGYP (SEQ ID NO:295) and having a length of 85 amino acids.

As another example, in some cases, an immunogenic composition of the present disclosure comprises: a) i) an HCV E1/E2 heterodimeric polypeptide; ii) an HCV E2 polypeptide; or iii) an HCV E1 polypeptide; b) a T-cell epitope comprising, in order from N-terminus to C-terminus: i) a TP50C polypeptide, as described above (e.g., a polypeptide having the following amino acid sequence: GVYLLPRRGPRLGVRATRKTSERSQPR-GRRQPIPKARRSEGRSWAQPGYP (SEQ ID NO:148); and having a length of 50 amino acids; and ii) a TP35-NS3 polypeptide, as described above (e.g., a polypeptide having the following amino acid sequence: KSTKVPAAYAAQGYKVLVLNPSVAATLGFGAYMSK (SEQ ID NO:133); and having a length of 35 amino acids). Thus, e.g., in some cases, an immunogenic composition of the present disclosure comprises: a) i) an HCV E1/E2 heterodimeric polypeptide; ii) an HCV E2 polypeptide; or iii) an HCV E1 polypeptide; b) a T-cell epitope comprising a polypeptide having at least 20% (at least 20%, at least 30%, at least 40%, at least 50%, at least 60%, at least 70%, at least 80%, at least 90%, at least 95%, at least 98%, or 100%) amino acid identity to: GVYLL-PRRGPRLGVRATRKTSERSQPRGRRQPIPKARRSEG-RSWAQPGYPKSTKVPAAY AAQGYKVLVLNPSVAATLGFGAYMSK (SEQ ID NO:296) and having a length of 85 amino acids.

As another example, in some cases, an immunogenic composition of the present disclosure comprises: a) i) an HCV E1/E2 heterodimeric polypeptide; ii) an HCV E2 polypeptide; or iii) an HCV E1 polypeptide; b) a T-cell epitope comprising, in order from N-terminus to C-terminus: i) a TP35-NS3 polypeptide, as described above (e.g., a polypeptide having the following amino acid sequence: KSTKVPAAYAAQGYKVLVLNPSVAATLGFGAYMSK (SEQ ID NO:133); and having a length of 35 amino acids);

ii) a TP50C polypeptide, as described above (e.g., a polypeptide having the following amino acid sequence: GVYLL-PRRGPRLGVRATRKTSERSQPRGRRQPIPKARRSEG-RSWAQPGYP (SEQ ID NO:148); and having a length of 50 amino acids; and iii) a TP23 polypeptide, as described above (e.g., a polypeptide having the following amino acid sequence: DVVVVATDALMTGFTGDFDSVID (SEQ ID NO:186); and having a length of 23 amino acids). Thus, e.g., in some cases, an immunogenic composition of the present disclosure comprises: a) i) an HCV E1/E2 heterodimeric polypeptide; ii) an HCV E2 polypeptide; or iii) an HCV E1 polypeptide; b) a T-cell epitope comprising a polypeptide having at least 20% (at least 20%, at least 30%, at least 40%, at least 50%, at least 60%, at least 70%, at least 80%, at least 90%, at least 95%, at least 98%, or 100%) amino acid identity to: KSTKVPAAYAAQGYKVLVLNPSVAATLGF-GAYMSKGVYLLPRRGPRLGVRATRKTSE RSQPR-GRRQPIPKARRSEGRSWAQPGYPDVVV-VATDALMTGFTGDFDSVID (SEQ ID NO:295) and having a length of 108 amino acids.

As another example, in some cases, an immunogenic composition of the present disclosure comprises: a) i) an HCV E1/E2 heterodimeric polypeptide; ii) an HCV E2 polypeptide; or iii) an HCV E1 polypeptide; b) a T-cell epitope comprising, in order from N-terminus to C-terminus: i) a TP35-NS3 polypeptide, as described above (e.g., a polypeptide having the following amino acid sequence: KSTKVPAAYAAQGYKVLVLNPSVAATLGFGAYMSK (SEQ ID NO:133); and having a length of 35 amino acids); ii) a TP50C polypeptide, as described above (e.g., a polypeptide having the following amino acid sequence: GVYLL-PRRGPRLGVRATRKTSERSQPRGRRQPIPKARRSEG-RSWAQPGYP (SEQ ID NO:148); and having a length of 50 amino acids; iii) a TP23 polypeptide, as described above (e.g., a polypeptide having the following amino acid sequence: DVVVVATDALMTGFTGDFDSVID (SEQ ID NO:186); and having a length of 23 amino acids); and iv) a TP27 polypeptide, as described above (e.g., a polypeptide having the following amino acid sequence: LEQIKG-GRHLIFCHSKKKCDELAAKLT (SEQ ID NO:188); and having a length of 27 amino acids). Thus, e.g., in some cases, an immunogenic composition of the present disclosure comprises: a) i) an HCV E1/E2 heterodimeric polypeptide; ii) an HCV E2 polypeptide; or iii) an HCV E1 polypeptide; b) a T-cell epitope comprising a polypeptide having at least 20% (at least 20%, at least 30%, at least 40%, at least 50%, at least 60%, at least 70%, at least 80%, at least 90%, at least 95%, at least 98%, or 100%) amino acid identity to: KSTKVPAAYAAQGYKVLVLNPSVAATLGF-GAYMSKGVYLLPRRGPRLGVRATRKTSE RSQPR-GRRQPIPKARRSEGRSWAQPGYPDVVV-VATDALMTGFTGDFDSVIDLEQIKGGR HLIFCHSKKKCDELAAKLT SEQ ID NO:298) and having a length of 135 amino acids.

As another example, in some cases, an immunogenic composition of the present disclosure comprises: a) i) an HCV E1/E2 heterodimeric polypeptide; ii) an HCV E2 polypeptide; or iii) an HCV E1 polypeptide; b) a T-cell epitope comprising, in order from N-terminus to C-terminus: i) a TP35-NS3 polypeptide, as described above (e.g., a polypeptide having the following amino acid sequence: KSTKVPAAYAAQGYKVLVLNPSVAATLGFGAYMSK (SEQ ID NO:133); and having a length of 35 amino acids); ii) a TP50C polypeptide, as described above (e.g., a polypeptide having the following amino acid sequence: GVYLL-PRRGPRLGVRATRKTSERSQPRGRRQPIPKARRSEG-RSWAQPGYP (SEQ ID NO:148); and having a length of 50 amino acids; iii) a TP23 polypeptide, as described above (e.g., a polypeptide having the following amino acid sequence: DVVVVATDALMTGFTGDFDSVID (SEQ ID NO:186); and having a length of 23 amino acids); iv) a TP27 polypeptide, as described above (e.g., a polypeptide having the following amino acid sequence: LEQIKGGRHLIFCHS-KKKCDELAAKLT (SEQ ID NO:188); and having a length of 27 amino acids); and v) a TP35-NS4 polypeptide, as described above (e.g., a polypeptide having the following amino acid sequence: ILRRHVGPGEGAVQWMNRLIA-FASRGNHVSPTHYV (SEQ ID NO:203); and having a length of 35 amino acids. Thus, e.g., in some cases, an immunogenic composition of the present disclosure comprises: a) i) an HCV E1/E2 heterodimeric polypeptide; ii) an HCV E2 polypeptide; or iii) an HCV E1 polypeptide; b) a T-cell epitope comprising a polypeptide having at least 20% (at least 20%, at least 30%, at least 40%, at least 50%, at least 60%, at least 70%, at least 80%, at least 90%, at least 95%, at least 98%, or 100%) amino acid identity to: KSTKVPAAYAAQGYKVLVLNPSVAATLGF-GAYMSKGVYLLPRRGPRLGVRATRKTSE RSQPR-GRRQPIPKARRSEGRSWAQPGYPDVVV-VATDALMTGFTGDFDSVIDLEQIKGGR HLIFCHSKKKCDELAAKLTILR-RHVGPGEGAVQWMNRLIAFASRGNHVSPTHYV (SEQ ID NO:299) and having a length of 170 amino acids.

As another example, in some cases, an immunogenic composition of the present disclosure comprises: a) i) an HCV E1/E2 heterodimeric polypeptide; ii) an HCV E2 polypeptide; or iii) an HCV E1 polypeptide; b) a T-cell epitope comprising, in order from N-terminus to C-terminus: i) a TP35-NS3 polypeptide, as described above (e.g., a polypeptide having the following amino acid sequence: KSTKVPAAYAAQGYKVLVLNPSVAATLGFGAYMSK (SEQ ID NO:133); and having a length of 35 amino acids); ii) a TP50C polypeptide, as described above (e.g., a polypeptide having the following amino acid sequence: GVYLL-PRRGPRLGVRATRKTSERSQPRGRRQPIPKARRSEG-RSWAQPGYP (SEQ ID NO:148); and having a length of 50 amino acids; iii) a TP42 polypeptide as described above (e.g., a polypeptide having following amino acid sequence: GTEGEIPFYGKAIPLEQIKGGRHLIFCHSKKKCDE-LAAKLTG (SEQ ID NO:228); and having a length of 42 amino acids); and iv) a TP48 polypeptide as described above (e.g., a polypeptide having following amino acid sequence: ILRRHVGPGEGAVQWMNRLIAFAS-RGNHVSPTHYVPESDAAARVTQIL (SEQ ID NO:268); and having a length of 48 amino acids).

As another example, in some cases, an immunogenic composition of the present disclosure comprises: a) i) an HCV E1/E2 heterodimeric polypeptide; ii) an HCV E2 polypeptide; or iii) an HCV E1 polypeptide; b) a T-cell epitope polypeptide comprising, in order from N-terminus to C-terminus: i) a TP35-NS3 polypeptide, as described above (e.g., a polypeptide having the following amino acid sequence: KSTKVPAAYAAQGYKVLVLNPSVAATLGF-GAYMSK (SEQ ID NO:133); and having a length of 35 amino acids); ii) a TP50C polypeptide, as described above (e.g., a polypeptide having the following amino acid sequence: GVYLLPRRGPRLGVRATRKTSERSQPR-GRRQPIPKARRSEGRSWAQPGYP (SEQ ID NO:148); and having a length of 50 amino acids; iii) a TP42 polypeptide as described above (e.g., a polypeptide having following amino acid sequence: GTEGEIPFYGKAI-PLEQIKGGRHLIFCHSKKKCDELAAKLTG (SEQ ID NO:228); and having a length of 42 amino acids); iv) a TP48 polypeptide as described above (e.g., a polypeptide having following amino acid sequence: ILRRHVGPGEGAVQWMNRLIAFASRGNHVSPTHYVPESDAAARVTQIL (SEQ ID NO:268); and having a length of 48 amino acids); and v) a TP42-2 polypeptide, as described above (e.g., a polypeptide having the following amino acid sequence: KGGRHLIFCHSKKKCDELAAKLTGLGLNAVAYYRGLDVSVIP (SEQ ID NO:291); and having a length of 42 amino acids.

Fusion Polypeptides

In some cases, a T-cell epitope polypeptide suitable for inclusion in an immunogenic composition of the present disclosure is present in a fusion polypeptide comprising: a) the T-cell epitope polypeptide; and b) a heterologous fusion partner polypeptide.

Thus, in some cases, an immunogenic composition of the present disclosure includes: a) i) an HCV E1/E2 heterodimer; ii) an HCV E1 polypeptide; or iii) an HCV E2 polypeptide; and b) a fusion polypeptide comprising: i) T-cell epitope polypeptide that comprises one or more T-cell epitopes (e.g., one or more T cell epitopes present in an HCV polypeptide other than an HCV E1 polypeptide or an HCV E2 polypeptide); and ii) a heterologous fusion partner polypeptide.

Suitable heterologous fusion partner polypeptides include, but are not limited to: i) a polypeptide that increases solubility of the T-cell epitope polypeptide in aqueous solution; ii) a polypeptide that facilitates synthesis and/or purification of the T-cell epitope polypeptide; and iii) a polypeptide that presents one or more additional T-cell epitopes other than HCV T-cell epitopes.

As noted above, in some cases, an immunogenic composition of the present disclosure includes: a) i) an HCV E1/E2 heterodimer; ii) an HCV E1 polypeptide; or iii) an HCV E2 polypeptide; and b) a fusion polypeptide comprising: i) T-cell epitope polypeptide that comprises one or more T-cell epitopes (e.g., one or more T cell epitopes present in an HCV polypeptide other than an HCV E1 polypeptide or an HCV E2 polypeptide); and ii) a heterologous fusion partner polypeptide that presents one or more additional T-cell epitopes. In some cases, the heterologous fusion partner polypeptide comprises one or more T cell epitopes present in: a) cholera toxin or toxoid; and/or b) tetanus toxin or toxoid; and/or c) diphtheria toxin or toxoid; and/or d) a meningococcal outer membrane protein.

In some cases, a suitable tetanus toxoid polypeptide comprises the amino acid sequence QYIKANSKFIGIFE (SEQ ID NO:132). In some cases, a suitable tetanus toxoid polypeptide comprises the amino acid sequence QYIKANSKFIGITE (SEQ ID NO:64).

In some cases, a heterologous fusion partner polypeptide can comprise cholera toxin (or toxoid) epitope. In some cases, a suitable heterologous fusion partner polypeptide comprising a cholera toxoid epitope comprises a fragment of cholera toxin-B subunit (CT-B), e.g., a fragment of from 5 amino acids to 25 amino acids, or from 25 amino acids to 50 amino acids, of the following amino acid sequence: MIKLKFGVFF TVLLSSAYAH GTPQNITDLC AEYHNTQIHT LNDKIFSYTE SLAGKREMAI ITFKNGATFQ VEVPGSQHID SQKKAIERMK DTLRIAYLTE AKVEKLCVWN NKTPHAIAAI SMAN (SEQ ID NO:65).

In some cases, a heterologous fusion partner polypeptide can comprise a tetanus toxin (or toxoid) T-cell epitope. In some cases, a suitable heterologous fusion partner polypeptide comprising a tetanus toxin T-cell epitope comprises the amino acid sequence: ILMQYIKANSKFIGI (SEQ ID NO:66); and has a length of from 15 amino acids to 20 amino acids. In some cases, a suitable heterologous fusion partner polypeptide comprising a tetanus toxin T-cell epitope comprises the amino acid sequence: VNNESSE (SEQ ID NO:67). In some cases, a suitable heterologous fusion partner polypeptide comprising a tetanus toxin T-cell epitope comprises the amino acid sequence: PGINGKAIHLVNNESSE (SEQ ID NO:68). In some cases, a suitable heterologous fusion partner polypeptide comprising a tetanus toxin T-cell epitope comprises the amino acid sequence: PNRDIL (SEQ ID NO:69). In some cases, a suitable heterologous fusion partner polypeptide comprising a tetanus toxin T-cell epitope comprises the amino acid sequence: FIGITEL (SEQ ID NO:70). In some cases, a suitable tetanus toxin T-cell epitope comprises the amino acid sequence: SYFPSV (SEQ ID NO:71). In some cases, a suitable heterologous fusion partner polypeptide comprising a tetanus toxin T-cell epitope comprises the amino acid sequence: NSVDDALINSTKIYSYFPSV (SEQ ID NO:72). In some cases, a suitable heterologous fusion partner polypeptide comprising a tetanus toxin T-cell epitope comprises the amino acid sequence: IDKISDVSTIVPYIGPALNI (SEQ ID NO:73).

In some cases, a heterologous fusion partner polypeptide can comprise a diphtheria toxin T-cell epitope In some cases, a suitable heterologous polypeptide comprising a diphtheria toxin T-cell epitope comprises the amino acid sequence: QSIALSSLMVAQAIP (SEQ ID NO:74); and has a length of from 15 amino acids to 20 amino acids. In some cases, a suitable fusion partner heterologous polypeptide comprising a diphtheria toxin T-cell epitope comprises the amino acid sequence: PVFAGANYAAWAVNVAQVI (SEQ ID NO:75). In some cases, a suitable heterologous fusion partner polypeptide comprising a diphtheria toxin T-cell epitope comprises the amino acid sequence: VHHNTEEIVAQSIALSSLMV (SEQ ID NO:76). In some cases, a suitable heterologous fusion partner polypeptide comprising a diphtheria toxin T-cell epitope comprises the amino acid sequence: QSIALSSLMVAQAIPLVGEL (SEQ ID NO:77). In some cases, a suitable heterologous fusion partner polypeptide comprising a diphtheria toxin T-cell epitope comprises the amino acid sequence: VDIGFAAYNFVESIINLFQV (SEQ ID NO:78). In some cases, a suitable heterologous fusion partner polypeptide comprising a diphtheria toxin T-cell epitope comprises the amino acid sequence: QGESGHDIKITAENTPLPIA (SEQ ID NO:79). In some cases, a suitable heterologous fusion partner polypeptide comprising a diphtheria toxin T-cell epitope comprises the amino acid sequence: GVLLPTIPGKLDVNKSKTHI (SEQ ID NO:80). In some cases, a suitable heterologous fusion partner polypeptide comprising a diphtheria toxin T-cell epitope comprises the amino acid sequence of CRM197 (see, e.g., Giannini et al. (1984) *Nucl. Acids. Res.* 12:4063).

The amino acid sequence of CRM197 is as follows:

```
                                        (SEQ ID NO: 81)
ADDVVDSSKSFVMENFSSYHGTKPGYVDSIQKGIQKPKSGTQGNYDDDWK

EFYSTDNKYDAAGYSVDNENPLSGKAGGVVKVTYPGLTKVLALKVDNAET

IKKELGLSLTEPLMEQVGTEEFIKRFGDGASRVVLSLPFAEGSSSVEYIN

NWEQAKALSVELEINFETRGKRGQDAMYEYMAQACAGNRVRRSVGSSLSC

INLDWDVIRDKTKTKIESLKEHGPIKNKMSESPNKTVSEEKAKQYLEEFH

QTALEHPELSELKTVTGTNPVFAGANYAAWAVNVAQVIDSETADNLEKTT
```

-continued

AALSILPGIGSVMGIADGAVHENTEEIVAQSIALSSLMVAQAIPLVGELV

DIGFAAYNFVESIINLFQVVHNSYNRPAYSPGHKTQPFLHDGYAVSWNTV

EDSIIRTGFQGESGHDIKITAENTPLPIAGVLLPTIPGKLDVNKSKTHIS

VNGRKIRMRCRAIDGDVTFCRPKSPVYVGNGVHANLHVAFHRSSSEKIHS

NEISSDSIGVLGYQKTVDHTKVNSKLSLFFEIKS.

In some cases, a heterologous fusion partner polypeptide can comprise a tetanus toxin T-cell epitope and a diphtheria toxin T-cell epitope. In some of these cases, the heterologous fusion partner polypeptide can comprise the amino acid sequence: IMQYIKANSKFIGIQSIALSSLMVAQ (SEQ ID NO:82); and can have a length of from 26 amino acids to 30 amino acids.

In some cases, the fusion partner is a poly(Lys) peptide. The fusion partner can be (Lys)n, where n is an integer from 1 to 10. For example, the fusion partner can be (Lys)n, where n is 1, 2, 3, 4, 5, 6, 7, 8, 9, or 10. For example, the fusion partner can be (Lys)n, where n is 3.

TP35-NS3 with Poly(Lysine)

In some cases, a fusion polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: KSTKVPAAYAAQGYKVLVLNPSVAATLGF-GAYMSK(K)n (SEQ ID NO:300), where n is 2, 3, 4, 5, 6, 7, 8, 9, or 10 (e.g., where n is 3, or where n is 5); and has a length of from 37 amino acids to about 45 amino acids. In some cases, a fusion polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: KSTKVPAAYAAQGYKVLVLNPSVAATLGF-GAYMSKKKK (SEQ ID NO:302); and has a length of from 38 amino acids to about 43 amino acids, where the C-terminal 3 amino acids are KKK. In some cases, a T-cell epitope polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: KSTKVPAAYAAQGYKVLVLNPSVAATLGF-GAYMSKKKK (SEQ ID NO:302); and has a length of 38 amino acids, where the C-terminal 3 amino acids are KKK. In some cases, a T-cell epitope polypeptide suitable for inclusion in a composition of the present disclosure comprises the amino acid sequence KSTKVPAAYAAQGYKVLVLNPSVAATLGF-GAYMSKKKK (SEQ ID NO:302); and has a length of 38 amino acids.

TP42 with Poly(Lysine)

In some cases, a fusion polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: GTEGEIPFYGKAIPLEQIKGGRHLIFCHS-KKKCDELAAKLTG(K)n (SEQ ID NO:301), where n is 2, 3, 4, 5, 6, 7, 8, 9, or 10 (e.g., where n is 3, or where n is 5); and has a length of from 44 amino acids to about 52 amino acids. In some cases, a fusion polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: GTEGEIPFYGKAIPLEQIKG-GRHLIFCHSKKKCDELAAKLTGKKK (SEQ ID NO:231); and has a length of from 45 amino acids to about 53 amino acids, where the C-terminal 3 amino acids are KKK. In some cases, a T-cell epitope polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: GTEGEIPFYGKAIPLEQIKG-GRHLIFCHSKKKCDELAAKLTGKKK (SEQ ID NO:231); and has a length of 45 amino acids, where the C-terminal 3 amino acids are KKK. In some cases, a T-cell epitope polypeptide suitable for inclusion in a composition of the present disclosure comprises the amino acid sequence GTEGEIPFYGKAIPLEQIKGGRHLIFCHSKKKCDE-LAAKLTGKKK (SEQ ID NO:231); and has a length of 45 amino acids.

TP45 with Poly(Lysine)

In some cases, a fusion polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: LNAVAYYRGLDVSVIPTSGDVVV-VATDALMTGFTGDFDSVIDCNV(K)n (SEQ ID NO:304), where n is 2, 3, 4, 5, 6, 7, 8, 9, or 10 (e.g., where n is 3, or where n is 5); and has a length of from 47 amino acids to about 57 amino acids. In some cases, a fusion polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: LNAVAYYR-GLDVSVIPTSGDVVV-VATDALMTGFTGDFDSVIDCNVKKK (SEQ ID NO:251); and has a length of from 48 amino acids to about 53 amino acids, where the C-terminal 3 amino acids are KKK. In some cases, a T-cell epitope polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: LNAVAYYR-GLDVSVIPTSGDVVV-VATDALMTGFTGDFDSVIDCNVKKK (SEQ ID NO:251); and has a length of 48 amino acids, where the C-terminal 3 amino acids are KKK. In some cases, a T-cell epitope polypeptide suitable for inclusion in a composition of the present disclosure comprises the amino acid sequence LNAVAYYRGLDVSVIPTSGDVVV-VATDALMTGFTGDFDSVIDCNVKKK (SEQ ID NO:251); and has a length of 48 amino acids.

In some cases, a fusion polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: LNAVAYYRGLDVSVIPTSGDVVV-VATDALMTGFTGDFDSVID(K)n (SEQ ID NO:305), where n is 2, 3, 4, 5, 6, 7, 8, 9, or 10 (e.g., where n is 3, or where n is 5); and has a length of from 45 amino acids to about 55 amino acids. In some cases, a fusion polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: LNAVAYYR-GLDVSVIPTSGDVVV-VATDALMTGFTGDFDSVIDKKK (SEQ ID NO:248); and has a length of from 45 amino acids to about 55 amino acids, where the C-terminal 3 amino acids are KKK. In some cases, a T-cell epitope polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: LNAVAYYRGLDVSVIPTSGDVVV-VATDALMTGFTGDFDSVIDKKK (SEQ ID NO:248); and has a length of 45 amino acids, where the C-terminal 3 amino acids are KKK. In some cases, a T-cell epitope polypeptide suitable for inclusion in a composition of the present disclosure comprises the amino acid sequence LNAVAYYRGLDVSVIPTSGDVVV-VATDALMTGFTGDFDSVIDCNVKKK (SEQ ID NO:251); and has a length of 48 amino acids.

TP48 with Poly(Lysine)

In some cases, a fusion polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: ILRRHVGPGEGAVQWMNRLIAFAS-RGNHVSPTHYVPESDASARVTQIL(K)n (SEQ ID NO:306), where n is 2, 3, 4, 5, 6, 7, 8, 9, or 10 (e.g., where n is 3, or where n is 5); and has a length of from 50 amino acids to about 58 amino acids. In some cases, a fusion polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: ILR-RHVGPGEGAVQWMNRLIAFASRGNHVSPTHYVPES-DASARVTQILKKK (SEQ ID NO:257); and has a length of from 51 amino acids to about 58 amino acids, where the C-terminal 3 amino acids are KKK. In some cases, a T-cell epitope polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: ILR-RHVGPGEGAVQWMNRLIAFASRGNHVSPTHYVPES-DASARVTQILKKK (SEQ ID NO:257); and has a length of 51 amino acids, where the C-terminal 3 amino acids are KKK. In some cases, a T-cell epitope polypeptide suitable for inclusion in a composition of the present disclosure comprises the amino acid sequence ILR-RHVGPGEGAVQWMNRLIAFASRGNHVSPTHYVPES-DASARVTQILKKK (SEQ ID NO:257); and has a length of 51 amino acids.

TP50-C with Poly(Lysine)

In some cases, a fusion polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: GVYLLPRRGPRLGVRATRKTSERSQPR-GRRQPIPKARRSEGRSWAQPGYP(K)n (SEQ ID NO:258), where n is 2, 3, 4, 5, 6, 7, 8, 9, or 10 (e.g., where n is 3, or where n is 5); and has a length of from 52 amino acids to about 62 amino acids. In some cases, a fusion polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: GVYLL-PRRGPRLGVRATRKTSERSQPRGRRQPIPKARRSEG-RSWAQPGYPKKK (SEQ ID NO:259); and has a length of from 53 amino acids to about 58 amino acids, where the C-terminal 3 amino acids are KKK. In some cases, a T-cell epitope polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: GVYLL-PRRGPRLGVRATRKTSERSQPRGRRQPIPKARRSEG-RSWAQPGYPKKK (SEQ ID NO:259); and has a length of 53 amino acids, where the C-terminal 3 amino acids are KKK. In some cases, a T-cell epitope polypeptide suitable for inclusion in a composition of the present disclosure comprises the amino acid sequence GVYLL-PRRGPRLGVRATRKTSERSQPRGRRQPIPKARRSEG-RSWAQPGYPKKK (SEQ ID NO:259); and has a length of 53 amino acids.

TP23 with Poly(Lysine)

In some cases, a fusion polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: DVVVVATDALMTGFTGDFDSVID(K)n (SEQ ID NO:260), where n is 2, 3, 4, 5, 6, 7, 8, 9, or 10 (e.g., where n is 3, or where n is 5); and has a length of from 25 amino acids to about 33 amino acids. In some cases, a fusion polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: DVVV-VATDALMTGFTGDFDSVIDKKK (SEQ ID NO:261); and has a length of from 26 amino acids to about 30 amino acids, where the C-terminal 3 amino acids are KKK. In some cases, a T-cell epitope polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: DVVVVATDALMTGFTGDFDSVIDKKK (SEQ ID NO:261); and has a length of 26 amino acids, where the C-terminal 3 amino acids are KKK. In some cases, a T-cell epitope polypeptide suitable for inclusion in a composition of the present disclosure comprises the amino acid sequence DVVVVATDALMTGFTGDFDSVIDKKK (SEQ ID NO:261); and has a length of 26 amino acids.

TP27 with Poly(Lys)

In some cases, a fusion polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: LEQIKGGRHLIFCHSKKKCDELAAKLT(K)n (SEQ ID NO:262), where n is 2, 3, 4, 5, 6, 7, 8, 9, or 10 (e.g., where n is 3, or where n is 5); and has a length of from 30 amino acids to about 37 amino acids. In some cases, a fusion polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: LEQIKG-GRHLIFCHSKKKCDELAAKLTKKK (SEQ ID NO:263); and has a length of from 30 amino acids to about 35 amino acids, where the C-terminal 3 amino acids are KKK. In some cases, a T-cell epitope polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: LEQIKGGRHLIFCHSKKKCDELAAKLTKKK (SEQ ID NO:263); and has a length of 30 amino acids, where the C-terminal 3 amino acids are KKK. In some cases, a T-cell epitope polypeptide suitable for inclusion in a composition of the present disclosure comprises the amino acid sequence LEQIKGGRHLIFCHSKKKCDELAAKLTKKK (SEQ ID NO:263); and has a length of 30 amino acids.

TP35-NS4 with Poly(Lys)

In some cases, a fusion polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: ILRRHVGPGEGAVQWMNRLIAFAS-RGNHVSPTHYV(K)n (SEQ ID NO:264), where n is 2, 3, 4, 5, 6, 7, 8, 9, or 10 (e.g., where n is 3, or where n is 5); and has a length of from 38 amino acids to about 48 amino acids. In some cases, a fusion polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

ILRRHVGPGEGAVQWMNRLIAFAS-
RGNHVSPTHYVKKK (SEQ ID NO:265); and has a length of from 38 amino acids to about 45 amino acids, where the C-terminal 3 amino acids are KKK. In some cases, a T-cell epitope polypeptide suitable for inclusion in a composition of the present disclosure comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: ILR-RHVGPGEGAVQWMNRLIAFASRGNHVSPTHYVKKK (SEQ ID NO:265); and has a length of 38 amino acids, where the C-terminal 3 amino acids are KKK. In some cases, a T-cell epitope polypeptide suitable for inclusion in a composition of the present disclosure comprises the amino acid sequence ILRRHVGPGEGAVQWMNRLIAFAS-RGNHVSPTHYVKKK (SEQ ID NO:265); and has a length of 38 amino acids.

Mixtures of Heterologous Polypeptides (T-Cell Epitope Polypeptides)

In some cases, an immunogenic composition of the present disclosure comprises two or more different T-cell epitope polypeptides comprising a T-cell epitope present in an HCV protein other than E1 and E2 (e.g., a mixture of two or more different heterologous polypeptides comprising a T-cell epitope present in an HCV protein other than E1 and E2). In some cases, an immunogenic composition of the present disclosure comprises two different T-cell epitope polypeptides comprising a T-cell epitope present in an HCV protein other than E1 and E2 (e.g., a mixture of two different heterologous polypeptides comprising a T-cell epitope present in an HCV protein other than E1 and E2). In some cases, an immunogenic composition of the present disclosure comprises three different T-cell epitope polypeptides comprising a T-cell epitope present in an HCV protein other than E1 and E2 (e.g., a mixture of three different heterologous polypeptides comprising a T-cell epitope present in an HCV protein other than E1 and E2). In some cases, an immunogenic composition of the present disclosure comprises four different T-cell epitope polypeptides comprising a T-cell epitope present in an HCV protein other than E1 and E2 (e.g., a mixture of four different heterologous polypeptides comprising a T-cell epitope present in an HCV protein other than E1 and E2). In some cases, an immunogenic composition of the present disclosure comprises five different T-cell epitope polypeptides comprising a T-cell epitope present in an HCV protein other than E1 and E2 (e.g., a mixture of five different heterologous polypeptides comprising a T-cell epitope present in an HCV protein other than E1 and E2). In some cases, an immunogenic composition of the present disclosure comprises six different T-cell epitope polypeptides comprising a T-cell epitope present in an HCV protein other than E1 and E2 (e.g., a mixture of six different heterologous polypeptides comprising a T-cell epitope present in an HCV protein other than E1 and E2). In some cases, the immunogenic composition comprises an adjuvant.

For example, in some cases, an immunogenic composition of the present disclosure comprises: a) an HCV E1/E2 heterodimeric polypeptide; b) two or more different heterologous polypeptides comprising a T-cell epitope present in an HCV protein other than E1 and E2; and c) a pharmaceutically acceptable excipient. In some cases, an immunogenic composition of the present disclosure comprises: a) an HCV E2 polypeptide; b) two or more different heterologous polypeptides comprising a T-cell epitope present in an HCV protein other than E1 and E2; and c) a pharmaceutically acceptable excipient. In some cases, an immunogenic composition of the present disclosure comprises: a) an HCV E1 polypeptide; b) two or more different heterologous polypeptides comprising a T-cell epitope present in an HCV protein other than E1 and E2; and c) a pharmaceutically acceptable excipient. In some cases, at least one of the two or more different heterologous polypeptides comprises a fusion partner. In some cases, at least one of the two or more different heterologous polypeptides comprises a C-terminal poly (Lys), e.g., comprises a stretch of 2, 3, 4, 5, 6, 7, 8, 9, or 10 C-terminal Lys. In some cases, the immunogenic composition comprises an adjuvant.

The following compositions, numbered Compositions 1-38, are non-limiting examples. In some cases, any one of Compositions 1-38 does not include: i) an HCV E1/E2 heterodimeric polypeptide; ii) an HCV E2 polypeptide; or iii) an HCV E1 polypeptide.

Composition 1. As one example, an immunogenic composition of the present disclosure comprises: a) i) an HCV E1/E2 heterodimeric polypeptide; ii) an HCV E2 polypeptide; or iii) an HCV E1 polypeptide; b) a first T-cell epitope polypeptide comprising an amino acid sequence having at least 20% amino acid sequence identity to: KSTKVPAAYAAQGYKVLVLNPSVAATLGFGAYMSK (SEQ ID NO:133); c) a second T-cell epitope polypeptide comprising an amino acid sequence having at least 20% amino acid sequence identity to: GVYLL-PRRGPRLGVRATRKTSERSQPRGRRQPIPKARRSEG-RSWAQPGYP (SEQ ID NO:148); and d) a pharmaceutically acceptable excipient. The first T-cell epitope polypeptide can have a length of 35 amino acids; and the second T-cell epitope polypeptide can have a length of 50 amino acids. As an example, an immunogenic composition of the present disclosure can comprise: a) i) an HCV E1/E2 heterodimeric polypeptide; ii) an HCV E2 polypeptide; or iii) an HCV E1 polypeptide; b) a first T-cell epitope polypeptide comprising the following amino acid sequence: KSTKVPAAYAAQGYKVLVLNPSVAATLGFGAYMSK (SEQ ID NO:133) and having a length of 35 amino acids; c) a second T-cell epitope polypeptide comprising the following amino acid sequence: GVYLLPRRGPRLGVRATRKT-SERSQPRGRRQPIPKARRSEGRSWAQPGYP (SEQ ID NO:148) and having a length of 50 amino acids; and d) a pharmaceutically acceptable excipient. In some cases, the composition comprises an adjuvant. In some cases, at least one of the T cell epitope polypeptides comprises a fusion partner. In some cases, at least one of the T cell epitope polypeptides comprises a C-terminal poly(Lys), e.g., comprises a stretch of 2, 3, 4, 5, 6, 7, 8, 9, or 10 C-terminal Lys. In some cases, the immunogenic composition does not include any HCV polypeptides other than: a) i) an HCV E1/E2 heterodimeric polypeptide; ii) an HCV E2 polypeptide; or iii) an HCV E1 polypeptide; b) the first T-cell epitope polypeptide; and c) the second T-cell epitope polypeptide. In some cases, the immunogenic composition does not include any polypeptides other than: a) i) an HCV E1/E2 heterodimeric polypeptide; ii) an HCV E2 polypeptide; or iii) an HCV E1 polypeptide; b) the first T-cell epitope polypeptide; and c) the second T-cell epitope polypeptide.

Composition 2. As one example, an immunogenic composition of the present disclosure comprises: a) i) an HCV E1/E2 heterodimeric polypeptide; ii) an HCV E2 polypeptide; or iii) an HCV E1 polypeptide; b) a first T-cell epitope polypeptide comprising an amino acid sequence having at least 20% amino acid sequence identity to:

KSTKVPAAYAAQGYKVLVLNPSVAATLGFGAYMSK (SEQ ID NO:133); c) a second T-cell epitope polypeptide comprising an amino acid sequence having at least 20% amino acid sequence identity to: DVVVVATDALMTGFTGDFDSVID (SEQ ID NO:186); and d) a pharmaceutically acceptable excipient. The first T-cell epitope polypeptide can have a length of 35 amino acids; and the second T-cell epitope polypeptide can have a length of 23 amino acids. As an example, an immunogenic composition of the present disclosure can comprise: a) i) an HCV E1/E2 heterodimeric polypeptide; ii) an HCV E2 polypeptide; or iii) an HCV E1 polypeptide; b) a first T-cell epitope polypeptide comprising the following amino acid sequence: KSTKVPAAYAAQGYKVLVLNPSVAATLGFGAYMSK (SEQ ID NO:133) and having a length of 35 amino acids; c) a second T-cell epitope polypeptide comprising the following amino acid sequence: DVVVVATDALMTGFTGDFDSVID (SEQ ID NO:186) and having a length of 23 amino acids; and d) a pharmaceutically acceptable excipient. In some cases, the composition comprises an adjuvant. In some cases, at least one of the T cell epitope polypeptides comprises a fusion partner. In some cases, at least one of the T cell epitope polypeptides comprises a C-terminal poly(Lys), e.g., comprises a stretch of 2, 3, 4, 5, 6, 7, 8, 9, or 10 C-terminal Lys. In some cases, the immunogenic composition does not include any HCV polypeptides other than: a) i) an HCV E1/E2 heterodimeric polypeptide; ii) an HCV E2 polypeptide; or iii) an HCV E1 polypeptide; b) the first T-cell epitope polypeptide; and c) the second T-cell epitope polypeptide. In some cases, the immunogenic composition does not include any polypeptides other than: a) i) an HCV E1/E2 heterodimeric polypeptide; ii) an HCV E2 polypeptide; or iii) an HCV E1 polypeptide; b) the first T-cell epitope polypeptide; and c) the second T-cell epitope polypeptide.

Composition 3. As one example, an immunogenic composition of the present disclosure comprises: a) i) an HCV E1/E2 heterodimeric polypeptide; ii) an HCV E2 polypeptide; or iii) an HCV E1 polypeptide; b) a first T-cell epitope polypeptide comprising an amino acid sequence having at least 20% amino acid sequence identity to: KSTKVPAAYAAQGYKVLVLNPSVAATLGFGAYMSK (SEQ ID NO:133); c) a second T-cell epitope polypeptide comprising an amino acid sequence having at least 20% amino acid sequence identity to: LEQIKGGRHLIFCHSKKKCDELAAKLT (SEQ ID NO:188); and d) a pharmaceutically acceptable excipient. The first T-cell epitope polypeptide can have a length of 35 amino acids; and the second T-cell epitope polypeptide can have a length of 27 amino acids. As an example, an immunogenic composition of the present disclosure can comprise: a) i) an HCV E1/E2 heterodimeric polypeptide; ii) an HCV E2 polypeptide; or iii) an HCV E1 polypeptide; b) a first T-cell epitope polypeptide comprising the following amino acid sequence: KSTKVPAAYAAQGYKVLVLNPSVAATLGFGAYMSK (SEQ ID NO:133) and having a length of 35 amino acids; c) a second T-cell epitope polypeptide comprising the following amino acid sequence: LEQIKGGRHLIFCHSKKKCDELAAKLT (SEQ ID NO:188) and having a length of 27 amino acids; and d) a pharmaceutically acceptable excipient. In some cases, the composition comprises an adjuvant. In some cases, at least one of the T cell epitope polypeptides comprises a fusion partner. In some cases, at least one of the T cell epitope polypeptides comprises a C-terminal poly (Lys), e.g., comprises a stretch of 2, 3, 4, 5, 6, 7, 8, 9, or 10 C-terminal Lys. In some cases, the immunogenic composition does not include any HCV polypeptides other than: a) i) an HCV E1/E2 heterodimeric polypeptide; ii) an HCV E2 polypeptide; or iii) an HCV E1 polypeptide; b) the first T-cell epitope polypeptide; and c) the second T-cell epitope polypeptide. In some cases, the immunogenic composition does not include any polypeptides other than: a) i) an HCV E1/E2 heterodimeric polypeptide; ii) an HCV E2 polypeptide; or iii) an HCV E1 polypeptide; b) the first T-cell epitope polypeptide; and c) the second T-cell epitope polypeptide.

Composition 4. As one example, an immunogenic composition of the present disclosure comprises: a) i) an HCV E1/E2 heterodimeric polypeptide; ii) an HCV E2 polypeptide; or iii) an HCV E1 polypeptide; b) a first T-cell epitope polypeptide comprising an amino acid sequence having at least 20% amino acid sequence identity to: KSTKVPAAYAAQGYKVLVLNPSVAATLGFGAYMSK (SEQ ID NO:133); c) a second T-cell epitope polypeptide comprising an amino acid sequence having at least 20% amino acid sequence identity to: ILRRHVGPGEGAVQWMNRLIAFASRGNHVSPTHYV (SEQ ID NO:203); and d) a pharmaceutically acceptable excipient. The first T-cell epitope polypeptide can have a length of 35 amino acids; and the second T-cell epitope polypeptide can have a length of 35 amino acids. As an example, an immunogenic composition of the present disclosure can comprise: a) i) an HCV E1/E2 heterodimeric polypeptide; ii) an HCV E2 polypeptide; or iii) an HCV E1 polypeptide; b) a first T-cell epitope polypeptide comprising the following amino acid sequence: KSTKVPAAYAAQGYKVLVLNPSVAATLGFGAYMSK (SEQ ID NO:133) and having a length of 35 amino acids; c) a second T-cell epitope polypeptide comprising the following amino acid sequence: ILRRHVGPGEGAVQWMNRLIAFASRGNHVSPTHYV (SEQ ID NO:203) and having a length of 35 amino acids; and d) a pharmaceutically acceptable excipient. In some cases, the composition comprises an adjuvant. In some cases, at least one of the T cell epitope polypeptides comprises a fusion partner. In some cases, at least one of the T cell epitope polypeptides comprises a C-terminal poly(Lys), e.g., comprises a stretch of 2, 3, 4, 5, 6, 7, 8, 9, or 10 C-terminal Lys. In some cases, the immunogenic composition does not include any HCV polypeptides other than: a) i) an HCV E1/E2 heterodimeric polypeptide; ii) an HCV E2 polypeptide; or iii) an HCV E1 polypeptide; b) the first T-cell epitope polypeptide; and c) the second T-cell epitope polypeptide. In some cases, the immunogenic composition does not include any polypeptides other than: a) i) an HCV E1/E2 heterodimeric polypeptide; ii) an HCV E2 polypeptide; or iii) an HCV E1 polypeptide; b) the first T-cell epitope polypeptide; and c) the second T-cell epitope polypeptide.

Composition 5. As one example, an immunogenic composition of the present disclosure comprises: a) i) an HCV E1/E2 heterodimeric polypeptide; ii) an HCV E2 polypeptide; or iii) an HCV E1 polypeptide; b) a first T-cell epitope polypeptide comprising an amino acid sequence having at least 20% amino acid sequence identity to: GVYLLPRRGPRLGVRATRKTSERSQPRGRRQPIPKARRSEGRSWAQPGYP (SEQ ID NO:148); c) a second T-cell epitope polypeptide comprising an amino acid sequence having at least 20% amino acid sequence identity to: DVVVVATDALMTGFTGDFDSVID (SEQ ID NO:186); and d) a pharmaceutically acceptable excipient. The first T-cell epitope polypeptide can have a length of 50 amino acids; and the second T-cell epitope polypeptide can have a length of 23 amino acids. As an example, an immunogenic composition of the present disclosure can comprise: a) i) an HCV E1/E2 heterodimeric polypeptide; ii) an HCV E2 polypeptide; or iii) an HCV E1 polypeptide; b) a first T-cell epitope polypeptide comprising the following amino acid sequence: GVYLLPRRGPRLGVRATRKTSERSQPR-GRRQPIPKARRSEGRSWAQPGYP (SEQ ID NO:148) and having a length of 50 amino acids; c) a second T-cell epitope polypeptide comprising the following amino acid sequence: DVVVVATDALMTGFTGDFDSVID (SEQ ID NO:186) and having a length of 23 amino acids; and d) a pharmaceutically acceptable excipient. In some cases, the composition comprises an adjuvant. In some cases, at least one of the T cell epitope polypeptides comprises a fusion partner. In some cases, at least one of the T cell epitope polypeptides comprises a C-terminal poly(Lys), e.g., comprises a stretch of 2, 3, 4, 5, 6, 7, 8, 9, or 10 C-terminal Lys. In some cases, the immunogenic composition does not include any HCV polypeptides other than: a) i) an HCV E1/E2 heterodimeric polypeptide; ii) an HCV E2 polypeptide; or iii) an HCV E1 polypeptide; b) the first T-cell epitope polypeptide; and c) the second T-cell epitope polypeptide. In some cases, the immunogenic composition does not include any polypeptides other than: a) i) an HCV E1/E2 heterodimeric polypeptide; ii) an HCV E2 polypeptide; or iii) an HCV E1 polypeptide; b) the first T-cell epitope polypeptide; and c) the second T-cell epitope polypeptide.

Composition 6. As one example, an immunogenic composition of the present disclosure comprises: a) i) an HCV E1/E2 heterodimeric polypeptide; ii) an HCV E2 polypeptide; or iii) an HCV E1 polypeptide; b) a first T-cell epitope polypeptide comprising an amino acid sequence having at least 20% amino acid sequence identity to: GVYLL-PRRGPRLGVRATRKTSERSQPRGRRQPIPKARRSEG-RSWAQPGYP (SEQ ID NO:148); c) a second T-cell epitope polypeptide comprising an amino acid sequence having at least 20% amino acid sequence identity to: LEQIKG-GRHLIFCHSKKKCDELAAKLT (SEQ ID NO:188); and d) a pharmaceutically acceptable excipient. The first T-cell epitope polypeptide can have a length of 50 amino acids; and the second T-cell epitope polypeptide can have a length of 27 amino acids. As an example, an immunogenic composition of the present disclosure can comprise: a) i) an HCV E1/E2 heterodimeric polypeptide; ii) an HCV E2 polypeptide; or iii) an HCV E1 polypeptide; b) a first T-cell epitope polypeptide comprising the following amino acid sequence: GVYLLPRRGPRLGVRATRKTSERSQPR-GRRQPIPKARRSEGRSWAQPGYP (SEQ ID NO:148) and having a length of 50 amino acids; c) a second T-cell epitope polypeptide comprising the following amino acid sequence: LEQIKGGRHLIFCHSKKKCDELAAKLT (SEQ ID NO:188) and having a length of 27 amino acids; and d) a pharmaceutically acceptable excipient. In some cases, the composition comprises an adjuvant. In some cases, at least one of the T cell epitope polypeptides comprises a fusion partner. In some cases, at least one of the T cell epitope polypeptides comprises a C-terminal poly(Lys), e.g., comprises a stretch of 2, 3, 4, 5, 6, 7, 8, 9, or 10 C-terminal Lys. In some cases, the immunogenic composition does not include any HCV polypeptides other than: a) i) an HCV E1/E2 heterodimeric polypeptide; ii) an HCV E2 polypeptide; or iii) an HCV E1 polypeptide; b) the first T-cell epitope polypeptide; and c) the second T-cell epitope polypeptide. In some cases, the immunogenic composition does not include any polypeptides other than: a) i) an HCV E1/E2 heterodimeric polypeptide; ii) an HCV E2 polypeptide; or iii) an HCV E1 polypeptide; b) the first T-cell epitope polypeptide; and c) the second T-cell epitope polypeptide.

Composition 7. As one example, an immunogenic composition of the present disclosure comprises: a) i) an HCV E1/E2 heterodimeric polypeptide; ii) an HCV E2 polypeptide; or iii) an HCV E1 polypeptide; b) a first T-cell epitope polypeptide comprising an amino acid sequence having at least 20% amino acid sequence identity to: GVYLL-PRRGPRLGVRATRKTSERSQPRGRRQPIPKARRSEG-RSWAQPGYP (SEQ ID NO:148); c) a second T-cell epitope polypeptide comprising an amino acid sequence having at least 20% amino acid sequence identity to: ILR-RHVGPGEGAVQWMNRLIAFASRGNHVSPTHYV (SEQ ID NO:203); and d) a pharmaceutically acceptable excipient. The first T-cell epitope polypeptide can have a length of 50 amino acids; and the second T-cell epitope polypeptide can have a length of 35 amino acids. As an example, an immunogenic composition of the present disclosure can comprise: a) i) an HCV E1/E2 heterodimeric polypeptide; ii) an HCV E2 polypeptide; or iii) an HCV E1 polypeptide; b) a first T-cell epitope polypeptide comprising the following amino acid sequence: GVYLLPRRGPRLGVRATRKTS-ERSQPRGRRQPIPKARRSEGRSWAQPGYP (SEQ ID NO:148) and having a length of 50 amino acids; c) a second T-cell epitope polypeptide comprising the following amino acid sequence: ILRRHVGPGEGAVQWMNRLIAFAS-RGNHVSPTHYV (SEQ ID NO:203) and having a length of 35 amino acids; and d) a pharmaceutically acceptable excipient. In some cases, the composition comprises an adjuvant. In some cases, at least one of the T cell epitope polypeptides comprises a fusion partner. In some cases, at least one of the T cell epitope polypeptides comprises a C-terminal poly(Lys), e.g., comprises a stretch of 2, 3, 4, 5, 6, 7, 8, 9, or 10 C-terminal Lys. In some cases, the immunogenic composition does not include any HCV polypeptides other than: a) i) an HCV E1/E2 heterodimeric polypeptide; ii) an HCV E2 polypeptide; or iii) an HCV E1 polypeptide; b) the first T-cell epitope polypeptide; and c) the second T-cell epitope polypeptide. In some cases, the immunogenic composition does not include any polypeptides other than: a) i) an HCV E1/E2 heterodimeric polypeptide; ii) an HCV E2 polypeptide; or iii) an HCV E1 polypeptide; b) the first T-cell epitope polypeptide; and c) the second T-cell epitope polypeptide.

Composition 8. As one example, an immunogenic composition of the present disclosure comprises: a) i) an HCV E1/E2 heterodimeric polypeptide; ii) an HCV E2 polypeptide; or iii) an HCV E1 polypeptide; b) a first T-cell epitope polypeptide comprising an amino acid sequence having at least 20% amino acid sequence identity to: DVVV-VATDALMTGFTGDFDSVID (SEQ ID NO:186); c) a second T-cell epitope polypeptide comprising an amino acid sequence having at least 20% amino acid sequence identity to: LEQIKGGRHLIFCHSKKKCDELAAKLT (SEQ ID NO:188); and d) a pharmaceutically acceptable excipient. The first T-cell epitope polypeptide can have a length of 23 amino acids; and the second T-cell epitope polypeptide can have a length of 27 amino acids. As an example, an immunogenic composition of the present disclosure can comprise: a) i) an HCV E1/E2 heterodimeric polypeptide; ii) an HCV E2 polypeptide; or iii) an HCV E1 polypeptide; b) a first T-cell epitope polypeptide comprising the following amino acid sequence: DVVVVATDALMTGFTGDFDSVID (SEQ ID NO:186) and having a length of 23 amino acids; c) a second T-cell epitope polypeptide comprising the following amino acid sequence: LEQIKGGRHLIFCHSKKKCDE-LAAKLT (SEQ ID NO:188) and having a length of 27 amino acids; and d) a pharmaceutically acceptable excipient. In some cases, the composition comprises an adjuvant. In some cases, at least one of the T cell epitope polypeptides comprises a fusion partner. In some cases, at least one of the T cell epitope polypeptides comprises a C-terminal poly (Lys), e.g., comprises a stretch of 2, 3, 4, 5, 6, 7, 8, 9, or 10 C-terminal Lys. In some cases, the immunogenic composition does not include any HCV polypeptides other than: a) i) an HCV E1/E2 heterodimeric polypeptide; ii) an HCV E2 polypeptide; or iii) an HCV E1 polypeptide; b) the first T-cell epitope polypeptide; and c) the second T-cell epitope polypeptide. In some cases, the immunogenic composition does not include any polypeptides other than: a) i) an HCV E1/E2 heterodimeric polypeptide; ii) an HCV E2 polypeptide; or iii) an HCV E1 polypeptide; b) the first T-cell epitope polypeptide; and c) the second T-cell epitope polypeptide.

Composition 9. As one example, an immunogenic composition of the present disclosure comprises: a) i) an HCV E1/E2 heterodimeric polypeptide; ii) an HCV E2 polypeptide; or iii) an HCV E1 polypeptide; b) a first T-cell epitope polypeptide comprising an amino acid sequence having at least 20% amino acid sequence identity to: DVVVVATDALMTGFTGDFDSVID (SEQ ID NO:186); c) a second T-cell epitope polypeptide comprising an amino acid sequence having at least 20% amino acid sequence identity to: ILRRHVGPGEGAVQWMNRLIAFASRGNHVSPTHYV (SEQ ID NO:203); and d) a pharmaceutically acceptable excipient. The first T-cell epitope polypeptide can have a length of 23 amino acids; and the second T-cell epitope polypeptide can have a length of 35 amino acids. As an example, an immunogenic composition of the present disclosure can comprise: a) i) an HCV E1/E2 heterodimeric polypeptide; ii) an HCV E2 polypeptide; or iii) an HCV E1 polypeptide; b) a first T-cell epitope polypeptide comprising the following amino acid sequence: DVVVVATDALMTGFTGDFDSVID (SEQ ID NO:186) and having a length of 23 amino acids; c) a second T-cell epitope polypeptide comprising the following amino acid sequence: ILRRHVGPGEGAVQWMNRLIAFASRGNHVSPTHYV (SEQ ID NO:203) and having a length of 35 amino acids; and d) a pharmaceutically acceptable excipient. In some cases, the composition comprises an adjuvant. In some cases, at least one of the T cell epitope polypeptides comprises a fusion partner. In some cases, at least one of the T cell epitope polypeptides comprises a C-terminal poly(Lys), e.g., comprises a stretch of 2, 3, 4, 5, 6, 7, 8, 9, or 10 C-terminal Lys. In some cases, the immunogenic composition does not include any HCV polypeptides other than: a) i) an HCV E1/E2 heterodimeric polypeptide; ii) an HCV E2 polypeptide; or iii) an HCV E1 polypeptide; b) the first T-cell epitope polypeptide; and c) the second T-cell epitope polypeptide. In some cases, the immunogenic composition does not include any polypeptides other than: a) i) an HCV E1/E2 heterodimeric polypeptide; ii) an HCV E2 polypeptide; or iii) an HCV E1 polypeptide; b) the first T-cell epitope polypeptide; and c) the second T-cell epitope polypeptide.

Composition 10. As one example, an immunogenic composition of the present disclosure comprises: a) i) an HCV E1/E2 heterodimeric polypeptide; ii) an HCV E2 polypeptide; or iii) an HCV E1 polypeptide; b) a first T-cell epitope polypeptide comprising an amino acid sequence having at least 20% amino acid sequence identity to: LEQIKGGRHLIFCHSKKKCDELAAKLT (SEQ ID NO:188); c) a second T-cell epitope polypeptide comprising an amino acid sequence having at least 20% amino acid sequence identity to: ILRRHVGPGEGAVQWMNRLIAFASRGNHVSPTHYV (SEQ ID NO:203); and d) a pharmaceutically acceptable excipient. The first T-cell epitope polypeptide can have a length of 27 amino acids; and the second T-cell epitope polypeptide can have a length of 35 amino acids. As an example, an immunogenic composition of the present disclosure can comprise: a) i) an HCV E1/E2 heterodimeric polypeptide; ii) an HCV E2 polypeptide; or iii) an HCV E1 polypeptide; b) a first T-cell epitope polypeptide comprising the following amino acid sequence: LEQIKGGRHLIFCHSKKKCDELAAKLT (SEQ ID NO:188) and having a length of 27 amino acids; c) a second T-cell epitope polypeptide comprising the following amino acid sequence: ILRRHVGPGEGAVQWMNRLIAFASRGNHVSPTHYV (SEQ ID NO:203) and having a length of 35 amino acids; and d) a pharmaceutically acceptable excipient. In some cases, the composition comprises an adjuvant. In some cases, at least one of the T cell epitope polypeptides comprises a fusion partner. In some cases, at least one of the T cell epitope polypeptides comprises a C-terminal poly(Lys), e.g., comprises a stretch of 2, 3, 4, 5, 6, 7, 8, 9, or 10 C-terminal Lys. In some cases, the immunogenic composition does not include any HCV polypeptides other than: a) i) an HCV E1/E2 heterodimeric polypeptide; ii) an HCV E2 polypeptide; or iii) an HCV E1 polypeptide; b) the first T-cell epitope polypeptide; and c) the second T-cell epitope polypeptide. In some cases, the immunogenic composition does not include any polypeptides other than: a) i) an HCV E1/E2 heterodimeric polypeptide; ii) an HCV E2 polypeptide; or iii) an HCV E1 polypeptide; b) the first T-cell epitope polypeptide; and c) the second T-cell epitope polypeptide.

Composition 11. As one example, an immunogenic composition of the present disclosure comprises: a) i) an HCV E1/E2 heterodimeric polypeptide; ii) an HCV E2 polypeptide; or iii) an HCV E1 polypeptide; b) a first T-cell epitope polypeptide comprising an amino acid sequence having at least 20% amino acid sequence identity to: KSTKVPAAYAAQGYKVLVLNPSVAATLGFGAYMSK (SEQ ID NO:133); c) a second T-cell epitope polypeptide comprising an amino acid sequence having at least 20% amino acid sequence identity to: GVYLLPRRGPRLGVRATRKTSERSQPRGRRQPIPKARRSEGRSWAQPGYP (SEQ ID NO:148); d) a third T-cell epitope polypeptide comprising an amino acid sequence having at least 20% amino acid sequence identity to: DVVVVATDALMTGFTGDFDSVID (SEQ ID NO:186); and e) a pharmaceutically acceptable excipient. The first T-cell epitope polypeptide can have a length of 35 amino acids; the second T-cell epitope polypeptide can have a length of 50 amino acids; and the third T-cell epitope polypeptide can have a length of 23 amino acids. As an example, an immunogenic composition of the present disclosure can comprise: a) i) an HCV E1/E2 heterodimeric polypeptide; ii) an HCV E2 polypeptide; or iii) an HCV E1 polypeptide; b) a first T-cell epitope polypeptide comprising the following amino acid sequence: KSTKVPAAYAAQGYKVLVLNPSVAATLGFGAYMSK (SEQ ID NO:133) and having a length of 35 amino acids; c) a second T-cell epitope polypeptide comprising the following amino acid sequence: GVYLLPRRGPRLGVRATRKTSERSQPRGRRQPIPKARRSEGRSWAQPGYP (SEQ ID NO:148) and having a length of 50 amino acids; d) a third T-cell epitope polypeptide comprising an amino acid sequence having at least 20% amino acid sequence identity to: DVVVVATDALMTGFTGDFDSVID (SEQ ID NO:186) and having a length of 23 amino acids; and e) a pharmaceutically acceptable excipient. In some cases, the composition comprises an adjuvant. In some cases, at least one of the T cell epitope polypeptides comprises a fusion partner. In some cases, at least one of the T cell epitope polypeptides comprises a C-terminal poly(Lys), e.g., comprises a stretch of 2, 3, 4, 5, 6, 7, 8, 9, or 10 C-terminal Lys. In some cases, the immunogenic composition does not include any HCV polypeptides other than: a) i) an HCV E1/E2 heterodimeric polypeptide; ii) an HCV E2 polypeptide; or iii) an HCV E1 polypeptide; b) the first T-cell epitope polypeptide; c) the second T-cell epitope polypeptide; and d) the third T-cell epitope polypeptide. In some cases, the immunogenic composition does not include any polypeptides other than: a) i) an HCV E1/E2 heterodimeric polypeptide; ii) an HCV E2 polypeptide; or iii) an HCV E1 polypeptide; b) the first T-cell epitope polypeptide; c) the second T-cell epitope polypeptide; and d) the third T-cell epitope polypeptide.

Composition 12. As one example, an immunogenic composition of the present disclosure comprises: a) i) an HCV E1/E2 heterodimeric polypeptide; ii) an HCV E2 polypeptide; or iii) an HCV E1 polypeptide; b) a first T-cell epitope polypeptide comprising an amino acid sequence having at least 20% amino acid sequence identity to: KSTKVPAAYAAQGYKVLVLNPSVAATLGFGAYMSK (SEQ ID NO:133); c) a second T-cell epitope polypeptide comprising an amino acid sequence having at least 20% amino acid sequence identity to: GVYLL-PRRGPRLGVRATRKTSERSQPRGRRQPIPKARRSEG-RSWAQPGYP (SEQ ID NO:148); d) a third T-cell epitope polypeptide comprising an amino acid sequence having at least 20% amino acid sequence identity to: LEQIKG-GRHLIFCHSKKKCDELAAKLT (SEQ ID NO:188); and e) a pharmaceutically acceptable excipient. The first T-cell epitope polypeptide can have a length of 35 amino acids; the second T-cell epitope polypeptide can have a length of 50 amino acids; and the third T-cell epitope polypeptide can have a length of 27 amino acids. As an example, an immunogenic composition of the present disclosure can comprise: a) i) an HCV E1/E2 heterodimeric polypeptide; ii) an HCV E2 polypeptide; or iii) an HCV E1 polypeptide; b) a first T-cell epitope polypeptide comprising the following amino acid sequence: KSTKVPAAYAAQGYKVLVLNPSVAATLGFGAYMSK (SEQ ID NO:133) and having a length of 35 amino acids; c) a second T-cell epitope polypeptide comprising the following amino acid sequence: GVYLLPRRGPRLGVRATRKT-SERSQPRGRRQPIPKARRSEGRSWAQPGYP (SEQ ID NO:148) and having a length of 50 amino acids; d) a third T-cell epitope polypeptide comprising an amino acid sequence having at least 20% amino acid sequence identity to: LEQIKGGRHLIFCHSKKKCDELAAKLT (SEQ ID NO:188) and having a length of 27 amino acids; and e) a pharmaceutically acceptable excipient. In some cases, the composition comprises an adjuvant. In some cases, at least one of the T cell epitope polypeptides comprises a fusion partner. In some cases, at least one of the T cell epitope polypeptides comprises a C-terminal poly(Lys), e.g., comprises a stretch of 2, 3, 4, 5, 6, 7, 8, 9, or 10 C-terminal Lys. In some cases, the immunogenic composition does not include any HCV polypeptides other than: a) i) an HCV E1/E2 heterodimeric polypeptide; ii) an HCV E2 polypeptide; or iii) an HCV E1 polypeptide; b) the first T-cell epitope polypeptide; c) the second T-cell epitope polypeptide; and d) the third T-cell epitope polypeptide. In some cases, the immunogenic composition does not include any polypeptides other than: a) i) an HCV E1/E2 heterodimeric polypeptide; ii) an HCV E2 polypeptide; or iii) an HCV E1 polypeptide; b) the first T-cell epitope polypeptide; c) the second T-cell epitope polypeptide; and d) the third T-cell epitope polypeptide.

Composition 13. As one example, an immunogenic composition of the present disclosure comprises: a) i) an HCV E1/E2 heterodimeric polypeptide; ii) an HCV E2 polypeptide; or iii) an HCV E1 polypeptide; b) a first T-cell epitope polypeptide comprising an amino acid sequence having at least 20% amino acid sequence identity to: KSTKVPAAYAAQGYKVLVLNPSVAATLGFGAYMSK (SEQ ID NO:133); c) a second T-cell epitope polypeptide comprising an amino acid sequence having at least 20% amino acid sequence identity to: GVYLL-PRRGPRLGVRATRKTSERSQPRGRRQPIPKARRSEG-RSWAQPGYP (SEQ ID NO:148); d) a third T-cell epitope polypeptide comprising an amino acid sequence having at least 20% amino acid sequence identity to: ILR-RHVGPGEGAVQWMNRLIAFASRGNHVSPTHYV (SEQ ID NO:203); and e) a pharmaceutically acceptable excipient. The first T-cell epitope polypeptide can have a length of 35 amino acids; the second T-cell epitope polypeptide can have a length of 50 amino acids; and the third T-cell epitope polypeptide can have a length of 35 amino acids. As an example, an immunogenic composition of the present disclosure can comprise: a) i) an HCV E1/E2 heterodimeric polypeptide; ii) an HCV E2 polypeptide; or iii) an HCV E1 polypeptide; b) a first T-cell epitope polypeptide comprising the following amino acid sequence: KSTKVPAAYAAQGYKVLVLNPSVAATLGFGAYMSK (SEQ ID NO:133) and having a length of 35 amino acids; c) a second T-cell epitope polypeptide comprising the following amino acid sequence: GVYLLPRRGPRLGVRATRKT-SERSQPRGRRQPIPKARRSEGRSWAQPGYP (SEQ ID NO:148) and having a length of 50 amino acids; d) a third T-cell epitope polypeptide comprising an amino acid sequence having at least 20% amino acid sequence identity to: ILRRHVGPGEGAVQWMNRLIAFAS-RGNHVSPTHYV (SEQ ID NO:203) and having a length of 35 amino acids; and e) a pharmaceutically acceptable excipient. In some cases, the composition comprises an adjuvant. In some cases, at least one of the T cell epitope polypeptides comprises a fusion partner. In some cases, at least one of the T cell epitope polypeptides comprises a C-terminal poly (Lys), e.g., comprises a stretch of 2, 3, 4, 5, 6, 7, 8, 9, or 10 C-terminal Lys. In some cases, the immunogenic composition does not include any HCV polypeptides other than: a) i) an HCV E1/E2 heterodimeric polypeptide; ii) an HCV E2 polypeptide; or iii) an HCV E1 polypeptide; b) the first T-cell epitope polypeptide; c) the second T-cell epitope polypeptide; and d) the third T-cell epitope polypeptide. In some cases, the immunogenic composition does not include any polypeptides other than: a) i) an HCV E1/E2 heterodimeric polypeptide; ii) an HCV E2 polypeptide; or iii) an HCV E1 polypeptide; b) the first T-cell epitope polypeptide; c) the second T-cell epitope polypeptide; and d) the third T-cell epitope polypeptide.

Composition 14. As one example, an immunogenic composition of the present disclosure comprises: a) i) an HCV E1/E2 heterodimeric polypeptide; ii) an HCV E2 polypeptide; or iii) an HCV E1 polypeptide; b) a first T-cell epitope polypeptide comprising an amino acid sequence having at least 20% amino acid sequence identity to: GVYLL-PRRGPRLGVRATRKTSERSQPRGRRQPIPKARRSEG-RSWAQPGYP (SEQ ID NO:148); c) a second T-cell epitope polypeptide comprising an amino acid sequence having at least 20% amino acid sequence identity to: DVVV-VATDALMTGFTGDFDSVID (SEQ ID NO:186); d) a third T-cell epitope polypeptide comprising an amino acid sequence having at least 20% amino acid sequence identity to: LEQIKGGRHLIFCHSKKKCDELAAKLT (SEQ ID NO:188); and e) a pharmaceutically acceptable excipient. The first T-cell epitope polypeptide can have a length of 50 amino acids; the second T-cell epitope polypeptide can have a length of 23 amino acids; and the third T-cell epitope polypeptide can have a length of 27 amino acids. As an example, an immunogenic composition of the present disclosure can comprise: a) i) an HCV E1/E2 heterodimeric polypeptide; ii) an HCV E2 polypeptide; or iii) an HCV E1 polypeptide; b) a first T-cell epitope polypeptide comprising the following amino acid sequence: GVYLL-PRRGPRLGVRATRKTSERSQPRGRRQPIPKARRSEG-RSWAQPGYP (SEQ ID NO:148) and having a length of 50 amino acids; c) a second T-cell epitope polypeptide comprising the following amino acid sequence: DVVV-VATDALMTGFTGDFDSVID (SEQ ID NO:186) and having a length of 23 amino acids; d) a third T-cell epitope polypeptide comprising an amino acid sequence having at least 20% amino acid sequence identity to: LEQIKG-GRHLIFCHSKKKCDELAAKLT (SEQ ID NO:188) and having a length of 27 amino acids; and e) a pharmaceutically acceptable excipient. In some cases, the composition comprises an adjuvant. In some cases, at least one of the T cell epitope polypeptides comprises a fusion partner. In some cases, at least one of the T cell epitope polypeptides comprises a C-terminal poly(Lys), e.g., comprises a stretch of 2, 3, 4, 5, 6, 7, 8, 9, or 10 C-terminal Lys. In some cases, the immunogenic composition does not include any HCV polypeptides other than: a) i) an HCV E1/E2 heterodimeric polypeptide; ii) an HCV E2 polypeptide; or iii) an HCV E1 polypeptide; b) the first T-cell epitope polypeptide; c) the second T-cell epitope polypeptide; and d) the third T-cell epitope polypeptide. In some cases, the immunogenic composition does not include any polypeptides other than: a) i) an HCV E1/E2 heterodimeric polypeptide; ii) an HCV E2 polypeptide; or iii) an HCV E1 polypeptide; b) the first T-cell epitope polypeptide; c) the second T-cell epitope polypeptide; and d) the third T-cell epitope polypeptide.

Composition 15. As one example, an immunogenic composition of the present disclosure comprises: a) i) an HCV E1/E2 heterodimeric polypeptide; ii) an HCV E2 polypeptide; or iii) an HCV E1 polypeptide; b) a first T-cell epitope polypeptide comprising an amino acid sequence having at least 20% amino acid sequence identity to: GVYLL-PRRGPRLGVRATRKTSERSQPRGRRQPIPKARRSEG-RSWAQPGYP (SEQ ID NO:148); c) a second T-cell epitope polypeptide comprising an amino acid sequence having at least 20% amino acid sequence identity to: DVVV-VATDALMTGFTGDFDSVID (SEQ ID NO:186); d) a third T-cell epitope polypeptide comprising an amino acid sequence having at least 20% amino acid sequence identity to: ILRRHVGPGEGAVQWMNRLIAFAS-RGNHVSPTHYV (SEQ ID NO:203); and e) a pharmaceutically acceptable excipient. The first T-cell epitope polypeptide can have a length of 50 amino acids; the second T-cell epitope polypeptide can have a length of 23 amino acids; and the third T-cell epitope polypeptide can have a length of 35 amino acids. As an example, an immunogenic composition of the present disclosure can comprise: a) i) an HCV E1/E2 heterodimeric polypeptide; ii) an HCV E2 polypeptide; or iii) an HCV E1 polypeptide; b) a first T-cell epitope polypeptide comprising the following amino acid sequence: GVYLLPRRGPRLGVRATRKTSERSQPR-GRRQPIPKARRSEGRSWAQPGYP (SEQ ID NO:148) and having a length of 50 amino acids; c) a second T-cell epitope polypeptide comprising the following amino acid sequence: DVVVVATDALMTGFTGDFDSVID (SEQ ID NO:186) and having a length of 23 amino acids; d) a third T-cell epitope polypeptide comprising an amino acid sequence having at least 20% amino acid sequence identity to: ILR-RHVGPGEGAVQWMNRLIAFASRGNHVSPTHYV (SEQ ID NO:203) and having a length of 35 amino acids; and e) a pharmaceutically acceptable excipient. In some cases, the composition comprises an adjuvant. In some cases, at least one of the T cell epitope polypeptides comprises a fusion partner. In some cases, at least one of the T cell epitope polypeptides comprises a C-terminal poly(Lys), e.g., comprises a stretch of 2, 3, 4, 5, 6, 7, 8, 9, or 10 C-terminal Lys. In some cases, the immunogenic composition does not include any HCV polypeptides other than: a) i) an HCV E1/E2 heterodimeric polypeptide; ii) an HCV E2 polypeptide; or iii) an HCV E1 polypeptide; b) the first T-cell epitope polypeptide; c) the second T-cell epitope polypeptide; and d) the third T-cell epitope polypeptide. In some cases, the immunogenic composition does not include any polypeptides other than: a) i) an HCV E1/E2 heterodimeric polypeptide; ii) an HCV E2 polypeptide; or iii) an HCV E1 polypeptide; b) the first T-cell epitope polypeptide; c) the second T-cell epitope polypeptide; and d) the third T-cell epitope polypeptide.

Composition 16. As one example, an immunogenic composition of the present disclosure comprises: a) i) an HCV E1/E2 heterodimeric polypeptide; ii) an HCV E2 polypeptide; or iii) an HCV E1 polypeptide; b) a first T-cell epitope polypeptide comprising an amino acid sequence having at least 20% amino acid sequence identity to: DVVV-VATDALMTGFTGDFDSVID (SEQ ID NO:186); c) a second T-cell epitope polypeptide comprising an amino acid sequence having at least 20% amino acid sequence identity to: LEQIKGGRHLIFCHSKKKCDELAAKLT (SEQ ID NO:188); d) a third T-cell epitope polypeptide comprising an amino acid sequence having at least 20% amino acid sequence identity to: ILRRHVGPGEGAVQWMNRLIA-FASRGNHVSPTHYV (SEQ ID NO:203); and e) a pharmaceutically acceptable excipient. The first T-cell epitope polypeptide can have a length of 23 amino acids; the second T-cell epitope polypeptide can have a length of 27 amino acids; and the third T-cell epitope polypeptide can have a length of 35 amino acids. As an example, an immunogenic composition of the present disclosure can comprise: a) i) an HCV E1/E2 heterodimeric polypeptide; ii) an HCV E2 polypeptide; or iii) an HCV E1 polypeptide; b) a first T-cell epitope polypeptide comprising the following amino acid sequence: DVVVVATDALMTGFTGDFDSVID (SEQ ID NO:186) and having a length of 23 amino acids; c) a second T-cell epitope polypeptide comprising the following amino acid sequence: LEQIKGGRHLIFCHSKKKCDELAAKLT (SEQ ID NO:188) and having a length of 27 amino acids; d) a third T-cell epitope polypeptide comprising an amino acid sequence having at least 20% amino acid sequence identity to: ILRRHVGPGEGAVQWMNRLIAFAS-RGNHVSPTHYV (SEQ ID NO:203) and having a length of 35 amino acids; and e) a pharmaceutically acceptable excipient. In some cases, the composition comprises an adjuvant. In some cases, at least one of the T cell epitope polypeptides comprises a fusion partner. In some cases, at least one of the T cell epitope polypeptides comprises a C-terminal poly (Lys), e.g., comprises a stretch of 2, 3, 4, 5, 6, 7, 8, 9, or 10 C-terminal Lys. In some cases, the immunogenic composition does not include any HCV polypeptides other than: a) i) an HCV E1/E2 heterodimeric polypeptide; ii) an HCV E2 polypeptide; or iii) an HCV E1 polypeptide; b) the first T-cell epitope polypeptide; c) the second T-cell epitope polypeptide; and d) the third T-cell epitope polypeptide. In some cases, the immunogenic composition does not include any polypeptides other than: a) i) an HCV E1/E2 heterodimeric polypeptide; ii) an HCV E2 polypeptide; or iii) an HCV E1 polypeptide; b) the first T-cell epitope polypeptide; c) the second T-cell epitope polypeptide; and d) the third T-cell epitope polypeptide.

Composition 17. As one example, an immunogenic composition of the present disclosure comprises: a) i) an HCV E1/E2 heterodimeric polypeptide; ii) an HCV E2 polypeptide; or iii) an HCV E1 polypeptide; b) a first T-cell epitope polypeptide comprising an amino acid sequence having at least 20% amino acid sequence identity to: KSTKVPAAYAAQGYKVLVLNPSVAATLGFGAYMSK (SEQ ID NO:133); c) a second T-cell epitope polypeptide comprising an amino acid sequence having at least 20% amino acid sequence identity to: GVYLLPRRGPRLGVRATRKTSERSQPRGRRQPIPKARRSEGRSWAQPGYP (SEQ ID NO:148); d) a third T-cell epitope polypeptide comprising an amino acid sequence having at least 20% amino acid sequence identity to: DVVVVATDALMTGFTGDFDSVID (SEQ ID NO:186); e) a fourth T-cell epitope polypeptide comprising an amino acid sequence having at least 20% amino acid sequence identity to: LEQIKGGRHLIFCHSKKKCDELAAKLT (SEQ ID NO:188); and f) a pharmaceutically acceptable excipient. The first T-cell epitope polypeptide can have a length of 35 amino acids; the second T-cell epitope polypeptide can have a length of 50 amino acids; the third T-cell epitope polypeptide can have a length of 23 amino acids; and the fourth T-cell epitope polypeptide can have a length of 27 amino acids. As an example, an immunogenic composition of the present disclosure can comprise: a) i) an HCV E1/E2 heterodimeric polypeptide; ii) an HCV E2 polypeptide; or iii) an HCV E1 polypeptide; b) a first T-cell epitope polypeptide comprising the following amino acid sequence: KSTKVPAAYAAQGYKVLVLNPSVAATLGFGAYMSK (SEQ ID NO:133) and having a length of 35 amino acids; c) a second T-cell epitope polypeptide comprising the following amino acid sequence: GVYLLPRRGPRLGVRATRKTSERSQPRGRRQPIPKARRSEGRSWAQPGYP (SEQ ID NO:148) and having a length of 50 amino acids; d) a third T-cell epitope polypeptide comprising an amino acid sequence having at least 20% amino acid sequence identity to: DVVVVATDALMTGFTGDFDSVID (SEQ ID NO:186) and having a length of 23 amino acids; e) a fourth T-cell epitope polypeptide comprising an amino acid sequence having at least 20% amino acid sequence identity to: LEQIKGGRHLIFCHSKKKCDELAAKLT (SEQ ID NO:188) and having a length of 27 amino acids; and f) a pharmaceutically acceptable excipient. In some cases, the composition comprises an adjuvant. In some cases, at least one of the T cell epitope polypeptides comprises a fusion partner. In some cases, at least one of the T cell epitope polypeptides comprises a C-terminal poly(Lys), e.g., comprises a stretch of 2, 3, 4, 5, 6, 7, 8, 9, or 10 C-terminal Lys. In some cases, the immunogenic composition does not include any HCV polypeptides other than: a) i) an HCV E1/E2 heterodimeric polypeptide; ii) an HCV E2 polypeptide; or iii) an HCV E1 polypeptide; b) the first T-cell epitope polypeptide; c) the second T-cell epitope polypeptide; d) the third T-cell epitope polypeptide; and e) the fourth T-cell epitope polypeptide. In some cases, the immunogenic composition does not include any polypeptides other than: a) i) an HCV E1/E2 heterodimeric polypeptide; ii) an HCV E2 polypeptide; or iii) an HCV E1 polypeptide; b) the first T-cell epitope polypeptide; c) the second T-cell epitope polypeptide; d) the third T-cell epitope polypeptide; and e) the fourth T-cell epitope polypeptide.

Composition 18. As one example, an immunogenic composition of the present disclosure comprises: a) i) an HCV E1/E2 heterodimeric polypeptide; ii) an HCV E2 polypeptide; or iii) an HCV E1 polypeptide; b) a first T-cell epitope polypeptide comprising an amino acid sequence having at least 20% amino acid sequence identity to: KSTKVPAAYAAQGYKVLVLNPSVAATLGFGAYMSK (SEQ ID NO:133); c) a second T-cell epitope polypeptide comprising an amino acid sequence having at least 20% amino acid sequence identity to: GVYLLPRRGPRLGVRATRKTSERSQPRGRRQPIPKARRSEGRSWAQPGYP (SEQ ID NO:148); d) a third T-cell epitope polypeptide comprising an amino acid sequence having at least 20% amino acid sequence identity to: DVVVVATDALMTGFTGDFDSVID (SEQ ID NO:186); e) a fourth T-cell epitope polypeptide comprising an amino acid sequence having at least 20% amino acid sequence identity to: ILRRHVGPGEGAVQWMNRLIAFASRGNHVSPTHYV (SEQ ID NO:203); and f) a pharmaceutically acceptable excipient. The first T-cell epitope polypeptide can have a length of 35 amino acids; the second T-cell epitope polypeptide can have a length of 50 amino acids; the third T-cell epitope polypeptide can have a length of 23 amino acids; and the fourth T-cell epitope polypeptide can have a length of 35 amino acids. As an example, an immunogenic composition of the present disclosure can comprise: a) i) an HCV E1/E2 heterodimeric polypeptide; ii) an HCV E2 polypeptide; or iii) an HCV E1 polypeptide; b) a first T-cell epitope polypeptide comprising the following amino acid sequence: KSTKVPAAYAAQGYKVLVLNPSVAATLGFGAYMSK (SEQ ID NO:133) and having a length of 35 amino acids; c) a second T-cell epitope polypeptide comprising the following amino acid sequence: GVYLLPRRGPRLGVRATRKTSERSQPRGRRQPIPKARRSEGRSWAQPGYP (SEQ ID NO:148) and having a length of 50 amino acids; d) a third T-cell epitope polypeptide comprising an amino acid sequence having at least 20% amino acid sequence identity to: DVVVVATDALMTGFTGDFDSVID (SEQ ID NO:186) and having a length of 23 amino acids; e) a fourth T-cell epitope polypeptide comprising an amino acid sequence having at least 20% amino acid sequence identity to: ILRRHVGPGEGAVQWMNRLIAFASRGNHVSPTHYV (SEQ ID NO:203) and having a length of 35 amino acids; and f) a pharmaceutically acceptable excipient. In some cases, the composition comprises an adjuvant. In some cases, at least one of the T cell epitope polypeptides comprises a fusion partner. In some cases, at least one of the T cell epitope polypeptides comprises a C-terminal poly(Lys), e.g., comprises a stretch of 2, 3, 4, 5, 6, 7, 8, 9, or 10 C-terminal Lys. In some cases, the immunogenic composition does not include any HCV polypeptides other than: a) i) an HCV E1/E2 heterodimeric polypeptide; ii) an HCV E2 polypeptide; or iii) an HCV E1 polypeptide; b) the first T-cell epitope polypeptide; c) the second T-cell epitope polypeptide; d) the third T-cell epitope polypeptide; and e) the fourth T-cell epitope polypeptide. In some cases, the immunogenic composition does not include any polypeptides other than: a) i) an HCV E1/E2 heterodimeric polypeptide; ii) an HCV E2 polypeptide; or iii) an HCV E1 polypeptide; b) the first T-cell epitope polypeptide; c) the second T-cell epitope polypeptide; d) the third T-cell epitope polypeptide; and e) the fourth T-cell epitope polypeptide.

Composition 19. As one example, an immunogenic composition of the present disclosure comprises: a) i) an HCV E1/E2 heterodimeric polypeptide; ii) an HCV E2 polypeptide; or iii) an HCV E1 polypeptide; b) a first T-cell epitope polypeptide comprising an amino acid sequence having at least 20% amino acid sequence identity to:

KSTKVPAAYAAQGYKVLVLNPSVAATLGFGAYMSK (SEQ ID NO:133); c) a second T-cell epitope polypeptide comprising an amino acid sequence having at least 20% amino acid sequence identity to: GVYLL-PRRGPRLGVRATRKTSERSQPRGRRQPIPKARRSEG-RSWAQPGYP (SEQ ID NO:148); d) a third T-cell epitope polypeptide comprising an amino acid sequence having at least 20% amino acid sequence identity to: LEQIKG-GRHLIFCHSKKKCDELAAKLT (SEQ ID NO:188); e) a fourth T-cell epitope polypeptide comprising an amino acid sequence having at least 20% amino acid sequence identity to: ILRRHVGPGEGAVQWMNRLIAFAS-RGNHVSPTHYV (SEQ ID NO:203); and f) a pharmaceutically acceptable excipient. The first T-cell epitope polypeptide can have a length of 35 amino acids; the second T-cell epitope polypeptide can have a length of 50 amino acids; the third T-cell epitope polypeptide can have a length of 27 amino acids; and the fourth T-cell epitope polypeptide can have a length of 35 amino acids. As an example, an immunogenic composition of the present disclosure can comprise: a) i) an HCV E1/E2 heterodimeric polypeptide; ii) an HCV E2 polypeptide; or iii) an HCV E1 polypeptide; b) a first T-cell epitope polypeptide comprising the following amino acid sequence: KSTKVPAAYAAQGYKVLVLNPSVAATLGFGAYMSK (SEQ ID NO:133) and having a length of 35 amino acids; c) a second T-cell epitope polypeptide comprising the following amino acid sequence: GVYLLPRRGPRLGVRATRKT-SERSQPRGRRQPIPKARRSEGRSWAQPGYP (SEQ ID NO:148) and having a length of 50 amino acids; d) a third T-cell epitope polypeptide comprising an amino acid sequence having at least 20% amino acid sequence identity to: LEQIKGGRHLIFCHSKKKCDELAAKLT (SEQ ID NO:188) and having a length of 27 amino acids; e) a fourth T-cell epitope polypeptide comprising an amino acid sequence having at least 20% amino acid sequence identity to: ILRRHVGPGEGAVQWMNRLIAFAS-RGNHVSPTHYV (SEQ ID NO:203) and having a length of 35 amino acids; and f) a pharmaceutically acceptable excipient. In some cases, the composition comprises an adjuvant. In some cases, at least one of the T cell epitope polypeptides comprises a fusion partner. In some cases, at least one of the T cell epitope polypeptides comprises a C-terminal poly (Lys), e.g., comprises a stretch of 2, 3, 4, 5, 6, 7, 8, 9, or 10 C-terminal Lys. In some cases, the immunogenic composition does not include any HCV polypeptides other than: a) i) an HCV E1/E2 heterodimeric polypeptide; ii) an HCV E2 polypeptide; or iii) an HCV E1 polypeptide; b) the first T-cell epitope polypeptide; c) the second T-cell epitope polypeptide; d) the third T-cell epitope polypeptide; and e) the fourth T-cell epitope polypeptide. In some cases, the immunogenic composition does not include any polypeptides other than: a) i) an HCV E1/E2 heterodimeric polypeptide; ii) an HCV E2 polypeptide; or iii) an HCV E1 polypeptide; b) the first T-cell epitope polypeptide; c) the second T-cell epitope polypeptide; d) the third T-cell epitope polypeptide; and e) the fourth T-cell epitope polypeptide.

Composition 20. As one example, an immunogenic composition of the present disclosure comprises: a) i) an HCV E1/E2 heterodimeric polypeptide; ii) an HCV E2 polypeptide; or iii) an HCV E1 polypeptide; b) a first T-cell epitope polypeptide comprising an amino acid sequence having at least 20% amino acid sequence identity to: KSTKVPAAYAAQGYKVLVLNPSVAATLGFGAYMSK (SEQ ID NO:133); c) a second T-cell epitope polypeptide comprising an amino acid sequence having at least 20% amino acid sequence identity to: GVYLL-PRRGPRLGVRATRKTSERSQPRGRRQPIPKARRSEG-RSWAQPGYP (SEQ ID NO:148); d) a third T-cell epitope polypeptide comprising an amino acid sequence having at least 20% amino acid sequence identity to: DVVV-VATDALMTGFTGDFDSVID (SEQ ID NO:186); e) a fourth T-cell epitope polypeptide comprising an amino acid sequence having at least 20% amino acid sequence identity to: LEQIKGGRHLIFCHSKKKCDELAAKLT (SEQ ID NO:188); f) a fifth T-cell epitope polypeptide comprising an amino acid sequence having at least 20% amino acid sequence identity to: ILRRHVGPGEGAVQWMNRLIA-FASRGNHVSPTHYV (SEQ ID NO:203); and g) a pharmaceutically acceptable excipient. The first T-cell epitope polypeptide can have a length of 35 amino acids; the second T-cell epitope polypeptide can have a length of 50 amino acids; the third T-cell epitope polypeptide can have a length of 23 amino acids; the fourth T-cell epitope polypeptide can have a length of 27 amino acids; and the fifth T-cell epitope polypeptide can have a length of 35 amino acids. As an example, an immunogenic composition of the present disclosure can comprise: a) i) an HCV E1/E2 heterodimeric polypeptide; ii) an HCV E2 polypeptide; or iii) an HCV E1 polypeptide; b) a first T-cell epitope polypeptide comprising the following amino acid sequence: KSTKVPAAYAAQGYKVLVLNPSVAATLGFGAYMSK (SEQ ID NO:133) and having a length of 35 amino acids; c) a second T-cell epitope polypeptide comprising the following amino acid sequence: GVYLLPRRGPRLGVRATRKT-SERSQPRGRRQPIPKARRSEGRSWAQPGYP (SEQ ID NO:148) and having a length of 50 amino acids; d) a third T-cell epitope polypeptide comprising an amino acid sequence having at least 20% amino acid sequence identity to: DVVVVATDALMTGFTGDFDSVID (SEQ ID NO:186) and having a length of 23 amino acids; e) a fourth T-cell epitope polypeptide comprising an amino acid sequence having at least 20% amino acid sequence identity to: LEQIKGGRHLIFCHSKKKCDELAAKLT (SEQ ID NO:188) and having a length of 27 amino acids; f) a fifth T-cell epitope polypeptide comprising an amino acid sequence having at least 20% amino acid sequence identity to: ILRRHVGPGEGAVQWMNRLIAFAS-RGNHVSPTHYV (SEQ ID NO:203) and having a length of 35 amino acids; and g) a pharmaceutically acceptable excipient. In some cases, the composition comprises an adjuvant. In some cases, at least one of the T cell epitope polypeptides comprises a fusion partner. In some cases, at least one of the T cell epitope polypeptides comprises a C-terminal poly(Lys), e.g., comprises a stretch of 2, 3, 4, 5, 6, 7, 8, 9, or 10 C-terminal Lys. In some cases, the immunogenic composition does not include any HCV polypeptides other than: a) i) an HCV E1/E2 heterodimeric polypeptide; ii) an HCV E2 polypeptide; or iii) an HCV E1 polypeptide; b) the first T-cell epitope polypeptide; c) the second T-cell epitope polypeptide; d) the third T-cell epitope polypeptide; e) the fourth T-cell epitope polypeptide; and f) the fifth T-cell epitope polypeptide. In some cases, the immunogenic composition does not include any polypeptides other than: a) i) an HCV E1/E2 heterodimeric polypeptide; ii) an HCV E2 polypeptide; or iii) an HCV E1 polypeptide; b) the first T-cell epitope polypeptide; c) the second T-cell epitope polypeptide; d) the third T-cell epitope polypeptide; e) the fourth T-cell epitope polypeptide; and f) the fifth T-cell epitope polypeptide.

Composition 21. As one example, an immunogenic composition of the present disclosure comprises: a) i) an HCV E1/E2 heterodimeric polypeptide; ii) an HCV E2 polypeptide; or iii) an HCV E1 polypeptide; b) a first T-cell epitope polypeptide comprising an amino acid sequence having at least 20% amino acid sequence identity to: KSTKVPAAYAAQGYKVLVLNPSVAATLGFGAYMSK (SEQ ID NO:133); c) a second T-cell epitope polypeptide comprising an amino acid sequence having at least 20% amino acid sequence identity to: GTEGEIPFYGKAI-PLEQIKGGRHLIFCHSKKKCDELAAKLTG(K)n (SEQ ID NO:301), where n is an integer from 2 to 10 (e.g., where n is 2, 3, 4, 5, 6, 7, 8, 9, or 10); and d) a pharmaceutically acceptable excipient. The first T-cell epitope polypeptide can have a length of 35 amino acids; and the second T-cell epitope polypeptide can have a length of from 44 amino acids to 52 amino acids. As an example, an immunogenic composition of the present disclosure can comprise: a) i) an HCV E1/E2 heterodimeric polypeptide; ii) an HCV E2 polypeptide; or iii) an HCV E1 polypeptide; b) a first T-cell epitope polypeptide comprising the following amino acid sequence: KSTKVPAAYAAQGYKVLVLNPSVAATLGF-GAYMSK (SEQ ID NO:133) and having a length of 35 amino acids; c) a second T-cell epitope polypeptide comprising the following amino acid sequence: GTEGEIPFYGKAIPLEQIKGGRHLIFCHSKKKCDE-LAAKLTGKKK (SEQ ID NO:231) and has a length of 45 amino acids; and d) a pharmaceutically acceptable excipient. In some cases, the composition comprises an adjuvant. In some cases, at least one of the T cell epitope polypeptides comprises a fusion partner. In some cases, the immunogenic composition does not include any HCV polypeptides other than: a) i) an HCV E1/E2 heterodimeric polypeptide; ii) an HCV E2 polypeptide; or iii) an HCV E1 polypeptide; b) the first T-cell epitope polypeptide; and c) the second T-cell epitope polypeptide. In some cases, the immunogenic composition does not include any polypeptides other than: a) i) an HCV E1/E2 heterodimeric polypeptide; ii) an HCV E2 polypeptide; or iii) an HCV E1 polypeptide; b) the first T-cell epitope polypeptide; and c) the second T-cell epitope polypeptide.

Composition 22. As one example, an immunogenic composition of the present disclosure comprises: a) i) an HCV E1/E2 heterodimeric polypeptide; ii) an HCV E2 polypeptide; or iii) an HCV E1 polypeptide; b) a first T-cell epitope polypeptide comprising an amino acid sequence having at least 20% amino acid sequence identity to: KSTKVPAAYAAQGYKVLVLNPSVAATLGFGAYMSK (SEQ ID NO:133); c) a second T-cell epitope polypeptide comprising an amino acid sequence having at least 20% amino acid sequence identity to: LNAVAYYR-GLDVSVIPTSGDVVV-VATDALMTGFTGDFDSVIDCNV(K)n (SEQ ID NO:304), where n is an integer from 2 to 10 (e.g., where n is 2, 3, 4, 5, 6, 7, 8, 9, or 10); and d) a pharmaceutically acceptable excipient. The first T-cell epitope polypeptide can have a length of 35 amino acids; and the second T-cell epitope polypeptide can have a length of from 47 amino acids to 57 amino acids. As an example, an immunogenic composition of the present disclosure can comprise: a) i) an HCV E1/E2 heterodimeric polypeptide; ii) an HCV E2 polypeptide; or iii) an HCV E1 polypeptide; b) a first T-cell epitope polypeptide comprising the following amino acid sequence: KSTKVPAAYAAQGYKVLVLNPSVAATLGFGAYMSK (SEQ ID NO:133) and having a length of 35 amino acids; c) a second T-cell epitope polypeptide comprising the following amino acid sequence: LNAVAYYR-GLDVSVIPTSGDVVV-VATDALMTGFTGDFDSVIDCNVKKK (SEQ ID NO:251) and having a length of 48 amino acids; and d) a pharmaceutically acceptable excipient. In some cases, the composition comprises an adjuvant. In some cases, at least one of the T cell epitope polypeptides comprises a fusion partner. In some cases, at least one of the T cell epitope polypeptides comprises a C-terminal poly(Lys), e.g., comprises a stretch of 2, 3, 4, 5, 6, 7, 8, 9, or 10 C-terminal Lys. In some cases, the immunogenic composition does not include any HCV polypeptides other than: a) i) an HCV E1/E2 heterodimeric polypeptide; ii) an HCV E2 polypeptide; or iii) an HCV E1 polypeptide; b) the first T-cell epitope polypeptide; and c) the second T-cell epitope polypeptide. In some cases, the immunogenic composition does not include any polypeptides other than: a) i) an HCV E1/E2 heterodimeric polypeptide; ii) an HCV E2 polypeptide; or iii) an HCV E1 polypeptide; b) the first T-cell epitope polypeptide; and c) the second T-cell epitope polypeptide.

Composition 23. As one example, an immunogenic composition of the present disclosure comprises: a) i) an HCV E1/E2 heterodimeric polypeptide; ii) an HCV E2 polypeptide; or iii) an HCV E1 polypeptide; b) a first T-cell epitope polypeptide comprising an amino acid sequence having at least 20% amino acid sequence identity to: KSTKVPAAYAAQGYKVLVLNPSVAATLGFGAYMSK (SEQ ID NO:133); c) a second T-cell epitope polypeptide comprising an amino acid sequence having at least 20% amino acid sequence identity to: ILR-RHVGPGEGAVQWMNRLIAFASRGNHVSPTHYVPES-DASARVTQIL(Lys)n (SEQ ID NO:308), where n is an integer from 2 to 10 (e.g., where n is 2, 3, 4, 5, 6, 7, 8, 9, or 10); and d) a pharmaceutically acceptable excipient. The first T-cell epitope polypeptide can have a length of 35 amino acids; and the second T-cell epitope polypeptide an have a length of from 50 amino acids to 58 amino acids. As an example, an immunogenic composition of the present disclosure can comprise: a) i) an HCV E1/E2 heterodimeric polypeptide; ii) an HCV E2 polypeptide; or iii) an HCV E1 polypeptide; b) a first T-cell epitope polypeptide comprising the following amino acid sequence: KSTKVPAAYAAQGYKVLVLNPSVAATLGFGAYMSK (SEQ ID NO:133) and having a length of 35 amino acids; c) a second T-cell epitope polypeptide comprising the following amino acid sequence: ILR-RHVGPGEGAVQWMNRLIAFASRGNHVSPTHYVPES-DASARVTQILKKK (SEQ ID NO:257) and having a length of 51 amino acids; and d) a pharmaceutically acceptable excipient. In some cases, the composition comprises an adjuvant. In some cases, at least one of the T cell epitope polypeptides comprises a fusion partner. In some cases, at least one of the T cell epitope polypeptides comprises a C-terminal poly(Lys), e.g., comprises a stretch of 2, 3, 4, 5, 6, 7, 8, 9, or 10 C-terminal Lys. In some cases, the immunogenic composition does not include any HCV polypeptides other than: a) i) an HCV E1/E2 heterodimeric polypeptide; ii) an HCV E2 polypeptide; or iii) an HCV E1 polypeptide; b) the first T-cell epitope polypeptide; and c) the second T-cell epitope polypeptide. In some cases, the immunogenic composition does not include any polypeptides other than: a) i) an HCV E1/E2 heterodimeric polypeptide; ii) an HCV E2 polypeptide; or iii) an HCV E1 polypeptide; b) the first T-cell epitope polypeptide; and c) the second T-cell epitope polypeptide.

Composition 24. As one example, an immunogenic composition of the present disclosure comprises: a) i) an HCV E1/E2 heterodimeric polypeptide; ii) an HCV E2 polypeptide; or iii) an HCV E1 polypeptide; b) a first T-cell epitope polypeptide comprising an amino acid sequence having at least 20% amino acid sequence identity to: GTEGEIPFYGKAIPLEQIKGGRHLIFCHSKKKCDE- LAAKLTG(K)n (SEQ ID NO:301), where n is an integer from 2 to 10 (e.g., where n is 2, 3, 4, 5, 6, 7, 8, 9, or 10); c) a second T-cell epitope polypeptide comprising an amino acid sequence having at least 20% amino acid sequence identity to: LNAVAYYRGLDVSVIPTSGDVVV-VATDALMTGFTGDFDSVIDCNV(K)n (SEQ ID NO:304), where n is an integer from 2 to 10 (e.g., where n is 2, 3, 4, 5, 6, 7, 8, 9, or 10); and d) a pharmaceutically acceptable excipient. The first T-cell epitope polypeptide can have a length of from 44 amino acids to 52 amino acids; and the second T-cell epitope polypeptide can have a length of from 47 amino acids to 57 amino acids. As an example, an immunogenic composition of the present disclosure can comprise: a) i) an HCV E1/E2 heterodimeric polypeptide; ii) an HCV E2 polypeptide; or iii) an HCV E1 polypeptide; b) a first T-cell epitope polypeptide comprising the following amino acid sequence: GTEGEIPFYGKAIPLEQIKG-GRHLIFCHSKKKCDELAAKLTGKKK (SEQ ID NO:231) and having a length of 45 amino acids; c) a second T-cell epitope polypeptide comprising the following amino acid sequence: LNAVAYYRGLDVSVIPTSGDVVV-VATDALMTGFTGDFDSVIDCNVKKK (SEQ ID NO:251) and having a length of 48 amino acids; and d) a pharmaceutically acceptable excipient. In some cases, the composition comprises an adjuvant. In some cases, at least one of the T cell epitope polypeptides comprises a fusion partner. In some cases, at least one of the T cell epitope polypeptides comprises a C-terminal poly(Lys), e.g., comprises a stretch of 2, 3, 4, 5, 6, 7, 8, 9, or 10 C-terminal Lys. In some cases, the immunogenic composition does not include any HCV polypeptides other than: a) i) an HCV E1/E2 heterodimeric polypeptide; ii) an HCV E2 polypeptide; or iii) an HCV E1 polypeptide; b) the first T-cell epitope polypeptide; and c) the second T-cell epitope polypeptide. In some cases, the immunogenic composition does not include any polypeptides other than: a) i) an HCV E1/E2 heterodimeric polypeptide; ii) an HCV E2 polypeptide; or iii) an HCV E1 polypeptide; b) the first T-cell epitope polypeptide; and c) the second T-cell epitope polypeptide.

Composition 25. As one example, an immunogenic composition of the present disclosure comprises: a) i) an HCV E1/E2 heterodimeric polypeptide; ii) an HCV E2 polypeptide; or iii) an HCV E1 polypeptide; b) a first T-cell epitope polypeptide comprising an amino acid sequence having at least 20% amino acid sequence identity to: GTEGEIPFYGKAIPLEQIKGGRHLIFCHSKKKCDE-LAAKLTG(K)n (SEQ ID NO:301), where n is an integer from 2 to 10 (e.g., where n is 2, 3, 4, 5, 6, 7, 8, 9, or 10); c) a second T-cell epitope polypeptide comprising an amino acid sequence having at least 20% amino acid sequence identity to: ILRRHVGPGEGAVQWMNRLIAFAS-RGNHVSPTHYVPESDASARVTQIL (SEQ ID NO:254); and d) a pharmaceutically acceptable excipient. The first T-cell epitope polypeptide can have a length of from 44 amino acids to 52 amino acids; and the second T-cell epitope polypeptide can have a length of 48 amino acids. As an example, an immunogenic composition of the present disclosure can comprise: a) i) an HCV E1/E2 heterodimeric polypeptide; ii) an HCV E2 polypeptide; or iii) an HCV E1 polypeptide; b) a first T-cell epitope polypeptide comprising the following amino acid sequence: GTEGEIPFYGKAI-PLEQIKGGRHLIFCHSKKKCDELAAKLTGKKK (SEQ ID NO:231) and having a length of 45 amino acids; c) a second T-cell epitope polypeptide comprising the following amino acid sequence: ILRRHVGPGEGAVQWMNRLIA-FASRGNHVSPTHYVPESDASARVTQIL(Lys)n (SEQ ID NO:308), where n is an integer from 2 to 10 (e.g., where n is 2, 3, 4, 5, 6, 7, 8, 9, or 10); and d) a pharmaceutically acceptable excipient. For example, in some cases, the second T-cell epitope polypeptide comprises the following amino acid sequence: ILRRHVGPGEGAVQWMNRLIA-FASRGNHVSPTHYVPESDASARVTQILKKK (SEQ ID NO:257) and has a length of 51 amino acids. In some cases, the composition comprises an adjuvant. In some cases, at least one of the T cell epitope polypeptides comprises a fusion partner. In some cases, at least one of the T cell epitope polypeptides comprises a C-terminal poly(Lys), e.g., comprises a stretch of 2, 3, 4, 5, 6, 7, 8, 9, or 10 C-terminal Lys. In some cases, the immunogenic composition does not include any HCV polypeptides other than: a) i) an HCV E1/E2 heterodimeric polypeptide; ii) an HCV E2 polypeptide; or iii) an HCV E1 polypeptide; b) the first T-cell epitope polypeptide; and c) the second T-cell epitope polypeptide. In some cases, the immunogenic composition does not include any polypeptides other than: a) i) an HCV E1/E2 heterodimeric polypeptide; ii) an HCV E2 polypeptide; or iii) an HCV E1 polypeptide; b) the first T-cell epitope polypeptide; and c) the second T-cell epitope polypeptide.

Composition 26. As one example, an immunogenic composition of the present disclosure comprises: a) i) an HCV E1/E2 heterodimeric polypeptide; ii) an HCV E2 polypeptide; or iii) an HCV E1 polypeptide; b) a first T-cell epitope polypeptide comprising an amino acid sequence having at least 20% amino acid sequence identity to: GTEGEIPFYGKAIPLEQIKGGRHLIFCHSKKKCDE-LAAKLTG(K)n (SEQ ID NO:301), where n is an integer from 2 to 10 (e.g., where n is 2, 3, 4, 5, 6, 7, 8, 9, or 10); c) a second T-cell epitope polypeptide comprising an amino acid sequence having at least 20% amino acid sequence identity to: GVYLLPRRGPRLGVRATRKTSERSQPR-GRRQPIPKARRSEGRSWAQPGYP (SEQ ID NO:148); and d) a pharmaceutically acceptable excipient. The first T-cell epitope polypeptide can have a length of from 44 amino acids to 52 amino acids; and the second T-cell epitope polypeptide can have a length of 50 amino acids. As an example, an immunogenic composition of the present disclosure can comprise: a) i) an HCV E1/E2 heterodimeric polypeptide; ii) an HCV E2 polypeptide; or iii) an HCV E1 polypeptide; b) a first T-cell epitope polypeptide comprising the following amino acid sequence: GTEGEIPFYGKAI-PLEQIKGGRHLIFCHSKKKCDELAAKLTGKKK (SEQ ID NO:231) and having a length of 45 amino acids; c) a second T-cell epitope polypeptide comprising the following amino acid sequence: GVYLLPRRGPRLGVRATRKTS-ERSQPRGRRQPIPKARRSEGRSWAQPGYP (SEQ ID NO:148) and having a length of 50 amino acids; and d) a pharmaceutically acceptable excipient. In some cases, the composition comprises an adjuvant. In some cases, at least one of the T cell epitope polypeptides comprises a fusion partner. In some cases, at least one of the T cell epitope polypeptides comprises a C-terminal poly(Lys), e.g., comprises a stretch of 2, 3, 4, 5, 6, 7, 8, 9, or 10 C-terminal Lys. In some cases, the immunogenic composition does not include any HCV polypeptides other than: a) i) an HCV E1/E2 heterodimeric polypeptide; ii) an HCV E2 polypeptide; or iii) an HCV E1 polypeptide; b) the first T-cell epitope polypeptide; and c) the second T-cell epitope polypeptide. In some cases, the immunogenic composition does not include any polypeptides other than: a) i) an HCV E1/E2 heterodimeric polypeptide; ii) an HCV E2 polypeptide; or iii) an HCV E1 polypeptide; b) the first T-cell epitope polypeptide; and c) the second T-cell epitope polypeptide.

Composition 27. As one example, an immunogenic composition of the present disclosure comprises: a) i) an HCV E1/E2 heterodimeric polypeptide; ii) an HCV E2 polypeptide; or iii) an HCV E1 polypeptide; b) a first T-cell epitope polypeptide comprising an amino acid sequence having at least 20% amino acid sequence identity to: ILR-RHVGPGEGAVQWMNRLIAFASRGNHVSPTHYVPES-DASARVTQIL(Lys)n (SEQ ID NO:308), where n is an integer from 2 to 10 (e.g., where n is 2, 3, 4, 5, 6, 7, 8, 9, or 10); c) a second T-cell epitope polypeptide comprising an amino acid sequence having at least 20% amino acid sequence identity to: GVYLLPRRGPRLGVRATRKTSER-SQPRGRRQPIPKARRSEGRSWAQPGYP (SEQ ID NO:148); and d) a pharmaceutically acceptable excipient. The first T-cell epitope polypeptide can have a length of from 50 amino acids to 58 amino acids s; and the second T-cell epitope polypeptide can have a length of 50 amino acids. As an example, an immunogenic composition of the present disclosure can comprise: a) i) an HCV E1/E2 heterodimeric polypeptide; ii) an HCV E2 polypeptide; or iii) an HCV E1 polypeptide; b) a first T-cell epitope polypeptide comprising the following amino acid sequence: ILR-RHVGPGEGAVQWMNRLIAFASRGNHVSPTHYVPES-DASARVTQILKKK (SEQ ID NO:257) and having a length of 51 amino acids; c) a second T-cell epitope polypeptide comprising the following amino acid sequence: GVYLL-PRRGPRLGVRATRKTSERSQPRGRRQPIPKARRSEG-RSWAQPGYP (SEQ ID NO:148) and having a length of 50 amino acids; and d) a pharmaceutically acceptable excipient. In some cases, the composition comprises an adjuvant. In some cases, at least one of the T cell epitope polypeptides comprises a fusion partner. In some cases, at least one of the T cell epitope polypeptides comprises a C-terminal poly (Lys), e.g., comprises a stretch of 2, 3, 4, 5, 6, 7, 8, 9, or 10 C-terminal Lys. In some cases, the immunogenic composition does not include any HCV polypeptides other than: a) i) an HCV E1/E2 heterodimeric polypeptide; ii) an HCV E2 polypeptide; or iii) an HCV E1 polypeptide; b) the first T-cell epitope polypeptide; and c) the second T-cell epitope polypeptide. In some cases, the immunogenic composition does not include any polypeptides other than: a) i) an HCV E1/E2 heterodimeric polypeptide; ii) an HCV E2 polypeptide; or iii) an HCV E1 polypeptide; b) the first T-cell epitope polypeptide; and c) the second T-cell epitope polypeptide.

Composition 28. As one example, an immunogenic composition of the present disclosure comprises: a) i) an HCV E1/E2 heterodimeric polypeptide; ii) an HCV E2 polypeptide; or iii) an HCV E1 polypeptide; b) a first T-cell epitope polypeptide comprising an amino acid sequence having at least 20% amino acid sequence identity to: KSTKVPAAYAAQGYKVLVLNPSVAATLGF-GAYMSKKKK (SEQ ID NO:302); c) a second T-cell epitope polypeptide comprising an amino acid sequence having at least 20% amino acid sequence identity to: GTEGEIPFYGKAIPLEQIKGGRHLIFCHSKKKCDE-LAAKLTG(K)n (SEQ ID NO:301), where n is an integer from 2 to 10 (e.g., where n is 2, 3, 4, 5, 6, 7, 8, 9, or 10); and d) a pharmaceutically acceptable excipient. The first T-cell epitope polypeptide can have a length of 38 amino acids; and the second T-cell epitope polypeptide can have a length of from 44 amino acids to 52 amino acids. As an example, an immunogenic composition of the present disclosure can comprise: a) i) an HCV E1/E2 heterodimeric polypeptide; ii) an HCV E2 polypeptide; or iii) an HCV E1 polypeptide; b) a first T-cell epitope polypeptide comprising the following amino acid sequence: KSTKVPAAYAAQGYKVLVLNPSVAATLGF-GAYMSKKKK (SEQ ID NO:302) and having a length of 38 amino acids; c) a second T-cell epitope polypeptide comprising the following amino acid sequence: GTEGEIPFYGKAIPLEQIKGGRHLIFCHSKKKCDE-LAAKLTGKKK (SEQ ID NO:231) and having a length of 45 amino acids; and d) a pharmaceutically acceptable excipient. In some cases, the composition comprises an adjuvant. In some cases, the immunogenic composition does not include any HCV polypeptides other than: a) i) an HCV E1/E2 heterodimeric polypeptide; ii) an HCV E2 polypeptide; or iii) an HCV E1 polypeptide; b) the first T-cell epitope polypeptide; and c) the second T-cell epitope polypeptide. In some cases, the immunogenic composition does not include any polypeptides other than: a) i) an HCV E1/E2 heterodimeric polypeptide; ii) an HCV E2 polypeptide; or iii) an HCV E1 polypeptide; b) the first T-cell epitope polypeptide; and c) the second T-cell epitope polypeptide.

Composition 29. As one example, an immunogenic composition of the present disclosure comprises: a) i) an HCV E1/E2 heterodimeric polypeptide; ii) an HCV E2 polypeptide; or iii) an HCV E1 polypeptide; b) a first T-cell epitope polypeptide comprising an amino acid sequence having at least 20% amino acid sequence identity to: KSTKVPAAYAAQGYKVLVLNPSVAATLGF-GAYMSKKKK (SEQ ID NO:302); c) a second T-cell epitope polypeptide comprising an amino acid sequence having at least 20% amino acid sequence identity to: LNAVAYYRGLDVSVIPTSGDVVV-VATDALMTGFTGDFDSVIDCNVKKK (SEQ ID NO:251); and d) a pharmaceutically acceptable excipient. The first T-cell epitope polypeptide can have a length of 38 amino acids; and the second T-cell epitope polypeptide can have a length of 48 amino acids. As an example, an immunogenic composition of the present disclosure can comprise: a) i) an HCV E1/E2 heterodimeric polypeptide; ii) an HCV E2 polypeptide; or iii) an HCV E1 polypeptide; b) a first T-cell epitope polypeptide comprising the following amino acid sequence: KSTKVPAAYAAQGYKVLVLNPSVAATLGF-GAYMSKKKK (SEQ ID NO:302) and having a length of 38 amino acids; c) a second T-cell epitope polypeptide comprising the following amino acid sequence: LNAVAYYR-GLDVSVIPTSGDVVV-VATDALMTGFTGDFDSVIDCNVKKK (SEQ ID NO:251) and having a length of 48 amino acids; and d) a pharmaceutically acceptable excipient. In some cases, the composition comprises an adjuvant. In some cases, the immunogenic composition does not include any HCV polypeptides other than: a) i) an HCV E1/E2 heterodimeric polypeptide; ii) an HCV E2 polypeptide; or iii) an HCV E1 polypeptide; b) the first T-cell epitope polypeptide; and c) the second T-cell epitope polypeptide. In some cases, the immunogenic composition does not include any polypeptides other than: a) i) an HCV E1/E2 heterodimeric polypeptide; ii) an HCV E2 polypeptide; or iii) an HCV E1 polypeptide; b) the first T-cell epitope polypeptide; and c) the second T-cell epitope polypeptide.

Composition 30. As one example, an immunogenic composition of the present disclosure comprises: a) i) an HCV E1/E2 heterodimeric polypeptide; ii) an HCV E2 polypeptide; or iii) an HCV E1 polypeptide; b) a first T-cell epitope polypeptide comprising an amino acid sequence having at least 20% amino acid sequence identity to: KSTKVPAAYAAQGYKVLVLNPSVAATLGF-GAYMSKKKK (SEQ ID NO:302); c) a second T-cell epitope polypeptide comprising an amino acid sequence having at least 20% amino acid sequence identity to: ILR-RHVGPGEGAVQWMNRLIAFASRGNHVSPTHYVPES-DASARVTQILKKK (SEQ ID NO:257); and d) a pharmaceutically acceptable excipient. The first T-cell epitope polypeptide can have a length of 38 amino acids; and the second T-cell epitope polypeptide can have a length of 51 amino acids. As an example, an immunogenic composition of the present disclosure can comprise: a) i) an HCV E1/E2 heterodimeric polypeptide; ii) an HCV E2 polypeptide; or iii) an HCV E1 polypeptide; b) a first T-cell epitope polypeptide comprising the following amino acid sequence: KSTKVPAAYAAQGYKVLVLNPSVAATLGF-GAYMSKKKK (SEQ ID NO:302) and having a length of 38 amino acids; c) a second T-cell epitope polypeptide comprising the following amino acid sequence: ILRRHVGPGEGAVQWMNRLIAFASRGNHVSPTHYVPES-DASARVTQILKKK (SEQ ID NO:257) and having a length of 51 amino acids; and d) a pharmaceutically acceptable excipient. In some cases, the composition comprises an adjuvant. In some cases, the immunogenic composition does not include any HCV polypeptides other than: a) i) an HCV E1/E2 heterodimeric polypeptide; ii) an HCV E2 polypeptide; or iii) an HCV E1 polypeptide; b) the first T-cell epitope polypeptide; and c) the second T-cell epitope polypeptide. In some cases, the immunogenic composition does not include any polypeptides other than: a) i) an HCV E1/E2 heterodimeric polypeptide; ii) an HCV E2 polypeptide; or iii) an HCV E1 polypeptide; b) the first T-cell epitope polypeptide; and c) the second T-cell epitope polypeptide.

Composition 31. As one example, an immunogenic composition of the present disclosure comprises: a) i) an HCV E1/E2 heterodimeric polypeptide; ii) an HCV E2 polypeptide; or iii) an HCV E1 polypeptide; b) a first T-cell epitope polypeptide comprising an amino acid sequence having at least 20% amino acid sequence identity to: KSTKVPAAYAAQGYKVLVLNPSVAATLGF-GAYMSKKKK (SEQ ID NO:302); c) a second T-cell epitope polypeptide comprising an amino acid sequence having at least 20% amino acid sequence identity to: GVYLLPRRGPRLGVRATRKTSERSQPR-GRRQPIPKARRSEGRSWAQPGYP (SEQ ID NO:148); and d) a pharmaceutically acceptable excipient. The first T-cell epitope polypeptide can have a length of 38 amino acids; and the second T-cell epitope polypeptide can have a length of 50 amino acids. As an example, an immunogenic composition of the present disclosure can comprise: a) i) an HCV E1/E2 heterodimeric polypeptide; ii) an HCV E2 polypeptide; or iii) an HCV E1 polypeptide; b) a first T-cell epitope polypeptide comprising the following amino acid sequence: KSTKVPAAYAAQGYKVLVLNPSVAATLGF-GAYMSKKKK (SEQ ID NO:302) and having a length of 38 amino acids; c) a second T-cell epitope polypeptide comprising the following amino acid sequence: GVYLL-PRRGPRLGVRATRKTSERSQPRGRRQPIPKARRSEG-RSWAQPGYP (SEQ ID NO:148) and having a length of 50 amino acids; and d) a pharmaceutically acceptable excipient. In some cases, the composition comprises an adjuvant. In some cases, the immunogenic composition does not include any HCV polypeptides other than: a) i) an HCV E1/E2 heterodimeric polypeptide; ii) an HCV E2 polypeptide; or iii) an HCV E1 polypeptide; b) the first T-cell epitope polypeptide; and c) the second T-cell epitope polypeptide. In some cases, the immunogenic composition does not include any polypeptides other than: a) i) an HCV E1/E2 heterodimeric polypeptide; ii) an HCV E2 polypeptide; or iii) an HCV E1 polypeptide; b) the first T-cell epitope polypeptide; and c) the second T-cell epitope polypeptide.

Composition 32. In some cases, an immunogenic composition of the present disclosure comprises 5 different T-cell epitope polypeptides. Thus, in some cases, an immunogenic composition of the present disclosure comprises: a) i) an HCV E1/E2 heterodimeric polypeptide; ii) an HCV E2 polypeptide; or iii) an HCV E1 polypeptide; b) a first T-cell epitope polypeptide comprising an amino acid sequence having at least 20% (at least 20%, at least 30%, at least 40%, at least 50%, at least 60%, at least 70%, at least 80%, at least 90%, at least 95%, at least 98%, at least 99%, or 100%) amino acid sequence identity to: KSTKVPAAYAAQGYKVLVLNPSVAATLGFGAYMSK (SEQ ID NO:133), and having length of from 35 amino acids to 45 amino acids; c) a second T-cell epitope polypeptide comprising an amino acid sequence having at least 20% (at least 20%, at least 30%, at least 40%, at least 50%, at least 60%, at least 70%, at least 80%, at least 90%, at least 95%, at least 98%, at least 99%, or 100%) amino acid sequence identity to: GTEGEIPFYGKAIPLEQIKG-GRHLIFCHSKKKCDELAAKLTG(K)n (SEQ ID NO:301), where n is an integer from 2 to 10 (e.g., where n is 2, 3, 4, 5, 6, 7, 8, 9, or 10), and having a length of from 44 amino acids to 52 amino acids; d) a third T-cell epitope polypeptide comprising an amino acid sequence having at least 20% (at least 20%, at least 30%, at least 40%, at least 50%, at least 60%, at least 70%, at least 80%, at least 90%, at least 95%, at least 98%, at least 99%, or 100%) amino acid sequence identity to: LNAVAYYRGLDVSVIPTSGDVVV-VATDALMTGFTGDFDSVIDCNVKKK (SEQ ID NO:251), and having a length of from 48 amino acids to 55 amino acids; e) a fourth T-cell epitope polypeptide comprising an amino acid sequence having at least 20% (at least 20%, at least 30%, at least 40%, at least 50%, at least 60%, at least 70%, at least 80%, at least 90%, at least 95%, at least 98%, at least 99%, or 100%) amino acid sequence identity to: ILRRHVGPGEGAVQWMNRLIAFAS-RGNHVSPTHYVPESDASARVTQIL(Lys)n (SEQ ID NO:308), where n is an integer from 2 to 10 (e.g., where n is 2, 3, 4, 5, 6, 7, 8, 9, or 10), and having a length of from 50 amino acids to 58 amino acids; f) a fifth T-cell epitope polypeptide comprising an amino acid sequence having at least 20% (at least 20%, at least 30%, at least 40%, at least 50%, at least 60%, at least 70%, at least 80%, at least 90%, at least 95%, at least 98%, at least 99%, or 100%) amino acid sequence identity to: GVYLLPRRGPRLGVRATRKTSER-SQPRGRRQPIPKARRSEGRSWAQPGYP (SEQ ID NO:148), and having a length of from 50 amino acids to 60 amino acids; and g) a pharmaceutically acceptable excipient. In some cases, the composition comprises an adjuvant. For example, in some cases, the fourth T-cell epitope polypeptide comprises the following amino acid sequence: ILRRHVGPGEGAVQWMNRLIAFASRGNHVSPTHYVPES-DASARVTQILKKK (SEQ ID NO:257) and has a length of 51 amino acids. In some cases, the immunogenic composition does not include any HCV polypeptides other than: a) i) an HCV E1/E2 heterodimeric polypeptide; ii) an HCV E2 polypeptide; or iii) an HCV E1 polypeptide; b) the first T-cell epitope polypeptide; c) the second T-cell epitope polypeptide; d) the third T-cell epitope polypeptide; e) the fourth T-cell epitope polypeptide; and f) the fifth T-cell epitope polypeptide. In some cases, the immunogenic composition does not include any polypeptides other than: a) i) an HCV E1/E2 heterodimeric polypeptide; ii) an HCV E2 polypeptide; or iii) an HCV E1 polypeptide; b) the first T-cell epitope polypeptide; c) the second T-cell epitope polypeptide; d) the third T-cell epitope polypeptide; e) the fourth T-cell epitope polypeptide; and f) the fifth T-cell epitope polypeptide.

Composition 33. In some cases, an immunogenic composition of the present disclosure comprises 5 different T-cell epitope polypeptides. Thus, in some cases, an immunogenic composition of the present disclosure comprises: a) i) an HCV E1/E2 heterodimeric polypeptide; ii) an HCV E2 polypeptide; or iii) an HCV E1 polypeptide; b) a first T-cell epitope polypeptide comprising an amino acid sequence having at least 20% (at least 20%, at least 30%, at least 40%, at least 50%, at least 60%, at least 70%, at least 80%, at least 90%, at least 95%, at least 98%, at least 99%, or 100%) amino acid sequence identity to: KSTKVPAAYAAQGYKVLVLNPSVAATLGF-GAYMSKKKK (SEQ ID NO:302), and having a length of from 38 amino acids to 45 amino acids; c) a second T-cell epitope polypeptide comprising an amino acid sequence having at least 20% (at least 20%, at least 30%, at least 40%, at least 50%, at least 60%, at least 70%, at least 80%, at least 90%, at least 95%, at least 98%, at least 99%, or 100%) amino acid sequence identity to: GTEGEIPFYGKAI-PLEQIKGGRHLIFCHSKKKCDELAAKLTG(K)n (SEQ ID NO:301), where n is an integer from 2 to 10 (e.g., where n is 2, 3, 4, 5, 6, 7, 8, 9, or 10), and having a length of from 44 amino acids to 52 amino acids; d) a third T-cell epitope polypeptide comprising an amino acid sequence having at least 20% (at least 20%, at least 30%, at least 40%, at least 50%, at least 60%, at least 70%, at least 80%, at least 90%, at least 95%, at least 98%, at least 99%, or 100%) amino acid sequence identity to: LNAVAYYRGLDVSVIPTSGDVVV-VATDALMTGFTGDFDSVIDCNVKKK (SEQ ID NO:251), and having a length of from 48 amino acids to 55 amino acids; e) a fourth T-cell epitope polypeptide comprising an amino acid sequence having at least 20% (at least 20%, at least 30%, at least 40%, at least 50%, at least 60%, at least 70%, at least 80%, at least 90%, at least 95%, at least 98%, at least 99%, or 100%) amino acid sequence identity to: ILRRHVGPGEGAVQWMNRLIAFAS-RGNHVSPTHYVPESDASARVTQILKKK (SEQ ID NO:257), and having a length of from 51 amino acids to 58 amino acids; f) a fifth T-cell epitope polypeptide comprising an amino acid sequence having at least 20% (at least 20%, at least 30%, at least 40%, at least 50%, at least 60%, at least 70%, at least 80%, at least 90%, at least 95%, at least 98%, at least 99%, or 100%) amino acid sequence identity to: GVYLLPRRGPRLGVRATRKTSERSQPR-GRRQPIPKARRSEGRSWAQPGYP (SEQ ID NO:148), and having a length of from 50 amino acids to 60 amino acids; and g) a pharmaceutically acceptable excipient. In some cases, the composition comprises an adjuvant. In some cases, the immunogenic composition does not include any HCV polypeptides other than: a) i) an HCV E1/E2 heterodimeric polypeptide; ii) an HCV E2 polypeptide; or iii) an HCV E1 polypeptide; b) the first T-cell epitope polypeptide; c) the second T-cell epitope polypeptide; d) the third T-cell epitope polypeptide; e) the fourth T-cell epitope polypeptide; and f) the fifth T-cell epitope polypeptide. In some cases, the immunogenic composition does not include any polypeptides other than: a) i) an HCV E1/E2 heterodimeric polypeptide; ii) an HCV E2 polypeptide; or iii) an HCV E1 polypeptide; b) the first T-cell epitope polypeptide; c) the second T-cell epitope polypeptide; d) the third T-cell epitope polypeptide; e) the fourth T-cell epitope polypeptide; and f) the fifth T-cell epitope polypeptide.

Composition 34. In some cases, an immunogenic composition of the present disclosure comprises 5 different T-cell epitope polypeptides. Thus, in some cases, an immunogenic composition of the present disclosure comprises: a) i) an HCV E1/E2 heterodimeric polypeptide; ii) an HCV E2 polypeptide; or iii) an HCV E1 polypeptide; b) a first T-cell epitope polypeptide comprising an amino acid sequence having at least 20% (at least 20%, at least 30%, at least 40%, at least 50%, at least 60%, at least 70%, at least 80%, at least 90%, at least 95%, at least 98%, at least 99%, or 100%) amino acid sequence identity to: KSTKVPAAYAAQGYKVLVLNPSVAATLGFGAYMSK (SEQ ID NO:133), and having length of from 35 amino acids to 45 amino acids; c) a second T-cell epitope polypeptide comprising an amino acid sequence having at least 20% (at least 20%, at least 30%, at least 40%, at least 50%, at least 60%, at least 70%, at least 80%, at least 90%, at least 95%, at least 98%, at least 99%, or 100%) amino acid sequence identity to: GTEGEIPFYGKAIPLEQIKG-GRHLIFCHSKKKCDELAAKLTG(K)n (SEQ ID NO:301), where n is an integer from 2 to 10 (e.g., where n is 2, 3, 4, 5, 6, 7, 8, 9, or 10), and having a length of from 44 amino acids to 52 amino acids; d) a third T-cell epitope polypeptide comprising an amino acid sequence having at least 20% (at least 20%, at least 30%, at least 40%, at least 50%, at least 60%, at least 70%, at least 80%, at least 90%, at least 95%, at least 98%, at least 99%, or 100%) amino acid sequence identity to: LNAVAYYRGLDVSVIPTSGDVVV-VATDALMTGFTGDFDSVID (SEQ ID NO:253), and having a length of from 42 amino acids to 52 amino acids; e) a fourth T-cell epitope polypeptide comprising an amino acid sequence having at least 20% (at least 20%, at least 30%, at least 40%, at least 50%, at least 60%, at least 70%, at least 80%, at least 90%, at least 95%, at least 98%, at least 99%, or 100%) amino acid sequence identity to: ILR-RHVGPGEGAVQWMNRLIAFASRGNHVSPTHYVPES-DASARVTQIL(Lys)n (SEQ ID NO:308), where n is an integer from 2 to 10 (e.g., where n is 2, 3, 4, 5, 6, 7, 8, 9, or 10), and having a length of from 50 amino acids to 58 amino acids; f) a fifth T-cell epitope polypeptide comprising an amino acid sequence having at least 20% (at least 20%, at least 30%, at least 40%, at least 50%, at least 60%, at least 70%, at least 80%, at least 90%, at least 95%, at least 98%, at least 99%, or 100%) amino acid sequence identity to: GVYLLPRRGPRLGVRATRKTSERSQPR-GRRQPIPKARRSEGRSWAQPGYP (SEQ ID NO:148), and having a length of from 50 amino acids to 60 amino acids; and g) a pharmaceutically acceptable excipient. For example, in some cases, the fourth T-cell epitope polypeptide comprises the following amino acid sequence: ILR-RHVGPGEGAVQWMNRLIAFASRGNHVSPTHYVPES-DASARVTQILKKK (SEQ ID NO:257) and has a length of 51 amino acids. In some cases, the composition comprises an adjuvant. In some cases, at least one of the T cell epitope polypeptides comprises a fusion partner. In some cases, at least one of the T cell epitope polypeptides comprises a C-terminal poly(Lys), e.g., comprises a stretch of 2, 3, 4, 5, 6, 7, 8, 9, or 10 C-terminal Lys. In some cases, the immunogenic composition does not include any HCV polypeptides other than: a) i) an HCV E1/E2 heterodimeric polypeptide; ii) an HCV E2 polypeptide; or iii) an HCV E1 polypeptide; b) the first T-cell epitope polypeptide; c) the second T-cell epitope polypeptide; d) the third T-cell epitope polypeptide; e) the fourth T-cell epitope polypeptide; and f) the fifth T-cell epitope polypeptide. In some cases, the immunogenic composition does not include any polypeptides other than: a) i) an HCV E1/E2 heterodimeric polypeptide; ii) an HCV E2 polypeptide; or iii) an HCV E1 polypeptide; b) the first T-cell epitope polypeptide; c) the second T-cell epitope polypeptide; d) the third T-cell epitope polypeptide; e) the fourth T-cell epitope polypeptide; and f) the fifth T-cell epitope polypeptide.

Composition 35. In some cases, an immunogenic composition of the present disclosure comprises 4 different T-cell epitope polypeptides. Thus, in some cases, an immunogenic composition of the present disclosure comprises: a) i) an HCV E1/E2 heterodimeric polypeptide; ii) an HCV E2 polypeptide; or iii) an HCV E1 polypeptide; b) a first T-cell epitope polypeptide comprising an amino acid sequence having at least 20% (at least 20%, at least 30%, at least 40%, at least 50%, at least 60%, at least 70%, at least 80%, at least 90%, at least 95%, at least 98%, at least 99%, or 100%) amino acid sequence identity to: KSTKVPAAYAAQGYKVLVLNPSVAATLGFGAYMSK (SEQ ID NO:133), and having length of from 35 amino acids to 45 amino acids; c) a second T-cell epitope polypeptide comprising an amino acid sequence having at least 20% (at least 20%, at least 30%, at least 40%, at least 50%, at least 60%, at least 70%, at least 80%, at least 90%, at least 95%, at least 98%, at least 99%, or 100%) amino acid sequence identity to: GTEGEIPFYGKAIPLEQIKGGRHLIFCHSKKKCDELAAKLTG(K)n (SEQ ID NO:301), where n is an integer from 2 to 10 (e.g., where n is 2, 3, 4, 5, 6, 7, 8, 9, or 10), and having a length of from 44 amino acids to 52 amino acids; d) a third T-cell epitope polypeptide comprising an amino acid sequence having at least 20% (at least 20%, at least 30%, at least 40%, at least 50%, at least 60%, at least 70%, at least 80%, at least 90%, at least 95%, at least 98%, at least 99%, or 100%) amino acid sequence identity to: ILRRHVGPGEGAVQWMNRLIAFASRGNHVSPTHYVPESDASARVTQIL(Lys)n (SEQ ID NO:308), where n is an integer from 2 to 10 (e.g., where n is 2, 3, 4, 5, 6, 7, 8, 9, or 10), and having a length of from 50 amino acids to 58 amino acids; e) a fourth T-cell epitope polypeptide comprising an amino acid sequence having at least 20% (at least 20%, at least 30%, at least 40%, at least 50%, at least 60%, at least 70%, at least 80%, at least 90%, at least 95%, at least 98%, at least 99%, or 100%) amino acid sequence identity to: GVYLLPRRGPRLGVRATRKTSERSQPRGRRQPIPKARRSEGRSWAQPGYP (SEQ ID NO:148), and having a length of from 50 amino acids to 60 amino acids; and g) a pharmaceutically acceptable excipient. For example, in some cases, the third T-cell epitope polypeptide comprises the following amino acid sequence: ILRRHVGPGEGAVQWMNRLIAFASRGNHVSPTHYVPESDASARVTQILKKK (SEQ ID NO:257) and has a length of 51 amino acids. In some cases, the composition comprises an adjuvant. In some cases, at least one of the T cell epitope polypeptides comprises a fusion partner. In some cases, at least one of the T cell epitope polypeptides comprises a C-terminal poly(Lys), e.g., comprises a stretch of 2, 3, 4, 5, 6, 7, 8, 9, or 10 C-terminal Lys. In some cases, the immunogenic composition does not include any HCV polypeptides other than: a) i) an HCV E1/E2 heterodimeric polypeptide; ii) an HCV E2 polypeptide; or iii) an HCV E1 polypeptide; b) the first T-cell epitope polypeptide; c) the second T-cell epitope polypeptide; d) the third T-cell epitope polypeptide; and e) the fourth T-cell epitope polypeptide. In some cases, the immunogenic composition does not include any polypeptides other than: a) i) an HCV E1/E2 heterodimeric polypeptide; ii) an HCV E2 polypeptide; or iii) an HCV E1 polypeptide; b) the first T-cell epitope polypeptide; c) the second T-cell epitope polypeptide; d) the third T-cell epitope polypeptide; and e) the fourth T-cell epitope polypeptide.

Composition 36. In some cases, an immunogenic composition of the present disclosure comprises 4 different T-cell epitope polypeptides. Thus, in some cases, an immunogenic composition of the present disclosure comprises: a) i) an HCV E1/E2 heterodimeric polypeptide; ii) an HCV E2 polypeptide; or iii) an HCV E1 polypeptide; b) a first T-cell epitope polypeptide comprising an amino acid sequence having at least 20% (at least 20%, at least 30%, at least 40%, at least 50%, at least 60%, at least 70%, at least 80%, at least 90%, at least 95%, at least 98%, at least 99%, or 100%) amino acid sequence identity to: KSTKVPAAYAAQGYKVLVLNPSVAATLGFGAYMSK(K)n (SEQ ID NO:300), where n is an integer from 2 to 10 (e.g., where n is 2, 3, 4, 5, 6, 7, 8, 9, or 10) and having length of from 37 amino acids to 45 amino acids; c) a second T-cell epitope polypeptide comprising an amino acid sequence having at least 20% (at least 20%, at least 30%, at least 40%, at least 50%, at least 60%, at least 70%, at least 80%, at least 90%, at least 95%, at least 98%, at least 99%, or 100%) amino acid sequence identity to: GTEGEIPFYGKAIPLEQIKGGRHLIFCHSKKKCDELAAKLTG(K)n (SEQ ID NO:301), where n is an integer from 2 to 10 (e.g., where n is 2, 3, 4, 5, 6, 7, 8, 9, or 10), and having a length of from 44 amino acids to 52 amino acids; d) a third T-cell epitope polypeptide comprising an amino acid sequence having at least 20% (at least 20%, at least 30%, at least 40%, at least 50%, at least 60%, at least 70%, at least 80%, at least 90%, at least 95%, at least 98%, at least 99%, or 100%) amino acid sequence identity to: ILRRHVGPGEGAVQWMNRLIAFASRGNHVSPTHYVPESDASARVTQILKKK (SEQ ID NO:257), and having a length of from 51 amino acids to 58 amino acids; e) a fourth T-cell epitope polypeptide comprising an amino acid sequence having at least 20% (at least 20%, at least 30%, at least 40%, at least 50%, at least 60%, at least 70%, at least 80%, at least 90%, at least 95%, at least 98%, at least 99%, or 100%) amino acid sequence identity to: GVYLLPRRGPRLGVRATRKTSERSQPRGRRQPIPKARRSEGRSWAQPGYP (SEQ ID NO:148), and having a length of from 50 amino acids to 60 amino acids; and g) a pharmaceutically acceptable excipient. In some cases, the composition comprises an adjuvant. In some cases, at least one of the T cell epitope polypeptides comprises a fusion partner. In some cases, at least one of the T cell epitope polypeptides comprises a C-terminal poly(Lys), e.g., comprises a stretch of 2, 3, 4, 5, 6, 7, 8, 9, or 10 C-terminal Lys. In some cases, the immunogenic composition does not include any HCV polypeptides other than: a) i) an HCV E1/E2 heterodimeric polypeptide; ii) an HCV E2 polypeptide; or iii) an HCV E1 polypeptide; b) the first T-cell epitope polypeptide; c) the second T-cell epitope polypeptide; d) the third T-cell epitope polypeptide; and e) the fourth T-cell epitope polypeptide. In some cases, the immunogenic composition does not include any polypeptides other than: a) i) an HCV E1/E2 heterodimeric polypeptide; ii) an HCV E2 polypeptide; or iii) an HCV E1 polypeptide; b) the first T-cell epitope polypeptide; c) the second T-cell epitope polypeptide; d) the third T-cell epitope polypeptide; and e) the fourth T-cell epitope polypeptide.

Composition 37. As one example, an immunogenic composition of the present disclosure comprises: a) i) an HCV E1/E2 heterodimeric polypeptide; ii) an HCV E2 polypeptide; or iii) an HCV E1 polypeptide; b) a first T-cell epitope polypeptide comprising an amino acid sequence having at least 80% amino acid sequence identity to: KSTKVPX$_1$AYX$_2$X$_3$QGYX$_4$VLVLNPSVAATLGFGX$_5$X$_6$X$_7$SX$_8$ (SEQ ID NO:134), wherein X$_1$ is A or V; X$_2$ is A or V; X$_3$ is A or S; X$_4$ is K or N; X$_5$ is A or S; X$_6$ is Y or F; X$_7$ is M or L; and X$_8$ is K or R, where the TP35-NS3 T-cell epitope polypeptide has a length of from 28 amino acids to 35 amino acids; c) a second T-cell epitope polypeptide comprising an amino acid sequence having at least 80% amino acid sequence identity to: GVYX$_1$LPRRGPRLGVRX$_2$TRKX$_3$SERSQPR GRRQ$X_4$IPK$X_5X_6X_7X_8X_9$G$X_{10}X_{11}$W$X_{12}X_{13}$PGY P (SEQ ID NO:149), where $X_1$ is L or V; $X_2$ is A or G; $X_3$ is T or S; $X_4$ is P or R; $X_5$ is A or D; $X_6$ is R or A; $X_7$ is R, Q, or S; $X_8$ is S or P; $X_9$ is E, T, or Q; $X_1$ is R or K; $X_{11}$ is S, T, H, or A; $X_{12}$ is A or G; and $X_{13}$ is Q or K, where the TP50C T-cell epitope polypeptide has a length of from 40 amino acids to 50 amino acids; d) a third T-cell epitope polypeptide comprising an amino acid sequence having at least 80% amino acid sequence identity to: $X_1X_2X_3$RH$X_4$G$X_5X_6$EG$X_7X_8$QWMNRLIAFASR GNHV$X_9$PTHY$X_{10}X_{11}X_{12}X_{13}$DA$X_{14}X_{15}X_{16}$V$X_{17}$ $X_{18}X_{19}$L(K)n (SEQ ID NO:255), where $X_1$ is I or V; $X_2$ is L or I; $X_3$ is R or K; $X_4$ is V, I, or T; $X_5$ is P, Q, or T; $X_6$ is G, A, or S; $X_7$ is A or V; $X_8$ is V or T; $X_9$ is S or A; $X_{10}$ is V or I; $X_{11}$ is P, T, A, or Q, $X_{12}$ is E or D; $X_{13}$ is S, T, or D; $X_{14}$ is S or A; $X_{15}$ is A, Q, R, or K; $X_{16}$ is R, K, or X; $X_{17}$ is T or M; $X_{18}$ is Q, A, T, or G; and $X_{19}$ is I, L, or V, where n is an integer from 2 to 10, and wherein the TP48 T-cell epitope polypeptide has a length of from 38 amino acids to 48 amino acids; and e) a pharmaceutically acceptable excipient. For example, in some cases, the immunogenic composition comprises: a) i) an HCV E1/E2 heterodimeric polypeptide; ii) an HCV E2 polypeptide; or iii) an HCV E1 polypeptide; b) a first T-cell epitope polypeptide comprising the amino acid sequence: KSTKVPAAYAAQGYKVLVLNPSVAATLGFGAYMSK (SEQ ID NO:133), and having a length of 35 amino acids; c) a second T-cell epitope polypeptide comprising the amino acid sequence: GVYLLPRRGPRLGVRATRKTSERSQPRGRRQPIPKARRSEGRSWAQPGYP (SEQ ID NO:148), and having a length of 50 amino acids; d) a third T-cell epitope polypeptide comprising the amino acid sequence: ILRRHVGPGEGAVQWMNRLIAFASRGNHVSPTHYVPESDASARVTQILKKK (SEQ ID NO:257) and having a length of 51 amino acids; and e) a pharmaceutically acceptable excipient. In some cases, the composition comprises an adjuvant. In some cases, at least one of the T cell epitope polypeptides comprises a fusion partner. In some cases, the immunogenic composition does not include any HCV polypeptides other than: a) i) an HCV E1/E2 heterodimeric polypeptide; ii) an HCV E2 polypeptide; or iii) an HCV E1 polypeptide; b) the first T-cell epitope polypeptide; c) the second T-cell epitope polypeptide; and d) the third T-cell epitope polypeptide. In some cases, the immunogenic composition does not include any polypeptides other than: a) i) an HCV E1/E2 heterodimeric polypeptide; ii) an HCV E2 polypeptide; or iii) an HCV E1 polypeptide; b) the first T-cell epitope polypeptide; c) the second T-cell epitope polypeptide; d) the third T-cell epitope polypeptide; and e) the fourth T-cell epitope polypeptide.

Composition 38. As one example, an immunogenic composition of the present disclosure comprises: a) i) an HCV E1/E2 heterodimeric polypeptide; ii) an HCV E2 polypeptide; or iii) an HCV E1 polypeptide; b) a first T-cell epitope polypeptide comprising an amino acid sequence having at least 20% amino acid sequence identity to: KSTKVPAAYAAQGYKVLVLNPSVAATLGFGAYMSK (SEQ ID NO:133); c) a second T-cell epitope polypeptide comprising an amino acid sequence having at least 20% amino acid sequence identity to: GVYLLPRRGPRLGVRATRKTSERSQPRGRRQPIPKARRSEGRSWAQPGYP (SEQ ID NO:148); d) a third T-cell epitope polypeptide comprising an amino acid sequence having at least 20% amino acid sequence identity to: GTEGEIPFYGKAIPLEQIKGGRHLIFCHSKKKCDELAAKLTG (SEQ ID NO:228); e) a fourth T-cell epitope polypeptide comprising an amino acid sequence having at least 20% amino acid sequence identity to: KGGRHLIFCHSKKKCDELAAKLTGLGLNAVAYYRGLDVSVIP (SEQ ID NO:291); f) a fifth T-cell epitope polypeptide comprising an amino acid sequence having at least 20% amino acid sequence identity to: ILRRHVGPGEGAVQWMNRLIAFASRGNHVSPTHYVPESDASARVTQIL (SEQ ID NO:254); and g) a pharmaceutically acceptable excipient. The first T-cell epitope polypeptide can have a length of 35 amino acids; the second T-cell epitope polypeptide can have a length of 50 amino acids; the third T-cell epitope polypeptide can have a length of 42 amino acids; the fourth T-cell epitope polypeptide can have a length of 42 amino acids; and the fifth T-cell epitope polypeptide can have a length of 48 amino acids. As an example, an immunogenic composition of the present disclosure can comprise: a) i) an HCV E1/E2 heterodimeric polypeptide; ii) an HCV E2 polypeptide; or iii) an HCV E1 polypeptide; b) a first T-cell epitope polypeptide comprising the following amino acid sequence: KSTKVPAAYAAQGYKVLVLNPSVAATLGFGAYMSK (SEQ ID NO:133) and having a length of 35 amino acids; c) a second T-cell epitope polypeptide comprising the following amino acid sequence: GVYLLPRRGPRLGVRATRKTSERSQPRGRRQPIPKARRSEGRSWAQPGYP (SEQ ID NO:148) and having a length of 50 amino acids; d) a third T-cell epitope polypeptide comprising an amino acid sequence having at least 20% amino acid sequence identity to: GTEGEIPFYGKAIPLEQIKGGRHLIFCHSKKKCDELAAKLTG (SEQ ID NO:228) and having a length of 42 amino acids; e) a fourth T-cell epitope polypeptide comprising an amino acid sequence having at least 20% amino acid sequence identity to: KGGRHLIFCHSKKKCDELAAKLTGLGLNAVAYYRGLDVSVIP (SEQ ID NO:291) and having a length of 42 amino acids; f) a fifth T-cell epitope polypeptide comprising an amino acid sequence having at least 20% amino acid sequence identity to: ILRRHVGPGEGAVQWMNRLIAFASRGNHVSPTHYVPESDASARVTQIL (SEQ ID NO:254) and having a length of 48 amino acids; and g) a pharmaceutically acceptable excipient. In some cases, the composition comprises an adjuvant. In some cases, at least one of the T cell epitope polypeptides comprises a fusion partner. In some cases, at least one of the T cell epitope polypeptides comprises a C-terminal poly (Lys), e.g., comprises a stretch of 2, 3, 4, 5, 6, 7, 8, 9, or 10 C-terminal Lys. In some cases, the immunogenic composition does not include any HCV polypeptides other than: a) i) an HCV E1/E2 heterodimeric polypeptide; ii) an HCV E2 polypeptide; or iii) an HCV E1 polypeptide; b) the first T-cell epitope polypeptide; c) the second T-cell epitope polypeptide; d) the third T-cell epitope polypeptide; e) the fourth T-cell epitope polypeptide; and f) the fifth T-cell epitope polypeptide. In some cases, the immunogenic composition does not include any polypeptides other than: a) i) an HCV E1/E2 heterodimeric polypeptide; ii) an HCV E2 polypeptide; or iii) an HCV E1 polypeptide; b) the first T-cell epitope polypeptide; c) the second T-cell epitope polypeptide; d) the third T-cell epitope polypeptide; e) the fourth T-cell epitope polypeptide; and f) the fifth T-cell epitope polypeptide.

Composition 39. As one example, an immunogenic composition of the present disclosure comprises: a) i) an HCV E1/E2 heterodimeric polypeptide; ii) an HCV E2 polypeptide; or iii) an HCV E1 polypeptide; b) a first T-cell epitope polypeptide comprising an amino acid sequence having at least 20% amino acid sequence identity to: KSTKVPAAYAAQGYKVLVLNPSVAATLGFGAYMSK (SEQ ID NO:133); c) a second T-cell epitope polypeptide comprising an amino acid sequence having at least 20% amino acid sequence identity to: GVYLL-PRRGPRLGVRATRKTSERSQPRGRRQPIPKARRSEG-RSWAQPGYP (SEQ ID NO:148); d) a third T-cell epitope polypeptide comprising an amino acid sequence having at least 20% amino acid sequence identity to: GTEGEIPFYGKAIPLEQIKGGRHLIFCHSKKKCDE-LAAKLTG (SEQ ID NO:228); and e) a pharmaceutically acceptable excipient. The first T-cell epitope polypeptide can have a length of 35 amino acids; the second T-cell epitope polypeptide can have a length of 50 amino acids; and the third T-cell epitope polypeptide can have a length of 42 amino acids. As an example, an immunogenic composition of the present disclosure can comprise: a) i) an HCV E1/E2 heterodimeric polypeptide; ii) an HCV E2 polypeptide; or iii) an HCV E1 polypeptide; b) a first T-cell epitope polypeptide comprising the following amino acid sequence: KSTKVPAAYAAQGYKVLVLNPSVAATLGFGAYMSK (SEQ ID NO:133) and having a length of 35 amino acids; c) a second T-cell epitope polypeptide comprising the following amino acid sequence: GVYLLPRRGPRLGVRATRKT-SERSQPRGRRQPIPKARRSEGRSWAQPGYP (SEQ ID NO:148) and having a length of 50 amino acids; d) a third T-cell epitope polypeptide comprising an amino acid sequence having at least 20% amino acid sequence identity to: GTEGEIPFYGKAIPLEQIKGGRHLIFCHSKKKCDE-LAAKLTG (SEQ ID NO:228) and having a length of 42 amino acids; and e) a pharmaceutically acceptable excipient. In some cases, the composition comprises an adjuvant. In some cases, at least one of the T cell epitope polypeptides comprises a fusion partner. In some cases, at least one of the T cell epitope polypeptides comprises a C-terminal poly (Lys), e.g., comprises a stretch of 2, 3, 4, 5, 6, 7, 8, 9, or 10 C-terminal Lys. In some cases, the immunogenic composition does not include any HCV polypeptides other than: a) i) an HCV E1/E2 heterodimeric polypeptide; ii) an HCV E2 polypeptide; or iii) an HCV E1 polypeptide; b) the first T-cell epitope polypeptide; c) the second T-cell epitope polypeptide; and d) the third T-cell epitope polypeptide. In some cases, the immunogenic composition does not include any polypeptides other than: a) i) an HCV E1/E2 heterodimeric polypeptide; ii) an HCV E2 polypeptide; or iii) an HCV E1 polypeptide; b) the first T-cell epitope polypeptide; c) the second T-cell epitope polypeptide; and d) the third T-cell epitope polypeptide.

HCV E1/E2 Heterodimers; HCV E2 Polypeptides: HCV E1 Polypeptides

HCV E1/E2 heterodimers suitable for use in an immunogenic composition of the present disclosure include HCV E1/E2 heterodimers comprising wild-type HCV E1 polypeptides; HCV E1/E2 heterodimers comprising wild-type HCV E2 polypeptides; HCV E1/E2 heterodimers comprising variant HCV E1 polypeptides; and HCV E1/E2 heterodimers comprising variant HCV E2 polypeptides. HCV E2 polypeptides suitable for use in an immunogenic composition of the present disclosure include wild-type E2 polypeptides and variant E2 polypeptides. HCV E1 polypeptides suitable for use in an immunogenic composition of the present disclosure include wild-type E1 polypeptides and variant E1 polypeptides.

E2 Polypeptides

An E2 polypeptide suitable for inclusion in an E1/E2 heterodimer for inclusion in an immunogenic composition of the present disclosure, or for inclusion by itself in an immunogenic composition of the present disclosure, can have a length of from about 200 amino acids (aa) to about 250 aa, from about 250 aa to about 275 aa, from about 275 aa to about 300 aa, from about 300 aa to about 325 aa, from about 325 aa to about 350 aa, or from about 350 aa to about 365 aa. In some cases, an HCV E2 polypeptide suitable for inclusion in an immunogenic composition of the present disclosure is an HCV E2 ectodomain polypeptide. In some cases, an HCV E2 polypeptide suitable for inclusion in an immunogenic composition of the present disclosure is a full-length HCV E2 polypeptide.

Figure 1A:
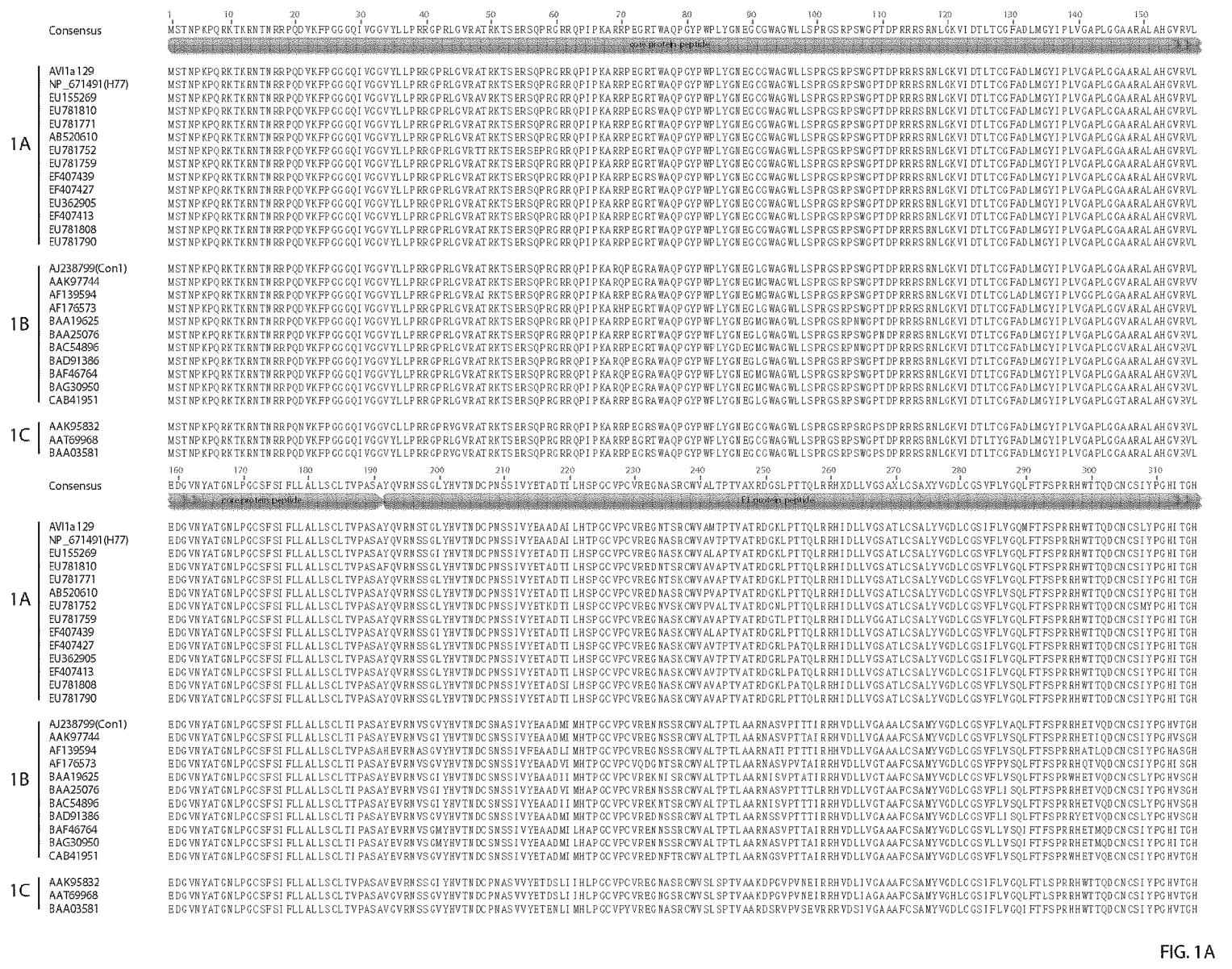
Figure 2A:
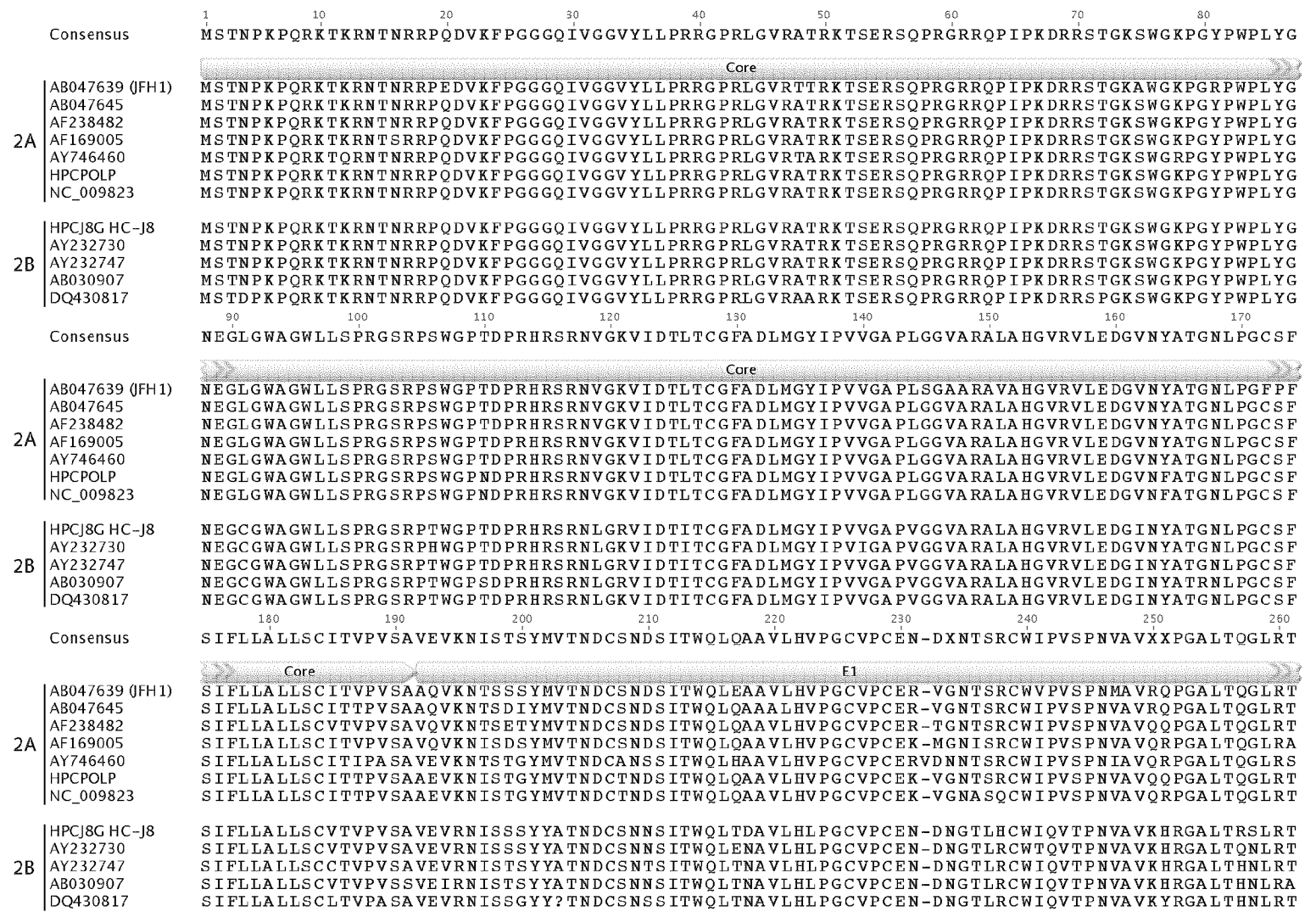
Figure 3B:
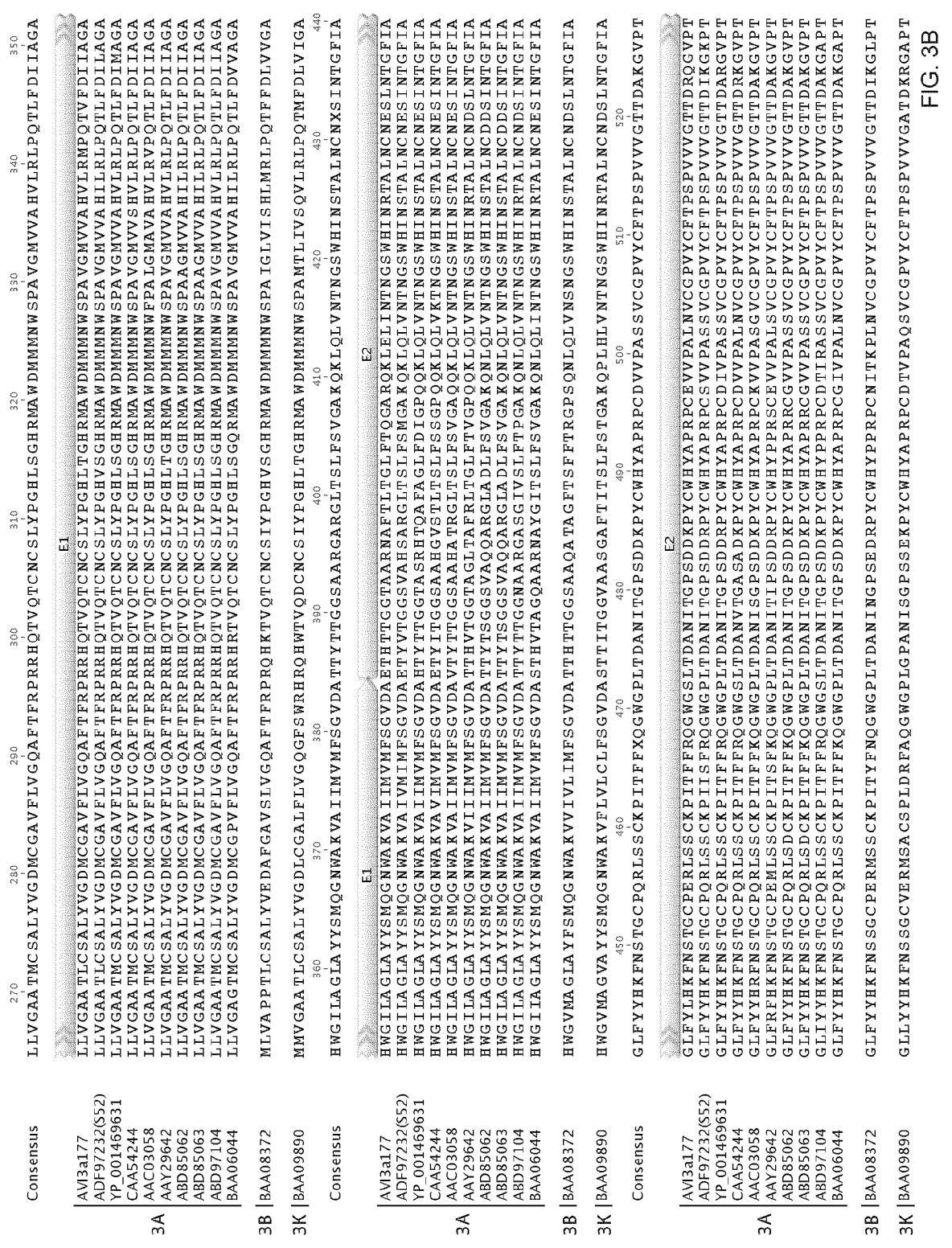
Figure 4B:
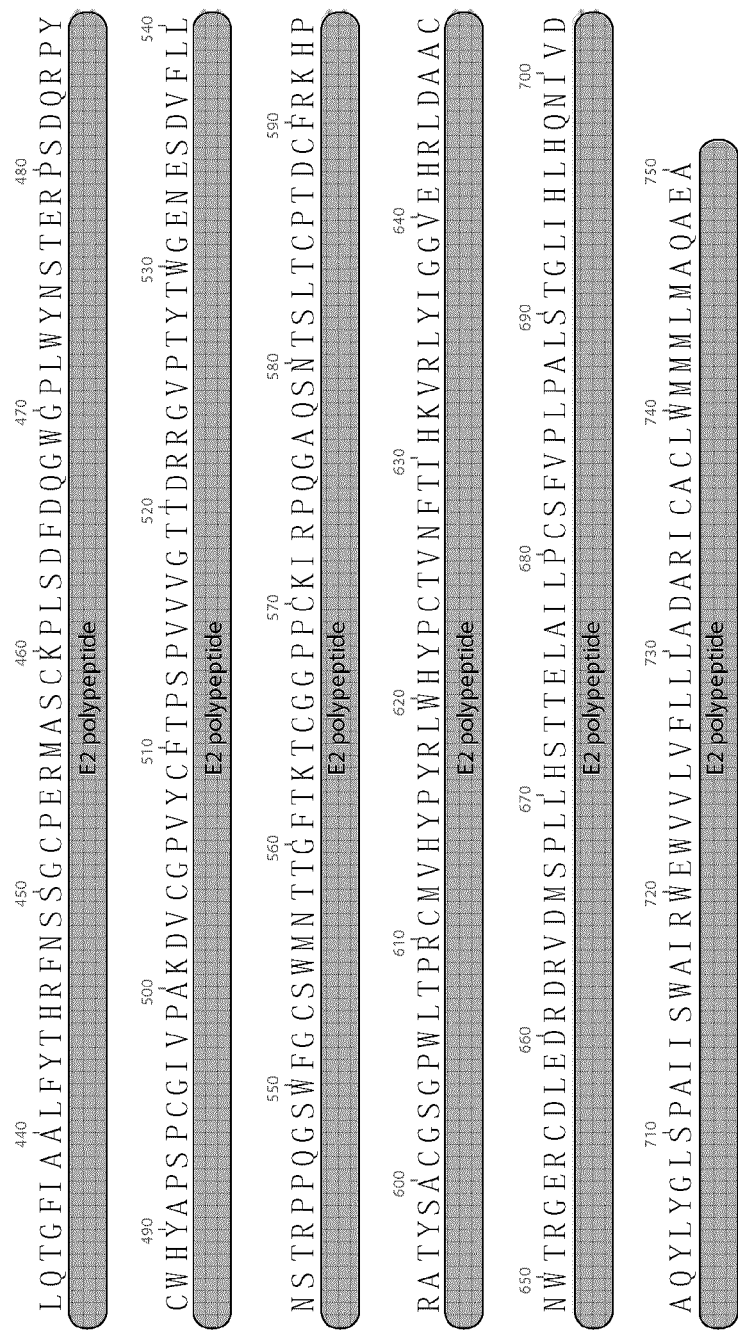
Figure 15:
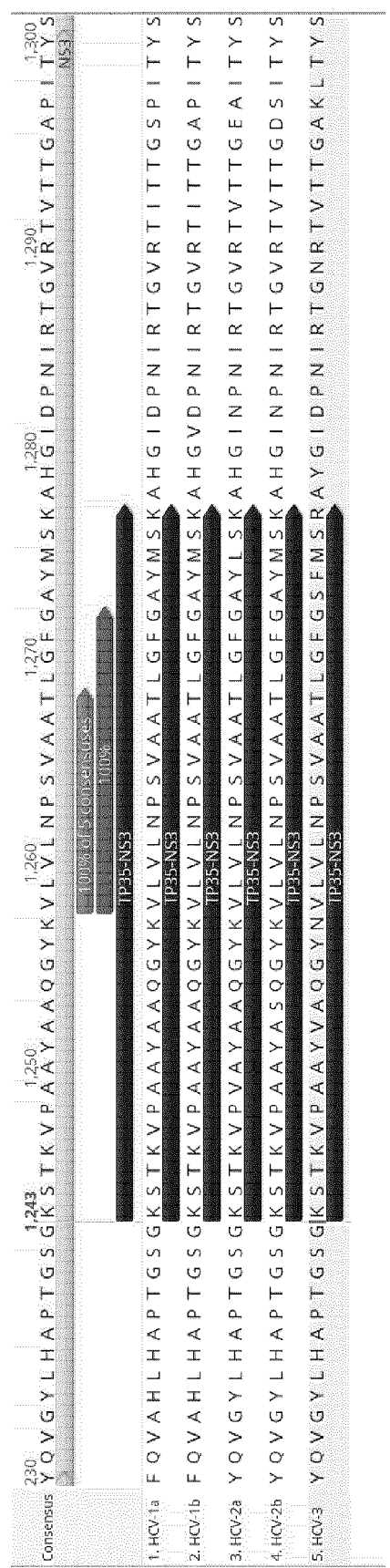
FIG. 15 provides an alignment of amino acid sequences of a portion of NS3 of HCV-1a, -1b, -2a, -2b, and -3, as well as a consensus sequence; and shows the positions of conserved MHC class II CD4-specific HCV epitopes, and conserved MHC class I CD8-specific HCV epitopes in TP35-NS3. Top to bottom: SEQ ID NOs:359-364. The upper bar ("100% of consensuses") indicates CD8 epitopes; the lower bar ("100%") indicates CD4 epitopes.
Figure 16:
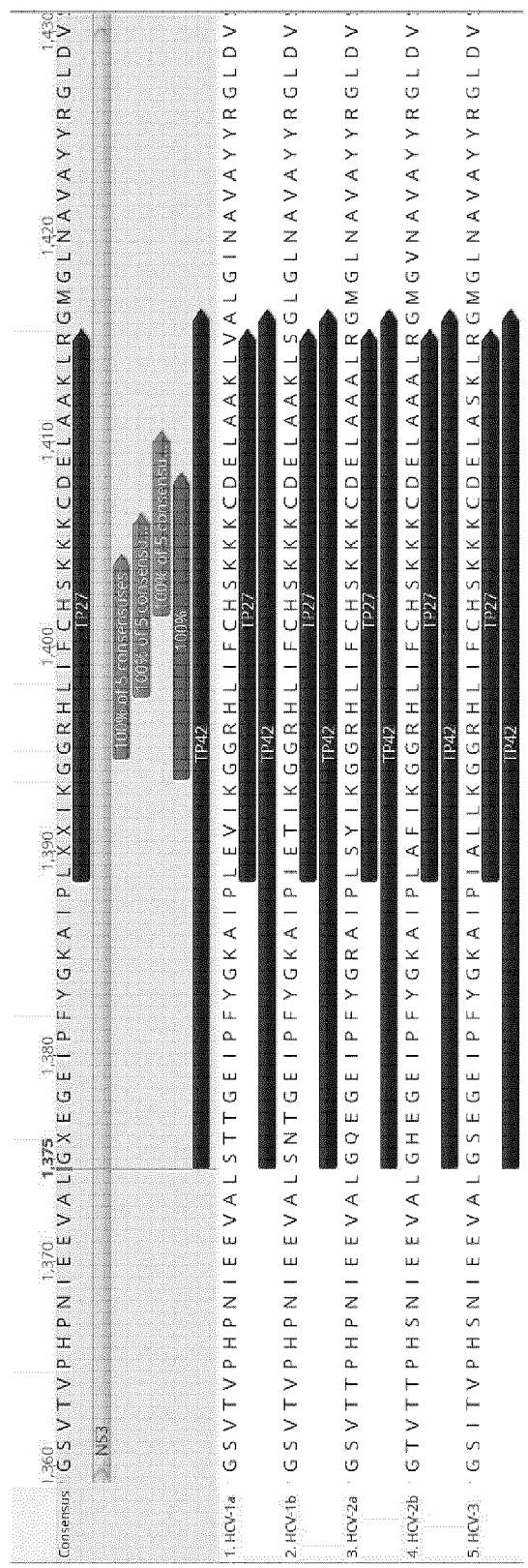
FIG. 16 provides an alignment of amino acid sequences of a portion of NS3 of HCV-1a, -1b, -2a, -2b, and -3, as well as a consensus sequence; and shows the positions of conserved MHC class II CD4-specific HCV epitopes, and conserved MHC class I CD8-specific HCV epitopes in TP27 and TP42. Top to bottom: SEQ ID NOs:365-370. The bars labeled "100% of 5 consensuses" indicate CD8 epitopes. The bar labeled "100%" indicates CD4 epitopes.
Figure 17:
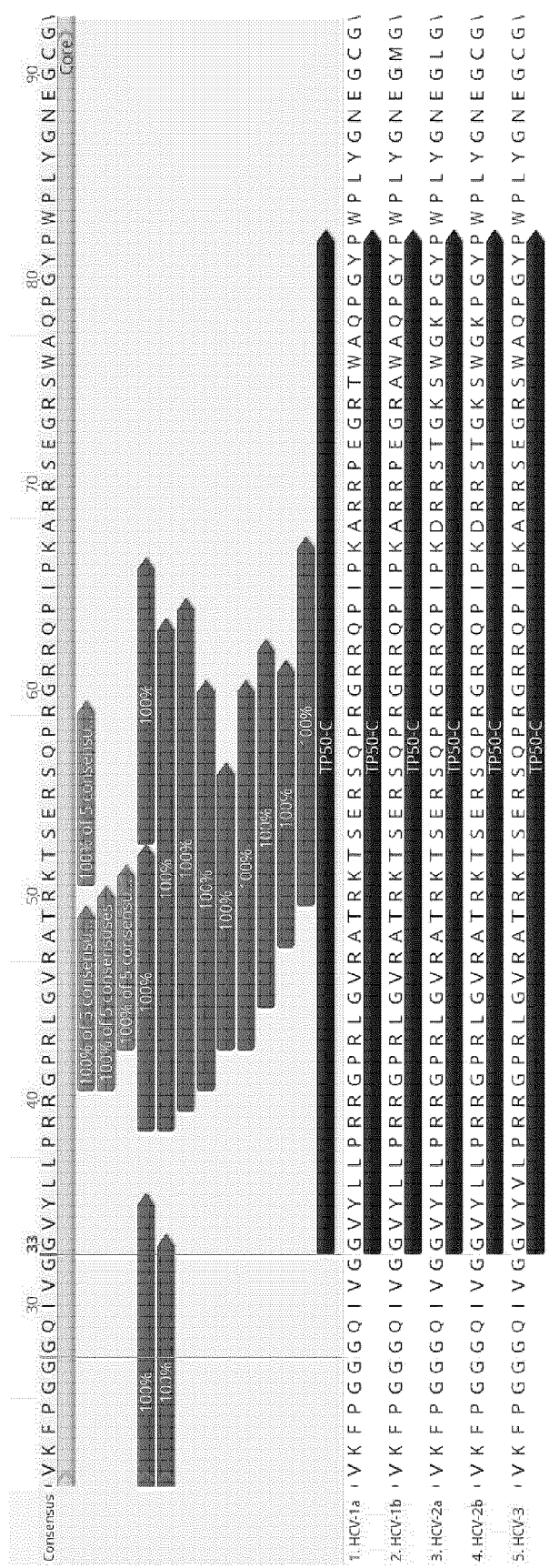
FIG. 17 provides an alignment of amino acid sequences of a portion of NS3 of HCV-1a, -1b, -2a, -2b, and -3, as well as a consensus sequence; and shows the positions of conserved MHC class II CD4-specific HCV epitopes, and conserved MHC class I CD8-specific HCV epitopes in TP50-C. Top to bottom: SEQ ID NOs:371-376. The bars labeled "100% of 5 consensuses" indicate CD8 epitopes. The bars labeled "100%" indicate CD4 epitopes.
Figure 18:
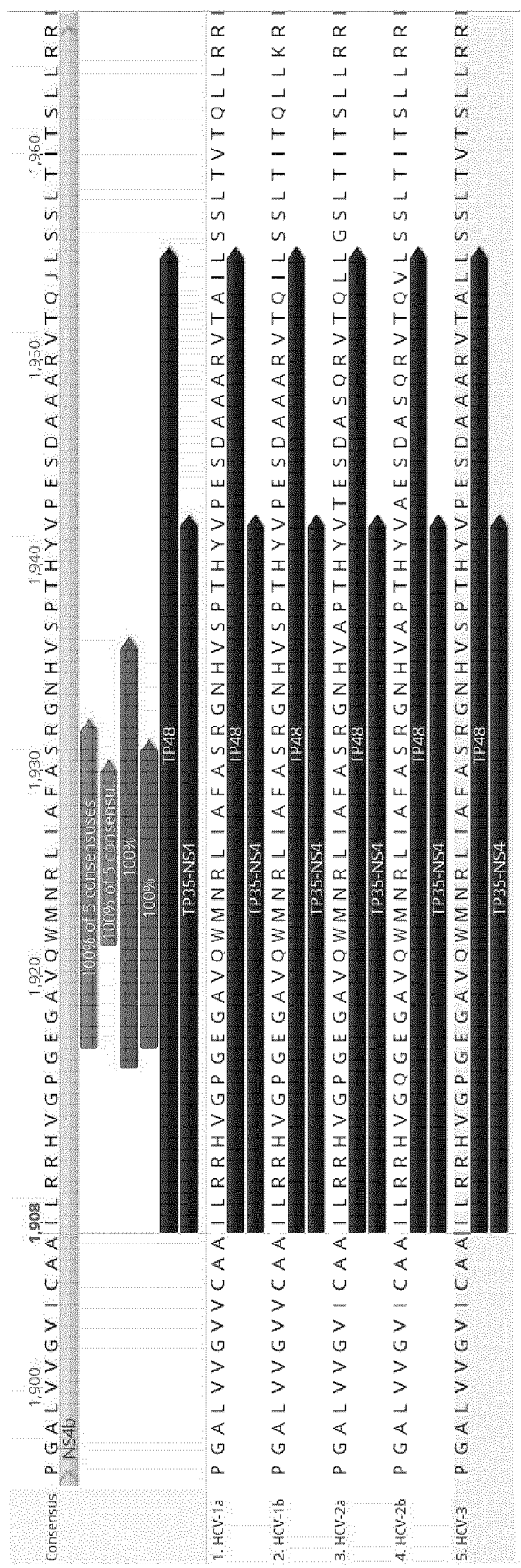
FIG. 18 provides an alignment of amino acid sequences of a portion of NS3 of HCV-1a, -1b, -2a, -2b, and -3, as well as a consensus sequence; and shows the positions of conserved MHC class II CD4-specific HCV epitopes, and conserved MHC class I CD8-specific HCV epitopes in TP35-NS4 and TP-48. Top to bottom: SEQ ID NOs:377-382. The bars labeled "100% of 5 consensuses" indicate CD8 epitopes. The bars labeled "100%" indicate CD4 epitopes.

In FIG. 1A-AC, the amino acid sequence of E2 is amino acid 384 to amino acid 746. In FIG. 2A-2B, the amino acid sequence of E2 is amino acid 384 to amino acid 751. In FIG. 3A-3C, the amino acid sequence of E2 is amino acid 385 to amino acid 754. In FIG. 4A-4B, the amino acid sequence of E2 is amino acid 384 to amino acid 750. As used herein, an "E2 polypeptide" includes a precursor E2 protein, including the signal sequence; includes a mature E2 polypeptide which lacks this sequence; and includes an E2 polypeptide with a heterologous signal sequence. An E2 polypeptide can include a C-terminal membrane anchor sequence which occurs at approximately amino acid positions 715-730 and may extend as far as approximately amino acid residue 746 (see, Lin et al., J. Virol. (1994) 68:5063-5073).

Figure 1B:
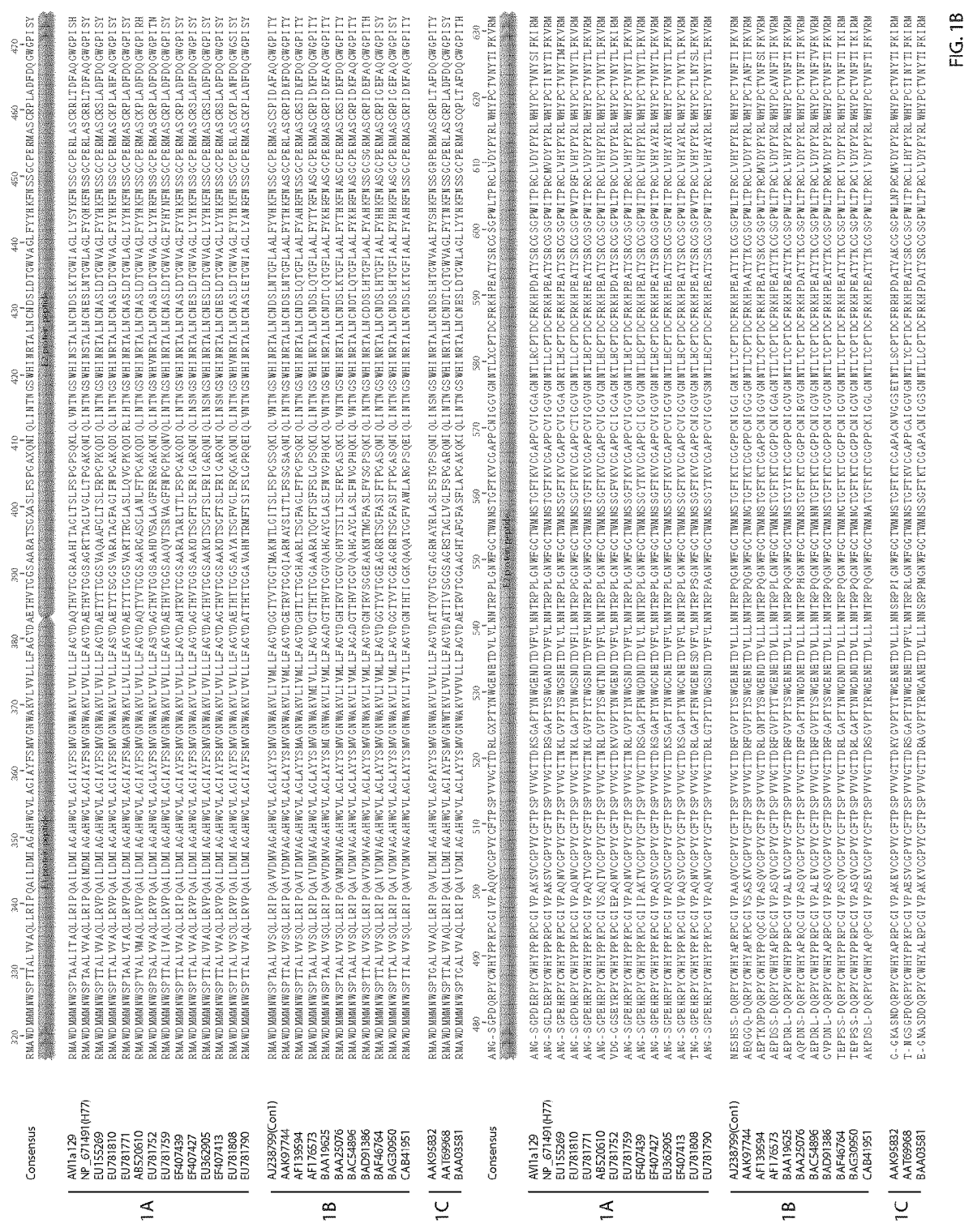
Figure 1C:
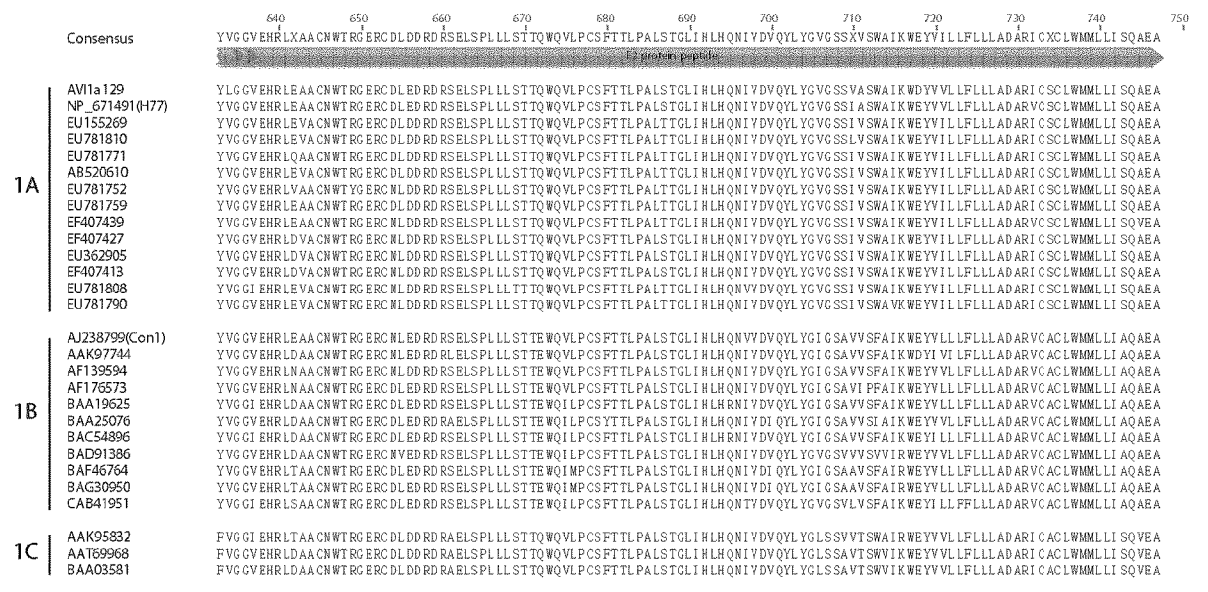

In some cases, a E2 polypeptide suitable for inclusion in an immunogenic composition of the present disclosure lacks a portion of its C-terminal region, e.g., from about amino acid 715 to the C-terminus; from about amino acid 625 to the C-terminus; from about amino acid 661 to the C-terminus; from about amino acid 655 to the C-terminus; from about amino acid 500 to the C-terminus, where the amino acid numbering is with reference to the numbering in FIG. 1A-1C. See, e.g., U.S. Pat. No. 6,521,423.

An E2 polypeptide suitable for inclusion in an immunogenic composition of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E2 polypeptide depicted in FIG. 1A-1C, FIG. 2A-2C, FIG. 3A-3C, or FIG. 4A-4B. An E2 polypeptide suitable for inclusion in an immunogenic composition of the present disclosure can comprise an amino acid sequence having at least about 20%, at least about 25%, at least about 30%, at least about 35%, at least about 40%, at least about 45%, at least about 50%, at least about 60%, at least about 70%, or at least about 75%, amino acid sequence identity to an amino acid sequence of an E2 polypeptide depicted in FIG. 1A-1C, FIG. 2A-2C, FIG. 3A-3C, or FIG. 4A-4B.

An E2 polypeptide suitable for inclusion in an immunogenic composition of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E2 polypeptide depicted in FIG. 1A-1C. For example, an E2 polypeptide of genotype 1 can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-746 of an amino acid sequence depicted in FIG. 1A-1C. For example, an E2 polypeptide of genotype 1A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-746 of an amino acid sequence identified as 1A and depicted in FIG. 1A-1C. For example, an E2 polypeptide of genotype 1B can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-746 of an amino acid sequence identified as 1B and depicted in FIG. 1A-1C. For example, an E2 polypeptide of genotype 1C can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-746 of an amino acid sequence identified as 1C and depicted in FIG. 1A-1C.

Figure 2C:
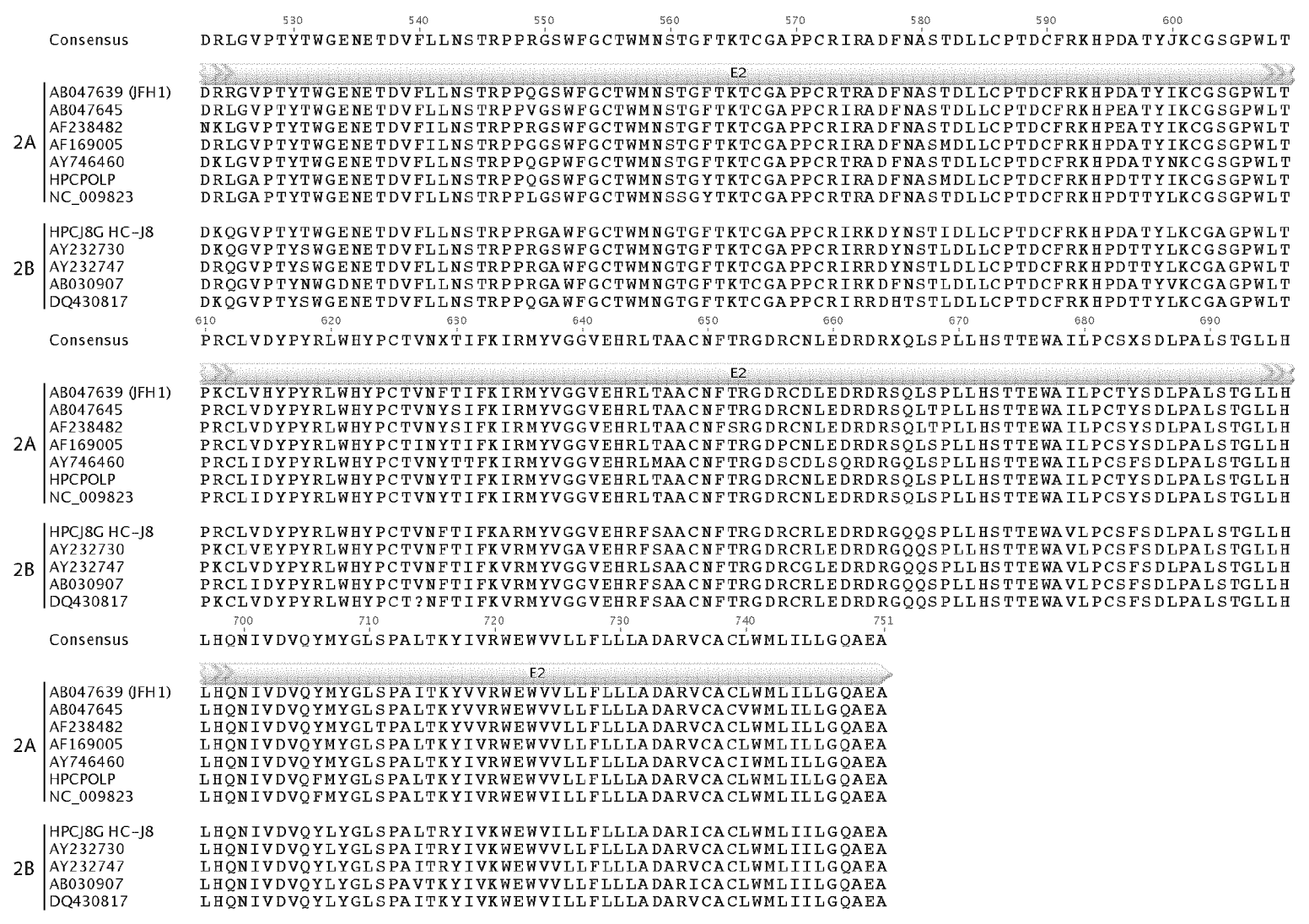

An E2 polypeptide suitable for inclusion in an immunogenic composition of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E2 polypeptide depicted in FIG. 2A-2C. For example, an E2 polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-751 of an amino acid sequence depicted in FIG. 2A-2C. For example, an E2 polypeptide of genotype 2A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-751 of the "consensus" amino acid sequence depicted in FIG. 2A-2C. For example, an E2 polypeptide of genotype 2B can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-751 of the "consensus" amino acid sequence depicted in FIG. 2A-2C.

An E2 polypeptide suitable for inclusion in an immunogenic composition of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E2 polypeptide depicted in FIG. 3A-3C. For example, an E2 polypeptide of genotype 3 can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 385-754 of an amino acid sequence depicted in FIG. 3A-3C. For example, an E2 polypeptide of genotype 3A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 385-754 of an amino acid sequence identified as 3A and depicted in FIG. 3A-3C. For example, an E2 polypeptide of genotype 3B can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 385-754 of the amino acid sequence identified as 3B and depicted in FIG. 3A-3C. For example, an E2 polypeptide of genotype 3K can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 385-754 of the amino acid sequence identified as 3K and depicted in FIG. 3A-3C.

An E2 polypeptide suitable for inclusion in an immunogenic composition of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the amino acid sequence of the E2 polypeptide depicted in FIG. 4A-4B. For example, an E2 polypeptide of genotype 7A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-750 of the amino acid sequence depicted in FIG. 4A-4B.

E1 Polypeptides

An HCV E1 polypeptide suitable for inclusion in an E1/E2 heterodimer for inclusion in an immunogenic composition of the present disclosure, or for inclusion by itself in an immunogenic composition of the present disclosure, can have a length of from about 100 amino acids (aa) to about 150 aa, from about 150 aa to about 175 aa, from about 175 aa to about 195 aa, from about 131 aa to about 175 aa, or from about 175 aa to about 193 aa. In some cases, an HCV E1 polypeptide suitable for inclusion in an E1/E2 heterodimer present in an immunogenic composition of the present disclosure is an HCV E1 ectodomain polypeptide. In some cases, an HCV E1 polypeptide suitable for inclusion in an E1/E2 heterodimer present in an immunogenic composition of the present disclosure is a full-length HCV E1 polypeptide.

In FIG. 1A-1C, the amino acid sequence of E1 is amino acid 192 to amino acid 383. In FIG. 2A-2C, the amino acid sequence of E1 is amino acid 192 to amino acid 383. In FIG. 3A-3C, the amino acid sequence of E1 is amino acid 192 to amino acid 384. In FIG. 4A-4B, the amino acid sequence of E1 is amino acid 192 to amino acid 383. Amino acids at around 170 through approximately 191 serve as a signal sequence for E1. As used herein, "E1 polypeptide" includes a precursor E1 protein, including the signal sequence; includes a mature E1 polypeptide which lacks this sequence; and includes an E1 polypeptide with a heterologous signal sequence. An E1 polypeptide can include a C-terminal membrane anchor sequence which occurs at approximately amino acid positions 360-383 (see, e.g., WO 96/04301). In some cases, a suitable E1 polypeptide lacks a C-terminal portion that includes a transmembrane region. For example, in some cases, a suitable E1 polypeptide lacks the C-terminal portion from amino acid 330 to amino acid 384, or from amino acid 360 to amino acid 384. E1 polypeptides can be an E1 polypeptide of any genotype, subtype or isolate of HCV. E1 polypeptides of genotype 1 and E1 polypeptides of genotype 3 are included in an E1/E2 heterodimer of the present disclosure.

An E1 polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E1 polypeptide depicted in FIG. 1A-IC, FIG. 2A-2C, FIG. 3A-3C, or FIG. 4A-4B.

An E1 polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E1 polypeptide depicted in FIG. 1A-1C. For example, an E1 polypeptide of genotype 1A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 192-383 of an amino acid sequence identified as 1A and depicted in FIG. 1A-1C. For example, an E1 polypeptide of genotype 1B can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 192-383 of an amino acid sequence identified as 1B and depicted in FIG. 1A-1C. For example, an E1 polypeptide of genotype 1C can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 192-383 of an amino acid sequence identified as 1C and depicted in FIG. 1A-1C.

An E1 polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E1 polypeptide depicted in FIG. 2A-2C. For example, an E1 polypeptide of genotype 2A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 192-383 of an amino acid sequence identified as 2A and depicted in FIG. 2A-2C. For example, an E1 polypeptide of genotype 2B can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 192-383 of an amino acid sequence identified as 2B and depicted in FIG. 2A-2C.

An E1 polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the consensus E1 polypeptide amino acid sequence depicted in FIG. 3A-3C.

An E1 polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E1 polypeptide depicted in FIG. 4A-4B. For example, an E1 polypeptide of genotype 7A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 192-383 of the amino acid sequence depicted in FIG. 4A-4B.

HCV E1 and E2 Polypeptides Comprising Amino Acids from a Proteolytically Cleavable Linker As described in more detail below, an HCV E1/E2 heterodimer can be generated using a method that involves an HCV E1 or an HCV E2 polypeptide comprising a heterologous proteolytically cleavable linker. Following enzymatic cleavage of the proteolytically cleavable linker, from 1 to 6 (e.g., 1, 2, 3, 4, 5, or 6) heterologous amino acids can remain on the HCV E1 or E2 polypeptide. For example, from 1 to 6 (e.g., 1, 2, 3, 4, 5, or 6) heterologous amino acids can remain at the N-terminus of an HCV E2 polypeptide. As another example, from 1 to 6 (e.g., 1, 2, 3, 4, 5, or 6) heterologous amino acids can remain at the C-terminus of an HCV E2 polypeptide. As another example, from 1 to 6 (e.g., 1, 2, 3, 4, 5, or 6) heterologous amino acids can remain at the N-terminus of an HCV E1 polypeptide. As another example, from 1 to 6 (e.g., 1, 2, 3, 4, 5, or 6) heterologous amino acids can remain at the C-terminus of an HCV E1 polypeptide.

In some cases, amino acids C-terminal to the proteolytic cleavage site in a proteolytically cleavable linker are Gly-Pro, Ser, Gly, or Gly-Ser. Thus, in some cases, a modified HCV E1 polypeptide comprises, appended to the N-terminus of an HCV E1 polypeptide: Gly-Pro, Ser, Gly, or Gly-Ser. In other words, in some cases, a modified HCV E1 polypeptide comprises, in order from N-terminus to C-terminus: a) Gly-Pro, Ser, Gly, or Gly-Ser; and b) an HCV E1 polypeptide.

In some cases, amino acids C-terminal to the proteolytic cleavage site in a proteolytically cleavable linker are Gly-Pro, Ser, Gly, or Gly-Ser. Thus, in some cases, a modified HCV E2 polypeptide comprises, appended to the N-terminus of an HCV E2 polypeptide: Gly-Pro, Ser, Gly, or Gly-Ser. In other words, in some cases, a modified HCV E2 polypeptide comprises, in order from N-terminus to C-terminus: a) Gly-Pro, Ser, Gly, or Gly-Ser; and b) an HCV E2 polypeptide.

In some cases, amino acids N-terminal to the proteolytic cleavage site in a proteolytically cleavable linker are LEVLFQ (SEQ ID NO:83), ENLYYFQ (SEQ ID NO:84), LVPR (SEQ ID NO:85), I(E/D)GR (SEQ ID NO:86), or DDDDK (SEQ ID NO:87). Thus, in some cases, a modified HCV E1 polypeptide comprises, appended to the C-terminus of an HCV E1 polypeptide: LEVLFQ (SEQ ID NO:83), ENLYYFQ (SEQ ID NO:84), LVPR (SEQ ID NO:85), I(E/D)GR (SEQ ID NO:86), or DDDDK (SEQ ID NO:87). In other words, in some cases, a modified HCV E1 polypeptide comprises, in order from N-terminus to C-terminus: a) an HCV E1 polypeptide; and b) LEVLFQ (SEQ ID NO:83), ENLYYFQ (SEQ ID NO:84), LVPR (SEQ ID NO:85), I(E/D)GR (SEQ ID NO:86), or DDDDK (SEQ ID NO:87).

In some cases, amino acids N-terminal to the proteolytic cleavage site in a proteolytically cleavable linker are LEVLFQ (SEQ ID NO:83), ENLYYFQ (SEQ ID NO:84), LVPR (SEQ ID NO:85), I(E/D)GR (SEQ ID NO:86), or DDDDK (SEQ ID NO:87). Thus, in some cases, a modified HCV E2 polypeptide comprises, appended to the C-terminus of an HCV E2 polypeptide: LEVLFQ (SEQ ID NO:83), ENLYYFQ (SEQ ID NO:84), LVPR (SEQ ID NO:85), I(E/D)GR (SEQ ID NO:86), or DDDDK (SEQ ID NO:87). In other words, in some cases, a modified HCV E2 polypeptide comprises, in order from N-terminus to C-terminus: a) an HCV E2 polypeptide; and b) LEVLFQ (SEQ ID NO:83), ENLYYFQ (SEQ ID NO:84), LVPR (SEQ ID NO:85), I(E/D)GR (SEQ ID NO:86), or DDDDK (SEQ ID NO:87).

In some cases, a flexible linker of from 1 to 10 amino acids is interposed between the proteolytically cleavable linker and the HCV E1 or E2 polypeptide. Flexible linkers are intrinsically disordered flexible linker domains or loops that vary in length and can be rich in polar uncharged amino acids. Flexible linkers include, e.g., glycine polymers $(G)_n$, glycine-serine polymers (including, for example, $(GS)_n$, $(GSGGS)_n$ (SEQ ID NO:88), $(GGSGGS)_n$ (SEQ ID NO:89), and $(GGGS)_n$ (SEQ ID NO:90), where n is an integer of at least one, e.g., where n is 1, 2, 3, 4, 5, or 6); glycine-alanine polymers, such as GAGAGAGA and the like; and alanine-serine polymers, e.g., SASASASA and the like. Exemplary linkers can comprise amino acid sequences including, but not limited to, GGSG (SEQ ID NO:91), GGSGG (SEQ ID NO:92), GSGSG (SEQ ID NO:93), GSGGG (SEQ ID NO:94), GGGSG (SEQ ID NO:95), GSSSG (SEQ ID NO:96), and the like.

For example, in some cases, a modified E1 polypeptide comprises, in order from N-terminus to C-terminus: a) Gly-Pro, Ser, Gly, or Gly-Ser; b) a flexible linker of from 1 to 10 amino acids; and c) an HCV E1 polypeptide.

As another example, in some cases, a modified E2 polypeptide comprises, in order from N-terminus to C-terminus: a) Gly-Pro, Ser, Gly, or Gly-Ser; b) a flexible linker of from 1 to 10 amino acids; and c) an HCV E2 polypeptide.

As another in some cases, a modified E1 polypeptide comprises, from N-terminus to C-terminus: a) an HCV E1 polypeptide; b) a flexible linker of from 1 to 10 amino acids; and c) LEVLFQ (SEQ ID NO:83), ENLYYFQ (SEQ ID NO:84), LVPR (SEQ ID NO:85), I(E/D)GR (SEQ ID NO:86), or DDDDK (SEQ ID NO:87).

As another in some cases, a modified E2 polypeptide comprises, from N-terminus to C-terminus: a) an HCV E2 polypeptide; b) a flexible linker of from 1 to 10 amino acids; and c) LEVLFQ (SEQ ID NO:83), ENLYYFQ (SEQ ID NO:84), LVPR (SEQ ID NO:85), I(E/D)GR (SEQ ID NO:86), or DDDDK (SEQ ID NO:87).

E2 with N-Terminal Heterologous Amino Acids

In some cases, an HCV E1/E2 heterodimer suitable for inclusion in an immunogenic composition of the present disclosure comprises a modified HCV E2 polypeptide with from 1 to 6 amino acids from the proteolytically cleavable linker on the N-terminus of the E2 polypeptide. In some cases, an HCV E1/E2 heterodimer suitable for inclusion in an immunogenic composition of the present disclosure comprises: a) an HCV E1 polypeptide; and b) a modified E2 polypeptide comprising, in order from N-terminus to C-terminus: i) from 1 to 6 heterologous amino acids wherein the from 1 to 6 heterologous amino acids are C-terminal to a site of proteolytic cleavage in a proteolytically cleavable linker; and ii) an HCV E2 polypeptide.

Proteolytically cleavable linkers are described elsewhere herein. Following proteolytic cleavage of a precursor polypeptide, as described herein, a modified E2 polypeptide is generated, which modified E2 polypeptide comprises, at its N-terminus, amino acids C-terminal to the protease cleavage site within the proteolytically cleavable linker.

For example, where the proteolytically cleavable linker comprises a PreScission cleavage site (LEVLFQGP; SEQ ID NO:97), where cleavage occurs between the glutamine and the glycine, a modified E2 polypeptide present in a heterodimeric E1/E2 polypeptide suitable for inclusion in an immunogenic composition of the present disclosure comprises, in order from N-terminus to C-terminus: a) Gly-Pro; and b) an HCV E2 polypeptide. As another example, where the proteolytically cleavable linker comprises a TEV cleavage site (ENLYFQS; SEQ ID NO:98), where cleavage occurs between the glutamine and the serine, a modified E2 polypeptide present in a heterodimeric E1/E2 polypeptide suitable for inclusion in an immunogenic composition of the present disclosure comprises, in order from N-terminus to C-terminus: a) Ser; and b) an HCV E2 polypeptide.

As another example, where the proteolytically cleavable linker comprises a TEV cleavage site (ENLYFQG; SEQ ID NO:99), where cleavage occurs between the glutamine and the glycine, a modified E2 polypeptide present in a heterodimeric E1/E2 polypeptide suitable for inclusion in an immunogenic composition of the present disclosure comprises, in order from N-terminus to C-terminus: a) Gly; and b) an HCV E2 polypeptide.

As another example, where the proteolytically cleavable linker comprises a thrombin cleavage site (LVPRGS; SEQ ID NO:100), where cleavage occurs between the arginine and the glycine, a modified E2 polypeptide present in a heterodimeric E1/E2 polypeptide suitable for inclusion in an immunogenic composition of the present disclosure comprises, in order from N-terminus to C-terminus: a) Gly-Ser; and an HCV E2 polypeptide.

As another example, where the proteolytically cleavable linker comprises a Factor Xa cleavage site (I(E/D)GRX, where X is any amino acid except arginine or proline; SEQ ID NO:101), where cleavage occurs between the arginine and the X, a modified E2 polypeptide present in a heterodimeric E1/E2 polypeptide suitable for inclusion in an immunogenic composition of the present disclosure comprises, in order from N-terminus to C-terminus: a) X (where X is any amino acid except arginine or proline); and an HCV E2 polypeptide.

Thus, for example, in some cases, an HCV E1/E2 heterodimer suitable for inclusion in an immunogenic composition of the present disclosure comprises: a) an HCV E1 polypeptide; and b) a modified E2 polypeptide comprising, in order from N-terminus to C-terminus: i) from 1 to 6 heterologous amino acids, wherein the from 1 to 6 (e.g., 1, 2, 3, 4, 5, or 6) heterologous amino acids are C-terminal to a site of proteolytic cleavage in a proteolytically cleavable linker; and ii) an HCV E2 polypeptide. In some cases, the 1 to 6 heterologous amino acids are Gly-Pro. In some cases, the 1 to 6 heterologous amino acids is Ser. In some cases, the 1 to 6 heterologous amino acids is Gly. In some cases, the 1 to 6 heterologous amino acids are Gly-Ser.

As another example, in some cases, an HCV E1/E2 heterodimer suitable for inclusion in an immunogenic composition of the present disclosure comprises: a) an HCV E2 polypeptide; and b) a modified E1 polypeptide comprising, in order from N-terminus to C-terminus: i) from 1 to 6 heterologous amino acids, wherein the from 1 to 6 (e.g., 1, 2, 3, 4, 5, or 6) heterologous amino acids are C-terminal to a site of proteolytic cleavage in a proteolytically cleavable linker; and ii) an HCV E1 polypeptide. In some cases, the 1 to 6 heterologous amino acids are Gly-Pro. In some cases, the 1 to 6 heterologous amino acids is Ser. In some cases, the 1 to 6 heterologous amino acids is Gly. In some cases, the 1 to 6 heterologous amino acids are Gly-Ser.

E1 with N-Terminal Heterologous Amino Acids

In some cases, an HCV E1/E2 heterodimer suitable for inclusion in an immunogenic composition of the present disclosure comprises a modified HCV E1 polypeptide with from 1 to 6 amino acids from a proteolytically cleavable linker on the N-terminus of the E1 polypeptide. In some cases, an HCV E1/E2 heterodimer suitable for inclusion in an immunogenic composition of the present disclosure comprises: a) an HCV E2 polypeptide; and b) a modified E1 polypeptide comprising, in order from N-terminus to C-terminus: i) from 1 to 6 heterologous amino acids wherein the from 1 to 6 heterologous amino acids are C-terminal to a site of proteolytic cleavage in a proteolytically cleavable linker; and ii) an HCV E1 polypeptide.

Proteolytically cleavable linkers are described elsewhere herein. Following proteolytic cleavage of a precursor polypeptide (e.g., a precursor polypeptide comprising, in order from N-terminus to C-terminus: a) an Fc polypeptide or an HCV E2 polypeptide; b) a proteolytically cleavable linker; and c) an HCV E1 polypeptide), a modified E1 polypeptide is generated, which modified E1 polypeptide comprises, at its N-terminus, amino acids C-terminal to the protease cleavage site within the proteolytically cleavable linker.

For example, where the proteolytically cleavable linker comprises a PreScission cleavage site (LEVLFQGP; SEQ ID NO:97), where cleavage occurs between the glutamine and the glycine, a modified E1 polypeptide present in an HCV E1/E2 heterodimer suitable for inclusion in an immunogenic composition of the present disclosure comprises, in order from N-terminus to C-terminus: a) Gly-Pro; and b) an HCV E1 polypeptide.

As another example, where the proteolytically cleavable linker comprises a TEV cleavage site (ENLYFQS; SEQ ID NO:98), where cleavage occurs between the glutamine and the serine, a modified E1 polypeptide present in an HCV E1/E2 heterodimer suitable for inclusion in an immunogenic composition of the present disclosure comprises, in order from N-terminus to C-terminus: a) Ser; and b) an HCV E1 polypeptide.

As another example, where the proteolytically cleavable linker comprises a TEV cleavage site (ENLYFQG; SEQ ID NO:99), where cleavage occurs between the glutamine and the glycine, a modified E1 polypeptide present in an HCV E1/E2 heterodimer suitable for inclusion in an immunogenic composition of the present disclosure comprises, in order from N-terminus to C-terminus: a) Gly; and b) an HCV E1 polypeptide.

As another example, where the proteolytically cleavable linker comprises a thrombin cleavage site (LVPRGS; SEQ ID NO:100), where cleavage occurs between the arginine and the glycine, a modified E1 polypeptide present in an HCV E1/E2 heterodimer suitable for inclusion in an immunogenic composition of the present disclosure comprises, in order from N-terminus to C-terminus: a) Gly-Ser; and an HCV E1 polypeptide.

As another example, where the proteolytically cleavable linker comprises a Factor Xa cleavage site (I(E/D)GRX, where X is any amino acid except arginine or proline; SEQ ID NO:101), where cleavage occurs between the arginine and the X, a modified E1 polypeptide present in an HCV E1/E2 heterodimer suitable for inclusion in an immunogenic composition of the present disclosure comprises, in order from N-terminus to C-terminus: a) X (where X is any amino acid except arginine or proline); and an HCV E1 polypeptide.

E2 with C-Terminal Heterologous Amino Acids

In some cases, an HCV E1/E2 heterodimer suitable for inclusion in an immunogenic composition of the present disclosure comprises a modified HCV E2 polypeptide with from 1 to 6 amino acids from a proteolytically cleavable linker on the C-terminus of the E2 polypeptide. In some cases, an HCV E1/E2 heterodimer suitable for inclusion in an immunogenic composition of the present disclosure comprises: a) an HCV E1 polypeptide; and b) a modified E2 polypeptide comprising, in order from N-terminus to C-terminus: i) an HCV E2 polypeptide; and ii) from 1 to 6 heterologous amino acids wherein the from 1 to 6 heterologous amino acids are N-terminal to a site of proteolytic cleavage in a proteolytically cleavable linker.

Proteolytically cleavable linkers are described elsewhere herein. Following proteolytic cleavage of a precursor polypeptide (e.g., a precursor polypeptide comprising, in order from N-terminus to C-terminus: a) HCV E2 polypeptide; b) a proteolytically cleavable linker; and c) an Fc polypeptide or an HCV E1 polypeptide), a modified E2 polypeptide is generated, which modified E2 polypeptide comprises, at its C-terminus, amino acids N-terminal to the protease cleavage site within the proteolytically cleavable linker.

For example, where the proteolytically cleavable linker comprises a PreScission cleavage site (LEVLFQGP; SEQ ID NO:97), where cleavage occurs between the glutamine and the glycine, a modified E2 polypeptide present in an HCV E1/E2 heterodimer suitable for inclusion in an immunogenic composition of the present disclosure comprises, in order from N-terminus to C-terminus: a) an HCV E2 polypeptide; and b) LEVLFQ (SEQ ID NO:83).

As another example, where the proteolytically cleavable linker comprises an enterokinase cleavage site (DDDDK; SEQ ID NO:87), where cleavage occurs C-terminal to the Lys, a modified E2 polypeptide present in an HCV E1/E2 heterodimer suitable for inclusion in an immunogenic composition of the present disclosure comprises, in order from N-terminus to C-terminus: a) an HCV E2 polypeptide; and b) DDDDK (SEQ ID NO:87).

As another example, where the proteolytically cleavable linker comprises a TEV cleavage site (ENLYFQG; SEQ ID NO:99), where cleavage occurs between the glutamine and the glycine, a modified E2 polypeptide present in an HCV E1/E2 heterodimer suitable for inclusion in an immunogenic composition of the present disclosure comprises, in order from N-terminus to C-terminus: a) an HCV E2 polypeptide; and b) ENLYFQ.

As another example, where the proteolytically cleavable linker comprises a thrombin cleavage site (LVPRGS; SEQ ID NO:100), where cleavage occurs between the arginine and the glycine, a modified E2 polypeptide present in an HCV E1/E2 heterodimer suitable for inclusion in an immunogenic composition of the present disclosure comprises, in order from N-terminus to C-terminus: a) an HCV E2 polypeptide; and LVPR (SEQ ID NO:85).

As another example, where the proteolytically cleavable linker comprises a Factor Xa cleavage site (I(E/D)GRX, where X is any amino acid except arginine or proline; SEQ ID NO:101), where cleavage occurs between the arginine and the X, a modified E2 polypeptide present in an HCV E1/E2 heterodimer suitable for inclusion in an immunogenic composition of the present disclosure comprises, in order from N-terminus to C-terminus: a) an HCV E2 polypeptide; and I(E/D)GR (SEQ ID NO:86).

E1 with C-Terminal Heterologous Amino Acids

In some cases, an HCV E1/E2 heterodimer suitable for inclusion in an immunogenic composition of the present disclosure comprises a modified HCV E1 polypeptide with from 1 to 6 amino acids from a proteolytically cleavable linker on the C-terminus of the E1 polypeptide. In some cases, an HCV E1/E2 heterodimer suitable for inclusion in an immunogenic composition of the present disclosure comprises: a) an HCV E2 polypeptide; and b) a modified E1 polypeptide comprising, in order from N-terminus to C-terminus: i) an HCV E1 polypeptide; and ii) from 1 to 6 heterologous amino acids wherein the from 1 to 6 heterologous amino acids are N-terminal to a site of proteolytic cleavage in a proteolytically cleavable linker.

Proteolytically cleavable linkers are described elsewhere herein. Following proteolytic cleavage of a precursor polypeptide (e.g., a precursor polypeptide comprising, in order from N-terminus to C-terminus: a) HCV E1 polypeptide; b) a proteolytically cleavable linker; and c) an Fc polypeptide or an HCV E2 polypeptide), a modified E1 polypeptide is generated, which modified E1 polypeptide comprises, at its C-terminus, amino acids N-terminal to the protease cleavage site within the proteolytically cleavable linker.

For example, where the proteolytically cleavable linker comprises a PreScission cleavage site (LEVLFQGP; SEQ ID NO:97), where cleavage occurs between the glutamine and the glycine, a modified E1 polypeptide present in an HCV E1/E2 heterodimer suitable for inclusion in an immunogenic composition of the present disclosure comprises, in order from N-terminus to C-terminus: a) an HCV E1 polypeptide; and b) LEVLFQ (SEQ ID NO:83).

As another example, where the proteolytically cleavable linker comprises an enterokinase cleavage site (DDDDK; SEQ ID NO:87), where cleavage occurs C-terminal to the Lys, a modified E1 polypeptide present in an HCV E1/E2 heterodimer suitable for inclusion in an immunogenic composition of the present disclosure comprises, in order from N-terminus to C-terminus: a) an HCV E1 polypeptide; and b) DDDDK (SEQ ID NO:87).

As another example, where the proteolytically cleavable linker comprises a TEV cleavage site (ENLYFQG; SEQ ID NO:99), where cleavage occurs between the glutamine and the glycine, a modified E1 polypeptide present in an HCV E1/E2 heterodimer suitable for inclusion in an immunogenic composition of the present disclosure comprises, in order from N-terminus to C-terminus: a) an HCV E1 polypeptide; and b) ENLYFQ (SEQ ID NO:102).

As another example, where the proteolytically cleavable linker comprises a thrombin cleavage site (LVPRGS; SEQ ID NO:100), where cleavage occurs between the arginine and the glycine, a modified E1 polypeptide present in an HCV E1/E2 heterodimer suitable for inclusion in an immunogenic composition of the present disclosure comprises, in order from N-terminus to C-terminus: a) an HCV E1 polypeptide; and LVPR (SEQ ID NO:85).

As another example, where the proteolytically cleavable linker comprises a Factor Xa cleavage site (I(E/D)GRX, where X is any amino acid except arginine or proline; SEQ ID NO:101), where cleavage occurs between the arginine and the X, a modified E1 polypeptide present in an HCV E1/E2 heterodimer suitable for inclusion in an immunogenic composition of the present disclosure comprises, in order from N-terminus to C-terminus: a) an HCV E1 polypeptide; and I(E/D)GR (SEQ ID NO:86).

Additional Polypeptides

In any of the above-described embodiments, one or both of the polypeptide chains of the E1/E2 heterodimer can include one or more additional polypeptides. For example, the E1 polypeptide, the E2 polypeptide, or both the E1 and the E2 polypeptide, can include an affinity tag. Suitable affinity tags include, e.g., immunoglobulin Fc polypeptides, a poly(histidine) tag (e.g., $His_6$), a maltose binding protein (MBP), a glutathione-S-transferase (GST) polypeptide, calmodulin-binding peptide (CBP), Streptavidin-binding peptide (SBP), Strep-tag II, FLAG (e.g., DYKDDDDK (SEQ ID NO:103), hemagglutinin (HA) (e.g., YPYDVPDYA (SEQ ID NO:104), c-myc T7 ((e.g., EQK-LISEEDL; SEQ ID NO:105), Glu-Glu, starch-binding domain (SBD), and Flag-Acidic-Target Tag (FATT), and the like.

In some cases, an E1/E2 heterodimer included in a composition of the present disclosure includes a variant E2 polypeptide. In some cases, the E1 polypeptide or the variant E2 polypeptide can include an Ig Fc polypeptide at the C-terminus of the E1 polypeptide or the variant E2 polypeptide. As another example, in some cases, the E1 polypeptide or the variant E2 polypeptide can include an Ig Fc polypeptide at the N-terminus of the E1 polypeptide or the variant E2 polypeptide. Ig Fc polypeptides are known in the art, and are described elsewhere herein.

Pharmaceutically Acceptable Excipients

The present disclosure provides an immunogenic composition comprising: a) one or more T-cell epitope polypeptides as described herein; and b) a pharmaceutically acceptable carrier. The present disclosure provides an immunogenic composition comprising: a) one or more T-cell epitope polypeptides as described herein; b) a pharmaceutically acceptable carrier; and c) an adjuvant. The present disclosure provides an immunogenic composition comprising: a) an HCV heterodimeric polypeptide comprising: i) an HCV E1 polypeptide; and ii) an HCV E2 polypeptide; b) a heterologous polypeptide comprising a T-cell epitope present in an HCV protein other than E1 and E2 ("a T-cell epitope polypeptide"); and c) a pharmaceutically acceptable carrier. The present disclosure provides an immunogenic composition comprising: a) an HCV E2 polypeptide; b) a heterologous polypeptide comprising a T-cell epitope present in an HCV protein other than E1 and E2; and c) a pharmaceutically acceptable carrier. The present disclosure provides an immunogenic composition comprising: a) an HCV E1 polypeptide; b) a heterologous polypeptide comprising a T-cell epitope present in an HCV protein other than E1 and E2; and c) a pharmaceutically acceptable carrier. The present disclosure provides an immunogenic composition comprising: a) an HCV E1 polypeptide; b) a heterologous polypeptide comprising a T-cell epitope present in an HCV protein other than E1 and E2; c) a pharmaceutically acceptable carrier; and d) an adjuvant (e.g., an immune-stimulating amount of an adjuvant).

An immunogenic composition of the present disclosure can comprise, in addition to the above-mentioned HCV polypeptides, one or more of: i) a buffer; ii) a salt; iii) a chelating agent; and iv) a non-ionic detergent. Suitable salts include, e.g., sodium citrate; sodium chloride, and the like. For example, the composition can comprise NaCl in a concentration of from about 50 mM to about 500 mM; e.g., an immunogenic composition of the present disclosure can include NaCl in a concentration of from about 50 mM to about 75 mM, from about 75 mM to about 100 mM, from about 100 mM to about 150 mM, from about 150 mM to about 200 mM, from about 200 mM to about 300 mM, from about 300 mM to about 400 mM, or from about 400 mM to about 500 mM. As one non-limiting example, an immunogenic composition of the present disclosure can comprise, in addition to the above-mentioned HCV polypeptides, the following components: 10 mM sodium citrate, 250 mM NaCl, 1 mM ethylenediaminetetraacetic acid (EDTA), 0.1% non-ionic detergent TWEEN® 80, pH 6.0. As another non-limiting example, an immunogenic composition of the present disclosure can comprise, in addition to the above-mentioned HCV polypeptides, the following components: 10 mM sodium citrate, 100 mM NaCl, 1 mM EDTA, 0.1% non-ionic detergent TWEEN® 80, pH 6.0. As another non-limiting example, an immunogenic composition of the present disclosure can comprise, in addition to the above-mentioned HCV polypeptides, the following components: 10 mM sodium citrate, 400 mM NaCl, 1 mM EDTA, 0.1% non-ionic detergent TWEEN® 80, pH 6.0.

In some cases, where an immunogenic composition of the present disclosure includes an HCV E1 polypeptide and an HCV E2 polypeptide, the ratio of HCV E2 polypeptide to HCV E1 polypeptide is in a range of from about 2:1 to 1:1, e.g., from about 2:1 to 1.5:1, or from 1.5:1 to 1:1. In some cases, where an immunogenic composition of the present disclosure includes an HCV E1 polypeptide and a HCV E2 polypeptide, the molar ratio of HCV E2 polypeptide to HCV E1 polypeptide is in a range of from about 1:1 to 1.5:1, from 1.5:1 to 2:1, from 2:1 to 3:1, from 3:1 to 4:1, from 4:1 to 6:1, or from 6:1 to 8:1.

HCV E1 polypeptides, HCV E2 polypeptides, and heterologous polypeptides (e.g., T-cell epitope polypeptide) can be formulated with a pharmaceutically acceptable excipient(s) to generate an immunogenic composition of the present disclosure. A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds 7th ed., Lippincott, Williams, & Wilkins; and Handbook of Pharmaceutical Excipients (2000) A. H. Kibbe et al., eds., 3rd ed. Amer. Pharmaceutical Assoc.

In some embodiments, an HCV E1 polypeptide, an HCV E2 polypeptide (e.g., as an HCV E1/E2 heterodimer), and a heterologous polypeptide (e.g., T-cell epitope polypeptide) are formulated in an aqueous buffer. Suitable aqueous buffers include, but are not limited to, acetate, succinate, citrate, and phosphate buffers varying in strengths from about 5 mM to about 100 mM. In some embodiments, the aqueous buffer includes reagents that provide for an isotonic solution. Such reagents include, but are not limited to, sodium chloride; and sugars e.g., mannitol, dextrose, sucrose, and the like. In some embodiments, the aqueous buffer further includes a non-ionic surfactant such as polysorbate 20 (TWEEN®20) or polysorbate 80 (TWEEN®80). For example, a formulation of an HCV E1 polypeptide, an HCV E2 polypeptide (e.g., as an HCV E1/E2 heterodimer), and a heterologous polypeptide (e.g., T-cell epitope polypeptide) in an aqueous buffer can include, e.g., from about 0.01% to about 0.05% polysorbate-20 (TWEEN®20) non-ionic detergent. Optionally the formulations may further include a preservative. Suitable preservatives include, but are not limited to, a benzyl alcohol, phenol, chlorobutanol, benzalkonium chloride, and the like. In many cases, the formulation is stored at about 4° C. Formulations may also be lyophilized, in which case they generally include cryoprotectants such as sucrose, trehalose, lactose, maltose, mannitol, and the like. Lyophilized formulations can be stored over extended periods of time, even at ambient temperatures. In some cases, the aqueous buffer further includes a non-ionic surfactant. In some cases, the aqueous buffer includes the non-ionic surfactant TRITON™ X-100, e.g., 0.1% TRITON™ X-100.

An HCV E1 polypeptide, an HCV E2 polypeptide (e.g., as an HCV E1/E2 heterodimer), and a heterologous polypeptide can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

An immunogenic composition of the present disclosure can include, e.g., pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

The concentration of an HCV E1 polypeptide, an HCV E2 polypeptide (e.g., as an HCV E1/E2 heterodimer), and a heterologous polypeptide in a formulation can vary widely (e.g., from less than about 0.1% to at least about 2%, to as much as 20% to 50% or more by weight) and can be selected primarily based on fluid volumes, viscosities, and patient-based factors in accordance with the particular mode of administration selected and the patient's needs.

An immunogenic composition of the present disclosure can be provided in the form of a solution, suspension, tablet, pill, capsule, powder, gel, cream, lotion, ointment, aerosol or the like. It is recognized that oral administration can require protection of the compositions from digestion. This is typically accomplished either by association of the composition with an agent that renders it resistant to acidic and enzymatic hydrolysis or by packaging the composition in an appropriately resistant carrier. Means of protecting from digestion are well known in the art.

An immunogenic composition of the present disclosure can also be provided so as to enhance serum half-life of the polypeptides (an HCV E1 polypeptide, an HCV E2 polypeptide (e.g., as an HCV E1/E2 heterodimer), and a heterologous polypeptide) following administration. For example, where an isolated HCV E1 polypeptide, an HCV E2 polypeptide (e.g., as an HCV E1/E2 heterodimer), and a heterologous polypeptide are formulated for injection, the polypeptides may be provided in a liposome formulation, prepared as a colloid, or other conventional techniques for extending serum half-life. A variety of methods are available for preparing liposomes, as described in, e.g., Szoka et al., Ann. Rev. Biophys. Bioeng. 9:467 (1980), U.S. Pat. Nos. 4,235,871, 4,501,728 and 4,837,028. The preparations may also be provided in controlled release or slow-release forms.

Adjuvants

An immunogenic composition of the present disclosure can include an adjuvant (e.g., an immunostimulating amount of an adjuvant). An immunogenic composition of the present disclosure can include an immune-stimulating amount of an adjuvant. Examples of known suitable adjuvants that can be used in humans include, but are not necessarily limited to, alum, aluminum phosphate, aluminum hydroxide, MF59 (4.3% w/v squalene, 0.5% w/v TWEEN™ 80, 0.5% w/v Span 85), CpG-containing nucleic acid (where the cytosine is unmethylated), QS21, monophosphoryl lipid A (MPL), 3-Q-desacyl-4'-monophosphoryl lipid A (3DMPL), extracts from Aquilla, immune-stimulating complexes (ISCOMS; complexes of cholesterol, phospholipids, and Quillaja saponins), LT/CT mutants, poly(D,L-lactide-co-glycolide) (PLG) microparticles, Quil A, interleukins, and the like. For experimental animals, one can use Freund's incomplete adjuvant, or Freund's complete adjuvant. Also suitable for use are N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria: monophosphoryl lipid A, trehalose dimycolate and cell wall skeleton (MPL+TDM+CWS) in a 2% squalene/TWEEN® 80 emulsion. The effectiveness of an adjuvant may be determined by one or more of: i) measuring the amount of antibodies directed against the immunogenic antigen or antigenic epitope thereof; ii) measuring a cytotoxic T lymphocyte response to the antigen; and iii) measuring a helper T cell response to the antigen.

Further exemplary adjuvants to enhance effectiveness of the composition include, but are not limited to: (1) oil-in-water emulsion formulations (with or without other specific immunostimulating agents such as muramyl peptides (see below) or bacterial cell wall components), such as for example (a) MF59™ (see, e.g., WO 90/14837), containing 5% Squalene, 0.5% TWEEN® 80, and 0.5% Span 85 (optionally containing MTP-PE) formulated into submicron particles using a microfluidizer, (b) SAF, containing 10% Squalane, 0.4% TWEEN® 80, 5% pluronic-blocked polymer L121, and thr-MDP either microfluidized into a submicron emulsion or vortexed to generate a larger particle size emulsion, and (c) RIBI™ adjuvant system (RAS), (Ribi Immunochem, Hamilton, Mont.) containing 2% Squalene, 0.2% TWEEN® 80, and one or more bacterial cell wall components such as monophosphorylipid A (MPL), trehalose dimycolate (TDM), and cell wall skeleton (CWS), e.g., MPL+CWS (Detox™); (2) saponin adjuvants, such as QS21 or StimulonT$^M$ (Cambridge Bioscience, Worcester, Mass.; a purified extract of Quillaja saponaria) may be used or particles generated therefrom such as ISCOMs (immunostimulating complexes), which ISCOMS may be devoid of additional detergent e.g. WO 00/07621; (3) Complete Freund's Adjuvant (CFA) and Incomplete Freund's Adjuvant (IFA); (4) cytokines, such as interleukins (e.g. IL-1, IL-2, IL-4, IL-5, IL-6, IL-7, IL-12 (WO99/44636), etc.), interferons (e.g. gamma interferon), macrophage colony stimulating factor (M-CSF), tumor necrosis factor (TNF), etc.; (5) monophosphoryl lipid A (MPL) or 3-O-deacylated MPL (3dMPL) e.g. GB-2220221, EP-A-0689454, optionally in the substantial absence of alum when used with pneumococcal saccharides e.g. WO 00/56358; (6) combinations of 3dMPL with, for example, QS21 and/or oil-in-water emulsions (see, e.g. EP-A-0835318, EP-A-0735898, EP-A-0761231); (7) oligonucleotides comprising a CpG motif containing at least one CG dinucleotide, where the cytosine is unmethylated (see, e.g., WO 96/02555, WO 98/16247, WO 98/18810, WO 98/40100, WO 98/55495, WO 98/37919 and WO 98/52581); (8) a polyoxyethylene ether or a polyoxyethylene ester (see, e.g. WO 99/52549); (9) a polyoxyethylene sorbitan ester surfactant in combination with an octoxynol (WO 01/21207) or a polyoxyethylene alkyl ether or ester surfactant in combination with at least one additional non-ionic surfactant such as an octoxynol (WO 01/21152); (10) a saponin and an immunostimulatory oligonucleotide (e.g. a CpG oligonucleotide) (WO 00/62800); (11) an immunostimulant and a particle of metal salt (see, e.g. WO 00/23105); (12) a saponin and an oil-in-water emulsion (see e.g. WO 99/11241); (13) a saponin (e.g. QS21)+3dMPL+IM2 (optionally including a sterol) (see, e.g. WO 98/57659); (14) other substances that act as immunostimulating agents to enhance the efficacy of the composition. Muramyl peptides include N-acetyl-muramyl-L-threonyl-D-isoglutamine (thr-MDP), N-25 acetyl-normuramyl-L-alanyl-D-isoglutamine (nor-MDP), N-acetylmuramyl-L-alanyl-D-isoglutarninyl-L-alanine-2-(1'-2'-dipalmitoyl-sn-glycero-3-hydroxyphosphoryloxy)-ethylamine MTP-PE), etc. Also suitable for use is Matrix-M™; Matrix-M™ is an adjuvant that comprises 40 nm nanoparticles comprising Quillaja saponins, cholesterol, and phospholipid. Adjuvants suitable for administration to a human are of particular interest. In some cases, the adjuvant is one that enhances a $CD4^+$ T helper response to the immunogen. Also suitable for use is a poly inosine:cytosine (poly I:C) nucleic acid. Poly I:C is a synthetic double-stranded RNA Also suitable for use is a cyclic dinucleotide activator of the STING pathway. Examples of suitable cyclic dinucleotide adjuvants include, but are not limited to: 1) bis-(3',5')-cyclic dimeric adenosine monophosphate (c-di-AMP); 2) bis-(3',5')-cyclic dimeric guanosine monophosphate (c-di-GMP); and bis-(3',5')-cyclic dimeric inosine monophosphate (c-di-IMP). Also suitable for use is poly (I:C).

QS21 has the following structure:

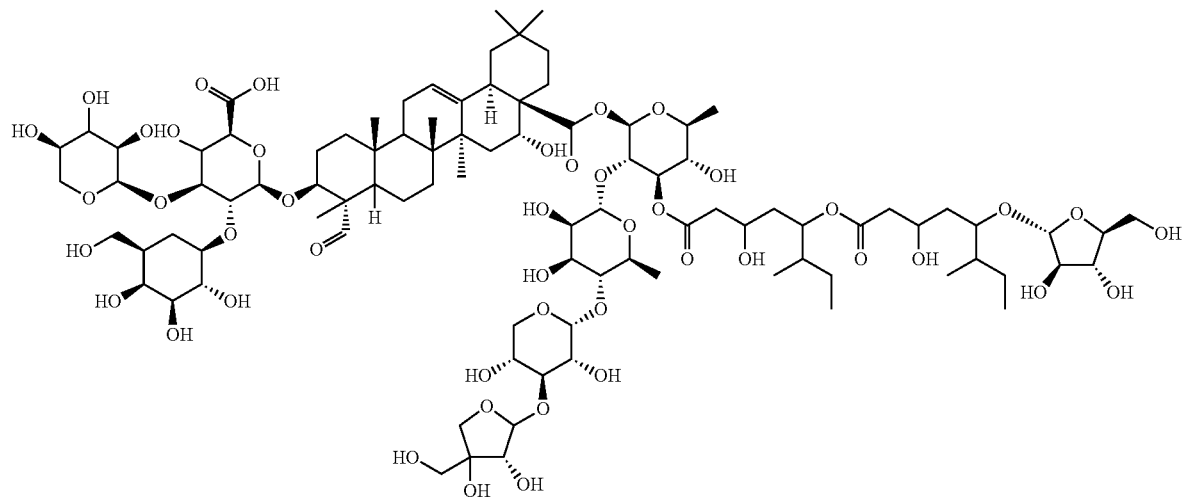

MPL has the following structure:

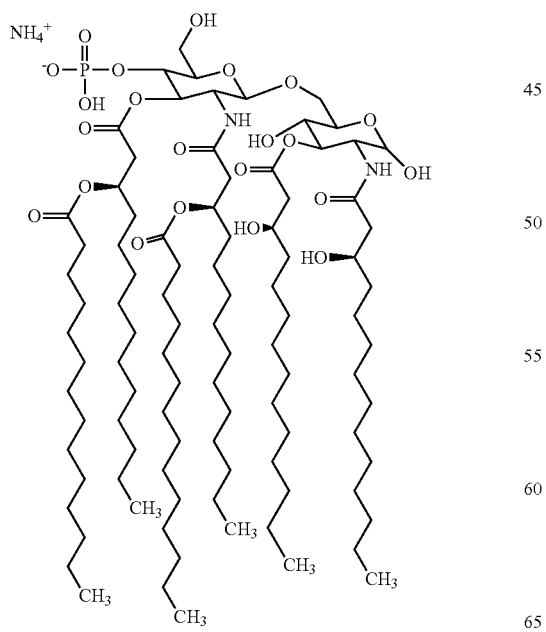

In some instances, the adjuvant is MF59, with or without a CpG-containing oligonucleotide. In other instances, the adjuvant is alum, with or without a CpG-containing oligonucleotide. In other instances, the adjuvant is poly(D,L-lactide-co-glycolide), with or without a CpG-containing oligonucleotide. In other instances, the adjuvant is MPL, with or without a CpG-containing oligonucleotide. In some cases, the adjuvant is Matrix-M™, with or without a CpG-containing oligonucleotide. In some cases, the adjuvant is keyhole limpet hemocyanin. In some cases, the adjuvant is alum. In some cases, the adjuvant is aluminum phosphate. In some cases, the adjuvant is aluminum hydroxide. In some cases, the adjuvant is alum+MPL. In some cases, the adjuvant is MF59. In some cases, the adjuvant is alum+MF59. In some cases, the adjuvant is AS01. AS01 contains QS-21 Stimulon® adjuvant, MPL, and liposomes. In some cases, the adjuvant comprises QS21 and MPL in a liposomal formulation. In some cases, the adjuvant is AS03. A dose of AS03 contains: 10.69 mg squalene; 11.86 mg DL-α-tocopherol; and 4.86 mg polysorbate-80. In some cases, the adjuvant comprises aluminum hydroxide and MPL. In some cases, the adjuvant is AS04. AS04 comprises aluminum hydroxide and MPL. In some cases, the adjuvant is AS15. AS15 is a combination of QS-21 Stimulon® adjuvant, monophosphoryl lipid A, and CpG7909 (an oligonucleotide of the sequence 5'-TCGTCGTTTTGTCGTTTTGTCGTT-3'; (SEQ ID NO: 106), in a liposomal formulation. In some instances, the adjuvant is a cyclic dinucleotide (CDN). Suitable CDNs are described below.

In some cases, the adjuvant is selected from the group consisting of an aluminum salt, RIBI, a toll-like receptor agonist, AS01, AS02, AS03, AS04, AS05, a CpG-oligodeoxynucleotide, MF-59, Montanide ISA-51 VG, Montanide ISA-720, Quil A, QS21, a synthetic saponin, an immunostimulatory complex, stearyl tyrosine, a virus-like particle, a reconstituted influenza virosome, a cytokine, mast cell activator compound 48/80, a liposome, a muramyl dipeptide, SAF-1, and combinations thereof. In some cases, the adjuvant is selected from the group consisting of an aluminum salt, alum, PHAD, a CDN, AS01, AS04, a CpG oligodeoxynucleotide, MF59, and combinations of two or more of the foregoing.

In some cases, the adjuvant is a disaccharide synthetic lipid compound, e.g., as described in U.S. Pat. No. 9,518,078. A disaccharide synthetic lipid compound can be a phosphorylated hexaacyl disaccharide (PHAD).

In some cases, the adjuvant is a PHAD of the following structure:

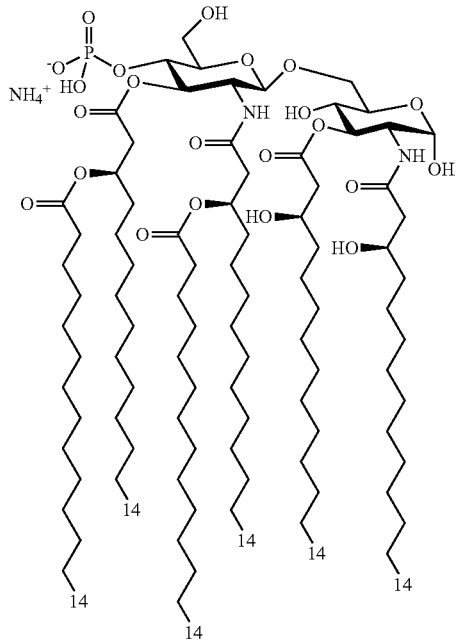

In some cases, a disaccharide synthetic lipid compound is a compound referred to as MPLA-B in U.S. Pat. No. 9,518,078; and has the following structure:

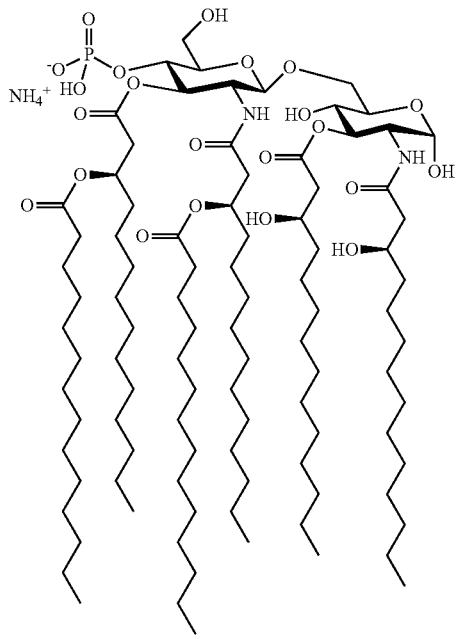

In some cases, a disaccharide synthetic lipid compound is a compound referred to as MPLA-D in U.S. Pat. No. 9,518,078; and has the following structure:

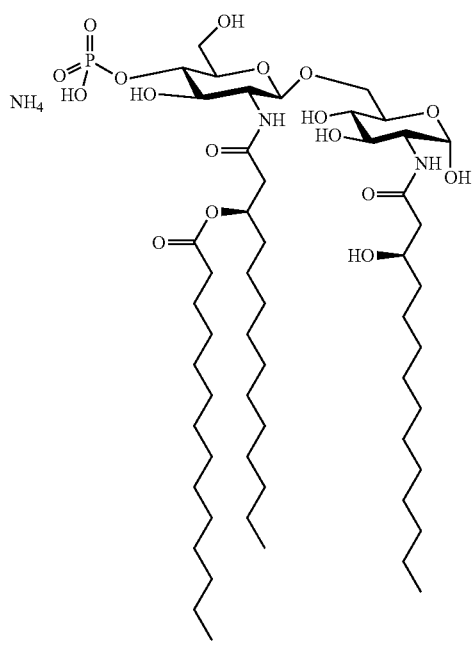

In some cases, a disaccharide synthetic lipid compound is a compound referred to as MPLA-C in U.S. Pat. No. 9,518,078; and has the following structure:

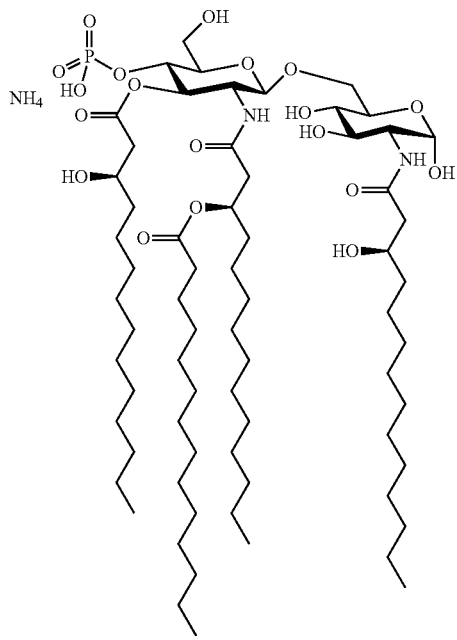

In some cases, the adjuvant is PHAD (also referred to as a glucopyranosyl lipid adjuvant (GLA)). In some cases, the adjuvant is a combination of alum and a PHAD.

Cyclic Dinucleotides

In some cases, an immunogenic composition of the present disclosure comprises a cyclic dinucleotide (CDN).

In some cases, a CDN suitable for use in an immunogenic composition of the present disclosure is of Formula (I):

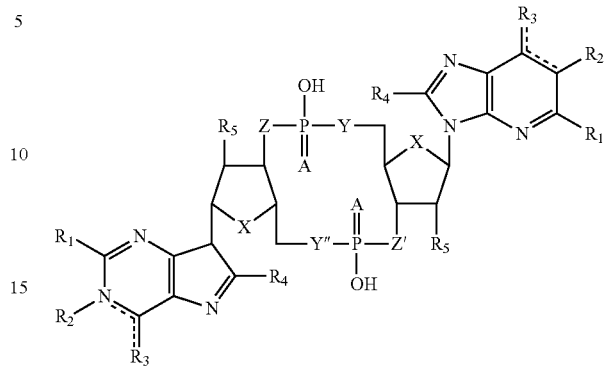

wherein:
A is S or O;
X is S, N, O, $CH_2$;
Y, Y is NH, $CH_2$, O;
Z, Z' is NH, $CH_2$, O;
R1 represents hydrogen or $NH_2$ which may be substituted;
R2 is hydrogen or absent;
R3 represents $NH_2$, O, OH, H, or a halogen;
R4 represents hydrogen, halogen, or a straight or branched $C_1$-$C_6$ alkyl group which may optionally be substituted;
R5 represents hydrogen, OH or a straight or branched $C_1$-$C_6$ alkyl chain or $C_1$-$C_6$ straight or branched alkoxy chain which may optionally be substituted;
----- is a single or double bond;
or conjugates thereof, and salts or solvates thereof. See, e.g., US 2008/0286296.

In formula (I), the purine residue is in some cases a guanine (G), adenine (A), xanthine or hypoxanthine (X), or inosine (I) residue. The compound can have identical purine residues, e.g. c-diGMP, c-diAMP, c-diIMP, or c-dXMP, or can contain different purine residues, e.g. c-GpAp, c-GpIp, c-GpXp, c-ApIp, c-ApXp, or c-IpXp. Further, R5 is in some cases an OH group. In addition, X is in some cases an oxygen atom. In one embodiment, Y, Y', Z, and Z' are an oxygen atom, O. Thus, in one embodiment, the compound of formula (I) is a cyclic bis(3'-5')diguanylic acid (c-diGMP) or conjugates thereof or a cyclic bis(3'-5')diadenylic acid (c-diAMP) or conjugates thereof, or salts or solvates thereof. In one embodiment, the compound of formula (I) is cyclic Bis(3'-5')adenylic acid, which is also referred to as c-di-AMP; or the pegylated conjugate. With the term "which may be substituted" is meant the substitution with a straight or branched C1-C6 alkyl group or a straight or branched C1-C6 alkoxy group and/or with a halogen, hydroxyl group or carboxyl group.

In some cases, a CDN suitable for use in an immunogenic composition of the present disclosure is selected from the group consisting of cyclic di-adenosine monophosphate (c-di-AMP), cyclic di-guanosine monophosphate (c-di-GMP), and cyclic guanosine monophosphate-adenosine monophosphate (cGAMP). In some cases, a CDN suitable for use in an immunogenic composition of the present disclosure is cGAMP (2'-3'-cyclic GMP-AMP) or cGAMP (3'-3'-cyclic GMP-AMP). In some cases, a CDN suitable for use in an immunogenic composition of the present disclosure is cGAMP (2'-3'-cyclic GMP-AMP). In some cases, a CDN suitable for use in an immunogenic composition of the present disclosure is cGAMP (3'-3'-cyclic GMP-AMP).

In some cases, a CDN suitable for use in an immunogenic composition of the present disclosure is of Formula (II):

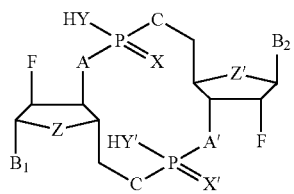

where:

A, C, A' and C' are independently selected from NH, O, and S;

X, Y, X', and Y' are independently selected from O or S;

Z and Z' are independently selected from O, S, NH, and $CH_2$; and $B_1$ and $B_2$ are independently a purine selected from:

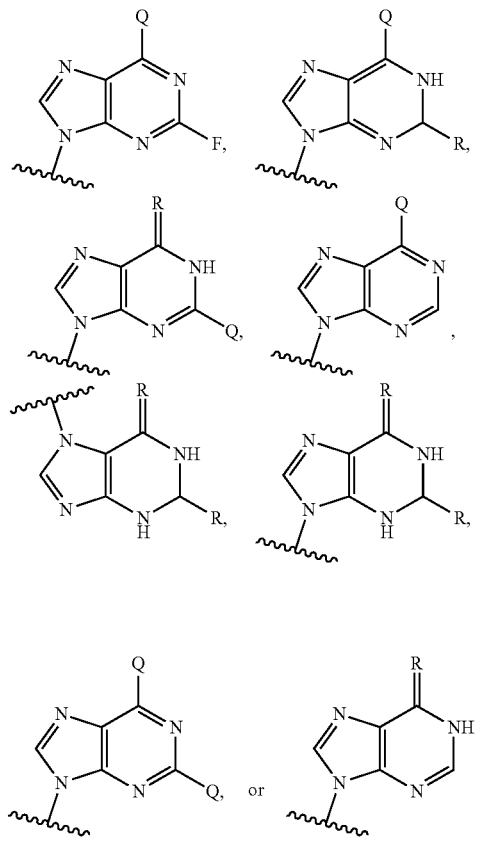

where:

Q is hydrogen or $NH_2$;

Nitrogen is optionally substituted with a $C_1$-$C_6$ alkyl or a $C_1$-$C_6$ acyl group; and R is O or S.

In some cases, a CDN suitable for inclusion in an immunogenic composition of the present disclosure is a fluorinated CND. In some cases, the fluorinated CDN is 2'-F-c-diGMP having the following structure:

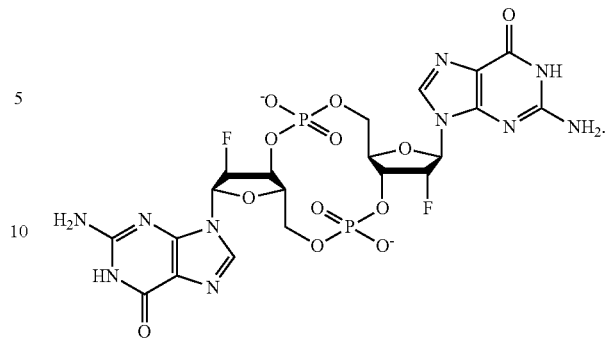

Archaeal Glycolipid

In some cases, an immunogenic composition of the present disclosure comprises an archaeosome. For example, in some cases, an immunogenic composition of the present disclosure comprises an archaeosome comprising at least one polar synthetic lipid, where the at least one polar synthetic lipid comprises at least one carbohydrate or anionic group linked by covalent bonding to at least one free hydroxyl group of an archaeal core lipid.

An archaeal lipid suitable for use in an immunogenic composition of the present disclosure comprises a polar lipid based on a 2, 3-dialkylglycerol skeleton. These 2, 3-dialkylglycerol groups are isoprenoid and the simplest molecules are derivatives or 2,3-dibiphytanyl-O-sn-glycerol (archeol); for instance, two isoprenoid units of 20 carbons joined at positions sn-2 and sn-3 of glycerol. These alkyl chains are generally saturated; nevertheless, some forms have double bonds in different positions. These lipids have one or two groups of polar head, which may be different with units 2, 3-sn-glycerol joined by C40 alkyl components which are also isoprenoid molecules. For instance, calarcheol (so called because it is the predominant form in some thermophile archaebacteria), has two C40 isoprenoid units bonded from positions 2 to 3' and from position 3 to 2'.

In some cases, an archaeal adjuvant suitable for use in an immunogenic composition of the present disclosure comprises multivalent cations in association with aggregates of a plurality of spherical archaeal polar lipid structures containing aqueous compartments (e.g., an "AMVAD structure"), where the archaeal polar lipid is a total polar lipids extract or archaetidyl glycerophosphate-O-methyl, obtained from an archaeal species. The multivalent cations can be divalent or trivalent cations. The multivalent cations can be divalent $Ca^{2+}$ or $Mg^2$, or trivalent $Al^{3+}$. The $Ca^{2+}$ can be provided as $CaCl_2$. The $Al^{3+}$ can be provided as $AlCl_3$ or $AlK(SO_4)_2$. In some cases, the total polar lipids extract from an archaeal species is mixed with neutral lipids from the archaeal species. See, e.g., U.S. Patent Publication No. 2013/0195932.

In some cases, lipids suitable for use in an immunogenic composition of the present disclosure comprises 1,2-di-O-hexadecyl-sn-glycero-3-phosphatidylcholine and 1,2-di-O-phytanyl-sn-glycero-3-phosphatidylethanolamine. In some cases, the 1,2-di-O-hexadecyl-sn-glycero-3-phosphatidylcholine and 1,2-di-O-phytanyl-sn-glycero-3-phosphatidylethanolamine form uniformly sized particles; for example, the particles can comprise: liposomes, nanoliposomes, niosomes, microspheres, nanospheres, nanoparticles, micelles or archaeosomes.

In some cases, an archaeosome comprises at least one polar synthetic lipid, where the at least one polar synthetic lipid comprises at least one carbohydrate or anionic group linked by covalent bonding to at least one free hydroxyl group of an archaeal core lipid. In some cases, the archaeal core lipid is archaeol (2,3-di-O-diphytanyl-sn-glycerol). In some cases, the archaeal core lipid is caldarchaeol (2,2',3, 3'-tetra-O-dibiphytanyl-sn-diglycerol). In some cases, the the carbohydrate group is selected from the group consisting of: β-D-Glc-(1,6)-β-D-Glc-; β-D-Glc-(1,6)-α-D-Glc-; α-D-Glc-(1,6)-β-D-Glc-; β-D-Glc-(1,4)-β-D-Glc-; α-D-Glc-(1,4)-β-D-Glc-; β-D-Gal-(1,4)-β-D-Glc-; α-D-Gal-(1,6)-β-D-Glc-; β-D-Glc-(1,6)-β-D-Glc-(1,6)-β-D-Glc-; α-D-Glc-(1,4)-α-D-Glc-(1,4)-β-D-Glc-; α-D-Man-(1,2)-α-D-Man-(1,2)-α-D-Man-; and α-D-Man-(1,2)-α-D-Man-(1,2)-α-D-Man-(1,2)-α-D-Man-. In some cases, the carbohydrate group comprises two or three β-D-Glc- units in (1,6) linkage. In some cases, the carbohydrate group is a Galactose-Glucose (gal-glc) group. In some cases, the anionic group is selected from the group consisting of phosphoserine, phosphoethanolamine, phosphoinositol and phosphoglycerol. In some cases, the at least one anionic lipid is selected from the group consisting of archaetidylglycerol, archaetidylglycerolphosphate-methyl, archaetidylserine, and archaetidylinositol. In some cases, the archaeosome comprises at least one conventional lipid. In some cases, the at least one conventional lipid is selected from a group consisting of phosphatidylglycerol, phosphatidylserine, sulfoquinovosyl diacylglycerol (SQDG), and cholesterol. In some cases, the at least one conventional lipid comprises cholesterol, and wherein cholesterol is present in an amount of between 10 and 45 mol % of the total lipid composition. In some cases, the phosphatidylglycerol is present in an amount of between 20 and 80 mol % of the lipid composition. In some cases, the phosphatidylserine is present in an amount of between 10 and 30 mol % of the lipid composition. In some cases, the at least one polar synthetic lipid comprises at least one synthetic immunoactive glycolipid and at least one anionic lipid, and the archaeosome further comprises at least one stabilizing lipid. In some cases, the at least one polar synthetic lipid comprises caldarchaeol having one carbohydrate head group and one anionic head group. In some cases, the carbohydrate head group comprises gentiobiose and the anionic head group comprises phosphoinositol. In some cases, the at least one polar synthetic lipid comprises a first caldarchaeol having two carbohydrate head groups and a second caldarchaeol having two anionic head groups, and wherein the at least one stabilizing lipid is the first and/or second caldarchaeol. In some cases, the at least one polar synthetic lipid comprises gentiotriose-archaeol and wherein the at least one stabilizing lipid comprises cholesterol and at least one of phosphatidylethanolamine, archaetidylglycerol, archaetidylserine or archaetidylglycerolphosphate-methyl.

Caldarchaeol is also known as dibiphytanyldiglycerol tetraether. Two glycerol units are linked together by two strains that consist of two phytanes linked together to form a linear chain of 32 carbon atoms. Caldarchaeol has the following structure:

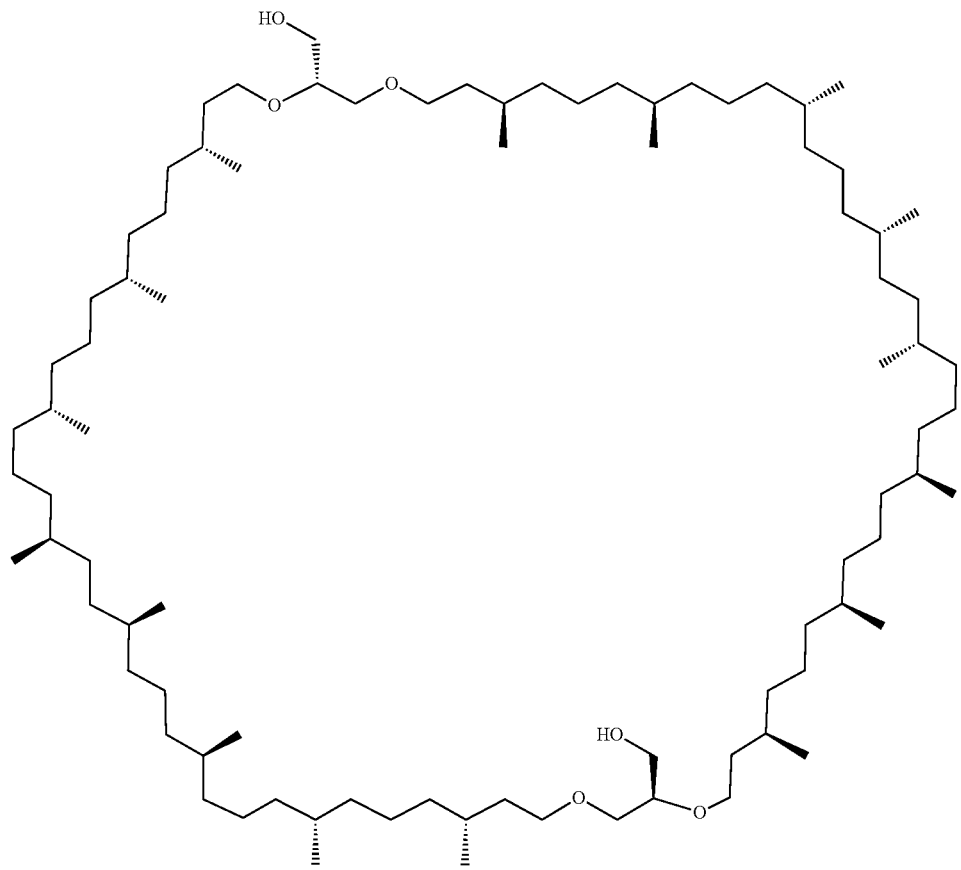 [SMILES: C[C@@H]1CCC[C@H](C)CCC[C@H](C)CC[C@@H](C)CCC[C@@H](C)CCC[C@@H](C)CCC[C@@H](C)CCO[C@H](CO)COCC[C@H](C)CCC[C@H](C)CCC[C@H](C)CCC[C@H](C)CC[C@@H](C)CCC[C@@H](C)CCC[C@@H](C)CCC[C@@H](C)CCO[C@H](CO)COCC[C@H](C)CCC1]

Archaeal lipids can be obtained from any archaea of the phyla Euryarchaeota, Crenarchaeota, Korarchaeota, or, Nanoarchaea. Archaeal lipids can be obtained from any archaea of the genus *Thermococcus, Sulfolobus, Halobac-* terium, *Methanococcus, Ferroglobus, Thermoplasma, Archaeoglobus, Haloquadratum*, or *Halorubrum*. Suitable sources of archaeal lipids include, but are not limited to, *Thermus aquaticus, Thermus thermophilus; Methanobrevibacter smithii; Thermoplasma acidophilum*; a *Sulfolobus* species, e.g. *Sulfolobus acidocaldarius, Sulfolobus solfataricus, Sulfolobus islandicus, Sulfolobus tokodaii*, etc.; a *Pyrobaculum* species, e.g. *Pyrobaculum islandicum* or *Pyrobaculum aerophilum*; a *Methanococcus* species, e.g., *Methanocaldococcus vulcanius, Methanocaldococcus jannaschii, Methanococcus aeolicus, Methanococcus voltae*; or a *Halobacterium* species such as *Halobacterium salinarum; Methanopyrus kandleri; Methanobacterium espanolae; Methanosphaera stadtmanae; Methanosarcina mazei; Natronobacterium magadii*; etc.

Total polar lipids (TPL) can be extracted from archaea and collected as the acetone-insoluble fraction. Choquet et al. (1994) *Appl. Microbiol. Biotechnol.* 42:375; Bligh and Dyer (1959) *Can. J. Biochem. Physiol.* 37:911. The polar lipids consist of regularly branched, and usually fully saturated, phytanyl chains of 20, 25, or 40 carbon length, with the 20 and 40 being most common. Archaeosomes can be prepared by hydrating TPL in a buffer (e.g., phosphate-buffered saline). The TPL-buffer solution can be sonicated (e.g., at 60 Hz for 10 min).

TPL can be extracted from archaea by stirring the cells (which may be lyophilized) with chloroform-methanol (2:1, v/v) for 1 hour at room temperature. The suspension is passed through a sintered glass filter, and the residue reextracted for an additional hour. Combined filtrates are evaporated, taken up in chloroform-methanol-water (60:30:4.5, v/v/v), and passed through Sephadex G-25 for removal of nonlipid contaminations. Langworthy et al. (1977) *J. Bacteriol.* 130:1326.

The mean diameter of archaeosomes in an archaeosomal formulation can range from about 50 nm to 600 nm, e.g., from 50 nm to 100 nm, from 100 nm to 150 nm, from 150 nm to 200 nm, from 200 nm to 250 nm, from 250 nm to 300 nm, from 300 nm to 400 nm, from 400 nm to 450 nm, from 450 nm to 500 nm, from 500 nm to 550 nm, or from 550 nm to 600 nm.

Containers

The present disclosure provides a container comprising an immunogenic composition of the present disclosure. The container can be sterile. The immunogenic composition can be sterile. The immunogenic composition can be suitable for administration to a human subject; e.g., the immunogenic composition can be free of pyrogens, allergens, or other substances that may be harmful to a human subject. Suitable containers include unit-dose containers, multi-dose sealed containers, ampules, vials, syringes, and the like. In some cases, the container is a syringe.

Methods of Making an HCV E1/E2 Heterodimer, and for Making a T-Cell Epitope Polypeptide An HCV E1/E2 heterodimer, an HCV E2 polypeptide, an HCV E1 polypeptide, and a T-cell epitope polypeptide, suitable for inclusion in an immunogenic composition of the present disclosure, can be generated using standard methods for producing a polypeptide in a host cell.

An HCV E1/E2 heterodimer, an HCV E2 polypeptide, an HCV E1 polypeptide, and a T-cell epitope polypeptide, suitable for inclusion in an immunogenic composition of the present disclosure, can be produced using any suitable method, including recombinant and non-recombinant methods (e.g., chemical synthesis). An HCV E1/E2 heterodimer, an HCV E1 polypeptide, and a T-cell epitope polypeptide, suitable for inclusion in an immunogenic composition of the present disclosure, can be generated using standard methods for producing a polypeptide in a host cell.

Where a polypeptide is chemically synthesized, the synthesis may proceed via liquid phase or solid-phase. Solid-phase peptide synthesis (SPPS) allows the incorporation of unnatural amino acids and/or peptide/protein backbone modification. Various forms of SPPS, such as Fmoc and Boc, are available for synthesizing polypeptides. Details of the chemical synthesis are known in the art (e.g., Ganesan A. 2006 Mini Rev. Med Chem. 6:3-10; Camarero J A et al. 2005 Protein Pept Lett. 12:723-8).

Where a polypeptide is produced using recombinant techniques, the polypeptide may be produced as an intracellular protein or as a secreted protein, using any suitable construct and any suitable host cell, which can be a prokaryotic or eukaryotic cell, such as a bacterial (e.g., *Escherichia coli*) cell or a yeast host cell, respectively. Other examples of eukaryotic cells that may be used as host cells include insect cells, mammalian cells, filamentous fungi, and plant cells. Suitable yeast cells include, e.g., *Saccharomyces cerevisiae* and *Pichia* (e.g., *Pichia pastoris*).

In some cases, the heterologous polypeptide is produced separately from (e.g., in a separate host cell) from the HCV E1/E2 heterodimer. In some cases, the heterologous polypeptide is produced in a first host cell; and the HCV E1/E2 heterodimer is produced in a second host cell. Once the HCV E1/E2 heterodimer and the heterologous polypeptide are separately produced, they can be combined, together with a pharmaceutically acceptable excipient, to generate an immunogenic composition of the present disclosure. In some cases, both the HCV E1/E2 heterodimer and the heterologous polypeptide are purified before being combined to generate an immunogenic composition. For example, both the HCV E1/E2 heterodimer and the heterologous polypeptide can be at least 80%, at least 85%, at least 90%, at least 95%, at least 98%, at least 99%, or more than 99%, pure, e.g., free from other polypeptides, other macromolecules, etc.

Methods of Making a T-Cell Epitope Polypeptide

A T-cell epitope polypeptide present in an immunogenic composition of the present disclosure can be generated using any known method for making a polypeptide. A T-cell epitope polypeptide can be chemically synthesized. A T-cell epitope polypeptide can be chemically synthesized via liquid phase or solid-phase. Solid-phase peptide synthesis (SPPS) allows the incorporation of unnatural amino acids and/or peptide/protein backbone modification. Various forms of SPPS, such as Fmoc and Boc, are available for synthesizing polypeptides. Details of the chemical synthesis are known in the art (e.g., Ganesan A. 2006 Mini Rev. Med Chem. 6:3-10 and Camarero J A et al. 2005 Protein Pept Lett. 12:723-8).

In some cases, a nucleic acid (e.g., a recombinant expression vector) comprising a nucleotide sequence encoding the T-cell epitope polypeptide is introduced into a host cell, generating a genetically modified (recombinant) host cell, where the recombinant expression vector provides for expression of the T-cell epitope polypeptide in the genetically modified host cell.

In some cases, the T-cell epitope polypeptide is produced as a fusion polypeptide comprising: a) the T-cell epitope polypeptide; and b) a fusion partner, where the fusion partner is an affinity tag. Suitable affinity tags include, e.g., immunoglobulin Fc polypeptides, a poly(histidine) tag (e.g., His$_6$), a maltose binding protein (MBP), a glutathione-S-transferase (GST) polypeptide, calmodulin-binding peptide (CBP), Streptavidin-binding peptide (SBP), Strep-tag II, FLAG (e.g., DYKDDDDK (SEQ ID NO:103), hemagglutinin (HA) (e.g., YPYDVPDYA (SEQ ID NO:104), c-myc T7 ((e.g., EQKLISEEDL; SEQ ID NO:105), Glu-Glu, starch-binding domain (SBD), and Flag-Acidic-Target Tag (FATT), and the like.

In some cases, the T-cell epitope polypeptide is produced as a fusion polypeptide comprising: a) the heterologous polypeptide; and b) a fusion partner (e.g., where the fusion partner is an Ig Fc polypeptide). In some cases, a proteolytically cleavable linker is interposed between the T-cell epitope polypeptide and the fusion partner, such that the fusion polypeptide comprises: a) the heterologous polypeptide; b) the proteolytically cleavable linker; and c) the fusion partner (e.g., Ig Fc polypeptide).

The proteolytically cleavable linker can include a protease recognition sequence recognized by a protease selected from the group consisting of alanine carboxypeptidase, *Armillaria mellea* astacin, bacterial leucyl aminopeptidase, cancer procoagulant, cathepsin B, clostripain, cytosol alanyl aminopeptidase, elastase, endoproteinase Arg-C, enterokinase, gastricsin, gelatinase, Gly-X carboxypeptidase, glycyl endopeptidase, human rhinovirus 3C protease, hypodermin C, IgA-specific serine endopeptidase, leucyl aminopeptidase, leucyl endopeptidase, lysC, lysosomal pro-X carboxypeptidase, lysyl aminopeptidase, methionyl aminopeptidase, myxobacter, nardilysin, pancreatic endopeptidase E, picornain 2A, picornain 3C, proendopeptidase, prolyl aminopeptidase, proprotein convertase I, proprotein convertase II, russellysin, saccharopepsin, semenogelase, T-plasminogen activator, thrombin, tissue kallikrein, tobacco etch virus (TEV), togavirin, tryptophanyl aminopeptidase, U-plasminogen activator, V8, venombin A, venombin AB, and Xaa-pro aminopeptidase.

For example, the proteolytically cleavable linker can comprise a matrix metalloproteinase cleavage site, e.g., a cleavage site for a MMP selected from collagenase-1, -2, and -3 (MMP-1, -8, and -13), gelatinase A and B (MMP-2 and -9), stromelysin 1, 2, and 3 (MMP-3, -10, and -11), matrilysin (MMP-7), and membrane metalloproteinases (MT1-MMP and MT2-MMP). For example, the cleavage sequence of MMP-9 is Pro-X-X-Hy (wherein, X represents an arbitrary residue; Hy, a hydrophobic residue), e.g., Pro-X-X-Hy-(Ser/Thr), e.g., Pro-Leu/Gln-Gly-Met-Thr-Ser (SEQ ID NO:107) or Pro-Leu/Gln-Gly-Met-Thr (SEQ ID NO:108). Another example of a protease cleavage site is a plasminogen activator cleavage site, e.g., a uPA or a tissue plasminogen activator (tPA) cleavage site. In some cases, the cleavage site is a furin cleavage site. Specific examples of cleavage sequences of uPA and tPA include sequences comprising Val-Gly-Arg. Another example of a protease cleavage site that can be included in a proteolytically cleavable linker is a tobacco etch virus (TEV) protease cleavage site, e.g., ENLYTQS (SEQ ID NO:109), where the protease cleaves between the glutamine and the serine. Another example of a protease cleavage site that can be included in a proteolytically cleavable linker is an enterokinase cleavage site, e.g., DDDDK (SEQ ID NO:87), where cleavage occurs after the lysine residue. Another example of a protease cleavage site that can be included in a proteolytically cleavable linker is a thrombin cleavage site, e.g., LVPR (SEQ ID NO:85). Additional suitable linkers comprising protease cleavage sites include linkers comprising one or more of the following amino acid sequences: LEVLFQGP (SEQ ID NO:97), cleaved by PreScission protease (a fusion protein comprising human rhinovirus 3C protease and glutathione-S-transferase; Walker et al. (1994) Biotechnol. 12:601); a thrombin cleavage site, e.g., CGLVPAGSGP (SEQ ID NO:110); SLLKSRMVPNFN (SEQ ID NO:111) or SLLIARRMPNFN (SEQ ID NO:112), cleaved by cathepsin B; SKLVQASASGVN (SEQ ID NO:113) or SSYLKAS-DAPDN (SEQ ID NO:114), cleaved by an Epstein-Barr virus protease; RPKPQQFFGLMN (SEQ ID NO:115) cleaved by MMP-3 (stromelysin); SLRPLALWRSFN (SEQ ID NO:116) cleaved by MMP-7 (matrilysin); SPQ-GIAGQRNFN (SEQ ID NO:117) cleaved by MMP-9; DVDERDVRGFASFL SEQ ID NO:118) cleaved by a thermolysin-like MMP; SLPLGLWAPNFN (SEQ ID NO:119) cleaved by matrix metalloproteinase 2 (MMP-2); SLLIFR-SWANFN (SEQ ID NO:120) cleaved by cathespin L; SGV-VIATVIVIT (SEQ ID NO:121) cleaved by cathepsin D; SLGPQGIWGQFN (SEQ ID NO:122) cleaved by matrix metalloproteinase 1 (MMP-1); KKSPGRVVGGSV (SEQ ID NO:123) cleaved by urokinase-type plasminogen activator; PQGLLGAPGILG (SEQ ID NO:124) cleaved by membrane type 1 matrixmetalloproteinase (MT-MMP); HGPEGLRVGFYESDVMGRGHARLVHVEEPHT (SEQ ID NO:125) cleaved by stromelysin 3 (or MMP-11), thermolysin, fibroblast collagenase and stromelysin-1; GPQGLAGQRGIV (SEQ ID NO:126) cleaved by matrix metalloproteinase 13 (collagenase-3); GGSGQRGRKALE (SEQ ID NO:127) cleaved by tissue-type plasminogen activator (tPA); SLSALLSSDIFN (SEQ ID NO:128) cleaved by human prostate-specific antigen; SLPRFKIIGGFN (SEQ ID NO:129) cleaved by kallikrein (hK3); SLLGIAVPGNFN (SEQ ID NO:130) cleaved by neutrophil elastase; and FFKNIVTPRTPP (SEQ ID NO:131) cleaved by calpain (calcium activated neutral protease).

Depending on the proteolytically cleavable linker, a heterologous polypeptide (a T-cell epitope polypeptide) can comprise, at its N-terminus or at its C-terminus, from 1 to 6 additional amino acids that are N-terminal or C-terminal to the cleavage site of the proteolytically cleavable linker. The following are non-limiting examples. In some cases, a heterologous polypeptide (a T-cell epitope polypeptide) is a modified T-cell epitope polypeptide that comprises from 1 to 6 additional amino acids at the N-terminus of the modified T-cell epitope polypeptide, where the from 1 to 6 additional amino acids are Gly-Pro, Ser, Gly, or Gly-Ser. In some cases, a heterologous polypeptide (a T-cell epitope polypeptide) is a modified T-cell epitope polypeptide that comprises from 1 to 6 additional amino acids at the C-terminus of the modified T-cell epitope polypeptide, where the from 1 to 6 additional amino acids are LEVLFQ (SEQ ID NO:83), ENLYYFQ (SEQ ID NO:84), LVPR (SEQ ID NO:85), I(E/D)GR (SEQ ID NO:86), or DDDDK (SEQ ID NO:87).

The Fc region can be a human IgG1 Fc, a human IgG2 Fc, a human IgG3 Fc, a human IgG4 Fc, etc. In some cases, the Fc region comprises an amino acid sequence having at least about 70%, at least about 75%, at least about 80%, at least about 85%, at least about 90%, at least about 95%, at least about 98%, at least about 99%, or 100%, amino acid sequence identity to an amino acid sequence of an Fc region depicted in FIG. 5A-5C. In some cases, the Fc region comprises an amino acid sequence having at least about 70%, at least about 75%, at least about 80%, at least about 85%, at least about 90%, at least about 95%, at least about 98%, at least about 99%, or 100%, amino acid sequence identity to the human IgG1 Fc polypeptide depicted in FIG. 5A. In some cases, the Fc region comprises an amino acid sequence having at least about 70%, at least about 75%, at least about 80%, at least about 85%, at least about 90%, at least about 95%, at least about 98%, at least about 99%, or 100%, amino acid sequence identity to the human IgG2 Fc polypeptide depicted in FIG. 5A; e.g., the Fc region comprises an amino acid sequence having at least about 70%, at least about 75%, at least about 80%, at least about 85%, at least about 90%, at least about 95%, at least about 98%, at least about 99%, or 100%, amino acid sequence identity to amino acids 99-325 of the human IgG2 Fc polypeptide depicted in FIG. 5A. In some cases, the Fc region comprises an amino acid sequence having at least about 70%, at least about 75%, at least about 80%, at least about 85%, at least about 90%, at least about 95%, at least about 98%, at least about 99%, or 100%, amino acid sequence identity to the human IgG3 Fc polypeptide depicted in FIG. 5A; e.g., the Fc region comprises an amino acid sequence having at least about 70%, at least about 75%, at least about 80%, at least about 85%, at least about 90%, at least about 95%, at least about 98%, at least about 99%, or 100%, amino acid sequence identity to amino acids 19-246 of the human IgG3 Fc polypeptide depicted in FIG. 5A.

Suitable expression vectors include, but are not limited to, baculovirus vectors, bacteriophage vectors, plasmids, phagemids, cosmids, fosmids, bacterial artificial chromosomes, viral vectors (e.g. viral vectors based on vaccinia virus, poliovirus, adenovirus, adeno-associated virus, SV40, herpes simplex virus, human immunodeficiency virus-based lentivirus vectors, murine leukemia virus (MVL)-based gamma retrovirus vectors, and the like), P1-based artificial chromosomes, yeast plasmids, yeast artificial chromosomes, and any other vectors specific for specific hosts of interest (such as *Escherichia coli*, mammalian cells, insect cells, or yeast cells).

Suitable host cells include eukaryotic cells, such as yeast cells, insect cells, and mammalian cells. In some cases, the host cell is a cell of a mammalian cell line. Suitable mammalian cell lines include human cell lines, non-human primate cell lines, rodent (e.g., mouse, rat) cell lines, and the like.

Suitable prokaryotic cells include, but are not limited to, any of a variety of laboratory strains of *Escherichia coli*, *Lactobacillus* sp., *Salmonella* sp., *Shigella* sp., and the like. See, e.g., Carrier et al. (1992) J. Immunol. 148:1176-1181; U.S. Pat. No. 6,447,784; and Sizemore et al. (1995) Science 270:299-302.

Suitable eukaryotic host cells include, but are not limited to, *Pichia pastoris*, *Pichia finlandica*, *Pichia trehalophila*, *Pichia koclamae*, *Pichia membranaefaciens*, *Pichia opuntiae*, *Pichia thermotolerans*, *Pichia salictaria*, *Pichia guercuum*, *Pichia pijperi*, *Pichia stiptis*, *Pichia methanolica*, *Pichia* sp., *Saccharomyces cerevisiae*, *Saccharomyces* sp., *Hansenula polymorpha*, *Kluyveromyces* sp., *Kluyveromyces lactis*, *Candida albicans*, *Aspergillus nidulans*, *Aspergillus niger*, *Aspergillus oryzae*, *Trichoderma reesei*, *Chrysosporium lucknowense*, *Fusarium* sp., *Fusarium gramineum*, *Fusarium venenatum*, *Neurospora crassa*, *Chlamydomonas reinhardtii*, and the like. Suitable yeast cells include, e.g., *Saccharomyces cerevisiae* and *Pichia* (e.g., *Pichia pastoris*).

Suitable insect cells include, e.g., *Spodoptera frugiperda* cells, e.g., Sf9 cells; *Spodoptera frugiperda* Sf-21 cells; *Trichoplusia ni* cells (e.g., Tn-368 cells; High-Five™ BTI-TN5B1-4 cells); etc.

Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, MRC4 fibroblast cells, and the like.

Methods for introduction of nucleic acids into host cells include, for example, transformation, electroporation, conjugation, calcium phosphate methods and the like. The method for transfer can be selected so as to provide for stable expression of the introduced polypeptide-encoding nucleic acid. The polypeptide-encoding nucleic acid can be provided as an inheritable episomal element (e.g., a plasmid) or can be genomically integrated.

In some cases, the T-cell epitope polypeptide is produced in a genetically modified host cell; and the heterologous polypeptide is purified from one or more of the cell culture medium and a cell lysate made from the genetically modified host cell. Methods of purifying a polypeptide from cell culture medium and/or a cell lysate are known in the art and include, e.g., affinity chromatography, size exclusion chromatography, In some cases, where the T-cell epitope polypeptide is a fusion protein comprising the T-cell epitope polypeptide and a fusion partner, the fusion protein is purified on an affinity column comprising an antibody specific for the fusion partner, or other affinity partner that binds the fusion partner, immobilized on an insoluble support. In some cases, where the T-cell epitope polypeptide is a fusion protein comprising the T-cell epitope polypeptide and a fusion partner, and where the fusion partner is an Ig Fc polypeptide, the fusion protein can be purified on a Protein A column (i.e., affinity chromatography using Protein A immobilized on an insoluble support).

In some cases, where the T-cell epitope polypeptide is a fusion protein comprising the heterologous polypeptide and a fusion partner, and where the fusion partner is an Ig Fc polypeptide, and where a proteolytically cleavable linker is interposed between the Ig Fc and the T-cell epitope polypeptide, the fusion protein can be purified on a Protein A column (i.e., affinity chromatography using Protein A immobilized on an insoluble support). The fusion protein can be immobilized on the Protein A column; and an enzyme that cleaves a proteolytic cleavage site in the proteolytically cleavable linker is applied to the column comprising the immobilized fusion protein; the enzyme releases the heterologous polypeptide from the Protein A column.

Methods of Making an HCV E1/E2 Heterodimer

An HCV E1/E2 heterodimer can be produced using any suitable method, including recombinant and non-recombinant methods (e.g., chemical synthesis).

Where a polypeptide is chemically synthesized, the synthesis may proceed via liquid phase or solid-phase. Solid-phase peptide synthesis (SPPS) allows the incorporation of unnatural amino acids and/or peptide/protein backbone modification. Various forms of SPPS, such as Fmoc and Boc, are available for synthesizing polypeptides. Details of the chemical synthesis are known in the art (e.g., Ganesan A. 2006 Mini Rev. Med Chem. 6:3-10 and Camarero J A et al. 2005 Protein Pept Lett. 12:723-8).

Where a polypeptide is produced using recombinant techniques, the polypeptide may be produced as an intracellular protein or as a secreted protein, using any suitable construct and any suitable host cell, which can be a prokaryotic or eukaryotic cell, such as a bacterial (e.g., *Escherichia coli*) cell or a yeast host cell, respectively. Other examples of eukaryotic cells that may be used as host cells include insect cells, mammalian cells, filamentous fungi, and plant cells. Suitable yeast cells include, e.g., *Saccharomyces cerevisiae* and *Pichia* (e.g., *Pichia pastoris*).

Suitable mammalian cells include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, MRC5 cells (ATCC No. CCL-171), and the like. Where mammalian host cells are used, such host cells may include human cells (e.g., HeLa, 293, H9 and Jurkat cells); mouse cells (e.g., NIH3T3, L cells, and C127 cells); primate cells (e.g., Cos 1, Cos 7 and CV1); MRC4 cells; and hamster cells (e.g., Chinese hamster ovary (CHO) cells).

A variety of host-vector systems suitable for the expression of a polypeptide may be employed according to standard procedures known in the art. See, e.g., Sambrook et al., 1989 Current Protocols in Molecular Biology Cold Spring Harbor Press, New York; Ausubel et al. 1995 Current Protocols in Molecular Biology, Eds. Wiley and Sons; "Protein Expression: A Practical Approach" (1999) S. J. Higgins and B. D. James, eds., Oxford University Press; "Protein Expression in Mammalian Cells: Methods and Protocols (Methods in Molecular Biology)" (2012) James L. Hartley, ed., Humana Press; and "Production of Recombinant Proteins" (2005) Gerd Gellisen, ed., Wiley-VCH. Methods for introduction of nucleic acids into host cells include, for example, transformation, electroporation, conjugation, calcium phosphate methods and the like. The method for transfer can be selected so as to provide for stable expression of the introduced polypeptide-encoding nucleic acid. The polypeptide-encoding nucleic acid can be provided as an inheritable episomal element (e.g., a plasmid) or can be genomically integrated. A variety of appropriate vectors for use in production of a peptide of interest are available commercially.

Suitable expression vectors include, but are not limited to, baculovirus vectors, bacteriophage vectors, plasmids, phagemids, cosmids, fosmids, bacterial artificial chromosomes, viral vectors (e.g. viral vectors based on vaccinia virus, poliovirus, adenovirus, adeno-associated virus, SV40, herpes simplex virus, HIV-based lentivirus vectors, murine leukemia virus (MVL)-based gamma retrovirus vectors, and the like), P1-based artificial chromosomes, yeast plasmids, yeast artificial chromosomes, and any other vectors specific for specific hosts of interest (such as *E. coli*, mammalian cells, insect cells, or yeast cells).

An E1 polypeptide, an E2 polypeptide, or an E1/E2 heterodimer can be produced by introducing a recombinant expression vector comprising a nucleotide sequence encoding the E1 polypeptide, E2 polypeptide, or E1/E2 heterodimer into an appropriate host cell, where the host cell produces the encoded E1 polypeptide, E2 polypeptide, or E1/E2 heterodimer. In the expression vector, a polynucleotide comprising a nucleotide sequence(s) encoding the E1 polypeptide, E2 polypeptide, or E1/E2 heterodimer is linked to a regulatory sequence as appropriate to obtain the desired expression properties. These regulatory sequences can include promoters, enhancers, terminators, operators, repressors, and inducers. The promoters can be regulated or constitutive. Expression vectors generally have convenient restriction sites located near the promoter sequence to provide for the insertion of nucleic acid sequences encoding a protein of interest. A selectable marker operative in the expression host cell may be present.

In some cases, the E1/E2 heterodimer is encoded in a recombinant expression vector suitable for expression in a eukaryotic host cell (e.g., an insect cell; a yeast cell; a mammalian host cell, such as CHO cells, HeLa cells, 293 cells, MRC5 cells, etc.). In some cases, a recombinant expression vector comprises a nucleotide sequence encoding E1 and E2 polypeptides (which may be wild-type or variant) as a single polypeptide chain; the recombinant expression vector is introduced into a eukaryotic host cell to generate a genetically modified host cell. In some cases, E1 and E2 polypeptides are initially produced as a single polypeptide chain, which is cleaved in the endoplasmic reticulum (ER) of the genetically modified host cell to produce separate E1 and E2 polypeptides. The separate E1 and E2 polypeptides can form a heterodimer (e.g., a non-covalently linked heterodimer) in the ER. The E1/E2 heterodimer can be isolated from the genetically modified host cell by, e.g., lysis using a non-ionic detergent, or using a freeze-thaw method. See, e.g., Frey et al. (2010) Vaccine 28:6367. The E1/E2 heterodimer can be purified from a cell lysate and/or cell culture medium using any of a variety of methods, including size exclusion chromatography, affinity chromatography, and the like, or combinations of such methods. In some cases, the E1/E2 heterodimer is purified from cell lysate and/or cell culture medium using *Galanthus nivalis* (GNA) lectin affinity chromatography. In some cases, the E1/E2 heterodimer is purified from a cell lysate. In some cases, the E1/E2 heterodimer is secreted from a cell and is purified from the cell culture medium. Suitable methods that can be used for purifying an E1/E2 heterodimer are described in, e.g., U.S. Pat. Nos. 6,121,020; 6,274,148; and Mazzocca et al. (2005) *J. Biol. Chem.* 280:11329. For example, in some cases, an E1/E2 heterodimer can be prepared in a method comprising cell disruption and debris removal by microfiltration, followed by purification using three subsequent chromatographic steps: lectin affinity chromatography, hydroxyapatite chromatography, and ion exchange chromatography.

Alternatively, the E1 and E2 polypeptides can be encoded on separate recombinant expression vectors; and produced in a cell (e.g., the same host cell or separate host cells) as separate polypeptides.

If full-length E1 and E2 polypeptides are expressed in a eukaryotic host cell, the E1 and E2 polypeptides remain bound to the endoplasmic reticulum (ER) membrane as asialoglycoproteins. If the E1 and E2 polypeptides have C-terminal truncations, such that the C-terminal transmembrane regions are removed, the truncated polypeptides are secreted and can acquire complex glycans such as sialic acid. Removal of approximately amino acids 660-746 of E2, or amino acids 715-746 of E2, and removal of approximately amino acids 330-383 of E1, results in secretion of E2 and E1 from a eukaryotic host cell. If E1 and E2 are co-expressed in 9 the same eukaryotic host cell as full-length polypeptides, they remain in the lumen of the ER as a heterodimer.

In some cases, an E2 polypeptide suitable for use in an E1/E2 heterodimer lacks a transmembrane region. For example, in some cases, an E2 polypeptide suitable for use in an E1/E2 heterodimer, comprises amino acids 384-659, and lacks amino acids 660-746 of a naturally-occurring E2 polypeptide; and may be referred to as "E2 ectodomain polypeptide." For example, in some cases, an E2 polypeptide suitable for use in an E1/E2 heterodimer comprises amino acids 384-659, lacks amino acids 660-746 of a naturally-occurring E2 polypeptide, and has a length of 276 amino acids.

In some cases, an E1 polypeptide suitable for use in an E1/E2 heterodimer lacks a transmembrane region. For example, in some cases, an E1 polypeptide suitable for use in an E1/E2 heterodimer comprises amino acids 191-329, and lacks amino acids 330-383 of a naturally-occurring E1 polypeptide; and may be referred to as an "E1 ectodomain polypeptide." For example, in some cases, an E1 polypeptide suitable for use in an E1/E2 heterodimer comprises amino acids 191-329, lacks amino acids 330-383 of a naturally-occurring E1 polypeptide, and has a length of 139 amino acids.

After production in a host cell, an E1 polypeptide, an E2 polypeptide, or an E1/E2 heterodimer (e.g., as separate polypeptides or as a heterodimer) can be purified from the host cell. Methods of purification of recombinantly produced polypeptides from a host cell are known in the art and include, e.g., detergent lysis (e.g., with a non-ionic detergent) or freeze-thaw lysis, followed by one or more of size exclusion column chromatography, high performance liquid chromatography, affinity chromatography, and the like.

In some cases, an E1/E2 heterodimer suitable for inclusion in an immunogenic composition of the present disclosure is produced by purifying an E1/E2 heterodimer on an affinity column, where the E1 or E2 polypeptide comprises an Ig Fc polypeptide linked to the E1 or E2 polypeptide via a proteolytically cleavable linker. For example, the method can comprise: A) culturing a genetically modified eukaryotic host cell that is genetically modified with a nucleic acid (e.g., recombinant expression vector) comprising a nucleotide sequence encoding an E1/E2 polypeptide that comprises, in order from N-terminus to C-terminus: a) a signal peptide that directs the E1/E2 polypeptide to the ER following translation of the E1/E2 polypeptide; b) an HCV E1 polypeptide; c) an Ig Fc region; d) a proteolytically cleavable linker; and e) an HCV E2 polypeptide); B) contacting a lysate of the cultured genetically modified eukaryotic host cell with a solid support comprising an Ig Fc binding moiety, generating an immobilized heterodimer comprising the HCV E1 polypeptide and a fusion polypeptide comprising: a) the Ig Fc; b) the proteolytically cleavable linker; and c) the E2 polypeptide; C) contacting the immobilized heterodimer with an enzyme that cleaves the proteolytically cleavable linker, thereby releasing the heterodimer; and D) collecting the released heterodimer.

In some cases, an E1/E2 heterodimer is produced using a method comprising: A) culturing a genetically modified eukaryotic host cell that is genetically modified with a nucleic acid (e.g., recombinant expression vector) comprising a nucleotide sequence encoding an E1/E2 polypeptide that comprises, in order from N-terminus to C-terminus: a) a signal peptide that directs the E1/E2 polypeptide to the ER following translation of the E1/E2 polypeptide; b) an HCV E1 polypeptide; c) an Ig Fc region; d) a proteolytically cleavable linker; and e) an HCV E2 polypeptide; B) contacting a lysate of the cultured genetically modified eukaryotic host cell with a solid support comprising an Ig Fc binding moiety, generating an immobilized heterodimer comprising the HCV E1 polypeptide and a fusion polypeptide comprising: a) the Ig Fc; b) the proteolytically cleavable linker; and c) the E2 polypeptide; C) contacting the immobilized heterodimer with an enzyme that cleaves the proteolytically cleavable linker, thereby releasing the heterodimer; and D) collecting the released heterodimer.

In some cases, an E1/E2 heterodimer is produced using a method comprising: A) culturing a genetically modified eukaryotic host cell that is genetically modified with a nucleic acid (e.g., recombinant expression vector) comprising a nucleotide sequence encoding an E1/E2 polypeptide that comprises, in order from N-terminus to C-terminus: a) a signal peptide that directs the E1/E2 polypeptide to the ER following translation of the E1/E2 polypeptide; b) an HCV E1 polypeptide; c) an Ig Fc region; d) a proteolytically cleavable linker comprising the amino acid sequence LEVLFQGP (SEQ ID NO:97), and having a length of from 8 amino acids to 15 amino acids; and e) an HCV E2 polypeptide; B) contacting a lysate of the cultured genetically modified eukaryotic host cell with a solid support comprising an Ig Fc binding moiety, generating an immobilized heterodimer comprising the HCV E1 polypeptide and a fusion polypeptide comprising: a) the Ig Fc; b) the proteolytically cleavable linker; and c) the E2 polypeptide; C) contacting the immobilized heterodimer with an enzyme (e.g., a rhinovirus 3C protease) that cleaves the proteolytically cleavable linker, thereby releasing the heterodimer; and D) collecting the released heterodimer.

In some cases, an E1/E2 heterodimer is produced using a method comprising: A) culturing a genetically modified eukaryotic host cell that is genetically modified with a nucleic acid (e.g., recombinant expression vector) comprising a nucleotide sequence encoding an E1/E2 polypeptide that comprises, in order from N-terminus to C-terminus: a) a signal peptide that directs the E1/E2 polypeptide to the ER following translation of the E1/E2 polypeptide; b) an HCV E1 polypeptide; c) an Ig Fc region; d) a proteolytically cleavable linker comprising the amino acid sequence LEVLFQGP (SEQ ID NO:97), and having a length of from 8 amino acids to 15 amino acids; and e) an HCV E2 polypeptide; B) contacting a lysate of the cultured genetically modified eukaryotic host cell with a solid support comprising an Ig Fc binding moiety, generating an immobilized heterodimer comprising the HCV E1 polypeptide and a fusion polypeptide comprising: a) the Ig Fc; b) the proteolytically cleavable linker; and c) the E2 polypeptide; C) contacting the immobilized heterodimer with an enzyme (e.g., a fusion polypeptide comprising a glutathione-S-transferase and a human rhinovirus 3C protease (GST-HRV3C protease)) that cleaves the proteolytically cleavable linker, thereby releasing the E1E2 heterodimer; and D) collecting the released E1E2 heterodimer. In some cases, a solution comprising the released E1E2 heterodimer is applied to glutathione immobilized on a solid support, to remove the GST-HRV3C protease. For example, a solution comprising the released heterodimer can be applied to a glutathione-Sepharose 4B column, where the GST-HRV3C binds to the glutathione-Sepharose 4B; the flow-through (unbound material) comprises the released E1E2 heterodimer. In some cases, the released E1E2 heterodimer is further subjected to hydroxyapatite chromatography. Hydroxyapatite chromatography can be carried out as described in, e.g., Mazzocca et al. (2005) *J. Biol. Chem.* 280:11329.

Suitable Ig Fc binding moieties include, but are not limited to, Protein A (Graille et al. (2000) *Proc. Natl. Acad. Sci. USA* 97:5399); Protein G (Sjobring et al. (1991) *J. Biol. Chem.* 266:399); and a Protein A/G fusion polypeptide (Eliasson et al. (1988) *J. Biol. Chem.* 263:4323).

The Ig Fc binding moiety can be immobilized onto a solid support, where the solid support can be of any of a variety of forms, e.g., a bead, a magnetic bead, a plate, and the like. The solid support can be made of any of a variety of materials, including, but not limited to, polystyrene, agarose, polyesters, polyethylene, and the like.

As an alternative to Fc, an affinity tag such as, e.g., polyhistidine (e.g., (His)$_6$), glutathione-S-transferase (GST), calmodulin-binding peptide (CBP), Streptavidin-binding peptide (SBP), Strep-tag II, FLAG (e.g., DYKDDDDK (SEQ ID NO:103), hemagglutinin (HA) (e.g., YPYDVPDYA (SEQ ID NO:104), c-myc T7 ((e.g., EQK-LISEEDL; SEQ ID NO:105), Glu-Glu, and the like, can be used. (Wood D. 2014. *Current Opinion in Structural Biology* 26 54-61; Kimple M E et al. 2013. *Current Protocols in Protein Science* 9.9.1-9.9.23). Other suitable affinity tags include, e.g., starch-binding domain (SBD); and Flag-Acidic-Target Tag (FATT). See, e.g., Wood D. 2014. *Current Opinion in Structural Biology* 26 54-61).

One or more additional purification steps can be carried out. For example, a solution comprising the released heterodimer, produced as described above, can be subjected to size exclusion chromatography, hydroxyapatite chromatography, and the like. Hydroxyapatite chromatography can be carried out as described in, e.g., Mazzocca et al. (2005) *J. Biol. Chem.* 280:11329.

An E1/E2 heterodimer can be purified such that the E1/E2 heterodimer is at least 60% pure, at least 65% pure, at least 70% pure, at least 75% pure, at least 80% pure, at least 85% pure, at least 90% pure, at least 95% pure, at least 98% pure, at least 99% pure, or greater than 99% pure.

Nucleic Acid Immunogenic Compositions

The present disclosure provides nucleic acid compositions comprising: a) one or more nucleic acids comprising a nucleotide sequence(s) encoding polypeptides (e.g., HCV E1/E2; HCV E1; HCV E2; a T-cell epitope polypeptide) as described above. The present disclosure provides an immunogenic composition comprising: a) a nucleic acid (e.g., a recombinant viral expression vector(s)) comprising nucleotide sequence(s) encoding one or more of: an HCV E1/E2 heterodimer; an HCV E1 polypeptide; an HCV E2 polypeptide; and a T-cell epitope polypeptide, where such polypeptides are described above. The polypeptides can be encoded in the same nucleic acid, or on separate nucleic acids. For example, where the nucleic acid(s) are recombinant expression vectors, the polypeptides can be encoded in the same or separate recombinant expression vectors.

In some cases, the nucleic acid(s) is/are DNA. In some cases, the nucleic acid(s) is/are RNA. In some cases, the nucleic acid(s) is/are present in expression vector(s), generating recombinant expression vector(s) comprising the nucleic acid(s). In some cases, the recombinant expression vector(s) is/are recombinant bacterial vectors. In some cases, the recombinant expression vector(s) is/are recombinant viral vector(s). In some cases, the recombinant viral vector(s) are packaged into viral particles. In some cases, the nucleic acid(s) are present in bacteria (e.g., non-pathogenic bacteria (e.g., attenuated bacteria) suitable for delivery of nucleic acids to an individual). Where the recombinant expression vector is a bacterial vector or a viral vector, the vector is suitably attenuated so as not to cause significant pathology in an individual.

In some cases, the nucleic acid is present in an expression vector. Suitable expression vectors include, but are not limited to, a replication-defective adenovirus vector; a replication-defective vaccinia virus vector; a lentivirus vector (e.g., a self-inactivating lentivirus vector); a retroviral vector (e.g., a self-inactivating retroviral vector); an adeno-associated virus vector; and the like. In some cases, the vector is a modified vaccinia Ankara (MVA) vector, or an MVA-based vector (see, e.g., Verheust et al. (2012) *Vaccine* 30:2623). In some cases, the vector is a replication-defective adenovirus vector. In some cases, the vector is a replication-defective adenovirus 6 (Ad6) vector. In some cases, the vector is a replication-defective simian adenovirus vector (e.g., ChAd3). Suitable viral vectors are described in, e.g., Zhou et al. (2012) *Invest. Ophthalmol. Vis. Sci.* 53:2804; Swadling et al. (2014) *Sci. Transl. Med.* 6:261ra153; and Choi and Chang (2013) *Clin. Exp. Vaccine Res.* 2:97. In many cases, the recombinant viral vectors are packaged into viral particles; and the viral particles are formulated in an immunogenic composition along with a pharmaceutically acceptable carrier. Suitable pharmaceutically acceptable carriers are described above.

In some cases, an immunogenic composition of the present disclosure comprises: a) a recombinant viral vector comprising nucleotide sequences encoding one or more of: an HCV E1/E2 heterodimer; an HCV E1 polypeptide; an HCV E2 polypeptide; and a T-cell epitope polypeptide; and b) a pharmaceutically acceptable excipient. In some cases, an immunogenic composition of the present disclosure comprises: a) a recombinant viral vector comprising nucleotide sequences encoding: an HCV E1/E2 heterodimer; and a T-cell epitope polypeptide; and b) a pharmaceutically acceptable excipient. In some cases, an immunogenic composition of the present disclosure comprises: a) a recombinant viral vector comprising nucleotide sequences encoding: an HCV E1 polypeptide; and a T-cell epitope polypeptide; and b) a pharmaceutically acceptable excipient. In some cases, an immunogenic composition of the present disclosure comprises: a) a recombinant viral vector comprising nucleotide sequences encoding: an HCV E2 polypeptide; and a T-cell epitope polypeptide; and b) a pharmaceutically acceptable excipient.

In some cases, the present disclosure provides: a) a first immunogenic composition comprising: i) a recombinant viral vector comprising nucleotide sequences encoding one or more of: an HCV E1/E2 heterodimer; an HCV E1 polypeptide; an HCV E2 polypeptide; and a T-cell epitope polypeptide; and ii) a pharmaceutically acceptable excipient; and b) a second immunogenic composition comprising: i) a recombinant viral vector comprising nucleotide sequences encoding one or more of: an HCV E1/E2 heterodimer; an HCV E1 polypeptide; an HCV E2 polypeptide; and a T-cell epitope polypeptide; and ii) a pharmaceutically acceptable excipient.

In some cases, the present disclosure provides: a) a first immunogenic composition comprising: i) a first recombinant viral vector comprising nucleotide sequences encoding one or more of: an HCV E1/E2 heterodimer; an HCV E1 polypeptide; an HCV E2 polypeptide; and a T-cell epitope polypeptide; and ii) a pharmaceutically acceptable excipient; and b) a second immunogenic composition comprising: i) a second recombinant viral vector comprising nucleotide sequences encoding one or more of: an HCV E1/E2 heterodimer; an HCV E1 polypeptide; an HCV E2 polypeptide; and a T-cell epitope polypeptide; and ii) a pharmaceutically acceptable excipient. In some cases, the first recombinant viral vector is a replication-defective adenovirus-based recombinant viral vector; and the second recombinant viral vector is an MVA-based recombinant viral vector. In some cases, the first recombinant viral vector is a chimpanzee adenovirus-based recombinant viral vector; and the second recombinant viral vector is an MVA-based recombinant viral vector.

In some cases, the nucleic acid(s) are present in bacteria (e.g., non-pathogenic bacteria suitable for delivery of nucleic acids to an individual). In some cases, the nucleic acid(s) are present in recombinant expression vector(s) present in bacteria (e.g., non-pathogenic bacteria suitable for delivery of nucleic acids to an individual). Thus, the present disclosure provides an immunogenic composition comprising a non-pathogenic, bacterium that harbors a nucleic acid(s) comprising nucleotide sequences encoding one or more of: an HCV E1/E2 heterodimer; an HCV E1 polypeptide; an HCV E2 polypeptide; and a T-cell epitope polypeptide, where such polypeptides are described above. The present disclosure provides an immunogenic composition comprising a non-pathogenic bacterium that harbors a recombinant expression vector(s) comprising nucleotide sequences encoding one or more of: an HCV E1/E2 heterodimer; an HCV E1 polypeptide; an HCV E2 polypeptide; and a T-cell epitope polypeptide, where such polypeptides are described above. In some cases, the bacteria are live. In some cases, the bacteria are live attenuated bacteria. In some cases, the bacteria are killed.

Bacteria suitable for delivery of nucleic acid(s) (which nucleic acid(s) may be present in expression vector(s)) include, but are not limited to, *Lactobacillus*; *Lactococcus* (e.g., *Lactococcus lactis*); *Salmonella*, e.g., attenuated, non-pathogenic *Salmonella*, e.g., *Salmonella enterica* serovar *Typhi*, *Salmonella enterica* serovar *Typhimurium*; non-pathogenic strains of *Francisella*; non-pathogenic strains of *Escherichia coli*; non-pathogenic strains of *Bordetella pertussis*; non-pathogenic strains of *Listeria*; non-pathogenic strains of *Shigella*; non-pathogenic strains of *Vibrio* (e.g., *Vibrio cholera*); *Streptococcus gordonii*; non-pathogenic strains of *Yersinia enterocolitica*; non-pathogenic strains of Shigellaflexneri; non-pathogenic strains of *Pseudomonas aeruginosa*; non-pathogenic strains of *Bacillus subtilis*; and the like.

In some cases, one or more virulence genes in the bacterium is all or partially deleted. For example, for *Salmonella enterica* serovar *Typhi* and *Salmonella enterica* serovar *Typhimurium*, an aroA, aroC, and aroD mutation can be made. Other mutations that can attenuate pathogenicity affect biosynthesis of the nucleotides adenine (pur) and guanine (guaBA), and outer membrane proteins C and F (ompC, ompF), as well as expression of the cAMP receptor (cya/crp), the conversion of UDP-galactose to UDP-glucose (galE), DNA recombination and repair (recA, recBC), and regulation of virulence genes (phoP, phoQ). For *Listeria monocytogenes*, attenuation can be achieved with auxotrophic mutants, or deletion of virulence factors such as the genes actA and internalin B (intB).

Methods of Inducing an Immune Response to Hcv

The present disclosure provides a method of inducing an immune response (e.g., a protective immune response) to at least one HCV genotype in a mammalian subject. In some cases, a method of the present disclosure for inducing an immune response in an individual to at least one HCV genotype comprises administering an immunogenic composition of the present disclosure, where the immunogenic composition comprises polypeptides (e.g., HCV E1/E2; HCV E1; HCV E2; T-cell epitope polypeptide). In some cases, a method of the present disclosure for inducing an immune response in an individual to at least one HCV genotype comprises administering an immunogenic composition of the present disclosure, where the immunogenic composition comprises one or more nucleic acids comprising nucleotide sequences encoding polypeptides (e.g., HCV E1/E2; HCV E1; HCV E2; T-cell epitope polypeptide).

Administering an Immunogenic Composition Comprising Polypeptides

In some cases, the methods comprise administering to an individual in need thereof an effective amount of an immunogenic composition of the present disclosure, where the immunogenic composition comprises: a) an HCV E1/E2 heterodimer; b) a T-cell epitope polypeptide comprising a T-cell epitope present in an HCV polypeptide other than E1 and E2; and c) a pharmaceutically acceptable excipient; or where the immunogenic composition comprises: a) an HCV E2 polypeptide; b) a T-cell epitope polypeptide comprising a T-cell epitope present in an HCV polypeptide other than E1 and E2; and c) a pharmaceutically acceptable excipient; or where the immunogenic composition comprises: a) an HCV E1 polypeptide; b) a T-cell epitope polypeptide comprising a T-cell epitope present in an HCV polypeptide other than E1 and E2; and c) a pharmaceutically acceptable excipient.

Administering an Immunogenic Composition Comprising Nucleic Acid(s)

In some cases, a method of the present disclosure for inducing an immune response to HCV in an individual comprises administering to the individual an effective amount of a nucleic acid(s) comprising nucleotide sequences encoding: 1) an HCV E1/E2 heterodimer and a T-cell epitope polypeptide; 2) an HCV E2 polypeptide and a T-cell epitope polypeptide; or 3) an HCV E1 polypeptide and a T-cell epitope polypeptide. The polypeptides can be encoded in the same nucleic acid, or on separate nucleic acids. For example, where the nucleic acid(s) are recombinant expression vectors, the polypeptides can be encoded in the same or separate recombinant expression vectors.

In some cases, the nucleic acid(s) is/are DNA. In some cases, the nucleic acid(s) is/are RNA. In some cases, the nucleic acid(s) is/are present in expression vector(s) such that a recombinant expression vector(s) comprising the nucleic acid(s) are administered. In some cases, the recombinant expression vector(s) is/are recombinant viral vector(s). In some cases, the recombinant viral vector(s) are packaged into viral particles. In some cases, the nucleic acid(s) are present in bacteria (e.g., non-pathogenic bacteria (e.g., attenuated bacteria) suitable for delivery of nucleic acids to an individual).

In some cases, the nucleic acid is present in an expression vector, thereby generating a recombinant expression vector. Suitable expression vectors include, but are not limited to, a replication-defective adenovirus vector; a replication-defective vaccinia virus vector; a lentivirus vector (e.g., a self-inactivating lentivirus vector); a retroviral vector (e.g., a self-inactivating retroviral vector); an adeno-associated virus vector; and the like. In some cases, the vector is a modified vaccinia Ankara (MVA) vector, or an MVA-based vector (see, e.g., Verheust et al. (2012) *Vaccine* 30:2623). In some cases, the vector is a replication-defective adenovirus vector. In some cases, the vector is a replication-defective adenovirus 6 (Ad6) vector. In some cases, the vector is a replication-defective simian adenovirus vector (e.g., ChAd3). Suitable viral vectors are described in, e.g., Zhou et al. (2012) *Invest. Ophthalmol. Vis. Sci.* 53:2804; Swadling et al. (2014) *Sci. Transl. Med.* 6:261ra153; and Choi and Chang (2013) *Clin. Exp. Vaccine Res.* 2:97. In many cases, the recombinant viral vectors are packaged into viral particles; and the viral particles are formulated in an immunogenic composition along with a pharmaceutically acceptable carrier.

In some cases, an HCV E1/E2 heterodimer is encoded by nucleotide sequences present in a first recombinant viral vector, e.g., an adenovirus vector, a vaccinia virus vector, an MVA vector or MVA-based vector; and a T-cell epitope polypeptide is encoded by nucleotide sequences present in a second recombinant viral vector, e.g., an adenovirus vector, a vaccinia virus vector, an MVA vector or MVA-based vector.

In some cases, a prime-boost vaccine protocol is used. In some cases, a first (priming) immunogenic composition is administered, where the first immunogenic composition comprises a recombinant viral vector comprising nucleotide sequences encoding one or more of: a) an HCV E1/E2 heterodimer; b) an HCV E2 polypeptide; c) an HCV E1 polypeptide; and d) a T-cell epitope polypeptide; and, after a time, a second (booster) immunogenic composition is administered, where the second immunogenic composition comprises a recombinant viral vector comprising nucleotide sequences encoding one or more of: a) an HCV E1/E2 heterodimer; b) an HCV E2 polypeptide; c) an HCV E1 polypeptide; and d) a T-cell epitope polypeptide. In some cases, the first recombinant viral vector and the second recombinant viral vector are the same. In some cases, the first recombinant viral vector and the second recombinant viral vector are different. For example, in some cases, the first recombinant viral vector is a vaccinia-based recombinant viral vector; and the second recombinant viral vector is an adenovirus-based recombinant viral vector. In general, the recombinant viral vectors are packaged into viral particles. A second immunogenic composition can be administered at a time period of from 1 day to 1 year following administration of the first immunogenic composition. For example, a second immunogenic composition can be administered at a time period of from 1 day to 1 week, from 1 week to 2 weeks, from 2 weeks to 1 month, from 1 month to 2 months, from 2 months to 6 months, or from 6 months to 1 year following administration of the first immunogenic composition.

For example, in some cases, a first (priming) vaccine comprising a recombinant adenovirus (e.g., Ad6 or chimpanzee Ad (e.g., ChAd3)) that comprises a nucleotide sequence encoding an HCV E1/E2 heterodimer is followed by a second (booster) vaccine comprising a recombinant MVA vector that comprises a nucleotide sequence encoding a T-cell epitope polypeptide. Other prime-boost protocols can be used. For example, multiple primes and/or multiple boosts can be administered.

In some cases, a first (priming) immunogenic composition is administered, where the first immunogenic composition comprises one or more of: a) an HCV E1/E2 heterodimer; b) an HCV E2 polypeptide; c) an HCV E1 polypeptide; and d) a T-cell epitope polypeptide, as described above; and a second (boosting) immunogenic composition is administered, where the second immunogenic composition comprises a recombinant viral vector comprising nucleotide sequence(s) encoding one or more of: a) an HCV E1/E2 heterodimer; b) an HCV E2 polypeptide; c) an HCV E1 polypeptide; and d) a T-cell epitope polypeptide, as described above.

In some cases, a first (priming) immunogenic composition is administered, where the first immunogenic composition comprises a recombinant viral vector comprising nucleotide sequence(s) encoding one or more of: a) an HCV E1/E2 heterodimer; b) an HCV E2 polypeptide; c) an HCV E1 polypeptide; and d) a T-cell epitope polypeptide, as described above; and a second (boosting) immunogenic composition is administered, where the second immunogenic composition comprises one or more of: a) an HCV E1/E2 heterodimer; b) an HCV E2 polypeptide; c) an HCV E1 polypeptide; and d) a T-cell epitope polypeptide, as described above.

In some cases, a co-immunization regimen is carried out, in which a polypeptide(s) per se is administered substantially concomitantly with a nucleic acid(s) encoding the polypeptide(s). For example, in some cases, a method of the present disclosure for inducing an immune response to an HCV polypeptide can comprise administering: a) a first immunogenic composition of the present disclosure, as described above, where the immunogenic composition comprises: i) an HCV E1/E2 heterodimer; ii) a T-cell epitope polypeptide; and iii) a pharmaceutically acceptable carrier; or i) an HCV E1 polypeptide; ii) a T-cell epitope polypeptide; and iii) a pharmaceutically acceptable carrier; or i) an HCV E2 polypeptide; ii) a T-cell epitope polypeptide; and iii) a pharmaceutically acceptable carrier; and b) a second immunogenic composition of the present disclosure, as described above, where the immunogenic composition comprises: i) one or more nucleic acids comprising nucleotide sequence encoding one or more of: an HCV E1/E2 heterodimer, an HCV E1 polypeptide, an HCV E2 polypeptide, and a T-cell epitope polypeptide; and ii) a pharmaceutically acceptable carrier. In some cases, the first and the second immunogenic compositions are in a single formulation. In some cases, the first and the second immunogenic compositions are in separate formulations. In some cases, the first and the second immunogenic compositions are administered via the same route of administration. In some cases, the first and the second immunogenic compositions are administered via different routes of administration. In some cases, the first and the second immunogenic compositions are in separate formulations that are administered substantially simultaneously, e.g., within 1 minute, within 1 minute to 5 minutes, within 5 minutes to 15 minutes, or within 15 minutes to 30 minutes, of one another. In some cases, the first and the second immunogenic compositions are administered multiple times to an individual.

In some cases, a co-immunization regimen is carried out, in which a polypeptide(s) per se is administered substantially concomitantly with a nucleic acid(s) encoding the polypeptide(s). For example, in some cases, a method of the present disclosure for inducing an immune response to an HCV polypeptide can comprise administering: a) a first immunogenic composition of the present disclosure, as described above, where the immunogenic composition comprises: i) an HCV E1/E2 heterodimer; ii) a T-cell epitope polypeptide; and iii) a pharmaceutically acceptable carrier; and b) a second immunogenic composition of the present disclosure, as described above, where the immunogenic composition comprises: i) one or more nucleic acids comprising nucleotide sequences encoding an HCV E1/E2 heterodimer and a T-cell epitope polypeptide; and ii) a pharmaceutically acceptable carrier. In some cases, the first and the second immunogenic compositions are in a single formulation. In some cases, the first and the second immunogenic compositions are in separate formulations. In some cases, the first and the second immunogenic compositions are administered via the same route of administration. In some cases, the first and the second immunogenic compositions are administered via different routes of administration. In some cases, the first and the second immunogenic compositions are in separate formulations that are administered substantially simultaneously, e.g., within 1 minute, within 1 minute to 5 minutes, within 5 minutes to 15 minutes, or within 15 minutes to 30 minutes, of one another. In some cases, the first and the second immunogenic compositions are administered multiple times to an individual. In some cases, the one or more nucleic acids are recombinant viral vectors.

In some cases, a method of the present disclosure for inducing an immune response to HCV in an individual comprises administering to the individual an effective amount of a nucleic acid(s) comprising nucleotide sequences encoding 1) an HCV E1/E2 heterodimer and a T-cell epitope polypeptide; 2) an HCV E2 polypeptide and a T-cell epitope polypeptide; or 3) an HCV E1 polypeptide and a T-cell epitope polypeptide. In some cases, the nucleic acid is an RNA comprising nucleotide sequences encoding a polypeptide of the present disclosure (e.g., an HCV E1/E2 heterodimer; an HCV E1 polypeptide; an HCV E2 polypeptide; a T-cell epitope polypeptide, as described herein. See, e.g., Weiner (2013) *Molec. Therapy* 21:506; and Ulmer et al. (2012) *Vaccine* 30:4414. In some cases, an RNA (e.g., a single mRNA molecule; or 2 mRNA molecules; or 3 mRNA molecules) comprising nucleotide sequences encoding a polypeptide of the present disclosure is formulated with a liposome. In some cases, an RNA (e.g., a single mRNA molecule; or 2 mRNA molecules) comprising nucleotide sequences encoding a polypeptide of the present disclosure is complexed with protamine. In some cases, an RNA (e.g., a single mRNA molecule; or 2 mRNA molecules) comprising nucleotide sequences encoding a polypeptide of the present disclosure is complexed with 1,2-dioleoyl-3-trimethylammonium-propane/1,2-dioleoyl-sn-glycero-3-phosphoethanolamine (DOTAP/DOPE).

In some cases, the nucleic acid(s) are present in bacteria (e.g., non-pathogenic bacteria suitable for delivery of nucleic acids to an individual). In some cases, the nucleic acid(s) are present in recombinant expression vector(s) present in bacteria (e.g., non-pathogenic bacteria suitable for delivery of nucleic acids to an individual). In some cases, the bacteria are live. In some cases, the bacteria are live attenuated bacteria. In some cases, the bacteria are killed. Bacteria suitable for delivery of nucleic acid(s) (which may be present in expression vectors) include, but are not limited to, *Lactobacillus; Lactococcus* (e.g., *Lactococcus lactis*); *Salmonella*, e.g., attenuated, non-pathogenic *Salmonella*, e.g., *Salmonella enterica* serovar *Typhi, Salmonella enterica* serovar *Typhimurium*; non-pathogenic strains of *Escherichia coli*; non-pathogenic strains of *Bordetella pertussis*; non-pathogenic strains of *Listeria*; non-pathogenic strains of *Shigella*; non-pathogenic strains of *Vibrio* (e.g., *Vibrio cholera*); *Streptococcus gordonii*; non-pathogenic strains of *Yersinia enterocolitica*; non-pathogenic strains of *Shigella flexneri*; non-pathogenic strains of *Pseudomonas aeruginosa*; non-pathogenic strains of *Bacillus subtilis*; and the like. In some cases, one or more virulence genes in the bacterium is all or partially deleted. For example, for *Salmonella enterica* serovar *Typhi* and *Salmonella enterica* serovar *Typhimurium*, an aroA, aroC, and aroD mutation can be made. Other mutations that can attenuate pathogenicity affect biosynthesis of the nucleotides adenine (pur) and guanine (guaBA), and outer membrane proteins C and F (ompC, ompF), as well as expression of the cAMP receptor (cya/crp), the conversion of UDP-galactose to UDP-glucose (galE), DNA recombination and repair (recA, recBC), and regulation of virulence genes (phoP, phoQ). For *Listeria monocytogenes*, attenuation can be achieved with auxotrophic mutants, or deletion of virulence factors such as the genes actA and internalin B (intB).

General Considerations

An immunogenic composition of the present disclosure is generally administered to a human subject who: i) has an HCV infection; or ii) is at risk of acquiring an HCV infection (e.g., is at greater risk than the general population of acquiring an HCV infection); or iii) is naïve with respect to HCV infection, so as to prevent or at least partially arrest the development of disease and its complications. An amount adequate to accomplish this is defined as a "therapeutically effective dose" or a "therapeutically effective amount." "Prophylactic" use of a subject immunogenic composition generally refers to administration to an individual who has not been infected with HCV (e.g., a "naïve" individual). "Therapeutic" use of a subject immunogenic composition can refer to "prophylactic" use (administration to an individual who has not been infected with HCV) and/or to administration to an individual who has an HCV infection. A "therapeutically effective amount" of an immunogenic composition of the present disclosure, can be an amount that, when administered in one or more doses to an individual who is not infected with HCV, is effective to induce an immune response in the individual to HCV. A "therapeutically effective amount" of an immunogenic composition of the present disclosure, can be an amount that, when administered in one or more doses to an individual who is infected with HCV, is effective to enhance an immune response in the individual to HCV.

Amounts effective for therapeutic use will depend on, e.g., the manner of administration, the weight and general state of health of the patient, and the judgment of the prescribing physician. Single or multiple doses of a subject immunogenic composition can be administered depending on the dosage and frequency required and tolerated by the patient, and route of administration.

In some cases, an effective amount of an immunogenic composition of the present disclosure is an amount that, when administered to an individual in one or more doses, is effective to induce an antibody response (e.g., a neutralizing antibody response) to HCV in the individual. For example, antibody to HCV (e.g., extracellular HCV), and/or to an HCV-infected cell, can be induced.

An effective amount of an immunogenic composition of the present disclosure can be an amount that, when administered to an individual in one or more doses, is effective to induce a neutralizing antibody response to HCV of a variety of genotypes (e.g., genotype 1; genotype 3; etc.). A neutralizing antibody response reduces binding of HCV to one or more host receptors for HCV and inhibits entry of HCV into a cell.

In some cases, an effective amount (e.g., a therapeutically effective amount) of an immunogenic composition of the present disclosure is an amount that, when administered to an individual in one or more doses, is effective to induce a cytotoxic T lymphocyte (CTL) response to HCV. For example, a CTL response to an HCV-infected cell can be induced.

In some cases, an effective amount (e.g., a therapeutically effective amount) of an immunogenic composition of the present disclosure is an amount that, when administered to an individual in one or more doses, is effective to induce a helper T lymphocyte (e.g., $CD4^+$ T cell) to HCV in an individual.

In some cases, an effective amount (e.g., a therapeutically effective amount) of an immunogenic composition of the present disclosure is an amount that, when administered to an individual in one or more doses, is effective to induce an antibody response (e.g., a neutralizing antibody response) and/or a CTL response and/or a helper T cell response to HCV genotype 1. In some cases, an effective amount (e.g., a therapeutically effective amount) of an immunogenic composition of the present disclosure is an amount that, when administered to an individual in one or more doses, is effective to induce an antibody response (e.g., a neutralizing antibody response) and/or a CTL response and/or a helper T cell response to HCV genotype 3. In some cases, an effective amount (e.g., a therapeutically effective amount) of an immunogenic composition of the present disclosure is an amount that, when administered to an individual in one or more doses, is effective to induce an antibody response (e.g., a neutralizing antibody response) and/or a CTL response and/or a helper T cell response to HCV genotype 1 and HCV genotype 3. In some cases, an effective amount (e.g., a therapeutically effective amount) of an immunogenic composition of the present disclosure is an amount that, when administered to an individual in one or more doses, is effective to induce an antibody response (e.g., a neutralizing antibody response) and/or a CTL response and/or a helper T cell response to HCV of any genotype.

An immunogenic composition of the present disclosure is generally administered in an amount effective to elicit an immune response, e.g., a humoral immune response (e.g., an antibody response) and/or a CTL response, in the mammalian subject. Effective amounts of E1/E2, E1, or E2 polypeptides for immunization will vary, and can generally range from about 1 µg to 100 µg per 70 kg patient, e.g., from about 5 µg/70 kg to about 50 µg/70 kg. Substantially higher dosages (e.g. 10 mg to 100 mg or more) of an HCV E1/E2, E1, or E2 polypeptide may be suitable in oral, nasal, or topical administration routes. In some cases, a dose of an immunogenic composition of the present disclosure comprises an HCV E1/E2 heterodimer in an amount of from 4 µg to 100 µg. For example, in some cases, a dose of an immunogenic composition of the present disclosure comprises an HCV E1/E2 heterodimer in an amount of from 4 µg to 5 µg, from 5 µg to 10 µg, from 10 µg to 15 µg, from 15 µg to 20 µg, from 20 µg to 25 µg, from 25 g to 30 µg, from 30 µg to 40 µg, from 40 µg to 50 µg, from 50 µg to 60 µg, from 60 µg to 70 µg, from 70 µg to 80 µg, from 80 µg to 90 µg, or from 90 µg to 100 µg. In some cases, a dose of an immunogenic composition of the present disclosure comprises an HCV E1/E2 heterodimer in an amount of from about 100 µg to about 200 µg.

In some cases, the amount of T-cell epitope polypeptide in a given dose ranges from 0.5 g to 125 µg; e.g., a suitable dose of T-cell epitope polypeptide ranges from 0.5 µg to 1 µg, from 1 µg to 5 µg, from 5 µg to 10 µg, from 10 µg to 15 µg, from 15 µg to 20 µg, from 20 µg to 25 µg, from 25 µg to 30 µg, from 30 µg to 40 µg, from 40 µg to 50 µg, from 50 µg to 60 µg, from 60 g to 75 µg, from 75 µg to 100 µg, or from 100 µg to 125 µg. In some cases, where two or more different T-cell epitope polypeptides are included in an immunogenic composition, a dose will include from 0.5 µg to 125 µg of each T-cell epitope polypeptide. In some cases, where two (or more) different T-cell epitope polypeptides are included in an immunogenic composition, a dose will include from 1 µg to 10 µg (e.g., 1 µg, 2 µg, 3 µg, 4 µg, 5 µg, 6 µg, 7 µg, 8 µg, 9 µg, or 10 g) of each T-cell epitope polypeptide. As one non-limiting example, where an immunogenic composition of the present disclosure includes 2 or more different T-cell epitope polypeptides, the composition can include 1 µg of each different T-cell epitope polypeptide. As another non-limiting example, where an immunogenic composition of the present disclosure includes 2 or more different T-cell epitope polypeptides, the composition can include 3 µg of each different T-cell epitope polypeptide. As another non-limiting example, where an immunogenic composition of the present disclosure includes 2 or more different T-cell epitope polypeptides, the composition can include 6 µg of each different T-cell epitope polypeptide.

In some cases, a single dose of an immunogenic composition of the present disclosure comprises: a) an HCV E1/E2 heterodimer in an amount of from about 10 µg to about 15 µg (e.g., g, 11 µg, 12 µg, 13 µg, 14 µg, or 15 µg E1/E2 heterodimer); and b) two or more different T-cell epitope polypeptides in an amount of from about 5 µg each different T-cell epitope polypeptide to about 15 µg each different T-cell epitope polypeptide (e.g., 5 µg, 6 µg, 7 µg, 8 µg, 9 µg, 10 µg, 11 µg, 12 µg, 13 µg, 14 µg, or 15 µg each different T-cell epitope polypeptide. As one non-limiting example, in some cases, a single dose of an immunogenic composition of the present disclosure comprises: a) 15 µg E1/E2 heterodimer; and b) 45 µg T-cell epitope polypeptides (9 µg each of TP35-NS3, TP50C, TP23, TP27, and TP35-NS4).

In some cases, dose of an immunogenic composition of the present disclosure comprises an E1/E2 heterodimer a T-cell epitope polypeptide, where the molar ratio of T-cell epitope polypeptide to E1/E2 heterodimer in the composition is from about 0.1:1 to about 25:1. For example, the molar ratio of T-cell epitope polypeptide to E1/E2 heterodimer in an immunogenic composition of the present disclosure is from about 0.1:1 to about 0.2:1, from about 0.2:1 to 0.3:1, from about 0.3:1 to about 0.4:1, from about 0.4:1 to about 0.5:1, or from about 0.5:1 to 1:1. Where different T-cell epitope polypeptides are present in an immunogenic composition of the present disclosure the molar ratio of the different T-cell epitope polypeptides to E1/E2 heterodimer can each be independently from about 0.1:1 to about 0.2:1, from about 0.2:1 to 0.3:1, from about 0.3:1 to about 0.4:1, from about 0.4:1 to about 0.5:1, or from about 0.5:1 to 1:1. As another example, the molar ratio of any given T-cell epitope polypeptide to E1/E2 heterodimer is from 1:1 to 25:1, e.g., from 1:1 to 5:1, from 5:1 to 10:1, from 10:1 to 15:1, from 15:1 to 20:1, or from 20:1 to 25:1. In some cases, the molar ratio of a T-cell epitope polypeptide to E1/E2 heterodimer in an immunogenic composition of the present disclosure is from about 10:1 to 20:1. In some cases, the molar ratio of a T-cell epitope polypeptide to E1/E2 heterodimer in an immunogenic composition of the present disclosure is from about 10:1 to 15:1. In some cases, the molar ratio of a T-cell epitope polypeptide to E1/E2 heterodimer in a composition of the present disclosure is 15:1.

The initial administration can be followed by booster immunization of the same immunogenic composition or a different immunogenic composition. In some instances, a subject method of inducing an immune response involves an initial administration of an immunogenic composition of the present disclosure, followed by at least one booster, and in some instances involves two or more (e.g., three, four, or five) boosters. The interval between an initial administration and a booster, or between a give booster and a subsequent booster, can be from about 1 week to about 12 weeks, e.g., from about 1 week to about 2 weeks, from about 2 weeks to about 4 weeks, from about 4 weeks to about 6 weeks, from about 6 weeks to about 8 weeks, from about 8 weeks to about 10 weeks, or from about 10 weeks to about 12 weeks. The interval between an initial administration and a booster, or between a give booster and a subsequent booster, can be from 4 months to 6 months, or from 6 months to 1 year.

In general, immunization can be accomplished by administration of an immunogenic composition of the present disclosure by any suitable route, including administration of the composition orally, nasally, nasopharyngeally, parenterally, enterically, gastrically, topically, transdermally, subcutaneously, intramuscularly, in tablet, solid, powdered, liquid, aerosol form, locally or systemically, with or without added excipients. Actual methods for preparing parenterally administrable compositions will be known or apparent to those skilled in the art and are described in more detail in such publications as Remington's Pharmaceutical Science, 15th ed., Mack Publishing Company, Easton, Pa. (1980). In some instances, immunization is accomplished by intramuscular injection of an immunogenic composition of the present disclosure.

Individuals Suitable for Administration

Individuals who are suitable for administration with an immunogenic composition of the present disclosure include immunologically naïve individuals (e.g., individuals who have not been infected with HCV and/or who have not been administered with an HCV vaccine). Individuals suitable for administration include humans.

Individuals who are suitable for administration with an immunogenic composition of the present disclosure composition of the present disclosure include individuals who are at greater risk than the general population of becoming infected with HCV, where such individuals include, e.g., intravenous drug users; individuals who are the recipients, or the prospective recipients, of blood or blood products from another (donor) individual(s); individuals who are the recipients, or the prospective recipients, of non-autologous cells, tissues, or organs from another (donor) individual; health care workers; emergency medical and non-medical personnel (e.g., first responders; fire fighters; emergency medical team personnel; etc.) and the like.

Individuals who are suitable for administration with an immunogenic composition of the present disclosure composition of the present disclosure include individuals who recently became exposed to HCV or who recently became infected with HCV. For example, a subject immunogenic composition can be administered to an individual within from about 24 hours to about 48 hours, from about 48 hours to about 1 week, or from about 1 week to about 4 weeks, following possible or suspected exposure to HCV or following infection with HCV.

Individuals who are suitable for administration with an immunogenic composition of the present disclosure composition of the present disclosure include individuals who were previously infected with HCV, who were treated for HCV, and who were cured.

Individuals who are suitable for administration with an immunogenic composition of the present disclosure composition of the present disclosure include individuals who have been diagnosed as having an HCV infection, and include chronically infected individuals. In some cases, an individual who has been diagnosed as having an HCV infection is treated with an anti-viral agent and an immunogenic composition of the present disclosure. Suitable anti-viral agents for treating HCV infection include, e.g., ribavirin (1-β-D-ribofuranosyl-1H-1,2,4-triazole-3-carboxamide); interferon-alpha (IFN-α) (where "IFN-α" includes IFN-α2a; IFN-α2b; IFN-α that is conjugated with poly (ethylene glycol) ("pegylated IFN-α), where the pegylated IFN-α can be pegylated IFN-α2a or pegylated IFN-α 2b); an HCV NS3 protease inhibitor (e.g., boceprevir; telaprevir); and an HCV NS5 protease inhibitor.

In some cases, an individual who has been diagnosed as having an HCV infection is treated with, e.g.: 1) IFN-α+ ribavirin; and an immunogenic composition of the present disclosure; 2) IFN-α+ribavirin+an HCV protease inhibitor (e.g., boceprevir or telaprevir); and an immunogenic composition of the present disclosure; 3) Harvoni; and an immunogenic composition of the present disclosure; 4) an inhibitor of HCV NS5B; and an immunogenic composition of the present disclosure; 5) an inhibitor of HCV NS5A; and an immunogenic composition of the present disclosure; or 6) an inhibitor of HCV NS5B+an inhibitor of HCV NS5A; and an immunogenic composition of the present disclosure. Suitable anti-viral agents for treating HCV infection include Sovaldi (Sofosbuvir; a nucleotide analog that functions as an NS5B polymerase inhibitor), alone or in combination with pegylated IFN-α and ribavirin; and Harvoni. Harvoni is a formulation comprising 90 mg ledipasvir and 400 mg sofosbuvir. Ledipasvir is an inhibitor of HCV NS5A.

Examples of Non-Limiting Aspects of the Disclosure

Aspects Set A

Aspects, including embodiments, of the present subject matter described above may be beneficial alone or in combination, with one or more other aspects or embodiments. Without limiting the foregoing description, certain non-limiting aspects of the disclosure numbered 1-27 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. An immunogenic composition comprising:
a) one or more T-cell epitope polypeptides selected from:
  i) a TP35-NS3 T-cell epitope polypeptide comprising an amino acid sequence having at least 80% (at least 80%, at least 90%, at least 95%, at least 98%, at least 99%, or 100%) amino acid sequence identity to: KSTKVPX$_1$AYX$_2$X$_3$QGYX$_4$VLVLNPSVAA TLGFGX$_5$X$_6$X$_7$SX$_8$ (SEQ ID NO:134), wherein X$_1$ is A or V; X$_2$ is A or V; X$_3$ is A or S; X$_4$ is K or N; X$_5$ is A or S; X$_6$ is Y or F; X$_7$ is M or L; and X$_8$ is K or R, wherein the TP35-NS3 T-cell epitope polypeptide has a length of from 28 amino acids to 35 amino acids; and
  ii) a TP50C T-cell epitope polypeptide comprising an amino acid sequence having at least 80% (at least 80%, at least 90%, at least 95%, at least 98%, at least 99%, or 100%) amino acid sequence identity to: GVYX$_1$LPRRGPRLGVRX$_2$TRKX$_3$SERSQ PRGRRQX$_4$IPKX$_5$X$_6$X$_7$X$_8$X$_9$GX$_{10}$X$_{11}$WX$_{12}$ X$_{13}$PGYP (SEQ ID NO:149), where X$_1$ is L or V; X$_2$ is A or G; X$_3$ is T or S; X$_4$ is P or R; X$_5$ is A or D; X$_6$ is R or A; X$_7$ is R, Q, or S; X$_8$ is S or P; X$_9$ is E, T, or Q; X$_{10}$ is R or K; X$_{11}$ is S, T, H, or A; X$_{12}$ is A or G; and X$_{13}$ is Q or K, wherein the TP50C T-cell epitope polypeptide has a length of from 40 amino acids to 50 amino acids;
  iii) a TP23 T-cell epitope polypeptide comprising an amino acid sequence having at least 80% (at least 80%, at least 90%, at least 95%, at least 98%, at least 99%, or 100%) amino acid sequence identity to: DVVVX$_1$X$_2$TDALMTGX$_3$TGDFDSVID (SEQ ID NO:171), wherein X$_1$ is V or C; X$_2$ is A or S; and X$_3$ is F or Y, wherein the TP23 T-cell epitope polypeptide has a length of from 18 amino acids to 23 amino acids;
  iv) a TP27 T-cell epitope polypeptide comprising an amino acid sequence having at least 80% (at least 80%, at least 90%, at least 95%, at least 98%, at least 99%, or 100%) amino acid sequence identity to: X$_1$X$_2$X$_3$X$_4$KGGRHLIFCHSKKKCDEX$_5$AX$_6$ X$_7$LX$_8$ (SEQ ID NO:189), where X$_1$ is L or I; X$_2$ is E, A, S, V, or Q; X$_3$ is Q, T, Y, F, or L; X$_4$ is I or L; X$_5$ is L or I; X$_6$ is A, K, or S; X$_7$ is K, Q, or A; and $X_8$ is T, R, or S, wherein the TP27 T-cell epitope polypeptide has a length of from 22 amino acids to 27 amino acids;

v) a TP35-NS4 T-cell epitope polypeptide comprising an amino acid sequence having at least 80% (at least 80%, at least 90%, at least 95%, at least 98%, at least 99%, or 100%) amino acid sequence identity to: $X_1X_2X_3RHX_4GX_5X_6EGX_7X_8QWMNRLIAFA$ SRGNHV$X_9$PTHY$X_{10}$ (SEQ ID NO:204), wherein $X_1$ is I or V; $X_2$ is L or I; $X_3$ is R or K; $X_4$ is V, I, or T; $X_5$ is P, Q, or T; $X_6$ is G, A, or S; $X_7$ is A or V; $X_8$ is V or T; $X_9$ is S or A; and $X_{10}$ is V or I, wherein the TP35-NS4 T-cell epitope polypeptide has a length of from 28 amino acids to 35 amino acids;

vi) a TP42 T-cell epitope polypeptide comprising an amino acid sequence having at least 80% (at least 80%, at least 90%, at least 95%, at least 98%, at least 99%, or 100%) amino acid sequence identity to: $X_1X_2X_3$GEIPFYG$X_4$AIP$X_5X_6X_7$XSKGGRH LIFCHSKKKCDE$X_9$A$X_{10}X_{11}$L$X_{12}X_{13}$(K)n (SEQ ID NO:229), where $X_1$ is G, P, or S; $X_2$ is T, N, Q, H, or S; $X_3$ is E, T, or D; $X_4$ is K or R; $X_5$ is L or I; $X_6$ is E, A, S, or Q; $X_7$ is Q, T, Y, F, or L; $X_8$ is I or L; $X_9$ is L or I; $X_{10}$ is A, K, or S; $X_1$ is K, Q, or A; $X_{12}$ is T, R, or S; and $X_{13}$ is G or S, wherein n is an integer from 2 to 10, and wherein the TP42 T-cell epitope polypeptide has a length of from 34 amino acids to 52 amino acids;

vii) a TP45 T-cell epitope polypeptide comprising an amino acid sequence having at least 80% (at least 80%, at least 90%, at least 95%, at least 98%, at least 99%, or 100%) amino acid sequence identity to: $X_1X_2$AVA$X_3$YRG$X_4$DV$X_5X_6$IP$X_7X_8$GDV VV$X_9X_{10}$TDALMTG$X_{11}$TGDFDSVID$X_{12}X_{13}$ $X_{14}$(K)n (SEQ ID NO:249), wherein $X_1$ is L or V; $X_2$ is N or T; $X_3$ is Y or F; $X_4$ is L or V; $X_5$ is S or A; $X_6$ is V or I; $X_7$ is T or A; $X_8$ is S, Q, or T; $X_9$ is V or C; $X_{10}$ is A or S; $X_{11}$ is F or Y; $X_{12}$ is C or K; $X_{13}$ is N or K; and $X_{14}$ is V or K, wherein n is an integer from 2 to 10, and wherein the TP45 T-cell epitope polypeptide has a length of from 36 amino acids to 55 amino acids; and viii) a TP48 T-cell epitope polypeptide comprising an amino acid sequence having at least 80% (at least 80%, at least 90%, at least 95%, at least 98%, at least 99%, or 100%) amino acid sequence identity to: $X_1X_2X_3$RH$X_4$G$X_5X_6$EG$X_7X_8$QWMNRL IAFASRGNHV$X_9$PTHY$X_{10}X_{11}X_{12}X_{13}$DA$X_{14}$ $X_{15}X_{16}$V$X_{17}X_{18}X_{19}$L(K)n (SEQ ID NO:255), wherein $X_1$ is I or V; $X_2$ is L or I; $X_3$ is R or K; $X_4$ is V, I, or T; $X_5$ is P, Q, or T; $X_6$ is G, A, or S; $X_7$ is A or V; $X_8$ is V or T; $X_9$ is S or A; $X_{10}$ is V or I; $X_1$ is P, T, A, or Q, $X_{12}$ is E or D; $X_{13}$ is S, T, or D; $X_{14}$ is S or A; $X_{15}$ is A, Q, R, or K; $X_{16}$ is R, K, or X; $X_{17}$ is T or M; $X_{18}$ is Q, A, T, or G; and $X_{19}$ is I, L, or V, wherein n is an integer from 2 to 10, and wherein the TP48 T-cell epitope polypeptide has a length of from 38 amino acids to 58 amino acids; and b) an immune-stimulating amount of an adjuvant.

Aspect 2. The immunogenic composition of aspect 1, wherein the one or more T-cell epitope polypeptides comprises a heterologous fusion partner.

Aspect 3. The immunogenic composition of aspect 2, wherein the heterologous fusion partner is (Lys)$_n$, wherein n is an integer from 2 to 10.

Aspect 4. The immunogenic composition of aspect 3, wherein n is 3, and wherein the fusion partner is at the C-terminus of the T-cell epitope polypeptide.

Aspect 5. The immunogenic composition of any one of aspects 1-4, wherein the composition comprises 2, 3, 4, or 5 different T-cell epitope polypeptides.

Aspect 6. The immunogenic composition of any one of aspects 1-5, wherein one or more T-cell epitope polypeptides comprise:

a) a TP35-NS3 T-cell epitope polypeptide comprising an amino acid sequence having at least 80% (at least 80%, at least 90%, at least 95%, at least 98%, at least 99%, or 100%) amino acid sequence identity to: KSTKVPAAYAAQGYKVLVLNPSVAATLGF-GAYMSK (SEQ ID NO:133), wherein the TP35-NS3 T-cell epitope polypeptide has a length of from 28 amino acids to 35 amino acids; and b) a TP50C T-cell epitope polypeptide comprising an amino acid sequence having at least 80% (at least 80%, at least 90%, at least 95%, at least 98%, at least 99%, or 100%) amino acid sequence identity to: GVYLLPRRGPRLGVRATRKTSERSQPR-GRRQPIPKARRSEGRSWAQPGYP (SEQ ID NO:148), wherein the TP50C T-cell epitope polypeptide has a length of from 40 amino acids to 50 amino acids.

Aspect 7. The immunogenic composition of any one of aspects 1-5, wherein the one or more T-cell epitope polypeptides comprise:

a) a TP35-NS3 T-cell epitope polypeptide comprising an amino acid sequence having at least 80% (at least 80%, at least 90%, at least 95%, at least 98%, at least 99%, or 100%) amino acid sequence identity to: KSTKVPAAYAAQGYKVLVLNPSVAATLGF-GAYMSK (SEQ ID NO:133), wherein the T-cell epitope polypeptide has a length of from 28 amino acids to 35 amino acids; and b) a TP50C T-cell epitope polypeptide comprising an amino acid sequence having at least 80% (at least 80%, at least 90%, at least 95%, at least 98%, at least 99%, or 100%) amino acid sequence identity to: GVYLLPRRGPRLGVRATRKTSERSQPR-GRRQPIPKARRSEGRSWAQPGYP (SEQ ID NO:148), wherein the T-cell epitope polypeptide has a length of from 40 amino acids to 50 amino acids; and c) one or more T-cell epitope polypeptides selected from:

i) a TP23 T-cell epitope polypeptide comprising an amino acid sequence having at least 80% (at least 80%, at least 90%, at least 95%, at least 98%, at least 99%, or 100%) amino acid sequence identity to: DVVVVATDALMTGFTGDFDSVID (SEQ ID NO:186), wherein the TP23 T-cell epitope polypeptide has a length of from 18 amino acids to 23 amino acids;

ii) a TP27 T-cell epitope polypeptide comprising an amino acid sequence having at least 80% (at least 80%, at least 90%, at least 95%, at least 98%, at least 99%, or 100%) amino acid sequence identity to: LEQIKGGRHLIFCHSKKKCDELAAKLT (SEQ ID NO:188), wherein the TP27 T-cell epitope polypeptide has a length of from 22 amino acids to 27 amino acids; and iii) a TP35-NS4 T-cell epitope polypeptide comprising an amino acid sequence having at least 80% (at least 80%, at least 90%, at least 95%, at least 98%, at least 99%, or 100%) amino acid sequence identity to: ILRRHVGPGEGAVQWMNRLIAFAS-RGNHVSPTHYV (SEQ ID NO:203), wherein the TP35-NS4 T-cell epitope polypeptide has a length of from 28 amino acids to 35 amino acids.

Aspect 8. The immunogenic composition of any one of aspects 1-5, wherein the one or more T-cell epitope polypeptides comprise:
- a) a TP35-NS3 T-cell epitope polypeptide comprising an amino acid sequence having at least 80% (at least 80%, at least 90%, at least 95%, at least 98%, at least 99%, or 100%) amino acid sequence identity to: KSTKVPAAYAAQGYKVLVLNPSVAATLGF-GAYMSK (SEQ ID NO:133), wherein the T-cell epitope polypeptide has a length of from 28 amino acids to 35 amino acids; and
- b) a TP50C T-cell epitope polypeptide comprising an amino acid sequence having at least 80% (at least 80%, at least 90%, at least 95%, at least 98%, at least 99%, or 100%) amino acid sequence identity to: GVYLLPRRGPRLGVRATRKTSERSQPR-GRRQPIPKARRSEGRSWAQPGYP (SEQ ID NO:148), wherein the T-cell epitope polypeptide has a length of from 40 amino acids to 50 amino acids; and
- c) a TP23 T-cell epitope polypeptide comprising an amino acid sequence having at least 80% (at least 80%, at least 90%, at least 95%, at least 98%, at least 99%, or 100%) amino acid sequence identity to: DVVV-VATDALMTGFTGDFDSVID (SEQ ID NO:186), wherein the TP23 T-cell epitope polypeptide has a length of from 18 amino acids to 23 amino acids;
- d) a TP27 T-cell epitope polypeptide comprising an amino acid sequence having at least 80% (at least 80%, at least 90%, at least 95%, at least 98%, at least 99%, or 100%) amino acid sequence identity to: LEQIKG-GRHLIFCHSKKKCDELAAKLT (SEQ ID NO:188), wherein the TP27 T-cell epitope polypeptide has a length of from 22 amino acids to 27 amino acids; and
- e) a TP35-NS4 T-cell epitope polypeptide comprising an amino acid sequence having at least 80% (at least 80%, at least 90%, at least 95%, at least 98%, at least 99%, or 100%) amino acid sequence identity to: ILR-RHVGPGEGAVQWMNRLIAFASRGNHVSPTHYV (SEQ ID NO:203), wherein the TP35-NS4 T-cell epitope polypeptide has a length of from 28 amino acids to 35 amino acids.

Aspect 9. The immunogenic composition of aspect 2, wherein heterologous fusion partner is one or more of:
- a) cholera toxin or toxoid;
- b) tetanus toxin or toxoid; and/or
- c) diphtheria toxin or toxoid; and/or
- d) CRM197.

Aspect 10. The immunogenic composition of any one of aspects 1-9, wherein the composition comprises a polypeptide comprising one or more T cell epitopes present in:
- a) cholera toxin or toxoid; and/or
- b) tetanus toxin or toxoid; and/or
- c) diphtheria toxin or toxoid; and/or
- d) CRM197.

Aspect 11. The immunogenic composition of any one of aspects 1-10, further comprising a hepatitis C virus (HCV) E1/E2 heterodimeric polypeptide comprising:
- i) an HCV E1 polypeptide; and
- ii) an HCV E2 polypeptide;

Aspect 12. The immunogenic composition of aspect 11, wherein the HCV E1 polypeptide comprises an amino acid sequence having at least 20% (at least 20%, at least 30%, at least 40%, at least 50%, at least 60%, at least 70%, at least 80%, at least 90%, at least 95%, at least 98%, at least 99%, or 100%) amino acid sequence identity to an E1 polypeptide depicted in FIG. 1A-IC, FIG. 2A-2C, FIG. 3A-3C, and FIG. 4A-4B.

Aspect 13. The immunogenic composition of aspect 11, wherein the HCV E2 polypeptide comprises an amino acid sequence having at least 20% (at least 20%, at least 30%, at least 40%, at least 50%, at least 60%, at least 70%, at least 80%, at least 90%, at least 95%, at least 98%, at least 99%, or 100%) amino acid sequence identity to an E2 polypeptide depicted in one of FIG. 1A-1C, FIG. 2A-2C, FIG. 3A-3C, and FIG. 4A-4B.

Aspect 14. The immunogenic composition of any one of aspects 11-13, wherein the E2 polypeptide and/or the E1 polypeptide lacks a C-terminal transmembrane domain.

Aspect 15. The immunogenic composition of any one of aspects 11-14, wherein the HCV E2 polypeptide and the HCV E1 polypeptide are derived from an HCV of the same genotype.

Aspect 16. The immunogenic composition of any one of aspects 11-15, wherein the HCV E2 polypeptide and the HCV E1 polypeptide are derived from an HCV of different genotypes.

Aspect 17. The immunogenic composition of any one of aspects 11-16, wherein the HCV E1/E2 heterodimeric polypeptide comprises:
- a) an HCV E1 polypeptide; and
- b) a modified E2 polypeptide comprising, in order from N-terminus to C-terminus:
  - i) from 1 to 6 heterologous amino acids, wherein the from 1 to 6 heterologous amino acids are C-terminal to a site of proteolytic cleavage in a proteolytically cleavable linker; and
  - ii) an HCV E2 polypeptide; or
- a) an HCV E2 polypeptide; and
- b) a modified E1 polypeptide comprising, in order from N-terminus to C-terminus:
  - i) from 1 to 6 heterologous amino acids, wherein the from 1 to 6 heterologous amino acids are C-terminal to a site of proteolytic cleavage in a proteolytically cleavable linker; and
  - ii) an HCV E1 polypeptide; or
- a) an HCV E1 polypeptide; and
- b) a modified E2 polypeptide comprising, in order from N-terminus to C-terminus:
  - i) an HCV E2 polypeptide; and
  - ii) from 1 to 6 heterologous amino acids, wherein the from 1 to 6 heterologous amino acids are N-terminal to a site of proteolytic cleavage in a proteolytically cleavable linker; or
- a) an HCV E2 polypeptide; and
- b) a modified E1 polypeptide comprising, in order from N-terminus to C-terminus:
  - i) an HCV E1 polypeptide; and
  - ii) from 1 to 6 heterologous amino acids, wherein the from 1 to 6 heterologous amino acids are N-terminal to a site of proteolytic cleavage in a proteolytically cleavable linker.

Aspect 18. The immunogenic composition of aspect 17, wherein:
- a) the from 1 to 6 heterologous amino acids at the N-terminus of the modified E2 polypeptide or the modified E1 polypeptide are Gly-Pro, Ser, Gly, or Gly-Ser; or
- b) the from 1 to 6 heterologous amino acids at the C-terminus of the modified E2 polypeptide or the modified E1 polypeptide are LEVLFQ (SEQ ID NO:83), ENLYYFQ (SEQ ID NO:84), LVPR (SEQ ID NO:85), I(E/D)GR (SEQ ID NO:86), or DDDDK (SEQ ID NO:87).

Aspect 19. The immunogenic composition of any one of aspects 1-18, wherein the adjuvant comprises: MF59; alum; poly(DL-lactide co-glycolide); a CpG oligonucleotide; a suspension of liposomes comprising 3'-O-desacyl-4'-monophosphoryl lipid A (MPL) and Quillaja saponaria 21 (QS21); a mixture of alum and MPL; a phosphorylated hexaacyl disaccharide (PHAD); a mixture of alum and PHAD; or a cyclic dinucleotide.

Aspect 20. The immunogenic composition of any one of aspects 1-18, wherein the adjuvant comprises MF59.

Aspect 21. The immunogenic composition of any one of aspects 1-18, wherein the adjuvant comprises alum.

Aspect 22. A method of inducing an immune response in an individual to a hepatitis C virus (HCV) polypeptide, the method comprising administering to the individual:
   a) an effective amount of the immunogenic composition of any one of aspects 1-21; or
   b) one or more nucleic acids comprising nucleotide sequences encoding the T-cell epitope polypeptide(s) and/or the HCV E1/E2 heterodimeric polypeptide.

Aspect 23. The method of aspect 22, wherein said administering is by intramuscular administration.

Aspect 24. The method of aspect 22, wherein said administering is by subcutaneous administration.

Aspect 25. A container comprising the immunogenic composition of any one of aspects 1-21.

Aspect 26. The container of aspect 25, wherein the container and the composition are sterile.

Aspect 27. The container of aspect 25 or aspect 26, wherein the container is a syringe.

Aspects Set B

Aspects, including embodiments, of the present subject matter described above may be beneficial alone or in combination, with one or more other aspects or embodiments. Without limiting the foregoing description, certain non-limiting aspects of the disclosure numbered 1-30 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. An immunogenic composition comprising:
   a) one or more T-cell epitope polypeptides selected from:
      i) a TP35-NS3 T-cell epitope polypeptide comprising an amino acid sequence having at least 80%, at least 90%, at least 95%, at least 98%, at least 99%, or 100%, amino acid sequence identity to: KSTKVPX$_1$AYX$_2$X$_3$QGYX$_4$VLVLNPSVA ATLGFGX$_5$X$_6$X$_7$SX$_8$ (SEQ ID NO:134), wherein X$_1$ is A or V; X$_2$ is A or V; X$_3$ is A or S; X$_4$ is K or N; X$_5$ is A or S; X$_6$ is Y or F; X$_7$ is M or L; and X$_8$ is K or R, wherein the TP35-NS3 T-cell epitope polypeptide has a length of from 28 amino acids to 35 amino acids; and
      ii) a TP50C T-cell epitope polypeptide comprising an amino acid sequence having at least 80%, at least 90%, at least 95%, at least 98%, at least 99%, or 100%, amino acid sequence identity to: GVYX$_1$LPRRGPRLGVRX$_2$TRKX$_3$SERSQ PRGRRQX$_4$IPKX$_5$X$_6$X$_7$X$_8$X$_9$GX$_{10}$X$_{11}$WX$_{12}$ X$_{13}$PGYP (SEQ ID NO:149), where X$_1$ is L or V; X$_2$ is A or G; X$_3$ is T or S; X$_4$ is P or R; X$_5$ is A or D; X$_6$ is R or A; X$_7$ is R, Q, or S; X$_8$ is S or P; X$_9$ is E, T, or Q; X$_{10}$ is R or K; X$_1$ is S, T, H, or A; X$_{12}$ is A or G; and X$_{13}$ is Q or K, wherein the TP50C T-cell epitope polypeptide has a length of from 40 amino acids to 50 amino acids;
      iii) a TP23 T-cell epitope polypeptide comprising an amino acid sequence having at least 80%, at least 90%, at least 95%, at least 98%, at least 99%, or 100%, amino acid sequence identity to: DVVVX$_1$X$_2$TDALMTGX$_3$TGDFDSVID (SEQ ID NO:171), wherein X$_1$ is V or C; X$_2$ is A or S; and X$_3$ is F or Y, wherein the TP23 T-cell epitope polypeptide has a length of from 18 amino acids to 23 amino acids;
      iv) a TP27 T-cell epitope polypeptide comprising an amino acid sequence having at least 80%, at least 90%, at least 95%, at least 98%, at least 99%, or 100%, amino acid sequence identity to: X$_1$X$_2$X$_3$X$_4$KGGRHLIFCHSKKKCDEX$_5$ AX$_6$X$_7$LX$_8$ (SEQ ID NO:189), where X$_1$ is L or I; X$_2$ is E, A, S, V, or Q; X$_3$ is Q, T, Y, F, or L; X$_4$ is I or L; X$_5$ is L or I; X$_6$ is A, K, or S; X$_7$ is K, Q, or A; and X$_8$ is T, R, or S, wherein the TP27 T-cell epitope polypeptide has a length of from 22 amino acids to 27 amino acids;
      v) a TP35-NS4 T-cell epitope polypeptide comprising an amino acid sequence having at least 80%, at least 90%, at least 95%, at least 98%, at least 99%, or 100%, amino acid sequence identity to: X$_1$X$_2$X$_3$RHX$_4$GX$_5$X$_6$EGX$_7$X$_8$QWMNRLIA FASRGNHVX$_9$PTHYX$_{10}$ (SEQ ID NO:204), wherein X$_1$ is I or V; X$_2$ is L or I; X$_3$ is R or K; X$_4$ is V, I, or T; X$_5$ is P, Q, or T; X$_6$ is G, A, or S; X$_7$ is A or V; X$_8$ is V or T; X$_9$ is S or A; and X$_{10}$ is V or I, wherein the TP35-NS4 T-cell epitope polypeptide has a length of from 28 amino acids to 35 amino acids;
      vi) a TP42 T-cell epitope polypeptide comprising an amino acid sequence having at least 80%, at least 90%, at least 95%, at least 98%, at least 99%, or 100%, amino acid sequence identity to: X$_1$X$_2$X$_3$GEIPFYGX$_4$AIPX$_5$X$_6$X$_7$X$_8$KGGR HLIFCHSKKKCDEX$_9$AX$_{10}$X$_{11}$LX$_{12}$X$_{13}$(K)n (SEQ ID NO:229), where X$_1$ is G, P, or S; X$_2$ is T, N, Q, H, or S; X$_3$ is E, T, or D; X$_4$ is K or R; X$_5$ is L or I; X$_6$ is E, A, S, or Q; X$_7$ is Q, T, Y, F, or L; X$_8$ is I or L; X$_9$ is L or I; X$_{10}$ is A, K, or S; X$_1$ is K, Q, or A; X$_{12}$ is T, R, or S; and X$_{13}$ is G or S, wherein n is an integer from 2 to 10, and wherein the TP42 T-cell epitope polypeptide has a length of from 34 amino acids to 52 amino acids;
      vii) a TP45 T-cell epitope polypeptide comprising an amino acid sequence having at least 80%, at least 90%, at least 95%, at least 98%, at least 99%, or 100%, amino acid sequence identity to: X$_1$X$_2$AVAX$_3$YRGX$_4$DVX$_5$X$_6$IPX$_7$X$_8$GD VVVX$_9$X$_{10}$TDALMTGX$_{11}$TGDFDSVIDX$_{12}$X$_{13}$ X$_{14}$(K)n (SEQ ID NO:249), wherein X$_1$ is L or V; X$_2$ is N or T; X$_3$ is Y or F; X$_4$ is L or V; X$_5$ is S or A; X$_6$ is V or I; X$_7$ is T or A; X$_8$ is S, Q, or T; X$_9$ is V or C; X$_{10}$ is A or S; X$_{11}$ is F or Y; X$_{12}$ is C or K; X$_{13}$ is N or K; and X$_{14}$ is V or K, wherein n is an integer from 2 to 10, and wherein the TP45 T-cell epitope polypeptide has a length of from 36 amino acids to 55 amino acids; and
      viii) a TP48 T-cell epitope polypeptide comprising an amino acid sequence having at least 80%, at least 90%, at least 95%, at least 98%, at least 99%, or 100%, amino acid sequence identity to: $X_1X_2X_3RHX_4GX_5X_6EGX_7X_8QWMNRLI$ AFASRGNHVX$_9$PTHYX$_{10}$X$_{11}$X$_{12}$X$_{13}$DAX$_{14}$ X$_{15}$X$_{16}$VX$_{17}$X$_{18}$X$_{19}$L(K)n (SEQ ID NO:255), wherein X$_1$ is I or V; X$_2$ is L or I; X$_3$ is R or K; X$_4$ is V, I, or T; X$_5$ is P, Q, or T; X$_6$ is G, A, or S; X$_7$ is A or V; X$_8$ is V or T; X$_9$ is S or A; X$_{10}$ is V or I; X$_1$ is P, T, A, or Q, X$_{12}$ is E or D; X$_{13}$ is S, T, or D; X$_{14}$ is S or A; X$_{15}$ is A, Q, R, or K; X$_{16}$ is R, K, or X; X$_{17}$ is T or M; X$_{18}$ is Q, A, T, or G; and X$_{19}$ is I, L, or V, wherein n is an integer from 2 to 10, and wherein the TP48 T-cell epitope polypeptide has a length of from 38 amino acids to 58 amino acids;

ix) a TP33 T-cell epitope polypeptide comprising an amino acid sequence having at least 80%, at least 90%, at least 95%, at least 98%, at least 99%, or 100%, amino acid sequence identity to: HSKKKCDELAX$_1$X$_2$LX$_3$X$_4$X$_5$GX$_6$NAVAY YRGLDVSX$_7$IP (SEQ ID NO:287), where X$_1$ is A or S; X$_2$ is K or A; X$_3$ is V, S, R, or T; X$_4$ is A or G; X$_5$ is L or M; X$_6$ is I, L, or V; and X$_7$ is V or I; wherein the TP33 T-cell epitope polypeptide has a length of from 30 amino acids to 36 amino acids;

x) a TP42-2 T-cell epitope polypeptide comprising an amino acid sequence having at least 80%, at least 90%, at least 95%, at least 98%, at least 99%, or 100%, amino acid sequence identity to: KGGRHLIFCHSKKKCDELAX$_1$X$_2$LX$_3$X$_4$ X$_5$GX$_6$NAVAYYRGLDVSX$_7$IP (SEQ ID NO:292), where X$_1$ is A or S; X$_2$ is K or A; X$_3$ is V, S, R, or T; X$_4$ is A or G; X$_5$ is L or M; X$_6$ is I, L, or V; and X$_7$ is V or I; wherein the TP42-2 T-cell epitope polypeptide has a length of from 38 amino acids to 46 amino acids; and b) an immune-stimulating amount of an adjuvant.

Aspect 2. The immunogenic composition of aspect 1, wherein the one or more T-cell epitope polypeptides comprises a heterologous fusion partner.

Aspect 3. The immunogenic composition of aspect 2, wherein the heterologous fusion partner is (Lys)$_n$, wherein n is an integer from 2 to 10.

Aspect 4. The immunogenic composition of aspect 3, wherein n is 3, and wherein the fusion partner is at the C-terminus of the T-cell epitope polypeptide.

Aspect 5. The immunogenic composition of any one of aspects 1-4, wherein the composition comprises 2, 3, 4, or 5 different T-cell epitope polypeptides.

Aspect 6. The immunogenic composition of any one of aspects 1-5, wherein one or more T-cell epitope polypeptides comprise:
a) a TP35-NS3 T-cell epitope polypeptide comprising an amino acid sequence having at least 80%, at least 90%, at least 95%, at least 98%, at least 99%, or 100%, amino acid sequence identity to: KSTKVPAAYAAQGYKVLVLNPSVAATLGF-GAYMSK (SEQ ID NO:133), wherein the TP35-NS3 T-cell epitope polypeptide has a length of from 28 amino acids to 35 amino acids; and
b) a TP50C T-cell epitope polypeptide comprising an amino acid sequence having at least 80%, at least 90%, at least 95%, at least 98%, at least 99%, or 100%, amino acid sequence identity to: GVYLLPRRGPRLGVRATRKTSERSQPR-GRRQPIPKARRSEGRSWAQPGYP (SEQ ID NO:148), wherein the TP50C T-cell epitope polypeptide has a length of from 40 amino acids to 50 amino acids.

Aspect 7. The immunogenic composition of any one of aspects 1-5, wherein the one or more T-cell epitope polypeptides comprise:
a) a TP35-NS3 T-cell epitope polypeptide comprising an amino acid sequence having at least 80%, at least 90%, at least 95%, at least 98%, at least 99%, or 100%, amino acid sequence identity to: KSTKVPAAYAAQGYKVLVLNPSVAATLGF-GAYMSK (SEQ ID NO:133), wherein the T-cell epitope polypeptide has a length of from 28 amino acids to 35 amino acids; and
b) a TP50C T-cell epitope polypeptide comprising an amino acid sequence having at least 80%, at least 90%, at least 95%, at least 98%, at least 99%, or 100%, amino acid sequence identity to: GVYLLPRRGPRLGVRATRKTSERSQPR-GRRQPIPKARRSEGRSWAQPGYP (SEQ ID NO:148), wherein the T-cell epitope polypeptide has a length of from 40 amino acids to 50 amino acids; and
c) one or more T-cell epitope polypeptides selected from:
i) a TP23 T-cell epitope polypeptide comprising an amino acid sequence having at least 80%, at least 90%, at least 95%, at least 98%, at least 99%, or 100%, amino acid sequence identity to: DVVV-VATDALMTGFTGDFDSVID (SEQ ID NO:186), wherein the TP23 T-cell epitope polypeptide has a length of from 18 amino acids to 23 amino acids;
ii) a TP27 T-cell epitope polypeptide comprising an amino acid sequence having at least 80%, at least 90%, at least 95%, at least 98%, at least 99%, or 100%, amino acid sequence identity to: LEQIKG-GRHLIFCHSKKKCDELAAKLT (SEQ ID NO:188), wherein the TP27 T-cell epitope polypeptide has a length of from 22 amino acids to 27 amino acids; and
iii) a TP35-NS4 T-cell epitope polypeptide comprising an amino acid sequence having at least 80%, at least 90%, at least 95%, at least 98%, at least 99%, or 100%, amino acid sequence identity to: ILR-RHVGPGEGAVQWMNRLIAFAS-RGNHVSPTHYV (SEQ ID NO:203), wherein the TP35-NS4 T-cell epitope polypeptide has a length of from 28 amino acids to 35 amino acids.

Aspect 8. The immunogenic composition of any one of aspects 1-5, wherein the one or more T-cell epitope polypeptides comprise:
a) a TP35-NS3 T-cell epitope polypeptide comprising an amino acid sequence having at least 80%, at least 90%, at least 95%, at least 98%, at least 99%, or 100%, amino acid sequence identity to: KSTKVPAAYAAQGYKVLVLNPSVAATLGF-GAYMSK (SEQ ID NO:133), wherein the T-cell epitope polypeptide has a length of from 28 amino acids to 35 amino acids; and
b) a TP50C T-cell epitope polypeptide comprising an amino acid sequence having at least 80%, at least 90%, at least 95%, at least 98%, at least 99%, or 100%, amino acid sequence identity to: GVYLLPRRGPRLGVRATRKTSERSQPR-GRRQPIPKARRSEGRSWAQPGYP (SEQ ID NO:148), wherein the T-cell epitope polypeptide has a length of from 40 amino acids to 50 amino acids; and
c) a TP23 T-cell epitope polypeptide comprising an amino acid sequence having at least 80%, at least 90%, at least 95%, at least 98%, at least 99%, or 100%, amino acid sequence identity to: DVVV-VATDALMTGFTGDFDSVID (SEQ ID NO:186), wherein the TP23 T-cell epitope polypeptide has a length of from 18 amino acids to 23 amino acids;
d) a TP27 T-cell epitope polypeptide comprising an amino acid sequence having at least 80%, at least 90%, at least 95%, at least 98%, at least 99%, or 100%, amino acid sequence identity to: LEQIKGGRHLIFCHS-KKKCDELAAKLT (SEQ ID NO:188), wherein the TP27 T-cell epitope polypeptide has a length of from 22 amino acids to 27 amino acids; and
e) a TP35-NS4 T-cell epitope polypeptide comprising an amino acid sequence having at least 80%, at least 90%, at least 95%, at least 98%, at least 99%, or 100%, amino acid sequence identity to: ILR-RHVGPGEGAVQWMNRLIAFASRGNHVSPTHYV (SEQ ID NO:203), wherein the TP35-NS4 T-cell epitope polypeptide has a length of from 28 amino acids to 35 amino acids.

Aspect 9. The immunogenic composition of any one of aspects 1-5, wherein the one or more T-cell epitope polypeptides comprise:
a) a TP35-NS3 T-cell epitope polypeptide comprising an amino acid sequence having at least 80%, at least 90%, at least 95%, at least 98%, at least 99%, or 100%, amino acid sequence identity to: KSTKVPAAYAAQGYKVLVLNPSVAATLGF-GAYMSK (SEQ ID NO:133), wherein the T-cell epitope polypeptide has a length of from 28 amino acids to 35 amino acids;
b) a TP50C T-cell epitope polypeptide comprising an amino acid sequence having at least 80%, at least 90%, at least 95%, at least 98%, at least 99%, or 100%, amino acid sequence identity to: GVYLLPRRGPRLGVRATRKTSERSQPR-GRRQPIPKARRSEGRSWAQPGYP (SEQ ID NO:148), wherein the T-cell epitope polypeptide has a length of from 40 amino acids to 50 amino acids;
c) a TP42 T-cell epitope polypeptide comprising an amino acid sequence having at least 80%, at least 90%, at least 95%, at least 98%, at least 99%, or 100%, amino acid sequence identity to: GTEGEIPFYGKAIPLEQIKG-GRHLIFCHSKKKCDELAAKLTG (SEQ ID NO:228), wherein the TP42 T-cell epitope polypeptide has a length of from 38 amino acids to 45 amino acids; and
d) a TP48 T-cell epitope polypeptide comprising an amino acid sequence having at least 80%, at least 90%, at least 95%, at least 98%, at least 99%, or 100%, amino acid sequence identity to: ILR-RHVGPGEGAVQWMNRLIAFAS-RGNHVSPTHYVPESDAAARVTQIL (SEQ ID NO:268), wherein the T-cell epitope polypeptide has a length of from 45 amino acids to 55 amino acids.

Aspect 10. The immunogenic composition of any one of aspects 1-5, wherein the one or more T-cell epitope polypeptides comprise:
a) a TP35-NS3 T-cell epitope polypeptide comprising an amino acid sequence having at least 80%, at least 90%, at least 95%, at least 98%, at least 99%, or 100%, amino acid sequence identity to: KSTKVPAAYAAQGYKVLVLNPSVAATLGF-GAYMSK (SEQ ID NO:133), wherein the TP35-NS3 T-cell epitope polypeptide has a length of from 28 amino acids to 35 amino acids; and
b) a TP50-C T-cell epitope polypeptide comprising an amino acid sequence having at least 80%, at least 90%, at least 95%, at least 98%, at least 99%, or 100%, amino acid sequence identity to: GVYLLPRRGPRLGVRATRKTSERSQPR-GRRQPIPKARRSEGRSWAQPGYP (SEQ ID NO:148), wherein the TP50-C T-cell epitope polypeptide has a length of from 40 amino acids to 50 amino acids;
c) a TP42 T-cell epitope polypeptide comprising an amino acid sequence having at least 80%, at least 90%, at least 95%, at least 98%, at least 99%, or 100%, amino acid sequence identity to: GTEGEIPFYGKAIPLEQIKG-GRHLIFCHSKKKCDELAAKLTG (SEQ ID NO:228), wherein the TP42 T-cell epitope polypeptide has a length of from 38 amino acids to 45 amino acids;
d) a TP48 T-cell epitope polypeptide comprising an amino acid sequence having at least 80%, at least 90%, at least 95%, at least 98%, at least 99%, or 100%, amino acid sequence identity to: ILR-RHVGPGEGAVQWMNRLIAFAS-RGNHVSPTHYVPESDAAARVTQIL (SEQ ID NO:268), wherein the T-cell epitope polypeptide has a length of from 45 amino acids to 55 amino acids; and
e) a TP42-2 T-cell epitope polypeptide comprising an amino acid sequence having at least 80%, at least 90%, at least 95%, at least 98%, at least 99%, or 100%, amino acid sequence identity to: KGGRHLIFCHS-KKKCDELAAKLTGLGLNAVAYYRGLDVSVIP (SEQ ID NO:291), wherein the TP42-2 T-cell epitope polypeptide has a length of from 38 amino acids to 45 amino acids.

Aspect 11. The immunogenic composition of any one of aspects 1-5, wherein the one or more T-cell epitope polypeptides comprise:
a) a TP35-NS3 T-cell epitope polypeptide comprising an amino acid sequence having at least 80%, at least 90%, at least 95%, at least 98%, at least 99%, or 100%, amino acid sequence identity to: KSTKVPAAYAAQGYKVLVLNPSVAATLGF-GAYMSK (SEQ ID NO:133), wherein the T-cell epitope polypeptide has a length of from 28 amino acids to 35 amino acids;
b) a TP50C T-cell epitope polypeptide comprising an amino acid sequence having at least 80%, at least 90%, at least 95%, at least 98%, at least 99%, or 100%, amino acid sequence identity to: GVYLLPRRGPRLGVRATRKTSERSQPR-GRRQPIPKARRSEGRSWAQPGYP (SEQ ID NO:148), wherein the T-cell epitope polypeptide has a length of from 40 amino acids to 50 amino acids; and
c) a TP42 T-cell epitope polypeptide comprising an amino acid sequence having at least 80%, at least 90%, at least 95%, at least 98%, at least 99%, or 100%, amino acid sequence identity to: GTEGEIPFYGKAIPLEQIKG-GRHLIFCHSKKKCDELAAKLTG (SEQ ID NO:228), wherein the T-cell epitope polypeptide has a length of from 38 amino acids to 45 amino acids.

Aspect 12. The immunogenic composition of aspect 2, wherein heterologous fusion partner is one or more of:
a) cholera toxin or toxoid;
b) tetanus toxin or toxoid; and
c) diphtheria toxin or toxoid; and
d) CRM197.

Aspect 13. The immunogenic composition of any one of aspects 1-12, wherein the composition comprises a polypeptide comprising one or more T cell epitopes present in:
  a) cholera toxin or toxoid; and/or
  b) tetanus toxin or toxoid; and/or
  c) diphtheria toxin or toxoid; and/or
  d) CRM197.

Aspect 14. The immunogenic composition of any one of aspects 1-13, further comprising a hepatitis C virus (HCV) E1/E2 heterodimeric polypeptide comprising: i) an HCV E1 polypeptide; and ii) an HCV E2 polypeptide;

Aspect 15. The immunogenic composition of aspect 14, wherein the HCV E1 polypeptide comprises an amino acid sequence having at least 20% (at least 20%, at least 30%, at least 40%, at least 50%, at least 60%, at least 70%, at least 80%, at least 90%, at least 95%, at least 98%, at least 99%, or 100%) amino acid sequence identity to an E1 polypeptide depicted in FIG. 1A-1C, FIG. 2A-2C, FIG. 3A-3C, and FIG. 4A-4B.

Aspect 16. The immunogenic composition of aspect 14, wherein the HCV E2 polypeptide comprises an amino acid sequence having at least 20% (at least 20%, at least 30%, at least 40%, at least 50%, at least 60%, at least 70%, at least 80%, at least 90%, at least 95%, at least 98%, at least 99%, or 100%) amino acid sequence identity to an E2 polypeptide depicted in one of FIG. 1A-1C, FIG. 2A-2C, FIG. 3A-3C, and FIG. 4A-4B.

Aspect 17. The immunogenic composition of any one of aspects 14-16, wherein the E2 polypeptide and/or the E1 polypeptide lacks a C-terminal transmembrane domain.

Aspect 18. The immunogenic composition of any one of aspects 14-17, wherein the HCV E2 polypeptide and the HCV E1 polypeptide are derived from an HCV of the same genotype.

Aspect 19. The immunogenic composition of any one of aspects 14-18, wherein the HCV E2 polypeptide and the HCV E1 polypeptide are derived from an HCV of different genotypes.

Aspect 20. The immunogenic composition of any one of aspects 14-19, wherein the HCV E1/E2 heterodimeric polypeptide comprises:
  a) an HCV E1 polypeptide; and
  b) a modified E2 polypeptide comprising, in order from N-terminus to C-terminus: i) from 1 to 6 heterologous amino acids, wherein the from 1 to 6 heterologous amino acids are C-terminal to a site of proteolytic cleavage in a proteolytically cleavable linker; and ii) an HCV E2 polypeptide; or
  a) an HCV E2 polypeptide; and
  b) a modified E1 polypeptide comprising, in order from N-terminus to C-terminus: i) from 1 to 6 heterologous amino acids, wherein the from 1 to 6 heterologous amino acids are C-terminal to a site of proteolytic cleavage in a proteolytically cleavable linker; and ii) an HCV E1 polypeptide; or
  a) an HCV E1 polypeptide; and
  b) a modified E2 polypeptide comprising, in order from N-terminus to C-terminus: i) an HCV E2 polypeptide; and ii) from 1 to 6 heterologous amino acids, wherein the from 1 to 6 heterologous amino acids are N-terminal to a site of proteolytic cleavage in a proteolytically cleavable linker; or
  a) an HCV E2 polypeptide; and
  b) a modified E1 polypeptide comprising, in order from N-terminus to C-terminus: i) an HCV E1 polypeptide; and ii) from 1 to 6 heterologous amino acids, wherein the from 1 to 6 heterologous amino acids are N-terminal to a site of proteolytic cleavage in a proteolytically cleavable linker.

Aspect 21. The immunogenic composition of aspect 20, wherein:
  a) the from 1 to 6 heterologous amino acids at the N-terminus of the modified E2 polypeptide or the modified E1 polypeptide are Gly-Pro, Ser, Gly, or Gly-Ser; or
  b) the from 1 to 6 heterologous amino acids at the C-terminus of the modified E2 polypeptide or the modified E1 polypeptide are LEVLFQ (SEQ ID NO:83), ENLYYFQ (SEQ ID NO:84), LVPR (SEQ ID NO:85), I(E/D)GR (SEQ ID NO:86), or DDDDK (SEQ ID NO:87).

Aspect 22. The immunogenic composition of any one of aspects 1-21, wherein the adjuvant comprises MF59; alum; poly(DL-lactide co-glycolide); a CpG oligonucleotide; a suspension of liposomes comprising 3'-O-desacyl-4'-monophosphoryl lipid A (MPL) and *Quillaja saponaria* 21 (QS21); a mixture of alum and MPL; a phosphorylated hexaacyl disaccharide (PHAD); a mixture of alum and PHAD; or a cyclic dinucleotide.

Aspect 23. The immunogenic composition of any one of aspects 1-21, wherein the adjuvant comprises MF59.

Aspect 24. The immunogenic composition of any one of aspects 1-21, wherein the adjuvant comprises alum.

Aspect 25. A method of inducing an immune response in an individual to a hepatitis C virus (HCV) polypeptide, the method comprising administering to the individual:
  a) an effective amount of the immunogenic composition of any one of aspects 1-24; or
  b) one or more nucleic acids comprising nucleotide sequences encoding the T-cell epitope polypeptide(s) and/or the HCV E1/E2 heterodimeric polypeptide.

Aspect 26. The method of aspect 25, wherein said administering is by intramuscular administration.

Aspect 27. The method of aspect 25, wherein said administering is by subcutaneous administration.

Aspect 28. A container comprising the immunogenic composition of any one of aspects 1-24.

Aspect 29. The container of aspect 28, wherein the container and the composition are sterile.

Aspect 30. The container of aspect 28 or aspect 29, wherein the container is a syringe.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s);

nt, nucleotide(s); i.m., intramuscular(ly); i.p., intraperitoneal(ly); s.c., subcutaneous(ly); and the like.

Example 1

All reported CD8 T cell epitopes until Jul. 12, 2013 were extracted from the Immune Epitope Database and Analysis Resource (IDEB). These CD8 epitopes were narrowed down through an alternative search performed based on the common HLA MHC class-I Alleles in North America. According to the latest demographic statistics from 2013, the population of USA as the representative of the North America comprises of different ethnic groups including White (64%), Black (12%), Hispanic (16%), Asian or Pacific Islanders (5%), and others including Natives, Alaskans, and etc. (3%) (https://en(dot)wikipedia(dot)org/wiki/Race_and_ ethnicity_in_the_United_States).

The first 30 common MHC-I alleles (frequency >~6-7%) for each of the first four common populations in USA were used in a search for any HCV epitopes that were reported for any of these individual alleles, which comprised of A*01:01, A*02:03, A*02:06, A*02:07, A*03:01, A*11:01, A*23:01, A*24:02, A*25:01, A*26:01, A*29:02, A*30:01, A*30:02, A*31:01, A*32:01, A*33:03, A*34:02, A*68:01, A*68:02, A*74:01, B*07:02, B*08:01, B*14:02, B*15:01, B*15:02, B*15:03, B*18:01, B*35:01, B*38:02, B*40:01, B*40:02, B*42:01, B*44:01, B*44:03, B*45:01, B*46:01, B*49:01, B*51:01, B*52:01, B*53:01, B*54:01, B*55:02, B*57:01, B*58:01, C*01:02, C*02:02, C*03:03, C*03:04, C*04:01, C*05:01, C*06:02, C*07:01, C*07:02, C*08:01, C*08:02, C*14:02, and C*16:01 (https(://)www(dot)proimmune(dot) com/ecommerce/page(dot)php@page-MHC_alleles) (https://www.proimmune.com/ecommerce/ page.php?page=MHC_alleles). Using IDEB database until Jul. 12, 2013, a total of 106 MHC-I CD8 T cell epitopes that were restricted to each of the afore-mentioned alleles were found. The sequence of each epitope was searched and entered in an alignment including sequences from HCV genotypes 1a, 1b, and 3 as the genotypes of interest for a vaccine that will be potentially used in North America. Out of 106 epitopes, 64 were located and annotated on the sequences of HCV genotypes of 1a, 1b, and 3. In the case of mismatch of 1-3 amino acids in the sequence of the epitope against the HCV sequences, the epitope was still included in the analysis. The excluded 42 epitopes were consisting of those that were located on structural regions of HCV polyprotein (core, E1, E2, and P7), were repeats of other epitopes, or were not found.

Example 2

T-cell epitope polypeptides TP35-NS3, TP35-NS3(Lys)$_3$, TP42, TP45 (with C-terminal CNV replaced with KKK), TP45(Lys)$_3$, TP48, TP48(Lys)$_3$, TP50C, TP23, TP23(Lys)$_3$, TP27, TP27(Lys)$_3$, TP35-NS4, and TP35-NS4(Lys)$_3$, were synthesized using solid-phase peptide synthesis. The solubility of these peptides was tested under various conditions and using various protocols.

Protocol 1 The solubility of the T-cell epitope polypeptides in E1E2 buffer was determined. E1E2 buffer: 10 mM sodium citrate, 250 mM NaCl, 1 mM ethylenediaminetetraacetic acid (EDTA), 0.1% non-ionic detergent TWEEN® 80, pH 6.0. Lyophilized T-cell epitope polypeptides were individually added to E1E2 buffer at a final concentration of 1 mg T-cell epitope polypeptide per ml E1E2 buffer, to generate T-cell epitope polypeptide/E1E2 solutions. The T-cell epitope polypeptide/E1E2 solutions were vortexed for 3 seconds. The T-cell epitope polypeptide/E1E2 solutions were then centrifuged at 10,000×g for 30 seconds. As precipitation was visible in the TP42, TP45-3+KKK, and TP48 solutions, 0.5 ml of E1E2 buffer was added and the solutions were vortexed and centrifuged again. After centrifugation, the concentration of peptides was measured using Nanodrop (Thermo Fisher).

The results are shown in FIG. 6. Solubility values shown in FIG. 6 are estimates based on A280 nm reading. As shown in FIG. 6, TP35-NS3, TP35-NS3-(Lys)$_3$, TP48-(Lys)$_3$, and TP50-C exhibit good solubility in E1E2 buffer. In contrast, TP42 and TP45 (with C-terminal CNV replaced with KKK) exhibited much lower solubility in E1E2 buffer than TP35-NS3, TP35-NS3-(Lys)$_3$, TP48-(Lys)$_3$, and TP50-C.

Protocol 2 All T-cell epitope peptides were lyophilized. E1E2 buffer was added to the lyophilized peptides to a concentration of 1 mg peptide/ml E1E2 buffer, to generate reconstituted T-cell epitope peptides ("TPs"). The reconstituted TPs were vortexed for 3 seconds, then incubated at room temperature for 30 minutes. After the 30-minute incubation period, all reconstituted TPs were centrifuged at 10,000×g for 30 seconds. Following centrifugation, the concentration of the TPs in the supernatant was measured using Nanodrop (Thermo Fisher).

The results are shown in FIG. 12. EC—extinction coefficient. EC was used to calculate the TP concentration.

Protocol 3 TP42, TP45(Lys)$_3$, and TP48 were lyophilized. The lyophilized peptides were reconstituted in: i) E1E2 buffer; or ii) E1E2 buffer without Tween; or iii) water. The reconstituted peptide solutions were vigorously vortexed for 20 seconds. After vortexing, the peptide solutions were incubated at room temperature with continuous shaking at 300 rpm for 2 hours 30 minutes. Afterwards, peptide solutions were centrifuged at 5000×g for 1 minute. After centrifugation, the concentration of the peptides in the supernatant was measured.

The results are shown in FIG. 13. The results indicate that TP42 and TP48 showed good solubility.

Protocol 4 TP45(Lys)$_3$, and TP48 were lyophilized. The lyophilized peptides were reconstituted in: i) E1E2 buffer; or ii) E1E2 buffer without Tween; or iii) water. The reconstituted peptide solutions were vigorously vortexed for 20 seconds. After vortexing, the peptide solutions were incubated at room temperature with continuous shaking at 300 rpm for 2 hours 30 minutes. Afterwards, peptide solutions were centrifuged at 5000×g for 1 minute. The results are shown in FIG. 14.

Example 3: Epitope-Based Design of TPs

Reported HCV MHC-I and MHC-H epitopes that are conserved for 5 genotypes of HCV: A further analysis was done to extend the conservancy of epitopes among 5 genotypes of HCV. First, all of the amino acid sequences for different HCV genotypes were extracted from NCBI. This step resulted in 526, 302, 24, 97, 36, 31, 6, 61, and 3 sequences for HCV genotypes 1a, 1b, 2a, 2b, 3, 4, 5, 6, and 7, respectively. Next, consensus sequences were built for each of the 5 genotypes of HCV1a, HCV-1b, HCV-2a, HCV-2b, and HCV-3. These consensus sequences were populated in one Genious alignment document.

Using IEDB software, all of the reported HCV MHC-I and MHC-II epitopes were extracted from database, which resulted in 744 MHC-I and 679 MHC-II epitopes. Next, all those epitopes were checked for conservancy against 5 consensus sequences. This resulted in 18 and 22 epitopes for MHC-I and MHC-II, respectively. Of those, 10 of MHC-I and 14 of MHC-II were located on the candidate TPs (TP50-C, TP35-NS3, TP42, and TP48). These epitopes are depicted in FIG. 15-18.

Predicted HCV MHC-I and MHC-II epitopes for designed 4 TPs. In a parallel analysis, potential predicted epitopes were searched for in the region of our already designed 4 TPs. To do this, the sequences of 4 TPs were checked against 87 common (a sum of the first 63 common HLAs in the USA population and the common HLAs recommended by IEDB). This analysis provided a list of 81,417 possible epitopes with different scores based on IC50 and percentile rank (depending on the applicable analysis method). To choose the high affinity epitopes, the following methods and thresholds were used according to the method that was available for each pair of epitope-allele and based on IEDB recommendation.

In 54 allele the ANN method was used to select epitopes with high affinity (an IC50<50 nm). This resulted in 82 allele-epitope pairs that included 69 unique epitopes and 23 unique alleles paired with each other. Using Consensus method for the same 54 alleles at Percentile Rank of <1%, 93 allele-epitope pairs selected that included 66 unique epitopes and 40 unique alleles paired with each other. Combining ANN and Consensus methods resulted in 104 unique epitopes that were paired with 42 unique alleles which resulted in 130 epitope-pair to be used for Population Coverage Analysis.

Of the 33 remaining epitopes, NetMHCpan method was used to select the epitopes with high affinity for 32 epitopes and SMM method was used for one epitope. A cutoff of a percentile rank of <1% and IC50<50 nm was used in NetMHCpan method. This resulted in 11 epitope-allele pairs that included 8 unique epitopes and 7 unique alleles that paired with each other. In the case of SMM method, using SMM percentile rank of <1% resulted in 1 epitope-allele pair. Both were combined and entered into Genious.

By pooling all the predicted epitopes and removing the repeated ones, a total of 104 epitopes selected for population coverage analysis which were predicted to be potentially recognized by 50 HLAs at high affinity, according to the cutoff recommended by each method.

Population Coverage Analysis Based on MHC-I Epitopes

Population coverage analysis was done for two groups of MHC-I epitope-HLA pairs. First, for the 10 reported MHC-I epitope-HLA pairs and second for the 104 predicted epitope-HLA pairs. The results are depicted in FIG. 19.

Memory Immune Response to TPs in Mice

Figure 20:
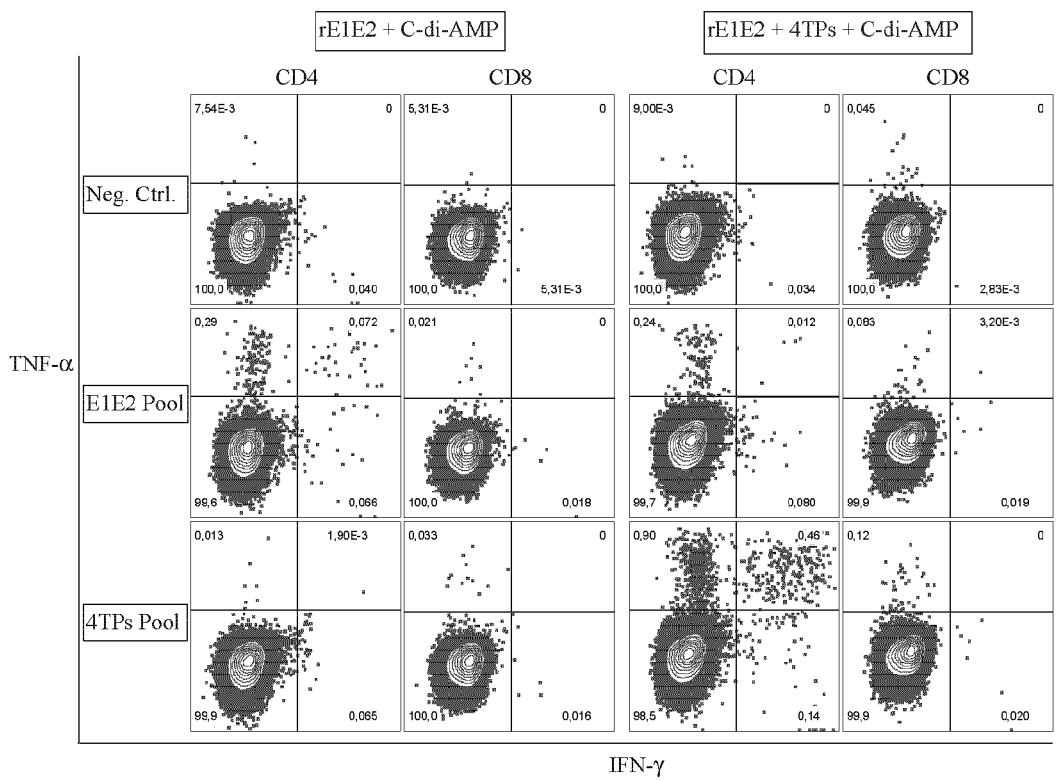
FIG. 20 depicts T-cell responses to various T-cell epitope polypeptides of the present disclosure in mice.

To check the solubility of a mixture of all 4 TPs (including TP50-C, TP35-NS3, TP42, and TP48) and the rE1E2 component of the vaccine, each TP was solubilized separately, as described above, and mixed with each other. The mixture of all 4 TPs was then further mixed with rE1E2. In the final solution of 4TPS and rE1E2 no visible precipitation observed. The mixture was used to immunize mice. After three immunization, the mice were sacrificed, the spleens were harvested, splenocytes were isolated and memory immune response was investigated via an in vitro assay by detecting polyfunctional T cells expressing IFN-γ and TNF-α in an intracellular cytokine assay protocol by flow cytometry. The results demonstrated a CD4 (but not CD8) T cell response following to re-stimulation of the splenocytes by a pool of peptides that spans the whole length of all 4 TPs (FIG. 20). The lack of a CD8 T cell response could be due to the lack of enough number of matching epitope-HLA pair in mice in comparison to human, since the TPs were basically designed based on the reported HCV epitopes according to human HLAs.

TP Analysis

Figure 21:
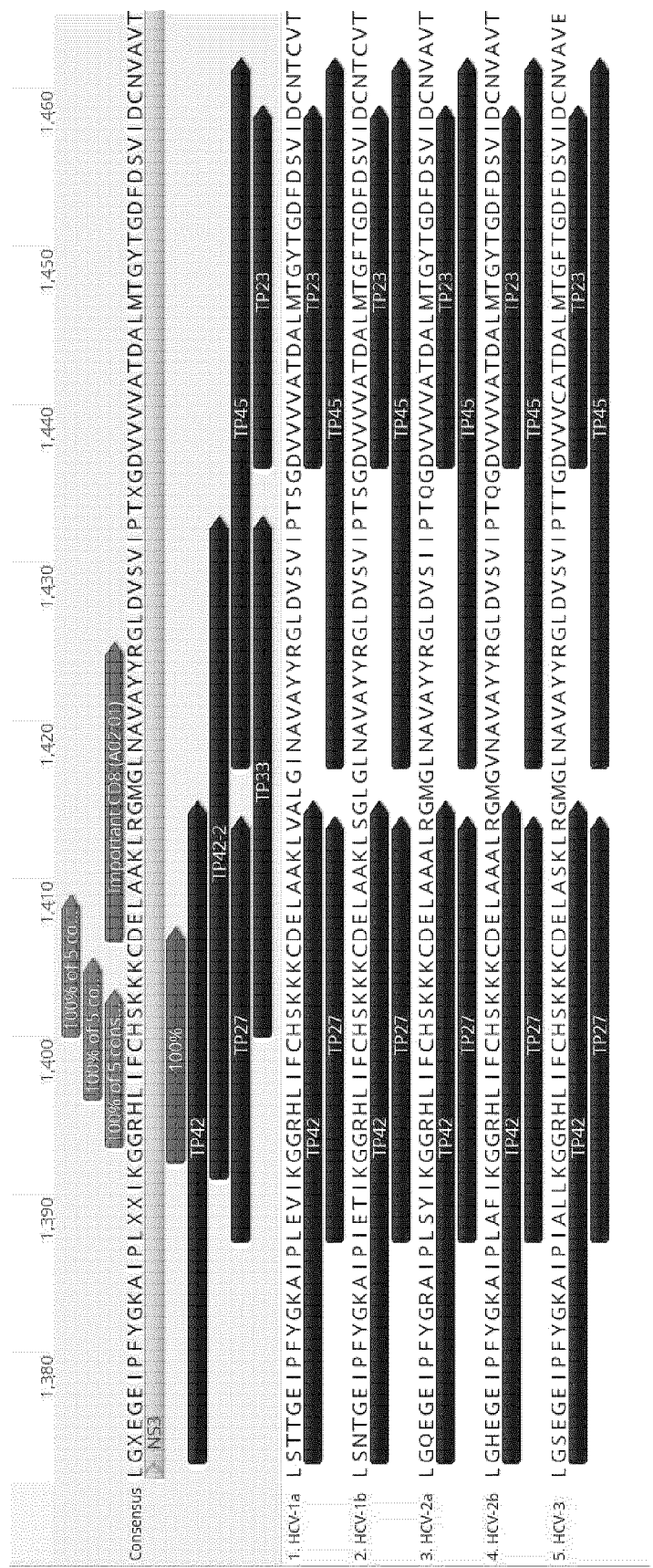
FIG. 21 provides an alignment of amino acid sequences of T-cell epitope polypeptides designated TP42, TP42-2, TP27, TP33, TP45, and TP23, from HCV-1a, HCV-1b, HCV-2a, HCV-2b, and HCV3. Top to Bottom: SEQ ID NOs:383-388. The bars labeled "100% of 5 co . . . " or "100% of 5 cons . . . " indicate CD8 epitopes. The bar labeled "100%" indicates CD4 epitopes.
Figure 22:
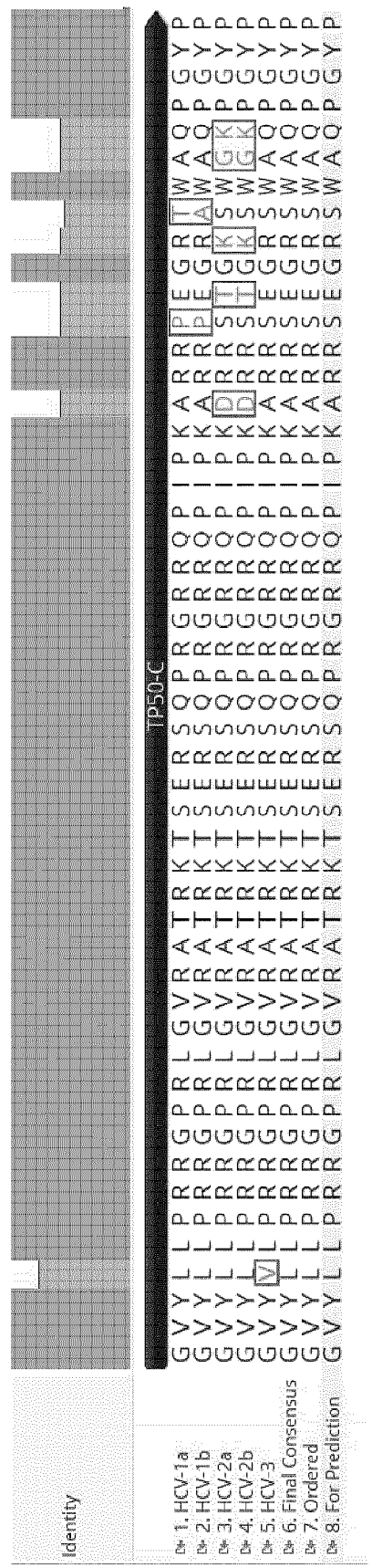
FIG. 22 provides an alignment of amino acid sequences of TP50-C T-cell epitope polypeptides from HCV-1a, HCV-1b, HCV-2a, HCV-2b, and HCV3; a final consensus sequence; an amino acid sequence of a TP50-C polypeptide on which solubility studies were conducted ("ordered"); and an amino acid sequence that was used for epitope prediction analyses ("for prediction"). Top to Bottom: SEQ ID NOs:389-396.
Figure 23:
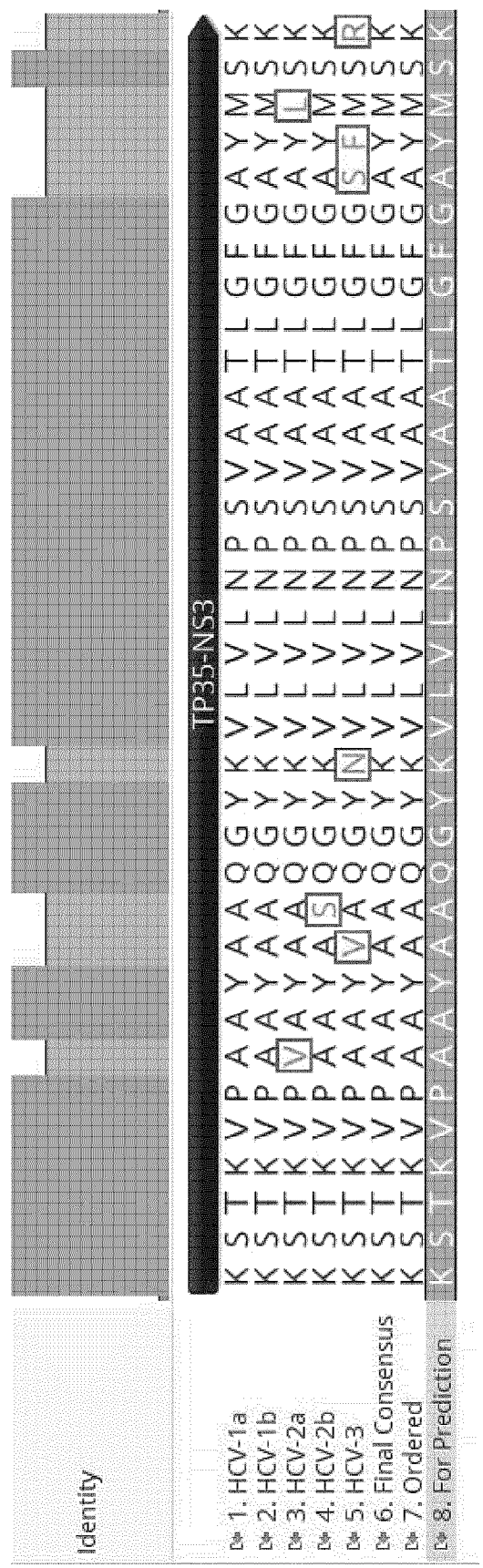
FIG. 23 provides an alignment of amino acid sequences of TP35-NS3 T-cell epitope polypeptides from HCV-1a, HCV-1b, HCV-2a, HCV-2b, and HCV3; a final consensus sequence; an amino acid sequence of a TP35-NS3 polypeptide on which solubility studies were conducted ("ordered"); and an amino acid sequence that was used for epitope prediction analyses ("for prediction"). Top to Bottom: SEQ ID NOs:397-404.

FIG. 21 depicts amino acid sequences of TP42, TP42-2, TP27, TP45, TP33, and TP23. FIG. 22-26 provide amino acid sequence alignments for TP50-C, TP35-NS3, TP42, TP42-2, and TP48, respectively. The "final consensus" sequences represent the consensus sequences for each of the TPs according to the most recent analysis. The "ordered" sequences represents the TP sequences that have been manufactured and tested for solubility. The "for prediction" sequences represent the TP sequences that were used in prediction analysis, to provide the predicted epitopes using IEDB software and its Databank.

Figure 24:
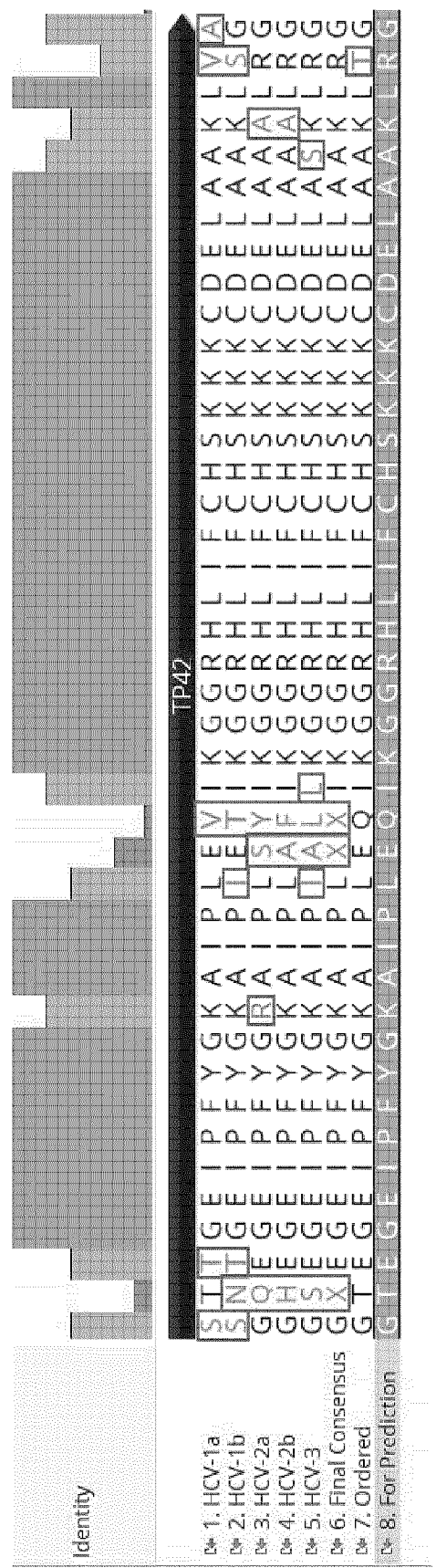
FIG. 24 provides an alignment of amino acid sequences of TP42 T-cell epitope polypeptides from HCV-1a, HCV-1b, HCV-2a, HCV-2b, and HCV3; a final consensus sequence; an amino acid sequence of a TP42 polypeptide on which solubility studies were conducted ("ordered"); and an amino acid sequence that was used for epitope prediction analyses ("for prediction"). Top to Bottom: SEQ ID NOs:405-412.
Figure 25:
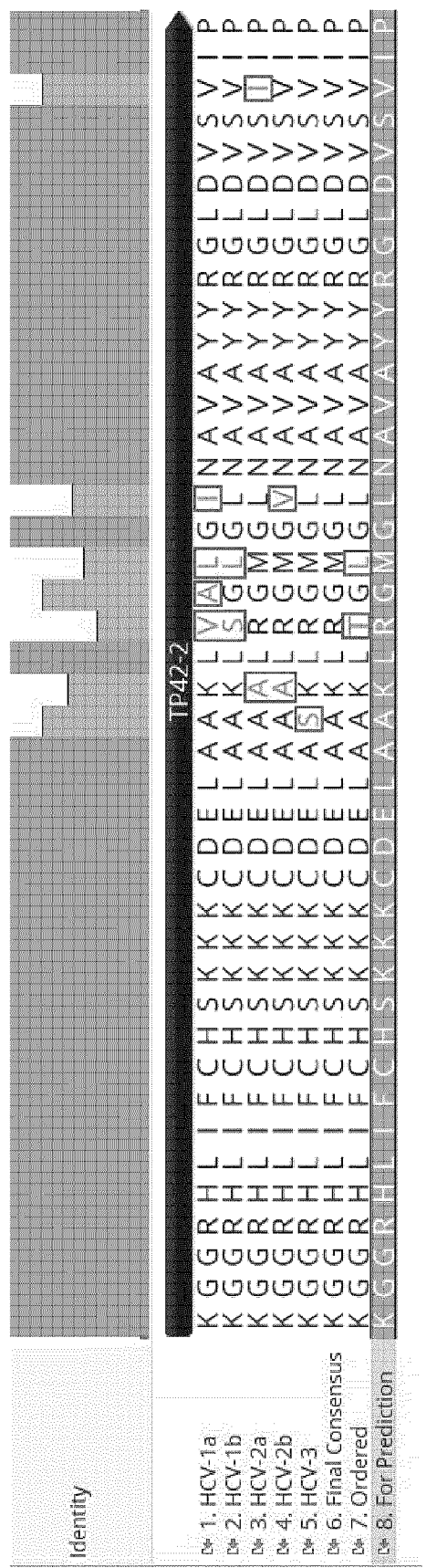
FIG. 25 provides an alignment of amino acid sequences of TP42-2 T-cell epitope polypeptides from HCV-1a, HCV-1b, HCV-2a, HCV-2b, and HCV3; a final consensus sequence; an amino acid sequence of a TP42-2 polypeptide on which solubility studies were conducted ("ordered"); and an amino acid sequence that was used for epitope prediction analyses ("for prediction"). Top to Bottom: SEQ ID NOs:413-420.
Figure 26:
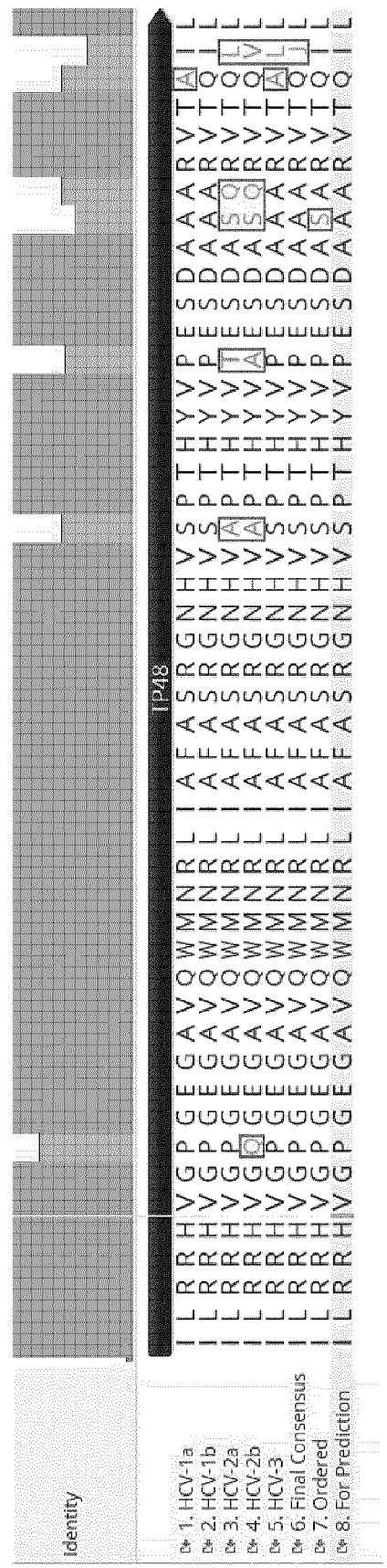
FIG. 26 provides an alignment of amino acid sequences of TP48 T-cell epitope polypeptides from HCV-1a, HCV-1b, HCV-2a, HCV-2b, and HCV3; a final consensus sequence; an amino acid sequence of a TP48 polypeptide on which solubility studies were conducted ("ordered"); and an amino acid sequence that was used for epitope prediction analyses ("for prediction"). Top to Bottom: SEQ ID NOs:421-428.

The Geneious software assigns letter "J" to any position of a consensus sequence, where the alternative amino acid could be "I" or "L" and assigns "X" where the alternative amino acid could be more than 3 different amino acids. Thus, in FIG. 26, a "J" indicates that the amino acid can be Ile or Leu. In FIG. 24, the "X" in position 2 can be any of Asn, Gln, His, Ser, or Thr.

Solubility of TP33 and TP42-2

TP33 and TP42-2 were reconstituted in a solution at 0.5 mg/mL. The solutions were vortexed vigorously for 20 seconds. After vortexing, the solutions were incubated at room temperature with continuous shaking at 300 rpm for 2 hours and 30 minutes. After incubation, the solutions were centrifuged at 5000×g for 1 minute, and evaluated for solubility, both visually and by Nanodrop.

The results are depicted in FIG. 27.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An immunogenic composition comprising:
   a) a TP35-NS3 T-cell epitope polypeptide comprising an amino acid sequence having at least 80% amino acid sequence identity to: KSTKVPAAYAAQGYKVLVLNPSVAATLGF-GAYMSK as set forth by SEQ ID NO:133, wherein the T-cell epitope polypeptide has a length of from 28 amino acids to 35 amino acids;
   b) a TP50C T-cell epitope polypeptide comprising an amino acid sequence having at least 80% amino acid sequence identity to: GVYLLPRRGPRLGVRATRKTSERSQPR-GRRQPIPKARRSEGRSWAQPGYP as set forth by SEQ ID NO:148, wherein the T-cell epitope polypeptide has a length of from 40 amino acids to 50 amino acids;
   c) a TP27 T-cell epitope polypeptide comprising an amino acid sequence having at least 80% amino acid sequence identity to: LEQIKGGRHLIFCHSKKKCDELAAKLT as set forth by SEQ ID NO:188, wherein the TP27 T-cell epitope polypeptide has a length of from 22 amino acids to 27 amino acids; and
   d) a TP48 T-cell epitope polypeptide comprising an amino acid sequence having at least 80% amino acid sequence identity to: ILRRHVGPGEGAVQWMNRLIAFAS-RGNHVSPTHYVPESDAAARVTQIL as set forth by SEQ ID NO:268, wherein the T-cell epitope polypeptide has a length of from 45 amino acids to 48 amino acids.

2. The immunogenic composition of claim 1, comprising:
   a) a TP35-NS3 T-cell epitope polypeptide comprising an amino acid sequence having at least 95% amino acid sequence identity to: KSTKVPAAYAAQGYKVLVLNPSVAATLGF-GAYMSK as set forth by SEQ ID NO:133, wherein the T-cell epitope polypeptide has a length of from 28 amino acids to 35 amino acids;
   b) a TP50C T-cell epitope polypeptide comprising an amino acid sequence having at least 95% amino acid sequence identity to: GVYLLPRRGPRLGVRATRKTSERSQPR-GRRQPIPKARRSEGRSWAQPGYP as set forth by SEQ ID NO:148, wherein the T-cell epitope polypeptide has a length of from 40 amino acids to 50 amino acids;
   c) a TP27 T-cell epitope polypeptide comprising an amino acid sequence having at least 95% amino acid sequence identity to: LEQIKGGRHLIFCHSKKKCDELAAKLT as set forth by SEQ ID NO:188, wherein the TP27 T-cell epitope polypeptide has a length of from 22 amino acids to 27 amino acids; and
   d) a TP48 T-cell epitope polypeptide comprising an amino acid sequence having at least 95% amino acid sequence identity to: ILRRHVGPGEGAVQWMNRLIAFAS- RGNHVSPTHYVPESDAAARVTQIL as set forth by SEQ ID NO:268, wherein the T-cell epitope polypeptide has a length of from 45 amino acids to 48 amino acids.

3. The immunogenic composition of claim 1, comprising:
a) a TP35-NS3 T-cell epitope polypeptide comprising an amino acid sequence having at least 95% amino acid sequence identity to: KSTKVPAAYAAQGYKVLVLNPSVAATLGF-GAYMSK as set forth by SEQ ID NO:133, wherein the T-cell epitope polypeptide has a length of 35 amino acids;
b) a TP50C T-cell epitope polypeptide comprising an amino acid sequence having at least 95% amino acid sequence identity to: GVYLLPRRGPRLGVRATRKTSERSQPR-GRRQPIPKARRSEGRSWAQPGYP as set forth by SEQ ID NO:148, wherein the T-cell epitope polypeptide has a length of 50 amino acids;
c) a TP27 T-cell epitope polypeptide comprising an amino acid sequence having at least 95% amino acid sequence identity to: LEQIKGGRHLIFCHSKKKCDELAAKLT as set forth by SEQ ID NO:188, wherein the TP27 T-cell epitope polypeptide has a length of 27 amino acids; and
d) a TP48 T-cell epitope polypeptide comprising an amino acid sequence having at least 95% amino acid sequence identity to: ILRRHVGPGEGAVQWMNRLIAFAS-RGNHVSPTHYVPESDAAARVTQIL as set forth by SEQ ID NO:268, wherein the T-cell epitope polypeptide has a length of 48 amino acids.

4. The immunogenic composition of claim 1, comprising:
a) a TP35-NS3 T-cell epitope polypeptide comprising the amino acid sequence: KSTKVPAAYAAQGYKVLVLNPSVAATLGF-GAYMSK as set forth by SEQ ID NO:133, wherein the T-cell epitope polypeptide has a length of 35 amino acids;
b) a TP50C T-cell epitope polypeptide comprising the amino acid sequence: GVYLLPRRGPRLGVRATRKTSERSQPR-GRRQPIPKARRSEGRSWAQPGYP as set forth by SEQ ID NO:148, wherein the T-cell epitope polypeptide has a length of 50 amino acids;
c) a TP27 T-cell epitope polypeptide comprising the amino acid sequence: LEQIKGGRHLIFCHS-KKKCDELAAKLT as set forth by SEQ ID NO:188, wherein the TP27 T-cell epitope polypeptide has a length of 27 amino acids; and
d) a TP48 T-cell epitope polypeptide comprising the amino acid sequence: ILR-RHVGPGEGAVQWMNRLIAFAS-RGNHVSPTHYVPESDAAARVTQIL as set forth by SEQ ID NO:268, wherein the T-cell epitope polypeptide has a length of 48 amino acids.

5. The immunogenic composition of claim 1, comprising:
a) a TP35-NS3 T-cell epitope polypeptide comprising the amino acid sequence: KSTKVPAAYAAQGYKVLVLNPSVAATLGF-GAYMSK as set forth by SEQ ID NO:133, wherein the T-cell epitope polypeptide has a length of 35 amino acids;
b) a TP50C T-cell epitope polypeptide comprising the amino acid sequence: GVYLLPRRGPRLGVRATRKTSERSQPR-GRRQPIPKARRSEGRSWAQPGYP as set forth by SEQ ID NO:148, wherein the T-cell epitope polypeptide has a length of 50 amino acids;
c) a TP27 T-cell epitope polypeptide comprising the amino acid sequence: LEQIKGGRHLIFCHS-KKKCDELAAKLR as set forth by SEO ID NO:188, wherein the TP27 T-cell epitope polypeptide has a length of 27 amino acids; and
d) a TP48 T-cell epitope polypeptide comprising the amino acid sequence: ILR-RHVGPGEGAVQWMNRLIAFAS-RGNHVSPTHYVPESDAAARVTQIL as set forth by SEQ ID NO:268, wherein the T-cell epitope polypeptide has a length of 48 amino acids.

6. The composition of claim 1, further comprising a hepatitis C virus (HCV) E1 polypeptide and/or an HCV E2 polypeptide.

7. The composition of claim 6, wherein the composition comprises an HCV E1 polypeptide and an HCV E2 polypeptide.

8. The composition of claim 7, wherein the HCV E1 polypeptide and the HCV E2 polypeptide are of the same genotype.

9. The composition of claim 7, wherein the HCV E1 polypeptide and the HCV E2 polypeptide are of different genotypes.

10. The composition of claim 1, wherein the adjuvant comprises MF59.

11. The composition of claim 1, wherein the adjuvant comprises alum.

12. The composition of claim 1, wherein the adjuvant comprises a glucopyranosyl lipid.

13. A container comprising the immunogenic composition of claim 1.

14. The container of claim 13, wherein the container and the composition are sterile.

15. The container of claim 13, wherein the container is a syringe.

16. A method of inducing an immune response in an individual to a hepatitis C virus (HCV) polypeptide, the method comprising administering to the individual an effective amount of the immunogenic composition of claim 1.

17. A method of inducing an immune response in an individual to a hepatitis C virus (HCV) polypeptide, the method comprising administering to the individual an effective amount of the immunogenic composition of claim 6.

18. A method of inducing an immune response in an individual to a hepatitis C virus (HCV) polypeptide, the method comprising administering to the individual an effective amount of the immunogenic composition of claim 7.

* * * * *